(12) United States Patent
Sydorenko et al.

(10) Patent No.: US 11,780,839 B2
(45) Date of Patent: Oct. 10, 2023

(54) COMPOUNDS FOR TREATING HUNTINGTON'S DISEASE

(71) Applicant: PTC THERAPEUTICS, INC., South Plainfield, NJ (US)

(72) Inventors: Nadiya Sydorenko, Princeton, NJ (US); Md Rauful Alam, Piscataway, NJ (US); Lukiana Amedzo, Somerset, NJ (US); Suresh Babu, Pennington, NJ (US); Ramil Y. Baiazitov, East Brunswick, NJ (US); Scott J. Barraza, Piscataway, NJ (US); Anuradha Bhattacharyya, Edison, NJ (US); Gary Mitchell Karp, Princeton Junction, NJ (US); Nathaniel T. Kenton, Highland Park, NJ (US); Anthony R. Mazzotti, Rahway, NJ (US); Young-Choon Moon, Belle Mead, NJ (US); Nicholas W. Mszar, New Brunswick, NJ (US); Jana Narasimhan, Scotch Plains, NJ (US); Sudipta Pal, Piscataway, NJ (US); Jigar S. Patel, Jersey City, NJ (US); Anthony Turpoff, Hillsborough, NJ (US); Matthew G. Woll, Dunellen, NJ (US); Zhenrong Xu, Chalfont, PA (US); Nanjing Zhang, Princeton, NJ (US)

(73) Assignee: PTC THERAPEUTICS, INC., South Plainfield, NJ (US)

( * ) Notice: Subject to any disclaimer, the term of this patent is extended or adjusted under 35 U.S.C. 154(b) by 0 days.

(21) Appl. No.: 17/040,104

(22) PCT Filed: Mar. 27, 2019

(86) PCT No.: PCT/US2019/024278
§ 371 (c)(1),
(2) Date: Sep. 22, 2020

(87) PCT Pub. No.: WO2019/191229
PCT Pub. Date: Oct. 3, 2019

(65) Prior Publication Data
US 2021/0024525 A1    Jan. 28, 2021

Related U.S. Application Data

(60) Provisional application No. 62/648,699, filed on Mar. 27, 2018.

(51) Int. Cl.
C07D 471/08 (2006.01)
C07D 401/14 (2006.01)
(Continued)

(52) U.S. Cl.
CPC ............ C07D 471/08 (2013.01); A61P 25/28 (2018.01); C07D 401/12 (2013.01);
(Continued)

(58) Field of Classification Search
CPC .. C07D 471/08; C07D 401/14; C07D 405/14; C07D 409/14; C07D 413/14;
(Continued)

(56) References Cited

U.S. PATENT DOCUMENTS 3,558,618 A   1/1971   Trepanier
4,122,274 A   10/1978  Juby
(Continued)

FOREIGN PATENT DOCUMENTS

CN   101360738 A   2/2009
CN   104768960 B   3/2017
(Continued)

OTHER PUBLICATIONS

Chemical Abstracts Registry No. 2107242-04-4, indexed in the Registry file on STN CAS Online Aug. 2, 2017. (Year: 2017).*
(Continued)

*Primary Examiner* — Laura L Stockton
(74) *Attorney, Agent, or Firm* — Hoffmann & Baron, LLP

(57) ABSTRACT

The present description relates to compounds, forms, and pharmaceutical compositions thereof and methods of using such compounds, forms, or compositions thereof for treating or ameliorating Huntington's disease.

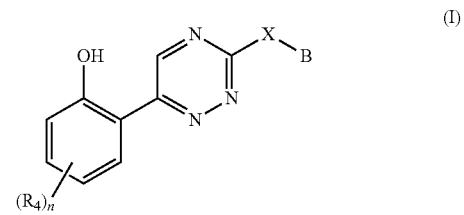

(I)

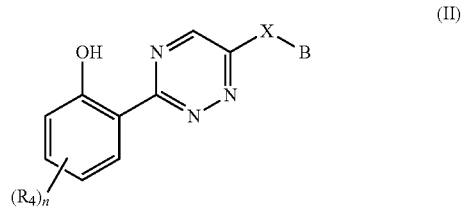

(II)

In particular, the present description relates to substituted monocyclic heteroaryl compounds of Formula (I) or Formula (II), forms and pharmaceutical compositions thereof and methods of using such compounds, forms, or compositions thereof for treating or ameliorating Huntington's disease.

12 Claims, No Drawings

(51) Int. Cl.
    *C07D 405/14* (2006.01)
    *C07D 409/14* (2006.01)
    *C07D 413/14* (2006.01)
    *C07D 417/14* (2006.01)
    *C07D 471/04* (2006.01)
    *C07D 471/10* (2006.01)
    *C07D 487/04* (2006.01)
    *C07D 491/107* (2006.01)
    *C07D 493/08* (2006.01)
    *C07D 498/04* (2006.01)
    *A61P 25/28* (2006.01)
    *C07D 401/12* (2006.01)

(52) U.S. Cl.
    CPC ......... *C07D 401/14* (2013.01); *C07D 405/14* (2013.01); *C07D 409/14* (2013.01); *C07D 413/14* (2013.01); *C07D 417/14* (2013.01); *C07D 471/04* (2013.01); *C07D 471/10* (2013.01); *C07D 487/04* (2013.01); *C07D 491/107* (2013.01); *C07D 493/08* (2013.01); *C07D 498/04* (2013.01)

(58) Field of Classification Search
    CPC .. C07D 417/14; C07D 471/04; C07D 471/10; C07D 487/04; C07D 491/107; C07D 493/08; C07D 498/04
    See application file for complete search history.

(56) References Cited

U.S. PATENT DOCUMENTS

| | | |
|---|---|---|
| 4,342,870 A | 8/1982 | Kennis et al. |
| 4,613,603 A | 9/1986 | Sanofi |
| 5,089,633 A | 2/1992 | Powers et al. |
| 5,599,816 A | 2/1997 | Chu et al. |
| 5,627,274 A | 5/1997 | Kole et al. |
| 5,665,593 A | 9/1997 | Kole et al. |
| 5,916,808 A | 6/1999 | Kole et al. |
| 5,916,916 A | 6/1999 | Hauser et al. |
| 5,976,879 A | 11/1999 | Kole et al. |
| 6,172,216 B1 | 1/2001 | Bennett et al. |
| 6,210,892 B1 | 4/2001 | Bennett et al. |
| 6,214,986 B1 | 4/2001 | Bennett et al. |
| 6,468,798 B1 | 10/2002 | Takehara et al. |
| 6,630,488 B1 | 10/2003 | Lamothe et al. |
| 6,977,255 B2 | 12/2005 | Robertson et al. |
| 7,326,711 B2 | 2/2008 | Wang et al. |
| 7,399,767 B2 | 7/2008 | Zhang et al. |
| 7,473,784 B2 | 1/2009 | Liu et al. |
| 7,569,337 B2 | 8/2009 | Auberson |
| 7,655,657 B2 | 2/2010 | Stoner et al. |
| 7,897,792 B2 | 3/2011 | Iikura et al. |
| 7,910,578 B2 | 3/2011 | Peters et al. |
| 8,143,274 B2 | 3/2012 | Kaisha |
| 8,314,119 B2 | 11/2012 | Schrimpf et al. |
| 8,337,941 B2 | 12/2012 | Gubernator et al. |
| 8,563,550 B2 | 10/2013 | Pevarello et al. |
| 8,633,019 B2 | 1/2014 | Paushkin et al. |
| 8,846,661 B2 | 9/2014 | Schrimpf et al. |
| 8,921,361 B2 | 12/2014 | Cmiljanovic et al. |
| 9,371,336 B2 | 6/2016 | Lee et al. |
| 9,399,649 B2 | 7/2016 | Chen et al. |
| 9,617,268 B2 | 4/2017 | Woll et al. |
| 9,969,754 B2 | 5/2018 | Ratni et al. |
| 2002/0099208 A1 | 7/2002 | Yu et al. |
| 2003/0004164 A1 | 1/2003 | Bebbington et al. |
| 2003/0199526 A1 | 10/2003 | Choquette et al. |
| 2005/0054836 A1 | 3/2005 | Krainer et al. |
| 2005/0074801 A1 | 4/2005 | Monia et al. |
| 2005/0159597 A1 | 7/2005 | Ji et al. |
| 2006/0172962 A1 | 8/2006 | Vickers et al. |
| 2006/0205741 A1 | 9/2006 | Zhang et al. |
| 2007/0078144 A1 | 4/2007 | Stockwell et al. |
| 2007/0105807 A1 | 5/2007 | Sazani et al. |
| 2007/0191374 A1 | 8/2007 | Hodgetts |
| 2008/0171792 A1 | 7/2008 | Jobdevairakkam et al. |
| 2008/0255162 A1 | 10/2008 | Bruendl et al. |
| 2009/0163464 A1 | 6/2009 | Black et al. |
| 2009/0163515 A1 | 6/2009 | Birault et al. |
| 2009/0170793 A1 | 7/2009 | Gaur |
| 2009/0264433 A1 | 10/2009 | Russell et al. |
| 2010/0004233 A1 | 1/2010 | Iikura et al. |
| 2010/0035279 A1 | 2/2010 | Gubernator et al. |
| 2010/0267721 A1 | 10/2010 | Hohlweg et al. |
| 2011/0086833 A1 | 4/2011 | Paushkin et al. |
| 2011/0118289 A1 | 5/2011 | Giordani et al. |
| 2012/0083495 A1 | 4/2012 | Heemskerk et al. |
| 2013/0046093 A1 | 2/2013 | Lee et al. |
| 2014/0051672 A1 | 2/2014 | Cheung et al. |
| 2014/0121197 A1 | 5/2014 | Usher, III |
| 2014/0206661 A1 | 7/2014 | Axford et al. |
| 2014/0329825 A1 | 11/2014 | Heback et al. |
| 2015/0005289 A1 | 1/2015 | Qi et al. |
| 2015/0018301 A1 | 1/2015 | Lee et al. |
| 2015/0057218 A1 | 2/2015 | Zhong et al. |
| 2015/0080383 A1 | 3/2015 | Yang et al. |
| 2015/0119380 A1 | 4/2015 | Woll et al. |
| 2016/0244762 A1 | 8/2016 | Vorechovsky et al. |
| 2017/0000794 A1 | 1/2017 | Naryshkin |
| 2017/0001995 A1 | 1/2017 | Metzger et al. |
| 2017/0002016 A1 | 1/2017 | Shishido et al. |
| 2017/0096411 A1 | 4/2017 | Vechorkin et al. |
| 2017/0121197 A1 | 5/2017 | Tale |
| 2017/0151225 A1 | 6/2017 | Dahl |
| 2017/0355989 A1 | 12/2017 | Konstantinova et al. |
| 2018/0118748 A1 | 5/2018 | Slaugenhaupt et al. |
| 2018/0161456 A1 | 6/2018 | Naryshkin et al. |
| 2018/0282347 A1 | 10/2018 | Arlt et al. |
| 2019/0264267 A1 | 8/2019 | Yang et al. |
| 2020/0056173 A1 | 2/2020 | Vargeese et al. |
| 2020/0080083 A1 | 3/2020 | Vargeese et al. |

FOREIGN PATENT DOCUMENTS

| | | |
|---|---|---|
| DE | 2345064 A1 | 4/1974 |
| EP | 1227084 A1 | 7/2002 |
| EP | 2560008 A2 | 2/2013 |
| EP | 2841428 B1 | 8/2018 |
| FR | 2914188 A1 | 10/2008 |
| GB | 1047935 | 11/1966 |
| GB | 1383409 | 2/1975 |
| JP | 1981-150091 A | 3/1983 |
| JP | S61-36282 | 2/1986 |
| JP | 2006219453 A | 8/2006 |
| JP | 2009-545540 | 12/2009 |
| JP | 2013-40945 | 2/2013 |
| JP | 2017-512834 | 5/2017 |
| WO | 1993/023398 A1 | 11/1993 |
| WO | 1994/026887 A1 | 11/1994 |
| WO | 1996/039407 A1 | 12/1996 |
| WO | 1998/025930 A1 | 6/1998 |
| WO | 2001/053266 A1 | 7/2001 |
| WO | 2002/062290 A2 | 8/2002 |
| WO | 2002/087589 A1 | 11/2002 |
| WO | 2004/009558 A1 | 1/2004 |
| WO | 2004/019002 A2 | 3/2004 |
| WO | 2004/029053 A1 | 4/2004 |
| WO | 2004/113335 A2 | 12/2004 |
| WO | 2005/012288 A1 | 2/2005 |
| WO | 2005/019215 A1 | 3/2005 |
| WO | 2005/061513 A1 | 7/2005 |
| WO | 2005/066166 A1 | 7/2005 |
| WO | 2005/072720 A1 | 8/2005 |
| WO | 2005/105801 A1 | 11/2005 |
| WO | 2006/131835 A2 | 12/2006 |
| WO | 2006/138418 A2 | 12/2006 |
| WO | 2007/003604 A2 | 1/2007 |
| WO | 2007/016392 A2 | 2/2007 |
| WO | 2007/018738 A1 | 2/2007 |
| WO | 2007/047913 A2 | 4/2007 |
| WO | 2007/065892 A1 | 6/2007 |
| WO | 2007/071055 A1 | 6/2007 |

(56) References Cited

FOREIGN PATENT DOCUMENTS

| | | |
|---|---|---|
| WO | 2007/089584 A2 | 8/2007 |
| WO | 2007/089611 A2 | 8/2007 |
| WO | 2007/090073 A2 | 8/2007 |
| WO | 2007/109211 A2 | 9/2007 |
| WO | 2007/110364 A1 | 10/2007 |
| WO | 2007/130383 A2 | 11/2007 |
| WO | 2007/133561 A2 | 11/2007 |
| WO | 2007/133756 A2 | 11/2007 |
| WO | 2007/135121 A1 | 11/2007 |
| WO | 2008/011109 A2 | 1/2008 |
| WO | 2008/014822 A1 | 2/2008 |
| WO | 2008/049864 A1 | 5/2008 |
| WO | 2008/077188 A1 | 7/2008 |
| WO | 2009/042907 A1 | 4/2009 |
| WO | 2009/085945 A1 | 7/2009 |
| WO | 2009/114874 A2 | 9/2009 |
| WO | 2009/126635 A1 | 10/2009 |
| WO | 2009/151546 A2 | 12/2009 |
| WO | 2009/156861 A2 | 12/2009 |
| WO | 2010/000032 A1 | 1/2010 |
| WO | 2010/019236 A1 | 2/2010 |
| WO | 2010/024903 A1 | 3/2010 |
| WO | 2010/045303 A2 | 4/2010 |
| WO | 2010/071819 A1 | 6/2010 |
| WO | 2010/093425 A1 | 8/2010 |
| WO | 2010/130934 A2 | 11/2010 |
| WO | 2010/145208 A1 | 12/2010 |
| WO | 2011/032045 A1 | 3/2011 |
| WO | 2011/050245 A1 | 4/2011 |
| WO | 2011/057204 A2 | 5/2011 |
| WO | 2011/062853 A1 | 5/2011 |
| WO | 2011/085990 A1 | 7/2011 |
| WO | 2011/097641 A1 | 8/2011 |
| WO | 2011/097643 A1 | 8/2011 |
| WO | 2011/097644 A2 | 8/2011 |
| WO | 2012/012467 A2 | 1/2012 |
| WO | 2012/019106 A2 | 2/2012 |
| WO | 2012/075393 A2 | 6/2012 |
| WO | 2012/103806 A1 | 8/2012 |
| WO | 2012/104823 A2 | 8/2012 |
| WO | 2012/109395 A1 | 8/2012 |
| WO | 2012/116965 A1 | 9/2012 |
| WO | 2013/019938 A1 | 2/2013 |
| WO | 2013/020993 A1 | 2/2013 |
| WO | 2013/022990 A1 | 2/2013 |
| WO | 2013/033223 A1 | 3/2013 |
| WO | 2013/059606 A1 | 4/2013 |
| WO | 2013/068769 A1 | 5/2013 |
| WO | 2013/101974 A1 | 7/2013 |
| WO | 2013/112788 A1 | 8/2013 |
| WO | 2013/119916 A1 | 8/2013 |
| WO | 2013/130689 A1 | 9/2013 |
| WO | 2013/142236 A1 | 9/2013 |
| WO | 2013/163190 A1 | 10/2013 |
| WO | 2014/012050 A2 | 1/2014 |
| WO | 2014/028459 A1 | 2/2014 |
| WO | 2014/059341 A2 | 4/2014 |
| WO | 2014/059356 A2 | 4/2014 |
| WO | 2014/066836 A1 | 5/2014 |
| WO | 2014/069675 A1 | 5/2014 |
| WO | 2014/116845 A1 | 7/2014 |
| WO | 2014/121287 A2 | 8/2014 |
| WO | 2014-135244 A1 | 9/2014 |
| WO | 2014/184163 A1 | 11/2014 |
| WO | 2014/209841 A2 | 12/2014 |
| WO | 2015/024876 A2 | 12/2014 |
| WO | 2015/017589 A1 | 2/2015 |
| WO | 2015/095446 A1 | 6/2015 |
| WO | 2015/095449 A1 | 6/2015 |
| WO | 2015/105657 A1 | 7/2015 |
| WO | 2015/107425 A2 | 7/2015 |
| WO | 2015/107494 A1 | 7/2015 |
| WO | 2015/110446 A1 | 7/2015 |
| WO | 2017/080967 A1 | 7/2015 |
| WO | 2015/143185 A1 | 9/2015 |
| WO | 2015/173181 A1 | 11/2015 |
| WO | 2015/197503 A1 | 12/2015 |
| WO | 2016/087417 A1 | 6/2016 |
| WO | 2016/128343 A1 | 8/2016 |
| WO | 2016/131776 A1 | 8/2016 |
| WO | 2016/144351 A1 | 9/2016 |
| WO | 2016/170163 A1 | 10/2016 |
| WO | 2016/184832 A1 | 11/2016 |
| WO | 2017/023987 A1 | 2/2017 |
| WO | 2017/081111 A1 | 5/2017 |
| WO | 2017/097728 A1 | 6/2017 |
| WO | 2017/100726 A1 | 6/2017 |
| WO | 2017/175068 A1 | 10/2017 |
| WO | 2017/189829 A1 | 11/2017 |
| WO | 2017/210134 A1 | 12/2017 |
| WO | 2018/081091 A1 | 5/2018 |
| WO | 2018/187209 A1 | 10/2018 |
| WO | 2018/218133 A1 | 11/2018 |
| WO | 2018/226622 A1 | 12/2018 |
| WO | 2019/005980 A1 | 1/2019 |
| WO | 2019/005993 A1 | 1/2019 |
| WO | 2019/028440 A1 | 2/2019 |
| WO | 2019/165073 A1 | 8/2019 |
| WO | 2019/183364 A1 | 9/2019 |
| WO | 2019/183367 A1 | 9/2019 |
| WO | 2019/191092 A1 | 10/2019 |
| WO | 2019/191229 A1 | 10/2019 |
| WO | 2020/005873 A1 | 1/2020 |
| WO | 2020/005877 A1 | 1/2020 |
| WO | 2020/005882 A1 | 1/2020 |
| WO | 2020/190793 A1 | 9/2020 |
| WO | 2020/231977 A1 | 11/2020 |
| WO | 2021/007378 A1 | 1/2021 |
| WO | 2021/084495 A1 | 5/2021 |
| WO | 2021/207453 A1 | 10/2021 |
| WO | 2022/103980 A1 | 5/2022 |
| WO | 2023/009816 A1 | 2/2023 |

OTHER PUBLICATIONS

Chloë Copin et al., "SnAr versus Buchwald-Hartwig Amination/Amidation in the Imidazo[2,1-b][1,3,4]thiadiazole Series", European Journal of Organic Chemistry, vol. 2015(31), Sep. 29, 2015, p. 6932-6942.

Database Registry, Chemical Abstracts Service, Feb. 22, 2018, Database Accession No. 2178867-25-7.

Database Registry, Chemical Abstracts Service, Sep. 18, 2017, Database Accession No. 2128311-64-6.

Database Registry, Chemical Abstracts Service, Sep. 24, 2017, Database Accession No. 2130300-22-8.

Database Registry, Chemical Abstracts Service, Sep. 25, 2017, Database Accession No. 2130694-60-7.

Fascio Mirta L et al, "Synthesis and antiviral activity of some imidazo[1,2-b][1,3,4]thiadiazole carbohydrate derivatives", Carbohydrate Research, vol. 480, May 21, 2019, p. 61-66.

Ingo Knepper et al., "3-Acylindoles as versatile starting materials for pyridine ring annulation: synthesis of 1-deazapurine isosteres", Tetrahedron, vol. 67(29):5293-5303, May 14, 2011.

K.K. Abdul Khader et al., "Regioselective synthesis of C-2 substituted imidazo[4,5-b]pyridines utilizing palladium catalysed C—N bond forming reactions with enolizable heterocy", Tetrahedron Letters, vol. 55(10):1778-1783, Feb. 1, 2014.

Mariusz Mojzych et al., "Synthesis of pyrazolo[4,3-e][1,2,4]triazine sulfonamides, novel Sildenafil analogs with tyrosinase inhibitory activity", Bioorganic & Medicinal Chemistry, vol. 22, pp. 6616-6624, Oct. 18, 2014.

Mazzone G et al, "Sintesi e valutazione biologica preliminare di imidazo[2,1-b]-1,3,4-tiadiazoli-2,6-diarilsostituti", Farmaco, Edizione Scientifica, Societa Chimica Italiana, Pavia, IT, vol. 39(7), Jan. 1, 1984, p. 585-598 English Abstract Only.

Patel Harun M et al, "2,5,6-Trisubstituted imidazo[2,1-b][1,3,4]thiadiazoles: Search for antihyperlipidemic agents", European Journal of Medicinal Chemistry, Editions Scientifique Elsevier, Paris, FR, vol. 65, Apr. 18, 2013, p. 119-133.

ISR in PCT/US2019/038889, dated Aug. 8, 2019.

(56) References Cited

OTHER PUBLICATIONS

WO in PCT/US2019/038889, dated Aug. 8, 2019.
ISR in PCT/US2019/038895, dated Aug. 14, 2019.
WO in PCT/US2019/038895, dated Aug. 14, 2019.
ISR in PCT/US19/38900, dated Aug. 20, 2019.
WO in PCT/US19/38900, dated Aug. 20, 2019.
J. S. Nair et al: "Synthesis and Fluorescence Properties of 3-Benzoxa- and Thiazol-2-ylquinoline-5 or 7-maleimides.", CHEMINFORM, vol. 36, No. 2, Sep. 1, 2004 (Sep. 1, 2004), pp. 1944-1949.
Naik et al: "Studies in the Vilsmeier-Haack reaction: Part XVI., Synthesis of 7-amino-3- hetrarylquinoline fluorophore and derivatives", Indian Journal of Chemistry, Council of Scientific and Industrial Research (CS I R), DE, vol. 15B, No. 6, Jan. 1, 1977 (Jan. 1, 1977), pp. 506-508.
USPTO, Office Action dated Feb. 4, 2021 in U.S. Appl. No. 16/617,450. See whole document in general and compounds on pp. 10-14 and 15-18 in particular.
Potkin et al., "New directions in therapeutics for Huntington disease", Future Neurology, vol. 13(2):101-121, May 2018.
Wermuth, "The Practice of Medicinal Chemistry", 2nd ed., 2003, Chapters 9-10.
H. Kubinyi, "3D QSAR in Drug Design—Theory Methods and Applications", pp. vii-ix and pp. 243-244, 1998.
International Search Report for PCT/EP2016/076905, dated Feb. 9, 2017.
Written Opinion of the International Searching Authority for PCT/EP2016/076905, dated Feb. 9, 2017.
International Search Report for PCT/EP2016/077190, dated Mar. 1, 2017.
Written Opinion of the International Searching Authority for PCT/EP2016/077190, dated Mar. 1, 2017.
International Search Report for PCT/EP2016/079816, dated Jan. 19, 2016.
Written Opinion of the International Searching Authority for PCT/EP2016/079816, dated Jan. 19, 2016.
International Search Report for PCT/US2013/025292, dated Aug. 30, 2013.
Written Opinion of the International Searching Authority for PCT/US2013/025292, dated Aug. 30, 2013.
International Search Report in PCT/US2018/039794, dated Oct. 25, 2018.
Written Opinion of the International Searching Authority in PCT/US2018/039794, dated Oct. 25, 2018.
International Search Report from PCT/US2020/041300, dated Oct. 16, 2020.
Written Opinion from PCT/US2020/041300, dated Oct. 16, 2020.
Pubchem, Substance Record for SID 249779947, Mar. 31, 2015, "4H-Quinolizin-4-one1; Hydrobromide".
MacDonald et al., "Quantification Assays for Total and Polyglutamine-Expanded Huntingtin Proteins", PLOS One, 2014, vol. 9(5), dated May 2014, e96854, pp. 1-17.
Palacino et al., "SMN2 splice modulators enhance U1-pre-mRNA association and rescue SM0A mice", Nature: Chemical Biology, pp. 511-517 and 5 Supplemental Pages + S1-S20, vol. 11, Jun. 1, 2015.
Pryor et al., "Huntingtin promotes mTORCl signaling in the pathogenesis of Huntington's disease", Sci. Signal, dated Oct. 28, 2014, vol. 7, Issue 349, ra103, pp. 1-12.
Cheung et al., "Discovery of Small Molecule Splicing Modulators of Survival Motor Neuron-2 (SMN2) for the Treatment of Spinal Muscular Atrophy (SMA)", J. Med. Chem. XXXX, XXX, XXX-XXX, Nov. 3, 2018 (published), pp. A-P.
Brunhilde Wirth et al., "Moving towards treatments for spinal muscular atrophy: hopes and limits", Expert Opinion on Emerging drugs, 20(3):353-356, Apr. 28, 2015.
Chiara Zanetta et al., "Molecular Therapeutic Strategies for Spinal Muscular Atrophies: Current and Future Clinical Trials", Clinical Therapeutics, 36(1):128-140, Dec. 17, 2013.
Coady et al., 2010, "Trans-splicing-mediated improvement in a severe mouse model of spinal muscular atrophy", J Neurosci., vol. 30(1), pp. 126-130, 2010.
Combrink Sombring et al., "Respiratory syncytial virus fusion inhibitors. Part 6: An examination of the effect of structural variation for the benzimidazol-2-one heterocycle moiety", Bioorganic & Medicinal Chemistry Letters, 17(17):4784-4790, Aug. 4, 2007.
European Patent Office, Communication pursuant to Article 94(3) EPC, European Application No. 14877918.4, dated Mar. 23, 2018.
Greene, Protective Groups in Organic Syntehsis, 1991, Wiley, New York, pp. v-xxi and 1-17.
Higuchi and W. Stella, "Pro-drugs as novel delivery systems", vol. 14 of the A.C.S., Symposium Series and in Bioreversible Carriers in Drug Design, ed., Edward B. Roche, American Pharmaceutical Association and Pergamon Press (1975).
Hua et al., "Peripheral SMN restoration is essential or long-term rescue of a severe SMA mouse model", Nature, vol. 478(7367), pp. 123-126, 2012.
Jarecki et al., "Diverse small-molecule modulators of SMN expression found by high-throughput compound screening: early leads towards a therapeutic for spinal muscular atrophy", Human molecular genetics, 14(14):2003-2018, 2005.
Knight et al., "Isoform-specific phosphoinositide 3-kinase inhibitors from an arylmorpholine scaffold", Bioorganic & Medicinal Chemistry, vol. 12(17):4749-4759, 2004.
Kocar, Transformations of 3-aminopyridazines. Synthesis of 4-oxo-4H-pyrimido [1,2-b]pyridazine and 1-(substituted pyridazin-3-yl)-1H-1,2,3-triazole derivatives, Arkivoc, vol. 8, 2002, 143-156.
Le et al., "SMND7, the major product of the centromeric survival motor neuron (SMN2) gene, extends survival in mice with spinal muscular atrophy and associates with full-length SMN", Human Molecular Genetics, vol. 14(5), pp. 845-857, 2005.
Liu et al., "A novel nuclear structure containing the survival of motor neurons protein", EMBO J. vol. 15(14), pp. 3555-3565 (1996).
Makhortova et al., "A screen for regulators of survival of motor neuron proteins levels", Nature chemical biology, vol. 7 (8):544-552, 2011.
Markus Riessland et al., "The benzamide M344, a novel histone deacetylase inhibitor, significantly increases SMN2 RNA/protein levels in spinal muscular atrophy cells", Hum Genet 120:101-110, May 26, 2006.
Naryshkin et al., "SMN2 splicing modifiers improve motor function and longevity in mice with spinal muscular atrophy", Science, vol. 345(6197):688-693, 2014 (including supplementary materials).
Passini et al., "Antisense Oligonucleotides delivered to the mouse CNS ameliorate symptoms of severe spinal muscular atrophy", Sci Transl. Med., vol. 3(72), 2001.
Peng, Lijie et al., "Identification of pyrido[1,2-alpha]pyrimidine-4-ones as new molecules improving the transcriptional functions of estrogen-related receptor alpha", Journal of medicinal chemistry, vol. 54(21):7729-7733, 2011.
PubChem/NCBI Database accession No. CID 377422 [online], 2005, retrieved on Jul. 4, 2016, URL http://pubchem.nci.nlm.nih.gov/compound/377422.
Seisuke Mimori et al., "Protective Effects of 4-phenylbutyrate derivatives on the neuronal cell death and endoplasmic reticulum stress," Biological & Pharmaceutical Bulletin of Japan, 35(1):84-90, Jan. 1, 2012.
Shao, Ning et al., "Synthesis and structure-activity relationship (SAR) study of 4-azabenzoxazole analogues as H3 antagonists", Bioorganic & Medicinal chemistry letters, vol. 22(5):2075-2078, 2012.
Sin et al., "Respiratory syncytial virus fusion inhibitors. Part 7: Structure-activity relationships associated with a series of isatin oximes that demonstrate antiviral activity in vivo", Bioorganic & Medicinal Chemistry Letters, 19 (16):4857-4862, Aug. 15, 2009.
Yuo et al., 2008, "5-(N-ethyl-N-isopropyl)-amiloride enhances SMN2 exon 7 inclusion and protein expression in spinal muscular atrophy cells". Annals of neurology, vol. 63(1):26-34, 2008.
Lazarev et al., "Factors Affecting Aggregate Formation in Cell Models of Huntington's Disease and Amyotrophic Lateral Sclerosis", Acta Naturae, vol. 5(2):81-89, Apr. 2013.
International Search Report for PCT/US2018/035954, dated Oct. 1, 2018.

(56) References Cited

OTHER PUBLICATIONS

Written Opinion of the International Searching Authority for PCT/US2018/035954, dated Oct. 1, 2018.
International Search Report for PCT/US2018/039775, dated Oct. 29, 2018.
Written Opinion of the International Searching Authority for PCT/US2018/039775, dated Oct. 29, 2018.
International Search Report in PCT/US2016/066042, dated Mar. 16, 2017.
Written Opinion of the International Searching Authority for PCT/US2016/066042, dated Mar. 16, 2017.
International Search Report for PCT/US2019/024068, dated Jul. 10, 2019.
Written Opinion of the International Searching Authority for PCT/US2019/024068, dated Jul. 10, 2019.
International Search Report for PCT/US2019/024278, dated May 28, 2019.
Written Opinion of the International Searching Authority for PCT/US2019/024278, dated May 28, 2019.
International Search Report for PCT/EP2012/065499, dated Sep. 28, 2012.
Written Opinion of the International Searching Authority for PCT/EP2012/065499, dated Sep. 28, 2012.
International Search Report for PCT/EP2014/059699, dated Aug. 25, 2014.
Written Opinion of the International Searching Authority for PCT/EP2014/059699, dated Aug. 25, 2014.
International Search Report for PCT/EP2015/051066, dated Feb. 19, 2015.
Written Opinion of the International Searching Authority for PCT/EP2015/051066, dated Feb. 19, 2015.
International Search Report for PCT/EP2015/060343, dated Jul. 13, 2015.
Written Opinion of the International Searching Authority for PCT/EP2015/060343, dated Jul. 13, 2015.
International Search Report for PCT/EP2016/060952, dated Jun. 29, 2016.
Written Opinion of the International Searching Authority for PCT/EP2016/060952, dated Jun. 29, 2016.
International Search Report for PCT/EP2015/063894, dated Aug. 6, 2015.
Written Opinion of the International Searching Authority for PCT/EP2015/063894, dated Aug. 6, 2015.
Andreassi, C. et al. 2001. Human Molecular Genetics 10, 2841-2849. "Aclarubicin treatment restores SMN levels to cells derived from type I spinal muscular atrophy patients."
Artursson P., et al. 1991. Biochem Biophys Res Comm 175, 880-5. "Correlation between oral drug absorption in humans and apparent drug permeability coefficients in human intestinal epithelial (Caco-2) cells."
Baldo, B. et al. 2012. J. Biol. Chem. 287, 1406-1414. "A screen for enhancers of clearance identifies huntingtin as a heat shock protein 90 (Hsp90) client protein."
Barbaro, B.A. et al. 2015. Human Molecular Genetics 24, 913-925 (published online Oct. 9, 2014). "Comparative study of naturally occurring huntingtin fragments in *Drosophila* points to exon 1 as the most pathogenic species in Huntington's disease."
Bates, G.P. et al. 2015. Nature Reviews, Disease Primers 1, 15005 (published online Apr. 23, 2015). "Huntington disease."
Bengart, P. et al. 2004. Nucleic Acids Res. 32, W154-W159. "Riboswitch finder—a tool for indentification of riboswitch RNAs."
Bhattacharyya, A. et al. 2007 Drug Discovery Today 12, 553-560. "Mining the GEMS—a novel platform technology targeting post-transcriptional control mechanisms."
Bibillo, A and Eickbush, T.H. 2002. J. Biol. Chem. 277, 34836-34845. "High Processivity of the Reverse Transcriptase from a Non-long Terminal Repeat Retrotransposon."
Carroll, J.B. et al. 2015. Lancet Neurol 14, 1135-1142 (No. 11—Nov. 2015). "Treating the whole body in Huntington's disease."

Cartegni, L. et al. 2003. Nucleic Acids Res. 31, 3568-3571. "ESEfinder: a web resource to identify exonic splicing enhancers."
Crooks, G. E., et al. 2004. Genome Research 14, 1188-1190. "WebLogo: a sequence logo generator."
Daguenet et al. 2015. EMBO reports 16, 1640-1655 (published online Nov. 13, 2015). "The pathogenicity of splicing defects: mechanistic insights into pre-mRNA processing inform novel therapeutic approaches."
Difiglia, et al. 1997. Science 277, 1990-1993. "Aggregation of Huntingtin in Neuronal Intranuclear Inclusions and Dystrophic Neurites in Brain".
Dobin, A. et al. 2013. Bioinformatics 29, 15-21. "STAR: ultrafast universal RNA-seq aligner."
Evers, M.M. et al. 2015. Molecular Neurodegeneration 10, Article No. 21 (published online Apr. 28, 2015). "Making (anti-) sense out of huntingtin levels in Huntington disease."
Fardaei, M. et al. 2002. Human Molecular Genetics 11, 805-814. "Three proteins, MBNL, MBLL and MBXL, co-localize in vivo with nuclear foci of expanded-repeat transcripts in DM1 and DM2 cells."
Fernandez-Nogales, M. et al. 2014. Nature Medicine 20, 881-885. "Huntington's disease is a four-repeat tauopathy with tau nuclear rods."
Gipson, T. A. et al. 2013. RNA Biology 10, 1647-1652. "Aberrantly spliced HTT, a new player in Huntington's disease pathogenesis."
Gray, M. et al. 2008. J. Neurosci. 28, 6182-6195. "Full-length human mutant huntingtin with a stable polyglutamine repeat can elicit progressive and selective neuropathogenesis in BACHD mice."
Griffiths-Jones, S. et al. 2005. Nucleic Acids Res. 33, D121-D124. "Rfam: annotating non-coding RNAs in complete genomes."
Griffiths-Jones, S. et al. 2006. Nucleic Acids Res. 34, D140-D144. "miRBase: microRNA sequences, targets and gene nomenclature."
Grillo, G. et al. 2003. Nucleic Acids Res. 31, 3608-3612. "PatSearch: a program for the detection of patterns and structural motifs in nucleotide sequences."
Grimson, A. et al. 2007. Molecular Cell 27, 91-105. "MicroRNA Targeting Specificity in Mammals: Determinants beyond Seed Pairing."
Heemskerk, J. et al. 2002. Nature Neuroscience Supplement 5, 1027-1029. "From chemical to drug: neurodegeneration drug screening and the ethics of clinical trials."
Heemskerk, J. et al. 2002. Trends Neurosci. 25, 494-496. "Teaching old drugs new tricks."
Heemskerk, J. et al. 2005. Chapter 16—"Therapeutics Development for Hereditary Disorders" in ed. Waxman, S. From Neuroscience to Neurology: Neuroscience, Molecular Medicine, and the Therapeutic Transformation of Neurology, pp. 285-291.
Hernandez-Imas, E. et al. 2015. PLoS One 10, e141735 (published online Oct. 28, 2015). "Functional Analysis of Mutations in Exon 9 of NF1 Revales the Presence of Several Elements Regulating Splicing."
Hodges, A. et al. 2006. Human Molecular Genetics 15, 965-977. "Regional and cellular gene expression changes in human Huntington's disease brain."
Hua et al. 2007. PLoS Biol 5, e73. Enhancement of SMN2 Exon 7 "Inclusion by Antisense Oligonucleotides Targeting the Exon."
Hua et al. 2008. American J. of Human Genetics 82, 834-848. "Antisense Masking of an hnRNP A1/A2 Intronic Splicing Silencer Corrects SMN2 Splicing in Transgenic Mice."
Hughes, A.C. et al. 2014. J. Mol. Biol. 426, 1428-1438. "Identification of Novel Alternative Splicing Events in the Huntingtin Gene and Assessment of the Functional Consequences Using Structural Protein Homology Modelling."
The Huntington's Disease Collaborative Research Group, 1993, Cell, 72, pp. 971-983 (1993). "A novel gene containing a trinucleotide repeat that is expanded and unstable on Huntington's Disease chromosomes."
Janas, A. M. 2015. "A Stem Cell Model of the Motor Circuit Reveals Distinct Requirements for SMN in Motor Neuron Survival and Function."
Jacobs, G.H. et al. 2006. Nucleic Acids Res. 34, suppl_1, D37-D40. "Transterm—extended search facilities and improved integration with other databases."

(56) References Cited

OTHER PUBLICATIONS

Kanadia, R.N. et al. 2003. Science 302, 1978-1980. "A Muscleblind Knockout Model for Myotonic Dystrophy."
Kaplan, A et al. 2012. Prog. Neurobiol. 99(3), 262-280. "Therapeutic approaches to preventing cell death in Huntington disease."
Kim, D. et al. 2013. Genome Biology 14, Article No. R36. "TopHat2: accurate alignment of transcriptomes in the presence of insertions, deletions and gene fusions."
Kordasiewicz, H.B. et al. 2012. Neuron, 74, 1031-1044. "Sustained Therapeutic Reversal of Huntington's Disease by Transient Repression of Huntingtin Synthesis"
Kuhn, A. et al. 2007. Human Molecular Genetics 16, 1845-1861. "Mutant huntingtin's effects on striatal gene expression in mice recapitulate changes observed in human Huntington's disease brain and do not differ with mutant huntingtin length or wild-type huntingtin dosage."
Labadorf, A.T. et al. 2015. Plos One 10(10): e0141298 (published online Oct. 23, 2015). "Evidence of Extensive Alternative Splicing in Post Mortem Human Brain HTT Transcription by mRNA Sequencing." (including supplemental information).
Labadorf, A. et al. 2015. PLoS One 10(12): e0143563 (published online Dec. 4, 2015). "RNA Sequence Analysis of Human Huntington Disease Brain Reveals an Extensive Increase in Inflammatory and Developmental Gene Expression."
Labbadia, J. et al. 2013. Trends Biochem. Sci. 38, 378-385. "Huntington's disease: underlying molecular mechanisms and emerging concepts."
Landles, C. et al. 2010. J. Bio. Chem. 285, 8808-8823. "Proteolysis of Mutant Huntington Produces an Exon 1 Fragment That Accumulates as an Aggregated Protein in Neuronal Nuclei in Huntington Disease."
Lei, et al. 2005. Nucleic Acids Res 33, 3897-3909. "Exonization of AluYa5 in the human ACE gene requires mutations in both 3' and 5' splice sites and is facilitated by a conserved splicing enhancer."
Liang, Y. et al. 2009. Brain Res. 2009 1286, 221-229. "ATF3 plays a protective role against toxicity by N-terminal fragment of mutant huntingtin in stable PC12 cell line."
Love, M. I. et al. 2014. Genome Biology 15, 550. "Moderated estimation of fold change and dispersion for RNA-seq data with DESeq2."
Lunkes, A. et al. 2002. Molecular Cell 10, 259-269. "Proteases Acting on Mutant Huntingtin Generate Cleaved Products that Differentially Build Up Cytoplasmic and Nuclear Inclusions."
Macke, T.J. 2001. Nucleic Acids Res. 29, 4724-4735. "RNAMotif, an RNA secondary structure definition and search algorithm."
Mahmood, I. et al. 1996. Xenobiotica 26, 887-895. "Interspecies scaling: predicting clearance of drugs in humans. Three different approaches."
Mahmood, I. 2006. Pharm. Sci. 95, 1810-1821. "Prediction of human drug clearance from animal data: Application of the rule of exponents and 'fu corrected intercept method' (FCIM)."
Mahmoudi, S et al. 2010. PLoS Biology 8(11), e10000521. "WRAP53 is Essential for Cajal Body and for Targeting the Survival of Motor Neuron Complex to Cajal Bodies."
Mangiarini, L. 1996. Cell 87, 493-506. "Exon 1 of the HD Gene with an Expanded CAG Repeat Is Sufficient to Cause a Progressive Neurological Phenotype in Transgenic Mice."
Mantione, K.J. et al. 2014. Med. Sci. Monit. Basic Res. 20, 138-141. "Comparing Bioinformation Gene Expression Profiling Methods: Microarray and RNA-Seq."
Mendoza, L.G. et al. 1999. BioTechniques 27, 778-788. "Hight-Throughput Microarray-Based Enzyme-Linked Immunosorbent Assay (ELISA)."
Mielcarek, M. et al. 2014. PLOS Genetics 10: 8e1004550. "Dysfunction of the CNS-Heart Axis in Mouse Models of Huntington's Disease."
Mignone, F. et al. 2005. Nucleic Acids Res. 33, D141-D146. "UTRdb and UTRsite: a collection of sequences and regulatory motifs of the untranslated regions of eukaryotic mRNAs."

Mort, M. et al. 2015. J. of Huntington's Disease 4(2 of 4), 161-171. "Huntingtin Exists as Multiple Splice Forms in Human Brain."
Neuder, A. et al. 2014. BMC Medical Genomics 7:60. "A common gene expression signature in Huntington's disease patient brain regions."
Paganetti, P. et al. 2009. ChemBioChem 10, 1678-1688. "Development of Method for the High-Throughput Quantification of Cellular Proteins."
Pouladi, M. et al. 2013. Nature Review Neuroscience 14, 709-721. "Choosing an animal model for the study of Huntington's disease."
Ratovitski, T. et al. 2012. Cell Cycle 11, 2006-2021. "Huntingtin protein interactions altered by polyglutamine expansion as determined by quantitative proteomic analysis."
Reiner, A. et al. 2011. International Review of Neurobiology 98, 325-372. "Genetics and neuropathology of Huntington's disease."
Ruzo, A. et al. 2015. PLoS One 10, e0127678 (published online May 26, 2015). "Discovery of Novel Isoforms of Huntingtin Reveals a New Hominid-Specific Exon."
Sadeghian, H. et al. 2011. Arch. Neurol. 68, 650-652. "Huntington Chorea Presenting with Motor Neuron Disease."
Sathasivam, K. et al. 2013. Proc. Natl. Acad. Sci. 110, 2366-2370. "Aberrant splicing of HTT generates the pathogenic exon 1 protein in Huntington disease."
Schilling, G. et al. 2007. J Neuropathol. Exp. Neurol. 66, 313-320. "Characterization of Huntingtin Pathologic Fragments in Human Huntington Disease, Transgenic Mice, and Cell Models."
Schwab, C. et al. 2008. J. Neuropathol Exp Neurol 67, 1159-1165. "Colocalization of Transactivation-Responsive DNA-Binding Protein 43 and Huntingtin in Inclusions of Huntington Disease."
Shlyakhtenko, L.S. et al. 2007. Nanomedicine: Nanotech., Bio., and Med. 3, 192-197. "Single-molecule selection and recovery of structure-specific antibodies using atomic force microscopy."
Southwell, A.L. et al. 2013. Hum. Mol. Genet. 22, 18-34. "A fully humanized transgenic mouse model of Huntington disease."
Stanek, L.M. et al. 2014. Human Gene Therapy 25, 461-474. "Silencing Mutant Huntingtin by Adeno-Associated Virus-Mediated RNA Interference Ameliorates Disease Manifestations in the YAC128 Mouse Model of Huntington's Disease."
Stoilov, P. et al. 2008. Proc. Natl. Acad. Sci. 105, 11218-11223. "A high-throughput screening strategy identifies cardiotonic steroids as alternative splicing modulators."
Taylor et al. 1999. Nat. Biotechnol. 17, 1097-1100 "Induction of endogenous Bcl-xS through the control of Bcl-x pre-mRNA splicing by antisense oligonucleotides."
Van der Burg, J.M.M. et al. 2009. The Lancet (Neurology) 8, 765-774. "Beyond the brain: widespread pathology in Huntington's disease."
Varma, H. et al. 2008. Comb Chem High Throughput Screen 11, 238-248. "High Throughput Screening for Neurodegeneration and Complex Disease Phenotypes."
Vickers et al., 2006. J. Immunol. 176, 3652-3661 "Modification of MyD88 mRNA splicing and inhibition of IL-1 beta signaling in cell culture and in mice with a 2'-O-methoxyethyl-modified oligonucleotide."
Wachter, A. 2014. Trends in Genetics 30, 172-181. "Gene regulation by structured mRNA elements."
Weiland, M. et al. 2012. Methods 56, 351-357. "Engineering of ribozyme-based riboswitches for mammalian cells."
Wild, E.J. et al. 2014. Movement Disorders 29, 1434-1445. "Targets for Future Clinical Trials in Huntington's Disease: What's in the Pipeline?"
Wilton et al. 1999. Neuromuscul. Disord. 9, 330-338. "Specific removal of the nonsense mutation from the mdx dystrophin mRNA using antisense oligonucleotides."
Xiong, H.Y. et al. 2015. Science 347, 1254806 (published online Dec. 18, 2014.) "The human splicing code reveals new insights into the genetic determinants of disease."
Yen, L. et al. 2004. Nature 431, 471-6. "Exogenous control of mammalian gene expression through modulation of RNA self-cleavage."
Yeo, G. et al. 2004. J. Comput. Biol. 11, 377-394. "Maximum entropy modeling of short sequence motifs with applications to RNA splicing signals."

(56) References Cited

OTHER PUBLICATIONS

Younis et al. 2010. Molecular and Cellular Biology 30, 1718-1728. "Rapid-Response Splicing Reporter Screens Identify Differential Regulators of Constitutive and Alternative Splicing."
Yu, S. et al. 2014. Trends in Pharmacological Sci. 35, 53-62. "Drugging unconventional targets: insights from Huntington's disease."
Zona, S. et al. 2014. Biochimica et Biophysica Acta 1839, 1316-1322. "FOXM1: An emerging master regulator of DNA damage response and genotoxic agent resistance."
Nair, A.B. et al. 2016. J. Basic and Clinical Pharmacy 7, 27-31. "A simple and practical guide for dose conversion between animals and human."
Neuder, A. et al. 2017. Scientific Reports 7, 1307 (published online May 2, 2017). "The pathogenic exon 1 HTT protein is produced by incomplete splicing in Huntington's disease patients."
Nopoulos, P. C. 2016. Dialogues Clin Neurosci 18, 91-98. "Huntington disease: a single-gene degenerative disorder of the striatum."
Ratni, H. et al. 2016. J. Med. Chem. 59, 6086-6100. "Specific Correction of Alternative Survival Motor Neuron 2 Splicing by Small Molecules: Discovery of a Potential Novel Medicine To Treat Spinal Muscular Atrophy."
Rüb, U. et al. 2016. Brain Pathol. 26, 726-740. "Huntington's disease (HD): the neuropathology of a multisystem neurodegenerative disorder of the human brain."
Saudou, F. et al. 2016. Neuron 89, 910-926. "The Biology of Huntingtin."
Wang, G. et al. 2016. Proc. Natl. Acad. Sci. 113, 3359-3364. "Ablation of huntingtin in adult neurons is nondeleterious but its depletion in young mice causes acute pancreatitis."
Woll, M.G. et al. 2016. J. Med. Chem. 59, 6070-6085. "Discovery and Optimization of Small Molecule Splicing Modifiers of Survival Motor Neuron 2 as a Treatment for Spinal Muscular Atrophy."
International Search Report for PCT/US20/32446, dated Jul. 7, 2020.
Written Opinion of the International Searching Authority in PCT/US20/32446, dated Jul. 7, 2020.
Daldin et al., "Polyglutamine expansion affects huntingtin conformation in multiple Huntington's disease models", Scientific Reports, vol. 7, 15 pages, 2017.
Gleave et al., "Synthesis and evaluation of 3-amino-6-aryl-pyridazines as selective CB2 agonists for the treatment of inflammatory pain", Bioorganic & Medicinal Chemistry Letters, vol. 20, pp. 465-468, 2010.
Kaida et al., "U1 snRNP protects pre-mRNAs from premature cleavage and polyadenylation"; Nature, vol. 468, pp. 664-669; Dec. 2, 2010.
Ross & Tabrizi, "Huntington's disease: from molecular pathogenesis to clinical treatment"; The Lancet Neurology, vol. 10, pp. 83-98, Jan. 2011.
Wang et al., "Mechanism of alternative splicing and its regulation (Review)", Biomedical Reports, vol. 3, pp. 152-158, 2015.
Berg, J.M., Tymoczko, J.L., & Stryer, L., *Biochemistry* (5th ed.), p. 798, 2002.
Opposition in European Patent No. 3,386,511, Feb. 25, 2022, 29 pages.
Bhattacharyya et al., Small molecule splicing modifiers with systemic HTT-lowering activity Nature Communications 12(7299), 2021.
Boudreau et al., 2009. "Nonallele-Specific Silencing of Mutant and Wild-Type Huntingtin Demonstrates Therapeutic Efficacy in Huntington''s Disease Mice." Molecular Therapy: The Journal of the American Society of Gene Therapy 17 (6): 1053-63.
Campagne et al., 2019. "Structural Basis of a Small Molecule Targeting RNA for a Specific Splicing Correction." Nature Chemical Biology 15 (12): 1191-98, 2019.
Connelly et al., 2016. "The Emerging Role of RNA as a Therapeutic Target for Small Molecules." Cell Chemical Biology 23 (9): 1077-90.

Effenberger et al., 2016. "Modulating Splicing with Small Molecular Inhibitors of the Spliceosome." Wiley Interdisciplinary Reviews. RNA 8 (2). https://doi.org/10.1002/wrna.1381.
Holste et al., 2008. "Strategies for Identifying RNA Splicing Regulatory Motifs and Predicting Alternative Splicing Events." PLoS Computational Biology 4 (1): e21.
Marxreiter et al., 2020. "Huntingtin Lowering Strategies." International Journal of Molecular Sciences 21 (6).
Mount et al., A catalogue of splice junction sequences Nucleic Acids Research 10(2):459-472 (Jan. 22, 1982).
Nishigaki et al., Syntheses of 9-Deazatheophyllines and 6-Deoxy-9-deazatheophyllines Chemical and Pharmaceutical Bulletin 28(5):1636-1641 (1980).
Ratni et al., Discovery of Risdiplam, a Selective Survival of Motor Neuron-2 (SMN2) Gene Splicing Modifier . . . , Journal of Medicinal Chemistry, 61(15), 6501-6517 (2018).
Ritz et al., Dose-Response Analysis Using R PLos ONE 10(12) (Dec. 30, 2015).
Romo et al., 2018. "A Fresh Look at Huntington mRNA Processing in Huntington''s Disease." Journal of Huntington''s Disease 7 (2): 101-8.
Schilling Judith, Meike Broemer, Ilian Atanassov, Yvonne Duernberger, Ina Vorberg, Christoph Dieterich, Alina Dagane, et al. 2019. "Deregulated Splicing Is a Major Mechanism of RNA-Induced Toxicity in Huntington''s Disease." Journal of Molecular Biology 431 (9): 1869-77.
Sibley et al., 2016. "Lessons from Non-Canonical Splicing." Nature Reviews. Genetics 17 (7): 407-21.
Sivaramakrishnan et al., Binding to SMN2 pre-mRNA-protein complex elicits specificity for small molecule splicing modifiers Nature Communications 8(1) (Nov. 2017).
Southwell et al. 2018. "Huntingtin Suppression Restores Cognitive Function in a Mouse Model of Huntington''s Disease." Science Translational Medicine (10) 1-12.
Southwell et al. 2017. "A Novel Humanized Mouse Model of Huntington Disease for Preclinical Development of Therapeutics Targeting Mutant Huntingtin Alleles." Human Molecular Genetics 26 (6): 1115-32.
Tabrizi et al., Huntington Lowering Strategies for Disease Modification in Huntington's Disease J. Neuron 101(5):801-819 (Mar. 6, 2019).
Wild et al., 2017. "Therapies Targeting DNA and RNA in Huntington''s Disease." Lancet Neurology 16 (10): 837-47.
International Search Report in PCT/US2021/059010, dated Apr. 26, 2022.
Written Opinion of the International Searching Authority in PCT/US2021/059010, dated Apr. 26, 2022.
Reply to Opposition in European Patent No. 3,386,511, Jul. 7, 2022, 427 pages.
EPO Board Communication in Opposition in European Patent No. 3,386,511, Oct. 18, 2022, 12 pages.
International Search Report in PCT/US2021/026316, dated Aug. 5, 2021.
Written Opinion of the International Searching Authority in PCT/US2021/026316, dated Aug. 5, 2021.
Burli et al., "Design, Synthesis, and Biological Evaluation of Potent and Selective Class IIa Histone Deacetylase (HDAC) Inhibitors as a Potential Therapy for Huntington's Disease", Journal of Medicinal Chemistry, vol. 56, pp. 9934-9954, 2013.
Chemical Abstracts Registry No. 1381103-87-2, indexed in the Registry file on STN CAS Online Jul. 4, 2012. (Year: 2012).
Chemical Abstracts Registry No. 1381109-95-0, indexed in the Registry file on STN CAS Online Jul. 4, 2012. (Year: 2012).
Chemical Abstracts Registry No. 1381103-06-5, indexed in the Registry file on STN CAS Online Jul. 4, 2012. (Year: 2012).
Chemical Abstracts Registry No. 1381085-12-6, indexed in the Registry file on STN CAS Online Jul. 4, 2012. (Year: 2012).
Chemical Abstracts Registry No. 1381084-38-3, indexed in the Registry file on STN CAS Online Jul. 4, 2012. (Year: 2012).
Chemical Abstracts Registry No. 1381084-19-0, indexed in the Registry file on STN CAS Online Jul. 4, 2012. (Year: 2012).
Chemical Abstracts Registry No. 1381069-02-8, indexed in the Registry file on STN CAS Online Jul. 4, 2012. (Year: 2012).

(56) References Cited

OTHER PUBLICATIONS

Chemical Abstracts Registry No. 1381060-23-6, indexed in the Registry file on STN CAS Online Jul. 4, 2012. (Year: 2012).
Chemical Abstracts Registry No. 1381036-73-2, indexed in the Registry file on STN CAS Online Jul. 4, 2012. (Year: 2012).
Chemical Abstracts Registry No. 1381033-11-9, indexed in the Registry file on STN CAS Online Jul. 4, 2012. (Year: 2012).
Chemical Abstracts Registry No. 1381016-89-2, indexed in the Registry file on STN CAS Online Jul. 4, 2012. (Year: 2012).
Chemical Abstracts Registry No. 1381016-41-6, indexed in the Registry file on STN CAS Online Jul. 4, 2012. (Year: 2012).
Chemical Abstracts Registry No. 1381013-97-3, indexed in the Registry file on STN CAS Online Jul. 4, 2012. (Year: 2012).
Chemical Abstracts Registry No. 1380991-96-7, indexed in the Registry file on STN CAS Online Jul. 4, 2012. (Year: 2012).
Chemical Abstracts Registry No. 1380991-09-2, indexed in the Registry file on STN CAS Online Jul. 4, 2012. (Year: 2012).
Chemical Abstracts Registry No. 1380955-66-7, indexed in the Registry file on STN CAS Online Jul. 4, 2012. (Year: 2012).
Chemical Abstracts Registry No. 1380889-28-0, indexed in the Registry file on STN CAS Online Jul. 3, 2012. (Year: 2012).
Chemical Abstracts Registry No. 1380857-75-9, indexed in the Registry file on STN CAS Online Jul. 3, 2012. (Year: 2012).
Chemical Abstracts Registry No. 1350420-68-6, indexed in the Registry file on STN CAS Online Dec. 7, 2011. (Year: 2011).
Chemical Abstracts Registry No. 1350191-80-8, indexed in the Registry file on STN CAS Online Dec. 7, 2011. (Year: 2011).
Chemical Abstracts Registry No. 919610-78-9, indexed in the Registry file on STN CAS Online Feb. 6, 2007. (Year: 2007).
Chemical Abstracts Registry No. 919610-77-8, indexed in the Registry file on STN CAS Online Feb. 6, 2007. (Year: 2007).
Chemical Abstracts Registry No. 919610-71-2, indexed in the Registry file on STN CAS Online Feb. 6, 2007. (Year: 2007).
Chemical Abstracts Registry No. 919610-70-1, indexed in the Registry file on STN CAS Online Feb. 6, 2007. (Year: 2007).
Chemical Abstracts Registry No. 919610-69-8, indexed in the Registry file on STN CAS Online Feb. 6, 2007. (Year: 2007).
Chemical Abstracts Registry No. 919494-40-9, indexed in the Registry file on STN CAS Online Feb. 6, 2007. (Year: 2007).
Chemical Abstracts Registry No. 919494-38-5, indexed in the Registry file on STN CAS Online Feb. 6, 2007. (Year: 2007).
Chemical Abstracts Registry No. 919494-22-7, indexed in the Registry file on STN CAS Online Feb. 6, 2007. (Year: 2007).
Chemical Abstracts Registry No. 1348577-48-9, indexed in the Registry file on STN CAS Online Dec. 4, 2011. (Year: 2011).
Chemical Abstracts Registry No. 1380990-95-3, indexed in the Registry file on STN CAS Online Jul. 4, 2012. (Year: 2012).
Chemical Abstracts Registry No. 1380944-26-2, indexed in the Registry file on STN CAS Online Jul. 4, 2012. (Year: 2012).
Chemical Abstracts Registry No. 1380879-49-1, indexed in the Registry file on STN CAS Online Jul. 3, 2012. (Year: 2012).
Chemical Abstracts Registry No. 1380858-18-3, indexed in the Registry file on STN CAS Online Jul. 3, 2012. (Year: 2012).
Chemical Abstracts Registry No. 1381109-36-9, indexed in the Registry file on STN CAS Online Jul. 4, 2012. (Year: 2012).
Chemical Abstracts Registry No. 1381106-70-2, indexed in the Registry file on STN CAS Online Jul. 4, 2012. (Year: 2012).
Chemical Abstracts Registry No. 1380864-49-2, indexed in the Registry file on STN CAS Online Jul. 3, 2012. (Year: 2012).
Chemical Abstracts Registry No. 1380859-62-0, indexed in the Registry file on STN CAS Online Jul. 3, 2012. (Year: 2012).
Chemical Abstracts Registry No. 1381035-24-0, indexed in the Registry file on STN CAS Online Jul. 4, 2012. (Year: 2012).
Chemical Abstracts Registry No. 2059673-20-8, indexed in the Registry file on STN CAS Online Jan. 26, 2017. (Year: 2017).
Chemical Abstracts Registry No. 2224380-48-5, indexed in the Registry file on STN CAS Online May 20, 2018.
Chemical Abstracts Registry No. 2055492-51-6, indexed in the Registry file on STN CAS Online Jan. 5, 2017.
Chemical Abstracts Registry No. 1608159-30-3, indexed in the Registry file on STN CAS Online May 22, 2014.
Chemical Abstracts Registry No. 1349790-59-5, indexed in the Registry file on STN CAS Online Dec. 6, 2011.
Chemical Abstracts Registry No. 1349075-20-2, indexed in the Registry file on STN CAS Online Dec. 5, 2011.
Chemical Abstracts Registry No. 1348522-09-7, indexed in the Registry file on STN CAS Online Dec. 4, 2011.
Chemical Abstracts Registry No. 1348048-78-1, indexed in the Registry file on STN CAS Online Dec. 4, 2011.
Chemical Abstracts Registry No. 1347905-79-6, indexed in the Registry file on STN CAS Online Dec. 4, 2011.
Chemical Abstracts Registry No. 1347641-28-4, indexed in the Registry file on STN CAS Online Dec. 2, 2011.
Chemical Abstracts Registry No. 1347614-67-8, indexed in the Registry file on STN CAS Online Dec. 2, 2011.
Chemical Abstracts Registry No. 1347467-65-5, indexed in the Registry file on STN CAS Online Dec. 2, 2011.
Chemical Abstracts Registry No. 2213453-82-6, indexed in the Registry file on STN CAS Online Apr. 16, 2018.
Chemical Abstracts Registry No. 2170880-44-9, indexed in the Registry file on STN CAS Online Jan. 24, 2018.
Chemical Abstracts Registry No. 2170880-30-3, indexed in the Registry file on STN CAS Online Jan. 24, 2018.
Chemical Abstracts Registry No. 2170880-29-0, indexed in the Registry file on STN CAS Online Jan. 24, 2018.
Chemical Abstracts Registry No. 2170876-00-1, indexed in the Registry file on STN CAS Online Jan. 24, 2018.
Chemical Abstracts Registry No. 2170875-99-5, indexed in the Registry file on STN CAS Online Jan. 24, 2018.
Chemical Abstracts Registry No. 2138484-61-2, indexed in the Registry file on STN CAS Online Nov. 3, 2017.
Chemical Abstracts Registry No. 2117679-02-2, indexed in the Registry file on STN CAS Online Aug. 21, 2017.
Chemical Abstracts Registry No. 2098833-57-7, indexed in the Registry file on STN CAS Online Jun. 21, 2017.
Chemical Abstracts Registry No. 2096985-34-9, indexed in the Registry file on STN CAS Online May 23, 2017.
Chemical Abstracts Registry No. 1957192-78-7, indexed in the Registry file on STN CAS Online Jul. 21, 2016.
Chemical Abstracts Registry No. 1579964-39-8, indexed in the Registry file on STN CAS Online Apr. 3, 2014.
Chemical Abstracts Registry No. 1381102-22-2, indexed in the Registry file on STN CAS Online Jul. 4, 2012.
Chemical Abstracts Registry No. 1381055-52-2, indexed in the Registry file on STN CAS Online Jul. 4, 2012.
Chemical Abstracts Registry No. 1380859-69-7, indexed in the Registry file on STN CAS Online Jul. 4, 2012.
Chemical Abstracts Registry No. 1283718-58-0, indexed in the Registry file on STN CAS Online Apr. 21, 2011.
Chemical Abstracts Registry No. 919610-72-3, indexed in the Registry file on STN CAS Online Feb. 6, 2007.
Chemical Abstracts Registry No. 919496-89-2, indexed in the Registry file on STN CAS Online Feb. 6, 2007.
Chemical Abstracts Registry No. 919494-45-4, indexed in the Registry file on STN CAS Online Feb. 6, 2007.
Chemical Abstracts Registry No. 919494-44-3, indexed in the Registry file on STN CAS Online Feb. 6, 2007.
Chemical Abstracts Registry No. 919494-39-6, indexed in the Registry file on STN CAS Online Feb. 6, 2007.
Chemical Abstracts Registry No. 949494-26-1, indexed in the Registry file on STN CAS Online Feb. 6, 2007.
Chemical Abstracts Registry No. 919494-23-8, indexed in the Registry file on STN CAS Online Feb. 6, 2007.
Chemical Abstracts Registry No. 919494-19-2, indexed in the Registry file on STN CAS Online Feb. 6, 2007.
Chemical Abstracts Registry No. 919493-72-4, indexed in the Registry file on STN CAS Online Feb. 6, 2007.
Chemical Abstracts Registry No. 919493-71-3, indexed in the Registry file on STN CAS Online Feb. 6, 2007.
Chemical Abstracts Registry No. 848953-00-4, indexed in the Registry file on STN CAS Online Apr. 21, 2005.

(56) References Cited

OTHER PUBLICATIONS

Chemical Abstracts Registry No. 848952-99-8, indexed in the Registry file on STN CAS Online Apr. 21, 2005.
Chemical Abstracts Registry No. 120821-79-6, indexed in the Registry file on STN CAS Online May 26, 1989.

* cited by examiner

COMPOUNDS FOR TREATING HUNTINGTON'S DISEASE

CROSS-REFERENCE TO RELATED APPLICATIONS

This application is a U.S. National Stage filing under 35 U.S.C. § 371 of International Application No. PCT/US2019/024278, filed Mar. 27, 2019, which in turn claims priority to U.S. Provisional Application No. 62/648,699, filed Mar. 27, 2018, the entire contents of which are incorporated by reference herein.

An aspect of the present description relates to compounds, forms, and pharmaceutical compositions thereof and methods of using such compounds, forms, or compositions thereof useful for treating or ameliorating Huntington's disease. In particular, another aspect of the present description relates to substituted monocyclic heteroaryl compounds, forms and pharmaceutical compositions thereof and methods of using such compounds, forms, or compositions thereof for treating or ameliorating Huntington's disease.

BACKGROUND

Huntington's disease (HD) is a progressive, autosomal dominant neurodegenerative disorder of the brain, having symptoms characterized by involuntary movements, cognitive impairment, and mental deterioration. Death, typically caused by pneumonia or coronary artery disease, usually occurs 13 to 15 years after the onset of symptoms. The prevalence of HD is between three and seven individuals per 100,000 in populations of western European descent. In North America, an estimated 30,000 people have HD, while an additional 200,000 people are at risk of inheriting the disease from an affected parent. The disease is caused by an expansion of uninterrupted trinucleotide CAG repeats in the "mutant" huntingtin (Htt) gene, leading to production of HTT (Htt protein) with an expanded poly-glutamine (polyQ) stretch, also known as a "CAG repeat" sequence. There are no current small molecule therapies targeting the underlying cause of the disease, leaving a high unmet need for medications that can be used for treating or ameliorating HD. Consequently, there remains a need to identify and provide small molecule compounds for treating or ameliorating HD.

All other documents referred to herein are incorporated by reference into the present application as though fully set forth herein.

SUMMARY

An aspect of the present description includes compounds comprising, a compound of Formula (I) or Formula (II):

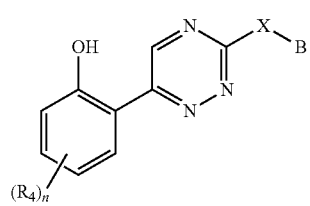

(I)

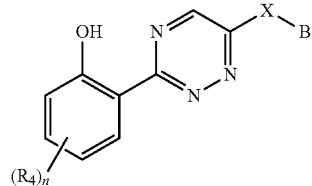

(II)

or a form thereof, wherein X, B, $R_4$, and n are as defined herein.

An aspect of the present description includes a method for treating or ameliorating HD in a subject in need thereof comprising, administering to the subject an effective amount of a compound of Formula (I) or Formula (II) or a form thereof.

An aspect of the present description includes a method for use of a compound of Formula (I) or Formula (II) or a form or composition thereof for treating or ameliorating HD in a subject in need thereof comprising, administering to the subject an effective amount of the compound of Formula (I) or Formula (II) or a form or composition thereof.

An aspect of the present description includes a use for a compound of Formula (I) or Formula (II) or a form thereof for treating or ameliorating HD in a subject in need thereof comprising, administering to the subject an effective amount of the compound of Formula (I) or Formula (II) or a form thereof.

An aspect of the present description includes a use for a compound of Formula (I) or Formula (II) or a form thereof in the manufacture of a medicament for treating or ameliorating HD in a subject in need thereof comprising, administering to the subject an effective amount of the medicament.

An aspect of the present description includes a use for a compound of Formula (I) or Formula (II) or a form thereof in a combination product with one or more therapeutic agents for treating or ameliorating HD in a subject in need thereof comprising, administering to the subject an effective amount of the compound of Formula (I) or Formula (II) or a form thereof in combination with an effective amount of the one or more agents.

DETAILED DESCRIPTION

An aspect of the present description relates to compounds comprising, a compound of Formula (I) or Formula (II):

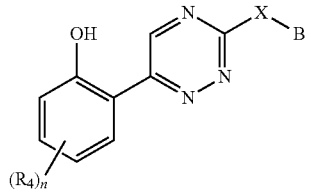

(I)

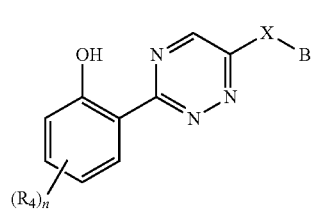

(II)

or a form thereof, wherein:

X is $CHR_{1a}$, $C=O$, O, $NR_{1b}$, or a bond;

$R_{1a}$ is hydrogen, halogen, hydroxyl, cyano, $C_{1-4}$alkyl, deutero-$C_{1-4}$alkyl, halo-$C_{1-4}$alkyl, amino or hydroxyl-$C_{1-4}$alkyl;

$R_{1b}$ is hydrogen, $C_{1-4}$alkyl, deutero-$C_{1-4}$alkyl, halo-$C_{1-4}$alkyl or hydroxyl-$C_{1-4}$alkyl;

B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, each optionally substituted with 1, 2, 3, 4, or 5 substituents each selected from $R_2$;

$R_2$ is independently selected from halogen, hydroxyl, cyano, $C_{1-4}$alkyl, deutero-$C_{1-4}$alkyl, halo-$C_{1-4}$alkyl, amino, $C_{1-4}$alkyl-amino, $(C_{1-6}$alkyl$)_2$-amino, halo-$C_{1-4}$alkyl-amino, (halo-$C_{1-6}$alkyl$)_2$-amino, hydroxy-$C_{1-4}$alkyl-amino, $C_{1-4}$alkoxy-$C_{1-4}$alkyl-amino, amino-$C_{1-4}$alkyl, $C_{1-4}$alkyl-amino-$C_{1-4}$alkyl, $(C_{1-4}$alkyl-amino$)_2$-$C_{1-4}$alkyl, $C_{1-4}$alkoxy, halo-$C_{1-4}$alkoxy, hydroxyl-$C_{1-4}$alkoxy, $C_{1-4}$alkyl-$C_{1-4}$alkoxy, $C_{3-10}$cycloalkyl, $C_{3-10}$cycloalkyl-amino, $C_{3-10}$cycloalkyl-amino-$C_{1-4}$alkyl, heteroaryl-$C_{1-4}$alkyl, heteroaryl-amino, heteroaryl-$C_{1-4}$alkyl-amino, heterocyclyl, heterocyclyl-$C_{1-4}$alkyl, heterocyclyl-amino, heterocyclyl-amino-$C_{1-4}$alkyl, heterocyclyl-$C_{1-4}$alkoxy, heterocyclyl-amino-$C_{3-10}$cycloalkyl, phenyl, and phenyl-$C_{1-4}$alkoxy, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, wherein $C_{3-10}$cycloalkyl is a saturated or partially unsaturated 3-7 membered monocyclic ring system, and wherein each instance of phenyl, heteroaryl, heterocyclyl, or $C_{3-10}$cycloalkyl is optionally substituted with 1 or 2 substituents each selected from $R_3$;

$R_3$ is independently selected from halogen, hydroxyl, cyano, $C_{1-4}$alkyl, deutero-$C_{1-4}$alkyl, halo-$C_{1-4}$alkyl, amino, $C_{1-4}$alkoxy, and halo-$C_{1-4}$alkoxy;

n is 0, 1, or 2;

$R_4$ is independently selected from halogen, hydroxyl, cyano, $C_{1-4}$alkyl, deutero-$C_{1-4}$alkyl, halo-$C_{1-4}$alkyl, amino, $C_{1-4}$alkyl-amino, $(C_{1-4}$alkyl$)_2$-amino, $C_{1-4}$alkoxy, halo-$C_{1-4}$alkoxy, heteroaryl, heterocyclyl, and phenyl, wherein heteroaryl is a saturated 3-6 membered monocyclic or 9-10 membered bicyclic ring system having 1, 2, 3, or 4 heteroatom ring members selected from N, O, and S, wherein heterocyclyl is a saturated or partially unsaturated 3-6 membered monocyclic or 9-10 membered bicyclic ring system having 1, 2, or 3 heteroatom ring members selected from N, O, and S, and wherein each instance of phenyl, heteroaryl or heterocyclyl is optionally substituted with 1, or 2 substituents each selected from $R_5$;

$R_5$ is independently selected from halogen, hydroxyl, cyano, nitro, $C_{1-4}$alkyl, deutero-$C_{1-4}$alkyl, halo-$C_{1-4}$alkyl, amino, $C_{1-4}$alkyl-amino, $(C_{1-4}$alkyl$)_2$-amino, amino-$C_{1-4}$alkyl, hydroxyl-$C_{1-4}$alkyl, $C_{1-4}$alkyl-carbonyl, $C_{1-4}$alkoxy, $C_{1-4}$alkylthio, halo-$C_{1-4}$alkoxy, and $C_{3-10}$cycloalkyl;

wherein a form of the compound is selected from the group consisting of a salt, hydrate, solvate, racemate, enantiomer, diastereomer, stereoisomer, and tautomer form thereof.

ASPECTS OF THE DESCRIPTION

Another aspect of the present description includes a compound of Formula (I) or Formula

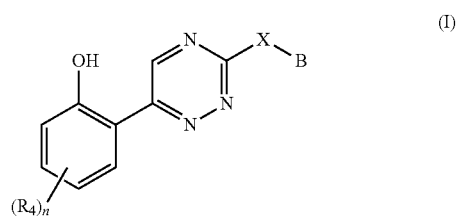

(I)

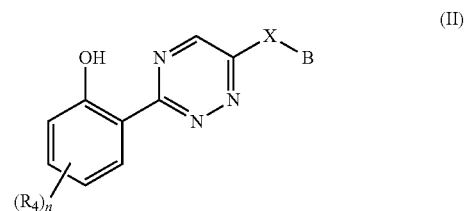

(II)

or a form thereof, wherein:

X is $CHR_{1a}$, $C=O$, O, $NR_{1b}$, or a bond;

$R_{1a}$ is hydrogen, halogen, hydroxyl, cyano, $C_{1-4}$alkyl, deutero-$C_{1-4}$alkyl, halo-$C_{1-4}$alkyl, amino or hydroxyl-$C_{1-4}$alkyl;

$R_{1b}$ is hydrogen, $C_{1-4}$alkyl, deutero-$C_{1-4}$alkyl, halo-$C_{1-4}$alkyl or hydroxyl-$C_{1-4}$alkyl;

B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, each optionally substituted with 1, 2, 3, 4, or 5 substituents each selected from $R_2$;

$R_2$ is independently selected from halogen, hydroxyl, cyano, $C_{1-4}$alkyl, deutero-$C_{1-4}$alkyl, halo-$C_{1-4}$alkyl, amino, $C_{1-4}$alkyl-amino, $(C_{1-6}$alkyl$)_2$-amino, halo-$C_{1-4}$alkyl-amino, (halo-$C_{1-6}$alkyl$)_2$-amino, hydroxy-$C_{1-4}$alkyl-amino, $C_{1-4}$alkoxy-$C_{1-4}$alkyl-amino, amino-$C_{1-4}$alkyl, $C_{1-4}$alkyl-amino-$C_{1-4}$alkyl, $(C_{1-4}$alkyl-amino$)_2$-$C_{1-4}$alkyl, $C_{1-4}$alkoxy, halo-$C_{1-4}$alkoxy, hydroxyl-$C_{1-4}$alkoxy, $C_{1-4}$alkyl-$C_{1-4}$alkoxy, $C_{3-10}$cycloalkyl, $C_{3-10}$cycloalkyl-amino, $C_{3-10}$cycloalkyl-amino-$C_{1-4}$alkyl, heteroaryl-$C_{1-4}$alkyl, heteroaryl-amino, heteroaryl-$C_{1-4}$alkyl-amino, heterocyclyl, heterocyclyl-$C_{1-4}$alkyl, heterocyclyl-amino, heterocyclyl-amino-$C_{1-4}$alkyl, heterocyclyl-$C_{1-4}$alkoxy, heterocyclyl-amino-$C_{3-10}$cycloalkyl, phenyl, and phenyl-$C_{1-4}$alkoxy, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S,
wherein $C_{3-10}$cycloalkyl is a saturated or partially unsaturated 3-7 membered monocyclic ring system, and
wherein each instance of phenyl, heteroaryl, heterocyclyl, or $C_{3-10}$cycloalkyl is optionally substituted with 1 or 2 substituents each selected from $R_3$;
$R_3$ is independently selected from halogen, hydroxyl, cyano, $C_{1-4}$alkyl, deutero-$C_{1-4}$alkyl, halo-$C_{1-4}$alkyl, amino, $C_{1-4}$alkoxy, and halo-$C_{1-4}$alkoxy;
n is 0, 1, or 2;
$R_4$ is independently selected from halogen, hydroxyl, cyano, $C_{1-4}$alkyl, deutero-$C_{1-4}$alkyl, halo-$C_{1-4}$alkyl, amino, $C_{1-4}$alkyl-amino, ($C_{1-4}$alkyl)$_2$-amino, $C_{1-4}$alkoxy, halo-$C_{1-4}$alkoxy, heteroaryl, heterocyclyl, and phenyl,
wherein heteroaryl is a 3-7 membered monocyclic or 6-10 membered bicyclic ring system having 1, 2, 3, or 4 heteroatom ring members independently selected from N, O, or S,
wherein heterocyclyl is a saturated or partially unsaturated 3-6 membered monocyclic or 9-10 membered bicyclic ring system having 1, 2, or 3 heteroatom ring members selected from N, O, and S, and
wherein each instance of phenyl, heteroaryl or heterocyclyl is optionally substituted with 1, or 2 substituents each selected from $R_5$;
$R_5$ is independently selected from halogen, hydroxyl, cyano, nitro, $C_{1-4}$alkyl, deutero-$C_{1-4}$alkyl, halo-$C_{1-4}$alkyl, amino, $C_{1-6}$alkyl-amino, ($C_{1-6}$alkyl)$_2$-amino, amino-$C_{1-4}$alkyl, hydroxyl-$C_{1-4}$alkyl, $C_{1-4}$alkyl-carbonyl, $C_{1-4}$alkoxy, $C_{1-4}$alkylthio, halo-$C_{1-4}$alkoxy, and $C_{3-10}$cycloalkyl.

One aspect includes a compound of Formula (I) or Formula (II), wherein X is selected from $CHR_{1a}$, C=O, O, $NR_{1b}$, and a bond.

Another aspect includes a compound of Formula (I) wherein X is $CHR_{1a}$.

Another aspect includes a compound of Formula (I) or Formula (II) wherein X is C=O.

Another aspect includes a compound of Formula (I) or Formula (II) wherein X is O.

Another aspect includes a compound of Formula (I) or Formula (II) wherein X is $NR_{1b}$.

Another aspect includes a compound of Formula (I) or Formula (II) wherein X is a bond.

One aspect includes a compound of Formula (I) or Formula (II), wherein $R_{1a}$ is selected from hydrogen, halogen, hydroxyl, cyano, $C_{1-4}$alkyl, deutero-$C_{1-4}$alkyl, halo-$C_{1-4}$alkyl, amino, and hydroxyl-$C_{1-4}$alkyl.

Another aspect includes a compound of Formula (I) or Formula (II), wherein $R_{1a}$ is selected from hydrogen, cyano, $C_{1-4}$alkyl, and amino.

Another aspect includes a compound of Formula (I) or Formula (II), wherein $R_{1a}$ is hydrogen.

Another aspect includes a compound of Formula (I) or Formula (II), wherein $R_{1a}$ is cyano.

Another aspect includes a compound of Formula (I) or Formula (II), wherein $R_{1a}$ is $C_{1-4}$alkyl selected from methyl, ethyl, propyl, isopropyl, butyl, and tert-butyl.

Another aspect includes a compound of Formula (I) or Formula (II), wherein $R_{1a}$ methyl.

Another aspect includes a compound of Formula (I) or Formula (II), wherein $R_{1a}$ is amino.

Another aspect includes a compound of Formula (I) or Formula (II), wherein $R_{1b}$ is selected from hydrogen and $C_{1-4}$alkyl.

Another aspect includes a compound of Formula (I) or Formula (II), wherein $R_{1b}$ is hydrogen.

Another aspect includes a compound of Formula (I) or Formula (II), wherein $R_{1b}$ is $C_{1-4}$alkyl selected from methyl, ethyl, propyl, isopropyl, butyl, and tert-butyl.

Another aspect includes a compound of Formula (I) or Formula (II), wherein $R_{1b}$ is methyl.

One aspect includes a compound of Formula (I) or Formula (II), wherein B is heterocyclyl,
wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, each optionally substituted with 1, 2, 3, 4, or 5 substituents each selected from $R_2$.

Another aspect includes a compound of Formula (I) or Formula (II), wherein B is heterocyclyl selected from azetidinyl, tetrahydrofuranyl, pyrrolidinyl, piperidinyl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, (3aS,6aS)-hexahydropyrrolo[3,4-b]pyrrol-(2H)-yl, hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-c]pyrrol-(1H)-yl, (3aR,6aS)-hexahydropyrrolo[3,4-c]pyrrol-(1H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(2H)-one, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, hexahydro-1H-cyclobuta[1.2-c:1,4-c']dipyrrol-(3H)-yl, (8aS)-octahydropyrrolo[1,2-a]pyrazin-(1H)-yl, (8aR)-octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 2-oxa-6-azaspiro[3.4]octanyl, 3-azabicyclo[3.1.0]hexanyl, 8-azabicyclo[3.2.1]octanyl, (1R,5S)-8-azabicyclo[3.2.1]octanyl, 8-azabicyclo[3.2.1]oct-2-en-yl, (1R,5S)-8-azabicyclo[3.2.1]oct-2-en-yl, 9-azabicyclo[3.3.1]nonanyl, (1R,5S)-9-azabicyclo[3.3.1]nonanyl, 2,5-diazabicyclo[2.2.1]heptanyl, (1S,4S)-2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, (1R,5S)-3,8-diazabicyclo[3.2.1]octanyl, 1,4-diazabicyclo[3.2.2]nonanyl, azaspiro[3.3]heptanyl, 4,7-diazaspiro[2.5]octanyl, 2,6-diazaspiro[3.3]heptanyl, 2,6-diazaspiro[3.4]octanyl, 1,7-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, and 7-azadispiro[5.1.5$^8$.3$^6$]hexadecanyl, each optionally substituted with 1, 2, 3, 4, or 5 substituents each selected from $R_2$.

Another aspect includes a compound of Formula (I) or Formula (II), wherein B is heterocyclyl selected from pyrrolidinyl, piperidinyl, piperazinyl, hexahydrocyclopentapyrrol-(1H)-yl, hexahydropyrrolo[3,2-b]pyrrol-(2H)-yl, hexahydropyrrolo[3,4-b]pyrrol-(1H)-yl, (3aR,6aR)- hexahydropyrrolo[3,4-b]pyrrol-(1H)-yl, hexahydropyrrolo[3,4-c]pyrrol-(1H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(1H)-yl, hexahydropyrrolo[3,4-b][1,4]oxazin-(2H)-yl, 5-azaspiro[2.4]heptanyl, 2-oxa-6-azaspiro[3.4]octanyl, 3-azabicyclo[3.1.0]hexanyl, 8-azabicyclo[3.2.1]octanyl, 9-azabicyclo[3.3.1]nonanyl, 2,6-diazaspiro[3.3]heptanyl, 2,6-diazaspiro[3.4]octanyl, 1,7-diazaspiro[4.4]nonanyl, 1,7-diazaspiro[3.5]nonanyl, 2,6-diazaspiro[3.5]nonanyl, 2,7-diazaspiro[3.5]nonanyl, 2,7-diazaspiro[4.4]nonanyl, 2,7-diazaspiro[4.5]decanyl, 2,8-diazaspiro[4.5]decanyl, 6-oxa-2,9-diazaspiro[4.5]decanyl, and 2,9-diazaspiro[5.5]undecanyl, each optionally substituted with 1, 2, 3, 4, or 5 substituents each selected from $R_2$.

Another aspect includes a compound of Formula (I) or Formula (II), wherein B is heterocyclyl selected from pyrrolidinyl, piperidinyl, and 2,7-diazaspiro[3.5]nonanyl, each optionally substituted with 1, 2, 3, 4, or 5 substituents each selected from $R_2$.

Another aspect includes a compound of Formula (I) or Formula (II), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, (3aS,6aS)-hexahydropyrrolo[3,4-b]pyrrol-1(2H)-yl, hexahydropyrrolo[3,4-b]pyrrol-5(1H)-yl, (3aS,6aS)-hexahydropyrrolo[3,4-b]pyrrol-5(1H)-yl, (3aR,6aR)-hexahydropyrrolo[3,4-b]pyrrol-5(1H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, (3aR,6aS)-hexahydropyrrolo[3,4-c]pyrrol-2(1H)-yl, octahydro-2H-pyrrolo[3,4-c]pyridin-2-yl, octahydro-5H-pyrrolo[3,2-c]pyridin-5-yl, octahydro-6H-pyrrolo[3,4-b]pyridin-6-yl, (4aR,7aR)-octahydro-6H-pyrrolo[3,4-b]pyridin-6-yl, (4aS,7aS)-octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, (7R,8aS)-hexahydropyrrolo[1,2-a]pyrazin-2(1H)-yl, (8aS)-hexahydropyrrolo[1,2-a]pyrazin-2(1H)-yl, (8aR)-hexahydropyrrolo[1,2-a]pyrazin-2(1H)-yl, hexahydro-1H-cyclobuta[1.2-c:1,4-c']dipyrrol-2(3H)-yl, (8aS)-octahydropyrrolo[1,2-a]pyrazin-2(1H)-yl, (8aR)-octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 2-oxa-6-azaspiro[3.4]octan-6-yl, 3-azabicyclo[3.1.0]hexan-3-yl, 8-azabicyclo[3.2.1]octan-3-yl, (1R,5S)-8-azabicyclo[3.2.1]octan-3-yl, 8-azabicyclo[3.2.1]oct-2-en-3-yl, (1R,5S)-8-azabicyclo[3.2.1]oct-2-en-3-yl, 9-azabicyclo[3.3.1]nonan-3-yl, (1R,5S)-9-azabicyclo[3.3.1]nonan-3-yl, 2,5-diazabicyclo[2.2.1]heptan-2-yl, (1S,4S)-2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, (1R,5S)-3,8-diazabicyclo[3.2.1]octan-3-yl, 1,4-diazabicyclo[3.2.2]nonan-4-yl, azaspiro[3.3]heptan-2-yl, 4,7-diazaspiro[2.5]octan-4-yl, 4,7-diazaspiro[2.5]octan-7-yl, 2,6-diazaspiro[3.3]heptan-2-yl, 2,6-diazaspiro[3.4]octan-2-yl, 2,6-diazaspiro[3.4]octan-6-yl, 1,7-diazaspiro[4.4]nonan-1-yl, 1,7-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, yl, 5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, and 7-azadispiro[5.1.5$^8$.3$^6$]hexadecan-15-yl, each optionally substituted with 1, 2, 3, 4, or 5 substituents each selected from $R_2$.

Another aspect includes a compound of Formula (I) or Formula (II), wherein B is heterocyclyl selected from pyrrolidin-1-yl, pyrrolidin-3-yl, piperidin-4-yl, piperazin-1-yl, hexahydrocyclopentapyrrol-2(1H)-yl, hexahydropyrrolo[3,2-b]pyrrol-1(2H)-yl, hexahydropyrrolo[3,4-b]pyrrol-5(1H)-yl, (3aR,6aR)-hexahydropyrrolo[3,4-b]pyrrol-5(1H)-yl, hexahydropyrrolo[3,4-c]pyrrol-2(1H)-yl, octahydro-2H-pyrrolo[3,4-c]pyridin-2-yl, octahydro-5H-pyrrolo[3,2-c]pyridin-5-yl, octahydro-6H-pyrrolo[3,4-b]pyridin-6-yl, hexahydropyrrolo[1,2-a]pyrazin-2(1H)-yl, hexahydropyrrolo[3,4-b][1,4]oxazin-6(2H)-yl, 5-azaspiro[2.4]heptan-5-yl, 2-oxa-6-azaspiro[3.4]octan-6-yl, 3-azabicyclo[3.1.0]hexan-3-yl, 8-azabicyclo[3.2.1]octan-3-yl, 9-azabicyclo[3.3.1]nonan-3-yl, 2,6-diazaspiro[3.3]heptan-2-yl, 2,6-diazaspiro[3.4]octan-6-yl, 1,7-diazaspiro[4.4]nonan-7-yl, 1,7-diazaspiro[3.5]nonan-7-yl, 2,6-diazaspiro[3.5]nonan-2-yl, 1,7-diazaspiro[3.5]nonan-7-yl, 2,7-diazaspiro[3.5]nonan-2-yl, 2,7-diazaspiro[3.5]nonan-7-yl, 2,7-diazaspiro[4.4]nonan-2-yl, 2,7-diazaspiro[4.5]decan-2-yl, 2,8-diazaspiro[4.5]decan-8-yl, 6-oxa-2,9-diazaspiro[4.5]decan-2-yl, and 2,9-diazaspiro[5.5]undecan-9-yl, each optionally substituted with 1, 2, 3, 4, or 5 substituents each selected from $R_2$.

Another aspect includes a compound of Formula (I) or Formula (II), wherein B is heterocyclyl selected from pyrrolidin-1-yl, pyrrolidin-3-yl, piperidin-4-yl, 2,7-diazaspiro[3.5]nonan-2-yl, and 2,7-diazaspiro[3.5]nonan-7-yl, each optionally substituted with 1, 2, 3, 4, or 5 substituents each selected from $R_2$.

One aspect includes a compound of Formula (I) or Formula (II), wherein $R_2$ is selected from halogen, hydroxyl, cyano, $C_{1-4}$alkyl, deutero-$C_{1-4}$alkyl, halo-$C_{1-4}$alkyl, amino, $C_{1-4}$alkyl-amino, $(C_{1-6}$alkyl$)_2$-amino, halo-$C_{1-4}$alkyl-amino, (halo-$C_{1-6}$alkyl$)_2$-amino, hydroxy-$C_{1-4}$alkyl-amino, $C_{1-4}$alkoxy-$C_{1-4}$alkyl-amino, amino-$C_{1-4}$alkyl, $C_{1-4}$alkyl-amino-$C_{1-4}$alkyl, $(C_{1-4}$alkyl-amino$)_2$-$C_{1-4}$alkyl, $C_{1-4}$alkoxy, halo-$C_{1-4}$alkoxy, hydroxyl-$C_{1-4}$alkoxy, $C_{1-4}$alkyl-$C_{1-4}$alkoxy, $C_{3-10}$cycloalkyl, $C_{3-10}$cycloalkyl-amino, $C_{3-10}$cycloalkyl-amino-$C_{1-4}$alkyl, heteroaryl-$C_{1-4}$alkyl, heteroaryl-amino, heteroaryl-$C_{1-4}$alkyl-amino, heterocyclyl, heterocyclyl-$C_{1-4}$alkyl, heterocyclyl-amino, heterocyclyl-amino-$C_{1-4}$alkyl, heterocyclyl-$C_{1-4}$alkoxy, heterocyclyl-amino-$C_{3-10}$cycloalkyl, phenyl, and phenyl-$C_{1-4}$alkoxy, wherein heteroaryl is a saturated 3-7 membered monocyclic, 6-10 membered bicyclic or 13-16 membered polycyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, wherein $C_{3-10}$cycloalkyl is a saturated or partially unsaturated 3-7 membered monocyclic ring system, and wherein each instance of phenyl, heteroaryl, heterocyclyl, or $C_{3-10}$cycloalkyl is optionally substituted with 1 or 2 substituents each selected from $R_3$.

One aspect includes a compound of Formula (I) or Formula (II), wherein $R_2$ is selected from halogen, hydroxyl, $C_{1-4}$alkyl, amino, $C_{1-4}$alkyl-amino, $(C_{1-6}$alkyl$)_2$-amino, halo-$C_{1-4}$alkyl-amino, hydroxy-$C_{1-4}$alkyl-amino, $C_{1-4}$alkoxy-$C_{1-4}$alkyl-amino, $C_{1-4}$alkyl-amino-$C_{1-4}$alkyl, $(C_{1-4}$alkyl-amino$)_2$-$C_{1-4}$alkyl, $C_{1-4}$alkoxy, $C_{3-10}$cycloalkyl-amino, $C_{3-10}$cycloalkyl-amino-$C_{1-4}$alkyl, heteroaryl-$C_{1-4}$alkyl-amino, heterocyclyl-amino, heterocyclyl-amino-$C_{1-4}$alkyl, and heterocyclyl-amino-$C_{3-10}$cycloalkyl, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, wherein $C_{3-10}$cycloalkyl is a saturated or partially unsaturated 3-7 membered monocyclic ring system, and wherein each instance of heteroaryl, heterocyclyl, or $C_{3-10}$cycloalkyl is optionally substituted with 1 or 2 substituents each selected from $R_3$.

Another aspect includes a compound of Formula (I) or Formula (II), wherein $R_2$ is halogen selected from bromo, chloro, fluoro, and iodo.

Another aspect includes a compound of Formula (I) or Formula (II), wherein $R_2$ is fluoro.

Another aspect includes a compound of Formula (I) or Formula (II), wherein $R_2$ is hydroxyl.

Another aspect includes a compound of Formula (I) or Formula (II), wherein $R_2$ is $C_{1-4}$alkyl selected from methyl, ethyl, propyl, isopropyl, butyl, isobutyl, sec-butyl, and tert-butyl.

Another aspect includes a compound of Formula (I) or Formula (II), wherein $R_2$ is $C_{1-4}$alkyl selected from methyl or ethyl.

Another aspect includes a compound of Formula (I) or Formula (II), wherein $R_2$ is methyl.

Another aspect includes a compound of Formula (I) or Formula (II), wherein $R_2$ is ethyl.

Another aspect includes a compound of Formula (I) or Formula (II), wherein $R_2$ is amino.

Another aspect includes a compound of Formula (I) or Formula (II), wherein $R_2$ is $C_{1-6}$alkyl-amino, wherein $C_{1-6}$alkyl is selected from methyl, ethyl, propyl, isopropyl, butyl, isobutyl, sec-butyl, tert-butyl, 2-methylbutyl, and 3-methylpentyl.

Another aspect includes a compound of Formula (I) or Formula (II), wherein $R_2$ is $C_{1-6}$alkyl-amino, wherein $C_{1-6}$alkyl is selected from methyl, ethyl, isopropyl, tert-butyl, 2-methylbutyl, and 3-methylpentyl.

Another aspect includes a compound of Formula (I) or Formula (II), wherein $R_2$ is methylamino.

Another aspect includes a compound of Formula (I) or Formula (II), wherein $R_2$ is ethylamino.

Another aspect includes a compound of Formula (I) or Formula (II), wherein $R_2$ is isopropylamino.

Another aspect includes a compound of Formula (I) or Formula (II), wherein $R_2$ is tert-butylamino.

Another aspect includes a compound of Formula (I) or Formula (II), wherein $R_2$ is 2-methylbutyl-2-amino.

Another aspect includes a compound of Formula (I) or Formula (II), wherein $R_2$ is 3-methylpentyl-3-amino.

Another aspect includes a compound of Formula (I) or Formula (II), wherein $R_2$ is $(C_{1-6}$alkyl$)_2$-amino, wherein $C_{1-4}$alkyl is each independently selected from selected from methyl, ethyl, isopropyl, tert-butyl, 2-methylbutyl, and 3-methylpentyl.

Another aspect includes a compound of Formula (I) or Formula (II), wherein $R_2$ is $(C_{1-6}$alkyl$)_2$-amino, wherein $C_{1-4}$alkyl is methyl or ethyl.

Another aspect includes a compound of Formula (I) or Formula (II), wherein $R_2$ is dimethylamino or diethylamino.

Another aspect includes a compound of Formula (I) or Formula (II), wherein $R_2$ is dimethylamino.

Another aspect includes a compound of Formula (I) or Formula (II), wherein $R_2$ is diethylamino.

Another aspect includes a compound of Formula (I) or Formula (II), wherein $R_2$ is halo-$C_{1-4}$alkyl-amino, wherein $C_{1-4}$alkyl is selected from methyl, ethyl, propyl, isopropyl, butyl, isobutyl, sec-butyl, and tert-butyl, partially or completely substituted with one or more halogen atoms where allowed by available valences.

Another aspect includes a compound of Formula (I) or Formula (II), wherein $R_2$ is halo-$C_{1-4}$alkyl-amino, wherein $C_{1-4}$alkyl is selected from isopropyl and tert-butyl, partially or completely substituted with one or more halogen atoms where allowed by available valences.

Another aspect includes a compound of Formula (I) or Formula (II), wherein $R_2$ is 1-fluoro-2-methylpropan-2-amino or 1-fluoropropan-2-amino.

Another aspect includes a compound of Formula (I) or Formula (II), wherein $R_2$ is hydroxy-$C_{1-4}$alkyl-amino, wherein $C_{1-4}$alkyl is selected from methyl, ethyl, propyl, isopropyl, butyl, isobutyl, sec-butyl, and tert-butyl, partially or completely substituted with one or more hydroxy groups where allowed by available valences.

Another aspect includes a compound of Formula (I) or Formula (II), wherein $R_2$ is hydroxy-$C_{1-4}$alkyl-amino, wherein $C_{1-4}$alkyl is selected from ethyl and propyl, partially or completely substituted with one or more hydroxy groups where allowed by available valences.

Another aspect includes a compound of Formula (I) or Formula (II), wherein $R_2$ is 2-hydroxyethylamino or 3-hydroxypropylamino.

Another aspect includes a compound of Formula (I) or Formula (II), wherein $R_2$ is $C_{1-4}$alkoxy-$C_{1-4}$alkyl-amino, wherein $C_{1-4}$alkoxy is selected from methoxy, ethoxy, propoxy, isopropoxy, butoxy and tert-butoxy, and $C_{1-4}$alkyl is selected from methyl, ethyl, propyl, isopropyl, butyl, isobutyl, sec-butyl, and tert-butyl.

Another aspect includes a compound of Formula (I) or Formula (II), wherein $R_2$ is $C_{1-4}$alkoxy-$C_{1-4}$alkyl-amino, wherein $C_{1-4}$alkoxy is methoxy and $C_{1-4}$alkyl is selected propyl, isopropyl, and tert-butyl.

Another aspect includes a compound of Formula (I) or Formula (II), wherein $R_2$ is 1-methoxypropan-2-amino or 1-methoxy-2-methylpropan-2-amino.

Another aspect includes a compound of Formula (I) or Formula (II), wherein $R_2$ is $C_{1-4}$alkyl-amino-$C_{1-4}$alkyl, wherein each $C_{1-4}$alkyl is independently selected from methyl, ethyl, propyl, isopropyl, butyl, isobutyl, sec-butyl, and tert-butyl.

Another aspect includes a compound of Formula (I) or Formula (II), wherein $R_2$ is $C_{1-4}$alkyl-amino-$C_{1-4}$alkyl, wherein each $C_{1-4}$alkyl is independently selected from methyl, ethyl, isopropyl, and tert-butyl.

Another aspect includes a compound of Formula (I) or Formula (II), wherein $R_2$ is methylaminomethyl, propan-2-yl-aminomethyl, propan-2-yl-aminoethyl, or tert-butylaminomethyl.

Another aspect includes a compound of Formula (I) or Formula (II), wherein $R_2$ is $(C_{1-4}alkyl-amino)_2-C_{1-4}alkyl$, wherein each $C_{1-4}alkyl$ is independently selected from methyl, ethyl, propyl, isopropyl, butyl, isobutyl, sec-butyl, and tert-butyl.

Another aspect includes a compound of Formula (I) or Formula (II), wherein $R_2$ is $(C_{1-4}alkyl-amino)_2-C_{1-4}alkyl$, wherein each $C_{1-4}alkyl$ is methyl.

Another aspect includes a compound of Formula (I) or Formula (II), wherein $R_2$ is dimethylaminomethyl.

Another aspect includes a compound of Formula (I) or Formula (II), wherein $R_2$ is $C_{1-4}alkoxy$ selected from methoxy, ethoxy, propoxy, isopropoxy, butoxy and tert-butoxy.

Another aspect includes a compound of Formula (I) or Formula (II), wherein $R_2$ methoxy.

Another aspect includes a compound of Formula (I) or Formula (II), wherein $R_2$ is $C_{3-10}cycloalkyl-amino$, wherein $C_{3-10}cycloalkyl$ is selected from cyclopropyl, cylcobutyl, cyclopentyl, cyclohexyl, cycloheptyl, cyclooctyl, bicyclo[2.2.1]hexanyl, and adamantyl.

Another aspect includes a compound of Formula (I) or Formula (II), wherein $R_2$ is $C_{3-10}cycloalkyl-amino$, wherein $C_{3-10}cycloalkyl$ is selected from cyclopropyl, cylcobutyl, cyclopentyl, bicyclo[2.2.1]hexanyl, and adamantyl.

Another aspect includes a compound of Formula (I) or Formula (II), wherein $R_2$ is $C_{3-10}cycloalkyl-amino-C_{1-4}alkyl$, wherein $C_{3-10}cycloalkyl$ is selected from cyclopropyl, cylcobutyl, cyclopentyl, cyclohexyl, cycloheptyl, cyclooctyl, bicyclo[2.2.1]hexanyl, and adamantyl and $C_{1-4}alkyl$ is selected from methyl, ethyl, propyl, and butyl.

Another aspect includes a compound of Formula (I) or Formula (II), wherein $R_2$ is $C_{3-10}cycloalkyl-amino-C_{1-4}alkyl$, wherein $C_{3-10}cycloalkyl$ is selected from cyclopropyl, cylcobutyl, and cyclopentyl, and $C_{1-4}alkyl$ is methyl.

Another aspect includes a compound of Formula (I) or Formula (II), wherein $R_2$ is cyclopropylaminomethyl, cyclobutylaminomethyl, or cyclopentylaminomethyl.

Another aspect includes a compound of Formula (I) or Formula (II), wherein $R_2$ is heteroaryl-$C_{1-4}alkyl-amino$, wherein heteroaryl is selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-tetrazolyl, 2H-tetrazolyl, pyridinyl, pyrimidinyl, pyridazinyl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, quinolinyl, isoquinolinyl, and quinoxalinyl, and $C_{1-4}alkyl$ is selected from methyl, ethyl, propyl, and butyl.

Another aspect includes a compound of Formula (I) or Formula (II), wherein $R_2$ is heteroaryl-$C_{1-4}alkyl-amino$, wherein heteroaryl is pyridinyl, and $C_{1-4}alkyl$ is methyl.

Another aspect includes a compound of Formula (I) or Formula (II), wherein $R_2$ is pyridin-2-yl-methylamino.

Another aspect includes a compound of Formula (I) or Formula (II), wherein $R_2$ is heterocyclyl-amino, wherein heterocyclyl is selected from azetidinyl, oxetanyl, pyrrolidinyl, tetrahydrofuranyl, piperidinyl, tetrahydropyranyl, 8-azabicyclo[3.2.1]octanyl, and 8-oxabicyclo[3.2.1]octanyl.

Another aspect includes a compound of Formula (I) or Formula (II), wherein $R_2$ is heterocyclyl-amino, wherein heterocyclyl is selected from oxetanyl and tetrahydropyranyl.

Another aspect includes a compound of Formula (I) or Formula (II), wherein $R_2$ is oxetanylamino or tetrahyropyranylamino.

Another aspect includes a compound of Formula (I) or Formula (II), wherein $R_2$ is heterocyclyl-amino-$C_{1-4}alkyl$, wherein heterocyclyl is selected from azetidinyl, oxetanyl, pyrrolidinyl, tetrahydrofuranyl, piperidinyl, oxanyl, 8-azabicyclo[3.2.1]octanyl, and 8-oxabicyclo[3.2.1]octanyl, and $C_{1-4}alkyl$ is selected from methyl, ethyl, propyl, and butyl.

Another aspect includes a compound of Formula (I) or Formula (II), wherein $R_2$ is heterocyclyl-amino-$C_{1-4}alkyl$, wherein heterocyclyl is selected from tetrahydrofuranyl, oxanyl, and 8-oxabicyclo[3.2.1]octanyl, and $C_{1-4}alkyl$ is methyl.

Another aspect includes a compound of Formula (I) or Formula (II), wherein $R_2$ is oxanylaminomethyl, tetrahydrofuranylaminomethyl, and 8-oxabicyclo[3.2.1]octanylamino.

Another aspect includes a compound of Formula (I) or Formula (II), wherein $R_2$ is heterocyclyl-amino-$C_{3-10}cycloalkyl$, wherein heterocyclyl is selected from azetidinyl, oxetanyl, pyrrolidinyl, tetrahydrofuranyl, piperidinyl, oxanyl, 8-azabicyclo[3.2.1]octanyl, and 8-oxabicyclo[3.2.1]octanyl, and $C_{3-10}cycloalkyl$ is selected from cyclopropyl, cylcobutyl, cyclopentyl, and cyclohexyl.

Another aspect includes a compound of Formula (I) or Formula (II), wherein $R_2$ is heterocyclyl-amino-$C_{3-10}cycloalkyl$, wherein heterocyclyl is oxanyl, and $C_{3-10}cycloalkyl$ is cyclopropyl.

Another aspect includes a compound of Formula (I) or Formula (II), wherein $R_2$ is oxanylaminocyclopropyl.

One aspect includes a compound of Formula (I) or Formula (II), wherein $R_3$ is halogen, hydroxyl, cyano, $C_{1-4}alkyl$, deutero-$C_{1-4}alkyl$, halo-$C_{1-4}alkyl$, amino, $C_{1-4}alkoxy$, and halo-$C_{1-4}alkoxy$.

Another aspect includes a compound of Formula (I) or Formula (II), wherein $R_3$ is halogen and $C_{1-4}alkyl$.

Another aspect includes a compound of Formula (I) or Formula (II), wherein $R_3$ is halogen selected from bromo, chloro, fluoro, and iodo.

Another aspect includes a compound of Formula (I) or Formula (II), wherein $R_3$ is fluoro.

Another aspect includes a compound of Formula (I) or Formula (II), wherein $R_3$ is $C_{1-4}alkyl$ selected from methyl, ethyl, propyl, isopropyl, butyl, isobutyl, sec-butyl, and tert-butyl.

Another aspect includes a compound of Formula (I) or Formula (II), wherein $R_3$ is methyl.

One aspect includes a compound of Formula (I) or Formula (II), wherein $R_4$ is selected from halogen, hydroxyl, cyano, $C_{1-4}alkyl$, deutero-$C_{1-4}alkyl$, halo-$C_{1-4}alkyl$, amino, $C_{1-4}alkyl-amino$, $(C_{1-4}alkyl)_2-amino$, $C_{1-4}alkoxy$, halo-$C_{1-4}alkoxy$, heteroaryl, heterocyclyl, and phenyl, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-6 membered monocyclic or 9-10 membered bicyclic ring system having 1, 2, or 3 heteroatom ring members selected from N, O, and S, and wherein each instance of phenyl, heteroaryl or heterocyclyl is optionally substituted with 1 or 2 substituents each selected from $R_5$.

Another aspect includes a compound of Formula (I) or Formula (II), wherein $R_4$ is selected from halogen, $C_{1-4}alkoxy$, heteroaryl, and phenyl.

Another aspect includes a compound of Formula (I) or Formula (II), wherein $R_4$ is halogen selected from bromo, chloro, fluoro, and iodo.

Another aspect includes a compound of Formula (I) or Formula (II), wherein $R_4$ is fluoro.

Another aspect includes a compound of Formula (I) or Formula (II), wherein $R_4$ is $C_{1-4}$alkoxy selected from methoxy, ethoxy, propoxy, isopropoxy, butoxy, and tert-butoxy.

Another aspect includes a compound of Formula (I) or Formula (II), wherein $R_4$ methoxy.

Another aspect includes a compound of Formula (I) or Formula (II), wherein $R_4$ is heteroaryl,
wherein heteroaryl is a 3-7 membered monocyclic or 6-10 membered bicyclic ring system having 1, 2, 3, or 4 heteroatom ring members independently selected from N, O, or S, optionally substituted with 1 or 2 substituents each selected from $R_5$.

Another aspect includes a compound of Formula (I) or Formula (II), wherein $R_4$ is heteroaryl selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-1,2,3-triazolyl, 2H-1,2,3-triazolyl, 1H-1,2,4-triazolyl, 1H-tetrazolyl, 2H-tetrazolyl, pyridinyl, pyridin-2(1H)-on-yl, pyrimidinyl, pyrimidin-4(3H)-on-yl, pyridazinyl, pyridazin-3(2H)-on-yl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, furo[3,2-b]pyridinyl, furo[3,2-c]pyridinyl, furo[2,3-c]pyridinyl, 1,3-oxazolo[5,4-b]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridin-yl, pyrazolo[1,5-a]pyridinyl, 1H-pyrazolo[3,4-b]pyrazinyl, 1H-pyrazolo[3,4-b]pyridinyl, 1H-pyrazolo[3,4-b]pyridinyl, 1H-pyrazolo[3,4-c]pyridinyl, 1H-pyrazolo[3,4-c]pyridinyl, 1H-pyrazolo[4,3-b]pyridinyl, 1H-pyrazolo[4,3-b]pyridinyl, 1H-pyrazolo[4,3-d]pyrimidinyl, 2H-pyrazolo[4,3-b]pyridinyl, 2H-pyrazolo[4,3-c]pyridin-yl, 5H-pyrrolo[2,3-b]pyrazinyl, pyrazolo[1,5-a]pyrazinyl, imidazo[1,2-a]pyridinyl, imidazo[1,2-a]pyridinyl, imidazo[1,2-a]pyrimidinyl, imidazo[1,2-a]pyrimidinyl, imidazo[1,2-c]pyrimidinyl, imidazo[1,2-b]pyridazinyl, imidazo[1,2-b]pyridazinyl, imidazo[1,2-a]pyrazinyl, imidazo[1,2-a]pyrazinyl, 1H-imidazo[4,5-b]pyridinyl, 3H-imidazo[4,5-b]pyridinyl, imidazo[2,1-b][1,3]thiazolyl, imidazo[2,1-b][1,3,4]thiadiazolyl, [1,3]oxazolo[4,5-b]pyridinyl, [1,2,3]triazolo[1,5-a]pyridinyl, [1,2,3]triazolo[1,5-a]pyridinyl, 1H-[1,2,3]triazolo[4,5-b]pyridinyl, 3H-[1,2,3]triazolo[4,5-b]pyridinyl, tetrazolo[1,5-a]pyridinyl, tetrazolo[1,5-b]pyridazinyl, quinolinyl, isoquinolinyl, and quinoxalinyl, optionally substituted with 1 or 2 substituents each selected from $R_5$.

Another aspect includes a compound of Formula (I) or Formula (II), wherein $R_4$ is heteroaryl selected from thienyl, 1H-pyrazolyl, 1H-imidazolyl, 1,3-thiazolyl, oxazolyl, 1,3,4-oxadiazolyl, 1,2,4-thiadiazolyl, 1H-1,2,3-triazolyl, 2H-1,2,3-triazolyl, 1H-1,2,4-triazolyl, 2H-tetrazolyl, pyridinyl, pyrimidinyl, pyrimidin-4(3H)-on-yl, pyridazinyl, pyridazin-3(2H)-on-yl, 1,2,4-triazinyl, 1,3,5-triazinyl, 1H-indazolyl, 1H-benzimidazolyl, 1,3-benzoxazolyl, 1,3-benzodioxolyl, 1,2,3-benzotriazolyl, 1,3-oxazolo[5,4-b]pyridinyl, 1H-pyrazolo[3,4-b]pyrazinyl, 1H-pyrazolo[3,4-b]pyridinyl, 1H-pyrazolo[3,4-c]pyridinyl, 1H-pyrazolo[4,3-b]pyridinyl, 1H-pyrazolo[4,3-d]pyrimidinyl, 5H-pyrrolo[2,3-b]pyrazinyl, imidazo[1,2-a]pyridinyl, imidazo[1,2-b]pyridazinyl, imidazo[1,2-a]pyrazinyl, 1H-imidazo[4,5-b]pyridinyl, 3H-imidazo[4,5-b]pyridinyl, [1,2,3]triazolo[1,5-a]pyridinyl, 1H-[1,2,3]triazolo[4,5-b]pyridinyl, 3H-[1,2,3]triazolo[4,5-b]pyridinyl, tetrazolo[1,5-a]pyridinyl, tetrazolo[1,5-b]pyridazinyl, and quinolinyl, optionally substituted with 1 or 2 substituents each selected from $R_5$.

Another aspect includes a compound of Formula (I) or Formula (II), wherein $R_4$ is heteroaryl selected from thien-2-yl, thien-3-yl, 1H-pyrazol-1-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,3-thiazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, 1,2,4-thiadiazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 1H-1,2,4-triazol-5-yl, 1H-tetrazol-1-yl, 1H-tetrazol-5-yl, 2H-tetrazol-2-yl, 2H-tetrazol-5-yl, pyridin-2-yl, pyridin-3-yl, pyridin-4-yl, pyridin-2(1H)-on-4-yl, pyridin-2(1H)-on-5-yl, pyridin-2(1H)-on-6-yl, pyrimidin-2-yl, pyrimidin-4-yl, pyrimidin-5-yl, pyrimidin-4(3H)-on-6-yl, pyridazin-3-yl, pyridazin-4-yl, pyridazin-3(2H)-on-5-yl, 1,2,4-triazin-3-yl, 1,3,5-triazin-2-yl, 1H-indol-3-yl, 1H-indol-4-yl, 1H-indol-5-yl, 1H-indol-6-yl, 1H-indazol-5-yl, 2H-indazol-5-yl, indolizin-2-yl, benzofuran-2-yl, benzofuran-5-yl, benzothien-2-yl, benzothien-3-yl, 1H-benzimidazol-2-yl, 1H-benzimidazol-5-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 1,3-benzodioxol-5-yl, 1,2,3-benzotriazol-5-yl, 9H-purin-8-yl, furo[3,2-b]pyridin-2-yl, furo[3,2-c]pyridin-2-yl, furo[2,3-c]pyridin-2-yl, 1,3-oxazolo[5,4-b]pyridine-5-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyridin-5-yl, 1H-pyrazolo[3,4-b]pyrazin-5-yl, 1H-pyrazolo[3,4-b]pyridin-5-yl, 1H-pyrazolo[3,4-b]pyridin-6-yl, 1H-pyrazolo[3,4-c]pyridin-1-yl, 1H-pyrazolo[3,4-c]pyridin-5-yl, 1H-pyrazolo[4,3-b]pyridin-5-yl, 1H-pyrazolo[4,3-b]pyridin-6-yl, 1H-pyrazolo[4,3-d]pyrimidin-5-yl, 2H-pyrazolo[4,3-b]pyridin-5-yl, 2H-pyrazolo[4,3-c]pyridin-5-yl, 5H-pyrrolo[2,3-b]pyrazin-2-yl, pyrazolo[1,5-a]pyrazin-2-yl, imidazo[1,2-a]pyridin-2-yl, imidazo[1,2-a]pyridin-6-yl, imidazo[1,2-a]pyrimidin-2-yl, imidazo[1,2-a]pyrimidin-6-yl, imidazo[1,2-c]pyrimidin-2-yl, imidazo[1,2-b]pyridazin-2-yl, imidazo[1,2-b]pyridazin-6-yl, imidazo[1,2-a]pyrazin-2-yl, imidazo[1,2-a]pyrazin-6-yl, 1H-imidazo[4,5-b]pyridin-5-yl, 3H-imidazo[4,5-b]pyridin-5-yl, imidazo[2,1-b][1,3]thiazol-6-yl, imidazo[2,1-b][1,3,4]thiadiazol-6-yl, [1,3]oxazolo[4,5-b]pyridin-2-yl, [1,2,3]triazolo[1,5-a]pyridin-5-yl, [1,2,3]triazolo[1,5-a]pyridin-6-yl, 1H-[1,2,3]triazolo[4,5-b]pyridin-5-yl, 3H-[1,2,3]triazolo[4,5-b]pyridin-5-yl, tetrazolo[1,5-a]pyridin-7-yl, tetrazolo[1,5-b]pyridazin-7-yl, quinolin-6-yl, isoquinolin-6-yl, and quinoxalin-2-yl, optionally substituted with 1 or 2 substituents each selected from $R_5$.

Another aspect includes a compound of Formula (I) or Formula (II), wherein $R_4$ is heteroaryl selected from thien-2-yl, 1H-pyrazol-1-yl, 1H-pyrazol-3-yl, 1H-pyrazol-4-yl, 1H-imidazol-1-yl, 1H-imidazol-4-yl, 1,3-thiazol-2-yl, 1,3-thiazol-5-yl, 1,3-oxazol-2-yl, 1,3-oxazol-5-yl, 1,3,4-oxadiazol-2-yl, 1,2,4-thiadiazol-5-yl, 1H-1,2,3-triazol-4-yl, 2H-1,2,3-triazol-2-yl, 2H-1,2,3-triazol-4-yl, 1H-1,2,4-triazol-1-yl, 2H-tetrazol-2-yl, 2H-tetrazol-5-yl, pyridin-2-yl, pyridin-3-yl, pyridin-4-yl, pyrimidin-2-yl, pyrimidin-4-yl, pyrimidin-5-yl, pyrimidin-4(3H)-on-6-yl, pyridazin-3-yl, pyridazin-4-yl, pyridazin-3(2H)-on-5-yl, 1,2,4-triazin-3-yl, 1,3,5-triazin-2-yl, 1H-indazol-5-yl, 1H-benzimidazol-5-yl, 1,3-benzoxazol-6-yl, 1,3-benzodioxol-5-yl, 1,2,3-benzotriazol- 5-yl, 1,3-oxazolo[5,4-b]pyridine-5-yl, 1H-pyrazolo[3,4-b]pyrazin-5-yl, 1H-pyrazolo[3,4-b]pyridin-5-yl, 1H-pyrazolo[3,4-b]pyridin-6-yl, 1H-pyrazolo[3,4-c]pyridin-1-yl, 1H-pyrazolo[3,4-c]pyridin-5-yl, 1H-pyrazolo[4,3-b]pyridin-5-yl, 1H-pyrazolo[4,3-b]pyridin-6-yl, 1H-pyrazolo[4,3-d]pyrimidin-5-yl, 5H-pyrrolo[2,3-b]pyrazin-2-yl, imidazo[1,2-a]pyridin-2-yl, imidazo[1,2-b]pyridazin-6-yl, imidazo[1,2-a]pyrazin-2-yl, imidazo[1,2-a]pyrazin-6-yl, 1H-imidazo[4,5-b]pyridin-5-yl, 3H-imidazo[4,5-b]pyridin-5-yl, [1,2,3]triazolo[1,5-a]pyridin-5-yl, [1,2,3]triazolo[1,5-a]pyridin-6-yl, 1H-[1,2,3]triazolo[4,5-b]pyridin-5-yl, 3H-[1,2,3]triazolo[4,5-b]pyridin-5-yl, tetrazolo[1,5-a]pyridin-7-yl, tetrazolo[1,5-b]pyridazin-7-yl, quinolin-6-yl, and isoquinolin-6-yl, optionally substituted with 1 or 2 substituents each selected from $R_5$.

Another aspect includes a compound of Formula (I) or Formula (II), wherein $R_4$ is phenyl, 1 or 2 substituents each selected from $R_5$.

One aspect includes a compound of Formula (I) or Formula (II), wherein $R_5$ is selected from halogen, hydroxyl, cyano, nitro, $C_{1-4}$alkyl, deutero-$C_{1-4}$alkyl, halo-$C_{1-4}$alkyl, amino, $C_{1-4}$alkyl-amino, $(C_{1-4}alkyl)_2$-amino, amino-$C_{1-4}$alkyl, hydroxyl-$C_{1-4}$alkyl, $C_{1-4}$alkyl-carbonyl, $C_{1-4}$alkoxy, $C_{1-4}$alkylthio, halo-$C_{1-4}$alkoxy, and $C_{3-10}$cycloalkyl.

Another aspect includes a compound of Formula (I) or Formula (II), wherein $R_5$ is selected from halogen, hydroxyl, cyano, nitro, $C_{1-4}$alkyl, deutero-$C_{1-4}$alkyl, amino, $C_{1-4}$alkyl-amino, amino-$C_{1-4}$alkyl, hydroxyl-$C_{1-4}$alkyl, $C_{1-4}$alkyl-carbonyl, $C_{1-4}$alkoxy, $C_{1-4}$alkylthio, and $C_{3-10}$cycloalkyl.

Another aspect includes a compound of Formula (I) or Formula (II), wherein $R_5$ is halogen selected from bromo, chloro, fluoro, and iodo.

Another aspect includes a compound of Formula (I) or Formula (II), wherein $R_5$ is halogen selected from bromo, chloro and fluoro.

Another aspect includes a compound of Formula (I) or Formula (II), wherein $R_5$ is chloro.

Another aspect includes a compound of Formula (I) or Formula (II), wherein $R_5$ is fluoro.

Another aspect includes a compound of Formula (I) or Formula (II), wherein $R_5$ is hydroxy.

Another aspect includes a compound of Formula (I) or Formula (II), wherein $R_5$ is cyano.

Another aspect includes a compound of Formula (I) or Formula (II), wherein $R_5$ is nitro.

Another aspect includes a compound of Formula (I) or Formula (II), wherein $R_5$ is $C_{1-4}$alkyl selected from methyl, ethyl, propyl, isopropyl, butyl, isobutyl, sec-butyl, and tert-butyl.

Another aspect includes a compound of Formula (I) or Formula (II), wherein $R_5$ is methyl.

Another aspect includes a compound of Formula (I) or Formula (II), wherein $R_5$ is deutero-$C_{1-4}$alkyl wherein $C_{1-4}$alkyl is selected from methyl, ethyl, propyl, isopropyl, butyl, isobutyl, sec-butyl, and tert-butyl partially or completely substituted with one or more deuterium atoms where allowed by available valences.

Another aspect includes a compound of Formula (I) or Formula (II), wherein $R_5$ is ($^2H_3$)methyl.

Another aspect includes a compound of Formula (I) or Formula (II), wherein $R_5$ is amino.

Another aspect includes a compound of Formula (I) or Formula (II), wherein $R_5$ is $C_{1-6}$alkyl-amino wherein $C_{1-6}$alkyl is selected from methyl, ethyl, propyl, isopropyl, butyl, isobutyl, sec-butyl, tert-butyl, 2-methylbutyl, and 3-methylpentyl.

Another aspect includes a compound of Formula (I) or Formula (II), wherein $R_5$ is $C_{1-4}$alkyl-amino wherein $C_{1-4}$alkyl is methyl.

Another aspect includes a compound of Formula (I) or Formula (II), wherein $R_5$ is methylamino.

Another aspect includes a compound of Formula (I) or Formula (II), wherein $R_5$ is amino-$C_{1-4}$alkyl wherein $C_{1-4}$alkyl is selected from methyl, ethyl, propyl, isopropyl, butyl, isobutyl, sec-butyl, and tert-butyl.

Another aspect includes a compound of Formula (I) or Formula (II), wherein $R_5$ is amino-$C_{1-4}$alkyl wherein $C_{1-4}$alkyl is methyl.

Another aspect includes a compound of Formula (I) or Formula (II), wherein $R_5$ is aminomethyl.

Another aspect includes a compound of Formula (I) or Formula (II), wherein $R_5$ is hydroxyl-$C_{1-4}$alkyl, wherein $C_{1-4}$alkyl is selected from methyl, ethyl, propyl, isopropyl, butyl, isobutyl, sec-butyl, and tert-butyl partially or completely substituted with one or more hydroxyl groups where allowed by available valences.

Another aspect includes a compound of Formula (I) or Formula (II), wherein $R_5$ is hydroxyl-$C_{1-4}$alkyl, wherein $C_{1-4}$alkyl is methyl substituted with one hydroxyl group.

Another aspect includes a compound of Formula (I) or Formula (II), wherein $R_5$ is hydroxymethyl.

Another aspect includes a compound of Formula (I) or Formula (II), wherein $R_5$ is $C_{1-4}$alkyl-carbonyl, wherein $C_{1-4}$alkyl is selected from methyl, ethyl, propyl, isopropyl, butyl, isobutyl, sec-butyl, and tert-butyl.

Another aspect includes a compound of Formula (I) or Formula (II), wherein $R_5$ is $C_{1-4}$alkyl-carbonyl, wherein $C_{1-4}$alkyl is methyl.

Another aspect includes a compound of Formula (I) or Formula (II), wherein $R_5$ is $CH_3C(O)$—.

Another aspect includes a compound of Formula (I) or Formula (II), wherein $R_5$ is $C_{1-4}$alkoxy selected from methoxy, ethoxy, propoxy, isopropoxy, butoxy, and tert-butoxy.

Another aspect includes a compound of Formula (I) or Formula (II), wherein $R_5$ methoxy.

Another aspect includes a compound of Formula (I) or Formula (II), wherein $R_5$ is $C_{1-4}$alkylthio selected from methylthio, ethylthio, propylthio, isopropylthio, butylthio, and tert-butylthio.

Another aspect includes a compound of Formula (I) or Formula (II), wherein $R_5$ methylthio.

Another aspect includes a compound of Formula (I) or Formula (II), wherein $R_5$ is $C_{3-10}$cycloalkyl selected from cyclopropyl, cylcobutyl, cyclopentyl, cyclohexyl, cycloheptyl, cyclooctyl, bicyclo[2.2.1]hexanyl, and adamantyl.

Another aspect includes a compound of Formula (I) or Formula (II), wherein $R_5$ is cyclopropyl.

Another aspect of the compound of Formula (I) or Formula (II) includes the compound of Formula (I):

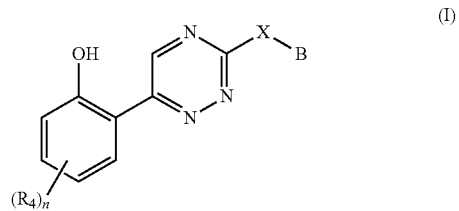

or a form thereof.

Another aspect of the compound of Formula (I) or Formula (II) includes the compound of Formula (II):
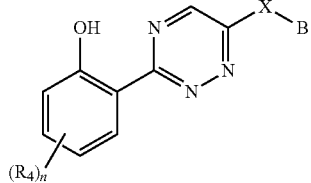
(II)
or a form thereof.
An aspect of the compound of Formula (I) or Formula (II) or a form thereof includes a compound selected from the group consisting of:
1
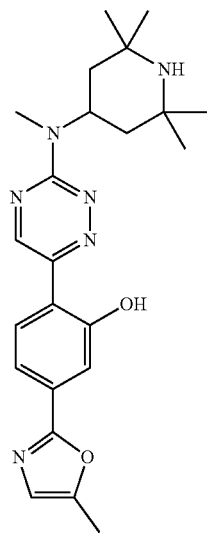
2
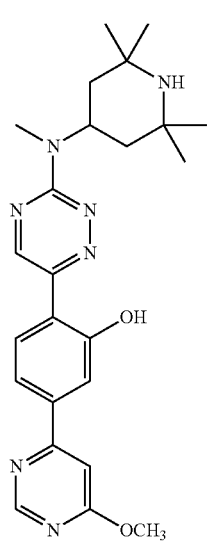
3
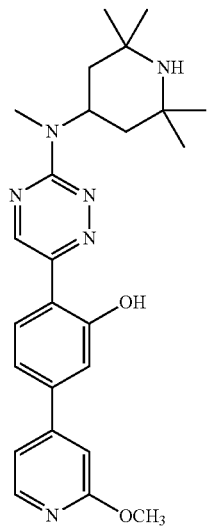
4
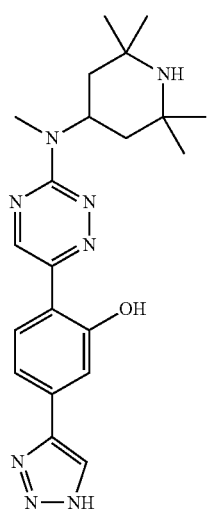
5
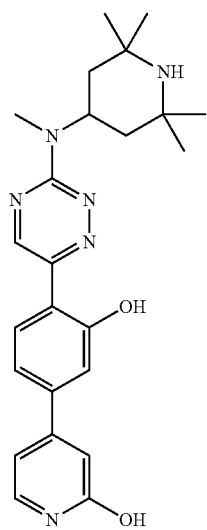

6
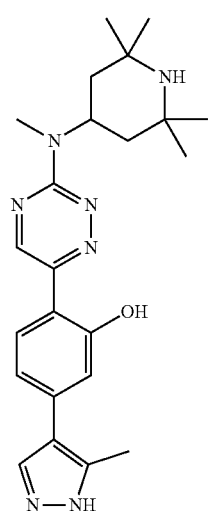
7
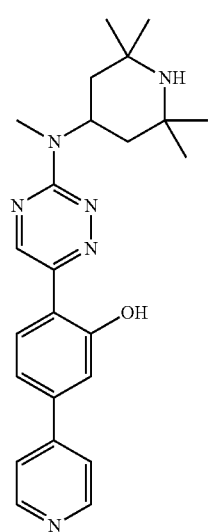
9
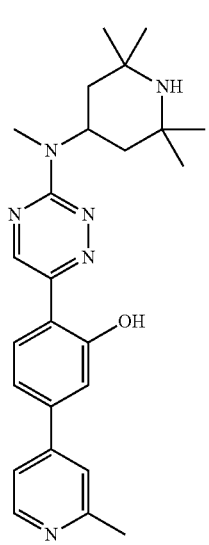
10
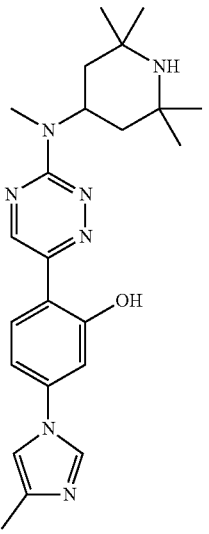
11
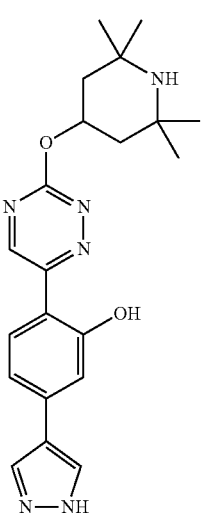

-continued
12
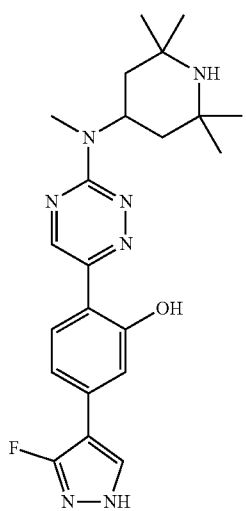
13
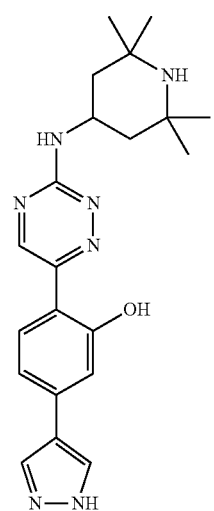
14
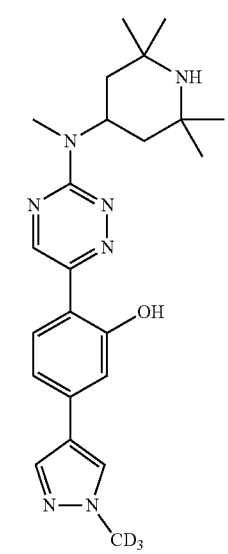
-continued
15
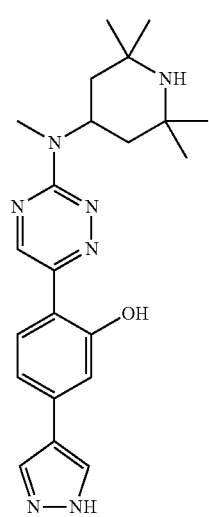
16
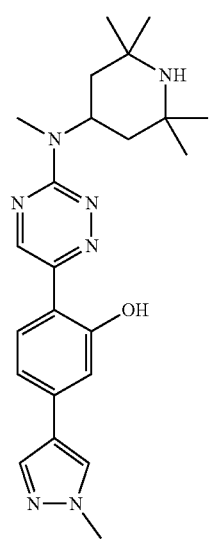
17
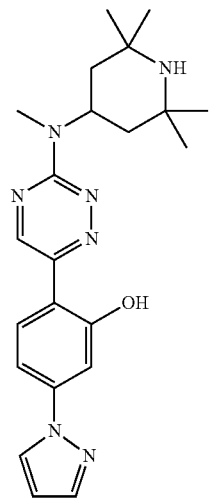

18
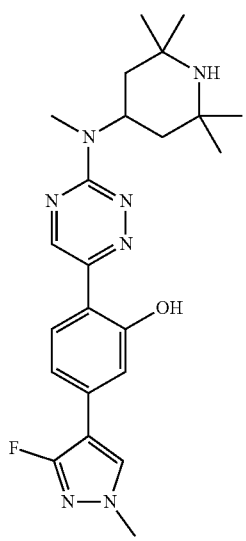
19
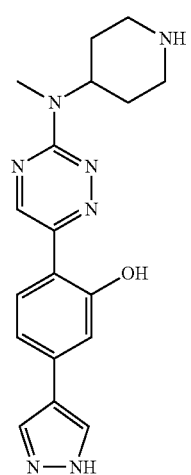
20
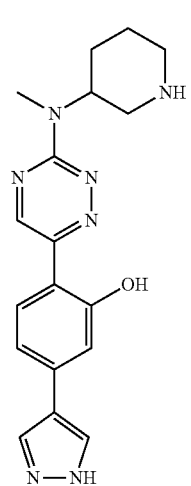
21
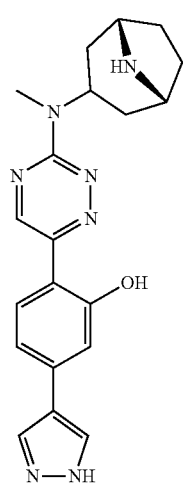
22
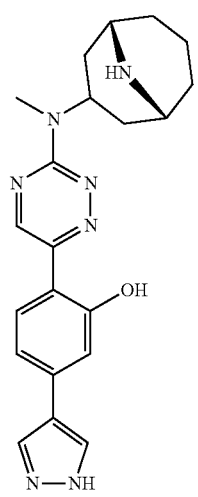
23
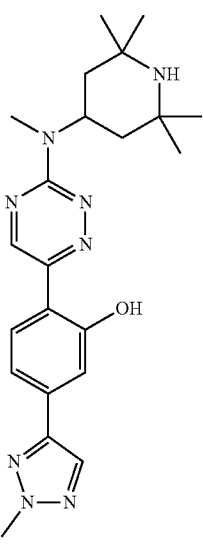

24
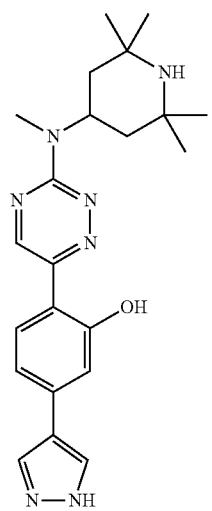
25
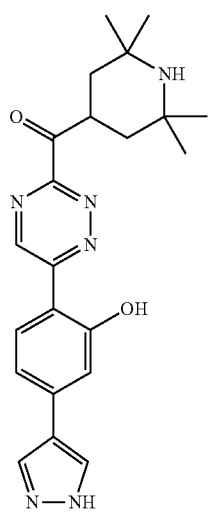
26
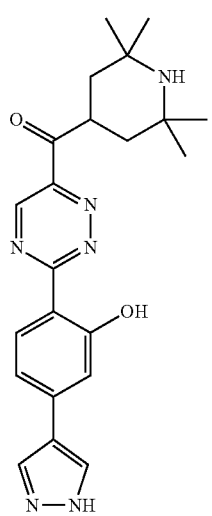
27
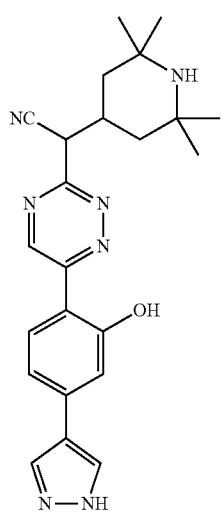
28
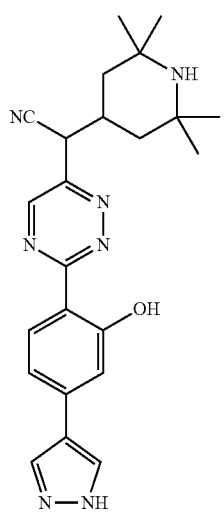
29
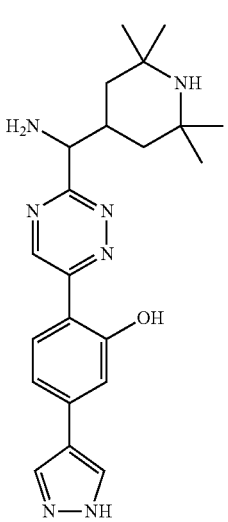

30
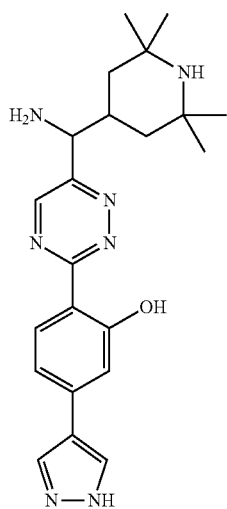
31
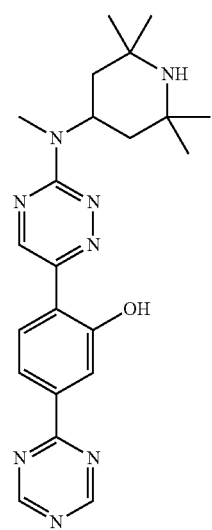
32
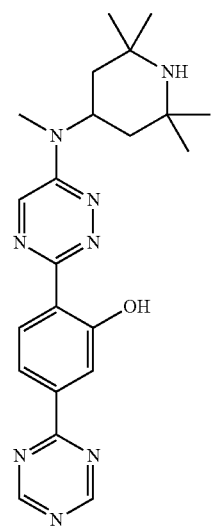
33
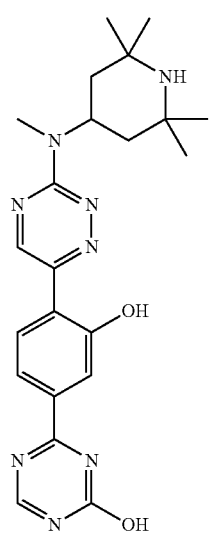
34
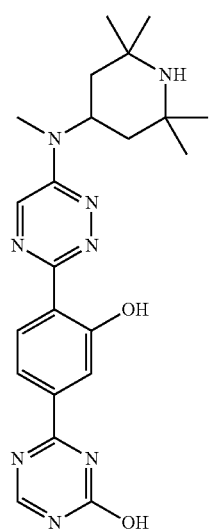
35
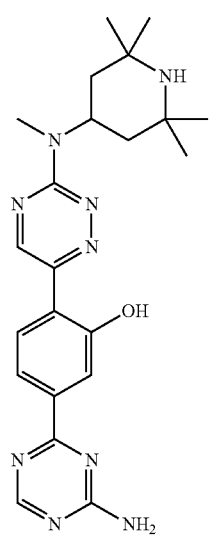

-continued
36
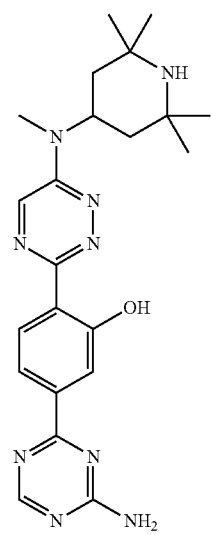
37
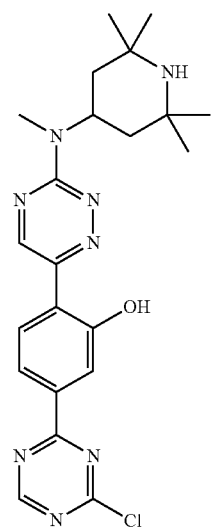
38
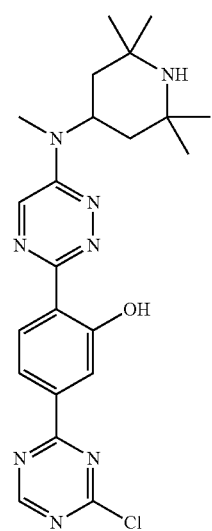
39
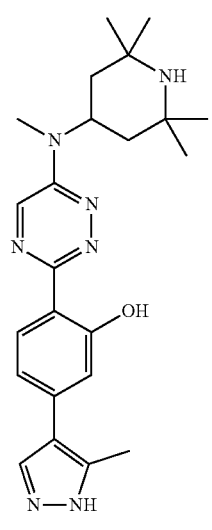
40
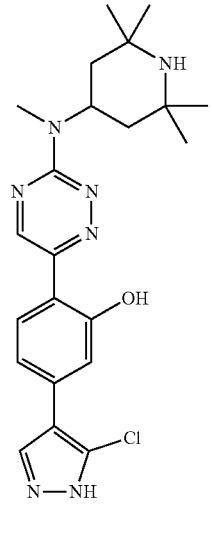
41
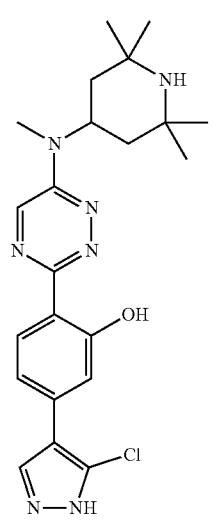

42
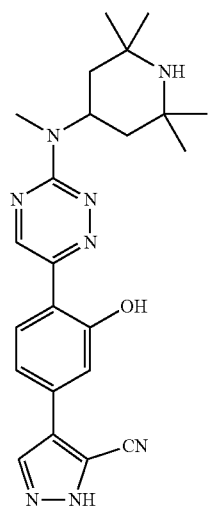
43
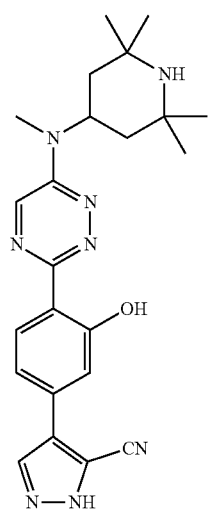
44
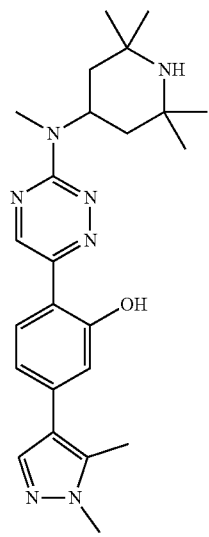
45
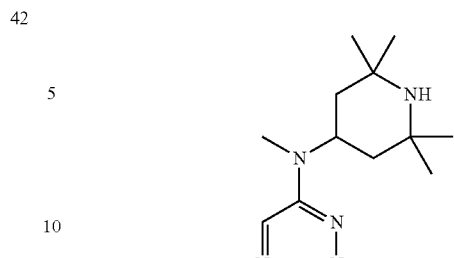
46
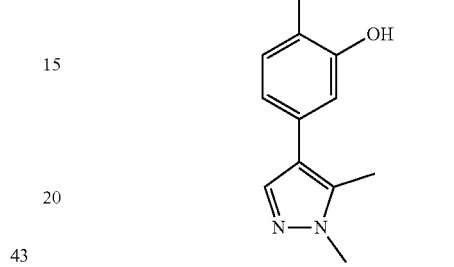
47
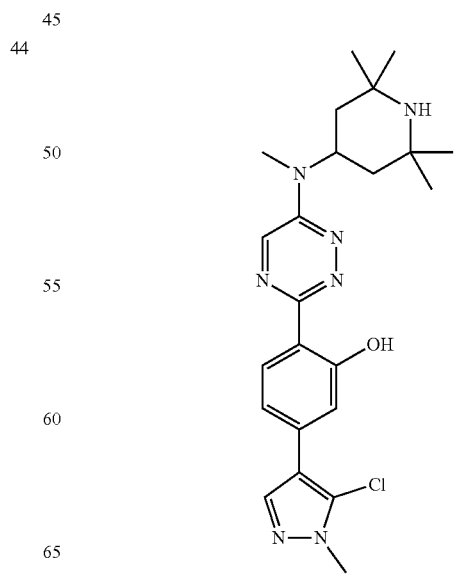

48 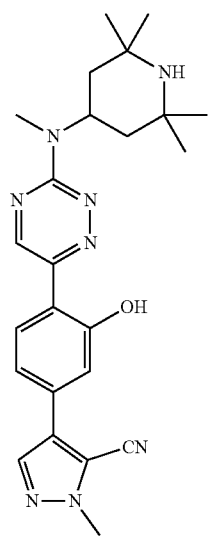
49 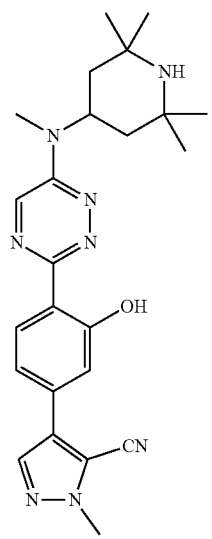
50 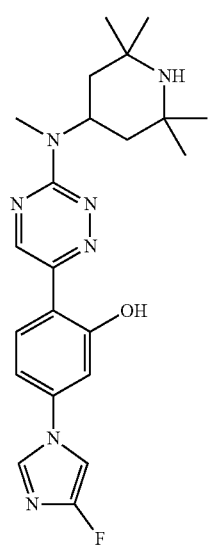
51 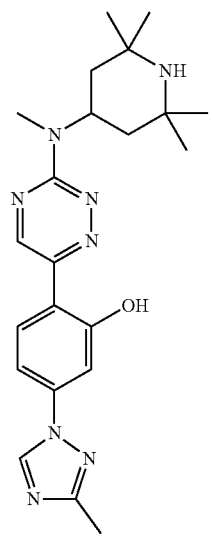
52 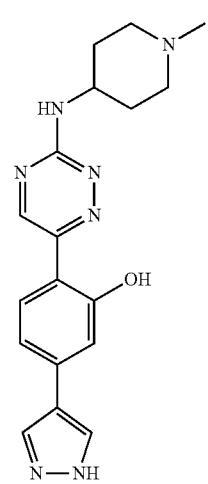
53 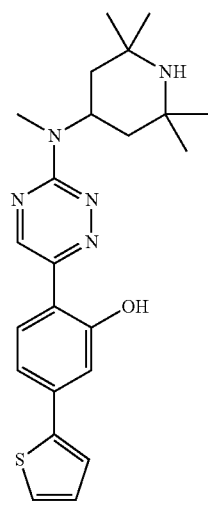

54
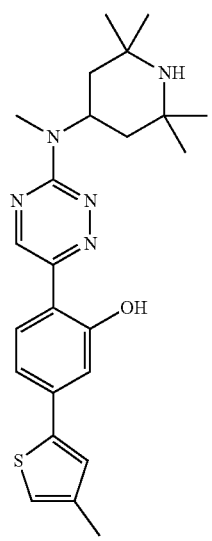
55
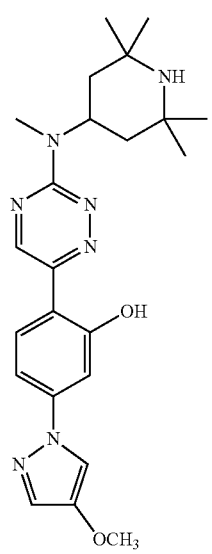
56
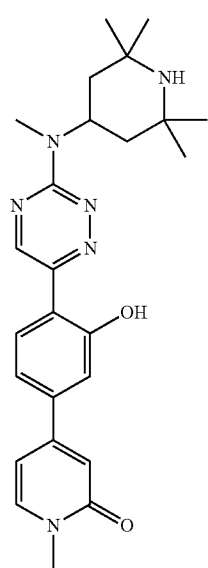
57
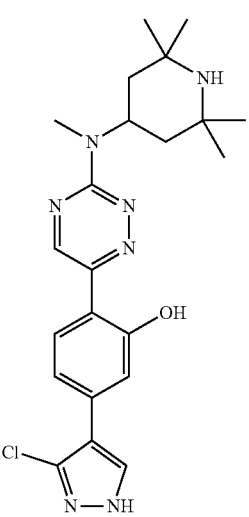
58
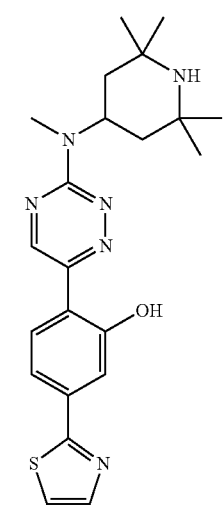
59
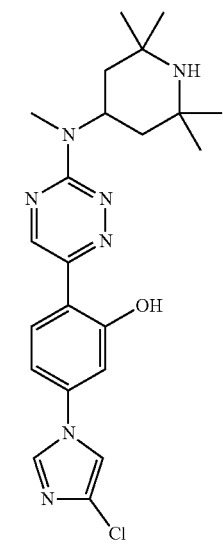

60
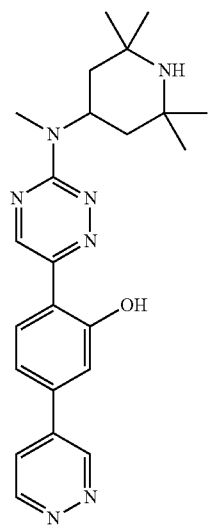
61
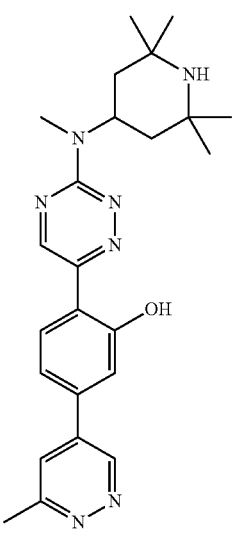
62
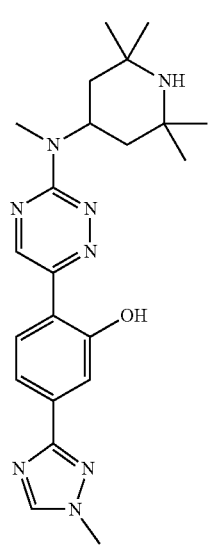
63
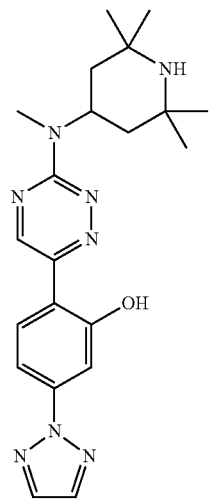
64
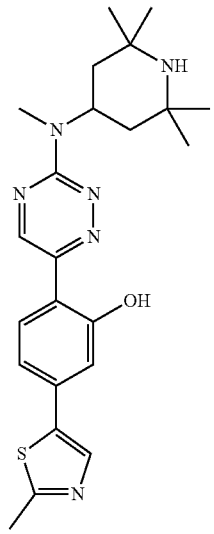
65
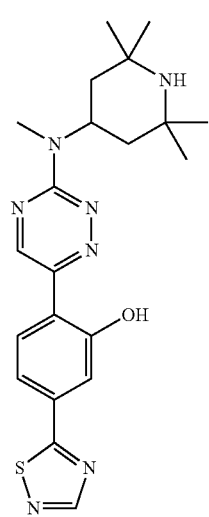

66
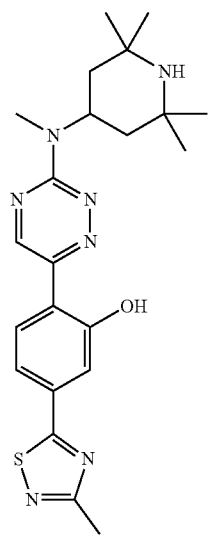
67
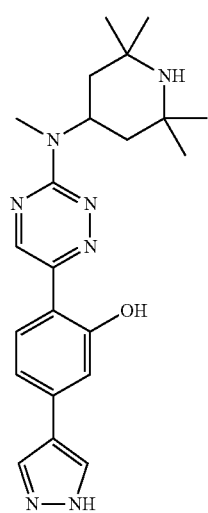
68
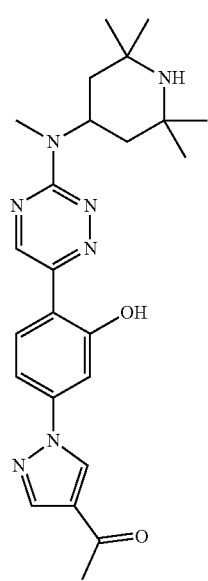
69
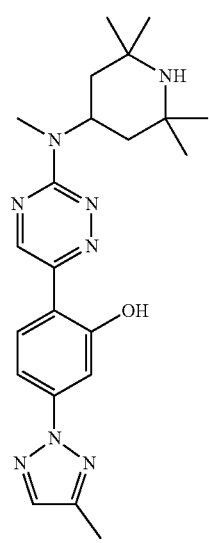
70
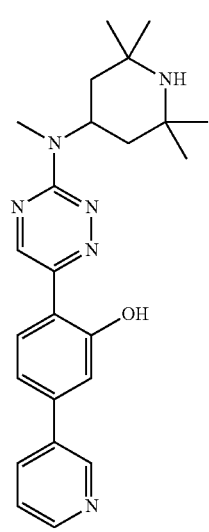
71

72
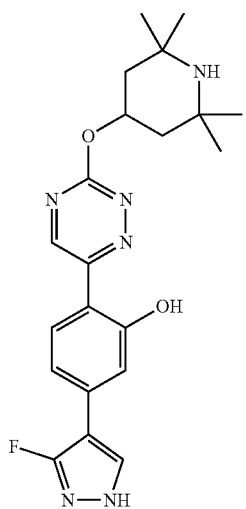
73
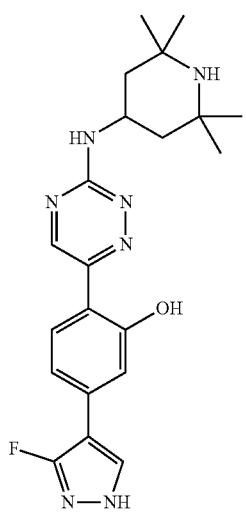
74
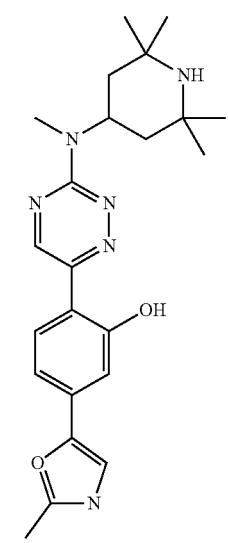
75
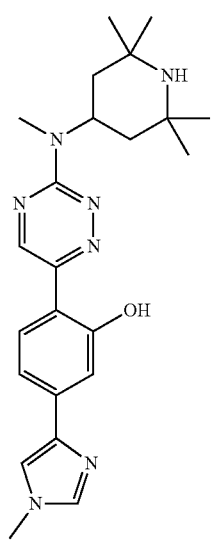
76
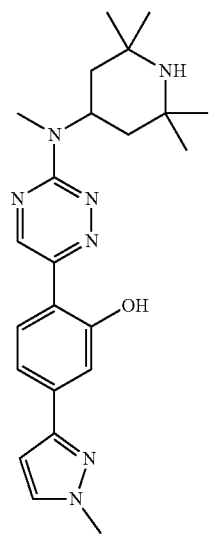
77
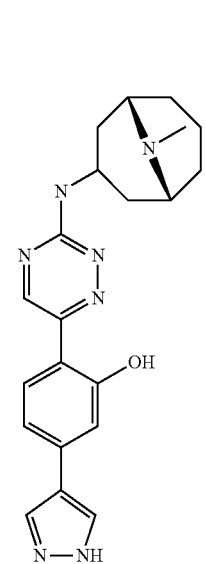

78
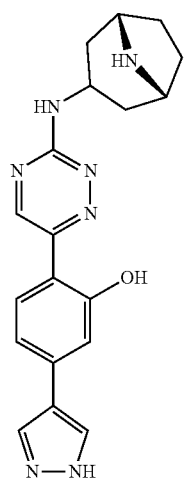
79
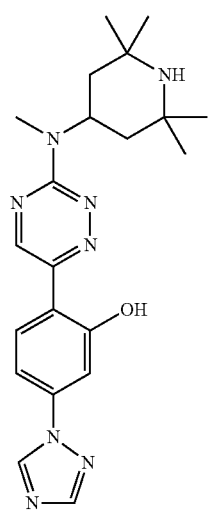
80
81
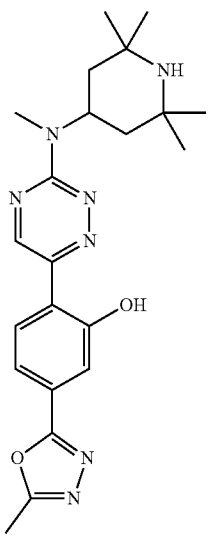
82
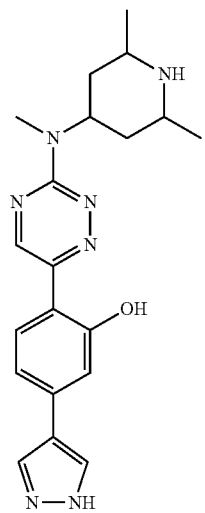
83
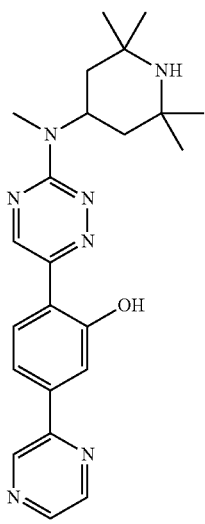

84
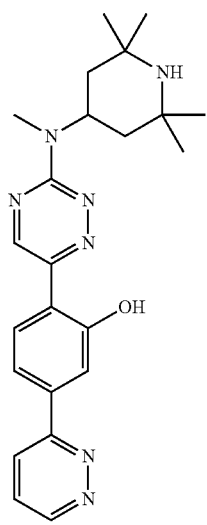
85
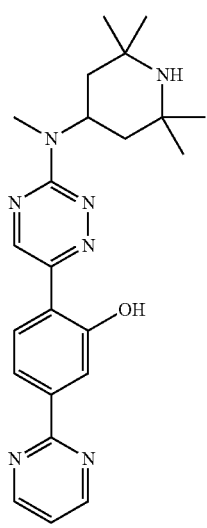
86
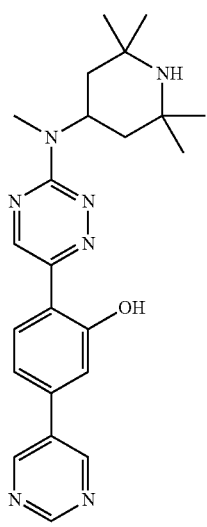
87
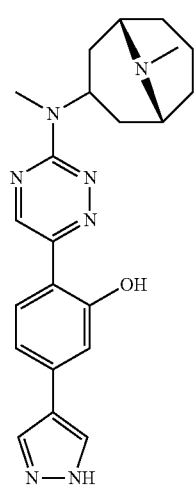
88
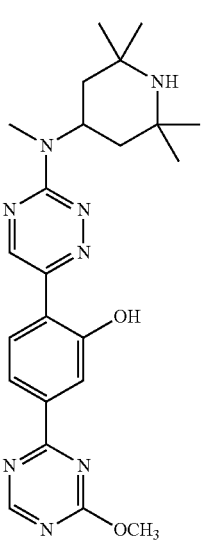
89
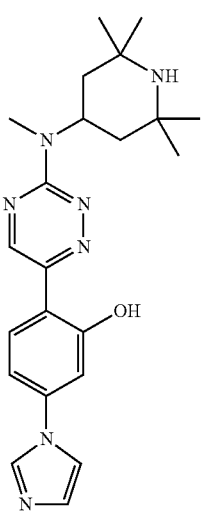

| 90 | 93 |
|---|---|
| 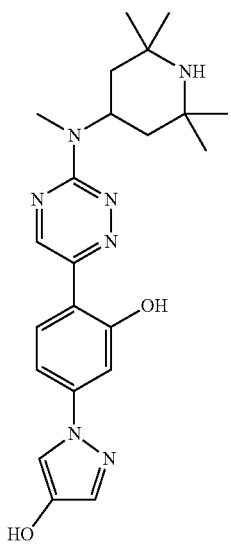 | 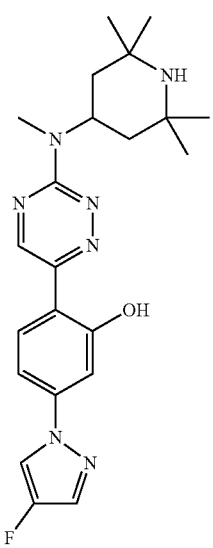 |
| 91 | 94 |
| 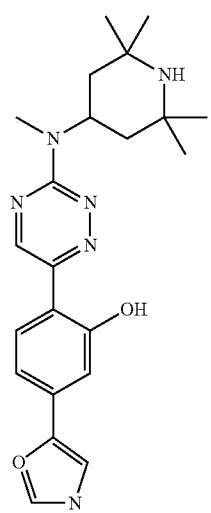 | 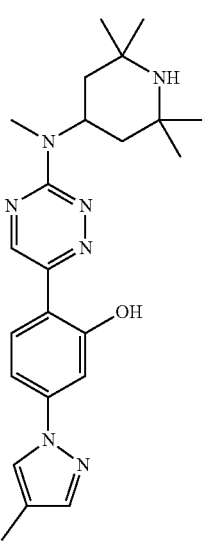 |
| 92 | 95 |
|  | 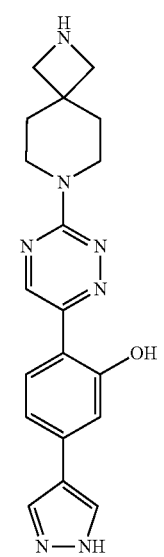 |

96 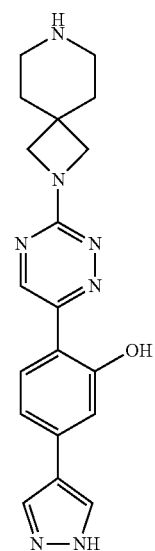
97 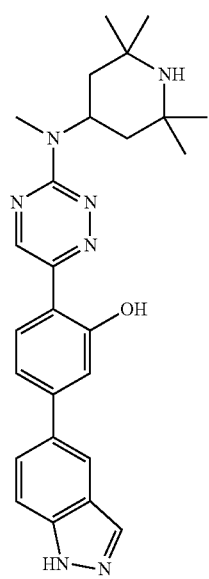
98 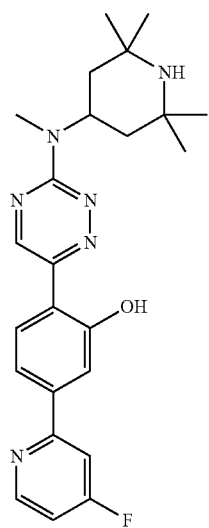
99 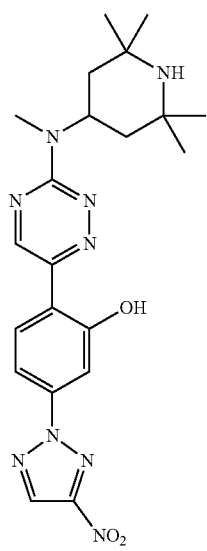
100 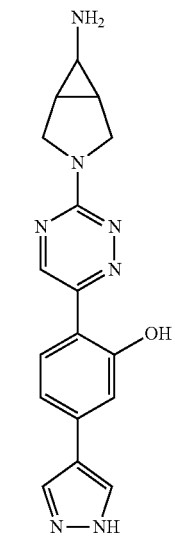
101 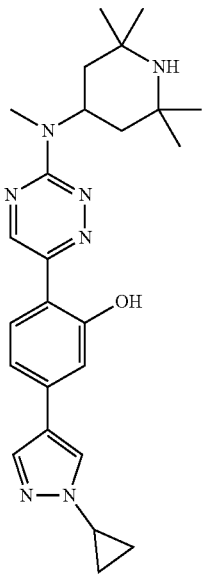

-continued
102
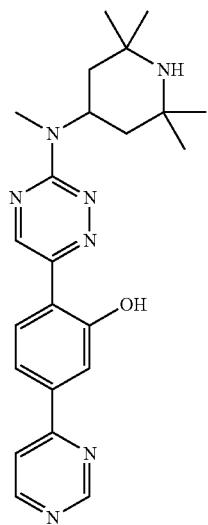
103
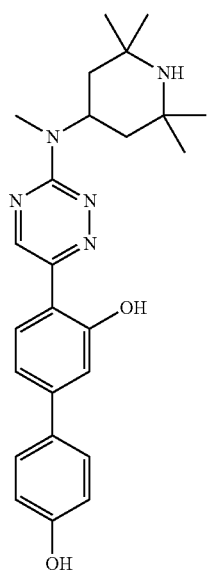
104
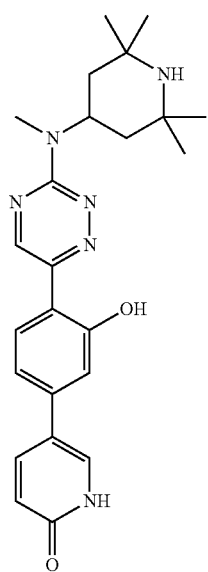
-continued
105
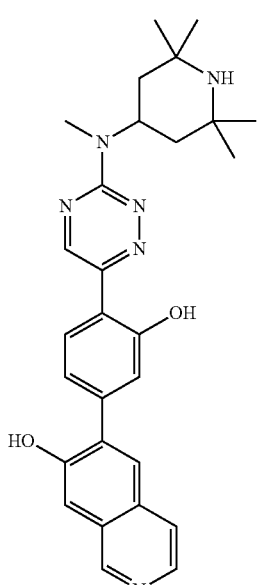
106
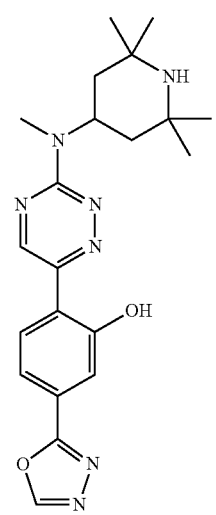
107
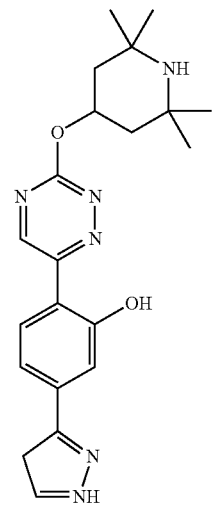

-continued
108
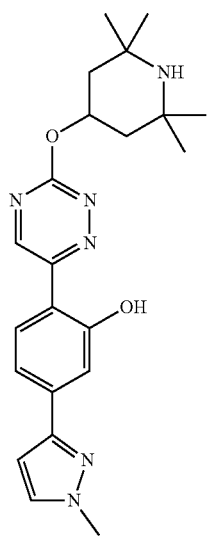
109
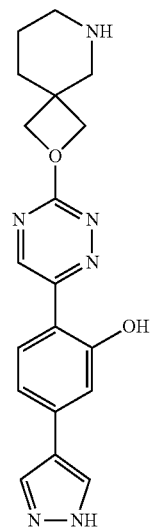
110
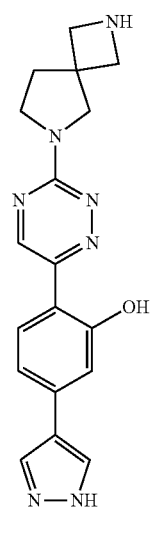
-continued
111
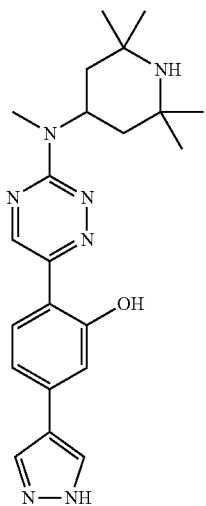
112
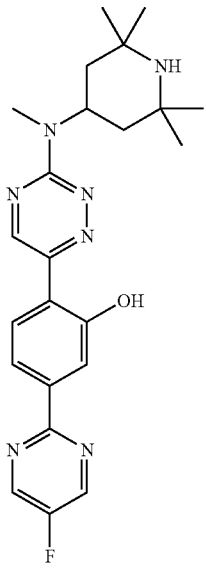
113
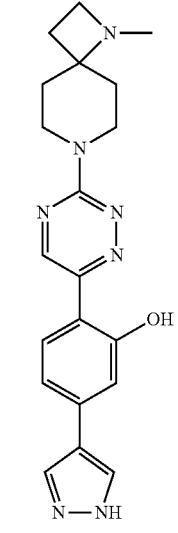

114 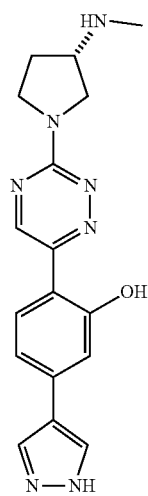
115 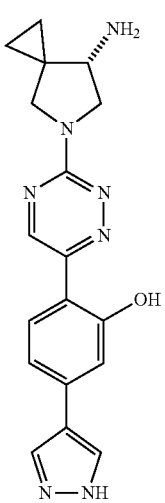
116 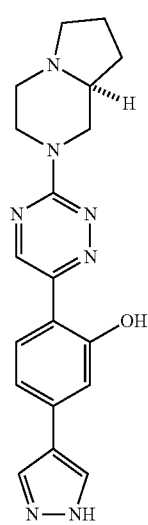
117 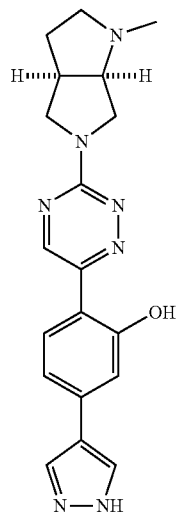
118 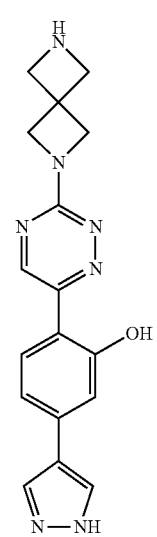
119 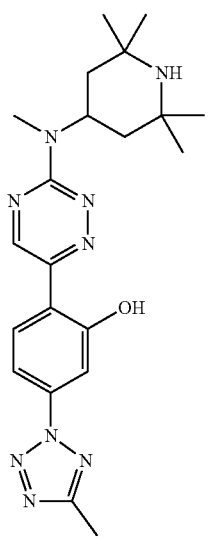

120 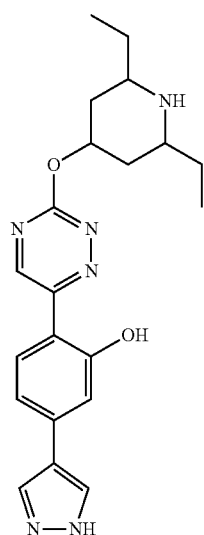
121 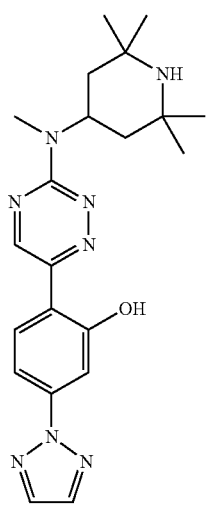
122 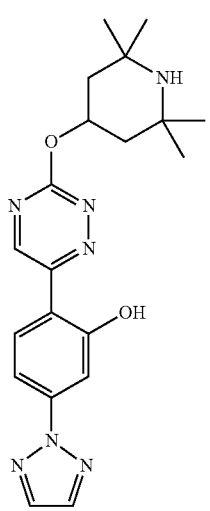
123 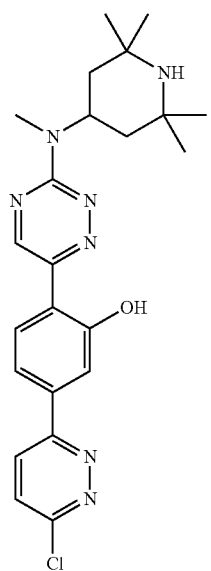
124 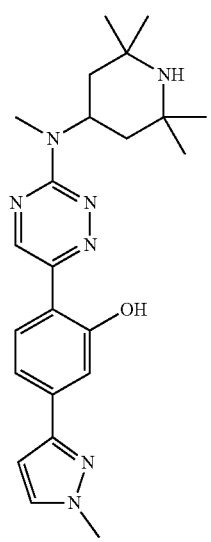
125 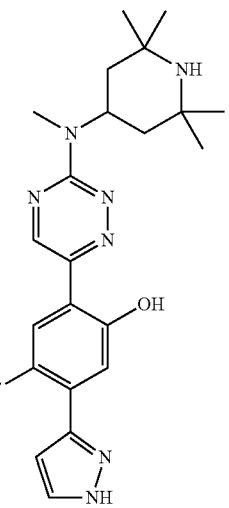

-continued
126 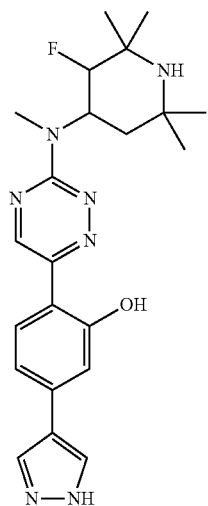
127 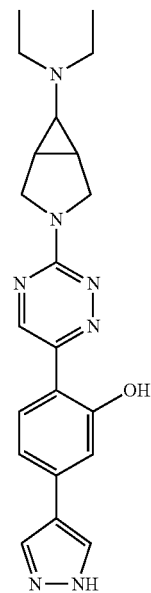
128 
-continued
129 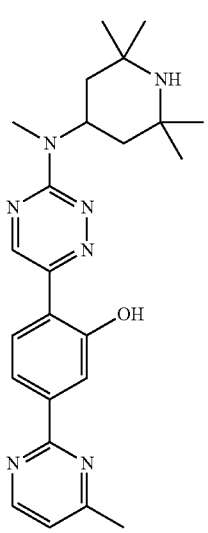
130 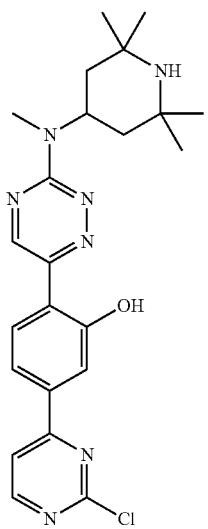
131 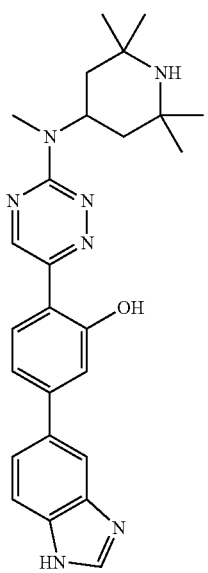

| 132 | 135 |
|---|---|
| 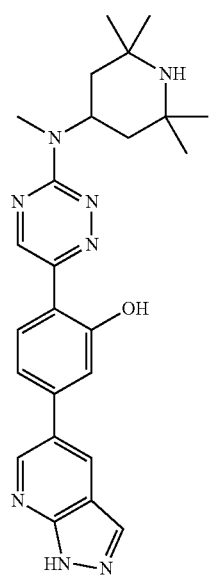 | 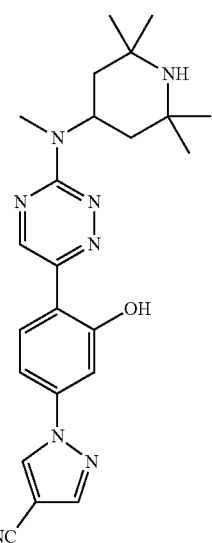 |
| 133 | 136 |
| 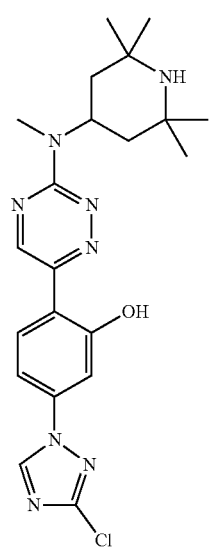 | 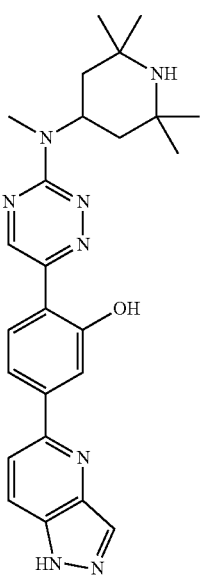 |
| 134 | 137 |
| 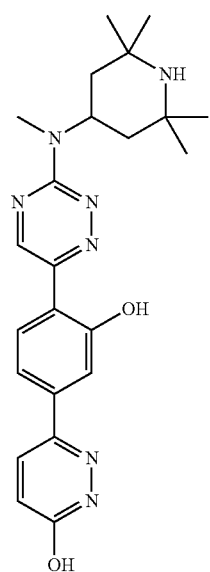 | 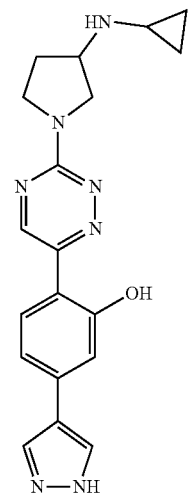 |

138
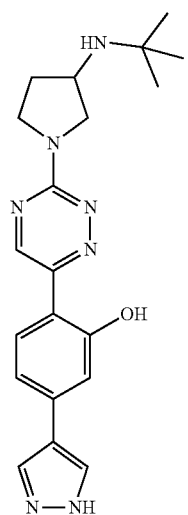
139
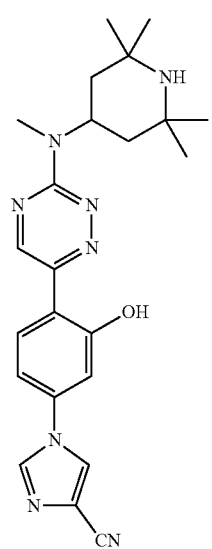
140
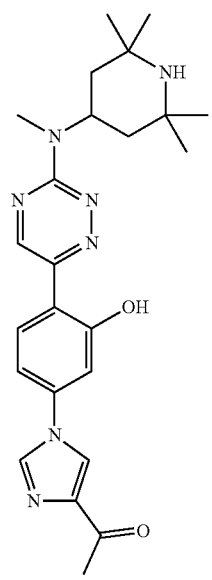
141
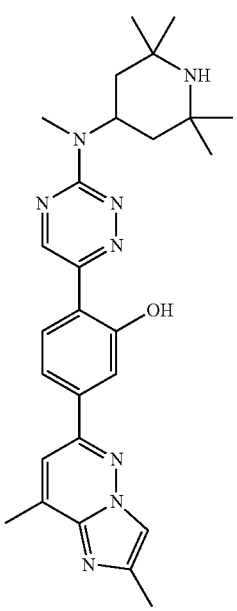
142
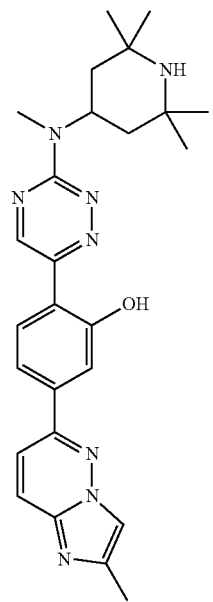

143 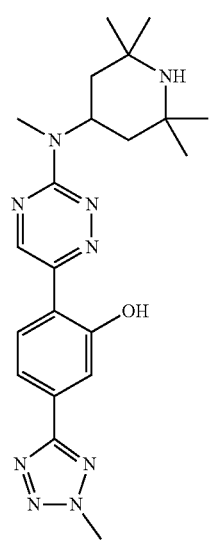
144 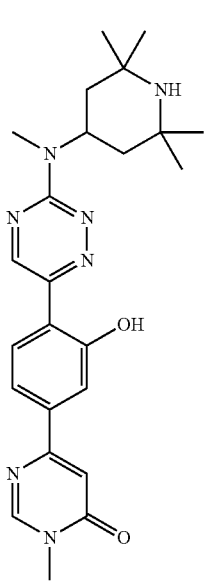
145 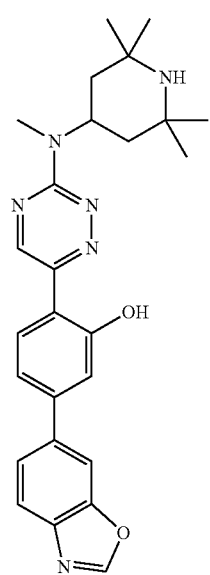
146 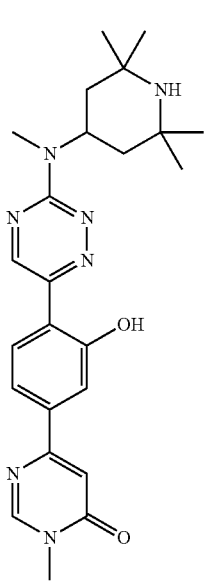
147 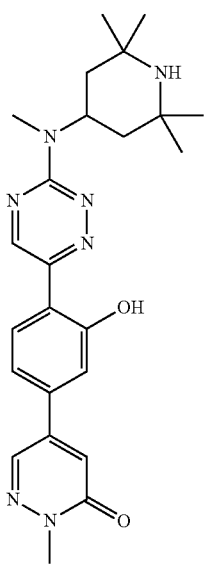
148 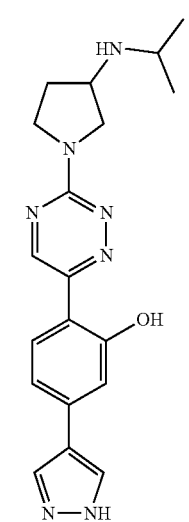

149
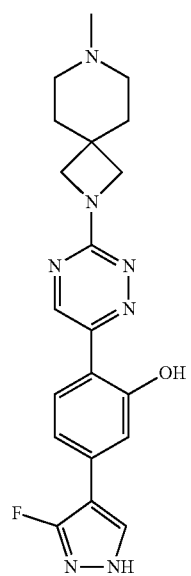
150
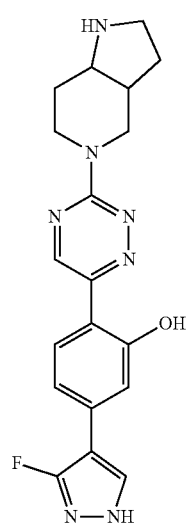
151
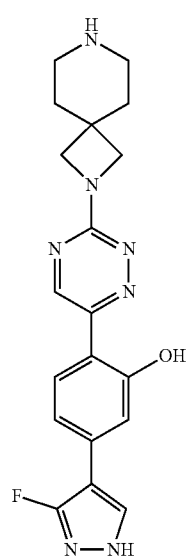
152
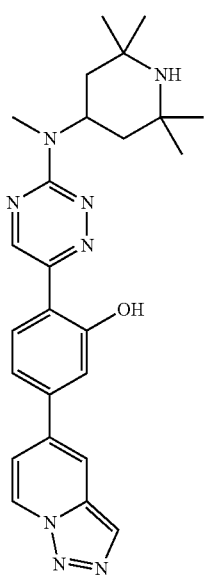
153
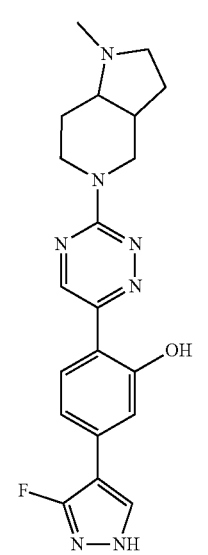
154
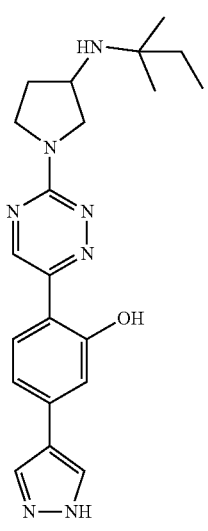

-continued
155
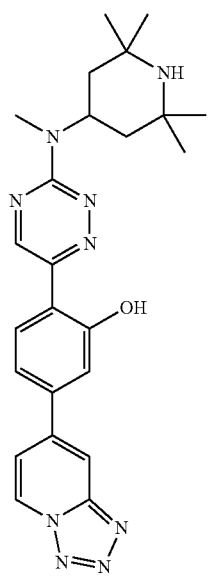
156
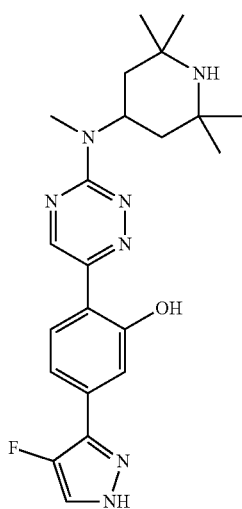
-continued
157
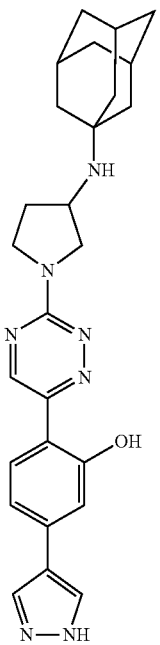
158
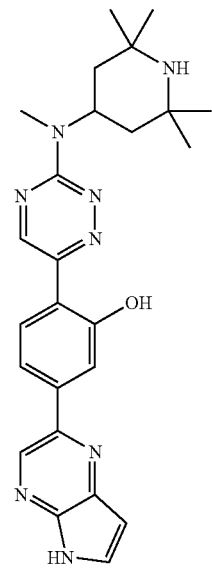

71
159
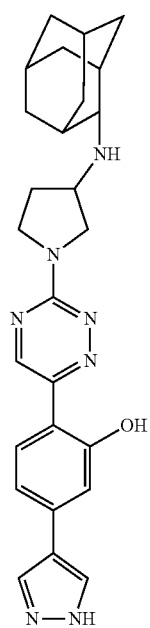
160
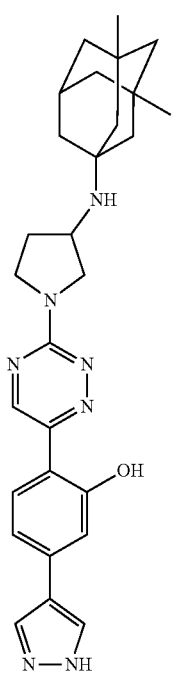
72
161
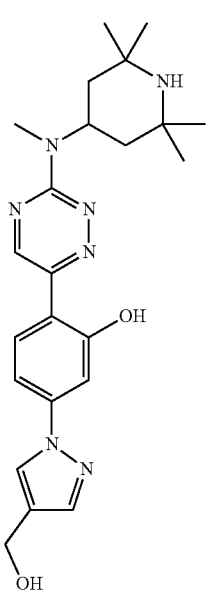
162
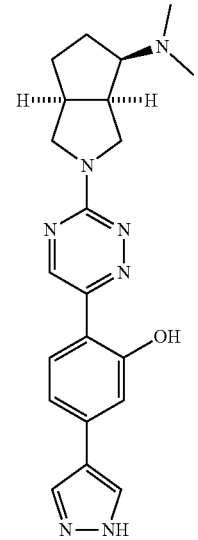

163 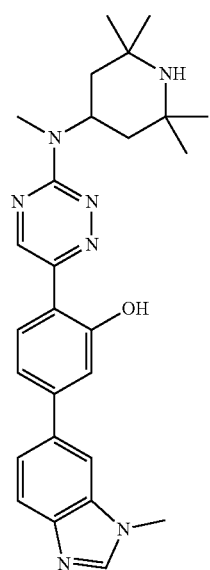
164 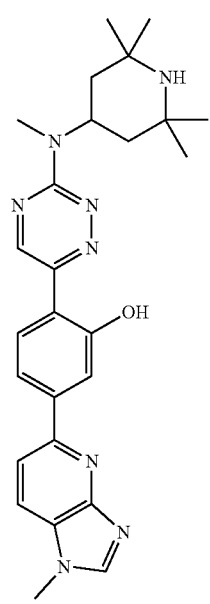
165 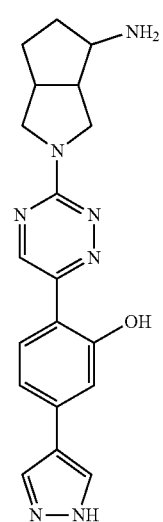
166 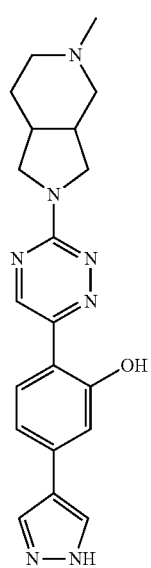
167 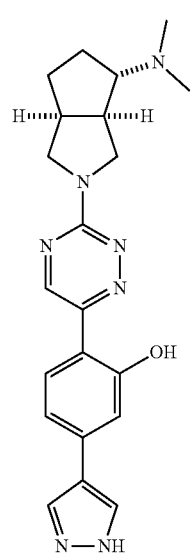
168 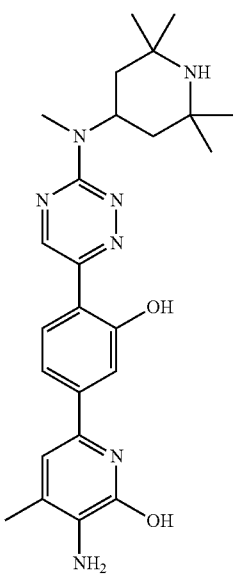

-continued
169 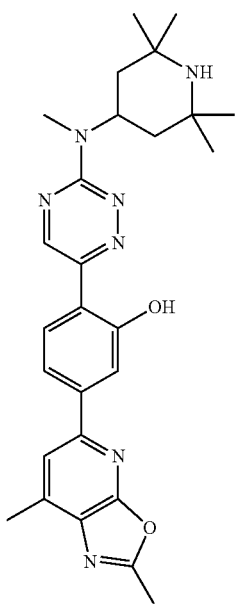
170 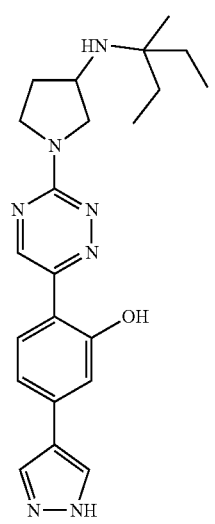
171 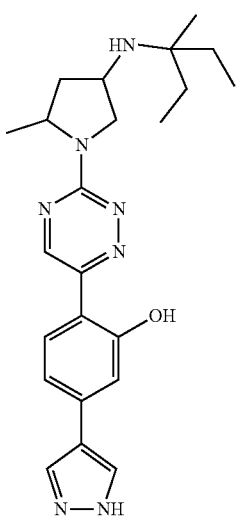
-continued
172 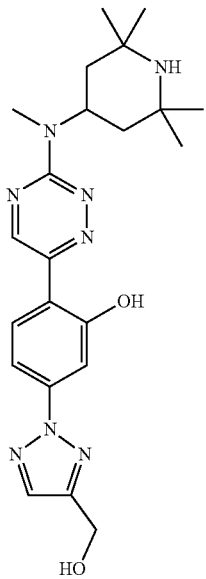
173 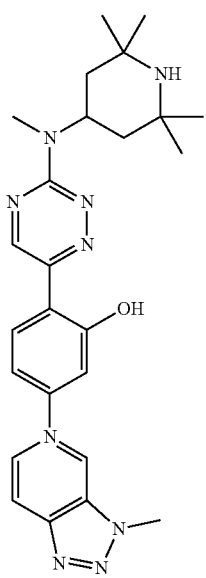
174 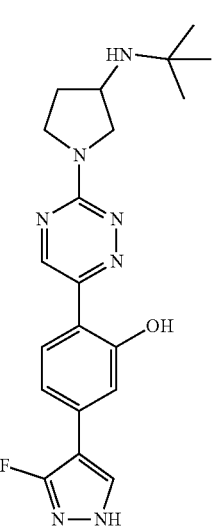

175
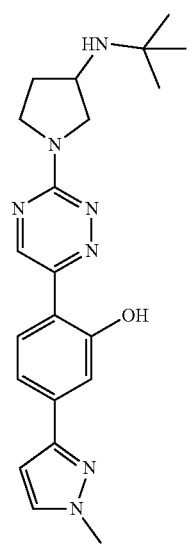
177
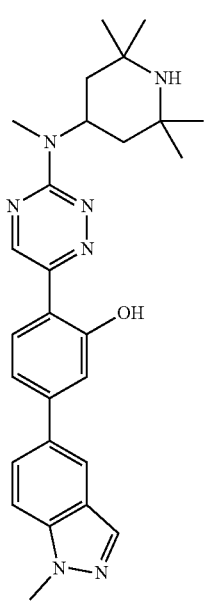
176
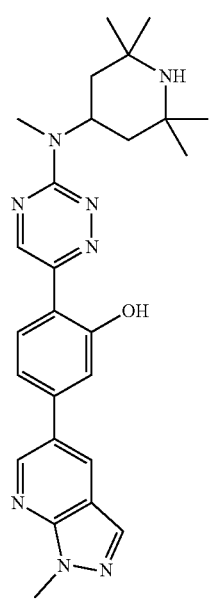
178
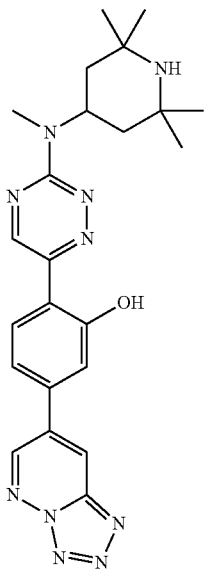

| 79 | 80 |
|---|---|
| -continued | -continued |
| 179 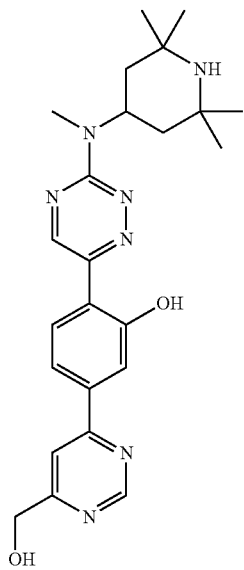 | 182 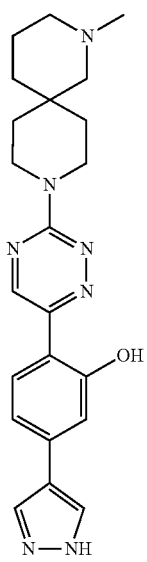 |
| 180 | |
| 181 | 183 |

184
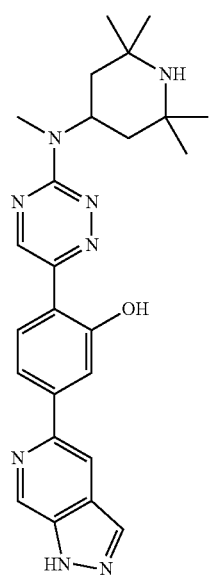
185
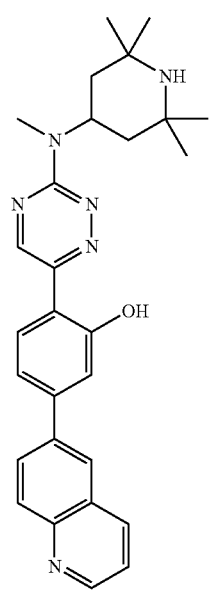
186
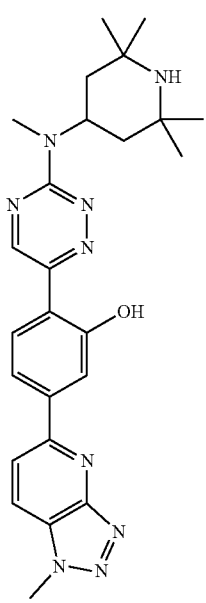
187
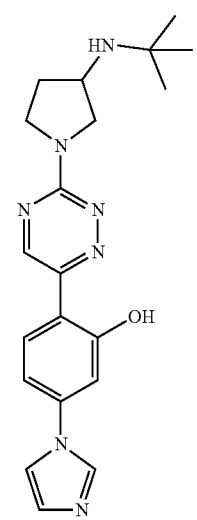
188
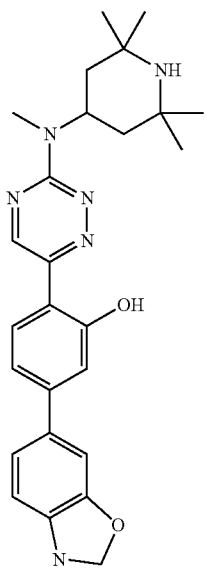

189
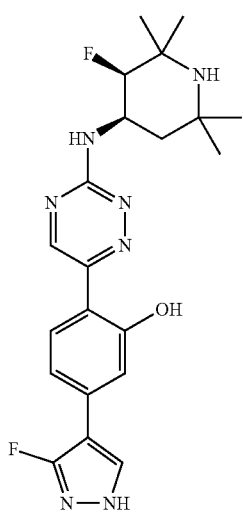
190
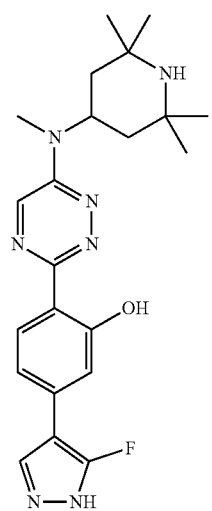
191
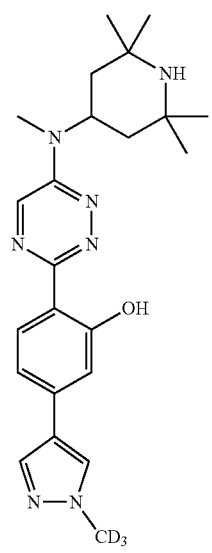
192
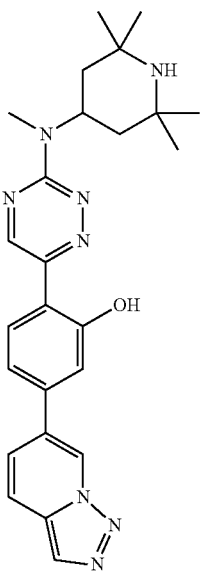
193
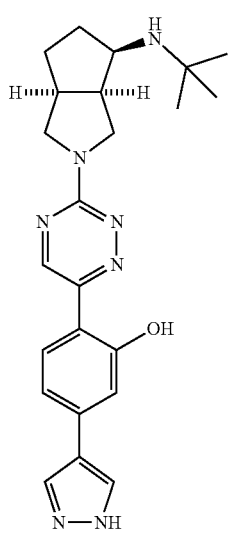
194
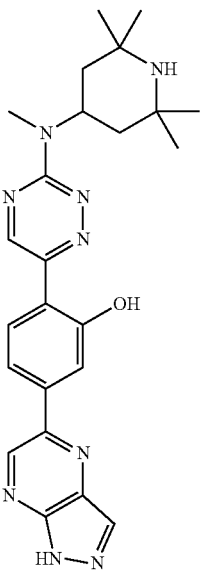

85
-continued
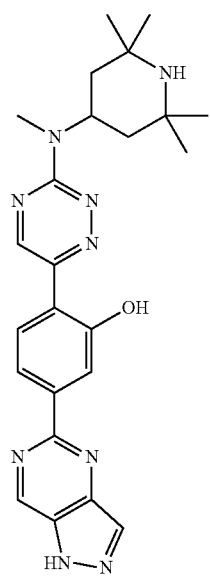
195
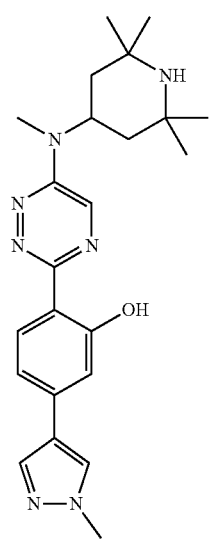
196
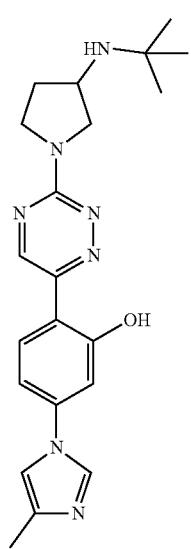
197
86
-continued
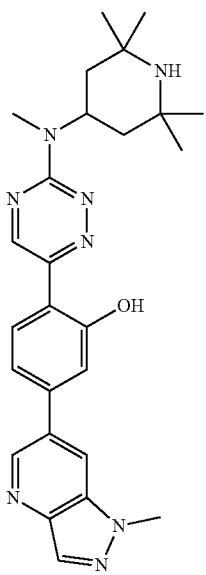
198
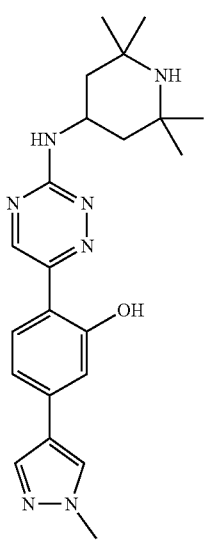
199

87
-continued
200 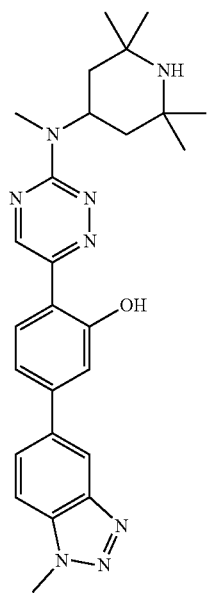
201 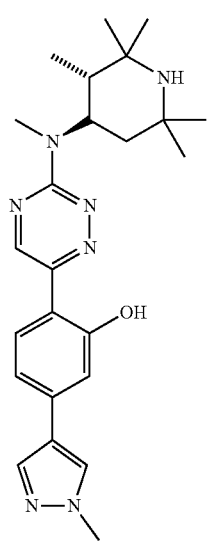
202 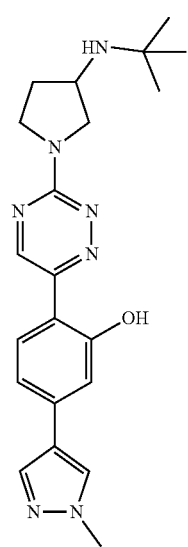
88
-continued
203 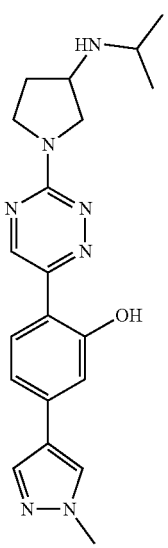
204 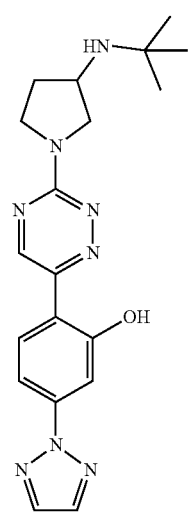
205 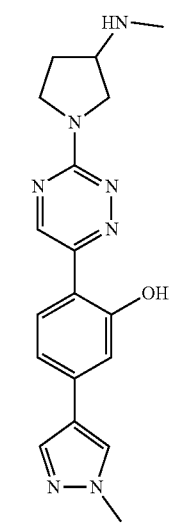

206
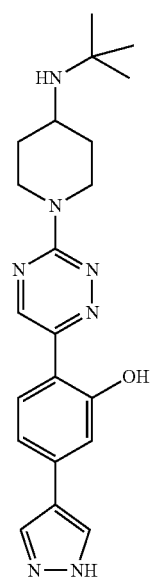
207
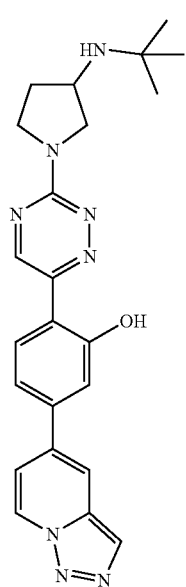
208
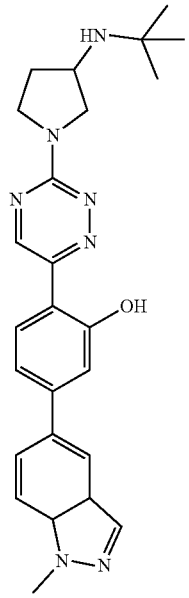
209
210

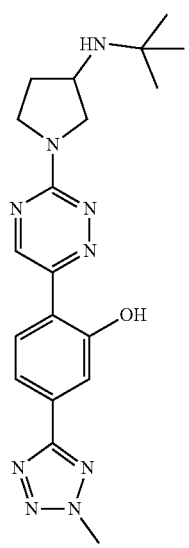
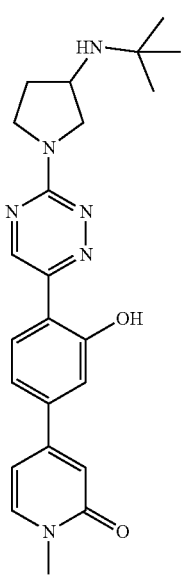

216 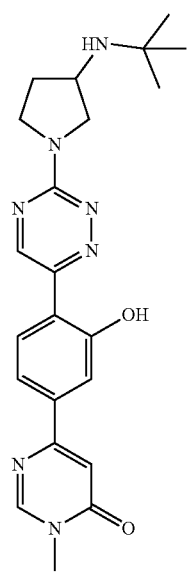
217 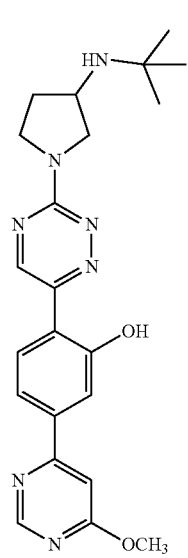
218 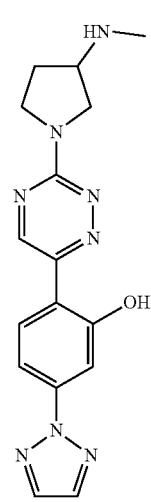
219 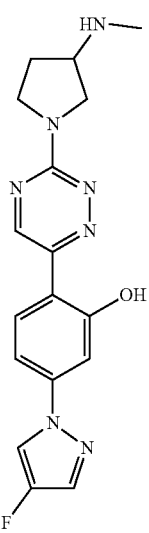
220 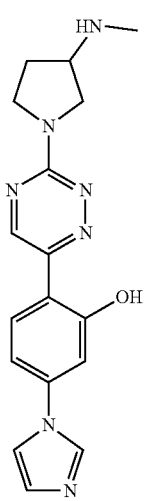
221 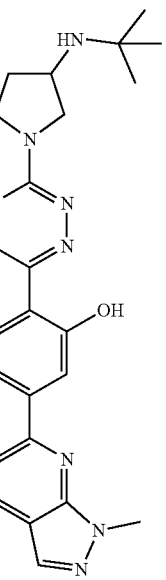

222
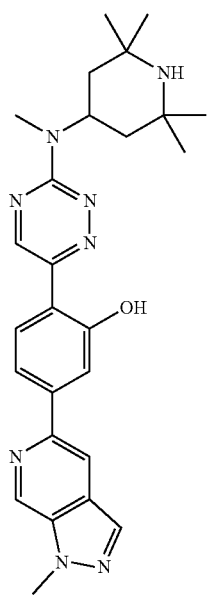
223
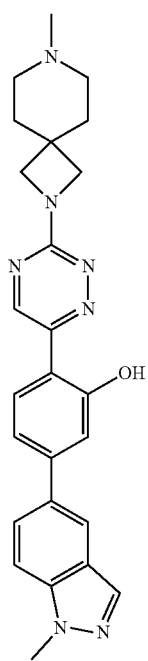
224
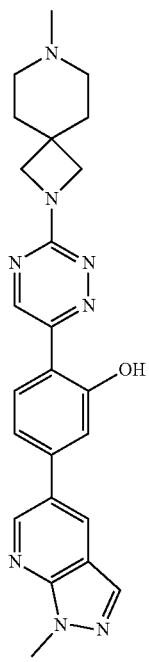
225
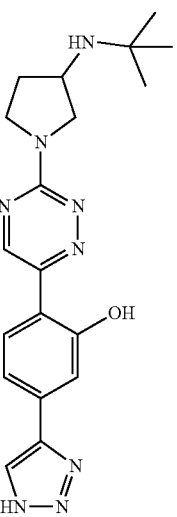

226
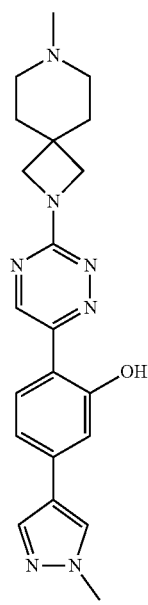
227
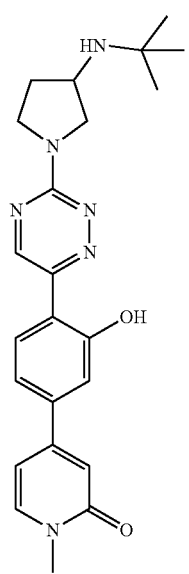
228
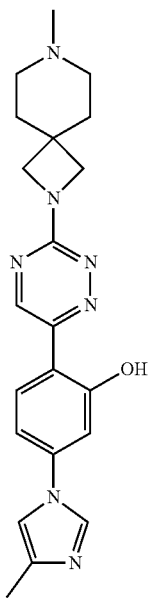
229
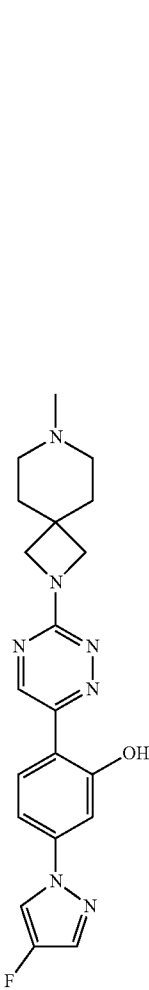

230
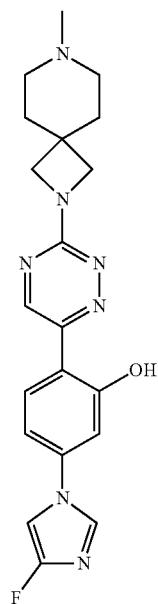
231
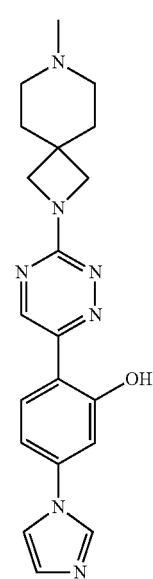
232
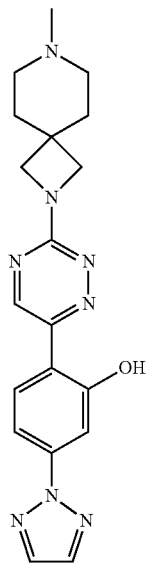
233
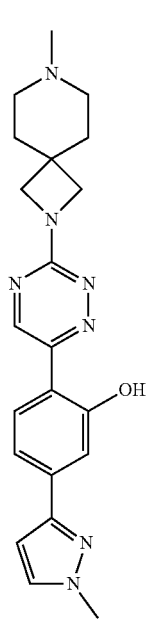

234 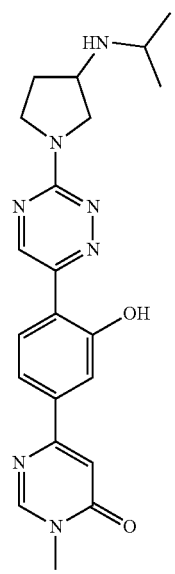
235 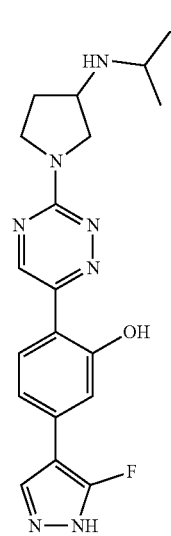
236 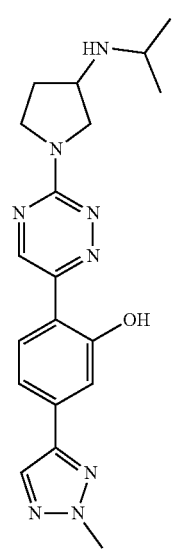
237 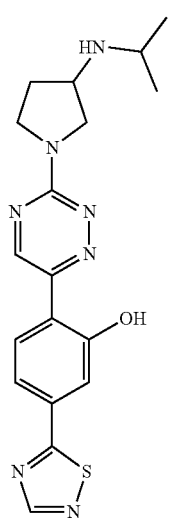
238 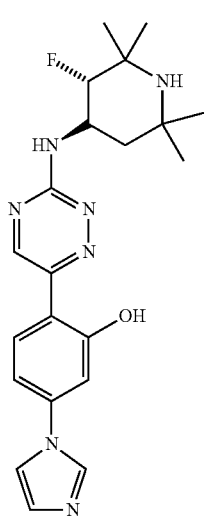
239 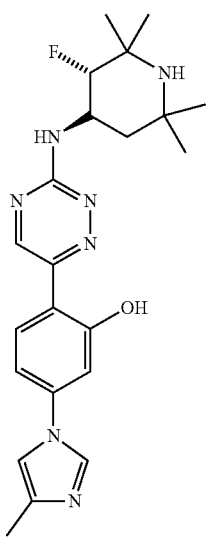

103
-continued
240
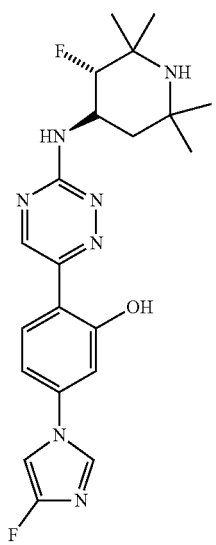
241
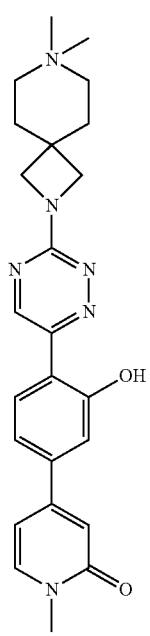
104
-continued
242
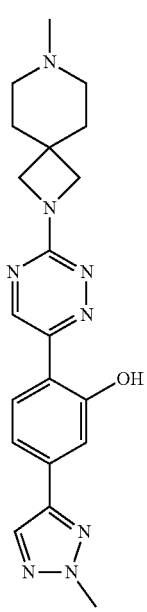
243
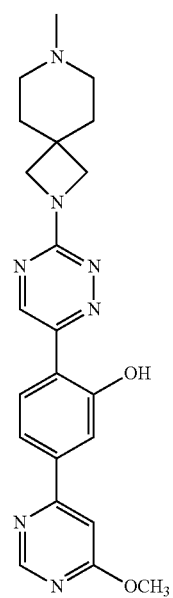

244
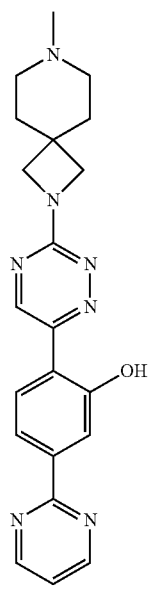
245
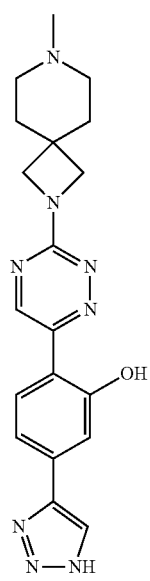
246
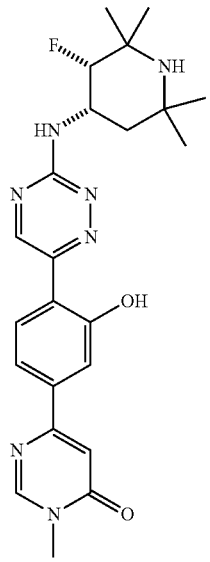
247
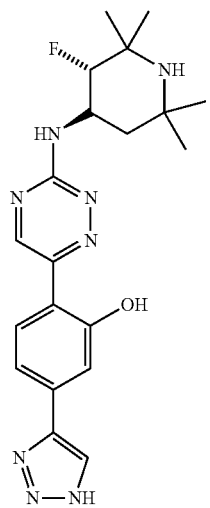
248
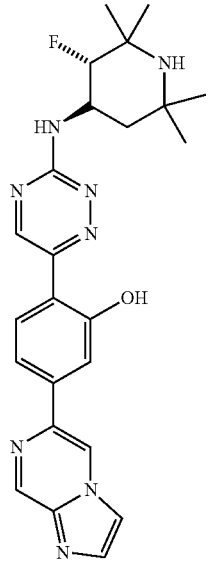

249 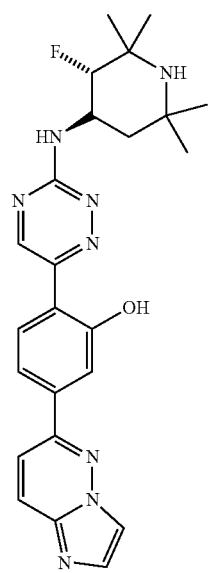
250 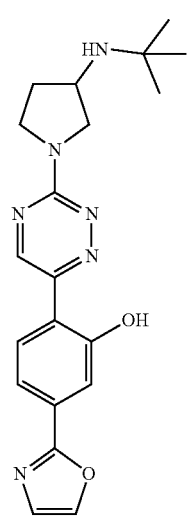
251 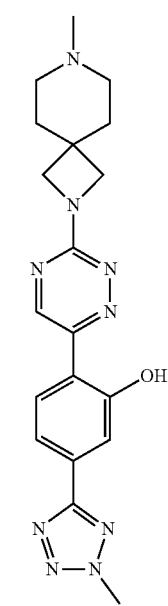
252 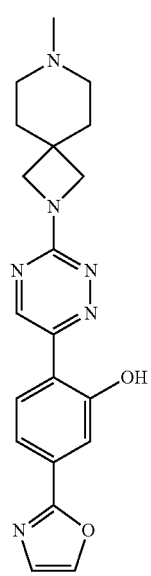
253 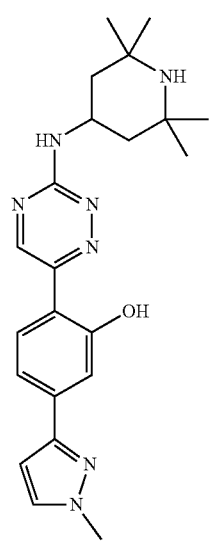
254 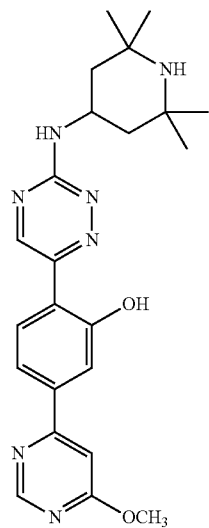

255
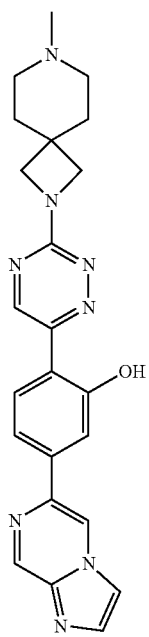
256
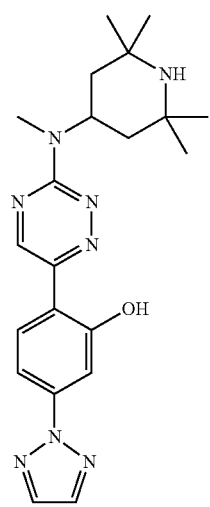
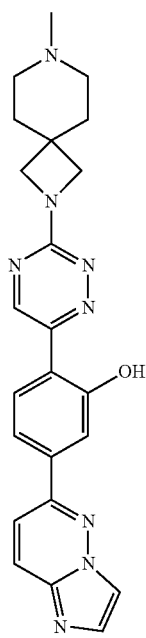
257
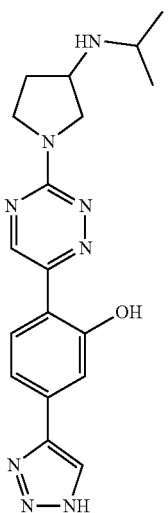
258

259 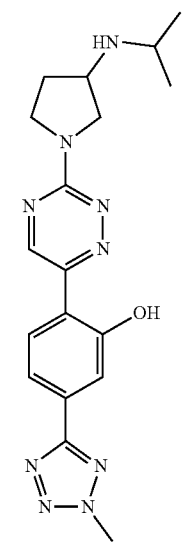
260 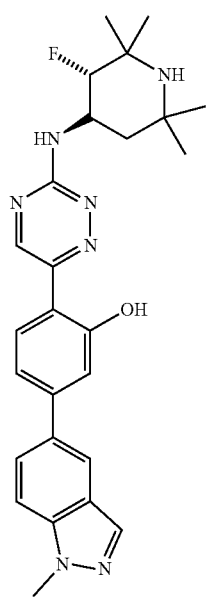
261 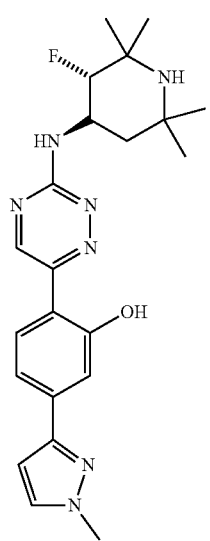
262 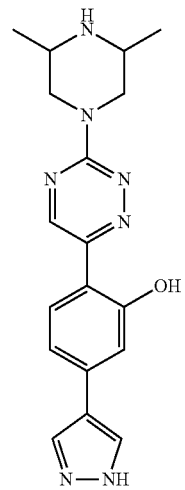
263 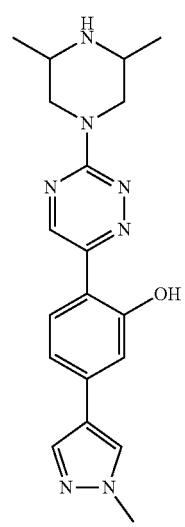
264 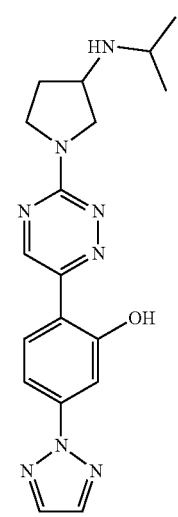

| 265 | 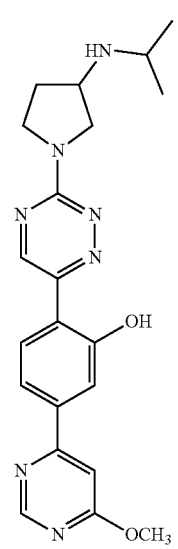 | 268 | 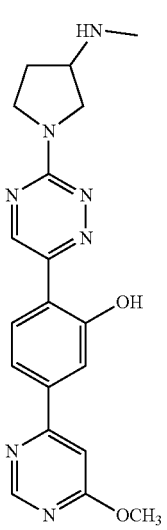 |
| 266 | 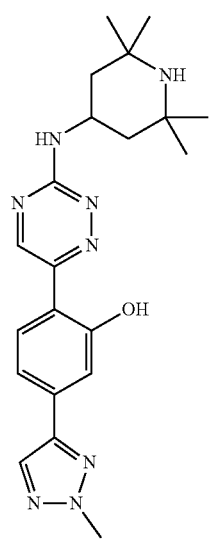 | 269 | 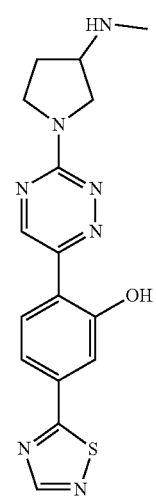 |
| 267 | 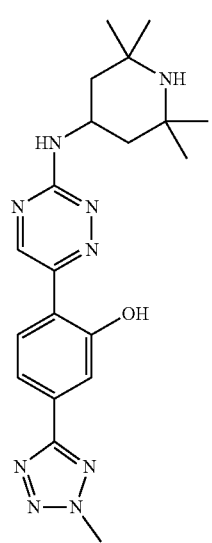 | 270 | 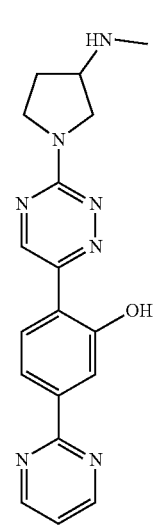 |

271 
272 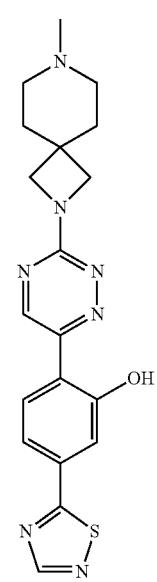
273 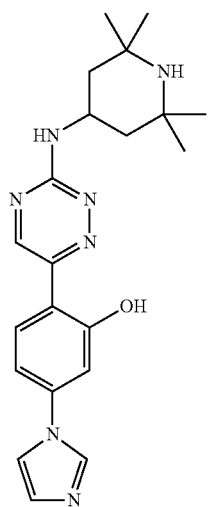
274 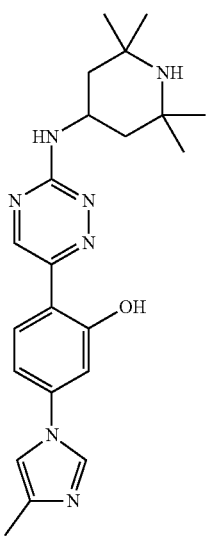
275 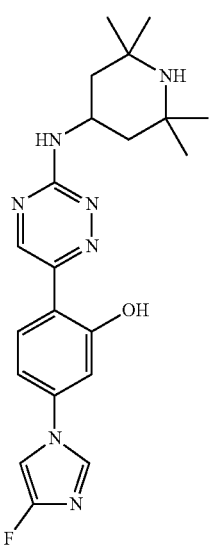
276 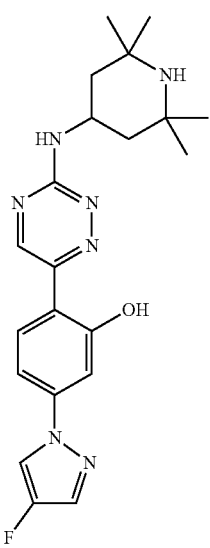

277 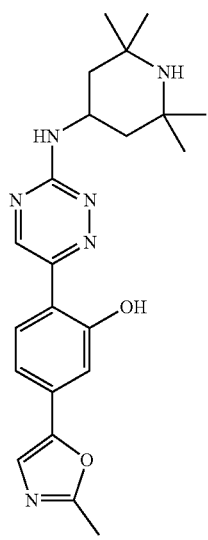
278 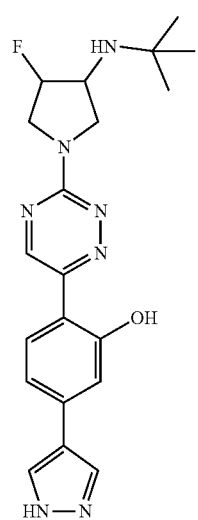
279 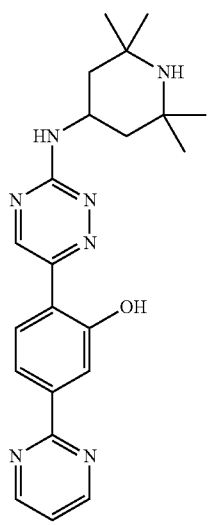
280 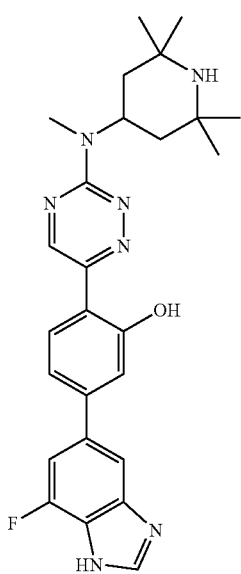
281 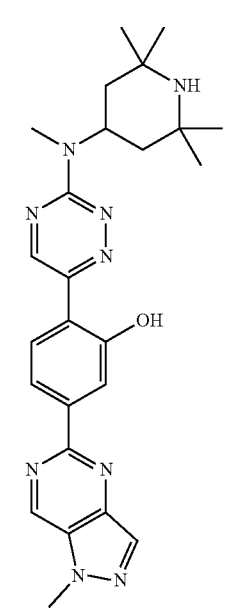
282 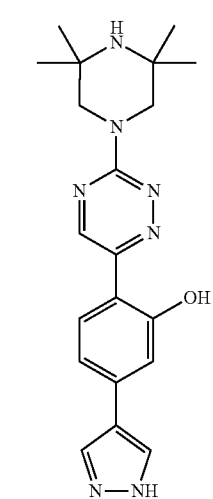

119
-continued
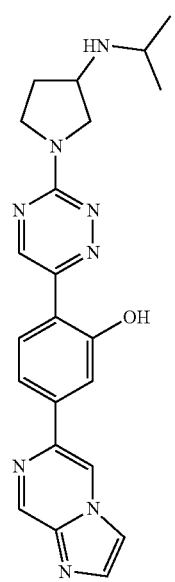
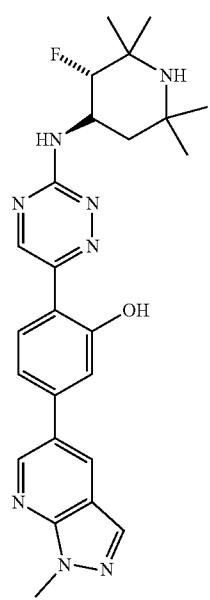
120
-continued
283
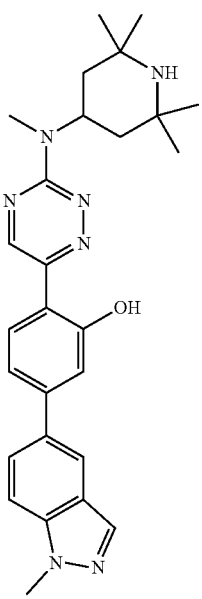
286
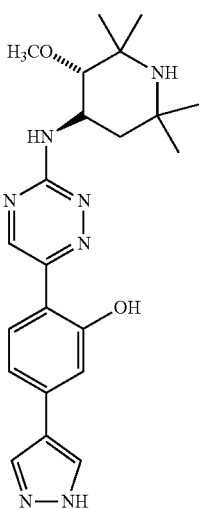
287
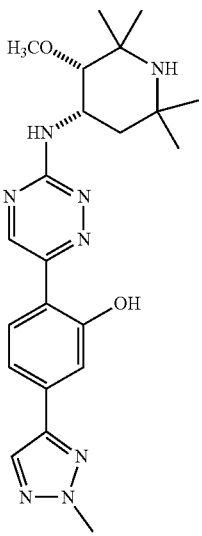

288
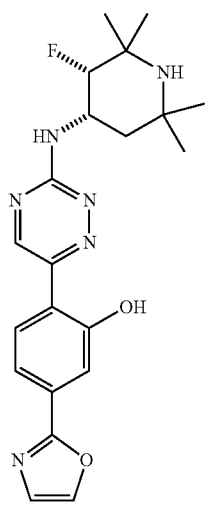
289
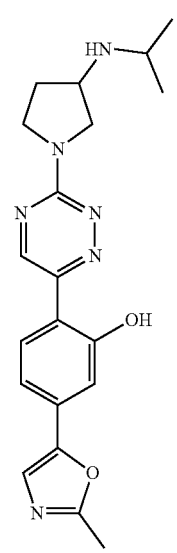
290
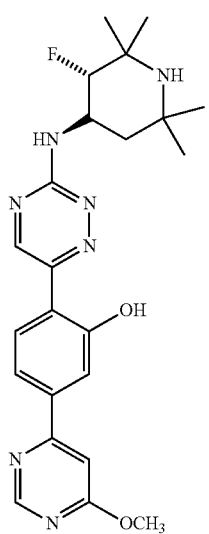
291
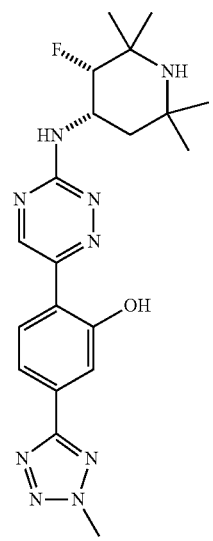
292
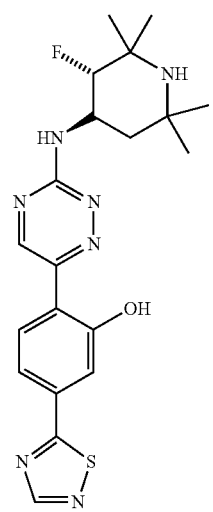
293
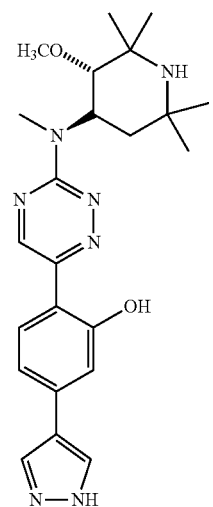

294
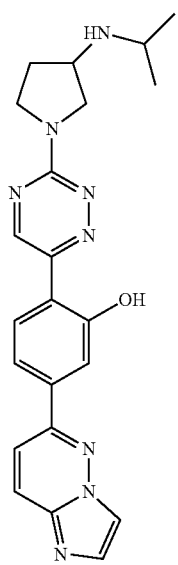
295
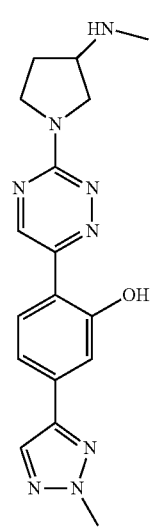
296
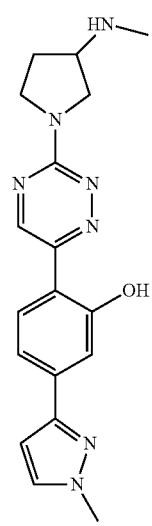
297
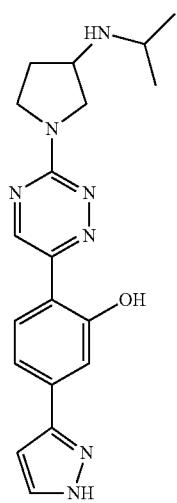
298
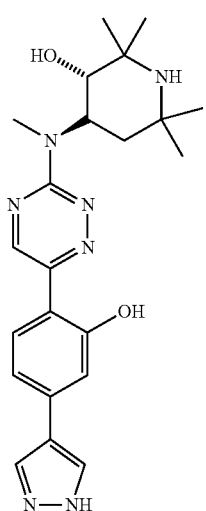
299
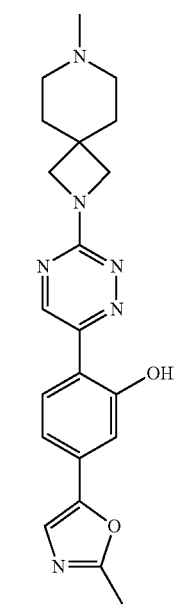

125
-continued
300
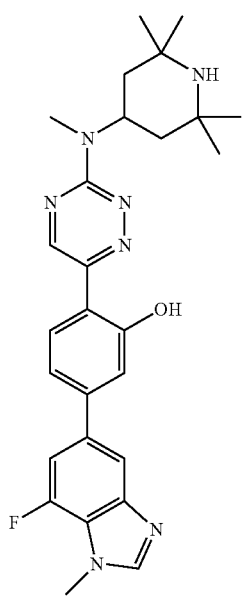
301
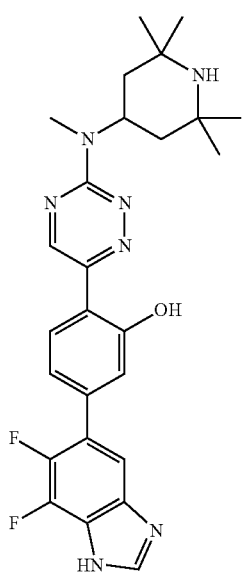
126
-continued
302
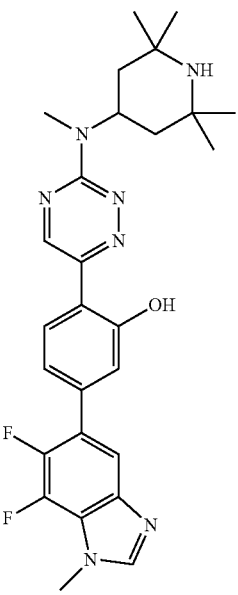
303
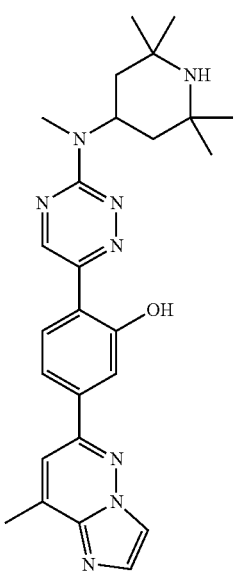

| 304 | 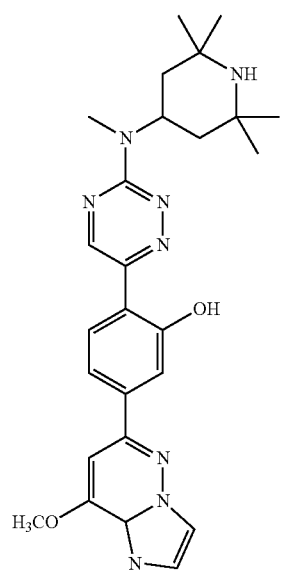 | 307 | 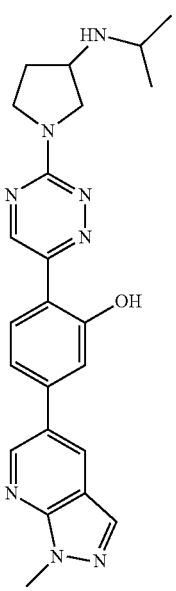 |
| 305 | 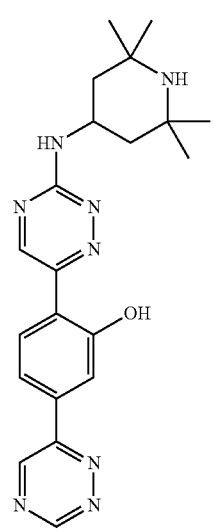 | 308 | 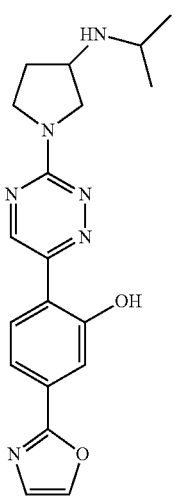 |
| 306 | 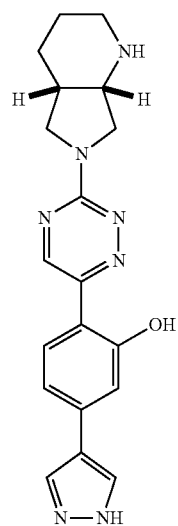 | 309 | 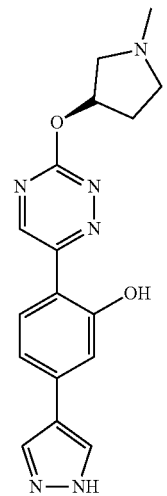 |

| 129 | 130 |
|---|---|
| 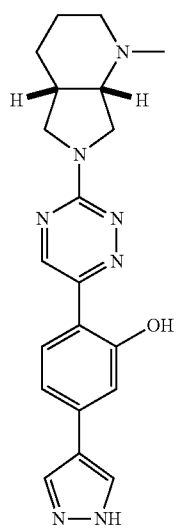 | 310 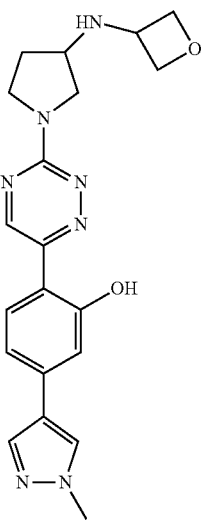 313 |
| 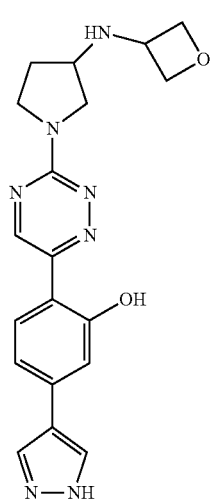 | 311 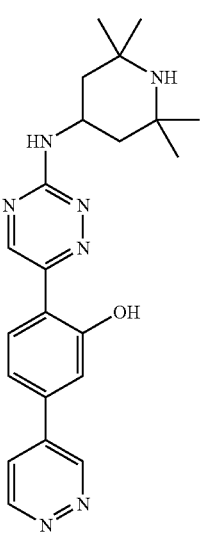 314 |
| | 312 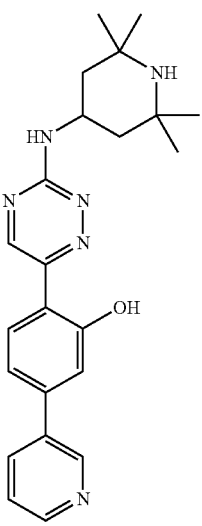 315 |

| 316 | 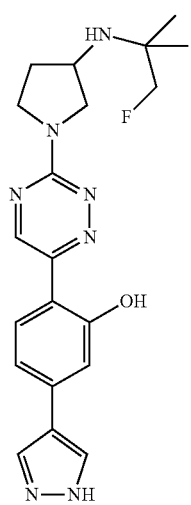 | 319 | 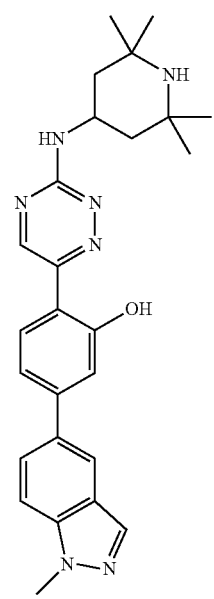 |
| 317 | 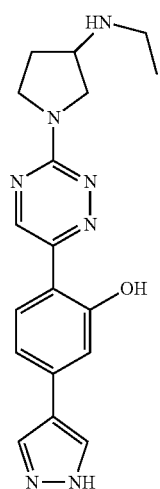 | | |
| 318 | 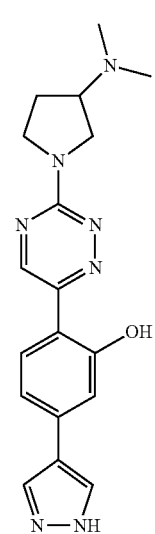 | 320 | 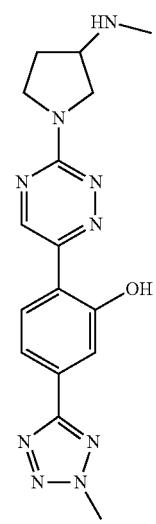 |

133
-continued
321 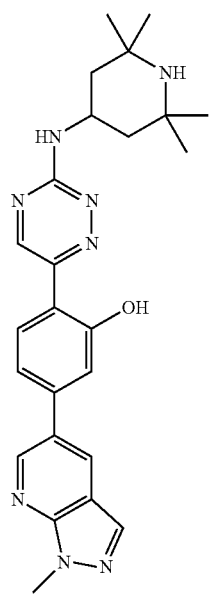
322
323
134
-continued
324 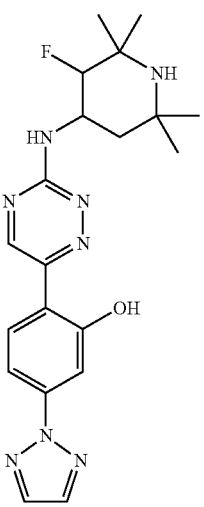
325 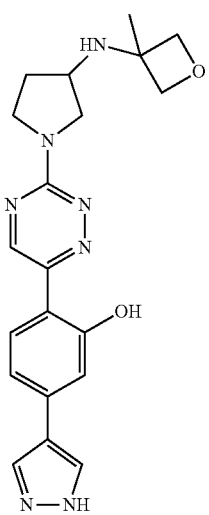
326 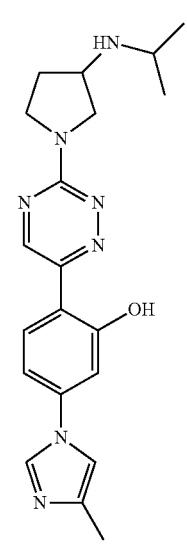

135 | 136
-continued | -continued
327 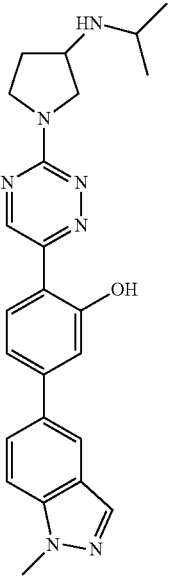
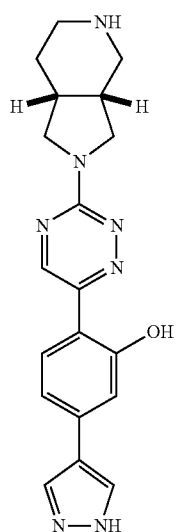
330 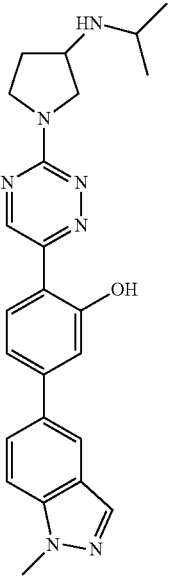
328 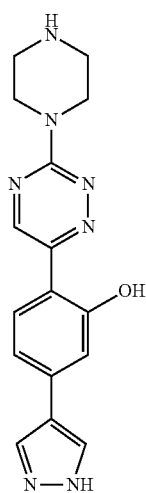
331 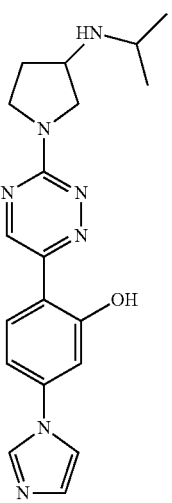
329 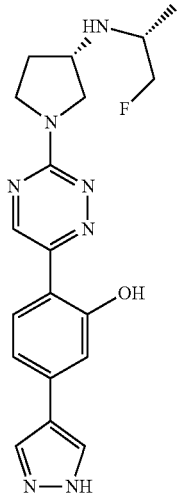
332 

| 333 | 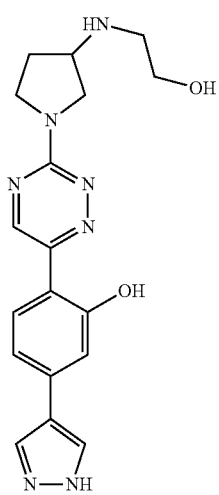 |
| --- | --- |
| 334 | 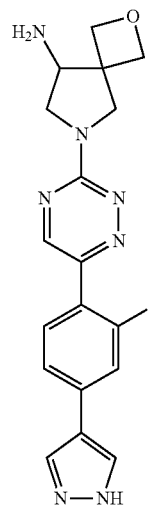 |
| 335 | 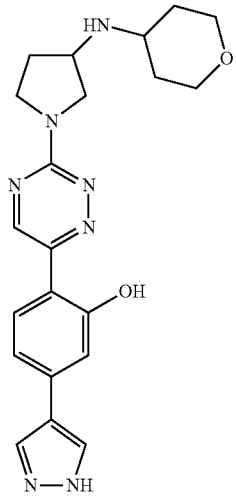 |
| 336 | 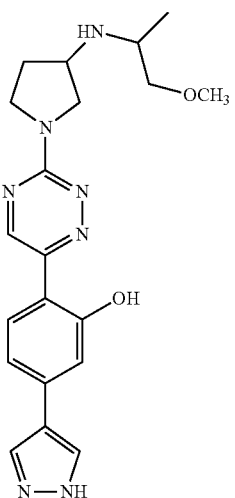 |
| --- | --- |
| 337 | |
| 338 | 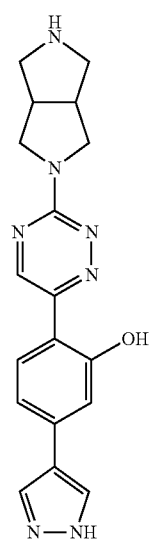 |

339
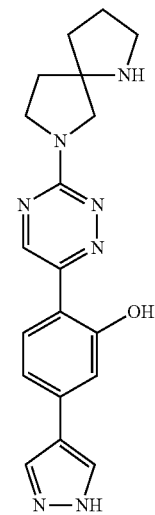
340
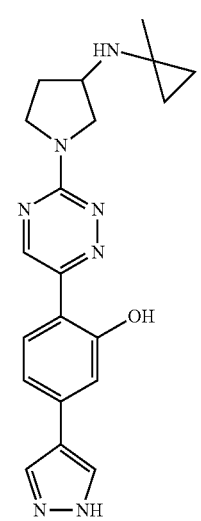
342
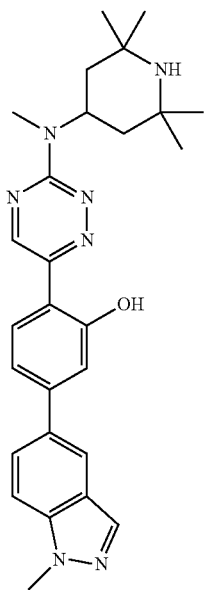
343
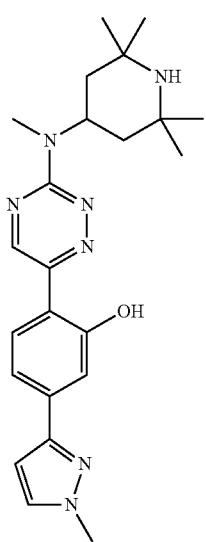

| 344 | 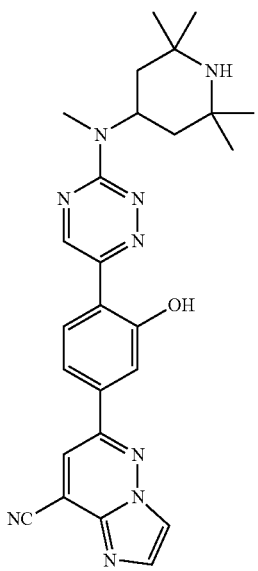 | 347 | 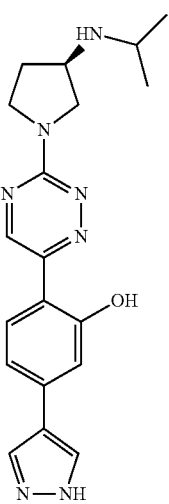 |
| 345 | 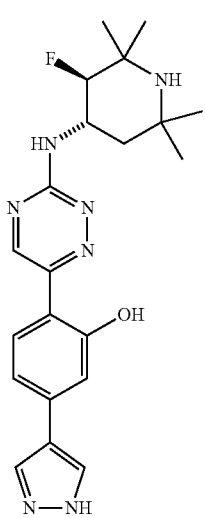 | 348 | 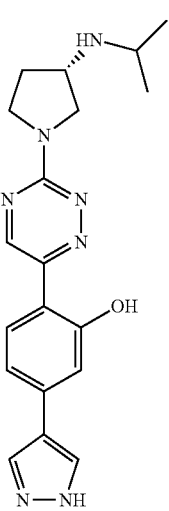 |
| 346 | 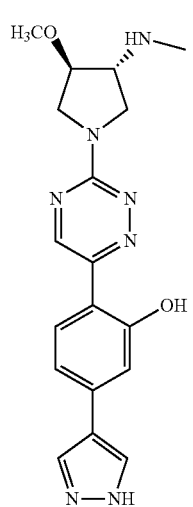 | 349 | 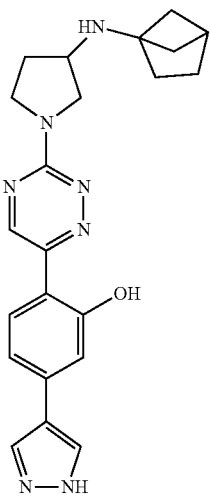 |

| 350 | 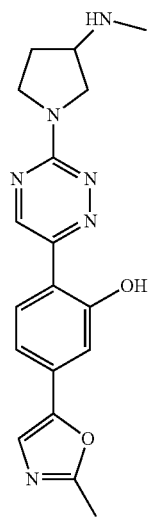 | 353 | 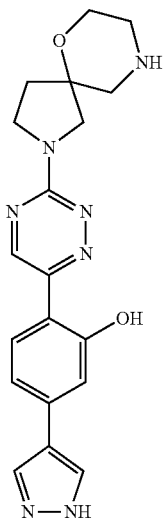 |
| 351 | 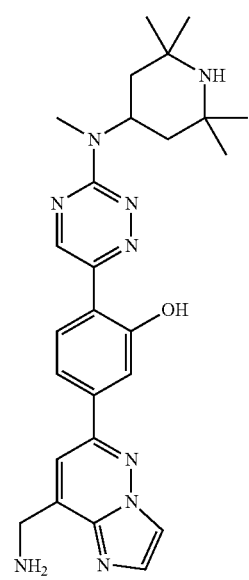 | 354 | 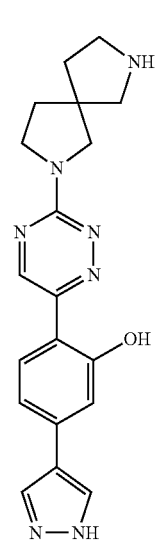 |
| 352 | 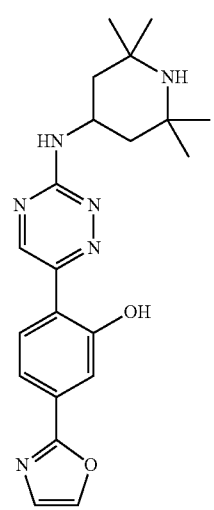 | 355 | 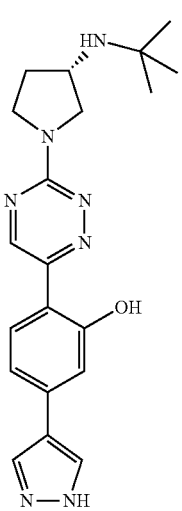 |

356 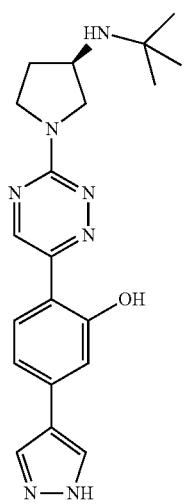
357 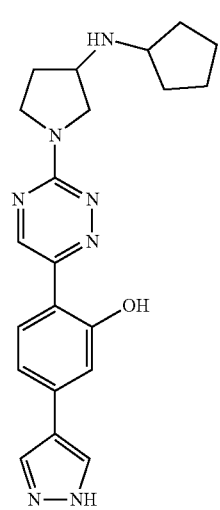
358 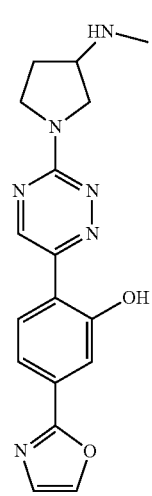
359 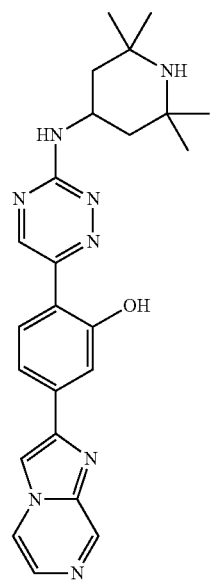
360 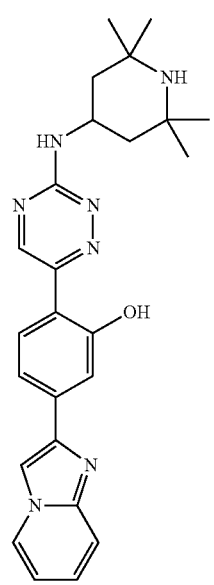
361 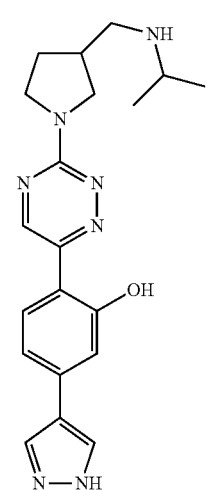

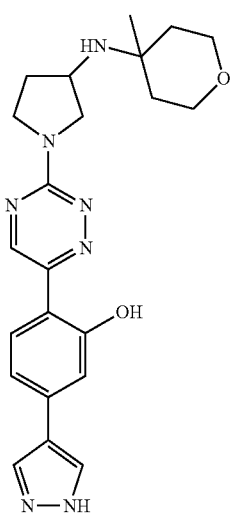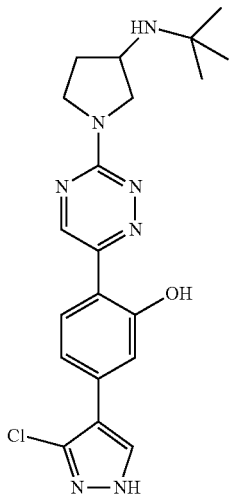

| 149 -continued | | 150 -continued | |
|---|---|---|---|
| 368 | 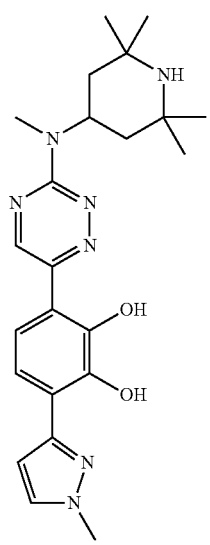 | 371 | 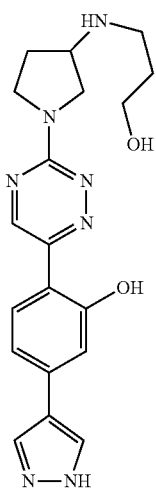 |
| 369 | 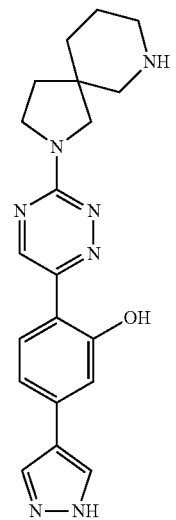 | 372 | 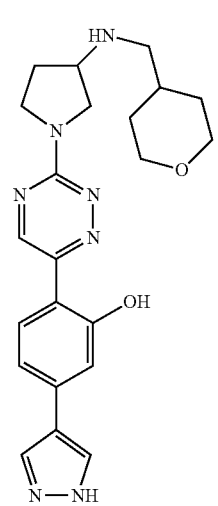 |
| 370 | 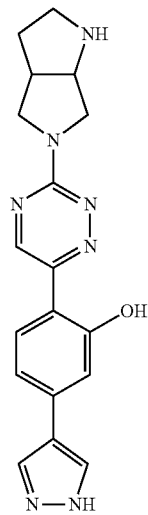 | 373 | 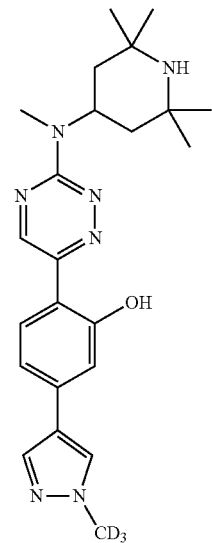 |

374 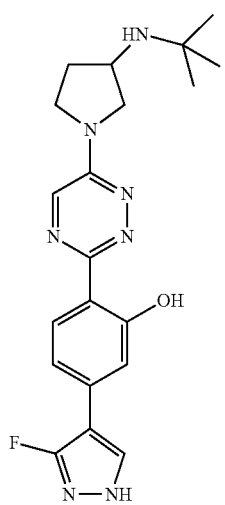
375 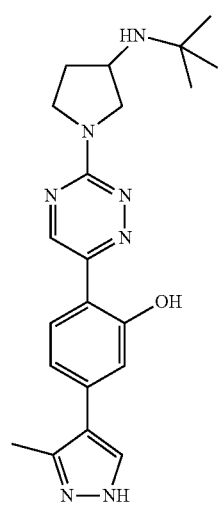
376 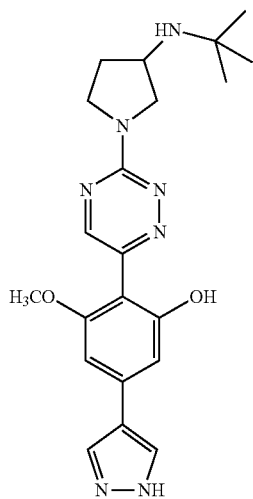
377 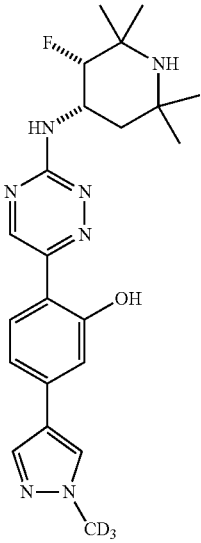
378 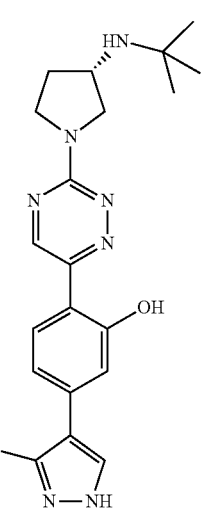
379 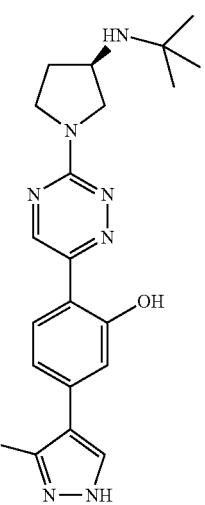

380 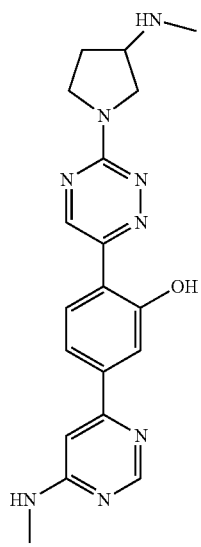
381 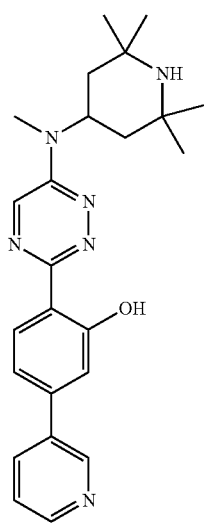
382
383 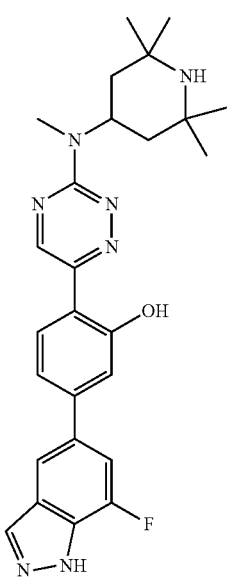
384 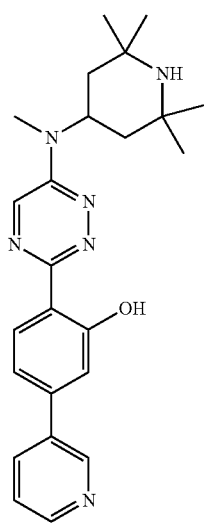
385 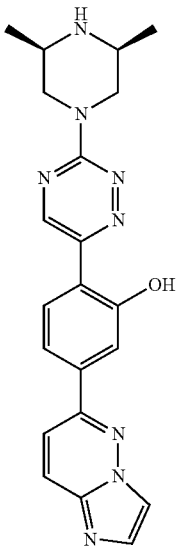

386
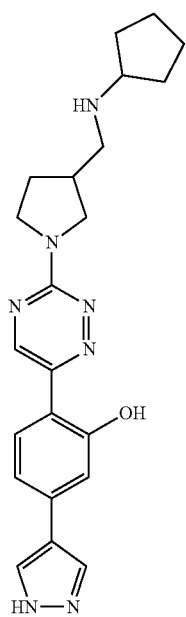
387
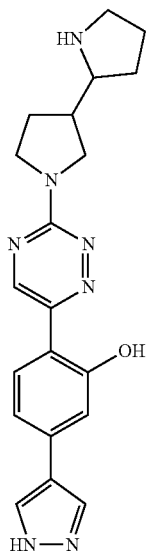
388
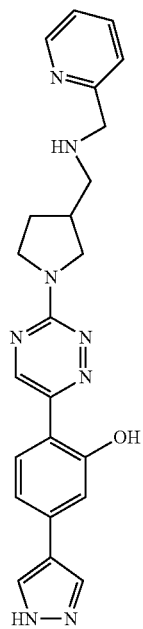
389
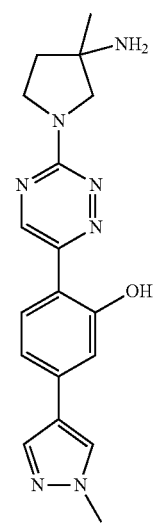

157
-continued
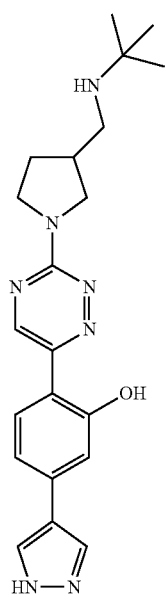
390
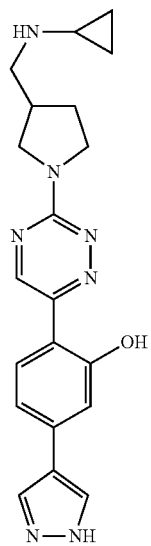
391
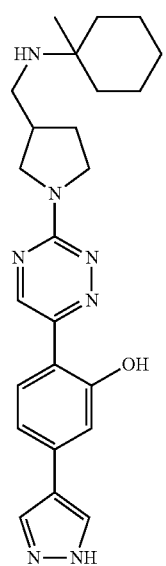
158
-continued
392
393
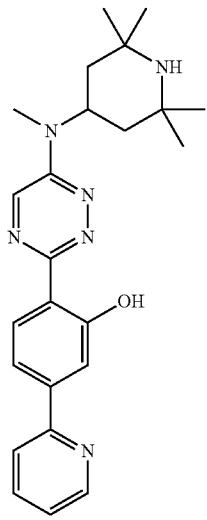
394

159
-continued
395
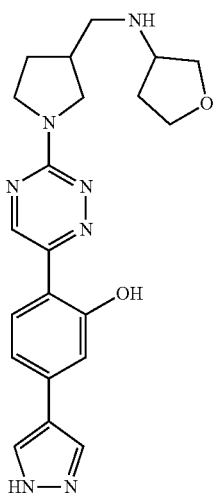
396
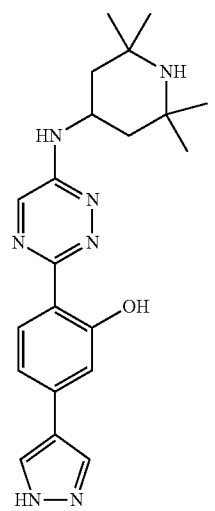
397
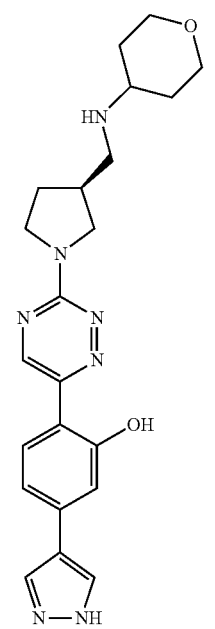
160
-continued
398
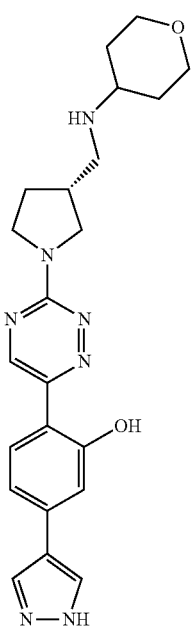
399
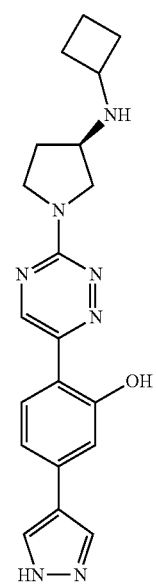

161 -continued
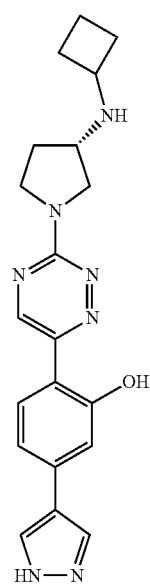
400
162 -continued
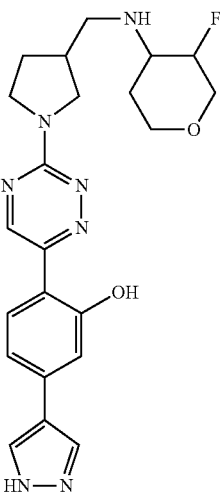
403
401
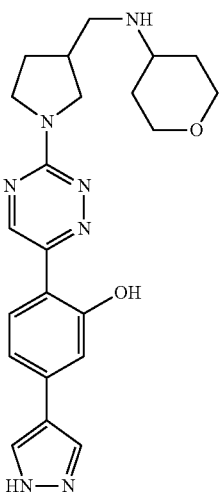
404
402
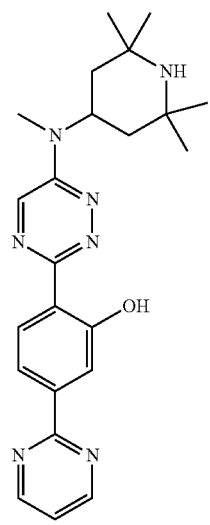
405

406
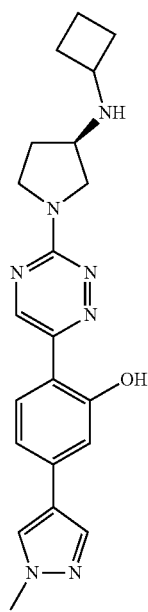
407
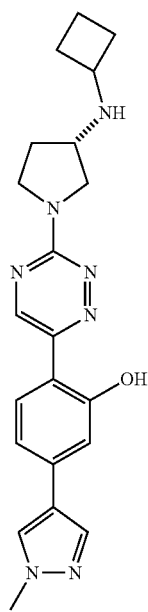
408
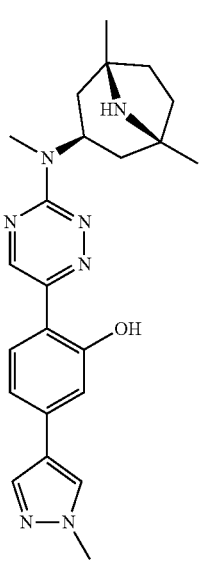
409
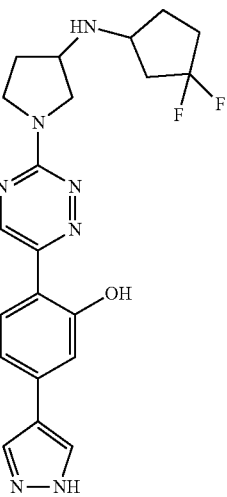
410

-continued
411 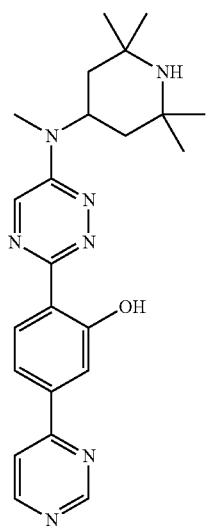
412 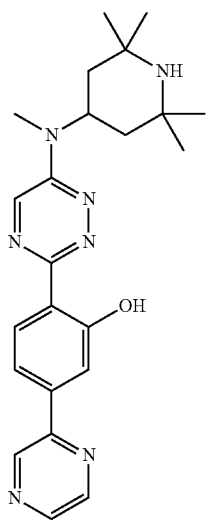
413 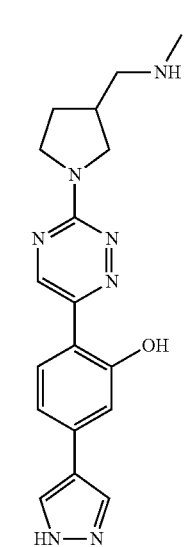
-continued
414 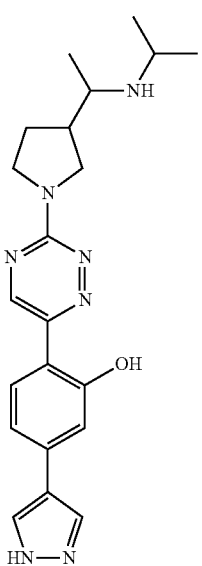
415 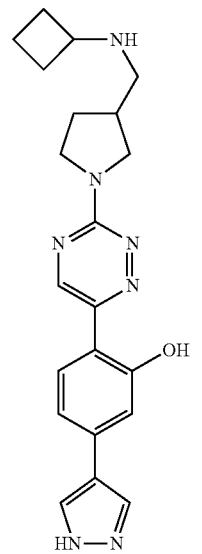

| 417 | 416 |
|---|---|
| 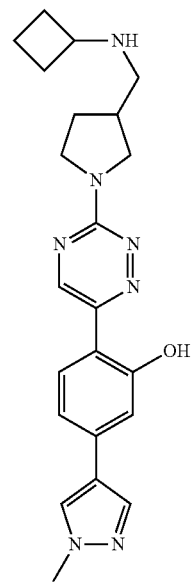 | 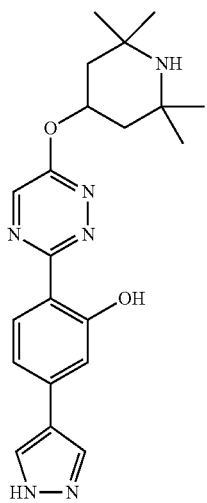 419 |
| 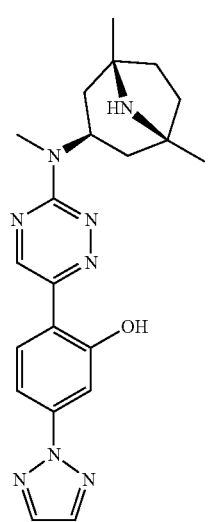 | 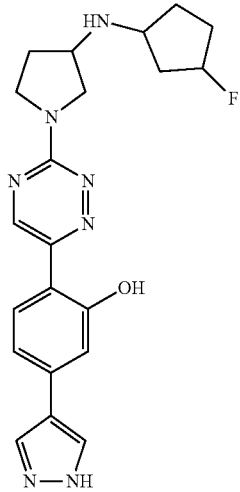 420 |
| 418 | 421 |
| 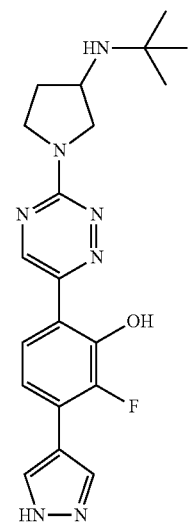 | 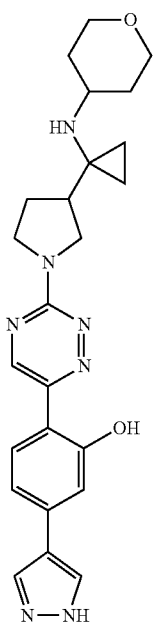 |

422

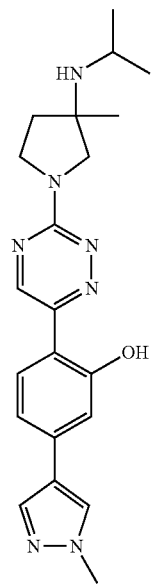

423

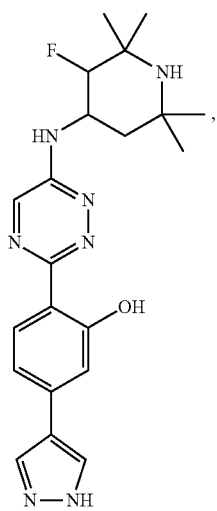

424

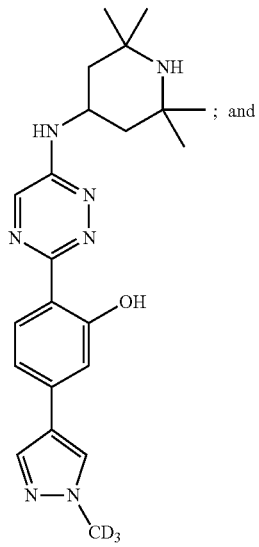

; and

425

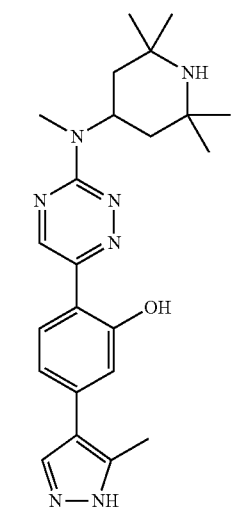

wherein a form of the compound is selected from the group consisting of a salt, hydrate, solvate, racemate, enantiomer, diastereomer, stereoisomer, and tautomer form thereof.

An aspect the compound of Formula (I) or Formula (II) or a form thereof (wherein compound number (#[1]) indicates that the salt form was isolated) includes a compound selected from the group consisting of:

| Cpd | Name |
|---|---|
| 1[1] | 5-(5-methyl-1,3-oxazol-2-yl)-2-{3-[methyl(2,2,6,6-tetramethylpiperidin-4-yl)amino]-1,2,4-triazin-6-yl}phenol |
| 2[1] | 5-(6-methoxypyrimidin-4-yl)-2-{3-[methyl(2,2,6,6-tetramethylpiperidin-4-yl)amino]-1,2,4-triazin-6-yl}phenol |
| 3[1] | 5-(2-methoxypyridin-4-yl)-2-{3-[methyl(2,2,6,6-tetramethylpiperidin-4-yl)amino]-1,2,4-triazin-6-yl}phenol |
| 4 | 2-{3-[methyl(2,2,6,6-tetramethylpiperidin-4-yl)amino]-1,2,4-triazin-6-yl}-5-(1H-1,2,3-triazol-4-yl)phenol |
| 5 | 4-(3-hydroxy-4-{3-[methyl(2,2,6,6-tetramethylpiperidin-4-yl)amino}-1,2,4-triazin-6-yl}phenyl)pyridin-2-ol |
| 6[1] | 5-(3-methyl-1H-pyrazol-4-yl)-2-{3-[methyl(2,2,6,6-tetramethylpiperidin-4-yl)amino]-1,2,4-triazin-6-yl}phenol |
| 7 | 2-{3-[methyl(2,2,6,6-tetramethylpiperidin-4-yl)amino]-1,2,4-triazin-6-yl}-5-(1,3-oxazol-2-yl)phenol |

-continued

| Cpd | Name |
|---|---|
| 8 | 2-{3-[methyl(2,2,6,6-tetramethylpiperidin-4-yl)amino]-1,2,4-triazin-6-yl}-5-(pyridin-4-yl)phenol |
| 9 | 5-(2-methylpyridin-4-yl)-2-{3-[methyl(2,2,6,6-tetramethylpiperidin-4-yl)amino]-1,2,4-triazin-6-yl}phenol |
| 10[1] | 5-(4-methyl-1H-imidazol-1-yl)-2-{3-[methyl(2,2,6,6-tetramethylpiperidin-4-yl)amino]-1,2,4-triazin-6-yl}phenol |
| 11[1] | 5-(1H-pyrazol-4-yl)-2-{3-[(2,2,6,6-tetramethylpiperidin-4-yl)oxy]-1,2,4-triazin-6-yl}phenol |
| 12[1] | 5-(3-fluoro-1H-pyrazol-4-yl)-2-{3-[methyl(2,2,6,6-tetramethylpiperidin-4-yl)amino]-1,2,4-triazin-6-yl}phenol |
| 13[1] | 5-(1H-pyrazol-4-yl)-2-{3-[(2,2,6,6-tetramethylpiperidin-4-yl)amino]-1,2,4-triazin-6-yl}phenol |
| 14[1] | 5-[1-($^2H_3$)methyl-1H-pyrazol-4-yl]-2-{3-[methyl(2,2,6,6-tetramethylpiperidin-4-yl)amino]-1,2,4-triazin-6-yl}phenol |
| 15[1] | 2-{3-[methyl(2,2,6,6-tetramethylpiperidin-4-yl)amino]-1,2,4-triazin-6-yl}-5-(1H-pyrazol-4-yl)phenol |
| 16[1] | 5-(1-methyl-1H-pyrazol-4-yl)-2-{3-[methyl(2,2,6,6-tetramethylpiperidin-4-yl)amino1-1,2,4-triazin-6-yl}phenol |
| 17[1] | 2-{3-[methyl(2,2,6,6-tetramethylpiperidin-4-yl)amino]-1,2,4-triazin-6-yl}-5-(1H-pyrazol-1-yl)phenol |
| 18[1] | 5-(3-fluoro-1-methyl-1H-pyrazol-4-yl)-2-{3-[methyl(2,2,6,6-tetramethylpiperidin-4-yl)amino]-1,2,4-triazin-6-yl}phenol |
| 19[1] | 2-{3-[methyl(piperidin-4-yl)amino]-1,2,4-triazin-6-yl}-5-(1H-pyrazol-4-yl)phenol |
| 20[1] | 2-{3-[methyl(piperidin-3-yl)amino]-1,2,4-triazin-6-yl}-5-(1H-pyrazol-4-yl)phenol |
| 21 | 2-(3-{[(1R,3S,5S)-8-azabicyclo[3.2.1]octan-3-yl](methyl)amino}-1,2,4-triazin-6-yl)-5-(1H-pyrazol-4-yl)phenol |
| 22 | 2-(3-{[(1R,3S,5S)-9-azabicyclo[3.3.1]nonan-3-yl](methyl)amino}-1,2,4-triazin-6-yl)-5-(1H-pyrazol-4-yl)phenol |
| 23[1] | 2-{3-[methyl(2,2,6,6-tetramethylpiperidin-4-yl)amino]-1,2,4-triazin-6-yl}-5-(2-methyl-2H-1,2,3-triazol-4-yl)phenol |
| 24[1] | 2-{6-[methyl(2,2,6,6-tetramethylpiperidin-4-yl)amino]-1,2,4-triazin-3-yl}-5-(1H-pyrazol-4-yl)phenol |
| 25 | (6-(2-hydroxy-4-(1H-pyrazol-4-yl)phenyl)-1,2,4-triazin-3-yl)(2,2,6,6-tetramethylpiperidin-4-yl)methanone |
| 26 | (3-(2-hydroxy-4-(1H-pyrazol-4-yl)phenyl)-1,2,4-triazin-6-yl)(2,2,6,6-tetramethylpiperidin-4-yl)methanone |
| 27 | 2-(6-(2-hydroxy-4-(1H-pyrazol-4-yl)phenyl)-1,2,4-triazin-3-yl)-2-(2,2,6,6-tetramethylpiperidin-4-yl)acetonitrile |
| 28 | 2-(3-(2-hydroxy-4-(1H-pyrazol-4-yl)phenyl)-1,2,4-triazin-6-yl)-2-(2,2,6,6-tetramethylpiperidin-4-yl)acetonitrile |
| 29 | 2-(3-(amino(2,2,6,6-tetramethylpiperidin-4-yl)methyl)-1,2,4-triazin-6-yl)-5-(1H-pyrazol-4-yl)phenol |
| 30 | 2-(6-(amino(2,2,6,6-tetramethylpiperidin-4-yl)methyl)-1,2,4-triazin-3-yl)-5-(1H-pyrazol-4-yl)phenol |
| 31 | 2-(3-(methyl(2,2,6,6-tetramethylpiperidin-4-yl)amino)-1,2,4-triazin-6-yl)-5-(1,3,5-triazin-2-yl)phenol |
| 32 | 2-(6-(methyl(2,2,6,6-tetramethylpiperidin-4-yl)amino)-1,2,4-triazin-3-yl)-5-(1,3,5-triazin-2-yl)phenol |
| 33[1] | 4-(3-hydroxy-4-{3-[methyl(2,2,6,6-tetramethylpiperidin-4-yl)amino]-1,2,4-triazin-6-yl}phenyl)-1,3,5-triazin-2-ol |
| 34 | 4-(3-hydroxy-4-(6-(methyl(2,2,6,6-tetramethylpiperidin-4-yl)amino)-1,2,4-triazin-3-yl)phenyl)-1,3,5-triazin-2-ol |
| 35 | 5-(4-amino-1,3,5-triazin-2-yl)-2-(3-(methyl(2,2,6,6-tetramethylpiperidin-4-yl)amino)-1,2,4-triazin-6-yl)phenol |
| 36 | 5-(4-amino-1,3,5-triazin-2-yl)-2-(6-(methyl(2,2,6,6-tetramethylpiperidin-4-yl)amino)-1,2,4-triazin-3-yl)phenol |
| 37 | 5-(4-chloro-1,3,5-triazin-2-yl)2-(3-(methyl(2,2,6,6-tetramethylpiperidin-4-yl)amino)-1,2,4-triazin-6-yl)phenol |
| 38 | 5-(4-chloro-1,3,5-triazin-2-yl)-2-(6-(methyl(2,2,6,6-tetramethylpiperidin-4-yl)amino)-1,2,4-triazin-3-yl)phenol |
| 39 | 2-(6-(methyl(2,2,6,6-tetramethylpiperidin-4-yl)amino)-1,2,4-triazin-3-yl)-5-(5-methyl-1H-pyrazol-4-yl)phenol |
| 40 | 5-(5-chloro-1H-pyrazol-4-yl)-2-(3-(methyl(2,2,6,6-tetramethylpiperidin-4-yl)amino)-1,2,4-triazin-6-yl)phenol |
| 41 | 5-(5-chloro-1H-pyrazol-4-yl)-2-(6-(methyl(2,2,6,6-tetramethylpiperidin-4-yl)amino)-1,2,4-triazin-3-yl)phenol |
| 42 | 4-(3-hydroxy-4-(3-(methyl(2,2,6,6-tetramethylpiperidin-4-yl)amino)-1,2,4-triazin-6-yl)phenyl)-1H-pyrazole-5-carbonitrile |
| 43 | 4-(3-hydroxy-4-(6-(methyl(2,2,6,6-tetramethylpiperidin-4-yl)amino)-1,2,4-triazin-3-yl)phenyl)-1H-pyrazole-5-carbonitrile |
| 44 | 5-(1,5-dimethyl-1H-pyrazol-4-yl)-2-(3-(methyl(2,2,6,6-tetramethylpiperidin-4-yl)amino)-1,2,4-triazin-6-yl)phenol |
| 45 | 5-(1,5-dimethyl-1H-pyrazol-4-yl)-2-(6-(methyl(2,2,6,6-tetramethylpiperidin-4-yl)amino)-1,2,4-triazin-3-yl)phenol |
| 46 | 5-(5-chloro-1-methyl-1H-pyrazol-4-yl)-2-(3-(methyl(2,2,6,6-tetramethylpiperidin-4-yl)amino)-1,2,4-triazin-6-yl)phenol |

| Cpd | Name |
|---|---|
| 47 | 5-(5-chloro-l-methyl-1H-pyrazol-4-yl)-2-(6-(methyl(2,2,6,6-tetramethylpiperidin-4-yl)amino)-1,2,4-triazin-3-yl)phenol |
| 48 | 4-(3-hydroxy-4-(3-(methyl(2,2,6,6-tetramethylpiperidin-4-yl)amino)-1,2,4-triazin-6-yl)phenyl)-1-methyl-1H-pyrazole-5-carbonitrile |
| 49 | 4-(3-hydroxy-4-(6-(methyl(2,2,6,6-tetramethylpiperidin-4-yl)amino)-1,2,4-triazin-3-yl)phenyl)-1-methyl-1H-pyrazole-5-carbonitrile |
| 50[1] | 5-(4-fluoro-1H-imidazol-1-yl)-2-{3-[methyl(2,2,6,6-tetramethylpiperidin-4-yl)amino]-1,2,4-triazin-6-yl}phenol |
| 51[1] | 2-{3-[methyl(2,2,6,6-tetramethylpiperidin-4-yl)amino]-1,2,4-triazin-6-yl}-5-(3-methyl-1H-1,2,4-triazol-1-yl)phenol |
| 52[1] | 2-{3-[(1-methylpiperidin-4-yl)amino]-1,2,4-triazin-6-yl}-5-(1H-pyrazol-4-yl)phenol |
| 53 | 2-{3-[methyl(2,2,6,6-tetramethylpiperidin-4-yl)amino]-1,2,4-triazin-6-yl}-5-(thiophen-2-yl)phenol |
| 54 | 2-{3-[methyl(2,2,6,6-tetramethylpiperidin-4-yl)amino]-1,2,4-triazin-6-yl}-5-(4-methylthiophen-2-yl)phenol |
| 55[1] | 5-(4-methoxy-1H-pyrazol-1-yl)-2-{3-[methyl(2,2,6,6-tetramethylpiperidin-4-yl)amino]-1,2,4-triazin-6-yl}phenol |
| 56 | 4-(3-hydroxy-4-{3-[methyl(2,2,6,6-tetramethylpiperidin-4-yl)amino1-1,2,4-triazin-6-yl}phenyl)-1-methylpyridin-2(1H)-one |
| 57[1] | 5-(3-chloro-1H-pyrazol-4-yl)-2-{3-[methyl(2,2,6,6-tetramethylpiperidin-4-yl)amino]-1,2,4-triazin-6-yl}phenol |
| 58[1] | 2-{3-[methyl(2,2,6,6-tetramethylpiperidin-4-yl)amino]-1,2,4-triazin-6-yl}-5-(1,3-thiazol-2-yl)phenol |
| 59[1] | 5-(4-chloro-1H-imidazol-1-yl)-2-{3-[methyl(2,2,6,6-tetramethylpiperidin-4-yl)amino]-1,2,4-triazin-6-yl}phenol |
| 60[1] | 2-{3-[methyl(2,2,6,6-tetramethylpiperidin-4-yl)amino]-1,2,4-triazin-6-yl}-5-(pyridazin-4-yl)phenol |
| 61[1] | 5-(6-methylpyridazin-4-yl)-2-{3-[methyl(2,2,6,6-tetramethylpiperidin-4-yl)amino]-1,2,4-triazin-6-yl}phenol |
| 62[1] | 2-{3-[methyl(2,2,6,6-tetramethylpiperidin-4-yl)amino]-1,2,4-triazin-6-yl}-5-(1-methyl-1H-1,2,4-triazol-3-yl)phenol |
| 63[1] | 2-{3-[methyl(2,2,6,6-tetramethylpiperidin-4-yl)amino]-1,2,4-triazin-6-yl}-5-(2H-1,2,3-triazol-2-yl)phenol |
| 64 | 2-{3-[methyl(2,2,6,6-tetramethylpiperidin-4-yl)amino]-1,2,4-triazin-6-yl}-5-(2-methyl-1,3-thiazol-5-yl)phenol |
| 65[1] | 2-{3-[methyl(2,2,6,6-tetramethylpiperidin-4-yl)amino]-1,2,4-triazin-6-yl}-5-(1,2,4-thiadiazol-5-yl)phenol |
| 66[1] | 2-{3-[methyl(2,2,6,6-tetramethylpiperidin-4-yl)amino]-1,2,4-triazin-6-yl}-5-(3-methyl-1,2,4-thiadiazol-5-yl)phenol |
| 67[1] | 2-{3-[(3-fluoro-2,6,6-tetramethylpiperidin-4-yl)(methyl)amino]-1,2,4-triazin-6-yl}-5-(1H-pyrazol-4-yl)phenol |
| 68[1] | 1-[1-(3-hydroxy-4-{3-[methyl(2,2,6,6-tetramethylpiperidin-4-yl)amino]-1,2,4-triazin-6-yl}phenyl)-1H-pyrazol-4-yl]ethan-l-one |
| 69[1] | 2-{3-[methyl(2,2,6,6-tetramethylpiperidin-4-yl)amino]-1,2,4-triazin-6-yl}-5-(4-methyl-2H-1,2,3-triazol-2-yl)phenol |
| 70 | 2-{3-[methyl(2,2,6,6-tetramethylpiperidin-4-yl)amino]-1,2,4-triazin-6-yl}-5-(pyridin-3-yl)phenol |
| 71[1] | 2-{3-[methyl(2,2,6,6-tetramethylpiperidin-4-yl)amino]-1,2,4-triazin-6-yl}-5-(pyridin-2-yl)phenol |
| 72[1] | 5-(3-fluoro-1H-pyrazol-4-yl)-2-{3-[(2,2,6,6-tetramethylpiperidin-4-yl)oxy]-1,2,4-triazin-6-yl}phenol |
| 73[1] | 5-(3-fluoro-1H-pyrazol-4-yl)-2-{3-[(2,2,6,6-tetramethylpiperidin-4-yl)amino]-1,2,4-triazin-6-yl}phenol |
| 74[1] | 5-(2-methyl-1,3-oxazol-5-yl)-2-{3-[methyl(2,2,6,6-tetramethylpiperidin-4-yl)amino]-1,2,4-triazin-6-yl}phenol |
| 75[1] | 5-(1-methyl-1H-imidazol-4-yl)-2-{3-[methyl(2,2,6,6-tetramethylpiperidin-4-yl)amino]-1,2,4-triazin-6-yl}phenol |
| 76[1] | 5-(1-methyl-1H-pyrazol-3-yl)-2-{3-[methyl(2,2,6,6-tetramethylpiperidin-4-yl)amino]-1,2,4-triazin-6-yl}phenol |
| 77[1] | 2-{3-{[(1R,3s,5S)-9-methyl-9-azabicyclo[3.3.1]nonan-3-yl]amino}-1,2,4-triazin-6-yl)-5-(1H-pyrazol-4-yl)phenol |
| 78 | 2-{3-{[1R,3r,5S)-8-azabicyclo[3.2.1]octan-3-yl]amino}-1,2,4-triazin-6-yl)-5-(1H-pyrazol-4-yl)phenol |
| 79[1] | 2-{3-[methyl(2,2,6,6-tetramethylpiperidin-4-yl)amino]-1,2,4-triazin-6-yl}-5-(1H-1,2,4-triazol-1-yl)phenol |
| 80[1] | 5-(imidazo[1,2-a]pyrazin-6-yl)-2-{3-[methyl(2,2,6,6-tetramethylpiperidin-4-yl)amino]-1,2,4-triazin-6-yl}phenol |
| 81[1] | 5-(5-methyl-1,3,4-oxadiazol-2-yl)-2-{3-[methyl(2,2,6,6-tetramethylpiperidin-4-yl)amino]-1,2,4-triazin-6-yl}phenol |
| 82[1] | 2-{3-[(2,6-dimethylpiperidin-4-yl)oxy]-1,2,4-triazin-6-yl}-5-(1H-pyrazol-4-yl)phenol |
| 83 | 2-{3-[methyl(2,2,6,6-tetramethylpiperidin-4-yl)amino]-1,2,4-triazin-6-yl}-5-(pyrazin-2-yl)phenol |
| 84[1] | 2-{3-[methyl(2,2,6,6-tetramethylpiperidin-4-yl)amino]-1,2,4-triazin-6-yl}-5-(pyridazin-3-yl)phenol |
| 85 | 2-{3-[methyl(2,2,6,6-tetramethylpiperidin-4-yl)amino]-1,2,4-triazin-6-yl}-5-(pyrimidin-2-yl)phenol |

-continued

| Cpd | Name |
|---|---|
| 86[1] | 2-{3-[methyl(2,2,6,6-tetramethylpiperidin-4-yl)amino]-1,2,4-triazin-6-yl}-5-(pyrimidin-5-yl)phenol |
| 87 | 2-(3-{methyl[(1R,3s,5S)-9-methyl-9-azabicyclo[3.3.1]nonan-3-yl]amino}-1,2,4-triazin-6-yl)-5-(1H-pyrazol-4-yl)phenol |
| 88[1] | 5-(4-methoxy-1,3,5-triazin-2-yl)-2-{3-[methyl(2,2,6,6-tetramethylpiperidin-4-yl)amino]-1,2,4-triazin-6-yl}phenol |
| 89[1] | 5-(1H-imidazol-1-yl)-2-{3-[methyl(2,2,6,6-tetramethylpiperidin-4-yl)amino]-1,2,4-triazin-6-yl}phenol |
| 90[1] | 1-(3-hydroxy-4-{3-[methyl(2,2,6,6-tetramethylpiperidin-4-yl)amino]-1,2,4-triazin-6-yl}phenyl)-1H-pyrazol-4-ol |
| 91[1] | 2-{3-[methyl(2,2,6,6-tetramethylpiperidin-4-yl)amino]-1,2,4-triazin-6-yl}-5-(1,3-oxazol-5-yl)phenol |
| 92[1] | 5-(imidazo[1,2-b]pyridazin-6-yl)-2-{3-[methyl(2,2,6,6-tetramethylpiperidin-4-yl)amino]-1,2,4-triazin-6-yl}phenol |
| 93[1] | 5-(4-fluoro-1H-pyrazol-1-yl)-2-{3-[methyl(2,2,6,6-tetramethylpiperidin-4-yl)amino]-1,2,4-triazin-6-yl}phenol |
| 94[1] | 5-(4-methyl-1H-pyrazol-1-yl)-2-{3-[methyl(2,2,6,6-tetramethylpiperidin-4-yl)amino]-1,2,4-triazin-6-yl}phenol |
| 95[1] | 2-[3-(2,7-diazaspiro[3.5]nonan-7-yl)-1,2,4-triazin-6-yl]-5-(1H-pyrazol-4-yl)phenol |
| 96[1] | 2-[3-(2,7-diazaspiro[3.5]nonan-2-yl)-1,2,4-triazin-6-yl]-5-(1H-pyrazol-4-yl)phenol |
| 97[1] | 5-(1H-indazol-5-yl)-2-{3-[methyl(2,2,6,6-tetramethylpiperidin-4-yl)amino]-1,2,4-triazin-6-yl}phenol |
| 98 | 5-(4-fluoropyridin-2-yl)-2-{3-[methyl(2,2,6,6-tetramethylpiperidin-4-yl)amino]-1,2,4-triazin-6-yl}phenol |
| 99[1] | 2-{3-[methyl(2,2,6,6-tetramethylpiperidin-4-yl)amino]-1,2,4-triazin-6-yl}-5-(4-nitro-2H-1,2,3-triazol-2-yl)phenol |
| 100 | 2-[3-(6-amino-3-azabicyclo[3.1.0]hexan-3-yl)-1,2,4-triazin-6-yl]-5-(1H-pyrazol-4-yl)phenol |
| 101[1] | 5-(1-cyclopropyl-1H-pyrazol-4-yl)-2-{3-[methyl(2,2,6,6-tetramethylpiperidin-4-yl)amino]-1,2,4-triazin-6-yl}phenol |
| 102[1] | 2-{3-[methyl(2,2,6,6-tetramethylpiperidin-4-yl)amino]-1,2,4-triazin-6-yl}-5-(pyrimidin-4-yl)phenol |
| 103[1] | 4-{3-[methyl(2,2,6,6-tetramethylpiperidin-4-yl)amino]-1,2,4-triazin-6-yl}[1,1'-biphenyl]-3,4'-diol |
| 104 | 5-(3-hydroxy-4-{3-[methyl(2,2,6,6-tetramethylpiperidin-4-yl)amino]-1,2,4-triazin-6-yl}phenyl)pyridin-2(1H)-one |
| 105[1] | 6-{3-[methyl(2,2,6,6-tetramethylpiperidin-4-yl)amino]-1,2,4-triazin-6-yl}quinolin-7-ol |
| 106 | 2-{3-[methyl(2,2,6,6-tetramethylpiperidin-4-yl)amino]-1,2,4-triazin-6-yl}-5-(1,3,4-oxadiazol-2-yl)phenol |
| 107[1] | 5-(1H-pyrazol-3-yl)-2-{3-[(2,2,6,6-tetramethylpiperidin-4-yl)oxy]-1,2,4-triazin-6-yl}phenol |
| 108[1] | 5-(1-methyl-1H-pyrazol-3-yl)-2-{3-[(2,2,6,6-tetramethylpiperidin-4-yl)oxy]-1,2,4-triazin-6-yl}phenol |
| 109[1] | 2-[3-(2,6-diazaspiro[3.5]nonan-2-yl)-1,2,4-triazin-6-yl]-5-(1H-pyrazol-4-yl)phenol |
| 110[1] | 2-[3-(2,6-diazaspiro[3.4]octan-6-yl)-1,2,4-triazin-6-yl]-5-(1H-pyrazol-4-yl)phenol |
| 111[1] | 2-{3-[methyl(2,2,6,6-tetramethylpiperidin-4-yl)amino]-1,2,4-triazin-6-yl}-5-(1H-pyrazol-3-yl)phenol |
| 112[1] | 5-(5-fluoropyrimidin-2-yl)-2-{3-[methyl(2,2,6,6-tetramethylpiperidin-4-yl)amino]-1,2,4-triazin-6-yl}phenol |
| 113[1] | 2-[3-(1-methyl-1,7-diazaspiro[3.5]nonan-7-yl)-1,2,4-triazin-6-yl]-5-(1H-pyrazol-4-yl)phenol |
| 114[1] | 2-{3-[(3S)-3-(methylamino)pyrrolidin-1-yl]-1,2,4-triazin-6-yl}-5-(1H-pyrazol-4-yl)phenol |
| 115[1] | 2-{3-[(7S)-7-amino-5-azaspiro[2.4]heptan-5-yl]-1,2,4-triazin-6-yl}-5-(1H-pyrazol-4-yl)phenol |
| 116[1] | 2-{3-[(8aS)-hexahydropyrrolo[1,2-a]pyrazin-2(1H)-yl]-1,2,4-triazin-6-yl}-5-(1H-pyrazol-4-yl)phenol |
| 117[1] | 2-{3-[(3aR,6aR)-1-methylhexahydropyrrolo[3,4-b]pyrrol-5(1H)-yl]-1,2,4-triazin-6-yl}-5-(1H-pyrazol-4-yl)phenol |
| 118[1] | 2-[3-(2,6-diazaspiro[3.3]heptan-2-yl)-1,2,4-triazin-6-yl]-5-(1H-pyrazol-4-yl)phenol |
| 119[1] | 2-{3-[methyl(2,2,6,6-tetramethylpiperidin-4-yl)amino]-1,2,4-triazin-6-yl}-5-(5-methyl-2H-tetrazol-2-yl)phenol |
| 120[1] | 2-{3-[(2R,4s,6S)-2,6-diethylpiperidin-4-yl]oxy]-1,2,4-triazin-6-yl)-5-(1H-pyrazol-4-yl)phenol |
| 121[1] | 2-{3-[(2,2,6,6-tetramethylpiperidin-4-yl)amino]-1,2,4-triazin-6-yl}-5-(2H-1,2,3-triazol-2-yl)phenol |
| 122[1] | 2-{3-[(2,2,6,6-tetramethylpiperidin-4-yl)oxy]-1,2,4-triazin-6-yl}-5-(2H-1,2,3-triazol-2-yl)phenol |
| 123[1] | 5-(6-chloropyridazin-3-yl)-2-{3-[methyl(2,2,6,6-tetramethylpiperidin-4-yl)amino]-1,2,4-triazin-6-yl}phenol |
| 124[1] | 5-(1-methyl-1H-pyrazol-5-yl)-2-{3-[methyl(2,2,6,6-tetramethylpiperidin-4-yl)amino]-1,2,4-triazin-6-yl}phenol |
| 125 | 4-fluoro-2-{3-[methyl(2,2,6,6-tetramethylpiperidin-4-yl)amino]-1,2,4-triazin-6-yl}-5-(1H-pyrazol-5-yl)phenol |
| 126[1] | 2-{3-[(3-fluoro-2,2,6,6-tetramethylpiperidin-4-yl)amino]-1,2,4-triazin-6-yl}-5-(1H-pyrazol-4-yl)phenol |

| Cpd | Name |
|---|---|
| 127[1] | 2-{3-[6-(diethylamino)-3-azabicyclo[3.1.0]hexan-3-yl]-1,2,4-triazin-6-yl}-5-(1H-pyrazol-4-yl)phenol |
| 128[1] | 5-(5-methylpyrimidin-2-yl)-2-{3-[methyl(2,2,6,6-tetramethylpiperidin-4-yl)amino]-1,2,4-triazin-6-yl}phenol |
| 129[1] | 5-(4-methylpyrimidin-2-yl)-2-{3-[methyl(2,2,6,6-tetramethylpiperidin-4-yl)amino]-1,2,4-triazin-6-yl}phenol |
| 130[1] | 5-(2-chloropyrimidin-4-yl)-2-{3-[methyl(2,2,6,6-tetramethylpiperidin-4-yl)amino]-1,2,4-triazin-6-yl}phenol |
| 131 | 5-(1H-benzimidazol-5-yl)-2-{3-[methyl(2,2,6,6-tetramethylpiperidin-4-yl)amino]-1,2,4-triazin-6-yl}phenol |
| 132[1] | 2-{3-[methyl(2,2,6,6-tetramethylpiperidin-4-yl)amino]-1,2,4-triazin-6-yl}-5-(1H-pyrazolo[3,4-b]pyridin-5-yl)phenol |
| 133[1] | 5-(3-chloro-1H-1,2,4-triazol-1-yl)-2-{3-[methyl(2,2,6,6-tetramethylpiperidin-4-yl)amino]-1,2,4-triazin-6-yl}phenol |
| 134[1] | 6-(3-hydroxy-4-{3-[methyl(2,2,6,6-tetramethylpiperidin-4-yl)amino]-1,2,4-triazin-6-yl}phenyl)pyridazin-3-ol |
| 135 | 1-(3-hydroxy-4-{3-[methyl(2,2,6,6-tetramethylpiperidin-4-yl)amino]-1,2,4-triazin-6-yl}phenyl)-1H-pyrazole-4-carbonitrile |
| 136 | 2-{3-[methyl(2,2,6,6-tetramethylpiperidin-4-yl)amino]-1,2,4-triazin-6-yl}-5-(1H-pyrazolo[4,3-b]pyridin-5-yl)phenol |
| 137 | 2-{3-[3-(cyclopropylamino)pyrrolidin-1-yl]-1,2,4-triazin-6-yl}-5-(1H-pyrazol-4-yl)phenol |
| 138 | 2-{3-[3-(tert-butylamino)pyrrolidin-1-yl]-1,2,4-triazin-6-yl}-5-(1H-pyrazol-4-yl)phenol |
| 139 | 1-(3-hydroxy-4-{3-[methyl(2,2,6,6-tetramethylpiperidin-4-yl)amino]-1,2,4-triazin-6-yl}phenyl)-1H-imidazole-4-carbonitrile |
| 140[1] | 1-[1-(3-hydroxy-4-{3-[methyl(2,2,6,6-tetramethylpiperidin-4-yl)amino]-1,2,4-triazin-6-yl}phenyl)-1H-imidazol-4-yl]ethan-1-one |
| 141[1] | 5-(2,8-dimethylimidazo[1,2-b]pyridazin-6-yl)-2-{3-[methyl(2,2,6,6-tetramethylpiperidin-4-yl)amino]-1,2,4-triazin-6-yl}phenol |
| 142[1] | 5-(2-methylimidazo[1,2-b]pyridazin-6-yl)-2-{3-[methyl(2,2,6,6-tetramethylpiperidin-4-yl)amino]-1,2,4-triazin-6-yl}phenol |
| 143[1] | 2-{3-[methyl(2,2,6,6-tetramethylpiperidin-4-yl)amino]-1,2,4-triazin-6-yl}-5-(2-methyl-2H-tetrazol-5-yl)phenol |
| 144 | 5-(6-methoxy-1,2,4-triazin-3-yl)-2-{3-[methyl(2,2,6,6-tetramethylpiperidin-4-yl)amino]-1,2,4-triazin-6-yl}phenol |
| 145 | 5-(1,3-benzoxazol-6-yl)-2-{3-[methyl(2,2,6,6-tetramethylpiperidin-4-yl)amino]-1,2,4-triazin-6-yl}phenol |
| 146[1] | 6-(3-hydroxy-4-{3-[methyl(2,2,6,6-tetramethylpiperidin-4-yl)amino]-1,2,4-triazin-6-yl}phenyl)-3-methylpyrimidin-4(3H)-one |
| 147[1] | 5-(3-hydroxy-4-{3-[methyl(2,2,6,6-tetramethylpiperidin-4-yl)amino]-1,2,4-triazin-6-yl}phenyl)-2-methylpyridazin-3(2H)-one |
| 148[1] | 2-(3-{3-[(propan-2-yl)amino]pyrrolidin-1-yl}-1,2,4-triazin-6-yl)-5-(1H-pyrazol-4-yl)phenol |
| 149 | 5-(3-fluoro-1H-pyrazol-4-yl)-2-[3-(7-methyl-2,7-diazaspiro[3.5]nonan-2-yl)-1,2,4-triazin-6-yl]phenol |
| 150 | 5-(3-fluoro-1H-pyrazol-4-yl)-2-{3-[(3aS,7aR)-octahydro-5H-pyrrolo[3,2-c]pyridin-5-yl]-1,2,4-triazin-6-yl}phenol |
| 151[1] | 2-[3-(2,7-diazaspiro[3.5]nonan-2-yl)-1,2,4-triazin-6-yl]-5-(3-fluoro-1H-pyrazol-4-yl)phenol |
| 152[1] | 2-{3-[methyl(2,2,6,6-tetramethylpiperidin-4-yl)amino]-1,2,4-triazin-6-yl}-5-([1,2,3]triazolo[1,5-a]pyridin-5-yl)phenol |
| 153[1] | 5-(3-fluoro-1H-pyrazol-4-yl)-2-{3-[(3aS,7aR)-1-methyloctahydro-5H-pyrrolo[3,2-c]pyridin-5-yl]-1,2,4-triazin-6-yl}phenol |
| 154 | 2-(3-{3-[(2-methylbutan-2-yl)amino]pyrrolidin-1-yl}-1,2,4-triazin-6-yl)-5-(1H-pyrazol-4-yl)phenol |
| 155[1] | 2-{3-[methyl(2,2,6,6-tetramethylpiperidin-4-yl)amino]-1,2,4-triazin-6-yl}-5-(tetrazolo[1,5-a]pyridin-7-yl)phenol |
| 156[1] | 5-(4-fluoro-1H-pyrazol-3-yl)-2-{3-[methyl(2,2,6,6-tetramethylpiperidin-4-yl)amino]-1,2,4-triazin-6-yl}phenol |
| 157[1] | 2-(3-{3-[(adamantan-1-yl)amino]pyrrolidin-1-yl}-1,2,4-triazin-6-yl)-5-(1H-pyrazol-4-yl)phenol |
| 158[1] | 2-{3-[methyl(2,2,6,6-tetramethylpiperidin-4-yl)amino]-1,2,4-triazin-6-yl}-5-(5H-pyrrolo[2,3-b]pyrazin-2-yl)phenol |
| 159[1] | 2-(3-{3-[(adamantan-2-yl)amino]pyrrolidin-1-yl}-1,2,4-triazin-6-yl)-5-(1H-pyrazol-4-yl)phenol |
| 160[1] | 2-(3-{3-[(3,5-dimethyladamantan-1-yl)amino]pyrrolidin-1-yl}-1,2,4-triazin-6-yl)-5-(1H-pyrazol-4-yl)phenol |
| 161[1] | 5-[4-(hydroxymethyl)-1H-pyrazol-1-yl]-2-{3-[methyl(2,2,6,6-tetramethylpiperidin-4-yl)amino]-1,2,4-triazin-6-yl}phenol |
| 162[1] | 2-{3-[(3aR,4R,6aS)-4-(dimethylamino)hexahydrocyclopenta[c]pyrrol-2(1H)-yl]-1,2,4-triazin-6-yl}-5-(1H-pyrazol-4-yl)phenol |
| 163 | 5-(3-methyl-3H-imidazo[4,5-b]pyridin-5-yl)-2-{3-[methyl(2,2,6,6-tetramethylpiperidin-4-yl)amino]-1,2,4-triazin-6-yl}phenol |
| 164[1] | 5-(1-methyl-1H-imidazo[4,5-b]pyridin-5-yl)-2-{3-[methyl(2,2,6,6-tetramethylpiperidin-4-yl)amino]-1,2,4-triazin-6-yl}phenol |

| Cpd | Name |
|---|---|
| 165[1] | 2-{3-[(3aR,4S,6aS)-4-aminohexahydrocyclopenta[c]pyrrol-2(1H)-yl]-1,2,4-triazin-6-yl}-5-(1H-pyrazol-4-yl)phenol |
| 166[1] | 2-[3-(5-methyloctahydro-2H-pyrrolo[3,4-c]pyridin-2-yl)-1,2,4-triazin-6-yl]-5-(1H-pyrazol-4-yl)phenol |
| 167[1] | 2-{3-[(3aR,4S,6aS)-4-(dimethylamino)hexahydrocyclopenta[c]pyrrol-2(1H)-yl]-1,2,4-triazin-6-yl}-5-(1H-pyrazol-4-yl)phenol |
| 168[1] | 3-amino-6-(3-hydroxy-4-{3-[methyl(2,2,6,6-tetramethylpiperidin-4-yl)amino]-1,2,4-triazin-6-yl}phenyl)-4-methylpyridin-2-ol |
| 169[1] | 5-(2,7-dimethyl[1,3]oxazolo[5,4-b]pyridin-5-yl)-2-{3-[methyl(2,2,6,6-tetramethylpiperidin-4-yl)amino]-1,2,4-triazin-6-yl}phenol |
| 170 | 2-(3-{3-[(3-methylpentan-3-yl)amino]pyrrolidin-1-yl}-1,2,4-triazin-6-yl)-5-(1H-pyrazol-4-yl)phenol |
| 171 | 2-{3-[4-(tert-butylamino)-2-methylpyrrolidin-1-yl]-1,2,4-triazin-6-yl}-5-(1H-pyrazol-4-yl)phenol |
| 172[1] | 5-[4-(hydroxymethyl)-2H-1,2,3-triazol-2-yl]-2-{3-[methyl(2,2,6,6-tetramethylpiperidin-4-yl)amino]-1,2,4-triazin-6-yl}phenol |
| 173[1] | 2-{3-[methyl(2,2,6,6-tetramethylpiperidin-4-yl)amino]-1,2,4-triazin-6-yl}-543-methyl-3H-[1,2,3]triazolo[4,5-b]pyridin-5-yl)phenol |
| 174[1] | 2-{3-[3-(tert-butylamino)pyrrolidin-1-yl]-1,2,4-triazin-6-yl}-5-(3-fluoro-1H-pyrazol-4-yl)phenol |
| 175[1] | 2-{3-[3-(tert-butylamino)pyrrolidin-1-yl]-1,2,4-triazin-6-yl}-5-(1-methyl-1H-pyrazol-3-yl)phenol |
| 176[1] | 5-(1-methyl-1H-pyrazolo[3,4-b]pyridin-5-yl)-2-{3-[methyl(2,2,6,6-tetramethylpiperidin-4-yl)amino]-1,2,4-triazin-6-yl}phenol |
| 177[1] | 5-(1-methyl-1H-indazol-5-yl)-2-{3-[methyl(2,2,6,6-tetramethylpiperidin-4-yl)amino]-1,2,4-triazin-6-yl}phenol |
| 178[1] | 2-{3-[methyl(2,2,6,6-tetramethylpiperidin-4-yl)amino]-1,2,4-triazin-6-yl}-5-(tetrazolo[1,5-b]pyridazin-6-yl)phenol |
| 179[1] | 5-[6-(hydroxymethyl)pyrimidin-4-yl]-2-{3-[methyl(2,2,6,6-tetramethylpiperidin-4-yl)amino]-1,2,4-triazin-6-yl}phenol |
| 180[1] | 2-[3-(2,9-diazaspiro[5.5]undecan-9-yl)-1,2,4-triazin-6-yl]-5-(1H-pyrazol-4-yl)phenol |
| 181[1] | 2-[3-(2,8-diazaspiro[4.5]decan-8-yl)-1,2,4-triazin-6-yl]-5-(1H-pyrazol-4-yl)phenol |
| 182[1] | 2-[3-(2-methyl-2,9-diazaspiro[5.5]undecan-9-yl)-1,2,4-triazin-6-yl]-5-(1H-pyrazol-4-yl)phenol |
| 183[1] | 2-[3-(2-methyl-2,8-diazaspiro[5.5]decan-8-yl)-1,2,4-triazin-6-yl]-5-(1H-pyrazol-4-yl)phenol |
| 184[1] | 2-{3-[methyl(2,2,6,6-tetramethylpiperidin-4-yl)amino]-1,2,4-triazin-6-yl}-5-(1H-pyrazolo[3,4-c]pyridin-5-yl)phenol |
| 185[1] | 2-{3-[methyl(2,2,6,6-tetramethylpiperidin-4-yl)amino]-1,2,4-triazin-6-yl}-5-(quinolin-6-yl)phenol |
| 186[1] | 2-{3-[methyl(2,2,6,6-tetramethylpiperidin-4-yl)amino]-1,2,4-triazin-6-yl}-5-(1-methyl-1H-[1,2,3]triazolo[4,5-b]pyridin-5-yl)phenol |
| 187[1] | 2-{3-[3-(tert-butylamino)pyrrolidin-l-yl]-1,2,4-triazin-6-yl}-5-(1H-imidazol-1-yl)phenol |
| 188[1] | 5-(2H-1,3-benzodioxol-5-yl)-2-{3-[methyl(2,2,6,6-tetramethylpiperidin-4-yl)amino]-1,2,4-triazin-6-yl}phenol |
| 189[1] | 5-(3-fluoro-1H-pyrazol-4-yl)-2-(3-{[(3R,4R)-3-fluoro-2,2,6,6-tetramethylpiperidin-4-yl]amino}-1,2,4-triazin-6-yl)phenol |
| 190[1] | 2-{3-{[(2S)-2-aminopropyl](methyl)amino}-1,2,4-triazin-6-yl)-5-(1H-pyrazol-4-yl)phenol |
| 191[1] | 5-(5-fluoro-1H-pyrazol-4-yl)-2-{6-[methyl(2,2,6,6-tetramethylpiperidin-4-yl)amino]-1,2,4-triazin-3-yl}phenol |
| 192 | 5-[1-($^2$H$_3$)methyl-1H-pyrazol-4-yl]-2-{6-[methyl(2,2,6,6-tetramethylpiperidin-4-yl)amino]-1,2,4-triazin-3-yl}phenol |
| 193[1] | 2-{3-[(3aR,4R,6aS)-4-(tert-butylamino)hexahydrocyclopenta[c]pyrrol-2(1H)-yl]-1,2,4-triazin-6-yl}-5-(1H-pyrazol-4-yl)phenol |
| 194[1] | 2-{3-[methyl(2,2,6,6-tetramethylpiperidin-4-yl)amino]-1,2,4-triazin-6-yl}-5-(1H-pyrazolo[3,4-b]pyrazin-5-yl)phenol |
| 195[1] | 2-{3-[methyl(2,2,6,6-tetramethylpiperidin-4-yl)amino]-1,2,4-triazin-6-yl}-5-(1H-pyrazolo[4,3-d]pyrimidin-5-yl)phenol |
| 196[1] | 5-(1-methyl-1H-pyrazol-4-yl)-2-{6-[methyl(2,2,6,6-tetramethylpiperidin-4-yl)amino]-1,2,4-triazin-3-yl}phenol |
| 197[1] | 2-{3-[3-(tert-butylamino)pyrrolidin-l-yl]-1,2,4-triazin-6-yl}-5-(4-methyl-1H-imidazol-1-yl)phenol |
| 198[1] | 5-(1-methyl-1H-pyrazolo[4,3-b]pyridin-5-yl)-2-{3-[methyl(2,2,6,6-tetramethylpiperidin-4-yl)amino]-1,2,4-triazin-6-yl}phenol |
| 199[1] | 5-(1-methyl-1H-pyrazol-4-yl)-2-{3-[(2,2,6,6-tetramethylpiperidin-4-yl)amino]-1,2,4-triazin-6-yl}phenol |
| 200[1] | 5-(1-methyl-1H-benzotriazol-5-yl)-2-{3-[methyl(2,2,6,6-tetramethylpiperidin-4-yl)amino]-1,2,4-triazin-6-yl}phenol |
| 201 | 2-(3-{[(3S,4S)-3-fluoro-2,2,6,6-tetramethylpiperidin-4-yl]amino}-1,2,4-triazin-6-yl)-5-(1-methyl-1H-pyrazol-4-yl)phenol |
| 202[1] | 2-{3-[3-(tert-butylamino)pyrrolidin-l-yl]-1,2,4-triazin-6-yl}-5-(1-methyl-1H-pyrazol-4-yl)phenol |
| 203[1] | 5-(1-methyl-1H-pyrazol-4-yl)-2-{3-[(propan-2-yl)amino]pyrrolidin-1-yl}-1,2,4-triazin-6-yl)phenol |

-continued

| Cpd | Name |
|---|---|
| 204[1] | 2-{3-[3-(tert-butylamino)pyrrolidin-1-yl]-1,2,4-triazin-6-yl}-5-(2H-1,2,3-triazol-2-yl)phenol |
| 205[1] | 2-{3-[3-(methylamino)pyrrolidin-1-yl]-1,2,4-triazin-6-yl}-5-(1-methyl-1H-pyrazol-4-yl)phenol |
| 206[1] | 2-{3-[4-(tert-butylamino)piperidin-1-yl]-1,2,4-triazin-6-yl}-5-(1H-pyrazol-4-yl)phenol |
| 207[1] | 2-{3-[3-(tert-butylamino)pyrrolidin-1-yl]-1,2,4-triazin-6-yl}-5-([1,2,3]triazolo[1,5-a]pyridin-5-yl)phenol |
| 208[1] | 2-{3-[3-(tert-butylamino)pyrrolidin-1-yl]-1,2,4-triazin-6-yl}-5-(1-methyl-1H-indazol-5-yl)phenol |
| 209[1] | 2-{3-[3-(tert-butylamino)pyrrolidin-1-yl]-1,2,4-triazin-6-yl}-5-(pyrimidin-2-yl)phenol |
| 210[1] | 2-{3-[3-(tert-butylamino)pyrrolidin-1-yl]-1,2,4-triazin-6-yl}-5-(2-methyl-2H-1,2,3-triazol-4-yl)phenol |
| 211[1] | 2-{3-[3-(tert-butylamino)pyrrolidin-1-yl]-1,2,4-triazin-6-yl}-5-(2-methyl-2H-tetrazol-5-yl)phenol |
| 212[1] | 2-{3-[3-(tert-butylamino)piperidin-1-yl]-1,2,4-triazin-6-yl}-5-(1H-pyrazol-4-yl)phenol |
| 213[1] | 5-(1-methyl-1H-pyrazol-3-yl)-2-(3-{3-[(propan-2-yl)amino]pyrrolidin-1-yl}-1,2,4-triazin-6-yl)phenol |
| 214[1] | 4-(4-{3-[3-(tert-butylamino)pyrrolidin-1-yl]-1,2,4-triazin-6-yl}-3-hydroxyphenyl)-1-methylpyridin-2(1H)-one |
| 215[1] | 2-{3-[3-(tert-butylamino)pyrrolidin1-yl]-1,2,4-triazin-6-yl}-5-(1-methyl-1H-[1,2,3]triazolo[4,5-b]pyridin-5-yl)phenol |
| 216[1] | 6-(4-{3-[3-(tert-butylamino)pyrrolidin-1-yl]-1,2,4-triazin-6-yl}-3-hydroxyphenyl)-3-methylpyrimidin-4(3H)-one |
| 217[1] | 2-{3-[3-(tert-butylamino)pyrrolidin-1-yl]-1,2,4-triazin-6-yl}-5-(6-methoxypyrimidin-4-yl)phenol |
| 218[1] | 2-{3-[3-(methylamino)pyrrolidin-1-yl]-1,2,4-triazin-6-yl}-5-(2H-1,2,3-triazol-2-yl)phenol |
| 219[1] | 5-(4-fluoro-1H-pyrazol-1-yl)-2-{3-[3-(methylamino)pyrrolidin-1-yl]-1,2,4-triazin-6-yl}phenol |
| 220[1] | 5-(1H-imidazol-1-yl)-2-{3-[3-(methylamino)pyrrolidin-1-yl]-1,2,4-triazin-6-yl}phenol |
| 221[1] | 2-{3-[3-(tert-butylamino)pyrrolidin-1-yl]-1,2,4-triazin-6-yl}-5-(1-methyl-1H-pyrazolo[3,4-b]pyridin-5-yl)phenol |
| 222[1] | 5-(1-methyl-1H-pyrazolo[3,4-c]pyridin-5-yl)-2-{3-[methyl(2,2,6,6-tetramethylpiperidin-4-yl)amino]-1,2,4-triazin-6-yl}phenol |
| 223[1] | 2-{3-[3-(7-methyl-2,7-diazaspiro[3.5]nonan-2-yl)-1,2,4-triazin-6-yl}-5-(1-methyl-1H-indazol-5-yl)phenol |
| 224[1] | 2-[3-(7-methyl-2,7-diazaspiro[3.5]nonan-2-yl)-1,2,4-triazin-6-yl]-5-(1-methyl-1H-pyrazolo[3,4-b]pyridin-5-yl)phenol |
| 225 | 2-{3-[3-(tert-butylamino)pyrrolidin-1-yl]-1,2,4-triazin-6-yl}-5-(1H-1,2,3-triazol-4-yl)phenol |
| 226[1] | 2-[3-(7-methyl-2,7-diazaspiro[3.5]nonan-2-yl)-1,2,4-triazin-6-yl]-5-(1-methyl-1H-pyrazol-4-yl)phenol |
| 227[1] | 4-[3-hydroxy-4-(3-{3-[(propan-2-yl)amino]pyrrolidin-1-yl}-1,2,4-triazin-6-yl)phenyl]-1-methylpyridin-2(1H)-one |
| 228[1] | 2-[3-(7-methyl-2,7-diazaspiro[3.5]nonan-2-yl)-1,2,4-triazin-6-yl]-5-(4-methyl-1H-imidazol-1-yl)phenol |
| 229[1] | 5-(4-fluoro-1H-pyrazol-1-yl)-2-[3-(7-methyl-2,7-diazaspiro[3.5]nonan-2-yl)-1,2,4-triazin-6-yl]phenol |
| 230[1] | 5-(4-fluoro-1H-imidazol-1-yl)-2-[3-(7-methyl-2,7-diazaspiro[3.5]nonan-2-yl)-1,2,4-triazin-6-yl]phenol |
| 231[1] | 5-(1H-imidazol-1-yl)-2-[3-(7-methyl-2,7-diazaspiro[3.5]nonan-2-yl)-1,2,4-triazin-6-yl]phenol |
| 232[1] | 2-[3-(7-methyl-2,7-diazaspiro[3.5]nonan-2-yl)-1,2,4-triazin-6-yl]-5-(2H-1,2,3-triazol-2-yl)phenol |
| 233[1] | 2-[3-(7-methyl-2,7-diazaspiro[3.5]nonan-2-yl)-1,2,4-triazin-6-yl]-5-(1-methyl-1H-pyrazol-3-yl)phenol |
| 234[1] | 6-[3-hydroxy-4-(3-{3-[(propan-2-yl)amino]pyrrolidin-1-yl}-1,2,4-triazin-6-yl)phenyl]-3-methylpyrimidin-4(3H)-one |
| 235[1] | 5-(5-fluoro-1H-pyrazol-4-yl)-2-(3-{3-[(propan-2-yl)amino]pyrrolidin-1-yl}-1,2,4-triazin-6-yl)phenol |
| 236[1] | 5-(2-methyl-2H-1,2,3-triazol-4-yl)-2-(3-{3-[(propan-2-yl)amino]pyrrolidin-1-yl}-1,2,4-triazin-6-yl)phenol |
| 237[1] | 2-(3-{3-[(propan-2-yl)amino]pyrrolidin-1-yl}-1,2,4-triazin-6-yl)-5-(1,2,4-thiadiazol-5-yl)phenol |
| 238[1] | 2-(3-{[(3S,4S)-3-fluoro-2,2,6,6-tetramethylpiperidin-4-yl]amino}-1,2,4-triazin-6-yl)-5-(1H-imidazol-1-yl)phenol |
| 239[1] | 2-{3-{[(3S,4S)-3-fluoro-2,2,6,6-tetramethylpiperidin-4-yl]amino}-1,2,4-triazin-6-yl)-5-(4-methyl-1H-imidazol-1-yl)phenol |
| 240[1] | 5-(4-fluoro-1H-imidazol-1-yl)-2-(3-{[(3S,4S)-3-fluoro-2,2,6,6-tetramethylpiperidin-4-yl]amino}-1,2,4-triazin-6-yl)phenol |
| 241[1] | 4-{3-hydroxy-4-[3-(7-methyl-2,7-diazaspiro[3.5]nonan-2-yl)-1,2,4-triazin-6-yl]phenyl}-1-methylpyridin-2(1H)-one |
| 242[1] | 2-[3-(7-methyl-2,7-diazaspiro[3.5]nonan-2-yl)-1,2,4-triazin-6-yl]-5-(2-methyl-2H-1,2,3-triazol-4-yl)phenol |
| 243[1] | 5-(6-methoxypyrimidin-4-yl)-2-[3-(7-methyl-2,7-diazaspiro[3.5]nonan-2-yl)-1,2,4-triazin-6-yl]phenol |

-continued

| Cpd | Name |
|---|---|
| 244[1] | 2-[3-(7-methyl-2,7-diazaspiro[3.5]nonan-2-yl)-1,2,4-triazin-6-yl]-5-(pyrimidin-2-yl)phenol |
| 245[1] | 2-[3-(7-methyl-2,7-diazaspiro[3.5]nonan-2-yl)-1,2,4-triazin-6-yl]-5-(1H-1,2,3-triazol-4-yl)phenol |
| 246[1] | 6-[4-(3-{[(3S,4S)-3-fluoro-2,2,6,6-tetramethylpiperidin-4-yl]amino}-1,2,4-triazin-6-yl)-3-hydroxyphenyl]-3-methylpyrimidin-4(3H)-one |
| 247[1] | 2-(3-{[(3S,4S)-3-fluoro-2,2,6,6-tetramethylpiperidin-4-yl]amino}-1,2,4-triazin-6-yl)-5-(1H-1,2,3-triazol-4-yl)phenol |
| 248 | 2-(3-{[(3S,4S)-3-fluoro-2,2,6,6-tetramethylpiperidin-4-yl]amino}-1,2,4-triazin-6-yl)-5-(imidazo[1,2-a]pyrazin-6-yl)phenol |
| 249[1] | 2-(3-{[(3S,4S)-3-fluoro-2,2,6,6-tetramethylpiperidin-4-yl]amino}-1,2,4-triazin-6-yl)-5-(imidazo[1,2-b]pyridazin-6-yl)phenol |
| 250[1] | 2-{3-[3-(tert-butylamino)pyrrolidin-1-yl]-1,2,4-triazin-6-yl}-5-(1,3-oxazol-2-yl)phenol |
| 251[1] | 2-[3-(7-methyl-2,7-diazaspiro[3.5]nonan-2-yl)-1,2,4-triazin-6-yl]-5-(2-methyl-2H-tetrazol-5-yl)phenol |
| 252[1] | 2-[3-(7-methyl-2,7-diazaspiro[3.5]nonan-2-yl)-1,2,4-triazin-6-yl]-5-(1,3-oxazol-2-yl)phenol |
| 253[1] | 5-(1-methyl-1H-pyrazol-3-yl)-2-{3-[(2,2,6,6-tetramethylpiperidin-4-yl)amino]-1,2,4-triazin-6-yl}phenol |
| 254[1] | 5-(6-methoxypyrimidin-4-yl)-2-{3-[(2,2,6,6-tetramethylpiperidin-4-yl)amino]-1,2,4-triazin-6-yl}phenol |
| 255 | 2-{6-[methyl(2,2,6,6-tetramethylpiperidin-4-yl)amino]-1,2,4-triazin-3-yl}-5-(2H-1,2,3-triazol-2-yl)phenol |
| 256[1] | 5-(imidazo[1,2-b]pyridazin-6-yl)-2-[3-(7-methyl-2,7-diazaspiro[3.5]nonan-2-yl)-1,2,4-triazin-6-yl]phenol |
| 257[1] | 5-(imidazo[1,2-a]pyrazin-6-yl)-2-[3-(7-methyl-2,7-diazaspiro[3.5]nonan-2-yl)-1,2,4-triazin-6-yl]phenol |
| 258[1] | 2-(3-{3-[(propan-2-yl)amino]pyrrolidin-1-yl}-1,2,4-triazin-6-yl)-5-(1H-1,2,3-triazol-4-yl)phenol |
| 259[1] | 5-(2-methyl-2H-tetrazol-5-yl)-2-(3-{3-[(propan-2-yl)amino]pyrrolidin-1-yl}-1,2,4-triazin-6-yl)phenol |
| 260[1] | 2-(3-{[(3S,4S)-3-fluoro-2,2,6,6-tetramethylpiperidin-4-yl]amino}-1,2,4-triazin-6-yl)-5-(1-methyl-1H-indazol-5-yl)phenol |
| 261[1] | 2-(3-{[(3S,4S)-3-fluoro-2,2,6,6-tetramethylpiperidin-4-yl]amino}-1,2,4-triazin-6-yl)-5-(1-methyl-1H-pyrazol-3-yl)phenol |
| 262[1] | 2-[3-(3,5-dimethylpiperazin-1-yl)-1,2,4-triazin-6-yl]-5-(1H-pyrazol-4-yl)phenol |
| 263[1] | 2-[3-(3,5-dimethylpiperazin-1-yl)-1,2,4-triazin-6-yl]-5-(1-methyl-1H-pyrazol-3-yl)phenol |
| 264[1] | 2-(3-{3-(propan-2-yl)amino]pyrrolidin-1-yl}-1,2,4-triazin-6-yl)-5-(2H-1,2,3-triazol-2-yl)phenol |
| 265[1] | 5-(6-methoxypyrimidin-4-yl)-2-(3-{3-[(propan-2-yl)amino]pyrrolidin-1-yl}-1,2,4-triazin-6-yl)phenol |
| 266[1] | 5-(2-methyl-2H-1,2,3-triazol-4-yl)-2-{3-[(2,2,6,6-tetramethylpiperidin-4-yl)amino]-1,2,4-triazin-6-yl}phenol |
| 267[1] | 5-(2-methyl-2H-tetrazol-5-yl)-2-{3-[(2,2,6,6-tetramethylpiperidin-4-yl)amino]-1,2,4-triazin-6-yl}phenol |
| 268[1] | 5-(6-methoxypyrimidin-4-yl)-2-{3-[(methylamino)pyrrolidin-1-yl]-1,2,4-triazin-6-yl}phenol |
| 269[1] | 2-{3-[3-(methylamino)pyrrolidin-1-yl]-1,2,4-triazin-6-yl}-5-(1,2,4-thiadiazol-5-yl)phenol |
| 270[1] | 2-{3-[3-(methylamino)pyrrolidin-1-yl]-1,2,4-triazin-6-yl}-5-(pyrimidin-2-yl)phenol |
| 271[1] | 2-{3-[3-(methylamino)pyrrolidin-1-yl]-1,2,4-triazin-6-yl}-5-(1-methyl-1H-pyrazolo[3,4-b]pyridin-5-yl)phenol |
| 272[1] | 2-[3-(7-methyl-2,7-diazaspiro[3.5]nonan-2-yl)-1,2,4-triazin-6-yl]-5-(1,2,4-thiadiazol-5-yl)phenol |
| 273[1] | 5-(1H-imidazol-1-yl)-2-{3-[(2,2,6,6-tetramethylpiperidin-4-yl)amino]-1,2,4-triazin-6-yl}phenol |
| 274[1] | 5-(4-methyl-1H-imidazol-1-yl)-2-{3-[(2,2,6,6-tetramethylpiperidin-4-yl)amino]-1,2,4-triazin-6-yl}phenol |
| 275[1] | 5-(4-fluoro-1H-imidazol-1-yl)-2-{3-[(2,2,6,6-tetramethylpiperidin-4-yl)amino]-1,2,4-triazin-6-yl}phenol |
| 276[1] | 5-(4-fluoro-1H-pyrazol-1-yl)-2-{3-[(2,2,6,6-tetramethylpiperidin-4-yl)amino]-1,2,4-triazin-6-yl}phenol |
| 277[1] | 5-(2-methyl-1,3-oxazol-5-yl)-2-{3-[(2,2,6,6-tetramethylpiperidin-4-yl)amino]1,2,4-triazin-6-yl}phenol |
| 278[1] | 2-{3-[3-(tert-butylamino)-4-fluoropyrrolidin-1-yl]-1,2,4-triazin-6-yl}-5-(1H-pyrazol-4-yl)phenol |
| 279[1] | 5-(pyrimidin-2-yl)-2-{3-[(2,2,6,6-tetramethylpiperidin-4-yl)amino]-1,2,4-triazin-6-yl}phenol |
| 280 | 5-(7-fluoro-1H-benzimidazol-5-yl)-2-{3-[methyl(2,2,6,6-tetramethylpiperidin-4-yl)amino]-1,2,4-triazin-6-yl}phenol |
| 281 | 5-(1-methyl-1H-pyrazolo[4,3-d]pyrimidin-5-yl)-2-{3-[methyl(2,2,6,6-tetramethylpiperidin-4-yl)amino]-1,2,4-triazin-6-yl}phenol |
| 282[1] | 5-(1H-pyrazol-4-yl)-2-[3-(3,3,5,5-tetramethylpiperazin-1-yl)-1,2,4-triazin-6-yl]phenol |
| 283[1] | 5-(imidazo[1,2-a]pyrazin-6-yl)-2-(3-{3-[(propan-2-yl)amino]pyrrolidin-1-yl}-1,2,4-triazin-6-yl)phenol |

-continued

| Cpd | Name |
|---|---|
| 284[1] | 2-(3-{[(3S,4S)-3-fluoro-2,2,6,6-tetramethylpiperidin-4-yl]amino}-1,2,4-triazin-6-yl)-5-(1-methyl-1H-pyrazolo[3,4-b]pyridin-5-yl)phenol |
| 285[1] | 5-(1-methyl-1H-benzimidazol-5-yl)-2-{3-[methyl(2,2,6,6-tetramethylpiperidin-4-yl)amino]-1,2,4-triazin-6-yl}phenol |
| 286 | 2-(3-{[(3S,4S)-3-methoxy-2,2,6,6-tetramethylpiperidin-4-yl]amino}-1,2,4-triazin-6-yl)-5-(1H-pyrazol-4-yl)phenol |
| 287[1] | 2-(3-{[(3S,4S)-3-fluoro-2,2,6,6-tetramethylpiperidin-4-yl]amino}-1,2,4-triazin-6-yl)-5-(2-methyl-2H-1,2,3-triazol-4-yl)phenol |
| 288[1] | 2-(3-{[(3S,4S)-3-fluoro-2,2,6,6-tetramethylpiperidin-4-yl]amino}-1,2,4-triazin-6-yl)-5-(1,3-oxazol-2-yl)phenol |
| 289[1] | 5-(2-methyl-1,3-oxazol-5-yl)-2-(3-{3-[(propan-2-yl)amino]pyrrolidin-l-yl}-1,2,4-triazin-6-yl)phenol |
| 290[1] | 2-(3-{[(3S,4S)-3-fluoro-2,2,6,6-tetramethylpiperidin-4-yl]amino}-1,2,4-triazin-6-yl)-5-(6-methoxypyrimidin-4-yl)phenol |
| 291[1] | 2-(3-{[(3S,4S)-3-fluoro-2,2,6,6-tetramethylpiperidin-4-yl]amino}-1,2,4-triazin-6-yl)-5-(2-methyl-2H-tetrazol-5-yl)phenol |
| 292[1] | 2-(3-{[(3S,4S)-3-fluoro-2,2,6,6-tetramethylpiperidin-4-yl]amino}-1,2,4-triazin-6-yl)-5-(1,2,4-thiadiazol-5-yl)phenol |
| 293[1] | 2-(3-{[(3S,4S)-3-methoxy-2,2,6,6-tetramethylpiperidin-4-yl](methyl)amino}-1,2,4-triazin-6-yl)-5-(1H-pyrazol-4-yl)phenol |
| 294[1] | 5-(imidazo[1,2-N]pyridazin-6-yl)-2-(3-{3-[(propan-2-yl)amino]pyrrolidin-l-yl}-1,2,4-triazin-6-yl)phenol |
| 295[1] | 2-{3-[3-(methylamino)pyrrolidin-1-yl]-1,2,4-triazin-6-yl}-5-(2-methyl-2H-1,2,3-triazol-4-yl)phenol |
| 296[1] | 2-{3-[3-(methylamino)pyrrolidin-1-yl]-1,2,4-triazin-6-yl}-5-(1-methyl-1H-pyrazol-3-yl)phenol |
| 297[1] | 2-(3-{3-[(2-methylpropyl)amino]pyrrolidin-1-yl}-1,2,4-triazin-6-yl)-5-(1H-pyrazol-4-yl)phenol |
| 298[1] | (3S,4S)-4-({6-[2-hydroxy-4-(1H-pyrazol-4-yl)phenyl]-1,2,4-triazin-3-yl}amino)-2,2,6,6-tetramethylpiperidin-3-ol |
| 299[1] | 2-[3-(7-methyl-2,7-diazaspiro[3.5]nonan-2-yl)-1,2,4-triazin-6-yl]-5-(2-methyl-1,3-oxazol-5-yl)phenol |
| 300[1] | 5-(7-fluoro-1-methyl-1H-benzimidazol-5-yl)-2-{3-[methyl(2,2,6,6-tetramethylpiperidin-4-yl)amino]-1,2,4-triazin-6-yl}phenol |
| 301[1] | 5-(6,7-difluoro-1H-benzimidazol-5-yl)-2-{3-[methyl(2,2,6,6-tetramethylpiperidin-4-yl)amino]-1,2,4-triazin-6-yl}phenol |
| 302[1] | 5-(6,7-difluoro-1-methyl-1H-benzimidazol-5-yl)-2-{3-[methyl(2,2,6,6-tetramethylpiperidin-4-yl)amino]-1,2,4-triazin-6-yl}phenol |
| 303[1] | 5-(8-methylimidazo[1,2-b]pyridazin-6-yl)-2-{3-[methyl(2,2,6,6-tetramethylpiperidin-4-yl)amino]-1,2,4-triazin-6-yl}phenol |
| 304[1] | 5-(8-methoxyimidazo[1,2-b]pyridazin-6-yl)-2-{3-[methyl(2,2,6,6-tetramethylpiperidin-4-yl)amino]-1,2,4-triazin-6-yl}phenol |
| 305[1] | 2-{3-[(2,2,6,6-tetramethylpiperidin-4-yl)amino]-1,2,4-triazin-6-yl}-5-(1,2,4-triazin-6-yl)phenol |
| 306[1] | 2-{3-[(4aS,7aS)-octahydro-6H-pyrrolo[3,4-b]pyridin-6-yl]-1,2,4-triazin-6-yl}-5-(1H-pyrazol-4-yl)phenol |
| 307[1] | 5-(1-methyl-1H-pyrazolo[3,4-b]pyridin-5-yl)-2-(3-{3-[(propan-2-yl)amino]pyrrolidin-1-yl}-1,2,4-triazin-6-yl)phenol |
| 308[1] | 5-(1,3-oxazol-2-yl)-2-(3-{3-[(propan-2-yl)amino]pyrrolidin-l-yl}-1,2,4-triazin-6-yl)phenol |
| 309[1] | 2-(3-{[(3S)-1-methylpyrrolidin-3-yl]oxy}-1,2,4-triazin-6-yl)-5-(1H-pyrazol-4-yl)phenol |
| 310[1] | 2-{3-[(4aS,7aS)-1-methyloctahydro-6H-pyrrolo[3,4-b]pyridin-6-yl]-1,2,4-triazin-6-yl}-5-(1H-pyrazol-4-yl)phenol |
| 311[1] | 2-{3-[(4aS,7aR)-4-methylhexahydropyrrolo[3,4-b][1,4]oxazin-6(2H)-yl]-1,2,4-triazin-6-yl}-5-(1H-pyrazol-4-yl)phenol |
| 312 | 2-(3-{3-[(oxetan-3-yl)amino]pyrrolidin-1-yl}-1,2,4-triazin-6-yl)-5-(1H-pyrazol-4-yl)phenol |
| 313 | 5-(1-methyl-1H-pyrazol-4-yl)-2-(3-{3-[(oxetan-3-yl)amino]pyrrolidin-1-yl}-1,2,4-triazin-6-yl)phenol |
| 314[1] | 5-(pyridazin-4-yl)-2-{3-[(2,2,6,6-tetramethylpiperidin-4-yl)amino]-1,2,4-triazin-6-yl}phenol |
| 315[1] | 5-[(pyridin-3-yl)amino]2-{3-[(2,2,6,6-tetramethylpiperidin-4-yl)amino]-1,2,4-triazin-6-yl}phenol |
| 316[1] | 2-(3-{3-[(1-fluoro-2-methylpropan-2-yl)amino]pyrrolidin-1-yl}-1,2,4-triazin-6-yl)-5-(1H-pyrazol-4-yl)phenol |
| 317[1] | 2-{3-[3-(ethylamino)pyrrolidin-1-yl]-1,2,4-triazin-6-yl}-5-(1H-pyrazol-4-yl)phenol |
| 318[1] | 2-{3-[3-(dimethylamino)pyrrolidin-1-yl]-1,2,4-triazin-6-yl}-5-(1H-pyrazol-4-yl)phenol |
| 319[1] | 5-(1-methyl-1H-indazol-5-yl)-2-{3-[(2,2,6,6-tetramethylpiperidin-4-yl)amino]-1,2,4-triazin-6-yl}phenol |
| 320[1] | 2-{3-[3-(methylamino)pyrrolidin-1-yl]-1,2,4-triazin-6-yl}-5-(2-methyl-2H-tetrazol-5-yl)phenol |
| 321[1] | 5-(1-methyl-1H-pyrazolo[3,4-b]pyridin-5-yl)-2-{3-[(2,2,6,6-tetramethylpiperidin-4-yl)amino]-1,2,4-triazin-6-yl}phenol |
| 322[1] | 2-(3-{[(3S,4S)-3-fluoro-2,2,6,6-tetramethylpiperidin-4-yl]amino}-1,2,4-triazin-6-yl)-5-(1H-pyrazol-4-yl)phenol |

-continued

| Cpd | Name |
|---|---|
| 323[1] | 2-(3-{[(3R,4R)-3-fluoro-2,2,6,6-tetramethylpiperidin-4-yl]amino}-1,2,4-triazin-6-yl)-5-(1H-pyrazol-4-yl)phenol |
| 324[1] | 2-{3-[(3-fluoro-2,2,6,6-tetramethylpiperidin-4-yl)amino]-1,2,4-triazin-6-yl}-5-(2H-1,2,3-triazol-2-yl)phenol |
| 325 | 2-{3-[(3-methyloxetan-3-yl)amino]pyrrolidin-1-yl}-1,2,4-triazin-6-yl)-5-(1H-pyrazol-4-yl)phenol |
| 326[1] | 5-(4-methyl-1H-imidazol-1-yl)-2-(3-{3-[(propan-2-yl)amino]pyrrolidin-1-yl}-1,2,4-triazin-6-yl)phenol |
| 327[1] | 2-{3-[(3aR,7aR)-octahydro-2H-pyrrolo[3,4-c]pyridin-2-yl]-1,2,4-triazin-6-yl}-5-(1H-pyrazol-4-yl)phenol |
| 328[1] | 2-[3-(piperazin-1-yl)-1,2,4-triazin-6-yl]-5-(1H-pyrazol-4-yl)phenol |
| 329[1] | 2-{3-[(3S)-3-{[(2R)-1-fluoropropan-2-yl]amino}pyrrolidin-1-yl]-1,2,4-triazin-6-yl}-5-(1H-pyrazol-4-yl)phenol |
| 330[1] | 5-(1-methyl-1H-indazol-5-yl)-2-(3-{3-[(propan-2-yl)amino]pyrrolidin-1-yl}-1,2,4-triazin-6-yl)phenol |
| 331[1] | 5-(1H-imidazol-1-yl)-2-(3-{3-(propan-2-yl)amino]pyrrolidin-1-yl}-1,2,4-triazin-6-yl)phenol |
| 332[1] | 2-{3-[(3aR,6aS)-hexahydropyrrolo[3,2-b]pyrrol-1(2H)-yl]-1,2,4-triazin-6-yl}-5-(1H-pyrazol-4-yl)phenol |
| 333[1] | 2-(3-{3-[(2-hydroxyethyl)amino]pyrrolidin-1-yl}-1,2,4-triazin-6-yl)-5-(1H-pyrazol-4-yl)phenol |
| 334[1] | 2-[3-(8-amino-2-oxa-6-azaspiro[3.4]octan-6-yl)-1,2,4-triazin-6-yl]-5-(1H-pyrazol-4-yl)phenol |
| 335[1] | 2-(3-{3-[(oxan-4-yl)amino]pyrrolidin-1-yl}-1,2,4-triazin-6-yl)-5-(1H-pyrazol-4-yl)phenol |
| 336[1] | 2-(3-{3-[(1-methoxypropan-2-yl)amino]pyrrolidin-1-yl}-1,2,4-triazin-6-yl)-5-(1H-pyrazol-4-yl)phenol |
| 337[1] | 2-[3-(hexahydropyrrolo[3,4-c]pyrrol-2(1H)-yl)-1,2,4-triazin-6-yl]-5-(1H-pyrazol-4-yl)phenol |
| 338[1] | 5-(4-fluoro-1H-pyrazol-1-yl)-2-(3-{3-[(propan-2-yl)amino]pyrrolidin-1-yl}-1,2,4-triazin-6-yl)phenol |
| 339[1] | 2-[3-(1,7-diazaspiro[4.4]nonan-7-yl)-1,2,4-triazin-6-yl]-5-(1H-pyrazol-4-yl)phenol |
| 340[1] | 2-(3-{3-[(1-methylcyclopropyl)amino]pyrrolidin-1-yl}-1,2,4-triazin-6-yl)-5-(1H-pyrazol-4-yl)phenol |
| 341[1] | 2-(3-{3-[(1-methoxy-2-methylpropan-2-yl)amino]pyrrolidin-1-yl}-1,2,4-triazin-6-yl)-5-(1H-pyrazol-4-yl)phenol |
| 342 | 5-(1-methyl-1H-indazol-5-yl)-2-{6-[methyl(2,2,6,6-tetramethylpiperidin-4-yl)amino]-1,2,4-triazin-3-yl}phenol |
| 343 | 5-(1-methyl-1H-pyrazol-3-yl)-2-{6-[methyl(2,2,6,6-tetramethylpiperidin-4-yl)amino]-1,2,4-triazin-3-yl}phenol |
| 344[1] | 6-(3-hydroxy-4-{3-[methyl(2,2,6,6-tetramethylpiperidin-4-yl)amino]-1,2,4-triazin-6-yl}phenyl)imidazo[1,2-b]pyridazine-8-carbonitrile |
| 345[1] | 2-(3-{[(3R,4S)-3-fluoropiperidin-4-yl]amino}-1,2,4-triazin-6-yl)-5-(1H-pyrazol-4-yl)phenol |
| 346[1] | 2-{3-[(3R,4R)-3-methoxy-4-(methylamino)pyrrolidin-1-yl]-1,2,4-triazin-6-yl}-5-(1H-pyrazol-4-yl)phenol |
| 347[1] | 2-(3-{(3S)-3-[(propan-2-yl)amino]pyrrolidin-1-yl}-1,2,4-triazin-6-yl)-5-(1H-pyrazol-4-yl)phenol |
| 348[1] | 2-(3-{(3R)-3-[(propan-2-yl)amino]pyrrolidin-1-yl}-1,2,4-triazin-6-yl)-5-(1H-pyrazol-4-yl)phenol |
| 349[1] | 2-(3-{3-[(bicyclo[1.1.1]pentan-1-yl)amino]pyrrolidin-1-yl}-1,2,4-triazin-6-yl)-5-(1H-pyrazol-4-yl)phenol |
| 350[1] | 2-{3-[3-(methylamino)pyrrolidin-1-yl]-1,2,4-triazin-6-yl}-5-(2-methyl-1,3-oxazol-5-yl)phenol |
| 351[1] | 5-[8-(aminomethyl)imidazo[1,2-b]pyridazin-6-yl]-2-{3-[methyl(2,2,6,6-tetramethylpiperidin-4-yl)amino]-1,2,4-triazin-6-yl}phenol |
| 352[1] | 5-(1,3-oxazol-2-yl)-2-{3-[(2,2,6,6-tetramethylpiperidin-4-yl)amino]-1,2,4-triazin-6-yl}phenol |
| 353[1] | 2-[3-(6-oxa-2,9-diazaspiro[4.5]decan-2-yl)-1,2,4-triazin-6-yl]-5-(1H-pyrazol-4-yl)phenol |
| 354[1] | 2-[3-(2,7-diazaspiro{4.4}nonan-2-yl)-1,2,4-triazin-6-yl]-5-(1H-pyrazol-4-yl)phenol |
| 355[1] | 2-{3-[(3S)-3-(tert-butylamino)pyrrolidin-1-yl]-1,2,4-triazin-6-yl}-5-(1H-pyrazol-4-yl)phenol |
| 356[1] | 2-{3-[(3R)-3-(tert-butylamino)pyrrolidin-1-yl]-1,2,4-triazin-6-yl}-5-(1H-pyrazol-4-yl)phenol |
| 357[1] | 2-{3-[3-(cyclopentylamino)pyrrolidin-1-yl]-1,2,4-triazin-6-yl}-5-(1H-pyrazol-4-yl)phenol |
| 358[1] | 2-{3-[3-(methylamino)pyrrolidin-1-yl]-1,2,4-triazin-6-yl}-5-(1,3-oxazol-2-yl)phenol |
| 359[1] | 5-(imidazo[1,2-a]pyrazin-2-yl)-2-{3-[(2,2,6,6-tetramethylpiperidin-4-yl)amino]-1,2,4-triazin-6-yl}phenol |
| 360[1] | 5-(imidazo[1,2-a]pyridin-2-yl)-2-{3-[(2,2,6,6-tetramethylpiperidin-4-yl)amino]-1,2,4-triazin-6-yl}phenol |
| 361[1] | 2-[3-(3-{[(propan-2-yl)amino]methyl}pyrrolidin-1-yl)-1,2,4-triazin-6-yl]-5-(1H-pyrazol-4-yl)phenol |
| 362[1] | 2-(3-{3-[(4-methyloxan-4-yl)amino]pyrrolidin-1-yl}-1,2,4-triazin-6-yl)-5-(1H-pyrazol-4-yl)phenol |

-continued

| Cpd | Name |
|---|---|
| 363[1] | 2-{6-[3-(tert-butylamino)pyrrolidin-l-yl]-1,2,4-triazin-3-yl}-5-(1H-pyrazol-4-yl)phenol |
| 364[1] | 2-{3-[3-(methylamino)pyrrolidin-l-yl]-1,2,4-triazin-6-yl}-5-[6-(methylsulfanyl)pyrimidin-4-yl]phenol |
| 365[1] | 2-{3-[3-(tert-butylamino)pyrrolidin-l-yl]-1,2,4-triazin-6-yl}-5-(3-chloro-1H-pyrazol-4-yl)phenol |
| 366[1] | 4-(4-{3-[3-(tert-butylamino)pyrrolidin-l-yl]-1,2,4-triazin-6-yl}-3-hydroxyphenyl)-1H-pyrazole-3-carbonitrile |
| 367[1] | 2-{3-[3-(tert-butylamino)pyrrolidin-l-yl]-1,2,4-triazin-6-yl}-5-[1-($^{2}H_{3}$)methyl-1H-pyrazol-4-yl]phenol |
| 368[1] | 3-(1-methyl-1H-pyrazol-3-yl)-6-{3-[methyl(2,2,6,6-tetramethylpiperidin-4-yl)amino]-1,2,4-triazin-6-yl}benzene-1,2-diol |
| 369[1] | 2-[3-(2,7-diazaspiro[4.5]decan-2-yl)-1,2,4-triazin-6-yl]-5-(1H-pyrazol-4-yl)phenol |
| 370[1] | 2-[3-(hexahydropyrrolo[3,4-b]pyrrol-5(1H)-yl)-1,2,4-triazin-6-yl]-5-(1H-pyrazol-4-yl)phenol |
| 371[1] | 2-(3-{3-[(3-hydroxypropyl)amino]pyrrolidin-1-yl}-1,2,4-triazin-6-yl)-5-(1H-pyrazol-4-yl)phenol |
| 372[1] | 2-[3-(3-{[(oxan-4-yl)amino]methyl}pyrrolidin-1-yl)-1,2,4-triazin-6-yl]-5-(1H-pyrazol-4-yl)phenol |
| 373[1] | 5-[1-($^{2}H_{3}$)methyl-1H-pyrazol-4-yl]-2-{3-[(2,2,6,6-tetramethylpiperidin-4-yl)amino]-1,2,4-triazin-6-yl}phenol |
| 374[1] | 2-{6-[3-(tert-butylamino)pyrrolidin-1-yl]-1,2,4-triazin-3-yl}-5-(3-fluoro-1H-pyrazol-4-yl)phenol |
| 375[1] | 2-{3-[3-(tert-butylamino)pyrrolidin-1-yl]-1,2,4-triazin-6-yl}-5-(3-methyl-1H-pyrazol-4-yl)phenol |
| 376[1] | 2-{3-[3-(tert-butylamino)pyrrolidin-1-yl]-1,2,4-triazin-6-yl}-3-methoxy-5-(1H-pyrazol-4-yl)phenol |
| 377[1] | 2-(3-{[(3S,4S)-3-fluoro-2,2,6,6-tetramethylpiperidin-4-yl]amino}-1,2,4-triazin-6-yl)-5-[1-($^{2}H_{3}$)methyl-1H-pyrazol-4-yl]phenol |
| 378[1] | 2-{3-[(3S)-3-(tert-butylamino)pyrrolidin-1-yl]-1,2,4-triazin-6-yl}-5-(3-fluoro-1H-pyrazol-4-yl)phenol |
| 379[1] | 2-{3-[(3R)-3-(tert-butylamino)pyrrolidin-1-yl]-1,2,4-triazin-6-yl}-5-(3-fluoro-1H-pyrazol-4-yl)phenol |
| 380 | 5-[6-(methylamino)pyrimidin-4-yl]-2-{3-[3-(methylamino)pyrrolidin-1-yl]-1,2,4-triazin-6-yl}phenol |
| 381[1] | 2-{3-[methyl(2,2,6,6-tetramethylpiperidin-4-yl)amino]-1,2,4-triazin-6-yl}-5-(1H-pyrazolo[3,4-c]pyridin-1-yl)phenol |
| 382 | 2-{6-[methyl(2,2,6,6-tetramethylpiperidin-4-yl)amino]-1,2,4-triazin-3-yl}-5-(pyridin-4-yl)phenol |
| 383 | 5-(7-fluoro-1H-indazol-5-yl)-2-{3-[methyl(2,2,6,6-tetramethylpiperidin-4-yl)amino]-1,2,4-triazin-6-yl}phenol |
| 384 | 2-{6-[methyl(2,2,6,6-tetramethylpiperidin-4-yl)amino]-1,2,4-triazin-3-yl}-5-(pyridin-3-yl)phenol |
| 385[1] | 2-{3-[(3R,5S)-3,5-dimethylpiperazin-1-yl]-1,2,4-triazin-6-yl}-5-(imidazo[1,2-b]pyridazin-6-yl)phenol |
| 386[1] | 2-(3-{3-[(cyclopentylamino)methyl]pyrrolidin-1-yl}-1,2,4-triazin-6-yl)-5-(1H-pyrazol-4-yl)phenol |
| 387[1] | 2-[3-([2,3'-bipyrrolidin]-1'-yl)-1,2,4-triazin-6-yl]-5-(1H-pyrazol-4-yl)phenol |
| 388[1] | 5-(1H-pyrazol-4-yl)-2-{3-[-({[(pyridin-2-yl)methyl]amino}methyl)pyrrolidin-1-yl]-1,2,4-triazin-6-yl}phenol |
| 389 | 2-[3-(3-amino-3-methylpyrrolidin-1-yl)-1,2,4-triazin-6-yl]-5-(1-methyl-1H-pyrazol-4-yl)phenol |
| 390[1] | 2-(3-{3-[(tert-butylamino)methyl]pyrrolidin-1-yl}-1,2,4-triazin-6-yl)-5-(1H-pyrazol-4-yl)phenol |
| 391[1] | 2-[3-(3-{[(4-methyloxan-4-yl)amino]methyl}pyrrolidin-1-yl)-1,2,4-triazin-6-yl]-5-(1H-pyrazol-4-yl)phenol |
| 392[1] | 2-(3-{3-[(cyclopropylamino)methyl]pyrrolidin-1-yl}-1,2,4-triazin-6-yl)-5-(1H-pyrazol-4-yl)phenol |
| 393 | 2-{6-[methyl(2,2,6,6-tetramethylpiperidin-4-yl)amino]-1,2,4-triazin-3-yl}-5-(pyridin-2-yl)phenol |
| 394 | 5-(1-methyl-1H-pyrazolo[4,3-b]pyridin-5-yl)-2-{6-[methyl(2,2,6,6-tetramethylpiperidin-4-yl)amino]-1,2,4-triazin-3-yl}phenol |
| 395[1] | 2-[3-(3-{[(oxolan-3-yl)amino]methyl}pyrrolidin-1-yl)-1,2,4-triazin-6-yl]-5-(1H-pyrazol-4-yl)phenol |
| 396[1] | 5-(1H-pyrazol-4-yl)-2-{6-[(2,2,6,6-tetramethylpiperidin-4-yl)amino]-1,2,4-triazin-3-yl}phenol |
| 397 | 2-{3-[(3S)-3-{[(oxan-4-yl)amino]methyl}pyrrolidin-1-yl]-1,2,4-triazin-6-yl}-5-(1H-pyrazol-4-yl)phenol |
| 398 | 2-{3-[(3R)-3-{[(oxan-4-yl)amino]methyl}pyrrolidin-1-yl]-1,2,4-triazin-6-yl}-5-(1H-pyrazol-4-yl)phenol |
| 399[1] | 2-{3-[(3R)-3-(cyclobutylamino)pyrrolidin-1-yl]-1,2,4-triazin-6-yl}-5-(1H-pyrazol-4-yl)phenol |
| 400[1] | 2-{3-[(3S)-3-(cyclobutylamino)pyrrolidin-1-yl]-1,2,4-triazin-6-yl}-5-(1H-pyrazol-4-yl)phenol |

-continued

| Cpd | Name |
|---|---|
| 401[1] | 2-{6-[(2,2,6,6-tetramethylpiperidin-4-yl)amino]-1,2,4-triazin-3-yl}-5-(2H-1,2,3-triazol-2-yl)phenol |
| 402 | 2-{6-[methyl(2,2,6,6-tetramethylpiperidin-4-yl)amino]-1,2,4-triazin-3-yl}-5-(pyrimidin-2-yl)phenol |
| 403[1] | 2-[3-(3-{[(3-fluorooxan-4-yl)amino]methyl}pyrrolidin-1-yl)-1,2,4-triazin-6-yl]-5-(1H-pyrazol-4-yl)phenol |
| 404[1] | 2-[3-(3-{[(oxan-3-yl)amino]methyl}pyrrolidin-1-yl)-1,2,4-triazin-6-yl]-5-(1H-pyrazol-4-yl)phenol |
| 405[1] | 2-[3-(3-{[(8-oxabicyclo[3.2.1]octan-3-yl)amino]methyl}pyrrolidin-1-yl)-1,2,4-triazin-6-yl]-5-(1H-pyrazol-4-yl)phenol |
| 406[1] | 2-{3-[(3R)-3-(cyclobutylamino)pyrrolidin-1-yl]-1,2,4-triazin-6-yl}-5-(1-methyl-1H-pyrazol-4-yl)phenol |
| 407[1] | 2-{3-[(3S)-3-(cyclobutylamino)pyrrolidin-1-yl]-1,2,4-triazin-6-yl}-5-(1-methyl-1H-pyrazol-4-yl)phenol |
| 408[1] | 2-(3-[(1R,3s,5S)-1,5-dimethyl-8-azabicyclo[3.2.1]octan-3-yl](methyl)amino}-1,2,4-triazin-6-yl)-5-(1-methyl-1H-pyrazol-4-yl)phenol |
| 409[1] | 2-(3-{3-[(3,3-difluorocyclopentyl)amino]pyrrolidin-1-yl}-1,2,4-triazin-6-yl)-5-(1H-pyrazol-4-yl)phenol |
| 410[1] | 2-(3-{3-[(dimethylamino)methyl]pyrrolidin-1-yl}-1,2,4-triazin-6-yl)-5-(1H-pyrazol-4-yl)phenol |
| 411 | 2-{6-[methyl(2,2,6,6-tetramethylpiperidin-4-yl)amino]-1,2,4-triazin-3-yl}-5-(pyrimidin-4-yl)phenol |
| 412 | 2-{6-[methyl(2,2,6,6-tetramethylpiperidin-4-yl)amino]-1,2,4-triazin-3-yl}-5-(pyrazin-2-yl)phenol |
| 413[1] | 2-(3-{3-[(methylamino)methyl]pyrrolidin-1-yl}-1,2,4-triazin-6-yl)-5-(1H-pyrazol-4-yl)phenol |
| 414[1] | 2-[3-(3-{1-[(propan-2-yl)amino]ethyl}pyrrolidin-1-yl)-1,2,4-triazin-6-yl]-5-(1H-pyrazol-4-yl)phenol |
| 415[1] | 2-(3-{3-[(cyclobutylamino)methyl]pyrrolidin-1-yl}-1,2,4-triazin-6-yl)-5-(1H-pyrazol-4-yl)phenol |
| 416[1] | 2-(3-{3-[(cyclobutylamino)methyl]pyrrolidin-1-yl}-1,2,4-triazin-6-yl)-5-(1-methyl-1H-pyrazol-4-yl)phenol |
| 417[1] | 2-(3-{[1R,3s,5S)-1,5-dimethyl-8-azabicyclo[3.2.1]octan-3-yl}(methyl)amino}-1,2,4-triazin-6-yl)-5-(2H-1,2,3-triazol-2-yl)phenol |
| 418[1] | 6-{3-[3-(tert-butylamino)pyrrolidin-1-yl]-1,2,4-triazin-6-yl}-2-fluoro-3-(1H-pyrazol-4-yl)phenol |
| 419[1] | 5-(1H-pyrazol-4-yl)-2-{6-[(2,2,6,6-tetramethylpiperidin-4-yl)oxy]-1,2,4-triazin-3-yl}phenol |
| 420[1] | 2-(3-{3-[(3-fluorocyclopentyl)amino]pyrrolidin-1-yl}-1,2,4-triazin-6-yl)-5-(1H-pyrazol-4-yl)phenol |
| 421[1] | 2-[3-(3-{1-[(oxan-4-yl)amino]cyclopropyl}pyrrolidin-1-yl)-1,2,4-triazin-6-yl]-5-(1H-pyrazol-4-yl)phenol |
| 422[1] | 2-(3-{3-methyl-3-[(propan-2-yl)aminolpyrrolidin-1-yl}-1,2,4-triazin-6-yl)-5-(1-methyl-1H-pyrazol-4-yl)phenol |
| 423[1] | 2-{6-[(3-fluoro-2,2,6,6-tetramethylpiperidin-4-yl)amino]-1,2,4-triazin-3-yl}-5-(1H-pyrazol-4-yl)phenol,and |
| 424[1] | 5-[1-($^{2}H_3$)methyl-1H-pyrazol-4-yl]-2-{6-[(2,2,6,6-tetramethylpiperidin-4-yl)amino]-1,2,4-triazin-3-yl}phenol; |
| 425 | 2-(3-(methyl(2,2,6,6-tetramethylpiperidin-4-yl)amino)-1,2,4-triazin-6-yl)-5-(5-methyl-1H-pyrazol-4-yl)phenol | wherein a form of the compound is selected from the group consisting of a salt, hydrate, solvate, racemate, enantiomer, diastereomer, stereoisomer, and tautomer form thereof.

Another aspect of the compound of Formula (I) or Formula (II) or a form thereof is a compound salt selected from the group consisting of:

| Cpd | Name |
|---|---|
| 1 | 5-(5-methyl-1,3-oxazol-2-yl)-2-{3-[methyl(2,2,6,6-tetramethylpiperidin-4-yl)amino]-1,2,4-triazin-6-yl}phenol hydrobromide |
| 2 | 5-(6-methoxypyrimidin-4-yl)-2-{3-[methyl(2,2,6,6-tetramethylpiperidin-4-yl)amino]-1,2,4-triazin-6-yl}phenol formate |
| 3 | 5-(2-methoxypyridin-4-yl)-2-{3-[methyl(2,2,6,6-tetramethylpiperidin-4-yl)amino]-1,2,4-triazin-6-yl}phenol formate |
| 6 | 5-(3-methyl-1H-pyrazol-4-yl)-2-{3-[methyl(2,2,6,6-tetramethylpiperidin-4-yl)amino]-1,2,4-triazin-6-yl}phenol formate |
| 10 | 5-(4-methyl-1H-imidazol-1-yl)-2-{3-[methyl(2,2,6,6-tetramethylpiperidin-4-yl)amino]-1,2,4-triazin-6-yl}phenol hydrochloride |
| 11 | 5-(1H-pyrazol-4-yl)-2-{3-[(2,2,6,6-tetramethylpiperidin-4-yl)oxy]-1,2,4-triazin-6-yl}phenol dihydrochloride |

-continued

| Cpd | Name |
|---|---|
| 12 | 5-(3-fluoro-1H-pyrazol-4-yl)-2-{3-[methyl(2,2,6,6-tetramethylpiperidin-4-yl)amino]-1,2,4-triazin-6-yl}phenol ditrifluoroacetate |
| 13 | 5-(1H-pyrazol-4-yl)-2-{3-[(2,2,6,6-tetramethylpiperidin-4-yl)amino]-1,2,4-triazin-6-yl}phenol dihydrochloride |
| 14 | 5-[1-($^2$H$_3$)methyl-1H-pyrazol-4-yl]-2-{3-[methyl(2,2,6,6-tetramethylpiperidin-4-yl)amino]-1,2,4-triazin-6-yl}phenol dihydrochloride |
| 15 | 6-[2,3-difluoro-4-(1H-pyrazol-4-yl)phenyl]-N-methyl-N-(2,2,6,6-tetramethylpiperidin-4-yl)-1,2,4-triazin-3-amine hydrochloride |
| 16 | 2-{3-[methyl(2,2,6,6-tetramethylpiperidin-4-yl)amino]-1,2,4-triazin-6-yl}-5-(1H-pyrazol-4-yl)phenol hydrochloride |
| 18 | 5-(1-methyl-1H-pyrazol-4-yl)-2-{3-[methyl(2,2,6,6-tetramethylpiperidin-4-yl)amino]-1,2,4-triazin-6-yl}phenol dihydrochloride |
| 19 | 5-(3-fluoro-1-methyl-1H-pyrazol-4-yl)-2-{3-[methyl(2,2,6,6-tetramethylpiperidin-4-yl)amino]-1,2,4-triazin-6-yl}phenol hydrochloride |
| 20 | 2-{3-[methyl(piperidin-4-yl)amino]-1,2,4-triazin-6-yl}-5-(1H-pyrazol-4-yl)phenol dihydrochloride |
| 23 | 2-{3-[methyl(piperidin-3-yl)amino]-1,2,4-triazin-6-yl}-5-(1H-pyrazol-4-yl)phenol dihydrochloride |
| 24 | 2-{3-[methyl(2,2,6,6-tetramethylpiperidin-4-yl)amino]-1,2,4-triazin-6-yl}-5-(2-methyl-2H-1,2,3-triazol-4-yl)phenol hydrochloride |
| 50 | 5-(4-fluoro-1H-imidazol-1-yl)-2-{3-[methyl(2,2,6,6-tetramethylpiperidin-4-yl)amino]-1,2,4-triazin-6-yl}phenol dihydrochloride |
| 51 | 2-{3-[methyl(2,2,6,6-tetramethylpiperidin-4-yl)amino]-1,2,4-triazin-6-yl}-5-(3-methyl-1H-1,2,4-triazol-1-yl)phenol hydrochloride |
| 52 | 2-{3-[(1-methylpiperidin-4-yl)amino]-1,2,4-triazin-6-yl}-5-(1H-pyrazol-4-yl)phenol trihydrochloride |
| 55 | 5-(4-methoxy-1H-pyrazol-1-yl)-2-{3-[methyl(2,2,6,6-tetramethylpiperidin-4-yl)amino]-1,2,4-triazin-6-yl}phenol dihydrochloride |
| 57 | 5-(3-chloro-1H-pyrazol-4-yl)-2-{3-[methyl(2,2,6,6-tetramethylpiperidin-4-yl)amino]-1,2,4-triazin-6-yl}phenol hydrochloride |
| 58 | 2-{3-[methyl(2,2,6,6-tetramethylpiperidin-4-yl)amino]-1,2,4-triazin-6-yl}-5-(1,3-thiazol-2-yl)phenol hydrochloride |
| 59 | 5-(4-chloro-1H-imidazol-1-yl)-2-{3-[methyl(2,2,6,6-tetramethylpiperidin-4-yl)amino]-1,2,4-triazin-6-yl}phenol dihydrochloride |
| 60 | 2-{3-[methyl(2,2,6,6-tetramethylpiperidin-4-yl)amino]-1,2,4-triazin-6-yl}-5-(pyridazin-4-yl)phenol dihydrochloride |
| 61 | 5-(6-methylpyridazin-4-yl)-2-{3-[methyl(2,2,6,6-tetramethylpiperidin-4-yl)amino]-1,2,4-triazin-6-yl}phenol dihydrochloride |
| 62 | 2-{3-[methyl(2,2,6,6-tetramethylpiperidin-4-yl)amino]-1,2,4-triazin-6-yl}-5-(1-methyl-1H-1,2,4-triazol-3-yl)phenol dihydrochloride |
| 63 | 2-{3-[methyl(2,2,6,6-tetramethylpiperidin-4-yl)amino]-1,2,4-triazin-6-yl}-5-(2H-1,2,3-triazol-2-yl)phenol dihydrochloride |
| 65 | 2-{3-[methyl(2,2,6,6-tetramethylpiperidin-4-yl)amino]-1,2,4-triazin-6-yl}-5-(1,2,4-thiadiazol-5-yl)phenol hydrochloride |
| 66 | 2-{3-[methyl(2,2,6,6-tetramethylpiperidin-4-yl)amino]-1,2,4-triazin-6-yl}-5-(3-methyl-1,2,4-thiadiazol-5-yl)phenol hydrochloride |
| 67 | 2-{3-[(3-fluoro-2,2,6,6-tetramethylpiperidin-4-yl)(methyl)amino]-1,2,4-triazin-6-yl}-5-(1H-pyrazol-4-yl)phenol dihydrochloride |
| 68 | 1-[1-(3-hydroxy-4-{3-[methyl(2,2,6,6-tetramethylpiperidin-4-yl)amino]-1,2,4-triazin-6-yl}phenyl)-1H-pyrazol-4-yl]ethan-1-one dihydrochloride |
| 69 | 2-{3-[methyl(2,2,6,6-tetramethylpiperidin-4-yl)amino]-1,2,4-triazin-6-yl}-5-(4-methyl-2H-1,2,3-triazol-2-yl)phenol dihydrochloride |
| 71 | 2-{3-[methyl(2,2,6,6-tetramethylpiperidin-4-yl)amino]-1,2,4-triazin-6-yl}-5-(pyridin-2-yl)phenol formate |
| 72 | 5-(3-fluoro-1H-pyrazol-4-yl)-2-{3-[(2,2,6,6-tetramethylpiperidin-4-yl)oxy]-1,2,4-triazin-6-yl}phenol dihydrochloride |
| 73 | 5-(3-fluoro-1H-pyrazol-4-yl)-2-{3-[(2,2,6,6-tetramethylpiperidin-4-yl)amino]-1,2,4-triazin-6-yl}phenol trihydrochloride |
| 74 | 5-(2-methyl-1,3-oxazol-5-yl)-2-{3-[methyl(2,2,6,6-tetramethylpiperidin-4-yl)amino]-1,2,4-triazin-6-yl}phenol hydrochloride |
| 75 | 5-(1-methyl-1H-imidazol-4-yl)-2-{3-[methyl(2,2,6,6-tetramethylpiperidin-4-yl)amino]-1,2,4-triazin-6-yl}phenol hydrochloride |
| 76 | 5-(1-methyl-1H-pyrazol-3-yl)-2-{3-[methyl(2,2,6,6-tetramethylpiperidin-4-yl)amino]-1,2,4-triazin-6-yl}phenol hydrochloride |
| 77 | 2-(3-{[(1R,3s,5S)-9-methyl-9-azabicyclo[3.3.1]nonan-3-yl]amino}-1,2,4-triazin-6-yl)-5-(1H-pyrazol-4-yl)phenol dihydrochloride |
| 79 | 2-{3-[methyl(2,2,6,6-tetramethylpiperidin-4-yl)amino]-1,2,4-triazin-6-yl}-5-(1H-1,2,4-triazol-1-yl)phenol dihydrochloride |
| 80 | 5-(imidazo[1,2-a]pyrazin-6-yl)-2-{3-[methyl(2,2,6,6-tetramethylpiperidin-4-yl)amino]-1,2,4-triazin-6-yl}phenol dihydrochloride |
| 81 | 5-(5-methyl-1,3,4-oxadiazol-2-yl)-2-{3-[methyl(2,2,6,6-tetramethylpiperidin-4-yl)amino]-1,2,4-triazin-6-yl}phenol hydrochloride |
| 82 | 2-{3-[(2,6-dimethylpiperidin-4-yl)oxy]-1,2,4-triazin-6-yl}-5-(1H-pyrazol-4-yl)phenol dihydrochloride |
| 84 | 2-{3-[methyl(2,2,6,6-tetramethylpiperidin-4-yl)amino]-1,2,4-triazin-6-yl}-5-(pyridazin-3-yl)phenol formate |

-continued

| Cpd | Name |
|---|---|
| 86 | 2-{3-[methyl(2,2,6,6-tetramethylpiperidin-4-yl)amino]-1,2,4-triazin-6-yl}-5-(pyrimidin-5-yl)phenol formate |
| 88 | 5-(4-methoxy-1,3,5-triazin-2-yl)-2-{3-[methyl(2,2,6,6-tetramethylpiperidin-4-yl)amino]-1,2,4-triazin-6-yl}phenol dihydrochloride |
| 89 | 5-(1H-imidazol-1-yl)-2-{3-[methyl(2,2,6,6-tetramethylpiperidin-4-yl)amino]-1,2,4-triazin-6-yl}phenol dihydrochloride |
| 90 | 1-(3-hydroxy-4-{3-[methyl(2,2,6,6-tetramethylpiperidin-4-yl)amino]-1,2,4-triazin-6-yl}phenyl)-1H-pyrazol-4-ol dihydrochloride |
| 91 | 2-{3-[methyl(2,2,6,6-tetramethylpiperidin-4-yl)amino]-1,2,4-triazin-6-yl}-5-(1,3-oxazol-5-yl)phenol hydrochloride |
| 92 | 5-(imidazo[1,2-b]pyridazin-6-yl)-2-{3-[methyl(2,2,6,6-tetramethylpiperidin-4-yl)amino]-1,2,4-triazin-6-yl}phenol hydrochloride |
| 93 | 5-(4-fluoro-1H-pyrazol-1-yl)-2-{3-[methyl(2,2,6,6-tetramethylpiperidin-4-yl)amino]-1,2,4-triazin-6-yl}phenol dihydrochloride |
| 94 | 5-(4-methyl-1H-pyrazol-1-yl)-2-{3-[methyl(2,2,6,6-tetramethylpiperidin-4-yl)amino]-1,2,4-triazin-6-yl}phenol dihydrochloride |
| 95 | 2-[3-(2,7-diazaspiro[3.5]nonan-7-yl)-1,2,4-triazin-6-yl]-5-(1H-pyrazol-4-yl)phenol dihydrochloride |
| 96 | 2-[3-(2,7-diazaspiro[3.5]nonan-2-yl)-1,2,4-triazin-6-yl]-5-(1H-pyrazol-4-yl)phenol dihydrochloride |
| 97 | 5-(1H-indazol-5-yl)-2-{3-[methyl(2,2,6,6-tetramethylpiperidin-4-yl)amino]-1,2,4-triazin-6-yl}phenol dihydrochloride |
| 99 | 2-{3-[methyl(2,2,6,6-tetramethylpiperidin-4-yl)amino]-1,2,4-triazin-6-yl}-5-(4-nitro-2H-1,2,3-triazol-2-yl)phenol dihydrochloride |
| 101 | 5-(1-cyclopropyl-1H-pyrazol-4-yl)-2-{3-[methyl(2,2,6,6-tetramethylpiperidin-4-yl)amino]-1,2,4-triazin-6-yl}phenol hydrochloride |
| 102 | 2-{3-[methyl(2,2,6,6-tetramethylpiperidin-4-yl)amino]-1,2,4-triazin-6-yl}-5-(pyrimidin-4-yl)phenol formate |
| 103 | 4-{3-[methyl(2,2,6,6-tetramethylpiperidin-4-yl)amino]-1,2,4-triazin-6-yl}[1,1'-biphenyl]-3,4'-diol formate |
| 105 | 6-{3-[methyl(2,2,6,6-tetramethylpiperidin-4-yl)amino]-1,2,4-triazin-6-yl}quinolin-7-ol hydrobromide |
| 107 | 5-(1H-pyrazol-3-yl)-2-{3-[(2,2,6,6-tetramethylpiperidin-4-yl)oxy]-1,2,4-triazin-6-yl}phenol ditrifluoroacetate |
| 108 | 5-(1-methyl-1H-pyrazol-3-yl)-2-{3-[(2,2,6,6-tetramethylpiperidin-4-yl)oxy]-1,2,4-triazin-6-yl}phenol trifluoroacetate |
| 109 | 2-[3-(2,6-diazaspiro[3.5]nonan-2-yl)-1,2,4-triazin-6-yl]-5-(1H-pyrazol-4-yl)phenol dihydrochloride |
| 110 | 2-[3-(2,6-diazaspiro[3.4]octan-6-yl)-1,2,4-triazin-6-yl]-5-(1H-pyrazol-4-yl)phenol dihydrochloride |
| 111 | 2-{3-[methyl(2,2,6,6-tetramethylpiperidin-4-yl)amino]-1,2,4-triazin-6-yl}-5-(1H-pyrazol-3-yl)phenol trifluoroacetate |
| 112 | 5-(5-fluoropyrimidin-2-yl)-2-{3-[methyl(2,2,6,6-tetramethylpiperidin-4-yl)amino]-1,2,4-triazin-6-yl}phenol hydrochloride |
| 113 | 2-[3-(1-methyl-1,7-diazaspiro[3.5]nonan-7-yl)-1,2,4-triazin-6-yl]-5-(1H-pyrazol-4-yl)phenol dihydrochloride |
| 114 | 2-{3-[(3S)-3-(methylamino)pyrrolidin-1-yl]-1,2,4-triazin-6-yl}-5-(1H-pyrazol-4-yl)phenol dihydrochloride |
| 115 | 2-{3-[(7S)-7-amino-5-azaspiro[2.4]heptan-5-yl]-1,2,4-triazin-6-yl}-5-(1H-pyrazol-4-yl)phenol dihydrochloride |
| 116 | 2-{3-[(8aS)-hexahydropyrrolo[1,2-a]pyrazin-2(1H)-yl]-1,2,4-triazin-6-yl}-5-(1H-pyrazol-4-yl)phenol dihydrochloride |
| 117 | 2-{3-[(3aR,6aR)-1-methylhexahydropyrrolo[3,4-b]pyrrol-5(1H)-yl]-1,2,4-triazin-6-yl}-5-(1H-pyrazol-4-yl)phenol dihydrochloride |
| 118 | 2-[3-(2,6-diazaspiro[3.3]heptan-2-yl)-1,2,4-triazin-6-yl]-5-(1H-pyrazol-4-yl)phenol dihydrochloride |
| 119 | 2-{3-[methyl(2,2,6,6-tetramethylpiperidin-4-yl)amino]-1,2,4-triazin-6-yl}-5-(5-methyl-2H-tetrazol-2-yl)phenol dihydrochloride |
| 120 | 2-(3-{[(2R,4s,6S)-2,6-diethylpiperidin-4-yl]oxy}-1,2,4-triazin-6-yl)-5-(1H-pyrazol-4-yl)phenol trifluoroacetate |
| 121 | 2-{3-[(2,2,6,6-tetramethylpiperidin-4-yl)amino]-1,2,4-triazin-6-yl}-5-(2H-1,2,3-triazol-2-yl)phenol dihydrochloride |
| 122 | 2-{3-[(2,2,6,6-tetramethylpiperidin-4-yl)oxy]-1,2,4-triazin-6-yl}-5-(2H-1,2,3-triazol-2-yl)phenol hydrochloride |
| 123 | 5-(6-chloropyridazin-3-yl)-2-{3-[methyl(2,2,6,6-tetramethylpiperidin-4-yl)amino]-1,2,4-triazin-6-yl}phenol hydrochloride |
| 124 | 5-(1-methyl-1H-pyrazol-5-yl)-2-{3-[methyl(2,2,6,6-tetramethylpiperidin-4-yl)amino]-1,2,4-triazin-6-yl}phenol dihydrochloride |
| 126 | 2-{3-[(3-fluoro-2,2,6,6-tetramethylpiperidin-4-yl)amino]-1,2,4-triazin-6-yl}-5-(1H-pyrazol-4-yl)phenol dihydrochloride |
| 127 | 2-{3-[6-(diethylamino)-3-azabicyclo[3.1.0]hexan-3-yl]-1,2,4-triazin-6-yl}-5-(1H-pyrazol-4-yl)phenol hydrochloride |
| 128 | 5-(5-methylpyrimidin-2-yl)-2-{3-[methyl(2,2,6,6-tetramethylpiperidin-4-yl)amino]-1,2,4-triazin-6-yl}phenol hydrochloride |
| 129 | 5-(4-methylpyrimidin-2-yl)-2-{3-[methyl(2,2,6,6-tetramethylpiperidin-4-yl)amino]-1,2,4-triazin-6-yl}phenol hydrochloride |

-continued

| Cpd | Name |
|---|---|
| 130 | 5-(2-chloropyrimidin-4-yl)-2-{3-[methyl(2,2,6,6-tetramethylpiperidin-4-yl)amino]-1,2,4-triazin-6-yl}phenol hydrochloride |
| 132 | 2-{3-[methyl(2,2,6,6-tetramethylpiperidin-4-yl)amino]-1,2,4-triazin-6-yl}-5-(1H-pyrazolo[3,4-b]pyridin-5-yl)phenol formate |
| 133 | 5-(3-chloro-1H-1,2,4-triazol-1-yl)-2-{3-[methyl(2,2,6,6-tetramethylpiperidin-4-yl)amino]-1,2,4-triazin-6-yl}phenol dihydrochloride |
| 134 | 6-(3-hydroxy-4-{3-[methyl(2,2,6,6-tetramethylpiperidin-4-yl)amino]-1,2,4-triazin-6-yl}phenyl)pyridazin-3-ol hydrochloride |
| 140 | 1-[1-(3-hydroxy-4-{3-[methyl(2,2,6,6-tetramethylpiperidin-4-yl)amino]-1,2,4-triazin-6-yl}phenyl)-1H-imidazol-4-yl]ethan-1-one dihydrochloride |
| 141 | 5-(2,8-dimethylimidazo[1,2-b]pyridazin-6-yl)-2-{3-[methyl(2,2,6,6-tetramethylpiperidin-4-yl)amino]-1,2,4-triazin-6-yl}phenol dihydrochloride |
| 142 | 5-(2-methylimidazo[1,2-b]pyridazin-6-yl)-2-{3-[methyl(2,2,6,6-tetramethylpiperidin-4-yl)amino]-1,2,4-triazin-6-yl}phenol dihydrochloride |
| 143 | 2-{3-[methyl(2,2,6,6-tetramethylpiperidin-4-yl)amino]-1,2,4-triazin-6-yl}-5-(2-methyl-2H-tetrazol-5-yl)phenol dihydrochloride |
| 146 | 6-(3-hydroxy-4-{3-[methyl(2,2,6,6-tetramethylpiperidin-4-yl)amino]-1,2,4-triazin-6-yl}phenyl)-3-methylpyrimidin-4(3H)-one dihydrochloride |
| 147 | 5-(3-hydroxy-4-{3-[methyl(2,2,6,6-tetramethylpiperidin-4-yl)amino]-1,2,4-triazin-6-yl}phenyl)-2-methylpyridazin-3(2H)-one dihydrochloride |
| 148 | 2-(3-{3-[(propan-2-yl)amino]pyrrolidin-1-yl}-1,2,4-triazin-6-yl)-5-(1H-pyrazol-4-yl)phenol hydrochloride |
| 151 | 2-[3-(2,7-diazaspiro[3.5]nonan-2-yl)-1,2,4-triazin-6-yl]-5-(3-fluoro-1H-pyrazol-4-yl)phenol dihydrochloride |
| 152 | 2-{3-[methyl(2,2,6,6-tetramethylpiperidin-4-yl)amino]-1,2,4-triazin-6-yl}-5-([1,2,3]triazolo[1,5-a]pyridin-5-yl)phenol dihydrochloride |
| 153 | 5-(3-fluoro-1H-pyrazol-4-yl)-2-{3-[(3aS,7aR)-1-methyloctahydro-5H-pyrrolo[3,2-c]pyridin-5-yl]-1,2,4-triazin-6-yl}phenol dihydrochloride |
| 155 | 2-{3-[methyl(2,2,6,6-tetramethylpiperidin-4-yl)amino]-1,2,4-triazin-6-yl}-5-(tetrazolo[1,5-a]pyridin-7-yl)phenol dihydrochloride |
| 156 | 5-(4-fluoro-1H-pyrazol-3-yl)-2-{3-[methyl(2,2,6,6-tetramethylpiperidin-4-yl)amino]-1,2,4-triazin-6-yl}phenol trifluoroacetate |
| 157 | 2-(3-{3-[(adamantan-1-yl)amino]pyrrolidin-1-yl}-1,2,4-triazin-6-yl)-5-(1H-pyrazol-4-yl)phenol ditrifluoroacetate |
| 158 | 2-{3-[methyl(2,2,6,6-tetramethylpiperidin-4-yl)amino]-1,2,4-triazin-6-yl}-5-(5H-pyrrolo[2,3-b]pyrazin-2-yl)phenol formate |
| 159 | 2-(3-{3-[(adamantan-2-yl)amino]pyrrolidin-1-yl}-1,2,4-triazin-6-yl)-5-(1H-pyrazol-4-yl)phenol ditrifluoroacetate |
| 160 | 2-(3-{3-[(3,5-dimethyladamantan-1-yl)amino]pyrrolidin-1-yl}-1,2,4-triazin-6-yl)-5-(1H-pyrazol-4-yl)phenol ditrifluoroacetate |
| 161 | 5-[4-(hydroxymethyl)-1H-pyrazol-1-yl]-2-{3-[methyl(2,2,6,6-tetramethylpiperidin-4-yl)amino]-1,2,4-triazin-6-yl}phenol hydrochloride |
| 162 | 2-{3-[(3aR,4R,6aS)-4-(dimethylamino)hexahydrocyclopenta[c]pyrrol-2(1H)-yl]-1,2,4-triazin-6-yl}-5-(1H-pyrazol-4-yl)phenol dihydrochloride |
| 164 | 5-(1-methyl-1H-imidazo[4,5-b]pyridin-5-yl)-2-{3-[methyl(2,2,6,6-tetramethylpiperidin-4-yl)amino]-1,2,4-triazin-6-yl}phenol hydrochloride |
| 165 | 2-{3-[(3aR,4S,6aS)-4-aminohexahydrocyclopenta[c]pyrrol-2(1H)-yl]-1,2,4-triazin-6-yl}-5-(1H-pyrazol-4-yl)phenol dihydrochloride |
| 166 | 2-[3-(5-methyloctahydro-2H-pyrrolo[3,4-c]pyridin-2-yl)-1,2,4-triazin-6-yl]-5-(1H-pyrazol-4-yl)phenol dihydrochloride |
| 167 | 2-{3-[(3aR,4S,6aS)-4-(dimethylamino)hexahydrocyclopenta[c]pyrrol-2(1H)-yl]-1,2,4-triazin-6-yl}-5-(1H-pyrazol-4-yl)phenol dihydrochloride |
| 168 | 3-amino-6-(3-hydroxy-4-{3-[methyl(2,2,6,6-tetramethylpiperidin-4-yl)amino]-1,2,4-triazin-6-yl}phenyl)-4-methylpyridin-2-ol dihydrochloride |
| 169 | 5-(2,7-dimethyl[1,3]oxazolo[5,4-b]pyridin-5-yl)-2-{3-[methyl(2,2,6,6-tetramethylpiperidin-4-yl)amino]-1,2,4-triazin-6-yl}phenol diformate |
| 172 | 5-[4-(hydroxymethyl)-2H-1,2,3-triazol-2-yl]-2-{3-[methyl(2,2,6,6-tetramethylpiperidin-4-yl)amino]-1,2,4-triazin-6-yl}phenol hydrochloride |
| 173 | 2-{3-[methyl(2,2,6,6-tetramethylpiperidin-4-yl)amino]-1,2,4-triazin-6-yl}-5-(3-methyl-3H-[1,2,3]triazolo[4,5-b]pyridin-5-yl)phenol hydrochloride |
| 174 | 2-{3-[3-(tert-butylamino)pyrrolidin-1-yl]-1,2,4-triazin-6-yl}-5-(3-fluoro-1H-pyrazol-4-yl)phenol hydrochloride |
| 175 | 2-{3-[3-(tert-butylamino)pyrrolidin-1-yl]-1,2,4-triazin-6-yl}-5-(1-methyl-1H-pyrazol-3-yl)phenol trifluoroacetate |
| 176 | 5-(1-methyl-1H-pyrazolo[3,4-b]pyridin-5-yl)-2-{3-[methyl(2,2,6,6-tetramethylpiperidin-4-yl)amino]-1,2,4-triazin-6-yl}phenol formate |
| 177 | 5-(1-methyl-1H-indazol-5-yl)-2-{3-[methyl(2,2,6,6-tetramethylpiperidin-4-yl)amino]-1,2,4-triazin-6-yl}phenol formate |
| 178 | 2-{3-[methyl(2,2,6,6-tetramethylpiperidin-4-yl)amino]-1,2,4-triazin-6-yl}-5-(tetrazolo[1,5-b]pyridazin-6-yl)phenol dihydrochloride |
| 179 | 5-[6-(hydroxymethyl)pyrimidin-4-yl]-2-{3-[methyl(2,2,6,6-tetramethylpiperidin-4-yl)amino]-1,2,4-triazin-6-yl}phenol hydrochloride |
| 180 | 2-[3-(2,9-diazaspiro[5.5]undecan-9-yl)-1,2,4-triazin-6-yl]-5-(1H-pyrazol-4-yl)phenol dihydrochloride |
| 181 | 2-[3-(2,8-diazaspiro[4.5]decan-8-yl)-1,2,4-triazin-6-yl]-5-(1H-pyrazol-4-yl)phenol dihydrochloride |

| Cpd | Name |
|---|---|
| 182 | 2-[3-(2-methyl-2,9-diazaspiro[5.5]undecan-9-yl)-1,2,4-triazin-6-yl]-5-(1H-pyrazol-4-yl)phenol dihydrochloride |
| 183 | 2-[3-(2-methyl-2,8-diazaspiro[4.5]decan-8-yl)-1,2,4-triazin-6-yl]-5-(1H-pyrazol-4-yl)phenol dihydrochloride |
| 184 | 2-{3-[methyl(2,2,6,6-tetramethylpiperidin-4-yl)amino]-1,2,4-triazin-6-yl}-5-(1H-pyrazolo[3,4-c]pyridin-5-yl)phenol formate |
| 185 | 2-{3-[methyl(2,2,6,6-tetramethylpiperidin-4-yl)amino]-1,2,4-triazin-6-yl}-5-(quinolin-6-yl)phenol trifluoroacetate |
| 186 | 2-{3-[methyl(2,2,6,6-tetramethylpiperidin-4-yl)amino]-1,2,4-triazin-6-yl}-5-(1-methyl-1H-[1,2,3]triazolo[4,5-b]pyridin-5-yl)phenol hydrochloride |
| 187 | 2-{3-[3-(tert-butylamino)pyrrolidin-1-yl]-1,2,4-triazin-6-yl}-5-(1H-imidazol-1-yl)phenol ditrifluoroacetate |
| 188 | 5-(2H-1,3-benzodioxol-5-yl)-2-{3-[methyl(2,2,6,6-tetramethylpiperidin-4-yl)amino]-1,2,4-triazin-6-yl}phenol dihydrochloride |
| 189 | 5-(3-fluoro-1H-pyrazol-4-yl)-2-(3-{[(3R,4R)-3-fluoro-2,2,6,6-tetramethylpiperidin-4-yl]amino}-1,2,4-triazin-6-yl)phenol dihydrochloride |
| 190 | 2-(3-{[(2S)-2-aminopropyl](methyl)amino}-1,2,4-triazin-6-yl)-5-(1H-pyrazol-4-yl)phenol dihydrochloride |
| 191 | 5-(5-fluoro-1H-pyrazol-4-yl)-2-{6-[methyl(2,2,6,6-tetramethylpiperidin-4-yl)amino]-1,2,4-triazin-3-yl}phenol hydrochloride |
| 193 | 2-{3-[(3aR,4R,6aS)-4-(tert-butylamino)hexahydrocyclopenta[c]pyrrol-2(1H)-yl]-1,2,4-triazin-6-yl}-5-(1H-pyrazol-4-yl)phenol dihydrochloride |
| 194 | 2-{3-[methyl(2,2,6,6-tetramethylpiperidin-4-yl)amino]-1,2,4-triazin-6-yl}-5-(1H-pyrazolo[3,4-b]pyrazin-5-yl)phenol formate |
| 195 | 2-{3-[methyl(2,2,6,6-tetramethylpiperidin-4-yl)amino]-1,2,4-triazin-6-yl}-5-(1H-pyrazolo[4,3-d]pyrimidin-5-yl)phenol formate |
| 196 | 5-(1-methyl-1H-pyrazol-4-yl)-2-{6-[methyl(2,2,6,6-tetramethylpiperidin-4-yl)amino]-1,2,4-triazin-3-yl}phenol hydrochloride |
| 197 | 2-{3-[3-(tert-butylamino)pyrrolidin-1-yl]-1,2,4-triazin-6-yl}-5-(4-methyl-1H-imidazol-1-yl)phenol ditrifluoroacetate |
| 198 | 5-(1-methyl-1H-pyrazolo[4,3-b]pyridin-5-yl)-2-{3-[methyl(2,2,6,6-tetramethylpiperidin-4-yl)amino]-1,2,4-triazin-6-yl}phenol formate |
| 199 | 5-(1-methyl-1H-pyrazol-4-yl)-2-{3-[(2,2,6,6-tetramethylpiperidin-4-yl)amino]-1,2,4-triazin-6-yl}phenol hydrochloride |
| 200 | 5-(1-methyl-1H-benzotriazol-5-yl)-2-{3-[methyl(2,2,6,6-tetramethylpiperidin-4-yl)amino]-1,2,4-triazin-6-yl}phenol hydrochloride |
| 202 | 2-{3-[3-(tert-butylamino)pyrrolidin-1-yl]-1,2,4-triazin-6-yl}-5-(1-methyl-1H-pyrazol-4-yl)phenol hydrochloride |
| 203 | 5-(1-methyl-1H-pyrazol-4-yl)-2-(3-{3-[(propan-2-yl)amino]pyrrolidin-1-yl}-1,2,4-triazin-6-yl)phenol hydrochloride |
| 204 | 2-{3-[3-(tert-butylamino)pyrrolidin-1-yl]-1,2,4-triazin-6-yl}-5-(2H-1,2,3-triazol-2-yl)phenol hydrochloride |
| 205 | 2-{3-[3-(methylamino)pyrrolidin-1-yl]-1,2,4-triazin-6-yl}-5-(1-methyl-1H-pyrazol-4-yl)phenol hydrochloride |
| 206 | 2-{3-[4-(tert-butylamino)piperidin-1-yl]-1,2,4-triazin-6-yl}-5-(1H-pyrazol-4-yl)phenol trifluoroacetate |
| 207 | 2-{3-[3-(tert-butylamino)pyrrolidin-1-yl]-1,2,4-triazin-6-yl}-5-([1,2,3]triazolo[1,5-a]pyridin-5-yl)phenol dihydrochloride |
| 208 | 2-{3-[3-(tert-butylamino)pyrrolidin-1-yl]-1,2,4-triazin-6-yl}-5-(1-methyl-1H-indazol-5-yl)phenol dihydrochloride |
| 209 | 2-{3-[3-(tert-butylamino)pyrrolidin-1-yl]-1,2,4-triazin-6-yl}-5-(pyrimidin-2-yl)phenol dihydrochloride |
| 210 | 2-{3-[3-(tert-butylamino)pyrrolidin-1-yl]-1,2,4-triazin-6-yl}-5-(2-methyl-2H-1,2,3-triazol-4-yl)phenol dihydrochloride |
| 211 | 2-{3-[3-(tert-butylamino)pyrrolidin-1-yl]-1,2,4-triazin-6-yl}-5-(2-methyl-2H-tetrazol-5-yl)phenol dihydrochloride |
| 212 | 2-{3-[3-(tert-butylamino)piperidin-1-yl]-1,2,4-triazin-6-yl}-5-(1H-pyrazol-4-yl)phenol trifluoroacetate |
| 213 | 5-(1-methyl-1H-pyrazol-3-yl)-2-(3-{3-[(propan-2-yl)amino]pyrrolidin-1-yl}-1,2,4-triazin-6-yl)phenol hydrochloride |
| 214 | 4-(4-{3-[3-(tert-butylamino)pyrrolidin-1-yl]-1,2,4-triazin-6-yl}-3-hydroxyphenyl)-1-methylpyridin-2(1H)-one hydrochloride |
| 215 | 2-{3-[3-(tert-butylamino)pyrrolidin-1-yl]-1,2,4-triazin-6-yl}-5-(1-methyl-1H-[1,2,3]triazolo[4,5-b]pyridin-5-yl)phenol hydrochloride |
| 216 | 6-(4-{3-[3-(tert-butylamino)pyrrolidin-1-yl]-1,2,4-triazin-6-yl}-3-hydroxyphenyl)-3-methylpyrimidin-4(3H)-one hydrochloride |
| 217 | 2-{3-[3-(tert-butylamino)pyrrolidin-1-yl]-1,2,4-triazin-6-yl}-5-(6-methoxypyrimidin-4-yl)phenol ditrifluoroacetate |
| 218 | 2-{3-[3-(methylamino)pyrrolidin-1-yl]-1,2,4-triazin-6-yl}-5-(2H-1,2,3-triazol-2-yl)phenol trihydrochloride |
| 219 | 5-(4-fluoro-1H-pyrazol-1-yl)-2-{3-[3-(methylamino)pyrrolidin-1-yl]-1,2,4-triazin-6-yl}phenol trihydrochloride |
| 220 | 5-(1H-imidazol-1-yl)-2-{3-[3-(methylamino)pyrrolidin-1-yl]-1,2,4-triazin-6-yl}phenol trihydrochloride |
| 221 | 2-{3-[3-(tert-butylamino)pyrrolidin-1-yl]-1,2,4-triazin-6-yl}-5-(1-methyl-1H-pyrazolo[3,4-b]pyridin-5-yl)phenol dihydrochloride |

| Cpd | Name |
|---|---|
| 222 | 5-(1-methyl-1H-pyrazolo[3,4-c]pyridin-5-yl)-2-{3-[methyl(2,2,6,6-tetramethylpiperidin-4-yl)amino]-1,2,4-triazin-6-yl}phenol dihydrochloride |
| 223 | 2-[3-(7-methyl-2,7-diazaspiro[3.5]nonan-2-yl)-1,2,4-triazin-6-yl]-5-(1-methyl-1H-indazol-5-yl)phenol trifluoroacetate |
| 224 | 2-[3-(7-methyl-2,7-diazaspiro[3.5]nonan-2-yl)-1,2,4-triazin-6-yl]-5-(1-methyl-1H-pyrazolo[3,4-b]pyridin-5-yl)phenol trifluoroacetate |
| 226 | 2-[3-(7-methyl-2,7-diazaspiro[3.5]nonan-2-yl)-1,2,4-triazin-6-yl]-5-(1-methyl-1H-pyrazol-4-yl)phenol trifluoroacetate |
| 227 | 4-[3-hydroxy-4-(3-{3-[(propan-2-yl)amino]pyrrolidin-1-yl}-1,2,4-triazin-6-yl)phenyl]-1-methylpyridin-2(1H)-one hydrochloride |
| 228 | 2-[3-(7-methyl-2,7-diazaspiro[3.5]nonan-2-yl)-1,2,4-triazin-6-yl]-5-(4-methyl-1H-imidazol-1-yl)phenol hydrochloride |
| 229 | 5-(4-fluoro-1H-pyrazol-1-yl)-2-[3-(7-methyl-2,7-diazaspiro[3.5]nonan-2-yl)-1,2,4-triazin-6-yl]phenol hydrochloride |
| 230 | 5-(4-fluoro-1H-imidazol-1-yl)-2-[3-(7-methyl-2,7-diazaspiro[3.5]nonan-2-yl)-1,2,4-triazin-6-yl]phenol hydrochloride |
| 231 | 5-(1H-imidazol-1-yl)-2-[3-(7-methyl-2,7-diazaspiro[3.5]nonan-2-yl)-1,2,4-triazin-6-yl]phenol hydrochloride |
| 232 | 2-[3-(7-methyl-2,7-diazaspiro[3.5]nonan-2-yl)-1,2,4-triazin-6-yl]-5-(2H-1,2,3-triazol-2-yl)phenol hydrochloride |
| 233 | 2-[3-(7-methyl-2,7-diazaspiro[3.5]nonan-2-yl)-1,2,4-triazin-6-yl]-5-(1-methyl-1H-pyrazol-3-yl)phenol hydrochloride |
| 234 | 6-[3-hydroxy-4-(3-{3-[(propan-2-yl)amino]pyrrolidin-1-yl}-1,2,4-triazin-6-yl)phenyl]-3-methylpyrimidin-4(3H)-one hydrochloride |
| 235 | 5-(5-fluoro-1H-pyrazol-4-yl)-2-(3-{3-[(propan-2-yl)amino]pyrrolidin-1-yl}-1,2,4-triazin-6-yl)phenol hydrochloride |
| 236 | 5-(2-methyl-2H-1,2,3-triazol-4-yl)-2-(3-{3-[(propan-2-yl)amino]pyrrolidin-1-yl}-1,2,4-triazin-6-yl)phenol hydrochloride |
| 237 | 2-(3-{3-[(propan-2-yl)amino]pyrrolidin-1-yl}-1,2,4-triazin-6-yl)-5-(1,2,4-thiadiazol-5-yl)phenol hydrochloride |
| 238 | 2-(3-{[(3S,4S)-3-fluoro-2,2,6,6-tetramethylpiperidin-4-yl]amino}-1,2,4-triazin-6-yl)-5-(1H-imidazol-1-yl)phenol dihydrochloride |
| 239 | 2-(3-{[(3S,4S)-3-fluoro-2,2,6,6-tetramethylpiperidin-4-yl]amino}-1,2,4-triazin-6-yl)-5-(4-methyl-1H-imidazol-1-yl)phenol dihydrochloride |
| 240 | 5-(4-fluoro-1H-imidazol-1-yl)-2-(3-{[(3S,4S)-3-fluoro-2,2,6,6-tetramethylpiperidin-4-yl]amino}-1,2,4-triazin-6-yl)phenol dihydrochloride |
| 241 | 4-{3-hydroxy-4-[3-(7-methyl-2,7-diazaspiro[3.5]nonan-2-yl)-1,2,4-triazin-6-yl]phenyl}-1-methylpyridin-2(1H)-one hydrochloride |
| 242 | 2-[3-(7-methyl-2,7-diazaspiro[3.5]nonan-2-yl)-1,2,4-triazin-6-yl]-5-(2-methyl-2H-1,2,3-triazol-4-yl)phenol trifluoroacetate |
| 243 | 5-(6-methoxypyrimidin-4-yl)-2-[3-(7-methyl-2,7-diazaspiro[3.5]nonan-2-yl)-1,2,4-triazin-6-yl]phenol ditrifluoroacetate |
| 244 | 2-[3-(7-methyl-2,7-diazaspiro[3.5]nonan-2-yl)-1,2,4-triazin-6-yl]-5-(pyrimidin-2-yl)phenol trifluoroacetate |
| 245 | 2-[3-(7-methyl-2,7-diazaspiro[3.5]nonan-2-yl)-1,2,4-triazin-6-yl]-5-(1H-1,2,3-triazol-4-yl)phenol trifluoroacetate |
| 246 | 6-[4-(3-{[(3S,4S)-3-fluoro-2,2,6,6-tetramethylpiperidin-4-yl]amino}-1,2,4-triazin-6-yl)-3-hydroxyphenyl]-3-methylpyrimidin-4(3H)-one dihydrochloride |
| 247 | 2-(3-{[(3S,4S)-3-fluoro-2,2,6,6-tetramethylpiperidin-4-yl]amino}-1,2,4-triazin-6-yl)-5-(1H-1,2,3-triazol-4-yl)phenol dihydrochloride |
| 249 | 2-(3-{[(3S,4S)-3-fluoro-2,2,6,6-tetramethylpiperidin-4-yl]amino}-1,2,4-triazin-6-yl)-5-(imidazo[1,2-b]pyridazin-6-yl)phenol dihydrochloride |
| 250 | 2-{3-[3-(tert-butylamino)pyrrolidin-1-yl]-1,2,4-triazin-6-yl}-5-(1,3-oxazol-2-yl)phenol hydrochloride |
| 251 | 2-[3-(7-methyl-2,7-diazaspiro[3.5]nonan-2-yl)-1,2,4-triazin-6-yl]-5-(2-methyl-2H-tetrazol-5-yl)phenol trifluoroacetate |
| 252 | 2-[3-(7-methyl-2,7-diazaspiro[3.5]nonan-2-yl)-1,2,4-triazin-6-yl]-5-(1,3-oxazol-2-yl)phenol trifluoroacetate |
| 253 | 5-(1-methyl-1H-pyrazol-3-yl)-2-{3-[(2,2,6,6-tetramethylpiperidin-4-yl)amino]-1,2,4-triazin-6-yl}phenol formate |
| 254 | 5-(6-methoxypyrimidin-4-yl)-2-{3-[(2,2,6,6-tetramethylpiperidin-4-yl)amino]-1,2,4-triazin-6-yl}phenol formate |
| 256 | 5-(imidazo[1,2-b]pyridazin-6-yl)-2-[3-(7-methyl-2,7-diazaspiro[3.5]nonan-2-yl)-1,2,4-triazin-6-yl]phenol trifluoroacetate |
| 257 | 5-(imidazo[1,2-a]pyrazin-6-yl)-2-[3-(7-methyl-2,7-diazaspiro[3.5]nonan-2-yl)-1,2,4-triazin-6-yl]phenol hydrochloride |
| 258 | 2-(3-{3-[(propan-2-yl)amino]pyrrolidin-1-yl}-1,2,4-triazin-6-yl)-5-(1H-1,2,3-triazol-4-yl)phenol ditrifluoroacetate |
| 259 | 5-(2-methyl-2H-tetrazol-5-yl)-2-(3-{3-[(propan-2-yl)amino]pyrrolidin-1-yl}-1,2,4-triazin-6-yl)phenol trifluoroacetate |
| 260 | 2-(3-{[(3S,4S)-3-fluoro-2,2,6,6-tetramethylpiperidin-4-yl]amino}-1,2,4-triazin-6-yl)-5-(1-methyl-1H-indazol-5-yl)phenol dihydrochloride |
| 261 | 2-(3-{[(3S,4S)-3-fluoro-2,2,6,6-tetramethylpiperidin-4-yl]amino}-1,2,4-triazin-6-yl)-5-(1-methyl-1H-pyrazol-3-yl)phenol dihydrochloride |
| 262 | 2-[3-(3,5-dimethylpiperazin-1-yl)-1,2,4-triazin-6-yl]-5-(1H-pyrazol-4-yl)phenol dihydrochloride |

-continued

| Cpd | Name |
|---|---|
| 263 | 2-[3-(3,5-dimethylpiperazin-1-yl)-1,2,4-triazin-6-yl]-5-(1-methyl-1H-pyrazol-3-yl)phenol hydrochloride |
| 264 | 2-(3-{3-[(propan-2-yl)amino]pyrrolidin-1-yl}-1,2,4-triazin-6-yl)-5-(2H-1,2,3-triazol-2-yl)phenol hydrochloride |
| 265 | 5-(6-methoxypyrimidin-4-yl)-2-(3-{3-[(propan-2-yl)amino]pyrrolidin-1-yl}-1,2,4-triazin-6-yl)phenol hydrochloride |
| 266 | 5-(2-methyl-2H-1,2,3-triazol-4-yl)-2-{3-[(2,2,6,6-tetramethylpiperidin-4-yl)amino]-1,2,4-triazin-6-yl}phenol dihydrochloride |
| 267 | 5-(2-methyl-2H-tetrazol-5-yl)-2-{3-[(2,2,6,6-tetramethylpiperidin-4-yl)amino]-1,2,4-triazin-6-yl}phenol dihydrochloride |
| 268 | 5-(6-methoxypyrimidin-4-yl)-2-{3-[3-(methylamino)pyrrolidin-1-yl]-1,2,4-triazin-6-yl}phenol ditrifluoroacetate |
| 269 | 2-{3-[3-(methylamino)pyrrolidin-1-yl]-1,2,4-triazin-6-yl}-5-(1,2,4-thiadiazol-5-yl)phenol dihydrochloride |
| 270 | 2-{3-[3-(methylamino)pyrrolidin-1-yl]-1,2,4-triazin-6-yl}-5-(pyrimidin-2-yl)phenol dihydrochloride |
| 271 | 2-{3-[3-(methylamino)pyrrolidin-1-yl]-1,2,4-triazin-6-yl}-5-(1-methyl-1H-pyrazolo[3,4-b]pyridin-5-yl)phenol dihydrochloride |
| 272 | 2-[3-(7-methyl-2,7-diazaspiro[3.5]nonan-2-yl)-1,2,4-triazin-6-yl]-5-(1,2,4-thiadiazol-5-yl)phenol trifluoroacetate |
| 273 | 5-(1H-imidazol-1-yl)-2-{3-[(2,2,6,6-tetramethylpiperidin-4-yl)amino]-1,2,4-triazin-6-yl}phenol hydrochloride |
| 274 | 5-(4-methyl-1H-imidazol-1-yl)-2-{3-[(2,2,6,6-tetramethylpiperidin-4-yl)amino]-1,2,4-triazin-6-yl}phenol hydrochloride |
| 275 | 5-(4-fluoro-1H-imidazol-1-yl)-2-{3-[(2,2,6,6-tetramethylpiperidin-4-yl)amino]-1,2,4-triazin-6-yl}phenol hydrochloride |
| 276 | 5-(4-fluoro-1H-pyrazol-1-yl)-2-{3-[(2,2,6,6-tetramethylpiperidin-4-yl)amino]-1,2,4-triazin-6-yl}phenol hydrochloride |
| 277 | 5-(2-methyl-1,3-oxazol-5-yl)-2-{3-[(2,2,6,6-tetramethylpiperidin-4-yl)amino]-1,2,4-triazin-6-yl}phenol hydrochloride |
| 278 | 2-{3-[3-(tert-butylamino)-4-fluoropyrrolidin-1-yl]-1,2,4-triazin-6-yl}-5-(1H-pyrazol-4-yl)phenol hydrochloride |
| 279 | 5-(pyrimidin-2-yl)-2-{3-[(2,2,6,6-tetramethylpiperidin-4-yl)amino]-1,2,4-triazin-6-yl}phenol formate |
| 282 | 5-(1H-pyrazol-4-yl)-2-[3-(3,3,5,5-tetramethylpiperazin-1-yl)-1,2,4-triazin-6-yl]phenol dihydrochloride |
| 283 | 5-(imidazo[1,2-a]pyrazin-6-yl)-2-(3-{3-[(propan-2-yl)amino]pyrrolidin-1-yl}-1,2,4-triazin-6-yl)phenol hydrochloride |
| 284 | 2-(3-{[(3S,4S)-3-fluoro-2,2,6,6-tetramethylpiperidin-4-yl]amino}-1,2,4-triazin-6-yl)-5-(1-methyl-1H-pyrazolo[3,4-b]pyridin-5-yl)phenol dihydrochloride |
| 285 | 5-(1-methyl-1H-benzimidazol-5-yl)-2-{3-[methyl(2,2,6,6-tetramethylpiperidin-4-yl)amino]-1,2,4-triazin-6-yl}phenol formate |
| 287 | 2-(3-{[(3S,4S)-3-fluoro-2,2,6,6-tetramethylpiperidin-4-yl]amino}-1,2,4-triazin-6-yl)-5-(2-methyl-2H-1,2,3-triazol-4-yl)phenol trifluoroacetate |
| 288 | 2-(3-{[(3S,4S)-3-fluoro-2,2,6,6-tetramethylpiperidin-4-yl]amino}-1,2,4-triazin-6-yl)-5-(1,3-oxazol-2-yl)phenol trifluoroacetate |
| 289 | 5-(2-methyl-1,3-oxazol-5-yl)-2-(3-{3-[(propan-2-yl)amino]pyrrolidin-1-yl}-1,2,4-triazin-6-yl)phenol hydrochloride |
| 290 | 2-(3-{[(3S,4S)-3-fluoro-2,2,6,6-tetramethylpiperidin-4-yl]amino}-1,2,4-triazin-6-yl)-5-(6-methoxypyrimidin-4-yl)phenol trifluoroacetate |
| 291 | 2-(3-{[(3S,4S)-3-fluoro-2,2,6,6-tetramethylpiperidin-4-yl]amino}-1,2,4-triazin-6-yl)-5-(2-methyl-2H-tetrazol-5-yl)phenol trifluoroacetate |
| 292 | 2-(3-{[(3S,4S)-3-fluoro-2,2,6,6-tetramethylpiperidin-4-yl]amino}-1,2,4-triazin-6-yl)-5-(1,2,4-thiadiazol-5-yl)phenol trifluoroacetate |
| 293 | 2-(3-{[(3S,4S)-3-methoxy-2,2,6,6-tetramethylpiperidin-4-yl](methyl)amino}-1,2,4-triazin-6-yl)-5-(1H-pyrazol-4-yl)phenol dihydrochloride |
| 294 | 5-(imidazo[1,2-b]pyridazin-6-yl)-2-(3-{3-[(propan-2-yl)amino]pyrrolidin-1-yl}-1,2,4-triazin-6-yl)phenol hydrochloride |
| 295 | 2-{3-[3-(methylamino)pyrrolidin-1-yl]-1,2,4-triazin-6-yl}-5-(2-methyl-2H-1,2,3-triazol-4-yl)phenol dihydrochloride |
| 296 | 2-{3-[3-(methylamino)pyrrolidin-1-yl]-1,2,4-triazin-6-yl}-5-(1-methyl-1H-pyrazol-3-yl)phenol dihydrochloride |
| 297 | 2-(3-{3-[(2-methylpropyl)amino]pyrrolidin-1-yl}-1,2,4-triazin-6-yl)-5-(1H-pyrazol-4-yl)phenol dihydrochloride |
| 298 | (3S,4S)-4-({6-[2-hydroxy-4-(1H-pyrazol-4-yl)phenyl]-1,2,4-triazin-3-yl}amino)-2,2,6,6-tetramethylpiperidin-3-ol dihydrochloride |
| 299 | 2-[3-(7-methyl-2,7-diazaspiro[3.5]nonan-2-yl)-1,2,4-triazin-6-yl]-5-(2-methyl-1,3-oxazol-5-yl)phenol trifluoroacetate |
| 300 | 5-(7-fluoro-1-methyl-1H-benzimidazol-5-yl)-2-{3-[methyl(2,2,6,6-tetramethylpiperidin-4-yl)amino]-1,2,4-triazin-6-yl}phenol formate |
| 301 | 5-(6,7-difluoro-1H-benzimidazol-5-yl)-2-{3-[methyl(2,2,6,6-tetramethylpiperidin-4-yl)amino]-1,2,4-triazin-6-yl}phenol formate |
| 302 | 5-(6,7-difluoro-1-methyl-1H-benzimidazol-5-yl)-2-{3-[methyl(2,2,6,6-tetramethylpiperidin-4-yl)amino]-1,2,4-triazin-6-yl}phenol formate |
| 303 | 5-(8-methylimidazo[1,2-b]pyridazin-6-yl)-2-{3-[methyl(2,2,6,6-tetramethylpiperidin-4-yl)amino]-1,2,4-triazin-6-yl}phenol formate |

-continued

| Cpd | Name |
|---|---|
| 304 | 5-(8-methoxyimidazo[1,2-b]pyridazin-6-yl)-2-{3-[methyl(2,2,6,6-tetramethylpiperidin-4-yl)amino]-1,2,4-triazin-6-yl}phenol formate |
| 305 | 2-{3-[(2,2,6,6-tetramethylpiperidin-4-yl)amino]-1,2,4-triazin-6-yl}-5-(1,2,4-triazin-6-yl)phenol trifluoroacetate |
| 306 | 2-{3-[(4aS,7aS)-octahydro-6H-pyrrolo[3,4-b]pyridin-6-yl]-1,2,4-triazin-6-yl}-5-(1H-pyrazol-4-yl)phenol dihydrochloride |
| 307 | 5-(1-methyl-1H-pyrazolo[3,4-b]pyridin-5-yl)-2-(3-{3-[(propan-2-yl)amino]pyrrolidin-1-yl}-1,2,4-triazin-6-yl)phenol hydrochloride |
| 308 | 5-(1,3-oxazol-2-yl)-2-(3-{3-[(propan-2-yl)amino]pyrrolidin-1-yl}-1,2,4-triazin-6-yl)phenol hydrochloride |
| 309 | 2-(3-{[(3S)-1-methylpyrrolidin-3-yl]oxy}-1,2,4-triazin-6-yl)-5-(1H-pyrazol-4-yl)phenol hydrochloride |
| 310 | 2-{3-[(4aS,7aS)-1-methyloctahydro-6H-pyrrolo[3,4-b]pyridin-6-yl]-1,2,4-triazin-6-yl}-5-(1H-pyrazol-4-yl)phenol trihydrochloride |
| 311 | 2-{3-[(4aS,7aR)-4-methylhexahydropyrrolo[3,4-b][1,4]oxazin-6(2H)-yl]-1,2,4-triazin-6-yl}-5-(1H-pyrazol-4-yl)phenol trihydrochloride |
| 314 | 5-(pyridazin-4-yl)-2-{3-[(2,2,6,6-tetramethylpiperidin-4-yl)amino]-1,2,4-triazin-6-yl}phenol formate |
| 315 | 5-[(pyridin-3-yl)amino]-2-{3-[(2,2,6,6-tetramethylpiperidin-4-yl)amino]-1,2,4-triazin-6-yl}phenol formate |
| 316 | 2-(3-{3-[(1-fluoro-2-methylpropan-2-yl)amino]pyrrolidin-1-yl}-1,2,4-triazin-6-yl)-5-(1H-pyrazol-4-yl)phenol hydrochloride |
| 317 | 2-{3-[3-(ethylamino)pyrrolidin-1-yl]-1,2,4-triazin-6-yl}-5-(1H-pyrazol-4-yl)phenol dihydrochloride |
| 318 | 2-{3-[3-(dimethylamino)pyrrolidin-1-yl]-1,2,4-triazin-6-yl}-5-(1H-pyrazol-4-yl)phenol dihydroiodide |
| 319 | 5-(1-methyl-1H-indazol-5-yl)-2-{3-[(2,2,6,6-tetramethylpiperidin-4-yl)amino]-1,2,4-triazin-6-yl}phenol trihydrochloride |
| 320 | 2-{3-[3-(methylamino)pyrrolidin-1-yl]-1,2,4-triazin-6-yl}-5-(2-methyl-2H-tetrazol-5-yl)phenol trihydrochloride |
| 321 | 5-(1-methyl-1H-pyrazolo[3,4-b]pyridin-5-yl)-2-{3-[(2,2,6,6-tetramethylpiperidin-4-yl)amino]-1,2,4-triazin-6-yl}phenol trihydrochloride |
| 322 | 2-(3-{[(3S,4S)-3-fluoro-2,2,6,6-tetramethylpiperidin-4-yl]amino}-1,2,4-triazin-6-yl)-5-(1H-pyrazol-4-yl)phenol dihydrochloride |
| 323 | 2-(3-{[(3R,4R)-3-fluoro-2,2,6,6-tetramethylpiperidin-4-yl]amino}-1,2,4-triazin-6-yl)-5-(1H-pyrazol-4-yl)phenol dihydrochloride |
| 324 | 2-{3-[(3-fluoro-2,2,6,6-tetramethylpiperidin-4-yl)amino]-1,2,4-triazin-6-yl}-5-(2H-1,2,3-triazol-2-yl)phenol dihydrochloride |
| 326 | 5-(4-methyl-1H-imidazol-1-yl)-2-(3-{3-[(propan-2-yl)amino]pyrrolidin-1-yl}-1,2,4-triazin-6-yl)phenol hydrochloride |
| 327 | 2-{3-[(3aR,7aR)-octahydro-2H-pyrrolo[3,4-c]pyridin-2-yl]-1,2,4-triazin-6-yl}-5-(1H-pyrazol-4-yl)phenol trihydrochloride |
| 328 | 2-[3-(piperazin-1-yl)-1,2,4-triazin-6-yl]-5-(1H-pyrazol-4-yl)phenol dihydrochloride |
| 329 | 2-{3-[(3S)-3-{[(2R)-1-fluoropropan-2-yl]amino}pyrrolidin-1-yl]-1,2,4-triazin-6-yl}-5-(1H-pyrazol-4-yl)phenol dihydrochloride |
| 330 | 5-(1-methyl-1H-indazol-5-yl)-2-(3-{3-[(propan-2-yl)amino]pyrrolidin-1-yl}-1,2,4-triazin-6-yl)phenol hydrochloride |
| 331 | 5-(1H-imidazol-1-yl)-2-(3-{3-[(propan-2-yl)amino]pyrrolidin-1-yl}-1,2,4-triazin-6-yl)phenol hydrochloride |
| 332 | 2-{3-[(3aR,6aS)-hexahydropyrrolo[3,2-b]pyrrol-1(2H)-yl]-1,2,4-triazin-6-yl}-5-(1H-pyrazol-4-yl)phenol dihydrochloride |
| 333 | 2-(3-{3-[(2-hydroxyethyl)amino]pyrrolidin-1-yl}-1,2,4-triazin-6-yl)-5-(1H-pyrazol-4-yl)phenol dihydrochloride |
| 335 | 2-(3-{3-[(oxan-4-yl)amino]pyrrolidin-1-yl}-1,2,4-triazin-6-yl)-5-(1H-pyrazol-4-yl)phenol dihydrochloride |
| 336 | 2-(3-{3-[(1-methoxypropan-2-yl)amino]pyrrolidin-1-yl}-1,2,4-triazin-6-yl)-5-(1H-pyrazol-4-yl)phenol dihydrochloride |
| 337 | 2-[3-(hexahydropyrrolo[3,4-c]pyrrol-2(1H)-yl]-1,2,4-triazin-6-yl]-5-(1H-pyrazol-4-yl)phenol dihydrochloride |
| 338 | 5-(4-fluoro-1H-pyrazol-1-yl)-2-(3-{3-[(propan-2-yl)amino]pyrrolidin-1-yl}-1,2,4-triazin-6-yl)phenol hydrochloride |
| 339 | 2-[3-(1,7-diazaspiro[4.4]nonan-7-yl)-1,2,4-triazin-6-yl]-5-(1H-pyrazol-4-yl)phenol dihydrochloride |
| 340 | 2-(3-{3-[(1-methylcyclopropyl)amino]pyrrolidin-1-yl}-1,2,4-triazin-6-yl)-5-(1H-pyrazol-4-yl)phenol dihydrochloride |
| 341 | 2-(3-{3-[(1-methoxy-2-methylpropan-2-yl)amino]pyrrolidin-1-yl}-1,2,4-triazin-6-yl)-5-(1H-pyrazol-4-yl)phenol dihydrochloride |
| 344 | 6-(3-hydroxy-4-{3-[methyl(2,2,6,6-tetramethylpiperidin-4-yl)amino]-1,2,4-triazin-6-yl}phenyl)imidazo[1,2-b]pyridazine-8-carbonitrile formate |
| 345 | 2-(3-{[(3R,4S)-3-fluoropiperidin-4-yl]amino}-1,2,4-triazin-6-yl)-5-(1H-pyrazol-4-yl)phenol dihydrochloride |
| 346 | 2-{3-[(3R,4R)-3-methoxy-4-(methylamino)pyrrolidin-1-yl]-1,2,4-triazin-6-yl}-5-(1H-pyrazol-4-yl)phenol dihydrochloride |
| 347 | 2-(3-{(3S)-3-[(propan-2-yl)amino]pyrrolidin-1-yl}-1,2,4-triazin-6-yl)-5-(1H-pyrazol-4-yl)phenol trifluoroacetate |
| 348 | 2-(3-{(3R)-3-[(propan-2-yl)amino]pyrrolidin-1-yl}-1,2,4-triazin-6-yl)-5-(1H-pyrazol-4-yl)phenol trifluoroacetate |

-continued

| Cpd | Name |
|---|---|
| 349 | 2-[3-{3-[(bicyclo[1.1.1]pentan-1-yl)amino]pyrrolidin-1-yl]-1,2,4-triazin-6-yl)-5-(1H-pyrazol-4-yl)phenol trifluoroacetate |
| 350 | 2-{3-[3-(methylamino)pyrrolidin-1-yl]-1,2,4-triazin-6-yl}-5-(2-methyl-1,3-oxazol-5-yl)phenol dihydrochloride |
| 351 | 5-[8-(aminomethyl)imidazo[1,2-b]pyridazin-6-yl]-2-{3-[methyl(2,2,6,6-tetramethylpiperidin-4-yl)amino]-1,2,4-triazin-6-yl}phenol formate |
| 352 | 5-(1,3-oxazol-2-yl)-2-{3-[(2,2,6,6-tetramethylpiperidin-4-yl)amino]-1,2,4-triazin-6-yl}phenol formate |
| 353 | 2-[3-(6-oxa-2,9-diazaspiro[4.5]decan-2-yl)-1,2,4-triazin-6-yl]-5-(1H-pyrazol-4-yl)phenol dihydrochloride |
| 354 | 2-[3-(2,7-diazaspiro[4.4]nonan-2-yl)-1,2,4-triazin-6-yl]-5-(1H-pyrazol-4-yl)phenol dihydrochloride |
| 355 | 2-{3-[(3S)-3-(tert-butylamino)pyrrolidin-1-yl]-1,2,4-triazin-6-yl}-5-(1H-pyrazol-4-yl)phenol dihydrochloride |
| 356 | 2-{3-[(3R)-3-(tert-butylamino)pyrrolidin-1-yl]-1,2,4-triazin-6-yl}-5-(1H-pyrazol-4-yl)phenol dihydrochloride |
| 357 | 2-{3-[3-(cyclopentylamino)pyrrolidin-1-yl]-1,2,4-triazin-6-yl}-5-(1H-pyrazol-4-yl)phenol dihydrochloride |
| 358 | 2-{3-[3-(methylamino)pyrrolidin-1-yl]-1,2,4-triazin-6-yl}-5-(1,3-oxazol-2-yl)phenol dihydrochloride |
| 359 | 5-(imidazo[1,2-a]pyrazin-2-yl)-2-{3-[(2,2,6,6-tetramethylpiperidin-4-yl)amino]-1,2,4-triazin-6-yl}phenol hydrochloride |
| 360 | 5-(imidazo[1,2-a]pyridin-2-yl)-2-{3-[(2,2,6,6-tetramethylpiperidin-4-yl)amino]-1,2,4-triazin-6-yl}phenol hydrochloride |
| 361 | 2-[3-(3-{[(propan-2-yl)amino]methyl}pyrrolidin-1-yl)-1,2,4-triazin-6-yl]-5-(1H-pyrazol-4-yl)phenol dihydrochloride |
| 362 | 2-(3-{3-[(4-methyloxan-4-yl)amino]pyrrolidin-1-yl}-1,2,4-triazin-6-yl)-5-(1H-pyrazol-4-yl)phenol ditrifluoroacetate |
| 363 | 2-{6-[3-(tert-butylamino)pyrrolidin-1-yl]-1,2,4-triazin-3-yl}-5-(1H-pyrazol-4-yl)phenol dihydrochloride |
| 364 | 2-{3-[3-(methylamino)pyrrolidin-1-yl]-1,2,4-triazin-6-yl}-5-[6-(methylsulfanyl)pyrimidin-4-yl]phenol trihydrochloride |
| 365 | 2-{3-[3-(tert-butylamino)pyrrolidin-1-yl]-1,2,4-triazin-6-yl}-5-(3-chloro-1H-pyrazol-4-yl)phenol dihydrochloride |
| 366 | 4-(4-{3-[3-(tert-butylamino)pyrrolidin-1-yl]-1,2,4-triazin-6-yl}-3-hydroxyphenyl)-1H-pyrazole-3-carbonitrile dihydrochloride |
| 367 | 2-{3-[3-(tert-butylamino)pyrrolidin-1-yl]-1,2,4-triazin-6-yl}-5-[1-($^{2}H_{3}$)methyl-1H-pyrazol-4-yl]phenol hydrochloride |
| 368 | 3-(1-methyl-1H-pyrazol-3-yl)-6-{3-[methyl(2,2,6,6-tetramethylpiperidin-4-yl)amino]-1,2,4-triazin-6-yl}benzene-1,2-diol trifluoroacetate |
| 369 | 2-[3-(2,7-diazaspiro[4.5]decan-2-yl)-1,2,4-triazin-6-yl]-5-(1H-pyrazol-4-yl)phenol dihydrochloride |
| 370 | 2-[3-(hexahydropyrrolo[3,4-b]pyrrol-5(1H)-yl)-1,2,4-triazin-6-yl]-5-(1H-pyrazol-4-yl)phenol dihydrochloride |
| 371 | 2-(3-{3-[(3-hydroxypropyl)amino]pyrrolidin-1-yl}-1,2,4-triazin-6-yl)-5-(1H-pyrazol-4-yl)phenol dihydrochloride |
| 372 | 2-[3-(3-{[(oxan-4-yl)amino]methyl}pyrrolidin-1-yl)-1,2,4-triazin-6-yl]-5-(1H-pyrazol-4-yl)phenol ditrifluoroacetate |
| 373 | 5-[1-($^{2}H_{3}$)methyl-1H-pyrazol-4-yl]-2-{3-[(2,2,6,6-tetramethylpiperidin-4-yl)amino]-1,2,4-triazin-6-yl}phenol hydrochloride |
| 374 | 2-{6-[3-(tert-butylamino)pyrrolidin-1-yl]-1,2,4-triazin-3-yl}-5-(3-fluoro-1H-pyrazol-4-yl)phenol dihydrochloride |
| 375 | 2-{3-[3-(tert-butylamino)pyrrolidin-1-yl]-1,2,4-triazin-6-yl}-5-(3-methyl-1H-pyrazol-4-yl)phenol dihydrochloride |
| 376 | 2-{3-[3-(tert-butylamino)pyrrolidin-1-yl]-1,2,4-triazin-6-yl}-3-methoxy-5-(1H-pyrazol-4-yl)phenol trifluoroacetate |
| 377 | 2-(3-{[(3S,4S)-3-fluoro-2,2,6,6-tetramethylpiperidin-4-yl]amino}-1,2,4-triazin-6-yl)-5-[1-($^{2}H_{3}$)methyl-1H-pyrazol-4-yl]phenol hydrochloride |
| 378 | 2-{3-[(3S)-3-(tert-butylamino)pyrrolidin-1-yl]-1,2,4-triazin-6-yl}-5-(3-fluoro-1H-pyrazol-4-yl)phenol dihydrochloride |
| 379 | 2-{3-[(3R)-3-(tert-butylamino)pyrrolidin-1-yl]-1,2,4-triazin-6-yl}-5-(3-fluoro-1H-pyrazol-4-yl)phenol dihydrochloride |
| 381 | 2-{3-[methyl(2,2,6,6-tetramethylpiperidin-4-yl)amino]-1,2,4-triazin-6-yl}-5-(1H-pyrazolo[3,4-c]pyridin-1-yl)phenol formate |
| 385 | 2-{3-[(3R,5S)-3,5-dimethylpiperazin-1-yl]-1,2,4-triazin-6-yl}-5-(imidazo[1,2-b]pyridazin-6-yl)phenol trifluoroacetate |
| 386 | 2-(3-{3-[(cyclopentylamino)methyl]pyrrolidin-1-yl}-1,2,4-triazin-6-yl)-5-(1H-pyrazol-4-yl)phenol dihydrochloride |
| 387 | 2-[3-([2,3'-bipyrrolidin]-1'-yl)-1,2,4-triazin-6-yl]-5-(1H-pyrazol-4-yl)phenol dihydrochloride |
| 388 | 5-(1H-pyrazol-4-yl)-2-{3-[3-({[(pyridin-2-yl)methyl]amino}methyl)pyrrolidin-1-yl]-1,2,4-triazin-6-yl}phenol ditrifluoroacetate |
| 390 | 2-(3-{3-[(tert-butylamino)methyl]pyrrolidin-1-yl}-1,2,4-triazin-6-yl)-5-(1H-pyrazol-4-yl)phenol dihydrochloride |
| 391 | 2-[3-(3-{[(4-methyloxan-4-yl)amino]methyl}pyrrolidin-1-yl)-1,2,4-triazin-6-yl]-5-(1H-pyrazol-4-yl)phenol trifluoroacetate |

-continued

| Cpd | Name |
|---|---|
| 392 | 2-(3-{3-[(cyclopropylamino)methyl]pyrrolidin-1-yl}-1,2,4-triazin-6-yl)-5-(1H-pyrazol-4-yl)phenol formate |
| 395 | 2-[3-(3-{[(oxolan-3-yl)amino]methyl}pyrrolidin-1-yl)-1,2,4-triazin-6-yl]-5-(1H-pyrazol-4-yl)phenol hydrochloride |
| 396 | 5-(1H-pyrazol-4-yl)-2-{6-[(2,2,6,6-tetramethylpiperidin-4-yl)amino]-1,2,4-triazin-3-yl}phenol hydrochloride |
| 399 | 2-{3-[(3R)-3-(cyclobutylamino)pyrrolidin-1-yl]-1,2,4-triazin-6-yl}-5-(1H-pyrazol-4-yl)phenol dihydrochloride |
| 400 | 2-{3-[(3S)-3-(cyclobutylamino)pyrrolidin-1-yl]-1,2,4-triazin-6-yl}-5-(1H-pyrazol-4-yl)phenol dihydrochloride |
| 401 | 2-{6-[(2,2,6,6-tetramethylpiperidin-4-yl)amino]-1,2,4-triazin-3-yl}-5-(2H-1,2,3-triazol-2-yl)phenol hydrochloride |
| 403 | 2-[3-(3-{[(3-fluorooxan-4-yl)amino]methyl}pyrrolidin-1-yl)-1,2,4-triazin-6-yl]-5-(1H-pyrazol-4-yl)phenol hydrochloride |
| 404 | 2-[3-(3-{[(oxan-3-yl)amino]methyl}pyrrolidin-1-yl)-1,2,4-triazin-6-yl]-5-(1H-pyrazol-4-yl)phenol hydrochloride |
| 405 | 2-[3-(3-{[(8-oxabicyclo[3.2.1]octan-3-yl)amino]methyl}pyrrolidin-1-yl)-1,2,4-triazin-6-yl]-5-(1H-pyrazol-4-yl)phenol hydrochloride |
| 406 | 2-{3-[(3R)-3-(cyclobutylamino)pyrrolidin-1-yl]-l,2,4-triazin-6-yl}-5-(1-methyl-1H-pyrazol-4-yl)phenol hydrochloride |
| 407 | 2-{3-[(3S)-3-(cyclobutylamino)pyrrolidin-1-yl]-1,2,4-triazin-6-yl}-5-(1-methyl-1H-pyrazol-4-yl)phenol hydrochloride |
| 408 | 2-(3-{[(1R,3s,5S)-1,5-dimethyl-8-azabicyclo[3.2.1]octan-3-yl](methyl)amino}-1,2,4-triazin-6-yl)-5-(1-methyl-1H-pyrazol-4-yl)phenol trifluoroacetate |
| 409 | 2-(3-{3-[(3,3-difluorocyclopentyl)amino]pyrrolidin-1-yl}-1,2,4-triazin-6-yl)-5-(1H-pyrazol-4-yl)phenol dihydrochloride |
| 410 | 2-(3-{3-[(dimethylamino)methyl]pyrrolidin-1-yl}-1,2,4-triazin-6-yl)-5-(1H-pyrazol-4-yl)phenol dihydrochloride |
| 413 | 2-(3-{3-[(methylamino)methyl]pyrrolidin-1-yl}-1,2,4-triazin-6-yl)-5-(1H-pyrazol-4-yl)phenol dihydrochloride |
| 414 | 2-[3-(3-{1-[(propan-2-yl)amino]ethyl}pyrrolidin-1-yl)-1,2,4-triazin-6-yl]-5-(1H-pyrazol-4-yl)phenol dihydrochloride |
| 415 | 2-(3-{3-[(cyclobutylamino)methyl]pyrrolidin-1-yl}-1,2,4-triazin-6-yl)-5-(1H-pyrazol-4-yl)phenol dihydrochloride |
| 416 | 2-(3-{3-[(cyclobutylamino)methyl]pyrrolidin-1-yl}-1,2,4-triazin-6-yl)-5-(1-methyl-1H-pyrazol-4-yl)phenol hydrochloride |
| 417 | 2-(3-{[(1R,3s,5S)-1,5-dimethyl-8-azabicyclo[3.2.1]octan-3-yl](methyl)amino}-1,2,4-triazin-6-yl)-5-(2H-1,2,3-triazol-2-yl)phenol trifluoroacetate |
| 418 | 6-{3-[3-(tert-butylamino)pyrrolidin-1-yl]-1,2,4-triazin-6-yl}-2-fluoro-3-(1H-pyrazol-4-yl)phenol dihydrochloride |
| 419 | 5-(1H-pyrazol-4-yl)-2-{6-[(2,2,6,6-tetramethylpiperidin-4-yl)oxy]-1,2,4-triazin-3-yl}phenol hydrochloride |
| 420 | 2-(3-{3-[(3-fluorocyclopentyl)amino]pyrrolidin-1-yl}-1,2,4-triazin-6-yl)-5-(1H-pyrazol-4-yl)phenol dihydrochloride |
| 421 | 2-[3-(3-{1-[(oxan-4-yl)amino]cyclopropyl}pyrrolidin-1-yl)-1,2,4-triazin-6-yl]-5-(1H-pyrazol-4-yl)phenol dihydrochloride |
| 422 | 2-(3-{3-methyl-3-[(propan-2-yl)amino]pyrrolidin-1-yl}-1,2,4-triazin-6-yl)-5-(1-methyl-1H-pyrazol-4-yl)phenol trifluoroacetate |
| 423 | 2-{6-[(3-fluoro-2,2,6,6-tetramethylpiperidin-4-yl)amino]-1,2,4-triazin-3-yl}-5-(1H-pyrazol-4-yl)phenol hydrochloride, and |
| 424 | 5-[1-($^2$H$_3$)methyl-1H-pyrazol-4-yl]-2-{6-[(2,2,6,6-tetramethylpiperidin-4-yl)amino]-1,2,4-triazin-3-yl}phenol hydrochloride; | wherein a form of the compound is selected from the group consisting of a salt, hydrate, solvate, racemate, enantiomer, diastereomer, stereoisomer, and tautomer form thereof.

An aspect of the present description includes a method for preventing, treating or ameliorating HD in a subject in need thereof comprising, administering to the subject an effective amount of a compound of Formula (I) or Formula (II) or a form thereof.

An aspect of the present description includes a method for treating or ameliorating HD in a subject in need thereof comprising, administering to the subject an effective amount of a compound of Formula (I) or Formula (II) or a form thereof.

Another aspect of the present description includes a method for treating or ameliorating HD in a subject in need thereof comprising, administering to the subject an effective amount of a compound salt of Formula (I) or Formula (II) or a form thereof.

An aspect of the present description includes a method for use of a compound of Formula (I) or Formula (II) or a form or composition thereof for treating or ameliorating HD in a subject in need thereof comprising, administering to the subject an effective amount of the compound of Formula (I) or Formula (II) or a form or composition thereof.

Another aspect of the present description includes a method for use of a compound salt of Formula (I) or Formula (II) or a form or composition thereof for treating or ameliorating HD in a subject in need thereof comprising, administering to the subject an effective amount of the compound salt of Formula (I) or Formula (II) or a form thereof.

An aspect of the present description includes a use for a compound of Formula (I) or Formula (II) or a form thereof for treating or ameliorating HD in a subject in need thereof comprising, administering to the subject an effective amount of the compound of Formula (I) or Formula (II) or a form thereof.

Another aspect of the present description includes a use for a compound salt of Formula (I) or Formula (II) or a form thereof for treating or ameliorating HD in a subject in need thereof comprising, administering to the subject an effective amount of the compound salt of Formula (I) or Formula (II) or a form thereof.

An aspect of the present description includes a use for a compound of Formula (I) or Formula (II) or a form thereof in the manufacture of a medicament for treating or ameliorating HD in a subject in need thereof comprising, administering to the subject an effective amount of the medicament.

Another aspect of the present description includes a use for a compound salt of Formula (I) or Formula (II) or a form thereof in the manufacture of a medicament for treating or ameliorating HD in a subject in need thereof comprising, administering to the subject an effective amount of the medicament.

An aspect of the present description includes a use for a compound of Formula (I) or Formula (II) or a form thereof in a combination product with one or more therapeutic agents for treating or ameliorating HD in a subject in need thereof comprising, administering to the subject an effective amount of the compound of Formula (I) or Formula (II) or a form thereof in combination with an effective amount of the one or more agents.

Another aspect of the present description includes a use for a compound salt of Formula (I) or Formula (II) or a form thereof in a combination product with one or more therapeutic agents for treating or ameliorating HD in a subject in need thereof comprising, administering to the subject an effective amount of the compound salt of Formula (I) or Formula (II) or a form thereof in combination with an effective amount of the one or more agents.

Chemical Definitions

The chemical terms used above and throughout the description herein, unless specifically defined otherwise, shall be understood by one of ordinary skill in the art to have the following indicated meanings.

As used herein, the term "$C_{1-4}$alkyl" generally refers to saturated hydrocarbon radicals having from one to four carbon atoms in a straight or branched chain configuration, including, but not limited to, methyl, ethyl, n-propyl (also referred to as propyl or propanyl), isopropyl, n-butyl (also referred to as butyl or butanyl), isobutyl, sec-butyl, tert-butyl and the like. A $C_{1-4}$alkyl radical is optionally substituted with substituent species as described herein where allowed by available valences.

As used herein, the term "$C_{2-4}$alkenyl" generally refers to partially unsaturated hydrocarbon radicals having from two to four carbon atoms in a straight or branched chain configuration and one or more carbon-carbon double bonds therein, including, but not limited to, ethenyl (also referred to as vinyl), allyl, propenyl and the like. A $C_{2-4}$alkenyl radical is optionally substituted with substituent species as described herein where allowed by available valences.

As used herein, the term "$C_{2-8}$alkynyl" generally refers to partially unsaturated hydrocarbon radicals having from two to eight carbon atoms in a straight or branched chain configuration and one or more carbon-carbon triple bonds therein, including, but not limited to, ethynyl, propynyl, butynyl and the like. In certain aspects, $C_{2-8}$alkynyl includes, but is not limited to, $C_{2-6}$alkynyl, $C_{2-4}$alkynyl and the like. A $C_{2-8}$alkynyl radical is optionally substituted with substituent species as described herein where allowed by available valences.

As used herein, the term "$C_{1-4}$alkoxy" generally refers to saturated hydrocarbon radicals having from one to four carbon atoms in a straight or branched chain configuration of the formula: —O—$C_{1-4}$alkyl, including, but not limited to, methoxy, ethoxy, n-propoxy, isopropoxy, n-butoxy, isobutoxy, sec-butoxy, tert-butoxy and the like. A $C_{1-4}$alkoxy radical is optionally substituted with substituent species as described herein where allowed by available valences.

As used herein, the term "$C_{3-10}$cycloalkyl" generally refers to a saturated or partially unsaturated monocyclic, bicyclic or polycyclic hydrocarbon radical, including, but not limited to, cyclopropyl, cyclobutyl, cyclopentyl, cyclohexyl, cyclohexenyl, cycloheptyl, and the like. A $C_{3-10}$cycloalkyl radical is optionally substituted with substituent species as described herein where allowed by available valences.

As used herein, the term "aryl" generally refers to a monocyclic, bicyclic or polycyclic aromatic carbon atom ring structure radical, including, but not limited to, phenyl, naphthyl, anthracenyl, fluorenyl, azulenyl, phenanthrenyl and the like. An aryl radical is optionally substituted with substituent species as described herein where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including, but not limited to, furanyl, thienyl, pyrrolyl, pyrazolyl, imidazolyl, isoxazolyl, isothiazolyl, oxazolyl, 1,3-thiazolyl, triazolyl, oxadiazolyl, thiadiazolyl, tetrazolyl, pyridinyl, pyrimidinyl, pyrazinyl, pyridazinyl, triazinyl, indolyl, indazolyl, indolizinyl, isoindolyl, benzofuranyl, benzothienyl, benzoimidazolyl, 1,3-benzothiazolyl, 1,3-benzoxazolyl, purinyl, quinolinyl, isoquinolinyl, quinazolinyl, quinoxalinyl, 1,3-diazinyl, 1,2-diazinyl, 1,2-diazolyl, 1,4-diazanaphthalenyl, acridinyl, furo[3,2-b]pyridinyl, furo[3,2-c]pyridinyl, furo[2,3-c]pyridinyl, 6H-thieno[2,3-b]pyrrolyl, thieno[3,2-c]pyridinyl, thieno[2,3-d]pyrimidinyl, 1H-pyrrolo[2,3-b]pyridinyl, 1H-pyrrolo[2,3-c]pyridinyl, 1H-pyrrolo[3,2-b]pyridinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, 3H-imidazo[4,5-b]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,2,4]triazolo[1,5-a]pyridinyl, [1,2,4]triazolo[4,3-a]pyridinyl and the like. A heteroaryl radical is optionally substituted on a carbon or nitrogen atom ring member with substituent species as described herein where allowed by available valences.

In certain aspects, the nomenclature for a heteroaryl radical may differ, such as in non-limiting examples where furanyl may also be referred to as furyl, thienyl may also be referred to as thiophenyl, pyridinyl may also be referred to as pyridyl, benzothienyl may also be referred to as benzothiophenyl and 1,3-benzoxazolyl may also be referred to as 1,3-benzooxazolyl.

In certain other aspects, the term for a heteroaryl radical may also include other regioisomers, such as in non-limiting examples where the term pyrrolyl may also include 2H-pyrrolyl, 3H-pyrrolyl and the like, the term pyrazolyl may also include 1H-pyrazolyl and the like, the term imidazolyl may also include 1H-imidazolyl and the like, the term triazolyl may also include 1H-1,2,3-triazolyl and the like, the term oxadiazolyl may also include 1,2,4-oxadiazolyl, 1,3,4-oxadiazolyl and the like, the term tetrazolyl may also include 1H-tetrazolyl, 2H-tetrazolyl and the like, the term indolyl may also include 1H-indolyl and the like, the term indazolyl may also include 1H-indazolyl, 2H-indazolyl and the like, the term benzoimidazolyl may also include 1H-benzoimidazolyl and the term purinyl may also include 9H-purinyl and the like.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, but not limited to, oxiranyl, oxetanyl, azetidinyl, tetrahydrofuranyl, pyrrolinyl, pyrrolidinyl, pyrazolinyl, pyrazolidinyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, pyranyl, dihydro-2H-pyranyl, thiopyranyl, 1,3-dioxanyl, 1,2,5,6-tetrahydropyridinyl, 1,2,3,6-tetrahydropyridinyl, piperidinyl, piperazinyl, morpholinyl, thiomorpholinyl, 1,4-diazepanyl, 1,3-benzodioxolyl, 1,4-benzodioxanyl, 2,3-dihydro-1,4-benzodioxinyl, hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, (3aR,6aR)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, (3aR,6aR)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(H)-yl, hexahydropyrrolo[1,2-a]pyrazin-(2H)-one, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,6-diazaspiro[3.4]octyl, 2,7-diazaspiro[3.5]nonyl, 5,8-diazaspiro[3.5]nonyl, 2,7-diazaspiro[4.4]nonyl, 6,9-diazaspiro[4.5]decyl, 7-azadispiro[5.1.5$^8$.3$^6$]hexadecanyl and the like. A heterocyclyl radical is optionally substituted on a carbon or nitrogen atom ring member with substituent species as described herein where allowed by available valences.

In certain aspects, the nomenclature for a heterocyclyl radical may differ, such as in non-limiting examples where 1,3-benzodioxolyl may also be referred to as benzo[d][1,3]dioxolyl and 2,3-dihydro-1,4-benzodioxinyl may also be referred to as 2,3-dihydrobenzo[b][1,4]dioxinyl.

As used herein, the term "$C_{1-4}$alkoxy-$C_{1-4}$alkyl" refers to a radical of the formula: —$C_{1-4}$alkyl-O—$C_{1-4}$alkyl.

As used herein, the term "$C_{1-4}$alkoxy-$C_{1-4}$alkyl-amino" refers to a radical of the formula: —NH—$C_{1-4}$alkyl-O—$C_{1-4}$alkyl.

As used herein, the term "($C_{1-4}$alkoxy-$C_{1-4}$alkyl)$_2$-amino" refers to a radical of the formula: —N($C_{1-4}$alkyl-O—$C_{1-4}$alkyl)$_2$.

As used herein, the term "$C_{1-4}$alkoxy-$C_{1-4}$alkyl-amino-$C_{1-4}$alkoxy" refers to a radical of the formula: —O—$C_{1-4}$alkyl-NH—$C_{1-4}$alkyl-O—$C_{1-4}$alkyl.

As used herein, the term "($C_{1-4}$alkoxy-$C_{1-4}$alkyl)$_2$-amino-$C_{1-4}$alkoxy" refers to a radical of the formula: —O—$C_{1-4}$alkyl-N($C_{1-4}$alkyl-O—$C_{1-4}$alkyl)$_2$.

As used herein, the term "($C_{1-4}$alkoxy-$C_{1-4}$alkyl)($C_{1-4}$alkyl)amino-$C_{1-4}$alkoxy" refers to a radical of the formula: —O—$C_{1-4}$alkyl-N($C_{1-4}$alkyl)($C_{1-44}$alkyl-O—$C_{1-4}$alkyl).

As used herein, the term "$C_{1-4}$alkoxy-$C_{1-4}$alkyl-amino-$C_{1-4}$alkyl" refers to a radical of the formula: —$C_{1-4}$alkyl-NH—$C_{1-4}$alkyl-O—$C_{1-4}$alkyl.

As used herein, the term "($C_{1-4}$alkoxy-$C_{1-4}$alkyl)$_2$-amino-$C_{1-4}$alkyl" refers to a radical of the formula: —$C_{1-4}$alkyl-N($C_{1-4}$alkyl-O—$C_{1-4}$alkyl)$_2$.

As used herein, the term "($C_{1-4}$alkoxy-$C_{1-4}$alkyl)($C_{1-4}$alkyl)amino-$C_{1-4}$alkyl" refers to a radical of the formula: —$C_{1-4}$alkyl-N($C_{1-4}$alkyl)($C_{1-4}$alkyl-O—$C_{1-4}$alkyl).

As used herein, the term "$C_{1-4}$alkoxy-carbonyl" refers to a radical of the formula: —C(O)—O—$C_{1-4}$alkyl.

As used herein, the term "$C_{1-4}$alkoxy-carbonyl-$C_{2-8}$alkenyl" refers to a radical of the formula: —$C_{2-8}$alkenyl-C(O)—O—$C_{1-4}$alkyl.

As used herein, the term "$C_{1-4}$alkoxy-carbonyl-amino" refers to a radical of the formula: —NH—C(O)—O—$C_{1-4}$alkyl.

As used herein, the term "$C_{1-4}$alkyl-amino" refers to a radical of the formula: —NH—$C_{1-4}$alkyl.

As used herein, the term "($C_{1-4}$alkyl)$_2$-amino" refers to a radical of the formula: —N($C_{1-4}$alkyl)$_2$.

As used herein, the term "$C_{1-4}$alkyl-amino-$C_{2-8}$alkenyl" refers to a radical of the formula: —$C_{2-8}$alkenyl-NH—$C_{1-4}$alkyl.

As used herein, the term "($C_{1-4}$alkyl)$_2$-amino-$C_{2-8}$alkenyl" refers to a radical of the formula: —$C_{2-8}$alkenyl-N($C_{1-4}$alkyl)$_2$.

As used herein, the term "$C_{1-4}$alkyl-amino-$C_{1-4}$alkoxy" refers to a radical of the formula: —O—$C_{1-4}$alkyl-NH—$C_{1-4}$alkyl.

As used herein, the term "($C_{1-4}$alkyl)$_2$-amino-$C_{1-4}$alkoxy" refers to a radical of the formula: —O—$C_{1-4}$alkyl-N($C_{1-4}$alkyl)$_2$.

As used herein, the term "$C_{1-4}$alkyl-amino-$C_{1-4}$alkyl" refers to a radical of the formula: —$C_{1-4}$alkyl-NH—$C_{1-4}$alkyl.

As used herein, the term "($C_{1-4}$alkyl)$_2$-amino-$C_{1-4}$alkyl" refers to a radical of the formula: —$C_{1-4}$alkyl-N($C_{1-4}$alkyl)$_2$.

As used herein, the term "$C_{1-4}$alkyl-amino-$C_{1-4}$alkyl-amino" refers to a radical of the formula: —NH—$C_{1-4}$alkyl-NH—$C_{1-4}$alkyl.

As used herein, the term "($C_{1-4}$alkyl)$_2$-amino-$C_{1-4}$alkyl-amino" refers to a radical of the formula: —NH—$C_{1-4}$alkyl-N($C_{1-4}$alkyl)$_2$.

As used herein, the term "($C_{1-4}$alkyl-amino-$C_{1-4}$alkyl)$_2$-amino" refers to a radical of the formula: —N($C_{1-4}$alkyl-NH—$C_{1-4}$alkyl)$_2$.

As used herein, the term "[($C_{1-4}$alkyl)$_2$-amino-$C_{1-4}$alkyl]$_2$-amino" refers to a radical of the formula: —N[$C_{1-4}$alkyl-N($C_{1-4}$alkyl)$_2$]$_2$.

As used herein, the term "($C_{1-4}$alkyl-amino-$C_{1-4}$alkyl)($C_{1-4}$alkyl)amino" refers to a radical of the formula: —N($C_{1-4}$alkyl)($C_{1-4}$alkyl-NH—$C_{1-4}$alkyl).

As used herein, the term "[($C_{1-4}$alkyl)$_2$-amino-$C_{1-4}$alkyl]($C_{1-4}$alkyl)amino" refers to a radical of the formula: —N($C_{1-4}$alkyl)[$C_{1-4}$alkyl-N($C_{1-4}$alkyl)$_2$].

As used herein, the term "$C_{1-4}$alkyl-amino-$C_{2-8}$alkynyl" refers to a radical of the formula: —$C_{2-8}$alkynyl-NH—$C_{1-4}$alkyl.

As used herein, the term "($C_{1-4}$alkyl)$_2$-amino-$C_{2-8}$alkynyl" refers to a radical of the formula: —$C_{2-8}$alkynyl-N($C_{1-4}$alkyl)$_2$.

As used herein, the term "$C_{1-4}$alkyl-carbonyl" refers to a radical of the formula: —C(O)—$C_{1-4}$alkyl.

As used herein, the term "$C_{1-4}$alkyl-carbonyl-amino" refers to a radical of the formula: —NH—C(O)—$C_{1-4}$alkyl.

As used herein, the term "$C_{1-4}$alkyl-thio" refers to a radical of the formula: —S—$C_{1-4}$alkyl.

As used herein, the term "amino-$C_{2-8}$alkenyl" refers to a radical of the formula: —$C_{2-8}$alkenyl-NH$_2$.

As used herein, the term "amino-$C_{1-4}$alkoxy" refers to a radical of the formula: —O—$C_{1-4}$alkyl-NH$_2$.

As used herein, the term "amino-$C_{1-4}$alkyl" refers to a radical of the formula: —$C_{1-4}$alkyl-NH$_2$.

As used herein, the term "amino-$C_{1-4}$alkyl-amino" refers to a radical of the formula: —NH—$C_{1-4}$alkyl-NH$_2$.

As used herein, the term "(amino-$C_{1-4}$alkyl)$_2$-amino" refers to a radical of the formula: —N($C_{1-4}$alkyl-NH$_2$)$_2$.

As used herein, the term "(amino-$C_{1-4}$alkyl)($C_{1-4}$alkyl)amino" refers to a radical of the formula: —N($C_{1-4}$alkyl)($C_{1-4}$alkyl-NH$_2$).

As used herein, the term "amino-$C_{2-8}$alkynyl" refers to a radical of the formula: —$C_{2-8}$alkynyl-NH$_2$.

As used herein, the term "aryl-$C_{1-4}$alkoxy-carbonyl" refers to a radical of the formula: —C(O)—O—$C_{1-4}$alkyl-aryl.

As used herein, the term "aryl-$C_{1-4}$alkyl" refers to a radical of the formula: —$C_{1-4}$alkyl-aryl.

As used herein, the term "aryl-$C_{1-4}$alkyl-amino" refers to a radical of the formula: —NH—$C_{1-4}$alkyl-aryl.

As used herein, the term "(aryl-$C_{1-4}$alkyl)$_2$-amino" refers to a radical of the formula: —N($C_{1-4}$alkyl-aryl)$_2$.

As used herein, the term "(aryl-$C_{1-4}$alkyl)($C_{1-4}$alkyl)amino" refers to a radical of the formula: —N($C_{1-4}$alkyl)($C_{1-4}$alkyl-aryl).

As used herein, the term "aryl-$C_{1-4}$alkyl-amino-$C_{1-4}$alkyl" refers to a radical of the formula: —$C_{1-4}$alkyl-NH—$C_{1-4}$alkyl-aryl.

As used herein, the term "(aryl-$C_{1-4}$alkyl)$_2$-amino-$C_{1-4}$alkyl" refers to a radical of the formula: —$C_{1-4}$alkyl-N($C_{1-4}$alkyl-aryl)$_2$.

As used herein, the term "(aryl-$C_{1-4}$alkyl)($C_{1-4}$alkyl)amino-$C_{1-4}$alkyl" refers to a radical of the formula: —$C_{1-4}$alkyl-N($C_{1-4}$alkyl)($C_{1-4}$alkyl-aryl).

As used herein, the term "aryl-amino" refers to a radical of the formula: —NH-aryl.

As used herein, the term "aryl-amino-carbonyl" refers to a radical of the formula: —C(O)—NH-aryl.

As used herein, the term "aryl-sulfonyloxy-$C_{1-4}$alkyl" refers to a radical of the formula: —$C_{1-4}$alkyl-O—SO$_2$-aryl.

As used herein, the term "benzoxy-carbonyl" refers to a radical of the formula: —C(O)—O—CH$_2$-phenyl.

As used herein, the term "$C_{3-14}$cycloalkyl-$C_{1-4}$alkyl" refers to a radical of the formula: —$C_{1-4}$alkyl-$C_{3-14}$cycloalkyl.

As used herein, the term "$C_{3-14}$cycloalkyl-amino" refers to a radical of the formula: —NH—$C_{3-14}$cycloalkyl.

As used herein, the term "$C_{3-14}$cycloalkyl-oxy" refers to a radical of the formula: —O—$C_{3-14}$cycloalkyl.

As used herein, the term "deutero-$C_{1-4}$alkyl," refers to a radical of the formula: —$C_{1-4}$alkyl-deutero, wherein $C_{1-4}$alkyl is partially or completely substituted with one or more deuterium atoms where allowed by available valences.

As used herein, the term "halo" or "halogen" generally refers to a halogen atom radical, including fluoro, chloro, bromo and iodo.

As used herein, the term "halo-$C_{1-4}$alkoxy" refers to a radical of the formula: —O—$C_{1-4}$alkyl-halo, wherein $C_{1-4}$alkyl is partially or completely substituted with one or more halogen atoms where allowed by available valences.

As used herein, the term "halo-$C_{1-4}$alkyl" refers to a radical of the formula: —$C_{1-4}$alkyl-halo, wherein $C_{1-4}$alkyl is partially or completely substituted with one or more halogen atoms where allowed by available valences.

As used herein, the term "halo-$C_{1-4}$alkyl-amino" refers to a radical of the formula: —NH—$C_{1-4}$alkyl-halo.

As used herein, the term "(halo-$C_{1-4}$alkyl)($C_{1-4}$alkyl)amino" refers to a radical of the formula: —N($C_{1-4}$alkyl)($C_{1-4}$alkyl-halo).

As used herein, the term "(halo-$C_{1-4}$alkyl)$_2$-amino" refers to a radical of the formula: —N($C_{1-4}$alkyl-halo)$_2$.

As used herein, the term "heteroaryl-$C_{1-4}$alkoxy" refers to a radical of the formula: —O—$C_{1-4}$alkyl-heteroaryl.

As used herein, the term "heteroaryl-$C_{1-4}$alkyl" refers to a radical of the formula: —$C_{1-4}$alkyl-heteroaryl.

As used herein, the term "heteroaryl-$C_{1-4}$alkyl-amino" refers to a radical of the formula: —NH—$C_{1-4}$alkyl-heteroaryl.

As used herein, the term "(heteroaryl-$C_{1-4}$alkyl)$_2$-amino" refers to a radical of the formula: —N($C_{1-4}$alkyl-heteroaryl)$_2$.

As used herein, the term "(heteroaryl-$C_{1-4}$alkyl)($C_{1-4}$alkyl)amino" refers to a radical of the formula: —N($C_{1-4}$alkyl)($C_{1-4}$alkyl-heteroaryl).

As used herein, the term "heteroaryl-$C_{1-4}$alkyl-amino-$C_{1-4}$alkyl" refers to a radical of the formula: —$C_{1-4}$alkyl-NH—$C_{1-4}$alkyl-heteroaryl.

As used herein, the term "(heteroaryl-$C_{1-4}$alkyl)$_2$-amino-$C_{1-4}$alkyl" refers to a radical of the formula: —$C_{1-4}$alkyl-N($C_{1-4}$alkyl-heteroaryl)$_2$.

As used herein, the term "(heteroaryl-$C_{1-4}$alkyl)($C_{1-4}$alkyl)amino-$C_{1-4}$alkyl" refers to a radical of the formula: —$C_{1-4}$alkyl-N($C_{1-4}$alkyl)($C_{1-4}$alkyl-heteroaryl).

As used herein, the term "heteroaryl-amino" refers to a radical of the formula: —NH-heteroaryl.

As used herein, the term "heterocyclyl-$C_{1-4}$alkoxy" refers to a radical of the formula: —O—$C_{1-4}$alkyl-heterocyclyl.

As used herein, the term "heterocyclyl-$C_{1-4}$alkyl" refers to a radical of the formula: —$C_{1-4}$alkyl-heterocyclyl.

As used herein, the term "heterocyclyl-$C_{1-4}$alkyl-amino" refers to a radical of the formula: —NH—$C_{1-4}$alkyl-heterocyclyl.

As used herein, the term "(heterocyclyl-$C_{1-4}$alkyl)$_2$-amino" refers to a radical of the formula: —N($C_{1-4}$alkyl-heterocyclyl)$_2$.

As used herein, the term "(heterocyclyl-$C_{1-4}$alkyl)($C_{1-4}$alkyl)amino" refers to a radical of the formula: —N($C_{1-4}$alkyl)($C_{1-4}$alkyl-heterocyclyl).

As used herein, the term "heterocyclyl-$C_{1-4}$alkyl-amino-$C_{1-4}$alkyl" refers to a radical of the formula: —$C_{1-4}$alkyl-NH—$C_{1-4}$alkyl-heterocyclyl.

As used herein, the term "(heterocyclyl-$C_{1-4}$alkyl)$_2$-amino-$C_{1-4}$alkyl" refers to a radical of the formula: —$C_{1-4}$alkyl-N($C_{1-4}$alkyl-heterocyclyl)$_2$.

As used herein, the term "(heterocyclyl-$C_{1-4}$alkyl)($C_{1-4}$alkyl)amino-$C_{1-4}$alkyl" refers to a radical of the formula: —$C_{1-4}$alkyl-N($C_{1-4}$alkyl)($C_{1-4}$alkyl-heterocyclyl).

As used herein, the term "heterocyclyl-amino" refers to a radical of the formula: —NH-heterocyclyl.

As used herein, the term "(heterocyclyl)($C_{1-4}$alkyl)amino" refers to a radical of the formula: —N($C_{1-4}$alkyl)(heterocyclyl).

As used herein, the term "heterocyclyl-amino-$C_{1-4}$alkyl" refers to a radical of the formula: —$C_{1-4}$alkyl-NH-heterocyclyl.

As used herein, the term "heterocyclyl-carbonyl" refers to a radical of the formula: —C(O)-heterocyclyl.

As used herein, the term "heterocyclyl-carbonyl-oxy" refers to a radical of the formula: —O—C(O)-heterocyclyl.

As used herein, the term "heterocyclyl-oxy" refers to a radical of the formula: —O-heterocyclyl.

As used herein, the term "hydroxy" refers to a radical of the formula: —OH.

As used herein, the term "hydroxy-$C_{1-4}$alkoxy-$C_{1-4}$alkyl" refers to a radical of the formula: —$C_{1-4}$alkyl-O—$C_{1-4}$alkyl-OH.

As used herein, the term "hydroxy-$C_{1-4}$alkyl" refers to a radical of the formula: —$C_{1-4}$alkyl-OH, wherein $C_{1-4}$alkyl is partially or completely substituted with one or more hydroxy radicals where allowed by available valences.

As used herein, the term "hydroxy-$C_{1-4}$alkyl-amino" refers to a radical of the formula: —NH—$C_{1-4}$alkyl-OH.

As used herein, the term "(hydroxy-$C_{1-4}$alkyl)$_2$-amino" refers to a radical of the formula: —N($C_{1-4}$alkyl-OH)$_2$.

As used herein, the term "(hydroxy-$C_{1-4}$alkyl)($C_{1-4}$alkyl)amino" refers to a radical of the formula: —N($C_{1-4}$alkyl)($C_{1-4}$alkyl-OH).

As used herein, the term "hydroxy-$C_{1-4}$alkyl-amino-$C_{1-4}$alkyl" refers to a radical of the formula: —$C_{1-4}$alkyl-NH—$C_{1-4}$alkyl-OH.

As used herein, the term "(hydroxy-$C_{1-4}$alkyl)$_2$-amino-$C_{1-4}$alkyl" refers to a radical of the formula: —$C_{1-4}$alkyl-N($C_{1-4}$alkyl-OH)$_2$.

As used herein, the term "(hydroxy-$C_{1-4}$alkyl)($C_{1-4}$alkyl)amino-$C_{1-4}$alkyl" refers to a radical of the formula: —$C_{1-4}$alkyl-N($C_{1-4}$alkyl)($C_{1-4}$alkyl-OH).

As used herein, the term "hydroxy-$C_{1-4}$alkyl-amino-$C_{1-4}$alkoxy" refers to a radical of the formula: —O—$C_{1-4}$alkyl-NH—$C_{1-4}$alkyl-OH.

As used herein, the term "(hydroxy-$C_{1-4}$alkyl)$_2$-amino-$C_{1-4}$alkoxy" refers to a radical of the formula: —O—$C_{1-4}$alkyl-N($C_{1-4}$alkyl-OH)$_2$.

As used herein, the term "(hydroxy-$C_{1-4}$alkyl)($C_{1-4}$alkyl)amino-$C_{1-4}$alkoxy" refers to a radical of the formula: —O—$C_{1-4}$alkyl-N($C_{1-4}$alkyl)($C_{1-4}$alkyl-OH).

As used herein, the term "hydroxy-$C_{1-4}$alkyl-amino-$C_{1-4}$alkyl-amino" refers to a radical of the formula: —NH—$C_{1-4}$alkyl-NH—$C_{1-4}$alkyl-OH.

As used herein, the term "(hydroxy-$C_{1-4}$alkyl)$_2$-amino-$C_{1-4}$alkyl)$_2$-amino" refers to a radical of the formula: —N($C_{1-4}$alkyl-NH—$C_{1-4}$alkyl-OH)$_2$.

As used herein, the term "(hydroxy-$C_{1-4}$alkyl)$_2$-amino-$C_{1-4}$alkyl-amino" refers to a radical of the formula: —NH—$C_{1-4}$alkyl-N($C_{1-4}$alkyl-OH)$_2$.

As used herein, the term "(hydroxy-$C_{1-4}$alkyl-amino-$C_{1-4}$alkyl)($C_{1-4}$alkyl)amino" refers to a radical of the formula: —N($C_{1-4}$alkyl)($C_{1-4}$alkyl-NH—$C_{1-4}$alkyl-OH).

As used herein, the term "[(hydroxy-$C_{1-4}$alkyl)$_2$-amino-$C_{1-4}$alkyl]($C_{1-4}$alkyl)amino" refers to a radical of the formula: —N($C_{1-4}$alkyl)[$C_{1-4}$alkyl-N($C_{1-4}$alkyl-OH)$_2$].

As used herein, the term "(hydroxy-$C_{1-4}$alkyl)($C_{1-4}$alkyl)amino-$C_{1-4}$alkyl-amino" refers to a radical of the formula: —NH—$C_{1-4}$alkyl-N($C_{1-4}$alkyl,$C_{1-4}$alkyl-OH).

As used herein, the term "[(hydroxy-$C_{1-4}$alkyl)($C_{1-4}$alkyl)amino-$C_{1-4}$alkyl]-($C_{1-4}$alkyl)amino" refers to a radical of the formula: —N($C_{1-4}$alkyl)[$C_{1-4}$alkyl-N($C_{1-4}$alkyl)-($C_{1-4}$alkyl-OH)].

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. A person of ordinary skill in the art should note that any carbon as well as heteroatom with valences that appear to be unsatisfied as described or shown herein is assumed to have a sufficient number of hydrogen atom(s) to satisfy the valences described or shown. In certain instances one or more substituents having a double bond (e.g., "oxo" or "=O") as the point of attachment may be described, shown or listed herein within a substituent group, wherein the structure may only show a single bond as the point of attachment to the core structure of Formula (I) or Formula (II). A person of ordinary skill in the art would understand that, while only a single bond is shown, a double bond is intended for those substituents.

As used herein, the term "and the like," with reference to the definitions of chemical terms provided herein, means that variations in chemical structures that could be expected by one skilled in the art include, without limitation, isomers (including chain, branching or positional structural isomers), hydration of ring systems (including saturation or partial unsaturation of monocyclic, bicyclic or polycyclic ring structures) and all other variations where allowed by available valences which result in a stable compound.

For the purposes of this description, where one or more substituent variables for a compound of Formula (I) or Formula (II) or a form thereof encompass functionalities incorporated into a compound of Formula (I) or Formula (II), each functionality appearing at any location within the disclosed compound may be independently selected, and as appropriate, independently and/or optionally substituted.

As used herein, the terms "independently selected," or "each selected" refer to functional variables in a substituent list that may occur more than once on the structure of Formula (I) or Formula (II), the pattern of substitution at each occurrence is independent of the pattern at any other occurrence. Further, the use of a generic substituent variable on any formula or structure for a compound described herein is understood to include the replacement of the generic substituent with species substituents that are included within the particular genus, e.g., aryl may be replaced with phenyl or naphthalenyl and the like, and that the resulting compound is to be included within the scope of the compounds described herein.

As used herein, the terms "each instance of" or "in each instance, when present," when used preceding a phrase such as " . . . $C_{3-14}$cycloalkyl, $C_{3-14}$cycloalkyl-$C_{1-4}$alkyl, aryl, aryl-$C_{1-4}$alkyl, heteroaryl, heteroaryl-$C_{1-4}$alkyl, heterocyclyl and heterocyclyl-$C_{1-4}$alkyl," are intended to refer to the $C_{3-14}$cycloalkyl, aryl, heteroaryl and heterocyclyl ring systems when each are present either alone or as a substituent.

As used herein, the term "optionally substituted" means optional substitution with the specified substituent variables, groups, radicals or moieties.

Compound Forms

As used herein, the term "form" means a compound of Formula (I) or Formula (II) having a form selected from the group consisting of a free acid, free base, prodrug, salt, hydrate, solvate, clathrate, isotopologue, racemate, enantiomer, diastereomer, stereoisomer, polymorph and tautomer form thereof.

In certain aspects described herein, the form of the compound of Formula (I) or Formula (II) is a free acid, free base or salt thereof.

In certain aspects described herein, the form of the compound of Formula (I) or Formula (II) is a salt thereof.

In certain aspects described herein, the form of the compound of Formula (I) or Formula (II) is an isotopologue thereof.

In certain aspects described herein, the form of the compound of Formula (I) or Formula (II) is a stereoisomer, racemate, enantiomer or diastereomer thereof.

In certain aspects described herein, the form of the compound of Formula (I) or Formula (II) is a tautomer thereof.

In certain aspects described herein, the form of the compound of Formula (I) or Formula (II) is a pharmaceutically acceptable form.

In certain aspects described herein, the compound of Formula (I) or Formula (II) or a form thereof is isolated for use.

As used herein, the term "isolated" means the physical state of a compound of Formula (I) or Formula (II) or a form thereof after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterized by standard analytical techniques described herein or well known to the skilled artisan.

As used herein, the term "protected" means that a functional group in a compound of Formula (I) or Formula (II) or a form thereof is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, methoxymethanol, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters. In certain instances, the protecting group may also be a polymer resin, such as a Wang resin or a 2-chlorotrityl-chloride resin. Protecting groups may be added or removed in accordance with standard techniques, which are well-known to those skilled in the art and as described herein. It will also be appreciated by those skilled in the art, although such protected derivatives of compounds described herein may not possess pharmacological activity as such, they may be administered to a subject and thereafter metabolized in the body to form compounds described herein which are pharmacologically active. Such derivatives may therefore be described as "prodrugs". All prodrugs of compounds described herein are included within the scope of the use described herein.

As used herein, the term "prodrug" means a form of an instant compound (e.g., a drug precursor) that is transformed in vivo to yield an active compound of Formula (I) or Formula (II) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In one example, when a compound of Formula (I) or Formula (II) or a form thereof contains a carboxylic acid functional group, a prodrug can comprise an ester formed by the replacement of the hydrogen atom of the acid group with a functional group such as alkyl and the like. In another example, when a compound of Formula (I) or Formula (II) or a form thereof contains a hydroxyl functional group, a prodrug form can be prepared by replacing the hydrogen atom of the hydroxyl with another functional group such as alkyl, alkylcarbonyl or a phosphonate ester and the like. In another example, when a compound of Formula (I) or Formula (II) or a form thereof contains an amine functional group, a prodrug form can be prepared by replacing one or more amine hydrogen atoms with a functional group such as alkyl or substituted carbonyl. Pharmaceutically acceptable prodrugs of compounds of Formula (I) or Formula (II) or a form thereof include those compounds substituted with one or more of the following groups: carboxylic acid esters, sulfonate esters, amino acid esters, phosphonate esters and mono-, di- or triphosphate esters or alkyl substituents, where appropriate. As described herein, it is understood by a person of ordinary skill in the art that one or more of such substituents may be used to provide a compound of Formula (I) or Formula (II) or a form thereof as a prodrug.

One or more compounds described herein may exist in unsolvated as well as solvated forms with pharmaceutically acceptable solvents such as water, ethanol, and the like, and the description herein is intended to embrace both solvated and unsolvated forms.

As used herein, the term "solvate" means a physical association of a compound described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

As used herein, the term "hydrate" means a solvate wherein the solvent molecule is water.

The compounds of Formula (I) or Formula (II) can form salts, which are intended to be included within the scope of this description. Reference to a compound of Formula (I) or Formula (II) or a form thereof herein is understood to include reference to salt forms thereof, unless otherwise indicated. The term "salt(s)", as employed herein, denotes acidic salts formed with inorganic and/or organic acids, as well as basic salts formed with inorganic and/or organic bases. In addition, when a compound of Formula (I) or Formula (II) or a form thereof contains both a basic moiety, such as, without limitation an amine moiety, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds described herein that are safe and effective (i.e., non-toxic, physiologically acceptable) for use in mammals and that possess biological activity, although other salts are also useful. Salts of the compounds of the Formula (I) or Formula (II) may be formed, for example, by reacting a compound of Formula (I) or Formula (II) or a form thereof with an amount of acid or base, such as an equivalent amount, in a medium such as one in which the salt precipitates or in an aqueous medium followed by lyophilization.

Pharmaceutically acceptable salts include one or more salts of acidic or basic groups present in compounds described herein. Particular aspects of acid addition salts include, and are not limited to, acetate, ascorbate, benzoate, benzenesulfonate, bisulfate, bitartrate, borate, bromide, butyrate, chloride, citrate, camphorate, camphorsulfonate, ethanesulfonate, formate, fumarate, gentisinate, gluconate, glucaronate, glutamate, iodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate salts and the like. Certain particular aspects of acid addition salts include chloride or dichloride.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Suitable basic salts include, but are not limited to, aluminum, ammonium, calcium, lithium, magnesium, potassium, sodium and zinc salts.

All such acid salts and base salts are intended to be included within the scope of pharmaceutically acceptable salts as described herein. In addition, all such acid and base salts are considered equivalent to the free forms of the corresponding compounds for purposes of this description.

Compounds of Formula (I) or Formula (II) and forms thereof, may further exist in a tautomeric form. All such tautomeric forms are contemplated and intended to be included within the scope of the compounds of Formula (I) or Formula (II) or a form thereof as described herein.

The compounds of Formula (I) or Formula (II) or a form thereof may contain asymmetric or chiral centers, and, therefore, exist in different stereoisomeric forms. The present description is intended to include all stereoisomeric forms of the compounds of Formula (I) or Formula (II) as well as mixtures thereof, including racemic mixtures.

The compounds described herein may include one or more chiral centers, and as such may exist as racemic mixtures (RIS) or as substantially pure enantiomers and diastereomers. The compounds may also exist as substantially pure (R) or (S) enantiomers (when one chiral center is present). In one particular aspect, the compounds described herein are (S) isomers and may exist as enantiomerically pure compositions substantially comprising only the (S) isomer. In another particular aspect, the compounds described herein are (R) isomers and may exist as enantiomerically pure compositions substantially comprising only the (R) isomer. As one of skill in the art will recognize, when more than one chiral center is present, the compounds described herein may also exist as a (R,R), (R,S), (S,R) or (S,S) isomer, as defined by IUPAC Nomenclature Recommendations.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the description, a compound of Formula (I) or Formula (II) or a form thereof is a substantially pure (S) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the description, a compound of Formula (I) or Formula (II) or a form thereof is a substantially pure (R) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, or about 80/20.

In addition, the present description embraces all geometric and positional isomers. For example, if a compound of Formula (I) or Formula (II) or a form thereof incorporates a double bond or a fused ring, both the cis- and trans-forms, as well as mixtures, are embraced within the scope of the description. Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art. Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) or Formula (II) may be atropisomers (e.g., substituted biaryls) and are considered as part of this description.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this description, as are positional isomers (such as, for example, 4-pyridyl and 3-pyridyl). Individual stereoisomers of the compounds described herein may, for example, be substantially free of other isomers, or may be present in a racemic mixture, as described supra.

The use of the terms "salt", "solvate", "ester", "prodrug" and the like, is intended to equally apply to the salt, solvate, ester and prodrug of enantiomers, stereoisomers, rotamers, tautomers, positional isomers, racemates or isotopologues of the instant compounds.

The term "isotopologue" refers to isotopically-enriched compounds described herein which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, $^{35}Cl$ and $^{36}Cl$, respectively, each of which are also within the scope of this description.

Certain isotopically-enriched compounds described herein (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances.

Polymorphic crystalline and amorphous forms of the compounds of Formula (I) or Formula (II) and of the salts, solvates, hydrates, esters and prodrugs of the compounds of Formula (I) or Formula (II) are further intended to be included in the present description.

Compound Uses

In accordance with the intended scope of the present description, aspects of the present description include compounds that have been identified and have been demonstrated to be useful in selectively preventing, treating or ameliorating HD and have been provided for use for preventing, treating or ameliorating HD.

An aspect of the present description includes a method for preventing, treating or ameliorating HD in a subject in need thereof comprising, administering to the subject an effective amount of a compound of Formula (I) or Formula (II) or a form thereof.

An aspect of the present description includes a method for treating or ameliorating HD in a subject in need thereof comprising, administering to the subject an effective amount of a compound of Formula (I) or Formula (II) or a form thereof.

An aspect of the present description includes a method for preventing HD in a subject in need thereof comprising, administering to the subject an effective amount of a compound of Formula (I) or Formula (II) or a form thereof.

An aspect of the present description includes a method for treating HD in a subject in need thereof comprising, administering to the subject an effective amount of a compound of Formula (I) or Formula (II) or a form thereof.

An aspect of the present description includes a method for ameliorating HD in a subject in need thereof comprising, administering to the subject an effective amount of a compound of Formula (I) or Formula (II) or a form thereof.

Another aspect of the present description includes a method for treating or ameliorating HD in a subject in need thereof comprising, administering to the subject an effective amount of a compound salt of Formula (I) or Formula (II) or a form thereof.

An aspect of the present description includes a method for use of a compound of Formula (I) or Formula (II) or a form or composition thereof for treating or ameliorating HD in a subject in need thereof comprising, administering to the subject an effective amount of the compound of Formula (I) or Formula (II) or a form or composition thereof.

Another aspect of the present description includes a method for use of a compound salt of Formula (I) or Formula (II) or a form or composition thereof for treating or ameliorating HD in a subject in need thereof comprising, administering to the subject an effective amount of the compound salt of Formula (I) or Formula (II) or a form thereof.

An aspect of the present description includes a use for a compound of Formula (I) or Formula (II) or a form thereof for treating or ameliorating HD in a subject in need thereof comprising, administering to the subject an effective amount of the compound of Formula (I) or Formula (II) or a form thereof.

Another aspect of the present description includes a use for a compound salt of Formula (I) or Formula (II) or a form thereof for treating or ameliorating HD in a subject in need thereof comprising, administering to the subject an effective amount of the compound salt of Formula (I) or Formula (II) or a form thereof.

An aspect of the present description includes a use for a compound of Formula (I) or Formula (II) or a form thereof in the manufacture of a medicament for treating or ameliorating HD in a subject in need thereof comprising, administering to the subject an effective amount of the medicament.

Another aspect of the present description includes a use for a compound salt of Formula (I) or Formula (II) or a form thereof in the manufacture of a medicament for treating or ameliorating HD in a subject in need thereof comprising, administering to the subject an effective amount of the medicament.

An aspect of the present description includes in vitro or in vivo use of the compound of Formula (I) or Formula (II) or a form thereof having activity toward HD.

An aspect of the present description includes a use of the compound of Formula (I) or Formula (II) or a form thereof in a combination therapy to provide additive or synergistic activity, thus enabling the development of a combination product for treating or ameliorating HD.

Another aspect of the present description includes a combination therapy comprising compounds described herein in combination with one or more known drugs or one or more known therapies may be used to treat HD regardless of whether HD is responsive to the known drug.

An aspect of the present description includes a use for a compound of Formula (I) or Formula (II) or a form thereof in a combination product with one or more therapeutic agents for treating or ameliorating HD in a subject in need thereof comprising, administering to the subject an effective amount of the compound of Formula (I) or Formula (II) or a form thereof in combination with an effective amount of the one or more agents.

Another aspect of the present description includes a use for a compound salt of Formula (I) or Formula (II) or a form thereof in a combination product with one or more therapeutic agents for treating or ameliorating HD in a subject in need thereof comprising, administering to the subject an effective amount of the compound salt of Formula (I) or Formula (II) or a form thereof in combination with an effective amount of the one or more agents.

In an aspect of a use or method provided herein, compounds of Formula (I) or Formula (II) or a form thereof used in combination with one or more additional agents can be administered to a subject or contacted with a subject or patient cell(s) prior to, concurrently with, or subsequent to administering to the subject or patient or contacting the cell with an additional agent(s). A compound(s) of Formula (I) or Formula (II) or a form thereof and an additional agent(s) can be administered to a subject or contacted with a cell in single composition or different compositions. In a specific aspect, a compound(s) of Formula (I) or Formula (II) or a form thereof is used in combination with gene therapy to inhibit HTT expression (using, e.g., viral delivery vectors) or the administration of another small molecule HTT inhibitor. In another specific aspect, a compound(s) of Formula (I) or Formula (II) or a form thereof are used in combination with cell replacement using differentiated non-mutant HTT stem cells. In another specific aspect, a compound(s) of Formula (I) or Formula (II) or a form thereof are used in combination with cell replacement using differentiated HTT stem cells.

In one aspect, provided herein is the use of compounds of Formula (I) or Formula (II) or a form thereof in combination with supportive standard of care therapies, including palliative care.

An aspect of the present description includes a use for a compound of Formula (I) or Formula (II) or a form thereof in the preparation of a kit for treating or ameliorating HD in a subject in need thereof comprising, the compound of Formula (I) or Formula (II) or a form thereof and instructions for administering an effective amount of the compound of Formula (I) or Formula (II) or a form thereof.

An aspect of the present description includes a use for a compound of Formula (I) or Formula (II) or a form thereof in the preparation of a kit for treating or ameliorating HD in a subject in need thereof comprising, the compound of Formula (I) or Formula (II) or a form thereof and instructions for administering an effective amount of the compound of Formula (I) or Formula (II) or a form thereof; and optionally, for administering to the subject an effective amount of the compound of Formula (I) or Formula (II) or a form thereof in a combination product with an effective amount of one or more therapeutic agents.

An aspect of the present description includes a use for a compound of Formula (I) or Formula (II) or a form thereof in the preparation of a kit for treating or ameliorating HD in a subject in need thereof comprising, the compound of Formula (I) or Formula (II) or a form thereof and instructions for administering an effective amount of the compound of Formula (I) or Formula (II) or a form thereof; and optionally, for administering to the subject an effective amount of the compound of Formula (I) or Formula (II) or a form thereof in a combination product with an effective amount of the one or more therapeutic agents; and optionally, for administering to the subject an effective amount of the compound of Formula (I) or Formula (II) or a form thereof in a combination product with an effective amount of the one or more therapeutic agents in a combination therapy with a standard of care supportive therapy, wherein the standard of care supportive therapy is palliative care.

In one respect, for each of such aspects, the subject is treatment naive. In another respect, for each of such aspects, the subject is not treatment naive.

As used herein, the term "preventing" refers to keeping a disease, disorder or condition from occurring in a subject that may be predisposed to the disease, disorder and/or condition but has not yet been diagnosed as having the disease, disorder and/or condition.

As used herein, the term "treating" refers to inhibiting the progression of a disease, disorder or condition in a subject already exhibiting the symptoms of the disease, disorder and/or condition, i.e., arresting the development of a disease, disorder and/or condition that has already affected the subject.

As used herein, the term "ameliorating" refers to relieving the symptoms of a disease, disorder or condition in a subject already exhibiting the symptoms of the disease, disorder and/or condition, i.e., causing regression of the disease, disorder and/or condition that has already affected the subject.

As used herein, the term "subject" refers to an animal or any living organism having sensation and the power of voluntary movement, and which requires oxygen and organic food. Nonlimiting examples include members of the human, primate, equine, porcine, bovine, murine, *rattus*, canine and feline specie. In certain aspects, the subject is a mammal or a warm-blooded vertebrate animal. In other aspects, the subject is a human. As used herein, the term "patient" may be used interchangeably with "subject" and "human".

As used herein, the terms "effective amount" or "therapeutically effective amount" mean an amount of compound of Formula (I) or Formula (II) or a form, composition or medicament thereof that achieves a target plasma concentration that is effective in treating or ameliorating HD as described herein and thus producing the desired therapeutic, ameliorative, inhibitory or preventative effect in a subject in need thereof. In one aspect, the effective amount may be the amount required to treat HD in a subject or patient, more specifically, in a human.

In another aspect, the concentration-biological effect relationships observed with regard to a compound of Formula (I) or Formula (II) or a form thereof indicate a target plasma concentration ranging from approximately 0.001 µg/mL to approximately 50 µg/mL, from approximately 0.01 µg/mL to approximately 20 µg/mL, from approximately 0.05 µg/mL to approximately 10 µg/mL, or from approximately 0.1 µg/mL to approximately 5 µg/mL. To achieve such plasma concentrations, the compounds described herein may be administered at doses that vary, such as, for example, without limitation, from 1.0 ng to 10,000 mg.

In one aspect, the dose administered to achieve an effective target plasma concentration may be administered based upon subject or patient specific factors, wherein the doses administered on a weight basis may be in the range of from about 0.001 mg/kg/day to about 3500 mg/kg/day, or about 0.001 mg/kg/day to about 3000 mg/kg/day, or about 0.001 mg/kg/day to about 2500 mg/kg/day, or about 0.001 mg/kg/day to about 2000 mg/kg/day, or about 0.001 mg/kg/day to about 1500 mg/kg/day, or about 0.001 mg/kg/day to about 1000 mg/kg/day, or about 0.001 mg/kg/day to about 500 mg/kg/day, or about 0.001 mg/kg/day to about 250 mg/kg/day, or about 0.001 mg/kg/day to about 200 mg/kg/day, or about 0.001 mg/kg/day to about 150 mg/kg/day, or about 0.001 mg/kg/day to about 100 mg/kg/day, or about 0.001 mg/kg/day to about 75 mg/kg/day, or about 0.001 mg/kg/day to about 50 mg/kg/day, or about 0.001 mg/kg/day to about 25 mg/kg/day, or about 0.001 mg/kg/day to about 10 mg/kg/day, or about 0.001 mg/kg/day to about 5 mg/kg/day, or about 0.001 mg/kg/day to about 1 mg/kg/day, or about 0.001 mg/kg/day to about 0.5 mg/kg/day, or about 0.001 mg/kg/day to about 0.1 mg/kg/day, or from about 0.01 mg/kg/day to about 3500 mg/kg/day, or about 0.01 mg/kg/day to about 3000 mg/kg/day, or about 0.01 mg/kg/day to about 2500 mg/kg/day, or about 0.01 mg/kg/day to about 2000 mg/kg/day, or about 0.01 mg/kg/day to about 1500 mg/kg/day, or about 0.01 mg/kg/day to about 1000 mg/kg/day, or about 0.01 mg/kg/day to about 500 mg/kg/day, or about 0.01 mg/kg/day to about 250 mg/kg/day, or about 0.01 mg/kg/day to about 200 mg/kg/day, or about 0.01 mg/kg/day to about 150 mg/kg/day, or about 0.01 mg/kg/day to about 100 mg/kg/day, or about 0.01 mg/kg/day to about 75 mg/kg/day, or about 0.01 mg/kg/day to about 50 mg/kg/day, or about 0.01 mg/kg/day to about 25 mg/kg/day, or about 0.01 mg/kg/day to about 10 mg/kg/day, or about 0.01 mg/kg/day to about 5 mg/kg/day, or about 0.01 mg/kg/day to about 1 mg/kg/day, or about 0.01 mg/kg/day to about 0.5 mg/kg/day, or about 0.01 mg/kg/day to about 0.1 mg/kg/day, or from about 0.1 mg/kg/day to about 3500 mg/kg/day, or about 0.1 mg/kg/day to about 3000 mg/kg/day, or about 0.1 mg/kg/day to about 2500 mg/kg/day, or about 0.1 mg/kg/day to about 2000 mg/kg/day, or about 0.1 mg/kg/day to about 1500 mg/kg/day, or about 0.1 mg/kg/day to about 1000 mg/kg/day, or about 0.1 mg/kg/day to about 500 mg/kg/day, or about 0.1 mg/kg/day to about 250 mg/kg/day, or about 0.1 mg/kg/day to about 200 mg/kg/day, or about 0.1 mg/kg/day to about 150 mg/kg/day, or about 0.1 mg/kg/day to about 100 mg/kg/day, or about 0.1 mg/kg/day to about 75 mg/kg/day, or about 0.1 mg/kg/day to about 50 mg/kg/day, or about 0.1 mg/kg/day to about 25 mg/kg/day, or about 0.1 mg/kg/day to about 10 mg/kg/day, or about 0.1 mg/kg/day to about 5 mg/kg/day, or about 0.1 mg/kg/day to about 1 mg/kg/day, or about 0.1 mg/kg/day to about 0.5 mg/kg/day.

Effective amounts for a given subject may be determined by routine experimentation that is within the skill and judgment of a clinician or a practitioner skilled in the art in light of factors related to the subject. Dosage and administration may be adjusted to provide sufficient levels of the active agent(s) or to maintain the desired effect. Factors which may be taken into account include genetic screening, severity of the disease state, status of disease progression, general health of the subject, ethnicity, age, weight, gender, diet, time of day and frequency of administration, drug combination(s), reaction sensitivities, experience with other therapies, and tolerance/response to therapy.

The dose administered to achieve an effective target plasma concentration may be orally administered once (once in approximately a 24 hour period; i.e., "q.d."), twice (once in approximately a 12 hour period; i.e., "b.i.d." or "q.12 h"), thrice (once in approximately an 8 hour period; i.e., "t.i.d." or "q.8 h"), or four times (once in approximately a 6 hour period; i.e., "q.d.s.", "q.i.d." or "q.6 h") daily.

In certain aspects, the dose administered to achieve an effective target plasma concentration may also be administered in a single, divided, or continuous dose for a patient or subject having a weight in a range of between about 40 to about 200 kg (which dose may be adjusted for patients or subjects above or below this range, particularly children under 40 kg). The typical adult subject is expected to have a median weight in a range of about 70 kg. Long-acting pharmaceutical compositions may be administered every 2, 3 or 4 days, once every week, or once every two weeks depending on half-life and clearance rate of the particular formulation.

The compounds and compositions described herein may be administered to the subject via any drug delivery route known in the art. Nonlimiting examples include oral, ocular, rectal, buccal, topical, nasal, sublingual, transdermal, subcutaneous, intramuscular, intravenous (bolus and infusion), intracerebral, and pulmonary routes of administration.

In another aspect, the dose administered may be adjusted based upon a dosage form described herein formulated for delivery at about 0.02, 0.025, 0.03, 0.05, 0.06, 0.075, 0.08, 0.09, 0.10, 0.20, 0.25, 0.30, 0.50, 0.60, 0.75, 0.80, 0.90, 1.0, 1.10, 1.20, 1.25, 1.50, 1.75, 2.0, 3.0, 5.0, 10, 20, 30, 40, 50, 100, 150, 200, 250, 300, 400, 500, 1000, 1500, 2000, 2500, 3000 or 4000 mg/day.

For any compound, the effective amount can be estimated initially either in cell culture assays or in relevant animal models, such as a mouse, guinea pig, chimpanzee, marmoset or tamarin animal model. Relevant animal models may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is therapeutic index, and can be expressed as the ratio, $LD_{50}/ED_{50}$. In certain aspects, the effective amount is such that a large therapeutic index is achieved. In further particular aspects, the dosage is within a range of circulating concentrations that include an $ED_{50}$ with little or no toxicity. The dosage may vary within this range depending upon the dosage form employed, sensitivity of the patient, and the route of administration.

In one aspect, provided herein are methods for modulating the amount of HTT (huntingtin protein), comprising contacting a human cell with a compound of Formula (I) or Formula (II) or a form thereof. In a specific aspect, provided herein are methods for modulating the amount of HTT, comprising contacting a human cell with a compound of Formula (I) or Formula (II) or a form thereof that modulates the expression of HTT. The human cell can be contacted with a compound of Formula (I) or Formula (II) or a form thereof in vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of HTT expression and/or function. In another aspect, the human cell is from a human with HD. In another aspect, the human cell is in a human with HD. In one aspect, the compound is a form of the compound of Formula (I) or Formula (II).

In a specific aspect, provided herein is a method for enhancing the inhibition of mutant HTT transcribed from the Htt gene, comprising contacting a human cell with a compound of Formula (I) or Formula (II) or a form thereof. The human cell can be contacted with a compound of Formula (I) or Formula (II) or a form thereof in vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of wild-type "normal" HTT expression and/or function. In another aspect, the human cell is from a human with HD. In another aspect, the human cell is in a human with HD. In one aspect, the compound is a form of the compound of Formula (I) or Formula (II).

In another aspect, provided herein is a method for modulating the inhibition of mutant HTT transcribed from the Htt gene, comprising administering to a non-human animal model for HD a compound of Formula (I) or Formula (II) or a form thereof. In a specific aspect, provided herein is a method for modulating the inhibition of mutant HTT transcribed from the Htt gene, comprising administering to a non-human animal model for HD a compound of Formula (I) or Formula (II) or a form thereof. In a specific aspect, the compound is a form of the compound of Formula (I) or Formula (II).

In another aspect, provided herein is a method for decreasing the amount of mutant HTT, comprising contacting a human cell with a compound of Formula (I) or Formula (II) or a form thereof. In a specific aspect, provided herein is a method for decreasing the amount of mutant HTT, comprising contacting a human cell with a compound of Formula (I) or Formula (II) that inhibits the transcription of mutant HTT (huntingtin mRNA) from the Htt gene. In another specific aspect, provided herein is a method for decreasing the amount of HTT, comprising contacting a human cell with a compound of Formula (I) or Formula (II) that inhibits the expression of mutant HTT transcribed from the Htt gene. The human cell can be contacted with a compound of Formula (I) or Formula (II) or a form thereof in vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of HTT expression and/or function. In another aspect, the human cell is from a human with HD. In another aspect, the human cell is in a human with HD. In one aspect, the compound is a form of the compound of Formula (I) or Formula (II).

In certain aspects, treating or ameliorating HD with a compound of Formula (I) or Formula (II) or a form thereof (alone or in combination with an additional agent) has a therapeutic effect and/or beneficial effect. In a specific aspect, treating HD with a compound of Formula (I) or Formula (II) or a form thereof (alone or in combination with an additional agent) results in one, two or more of the following effects: (i) reduces or ameliorates the severity of HD; (ii) delays onset of HD; (iii) inhibits the progression of HD; (iv) reduces hospitalization of a subject; (v) reduces hospitalization length for a subject; (vi) increases the survival of a subject; (vii) improves the quality of life for a subject; (viii) reduces the number of symptoms associated with HD; (ix) reduces or ameliorates the severity of a symptom(s) associated with HD; (x) reduces the duration of a symptom associated with HD; (xi) prevents the recurrence of a symptom associated with HD; (xii) inhibits the development or onset of a symptom of HD; and/or (xiii) inhibits of the progression of a symptom associated with HD.

Metabolites

Another aspect included within the scope of the present description are the use of in vivo metabolic products of the compounds described herein. Such products may result, for example, from the oxidation, reduction, hydrolysis, amidation, esterification and the like of the administered compound, primarily due to enzymatic processes. Accordingly, the description includes the use of compounds produced by a process comprising contacting a compound described herein with a mammalian tissue or a mammal for a period of time sufficient to yield a metabolic product thereof.

Such products typically are identified by preparing a radio-labeled isotopologue (e.g., $^{14}$C or $^{3}$H) of a compound described herein, administering the radio-labeled compound in a detectable dose (e.g., greater than about 0.5 mg/kg) to a mammal such as a rat, mouse, guinea pig, dog, monkey or human, allowing sufficient time for metabolism to occur (typically about 30 seconds to about 30 hours), and identifying the metabolic conversion products from urine, bile, blood or other biological samples. The conversion products are easily isolated since they are "radiolabeled" by virtue of being isotopically-enriched (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds described herein even if they possess no biological activity of their own.

Pharmaceutical Compositions

In accordance with the intended scope of the present description, aspects of the present description include compounds that have been identified and have been demonstrated to be useful in selectively preventing, treating or ameliorating HD and have been provided for use as one or more pharmaceutical compositions for preventing, treating or ameliorating HD.

An aspect of the present description includes a use for a compound of Formula (I) or Formula (II) or a form thereof in the preparation of a pharmaceutical composition for treating or ameliorating HD in a subject in need thereof comprising, administering to the subject an effective amount of the compound of Formula (I) or Formula (II) or a form thereof in admixture with one or more pharmaceutically acceptable excipients.

An aspect of the present description includes a use for a pharmaceutical composition of the compound of Formula (I) or Formula (II) or a form thereof in the preparation of a kit for treating or ameliorating HD in a subject in need thereof comprising, the pharmaceutical composition of the compound of Formula (I) or Formula (II) or a form thereof and instructions for administering the pharmaceutical composition.

As used herein, the term "composition" means a product comprising the specified ingredients in the specified amounts, as well as any product which results, directly or indirectly, from combination of the specified ingredients in the specified amounts.

The pharmaceutical composition may be formulated to achieve a physiologically compatible pH, ranging from about pH 3 to about pH 11. In certain aspects, the pharmaceutical composition is formulated to achieve a pH of from about pH 3 to about pH 7. In other aspects, the pharmaceutical composition is formulated to achieve a pH of from about pH 5 to about pH 8.

The term "pharmaceutically acceptable excipient" refers to an excipient for administration of a pharmaceutical agent, such as the compounds described herein. The term refers to any pharmaceutical excipient that may be administered without undue toxicity. Pharmaceutically acceptable excipients may be determined in part by the particular composition being administered, as well as by the particular mode of administration and/or dosage form. Nonlimiting examples of pharmaceutically acceptable excipients include carriers, solvents, stabilizers, adjuvants, diluents, etc. Accordingly, there exists a wide variety of suitable formulations of pharmaceutical compositions for the instant compounds described herein (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive antibodies. Other exemplary excipients include antioxidants such as ascorbic acid; chelating agents such as EDTA; carbohydrates such as dextrin, hydroxyalkylcellulose, hydroxyalkylmethylcellulose (e.g., hydroxypropylmethylcellulose, also known as HPMC), stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended use described herein. Suitable formulations for oral administration include solids, liquid solutions, emulsions and suspensions, while suitable inhalable formulations for pulmonary administration include liquids and powders. Alternative formulations include syrups, creams, ointments, tablets, and lyophilized solids which can be reconstituted with a physiologically compatible solvent prior to administration.

When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents, and preserving agents, in order to provide a palatable preparation.

Pharmaceutically acceptable excipients suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid, or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate, or kaolin, or as soft gelatin capsules wherein the active ingredient is mixed with non-aqueous or oil medium, such as glycerin, propylene glycol, polyethylene glycol, peanut oil, liquid paraffin, or olive oil.

In other aspects, pharmaceutical compositions described herein may be formulated as suspensions comprising a compound of Formula (I) or Formula (II) or a form thereof in admixture with one or more pharmaceutically acceptable excipients suitable for the manufacture of a suspension. In yet other aspects, pharmaceutical compositions described herein may be formulated as dispersible powders and granules suitable for preparation of a suspension by the addition of one or more excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin, or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions described herein may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions described herein may be in the form of a sterile injectable preparation, such as a sterile injectable aqueous emulsion or oleaginous suspension. Such emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propanediol. The sterile injectable preparation may also be prepared as a lyophilized powder. Among the acceptable vehicles and solvents that may be employed are water, Ringer's solution and isotonic sodium chloride solution. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

The compounds described herein may be substantially insoluble in water and sparingly soluble in most pharmaceutically acceptable protic solvents and vegetable oils, but generally soluble in medium-chain fatty acids (e.g., caprylic and capric acids) or triglycerides and in propylene glycol esters of medium-chain fatty acids. Thus, contemplated in the description are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In certain aspects, the compound described herein is formulated for oral administration in a lipid-based composition suitable for low solubility compounds. Lipid-based formulations can generally enhance the oral bioavailability of such compounds. As such, pharmaceutical compositions described herein may comprise a effective amount of a compound of Formula (I) or Formula (II) or a form thereof, together with at least one pharmaceutically acceptable excipient selected from medium chain fatty acids or propylene glycol esters thereof (e.g., propylene glycol esters of edible fatty acids such as caprylic and capric fatty acids) and pharmaceutically acceptable surfactants, such as polysorbate 20 or 80 (also referred to as Tween® 20 or Tween® 80, respectively) or polyoxyl 40 hydrogenated castor oil.

In other aspects, the bioavailability of low solubility compounds may be enhanced using particle size optimization techniques including the preparation of nanoparticles or nanosuspensions using techniques known to those skilled in the art. The compound forms present in such preparations include amorphous, partially amorphous, partially crystalline or crystalline forms.

In alternative aspects, the pharmaceutical composition may further comprise one or more aqueous solubility enhancer(s), such as a cyclodextrin. Nonlimiting examples of cyclodextrin include hydroxypropyl, hydroxyethyl, glucosyl, maltosyl and maltotriosyl derivatives of α-, β-, and γ-cyclodextrin, and hydroxypropyl-β-cyclodextrin (HPBC). In certain aspects, the pharmaceutical composition further comprises HPBC in a range of from about 0.1% to about 20%, from about 1% to about 15%, or from about 2.5% to about 10%. The amount of solubility enhancer employed may depend on the amount of the compound in the composition.

Preparation of Compounds

General Synthetic Methods

As disclosed herein, general methods for preparing the compounds of Formula (I) or Formula (II) or a form thereof as described herein are available via standard, well-known synthetic methodology. Many of the starting materials are commercially available or, when not available, can be prepared using the routes described below using techniques known to those skilled in the art. The synthetic schemes provided herein comprise multiple reaction steps, each of which is intended to stand on its own and can be carried out with or without any preceding or succeeding step(s). In other words, each of the individual reaction steps of the synthetic schemes provided herein in isolation is contemplated.

Compounds of Formula (I), wherein B is heterocyclyl, X is O, NH or $NR_{1b}$, where $R_{1b}$ is $C_{1-4}$alkyl, may be prepared as described in Scheme A below.

Compound A1 (where $W_1$ is bromine, chlorine and the like) is converted to Compound A2 by a nucleophilic substitution with a primary or secondary amine or an alcohol (BXH) in the presence of a suitable base (such as $Et_3N$ and the like) in a suitable solvent (such as DMF and the like). Alternatively, Compound A1 is converted to Compound A2 via cross coupling with a primary or a secondary amine in the presence of a suitable catalyst (such as RuPhos Pd G2 and the like) and base (such as sodium tert-butoxide and the like) in an appropriate solvent such as 1,4-dioxane and the like). Compound A2 is converted to Compound A3 by halogenation upon treatment with an appropriate reagent (such as bromine and the like) in an appropriate solvent (such as methanol and the like). Compound A3 is converted to Compound A4 by a Suzuki coupling with an aryl- or heteroaryl-boronic acid (or pinacol boronic ester) in the presence of a catalyst (such as $Pd(dppf)Cl_2$ and the like) and base (such as aqueous $K_2CO_3$ and the like) in a suitable solvent (such as 1,4-dioxane and the like). Alternatively, Compound A3 is converted to Compound A4 by a Stille coupling with an aryl- or heteroaryl-stannane in the presence of a catalyst (such as $Pd_2(dba)_3$ and the like), a ligand (such as X-Phos and the like) and a base (such as CsF and the like) in a suitable solvent (such as 1,4-dioxane and the like). Any protecting groups may be removed upon treatment with a suitable reagent (such as HCl in dioxane for a Boc protecting group and the like) in a suitable solvent (such as dioxane and the like).

Scheme A

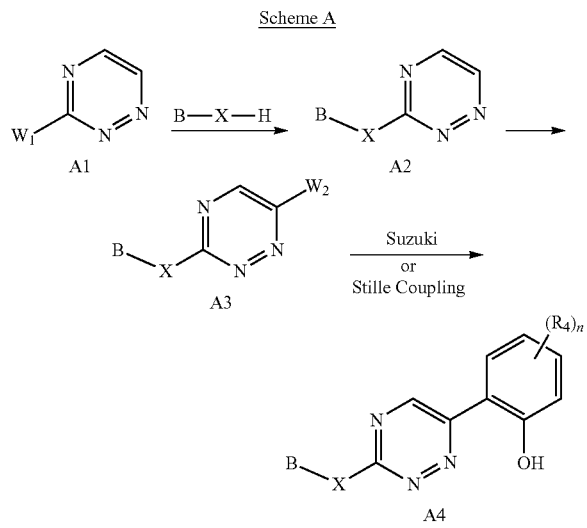

Scheme B

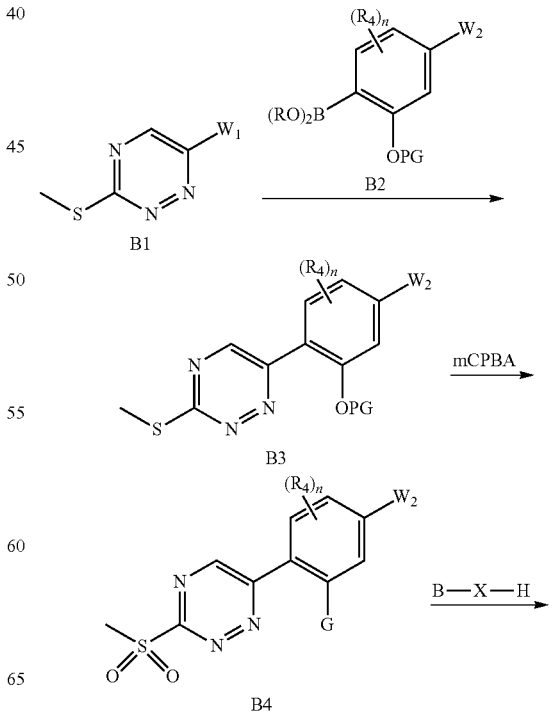

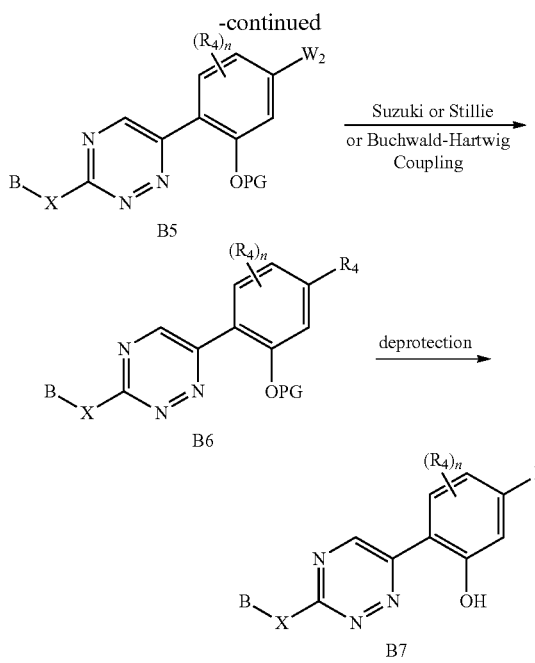

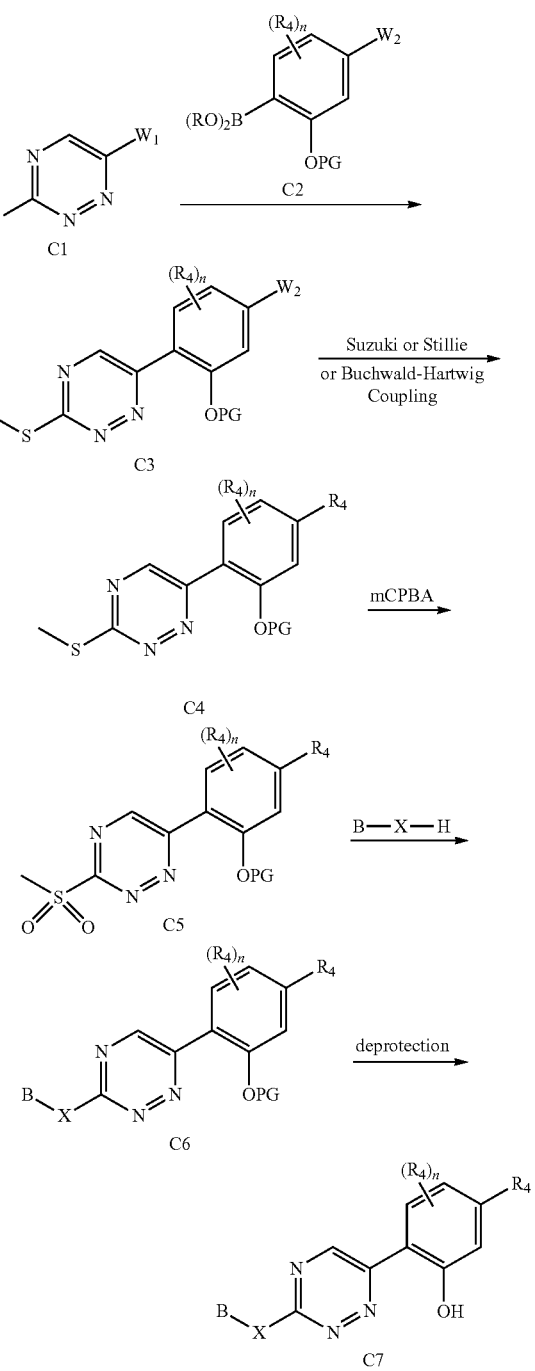

Compounds of Formula (I), wherein $(R_4)_n$ is hydrogen, halogen, hydroxy, or $C_{1-4}$alkoxy, n is 0 or 1, $R_4$ is heterocyclyl, heteroaryl, or phenyl, B is heterocyclyl; X is O, NH or $NR_{1b}$, and $R_{1b}$ is $C_{1-4}$alkyl, may be prepared as described in Scheme B below.

Compound B1 (where $W_1$ is bromine, chlorine and the like) is converted to Compound B3 by a Suzuki coupling with an aryl-boronic acid (or pinacol boronic ester) B2 (where $W_2$ is bromine, chlorine and the like; $(R_4)_n$ is hydrogen, halogen, hydroxy, or $C_{1-4}$alkoxy, and PG is a protecting group such as MOM and the like) in the presence of a catalyst (such as Pd(dppf)Cl$_2$ and the like) and base (such as aqueous K$_2$CO$_3$ and the like) in a suitable solvent (such as 1,4-dioxane and the like). Compound B3 is converted to Compound B4 by treatment with an oxidizing agent (such as mCPBA or oxone and the like) in a suitable solvent (such as dichloromethane and the like). Compound B4 is converted to Compound B5 by a nucleophilic substitution with a primary or a secondary amine or an alcohol (BXH, where X is O, NH or $NR_{1b}$, where $R_{1b}$ is $C_{1-4}$alkyl) in the presence of a suitable base (such as Et$_3$N and the like) in a suitable solvent (such as DMF and the like). Compound B5 is converted to Compound B6 by a Suzuki coupling with an aryl- or heteroaryl-boronic acid (or pinacol boronic ester) in the presence of a catalyst (such as Pd(dppf)Cl$_2$ and the like) and a base (such as aqueous K$_2$CO$_3$ and the like) in a suitable solvent (such as 1,4-dioxane and the like). Alternatively, Compound B5 is converted to Compound B6 by a Stille coupling with an aryl- or heteroaryl-stannane in the presence of a catalyst (such as Pd$_2$(dba)$_3$ and the like), a ligand (such as X-Phos and the like) and a base (such as CsF and the like) in a suitable solvent (such as 1,4-dioxane and the like). Alternatively, Compound B5 is converted to Compound B6 by treatment with pinacolatodiboron and a base (such as KOAc and the like) in the presence of a catalyst (such as Pd(dppf)Cl$_2$ and the like) in an appropriate solvent (such as 1,4-dioxane and the like), followed by addition of an aryl- or heteroaryl-halide. Alternatively, Compound B5 is converted to Compound B6 by a Buchwald-Hartwig coupling with a heteroaryl or amine in the presence of a catalyst (such as Pd$_2$(dba)$_3$ and the like), a ligand (such as tBuX-Phos and the like) and a base (such as K$_3$PO$_4$ and the like) in a suitable solvent (such as 1,4-dioxane and the like). Compound B6 is converted to Compound B7 upon treatment with conditions appropriate to the removal of the protecting groups (such as HCl in dioxane for a MOM protecting group) in a suitable solvent (such as dioxane and the like).

Following the general conditions described in Scheme B, but changing the order of steps 2 and 4, compound C1 can be converted to compound C7.

Scheme D

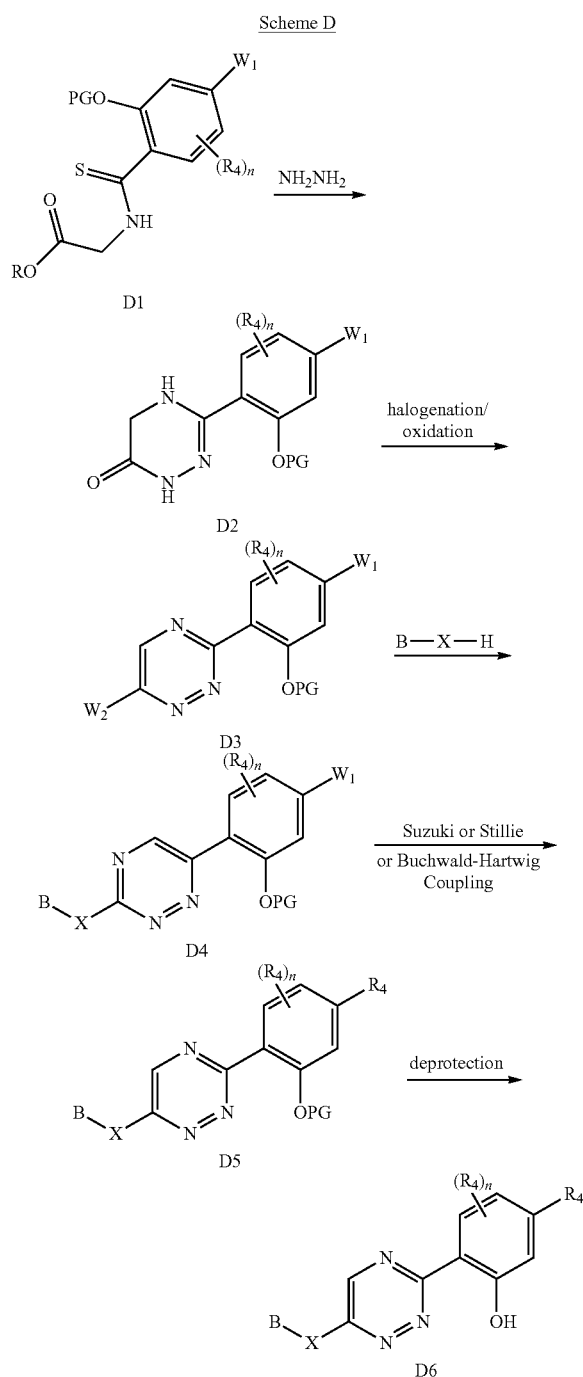

Compounds of Formula (II), wherein $(R_4)_n$ is hydrogen, halogen, hydroxy, or $C_{1-4}$alkoxy, n is 0 or 1, $R_4$ is heterocyclyl, heteroaryl, or phenyl, B is heterocyclyl; X is O, NH or $NR_{1b}$, and $R_{1b}$ is $C_{1-4}$alkyl, may be prepared as described in Scheme D below.

Compound D1 (where $W_1$, is bromine, chlorine and the like; $(R_4)_n$ is hydrogen, halogen, hydroxy, or $C_{1-4}$alkoxy; and PG is a protecting group such as MOM and the like) is converted to Compound D2 by a condensation/cyclization sequence in presence of hydrazine in a suitable solvent (such as ethanol and the like). Compound D2 is converted to Compound D3 by treatment with a dehydrative halogenating agent (such as $POCl_3$ and the like) followed by treatment with an oxidizing agent (such as manganese dioxide and the like). Compound D3 is converted to Compound D4 by a nucleophilic substitution with a primary or a secondary amine or an alcohol (BXH, where X is O, NH or $NR_{1b}$, where $R_{1b}$ is $C_{1-4}$alkyl) in the presence of a suitable base (such as $Et_3N$ and the like) in a suitable solvent (such as DMF and the like). Alternatively, Compound D3 is converted to Compound D4 via cross coupling with a primary amine or a secondary amine or an alcohol in the presence of a suitable catalyst (such as RuPhos Pd G2 and the like) and base (such as sodium tert-butoxide and the like) in an appropriate solvent such as 1,4-dioxane and the like). Compound D4 is converted to Compound D5 by a Suzuki coupling with an aryl- or heteroaryl-boronic acid (or pinacol boronic ester) in the presence of a catalyst (such as $Pd(dppf)Cl_2$ and the like) and base (such as aqueous $K_2CO_3$ and the like) in a suitable solvent (such as 1,4-dioxane and the like). Alternatively, Compound D4 is converted to Compound D5 by a Stille coupling with an aryl- or heteroaryl-stannane in the presence of a catalyst (such as $Pd_2(dba)_3$ and the like), a ligand (such as X-Phos and the like) and a base (such as CsF and the like) in a suitable solvent (such as 1,4-dioxane and the like). Alternatively, Compound D4 is converted to Compound D5 by treatment with pinacolatodiboron and a base (such as KOAc and the like) in the presence of a catalyst (such as $Pd(dppf)Cl_2$ and the like) in an appropriate solvent (such as 1,4-dioxane and the like), followed by addition of an aryl- or heteroaryl-halide. Alternatively, Compound D4 is converted to Compound D5 by a Buchwald-Hartwig coupling with a heteroaryl or amine in the presence of a catalyst (such as $Pd_2(dba)_3$ and the like), a ligand (such as tBuX-Phos and the like) and a base (such as $K_3PO_4$ and the like) in a suitable solvent (such as 1,4-dioxane and the like). Compound D5 is converted to Compound D6 upon treatment with conditions appropriate to the removal of the protecting groups (such as HCl in dioxane for a MOM protecting group) in a suitable solvent (such as dioxane and the like).

Specific Synthetic Examples

To describe in more detail and assist in understanding, the following non-limiting examples are offered to more fully illustrate the scope of compounds described herein and are not to be construed as specifically limiting the scope thereof. Such variations of the compounds described herein that may be now known or later developed, which would be within the purview of one skilled in the art to ascertain, are considered to fall within the scope of the compounds as described herein and hereinafter claimed. These examples illustrate the preparation of certain compounds. Those of skill in the art will understand that the techniques described in these examples represent techniques, as described by those of ordinary skill in the art, that function well in synthetic practice, and as such constitute preferred modes for the practice thereof. However, it should be appreciated that those of skill in the art should, in light of the present disclosure, appreciate that many changes can be made in the specific methods that are disclosed and still obtain a like or similar result without departing from the spirit and scope of the present description.

Other than in the following examples of the embodied compounds, unless indicated to the contrary, all numbers expressing quantities of ingredients, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and rounding techniques used by those of skill in the art.

While the numerical ranges and parameters setting forth the broad scope of the present description are approximations, the numerical values set forth in the examples set forth below are reported as precisely as possible. Any numerical value, however, inherently contains certain errors necessarily resulting from the standard deviation found in their respective testing measurements.

The starting materials used in the examples provided are commercially available or can be prepared according to methods known to one skilled in the art or can be prepared by the procedures disclosed herein.

Compound Examples

As used above, and throughout the present description, the following abbreviations, unless otherwise indicated, shall be understood to have the following meanings:

| Abbreviation | Meaning |
|---|---|
| Δ | heating (chemistry) or deletion (biology) |
| AcOH or HOAc | acetic acid |
| Ar | argon |
| ACN or CH$_3$CN | acetonitrile |
| aq. | aqueous |
| atm | atmosphere(s) |
| BBr$_3$ | boron tribromide |
| B$_2$pin$_2$ | bis(pinacolato)diboron |
| Boc | tert-butoxy-carbonyl |
| t-Bu | tert-butyl |
| t-BuOK or KOtBu | postassium tert-butoxide |
| BuOH or n-BuOH | n-butanol |
| ° C. | degrees Centigrade |
| Celite ® or Celite | diatomaceous earth |
| d/h/hr/hrs/min/s | day(d)/hour(h, hr or hrs)/minute(min)/second(s) |
| DCM or CH$_2$Cl$_2$ | dichloromethane |
| DMF | dimethylformamide |
| DMSO | dimethylsulfoxide |
| EtOAc | ethyl acetate |
| EtOH | ethanol |
| Et$_2$O | diethyl ether |
| equiv | equivalents |
| H$_2$ | hydrogen |
| HBr | hydrobromic acid |
| HCl | hydrochloric acid |
| H$_2$SO$_4$ | sulfuric acid |
| K$_2$CO$_3$ | potassium carbonate |
| KOAc | potassium acetate |
| KOH | potassium hydroxide |
| LC/MS, LCMS or LC-MS | liquid chromatographic mass spectroscopy |
| LiOt-Bu | lithium tert-butoxide |
| LiOH | lithium hydroxide |
| mCPBA | meta-chloroperoxybenzoic acid |
| MeOH | methanol |
| MeSO$_3$H | methanesulfonic acid |
| MgSO$_4$ | magnesium sulfate |
| mL | milliliter |
| MOM | methoxymethyl |

| Abbreviation | Meaning |
|---|---|
| MS | mass spectroscopy |
| NEt$_3$ | triethylamine |
| NH$_4$Cl | ammonium chloride |
| NH$_4$OAc | ammonium acetate |
| Na$_2$CO$_3$ | sodium carbonate |
| NaH | sodium hydride |
| NaHCO$_3$ | sodium bicarbonate |
| NaOH | sodium hydroxide |
| Na$_2$SO$_4$ | sodium sulfate |
| N$_2$ | nitrogen |
| NH$_4$Cl | ammoniuim chloride |
| NMP | N-methylpyrrolidone |
| NMR | nuclear magnetic resonance |
| Pd | palladium |
| Pd/C | palladium on carbon |
| Pd$_2$(dba)$_3$ | tris(dibenzylideneacetone)dipalladium(0) |
| Pd(dppf)Cl$_2$ or Pd(dppf)Cl$_2$—CH$_2$Cl$_2$ | [1,1'-bis(diphenylphosphino)ferrocene]dichloropalladium(II), complex with dichloromethane |
| PhMe | toluene |
| Psi | pounds per square inch pressure |
| QPhos | 1,2,3,4,5-pentaphenyl-1'-(di-tert-butylphosphino)ferrocene |
| Rt or rt | room temperature |
| S-Phos, SPhos or Sphos | 2-dicyclohexylphosphino-2',6'-dimethoxybiphenyl |
| S-Phos G$_2$ | chloro(2-dicyclohexylphosphino-2',6'-dimethoxy-1,1'-biphenyl)(2'-amino-1,1'-biphenyl-2-yl) palladium(II) |
| TBAF | tetrabutylammonium fluoride |
| TBS | tert-butyldimethylsilyl |
| TEA, Et$_3$N or NEt$_3$ | triethylamine |
| Tf | trifluoromethane sulfonyl or triflate |
| TFA | trifluoroacetic acid |
| THF | tetrahydrofuran |
| THP | tetrahydropyranyl |
| TIPS | tiisopropylsilane |
| TLC | thin layer chromatography |
| UPLC | Ulta performance liquid chromatography |

Preparation of Starting Material: 4-(3-(Methoxymethoxy)-4-(4,4,5,5-tetramethyl-1,3,2-dioxaborolan-2-yl)phenyl)-1-(tetrahydro-2H-pyran-2-yl)-1H-pyrazole

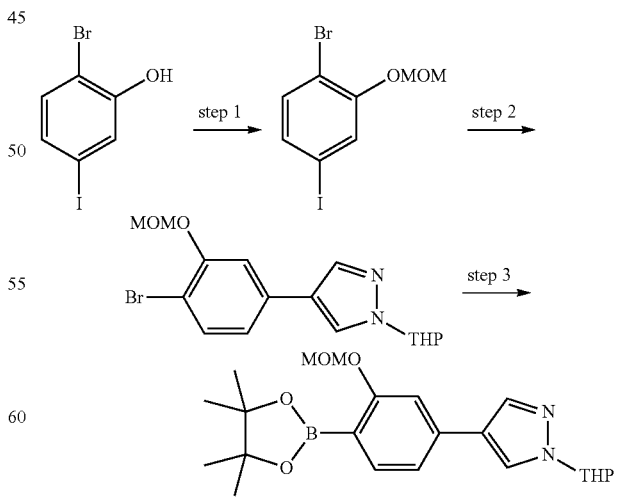

Step 1: 2-Bromo-5-iodophenol (54.9 g, 184 mmol), was dissolved in DMF (240 mL) at 0° C. Sodium tert-pentoxide (2.5 M in THF, 90 mL, 230 mmol) was added dropwise. This was stirred at 0° C. for 15 minutes after addition was complete. Chloromethyl methyl ether (18 mL, 225 mmol) was added dropwise over 30 minutes. The mixture was warmed to ambient temperature and was stirred for 16 hours. The mixture was diluted with 1.5 L of $H_2O$ and was extracted into 2×400 mL of EtOAc. The combined organic layers were washed with 300 mL of $H_2O$, and then with brine. The organic layer was dried over $MgSO_4$, filtered, and concentrated under vacuum. The residue was flushed through a silica plug using 0-10% $CH_2Cl_2$ in hexanes to yield 1-bromo-4-iodo-2-(methoxymethoxy)benzene (61 g, 97%) as a clear liquid.

$^1$H NMR (acetone-$d_6$): δ 7.56 (d, J=2 Hz, 1H), 7.38 (d, J=8 Hz, 1H), 7.33 (dd, J=8 Hz, 2 Hz, 1H), 5.35 (s, 2H), 3.50 (s, 3H).

Step 2: 1-Bromo-4-iodo-2-(methoxymethoxy)benzene (49 g, 143 mmol), 1-(tetrahydro-2H-pyran-2-yl)-4-(4,4,5,5-tetramethyl-1,3,2-dioxaborolan-2-yl)-1H-pyrazole (48.4 g, 174 mmol), Pd(dppf)Cl$_2$-dichloromethane adduct (3.1 g, 3.6 mmol), dioxane (500 mL), and aqueous $K_2CO_3$ (1M, 350 mL, 350 mmol) were heated at 90° C. for 2 hours. The reaction mixture was then partitioned between $H_2O$ and EtOAc. The organic layer was dried over $MgSO_4$, filtered, and concentrated under vacuum. The residue was purified by silica gel chromatography eluting with a EtOAc/hexanes gradient (20-50% EtOAc), followed by trituration with hexanes, yielding 4-(4-bromo-3-(methoxymethoxy)phenyl)-1-(tetrahydro-2H-pyran-2-yl)-1H-pyrazole (40.4 g, 77% yield) as an off-white solid.

$^1$H NMR (acetone-$d_6$): δ 8.22 (s, 1H), 7.88 (s, 1H), 7.55 (d, J=8.5 Hz, 1H), 7.47 (d, J=2 Hz, 1H), 7.23 (dd, J=8.5 Hz, 2 Hz, 1H), 5.44 (dd, J=9.5 Hz, 2.5 Hz, 1H), 5.38 (s, 2H), 4.01 (m, 1H), 3.72 (m, 1H), 3.51 (s, 3H), 2.1-2.23 (m, 1H), 2.0-2.1 (m, 2H), 1.7-1.8 (m, 1H), 1.6-1.7 (m, 2H).

Step 3: A flask containing potassium acetate (22 g, 224 mmol) was pumped dry at 180° C. for 2 hours, and then was filled with argon. 4-(4-Bromo-3-(methoxymethoxy)phenyl)-1-(tetrahydro-2H-pyran-2-yl)-1H-pyrazole (20 g, 54.5 mmol), Pd(dppf)Cl$_2$-dichloromethane adduct (1.22 g, 1.47 mmol), bis(pinacolato)diboron (20.8 g, 81.9 mmol), and dry toluene (200 mL) were added. This mixture was heated at 110° C. for 48 h. After cooling, the mixture was filtered through celite, followed by rinsing with ether. The filtrate was concentrated under vacuum, re-dissolved in ether, and was filtered again through celite to remove solid impurities. Purification by silica gel chromatography eluting with a gradient of EtOAc/hexane (20-50% EtOAc) yielded 12 g of crude title product. The crude material was dissolved in 100 mL ether and was back-washed with 2×1.5 L of dilute aqueous $NaHCO_3$. The ether layer was washed with brine, dried over $MgSO_4$, and was filtered. The filtrate was concentrated to a glassy semi-solid. This material was hexane-triturated to yield 4-(3-(methoxymethoxy)-4-(4,4,5,5-tetramethyl-1,3,2-dioxaborolan-2-yl)phenyl)-1-(tetrahydro-2H-pyran-2-yl)-1H-pyrazole as a white crystalline solid (7.05 g, 32% yield).

$^1$H NMR (acetone-$d_6$): δ 8.24 (s, 1H), 7.90 (s, 1H), 7.65 (d, J=8 Hz, 1H), 7.33 (d, J=1.5 Hz, 1H), 7.29 (dd, J=8 Hz, 1.5 Hz, 1H), 5.45 (dd, J=10 Hz, 2.5 Hz, 1H), 5.25 (s, 2H), 4.01 (m, 1H), 3.69-3.74 (m, 1H), 3.52 (s, 3H), 2.15-2.2 (m, 1H), 2.0-2.1 (m, 2H), 1.7-1.8 (m, 1H), 1.6-1.68 (m, 2H), 1.35 (s, 12H).

Using the procedure described, additional compounds described herein may be prepared by substituting the appropriate starting material, suitable reagents and reaction conditions, obtaining compounds such as those selected from:

| Structure | Data |
| --- | --- |
| 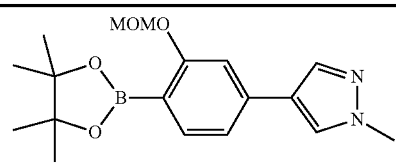 | MS m/z 345.5 [M + H]$^+$; $^1$H NMR (methanol-$d_4$) δ: 7.94-8.03 (m, 1H), 7.84 (s, 1H), 7.64 (br d, J = 7.6 Hz, 1H), 7.25 (s, 1H), 7.20 (d, J = 7.3 Hz, 1H), 5.25 (s, 2H), 3.81-3.98 (m, 3H), 3.53 (s, 3H), 1.36 (s, 12H) |
| 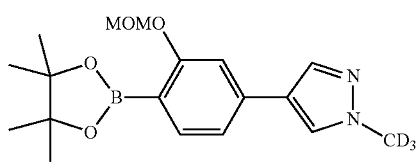 | MS m/z 348.5 [M + H]$^+$; $^1$H NMR (methanol-$d_4$) δ: 8.00 (s, 1H), 7.85 (s, 1H), 7.64 (br d, J = 7.6 Hz, 1H), 7.26 (s, 1H), 7.22 (d, J = 7.6 Hz, 1H), 5.26 (s, 2H), 4.86 (s, 3H), 1.37 (s, 12H) |
| 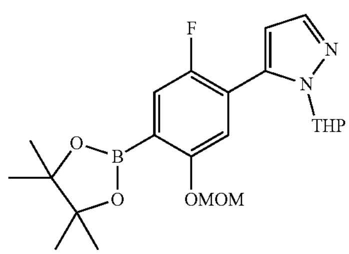 | MS m/z 349.2 [M − THP + H]$^+$ |
| 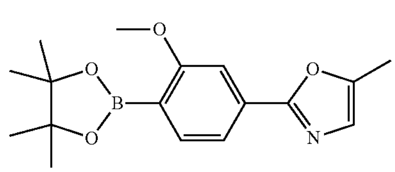 | MS m/z 316.6 [M + H]$^+$ |

Preparation of Starting Material: 1-(3-(Methoxymethoxy)-4-(4,4,5,5-tetramethyl-1,3,2-dioxaborolan-2-yl)phenyl)-4-methyl-1H-imidazole

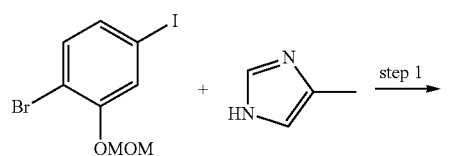

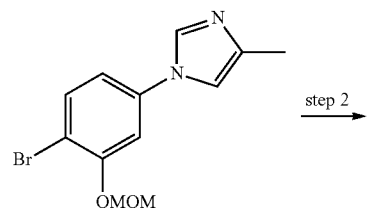

| Structure | Data |
|---|---|
| 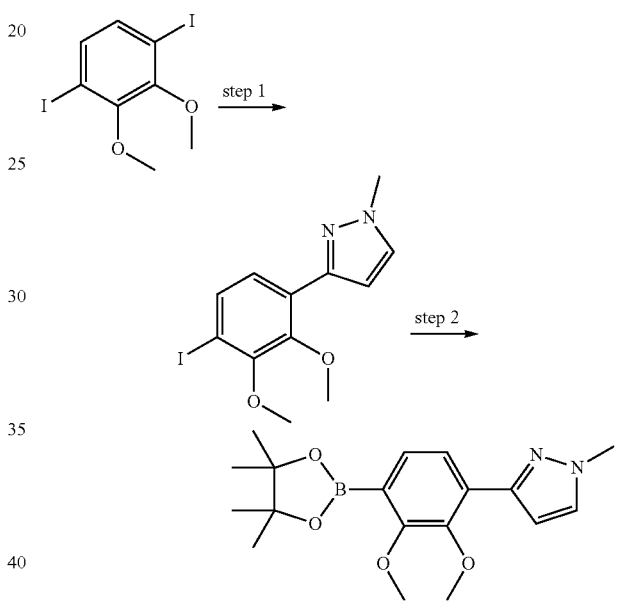 | MS m/z 349.4 [M + H]⁺ |

Preparation of Starting Material: 3-[2,3-Dimethoxy-4-(4,4,5,5-tetramethyl-1,3,2-dioxaborolan-2-yl)phenyl]-1-methyl-pyrazole Step 1: An oven-dried vial was equipped with a magnetic stir bar and charged with 1-bromo-4-iodo-2-(methoxymethoxy)benzene (0.7 g, 2.0 mmol), 4-methyl-1H-imidazole (0.2 g, 2.4 mmol), copper(I) oxide (0.015 g, 0.1 mmol), salicylaldoxime (0.057 g, 0.43 mmol), and cesium carbonate (1.35 g, 4.1 mmol). The reaction mixture was purged with argon, acetonitrile (6 mL) was added, and the reaction was stirred at 50° C. for 24 h. The reaction was diluted with water and then extracted with CH₂Cl₂. The organic layer was washed with water, dried over MgSO₄, filtered, and concentrated under reduced pressure. The crude oil was purified by silica gel chromatography eluting with a MeOH/CH₂Cl₂ gradient (0-15% MeOH) to afford 1-(4-bromo-3-(methoxymethoxy)phenyl)-4-methyl-1H-imidazole (0.38 g, 1.28 mmol, 60%). MS m/z 297.1, 299.1 [M+H]⁺.

Step 2: An oven-dried vial was equipped with a magnetic stir bar and charged with 1-(4-bromo-3-(methoxymethoxy) phenyl)-4-methyl-1H-imidazole (0.19 g, 0.64 mmol), bis (pinacolato)diboron (0.25 g, 0.98 mmol), [1,1'-bis(diphenylphosphino)ferrocene]dicholoropalladium(II) (0.06 g, 0.07 mmol), and potassium acetate (0.19 g, 1.94 mmol) and was purged with argon. Dioxane (5 mL) was added, and the reaction was stirred at 90° C. for 2 h. The crude mixture was purified by silica gel chromatography eluting with a MeOH/CH₂Cl₂ gradient (0-10% MeOH) to afford 1-(3-(methoxymethoxy)-4-(4,4,5,5-tetramethyl-1,3,2-dioxaborolan-2-yl)phenyl)-4-methyl-1H-imidazole (0.11 g, 0.32 mmol, 50%). MS m/z 345.2 [M+H]⁺.

Using the procedure described, additional compounds described herein may be prepared by substituting the appropriate starting material, suitable reagents and reaction conditions, obtaining compounds such as those selected from:

Step 1: A 25 mL round bottom flask was charged with 1,4-diiodo-2,3-dimethoxybenzene (460 mg, 1.17 mmol), 1-methyl-3-(4,4,5,5-tetramethyl-1,3,2-dioxaborolan-2-yl)-1h-pyrazole (180 mg, 0.87 mmol), 1,1'-bis(diphenylphosphino)ferrocene-palladium(II)dichloride dichloromethane complex (80 mg, 0.10 mmol) potassium carbonate (360 mg, 2.60 mmol), water (9.4 mL) and 1,4-dioxane (9.4 mL) and the reaction mixture was purged with N₂ for 15 minutes. The mixture was then heated at 80° C. for 2 hours. The reaction was cooled, concentrated and purified by silica gel chromatography eluting with a gradient of EtOAc/hexanes (30-100% EtOAc) to give 3-(4-iodo-2,3-dimethoxy-phenyl)-1-methyl-pyrazole (104 mg, 35% yield). MS m/z 345.0 [M+H]⁺.

Step 2: A screw-cap tube was charged with 3-(4-iodo-2, 3-dimethoxy-phenyl)-1-methyl-pyrazole (48 mg, 0.14 mmol), bis(pinacolato)diboron (0.04 ml, 0.30 mmol), triethylamine (0.05 ml, 0.40 mmol) and 1,4-dioxane (0.3 ml) and the headspace was purged with N₂ gas for 30 minutes. Then palladium(II) acetate (1.80 mg, 0.008 mmol) and 2-(dicyclohexylphosphino)biphenyl (5.2 mg, 0.02 mmol) were added and the reaction stirred at 80° C. for 1 h. The reaction was cooled, concentrated and purified by silica gel chromatography eluting with a EtOAc/hexanes gradient (0-100%

EtOAc) to give 3-[2,3-dimethoxy-4-(4,4,5,5-tetramethyl-1,3,2-dioxaborolan-2-yl)phenyl]-1-methyl-pyrazole (45 mg, 94% yield). MS m/z 345.2 [M+H]+.

Preparation of Starting Material: 4-[3,5-Dimethoxy-4-(4,4,5,5-tetramethyl-1,3,2-dioxaborolan-2-yl)phenyl]-1-tetrahydropyran-2-yl-pyrazole

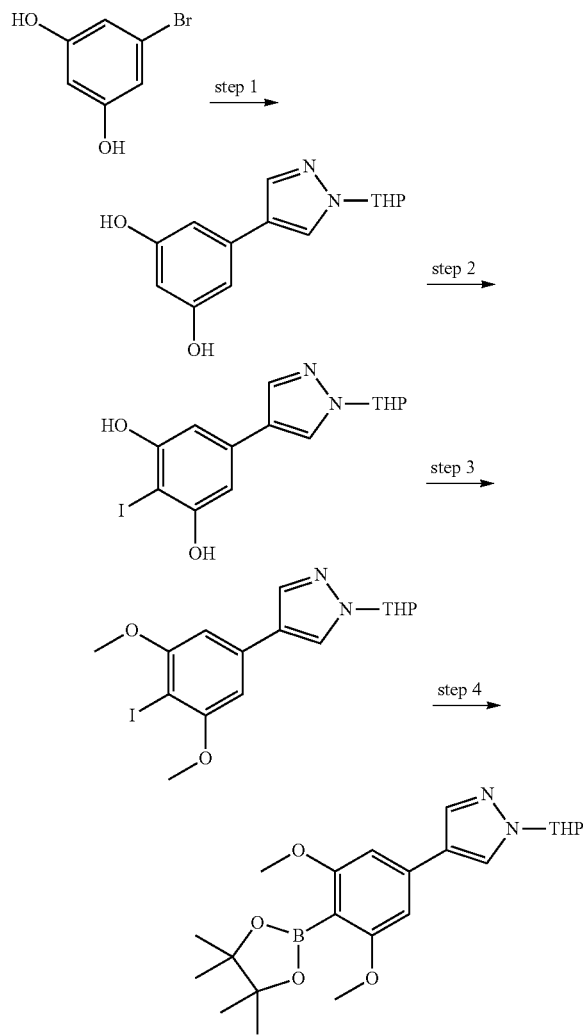

Step 1. A round bottom flask was charged with 5-bromobenzene-1,3-diol (600 mg, 3.02 mmol) 1-(tetrahydro-2h-pyran-2-yl)-4-(4,4,5,5-tetramethyl-1,3,2-dioxaborolan-2-yl)-1h-pyrazole (1.4 g, 4.8 mmol), chloro(2-dicyclohexylphosphino-2',6'-dimethoxy-1,1'-biphenyl)[2-(2'-amino-1,1'-biphenyl)]palladium(II) (220 mg, 0.302 mmol), potassium carbonate (1.3 g, 9.4 mmol), 1,4-dioxane (36 mL) and water (36 mL) and the reaction was purged with N₂ for 15 minutes. The mixture was stirred at 80° C. for 1 hour. The reaction was cooled, concentrated and purified by silica gel chromatography eluting with a MeOH/CH₂Cl₂ gradient (0 to 30% MeOH), to give 5-(1-tetrahydropyran-2-ylpyrazol-4-yl)benzene-1,3-diol (600 mg, 77% yield). MS m/z 261.1 [M+H]+.

Step 2. A solution of 5-(1-tetrahydropyran-2-ylpyrazol-4-yl)benzene-1,3-diol (600 mg, 2.31 mmol) in acetonitrile (4 mL) was cooled to 0° C. N-Iodosuccinimide (520 mg, 2.31 mmol) was added and the reaction was stirred at 0° C. for 5 minutes. The reaction was quenched with aqueous saturated sodium thiosulfate and extracted with dichloromethane. The organic layer was dried, concentrated and purified by silica gel chromatography eluting with a MeOH/CH₂Cl₂ gradient (0 to 30% MeOH) to give 2-iodo-5-(1-tetrahydropyran-2-ylpyrazol-4-yl)benzene-1,3-diol (800 mg, 90% yield). MS m/z 387.1 [M+H]+.

Step 3. A round bottom flask was charged with 2-iodo-5-(1-tetrahydropyran-2-ylpyrazol-4-yl)benzene-1,3-diol (400 mg, 1.04 mmol), iodomethane (0.14 mL, 2.2 mmol), potassium carbonate (310 mg, 2.24 mmol) and acetone (3.3 mL) and the mixture was heated at 50° C. for 12 hours. The reaction was cooled, concentrated and purified by silica gel chromatography eluting with a gradient of EtOAc/hexanes (30-100% EtOAc) to give 4-(4-iodo-3,5-dimethoxy-phenyl)-1-tetrahydropyran-2-yl-pyrazole (300 mg, 0.72 mmol, 70% yield). MS m/z 415.1 [M+H]+.

Step 4. A round bottom flask was charged with 4-(4-iodo-3,5-dimethoxy-phenyl)-1-tetrahydropyran-2-yl-pyrazole (50 mg, 0.12 mmol), bis(pinacolato)diboron (0.04 ml, 0.3 mmol), triethylamine (0.05 ml, 0.4 mmol), and 1,4-dioxane (0.3 ml) and the reaction was purged with N₂ for 15 minutes. Then 1,4-dioxane (0.3 mL) and 2-(dicyclohexylphosphino)biphenyl (4.5 mg, 0.013 mmol) was dissolved in 1,4-dioxane (0.3 mL) was added and the reaction was heated at 90° C. for 12 hours. The mixture was cooled, concentrated and purified by silica gel chromatography eluting with a gradient of EtOAc/hexanes (0-100% EtOAc) to give 4-[3,5-dimethoxy-4-(4,4,5,5-tetramethyl-1,3,2-dioxaborolan-2-yl)phenyl]-1-tetrahydropyran-2-yl-pyrazole (50 mg, 99% yield). MS m/z 415.4 [M+H]+.

Preparation of Starting Material: 2-[4-Chloro-3-fluoro-2-(methoxymethoxy)phenyl]-4,4,5,5-tetramethyl-1,3,2-dioxaborolane

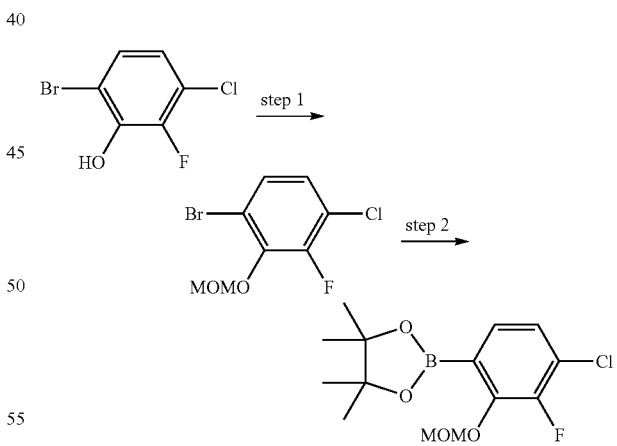

Step 1: 6-Bromo-3-chloro-2-fluoro-phenol (900 mg, 4.0 mmol) was dissolved in DMF (4.5 mL) at 0° C. Sodium tert-pentoxide (2.5 M in THF, 2 mL, 5.0 mmol) was added dropwise, followed by dropwise addition of chloromethyl methyl ether (405 μL, 5.34 mmol) and the reaction was stirred overnight at room temperature. The reaction mixture was partitioned between water and EtOAc. The organic layer was washed with water, and then brine. The organic layer was dried over MgSO₄, filtered, and concentrated under vacuum. The residue was purified by silica gel chromatography eluting with a EtOAc/hexanes gradient (30-100% EtOAc) to yield 1-bromo-4-chloro-3-fluoro-2-(methoxymethoxy)benzene (1.01 g, 94% yield) as a clear oil.

$^1$H NMR (acetone-$d_6$) δ: 7.50 (d, J=9 Hz, 1H), 7.28 (t, J=8 Hz, 1H), 5.26 (s, 2H), 3.62 (s, 3H).

Step 2: A mixture of dry KOAc (1.5 g, 15 mmol), bis(pinacolato)diboron (1.02 g, 4.02 mmol), Pd(dppf)Cl$_2$—CH$_2$Cl$_2$ (90 mg, 0.108 mmol), and a solution of 1-bromo-4-chloro-3-fluoro-2-(methoxymethoxy)benzene (900 mg, 3.3 mmol) in toluene (12 mL) was purged with argon for 15 min. The mixture was heated at 110° C. for 16 h. Upon completion, the reaction was diluted with EtOAc and was filtered through celite. The filtrate was concentrated and purified by silica chromatography eluting with a MeOH/CH$_2$Cl$_2$ gradient (0 to 5% MeOH) to yield 2-[4-chloro-3-fluoro-2-(methoxymethoxy)phenyl]-4,4,5,5-tetramethyl-1,3,2-dioxaborolane (524 mg, 47% yield) as a light orange oil.

$^1$H NMR (acetone-$d_6$) δ: 7.49 (d, J=8 Hz, 1H), 7.29 (t, J=7 Hz, 1H), 5.16 (s, 2H), 3.58 (s, 3H), 1.37 (s, 12H).

Preparation of Starting Material: 6-Chloro-8-methyl-imidazo[1,2-b]pyridazine

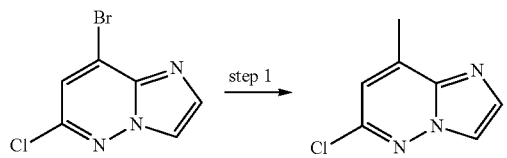

Step 1: A mixture of 8-bromo-6-chloro-imidazo[1,2-b]pyridazine (232 mg, 1.0 mmol), 2,4,4,5,5-pentamethyl-1,3,2-dioxaborolane (142 mg, 1.0 mmol), Pd(dppf)Cl$_2$ (150 mg, 0.20 mmol), and K$_2$CO$_3$ (285 mg, 2.1 mmol), in dioxane (5 mL) and water (1 mL) was purged with argon for 15 min and heated to 90° C. for 16 h. The reaction was diluted with water (50 mL), and then extracted with CH$_2$Cl$_2$ (3×30 mL). The organic layers were washed with brine (2×20 mL), dried over Na$_2$SO$_4$, and then filtered and concentrated. The residue was purified by silica gel column chromatography eluting with a MeOH/CH$_2$Cl$_2$ gradient (5 to 10% MeOH) to afford 6-chloro-8-methyl-imidazo[1,2-b]pyridazine (85 mg, 50% yield). MS m/z 168.0, 170.0 [M+H]$^+$.

Preparation of Starting Material: 6-Chloro-8-methyl-imidazo[1,2-b]pyridazine and tert-Butyl ((6-chloroimidazo[1,2-b]pyridazin-8-yl)methyl)carbamate

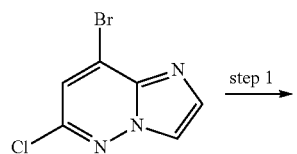

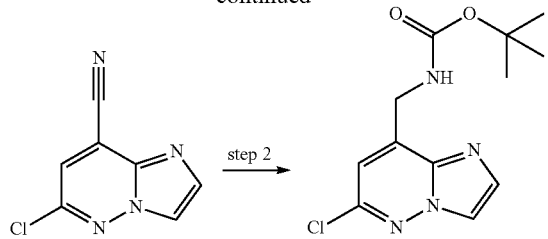

Step 1: A solution of 8-bromo-6-chloro-imidazo[1,2-b]pyridazine (232 mg, 1.0 mmol), dicyanozinc (150 mg, 1.2 mmol), and Pd(PPh$_3$)$_4$ (240 mg, 0.2 mmol) in dry DMF (4 mL) was heated in a microwave for 45 min at 100° C. The reaction was concentrated and purified by preparatory HPLC to afford 6-chloro-8-methyl-imidazo[1,2-b]pyridazine (85 mg, 50% yield). MS m/z 178.9, 181.1 [M+H]$^+$.

Step 2: A solution of 6-chloro-8-methyl-imidazo[1,2-b]pyridazine (80 mg, 0.45 mmol), di-tert-butyl dicarbonate (147 mg, 0.67 mmol), and Ni (16 mg) in THF (5 mL) was stirred at room temperature for 16 h. The reaction was filtered and concentrated. The residue was purified by preparatory HPLC (10% MeOH in CH$_2$Cl$_2$), to afford tert-butyl ((6-chloroimidazo[1,2-b]pyridazin-8-yl)methyl)carbamate (36 mg, 28% yield). MS m/z 282.9, 284.8 [M+H]$^+$.

Preparation of Starting Material: 6-Chloro-8-methoxy-imidazo[1,2-b]pyridazine

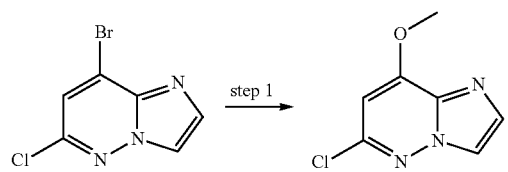

Step 1: A solution of 8-bromo-6-chloro-imidazo[1,2-b]pyridazine (234 mg, 1.0 mmol) and sodium methoxide (108 mg, 1.2 mmol) in methanol (4 mL) was heated to reflux for 12 h. The reaction was cooled to room temperature, concentrated, and then the residue was purified by preparatory HPLC to afford 6-chloro-8-methoxy-imidazo[1,2-b]pyridazine (100 mg, 54% yield). MS m/z 184.0, 186.0 [M+H]$^+$.

Preparation of Starting Material: 5-Bromo-7-fluoro-1-((2-(trimethylsilyl)ethoxy)methyl)-1H-benzo[d]imidazole

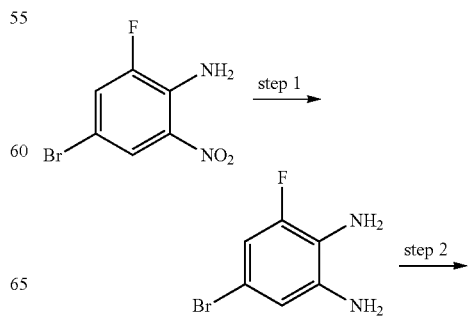

-continued

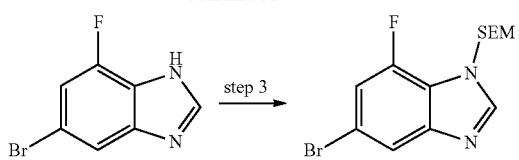

Step 1: To a solution of 4-bromo-2-fluoro-6-nitroaniline (600 mg, 2.6 mmol) in tetrahydrofuran (5 mL), ethanol (5 mL), and water (1 mL) was added iron (1.5 g, 27 mmol), and ammonium chloride (1.5 g, 28 mmol). The mixture was heated to reflux for 16 hours, then cooled to room temperature, filtered and concentrated. The crude product was purified by silica gel chromatography eluting with a MeOH/CH$_2$Cl$_2$ gradient (0 to 10% MeOH) to yield 5-bromo-3-fluorobenzene-1,2-diamine as a brown solid (400 mg, 76%). MS m/z 204.8, 206.8 [M+H]$^+$.

Step 2: A mixture of 5-bromo-3-fluorobenzene-1,2-diamine (400 mg, 2.0 mmol) and formic acid (5 mL) was stirred at 120° C. for 16 hours. After cooling, the solvent was removed and the residue was partitioned between EtOAc (200 mL) and sat. aq. NaHCO$_3$ (50 mL). The organic phase was dried over Na$_2$SO$_4$ and concentrated to afford crude 5-bromo-7-fluoro-1H-benzoimidazole as an off white solid (400 mg, 95%). MS m/z 215.0, 217.0 [M+H]$^+$.

Step 3: A solution of 5-bromo-7-fluoro-1H-benzimidazole (200 mg, 0.93 mmol) in tetrahydrofuran (5 mL) was cooled to 0° C. and sodium hydride (15 mg, 0.60 mmol) was added. The reaction was stirred at 0° C. for 20 minutes, then 2-(trimethylsilyl)ethoxymethyl chloride (0.08 g, 0.48 mmol) was added. The mixture was stirred at room temperature for 2 h. The reaction was quenched with ice water, and the aqueous phase was extracted with EtOAc. The organic phase was dried over Na$_2$SO$_4$, concentrated and the residue was purified by silica gel chromatography eluting with a MeOH/CH$_2$Cl$_2$ gradient (0 to 10% MeOH) to afford 5-bromo-7-fluoro-1-((2-(trimethylsilyl)ethoxy)methyl)-1H-benzo[d]imidazole (210 mg, 65%). MS m/z 345.0, 347.0 [M+H]$^+$.

Preparation of Starting Material:
5-Bromo-6,7-difluoro-1-methyl-benzimidazole

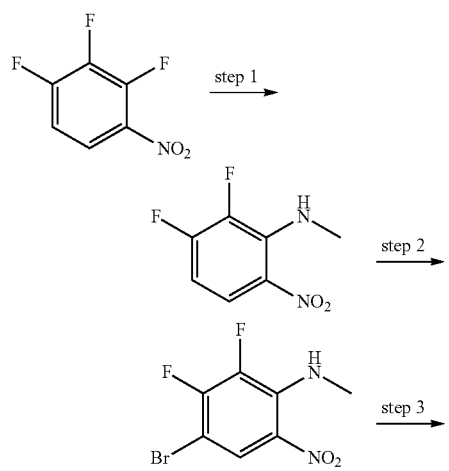

-continued

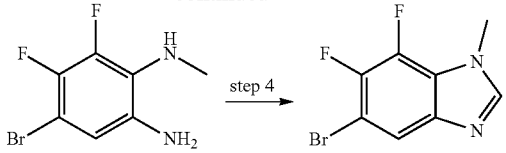

Step 1: To a solution of 1,2,3-trifluoro-4-nitro-benzene (1.00 g, 5.65 mmol) and methylamine hydrochloride (409 mg, 5.94 mmol) in acetonitrile (10.0 mL) was added DIPEA (3.66 g, 28.2 mmol). The mixture was stirred for 3 hours at 70° C., then cooled to room temperature. The mixture was concentrated and the residue was purified by silica gel chromatography eluting with a EtOAc/hexanes gradient (0-5% EtOAc) to afford 2,3-difluoro-N-methyl-6-nitro-aniline (1.06 g, 99% yield) as a yellow solid. MS m/z 189.0 [M+H]$^+$.

Step 2: To a solution of 2,3-difluoro-N-methyl-6-nitro-aniline (1.48 g, 7.87 mmol) in DMF (50.0 mL) was added NBS (1.79 g, 9.86 mmol). The mixture was stirred for 1 hour at 90° C., and then cooled to room temperature and quenched with brine (200 mL). The mixture was extracted with EtOAc (3×50 mL). The organic layers were dried over Na$_2$SO$_4$ and concentrated. The residue was purified by silica gel chromatography eluting with a EtOAc/hexanes gradient (0-5% EtOAc) to afford 4-bromo-2,3-difluoro-N-methyl-6-nitro-aniline (1.75 g, 83% yield) as a yellow solid. MS m/z 267.0, 269.0 [M+H]$^+$.

Step 3: A solution of 4-bromo-2,3-difluoro-N-methyl-6-nitro-aniline (1.85 g, 6.93 mmol) in tetrahydrofuran (50.0 mL) and methanol (50.0 mL) was cooled to 0° C. Then, Raney-nickel (500 mg) was added, followed by dropwise addition of hydrazine (227 mg, 6.94 mmol). The mixture was stirred for 15 min at 0° C. and filtered. The filtrate was concentrated to give crude 4-bromo-5,6-difluoro-N$^1$-methylbenzene-1,2-diamine (1.58 g, 96% yield) as a pale brown oil. MS m/z 237.0, 239.0 [M+H]$^+$.

Step 4: 5-Bromo-3,4-difluoro-N$_2$-methyl-benzene-1,2-diamine (1.58 g, 6.67 mmol) was suspended in formic acid (5 mL) and trimethyl orthoformate (5.0 mL, 46 mmol) was then added. The mixture was heated at reflux for 1 hour under a nitrogen atmosphere, and then cooled to room temperature. The mixture was concentrated and the residue was neutralized with sat. aq. NaHCO$_3$ to pH 8. The mixture was extracted with EtOAc (3×50 mL) and the organic layers were dried over Na$_2$SO$_4$, concentrated and purified by silica gel chromatography eluting with a EtOAc/hexanes gradient (0-65% EtOAc) to afford 5-bromo-6,7-difluoro-1-methyl-benzimidazole (1.52 g, 92% yield) as a pale brown solid. MS m/z 247.0, 249.0 [M+H]$^+$.

Preparation of Starting Material: Racemic (3S,4S)-3-fluoro-2,2,6,6-tetramethyl-piperidin-4-amine

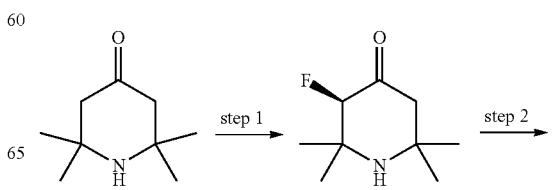

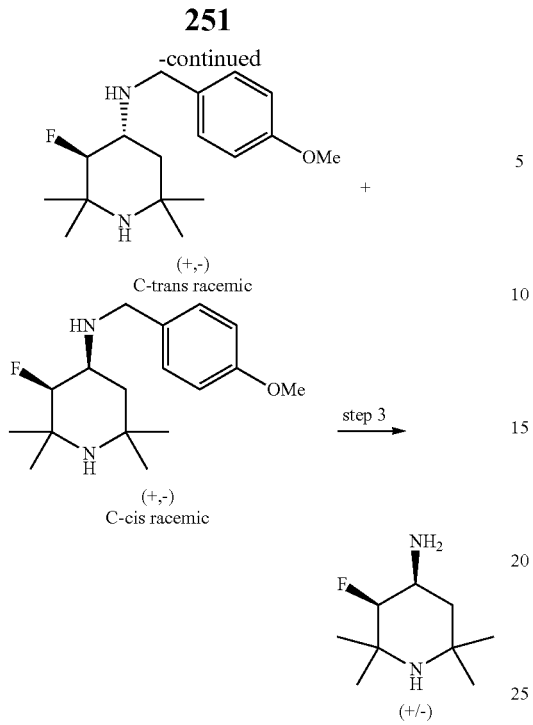

Step 1: To an oven-dried three-necked flask was added 2,2,6,6-tetramethylpiperidin-4-one (20.0 g, 129 mmol). After evacuating and back-filling with nitrogen 3 times, tetrahydrofuran (90 mL) was added under nitrogen. The solution was cooled to −78° C., and then lithium bis(trimethylsilyl)amide in tetrahydrofuran (193 mL, 193 mmol, 1 mol/L) was added dropwise. Following complete reaction, the mixture was stirred at −78° C. for 30 min. N-fluorobenzensulfonimide (42.6 g, 135 mol) was added potionwise as a solid over 20 min under nitrogen. The reaction was then gradually warmed to room temperature, and the mixture was further stirred at room temperature for 16 hours. The reaction was filtered to remove solid, and then the mixture was concentrated, and purified by flash chromatography using EtOAc and petroleum ether (0-10% EtOAc) as eluent to afford 3-fluoro-2,2,6,6-tetramethylpiperidin-4-one as a pale yellow solid (10.0 g, 45.5%). MS m/z: 174.1 [M+H]$^+$.

Step 2: 3-Fluoro-2,2,6,6-tetramethylpiperidin-4-one (7.2 g, 41.6 mmol) and (4-methoxyphenyl)methanamine (6.3 g, 45.8 mmol) were dissolved in methanol (40 mL). Acetic acid (6 mL, 104 mmol) was then added. The resulting mixture was stirred at room temperature for 1 h, then NaBH$_3$CN (3.9 g, 62.4 mmol) was added, and the mixture was stirred for an additional 16 hours. The solvent was removed under reduced pressure and the residue was purified by silica gel chromatography eluting with a EtOAc/hexanes gradient (10-30% EtOAc) to afford C-cis racemic (3S,4S)-3-fluoro-N-[(4-methoxyphenyl)methyl]-2,2,6,6-tetramethyl-piperidin-4-amine (5.0 g, 40.0%) and C-trans racemic (3S,4R)-3-fluoro-N-(4-methoxybenzyl)-2,2,6,6-tetramethylpiperidin-4-amine (2.7 g, 22.0%).

C-cis racemic (3S,4S)-3-fluoro-N-[(4-methoxyphenyl) methyl]-2,2,6,6-tetramethyl-piperidin-4-amine: MS m/z: 295.2 [M+H]$^+$; $^1$H NMR (DMSO-d$_6$) δ 7.23 (d, J=8.4 Hz, 2H), 6.86 (d, J=8.8 Hz, 2H), 3.95 (dd, J$_1$=9.6 Hz, J$_2$=51.2 Hz, 1H), 3.73-3.63 (m, 5H), 3.33 (br s, 1H), 3.03-2.97 (m, 1H), 1.87-1.83 (m, 2H), 1.65 (br, 1H), 1.09-1.04 (m, 12H).

C-trans racemic: (3S,4R)-3-fluoro-N-(4-methoxybenzyl)-2,2,6,6-tetramethylpiperidin-4-amine: MS m/z: 295.2 [M+H]$^+$; $^1$H NMR (DMSO-d$_6$) δ 7.25 (d, J=8.4 Hz, 2H), 6.86 (d, J=8.4 Hz, 2H), 4.33 (d, J=50.8 Hz, 1H), 3.72 (s, 5H), 3.33 (br s, 2H), 2.95 (dd, J$_1$=15.6 Hz, J$_2$=28.4 Hz, 1H), 1.53 (dd, J$_1$=4.0 Hz, J$_2$=8.8 Hz, 1H), 1.21-1.03 (m, 13H).

Step 3: To a three-neck round bottom flask charged with a thermometer, pressure drop funnel and hydrogen balloon was added racemic (3S,4S)-3-fluoro-N-[(4-methoxyphenyl) methyl]-2,2,6,6-tetramethyl-piperidin-4-amine (10.0 g, 33.97 mmol), MeOH (150 mL), palladium on carbon (10 wt %) (3.0 g, 2.8 mmol), and formic acid (0.20 g, 4.0 mmol). The flask was evacuated and backfilled with hydrogen twice. The mixture was stirred at 45° C. for 16 h. After cooling to room temperature, the mixture was filtered, and the filtrate was concentrated. The residue was purified by silica gel chromatography eluting with a gradient of MeOH/CH$_2$Cl$_2$ (0 to 100% MeOH) to yield racemic (3S,4S)-3-fluoro-2,2, 6,6-tetramethyl-piperidin-4-amine (4.8 g, 81%). MS m/z 175.2 [M+H]$^+$; $^1$H NMR (methanol-d$_4$) δ: 4.91 (d, J=48 Hz, 1H), 4.25 (dd, J$_1$=11.6 Hz, J$_2$=30 Hz, 1H), 2.14-2.00 (m, 2H). 1.62-1.57 (m, 12H); 3NHs not observed.

Preparation of Starting Material: (3S,4S)-3-Fluoro-2,2,6,6-tetramethylpiperidin-4-amine

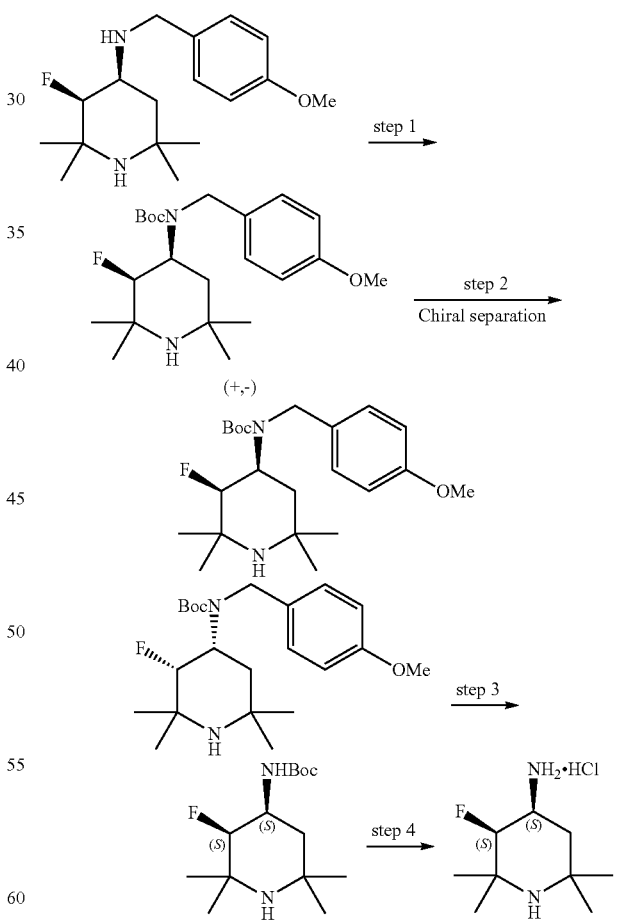

Step 1: Racemic (3S,4S)-3-fluoro-N-[(4-methoxyphenyl) methyl]-2,2,6,6-tetramethyl-piperidin-4-amine (5.0 g, 12.7 mmol) was dissolved in methanol (80 mL), then di-tert-butyl dicarbonate (4.1 g, 19.5 mmol) and triethyl amine (2.7 mmol, 19.5 mmol) were added sequentially. The resultant mixture was stirred at room temperature for 3 h. The solvent was removed under reduced pressure, the residue was purified by silica gel chromatography eluting with a EtOAc/hexanes gradient (0-50% EtOAc) to afford the desired tert-butyl ((3S,4S)-3-fluoro-2,2,6,6-tetramethylpiperidin-4-yl)(4-methoxybenzyl)carbamate (4.1 g, 61.0%) as a colorless oil. MS m/z: 395.2 [M+H]⁺.

Step 2: A total of 5 g of racemic tert-butyl ((3S,4S)-3-fluoro-2,2,6,6-tetramethylpiperidin-4-yl)(4-methoxybenzyl)carbamate were separated by chiral-Prep-HPLC (SFC-200, Thar, Waters) using a WHELK 50*250 mm, 10 um (Daicel) column with CO₂/IPA (0.2% Methanol Ammonia)=90/10 as the mobile phase to afford tert-butyl ((3S,4S)-3-fluoro-2,2,6,6-tetramethylpiperidin-4-yl)(4-methoxybenzyl)carbamate (2.2 g, 44% yield) and tert-butyl ((3R,4R)-3-fluoro-2,2,6,6-tetramethylpiperidin-4-yl)(4-methoxybenzyl)carbamate (1.8 g, 36%).

Step 3: tert-Butyl ((3S,4S)-3-fluoro-2,2,6,6-tetramethylpiperidin-4-yl)(4-methoxybenzyl) carbamate (2.2 g, 5.6 mmol) was dissolved in acetonitrile (40 mL), ammonium cerium(IV) nitrate (9.2 g, 16.8 mmol) was added, and the mixture was stirred at room temperature for 2 h. The mixture was concentrated and purified by silica gel chromatography eluting with a gradient of EtOAc/hexanes (0-80% EtOAc) to afford crude tert-butyl ((3S,4S)-3-fluoro-2,2,6,6-tetramethylpiperidin-4-yl)carbamate (1.5 g, 98% yield), which was used to the next step without further purification. MS m/z: 275.2 [M+H]⁺.

Step 4: The crude tert-butyl ((3S,4S)-3-fluoro-2,2,6,6-tetramethylpiperidin-4-yl)carbamate (1.5 g, 0.54 mmol) obtained in step 3 was dissolved in CH₂Cl₂ (20 mL), and then 2 mL of HCl in dioxane (4 mol/L) was added, and the mixture was stirred at room temperature for 16 h. The precipitate was filtered, washed with 5 mL of CH₂Cl₂ and dried to yield (3S,4S)-3-fluoro-2,2,6,6-tetramethylpiperidin-4-amine (533 mg, HCl salt, 47% yield) as a white solid.

MS m/z: 175.2 [M+H]⁺; ¹H NMR (methanol-d₄) δ: 4.91 (d, J=48 Hz, 1H), 4.25 (dd, J=11.6 Hz, 30 Hz, 1H), 2.14-2.00 (m, 2H). 1.62-1.57 (m, 12H); 3NHs not observed.

Using the procedure described, additional compounds described herein may be prepared by substituting the appropriate starting material, suitable reagents and reaction conditions, obtaining compounds such as those selected from:

| Structure | Data |
|---|---|
| NH₂•HCl structure with F, (R), (R) | MS m/z 175.2 [M + H]⁺; ¹H NMR (methanol-d₄) δ: 4.90 (d, J = 48 Hz, 1H), 4.25 (dd, J₁ = 10.8 Hz, J₂ = 28.8 Hz, 1H), 2.14-2.00 (m, 2H).1.64-1.50 (m, 12H), 3 NHs not observed. |

Preparation of Starting Material: Racemic (3R,4R)-4-amino-2,2,6,6-tetramethyl-piperidin-3-ol dihydrochloride

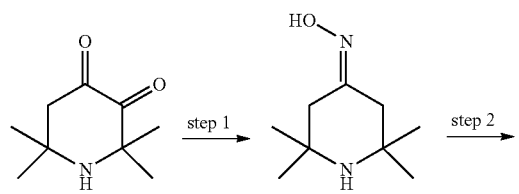

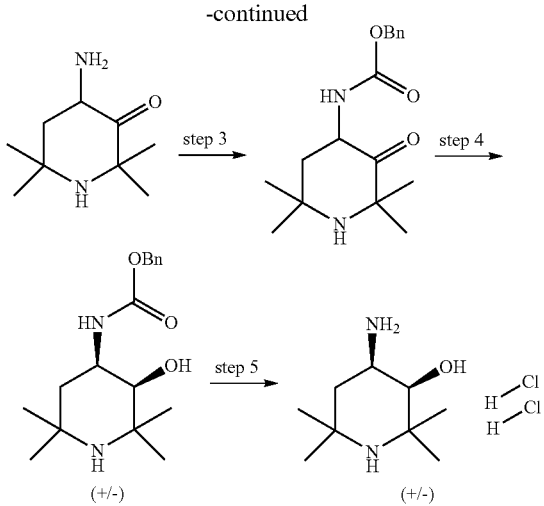

Step 1: 2,2,6,6-Tetramethylpiperidine-3,4-dione (2.98 g, 17.6 mmol) was dissolved in ethanol (15 mL), followed by the addition of aqueous hydroxylamine (1.2 mL, 20 mmol, 50 wt % in H₂O). The reaction was sealed and heated to 70° C. for 10 minutes, and then cooled to room temperature and concentrated providing crude (E)-4-(hydroxyimino)-2,2,6,6-tetramethylpiperidin-3-one (2.1 g, 63% yield) which was used directly in the next step. MS m/z 185.3 [M+H]⁺.

Step 2: (E)-4-(hydroxyimino)-2,2,6,6-tetramethylpiperidin-3-one (2.1 g, 11 mmol), zinc (4.5 g, 69 mmol), and aqueous sodium hydroxide (16 mL, 6.0 M) were combined and heated at 70° C. for 30 min and then cooled to room temperature. The reaction was filtered through a frit, rinsing with CH₂Cl₂/MeOH. The aqueous layer was extracted twice with CH₂Cl₂/MeOH (9:1) and three times with CHCl₃/iPrOH (7:3). The combined organic layers were dried over sodium sulfate, filtered and then concentrated to yield crude 4-amino-2,2,6,6-tetramethyl-piperidin-3-one (1.75 g, 90%) as an orange oil which was used directly in the next step without purification.

Step 3: 4-Amino-2,2,6,6-tetramethyl-piperidin-3-one (1.75 g, 10.3 mmol), DMF (6 mL), and N,N-diisopropyl-ethylamine (2.70 mL, 15.5 mmol) were stirred at room temperature and then cooled to 0° C. Benzyl chloroformate (2.20 mL, 15.5 mmol) was added dropwise. Stirring was continued at 0° C. for 25 min. The reaction was then partitioned between EtOAc and brine and the layers were separated. The aqueous layer was extracted twice with EtOAc and the combined organic layers were washed three times with brine. The organic layer was dried over sodium sulfate, filtered and concentrated. The residue was purified by silica gel column chromatography eluting with a EtOAc/hexanes gradient (0-100% EtOAc) to yield benzyl N-(2,2,6,6-tetramethyl-3-oxo-4-piperidyl)carbamate (1.45 g, 46%) as an orange solid.

MS m/z 305.6 [M+H]⁺; ¹H NMR (DMSO-d₆) δ: 7.55 (br d, J=8.5 Hz, 1H), 7.29-7.41 (m, 5H), 5.06 (s, 2H), 4.86-4.96 (m, 1H), 4.69 (s, 1H), 2.13 (dd, J=12.8, 8.9 Hz, 1H), 1.58 (dd, J=12.8, 7.3 Hz, 1H), 1.28 (d, J=1.8 Hz, 6H), 1.24 (s, 3H), 1.09 (s, 3H).

Step 4: Benzyl N-(2,2,6,6-tetramethyl-3-oxo-4-piperidyl)carbamate (1.20 g, 3.95 mmol) was dissolved in MeOH (5 mL), followed by the addition of sodium borohydride (247 mg, 6.54 mmol). The reaction was stirred at room temperature for 1 h, then acetone (3 mL) was added slowly and the reaction was concentrated. The residue was partitioned between EtOAc and H₂O and the layers were separated. The aqueous layer was extracted four times with EtOAc. The combined organic layers were dried over sodium sulfate, filtered and concentrated to yield crude racemic benzyl N-[(3R,4R)-3-hydroxy-2,2,6,6-tetramethyl-4-piperidyl]carbamate that was used directly in the next step.

MS m/z 307.5 [M+H]⁺; ¹H NMR (DMSO-d₆) δ 7.30-7.40 (m, 6H), 5.01 (d, J=5.8 Hz, 2H), 4.94-4.95 (m, 1H), 3.91-4.00 (m, 1H), 2.93 (br d, J=7.3 Hz, 1H), 1.76 (dd, J=12.2, 9.8 Hz, 1H), 1.46 (br dd, J=12.8, 5.5 Hz, 1H), 1.14 (s, 3H), 1.08 (s, 3H), 1.06 (s, 3H), 1.05 (s, 3H); 1H not observed (NH).

Step 5: The residue from Step 4 containing racemic benzyl N-[(3R,4R)-3-hydroxy-2,2,6,6-tetramethyl-4-piperidyl]carbamate was dissolved in methanol (5 mL), followed by the addition of 10% palladium on carbon (293 mg, 0.275 mmol). The reaction was stirred at room temperature while hydrogen gas was used to sparge the solution for 3 minutes. Stirring was continued under a hydrogen atmosphere at room temperature for 72 h. The reaction was filtered through celite and rinsed with methanol. Methanolic HCl (5 mL, 1.25 M) was added to the filtrate and the filtrate was concentrated to yield racemic (3R,4R)-4-amino-2,2,6,6-tetramethyl-piperidin-3-ol dihydrochloride (251 mg, 26% yield).

MS m/z 173.0 [M+H]⁺; ¹H NMR (1:1 chloroform-d:methanol-d₄) δ: 3.48 (q, J=7.6 Hz, 1H), 2.86 (d, J=7.6 Hz, 1H), 2.00 (dd, J=12.8, 8.5 Hz, 1H), 1.57 (dd, J=12.8, 7.3 Hz, 1H), 1.30 (d, J=2.1 Hz, 6H), 1.23 (s, 3H), 1.23 (s, 3H); 4Hs not observed (3NHs and OH).

Preparation of Starting Material: Racemic (3aR,4R, 6aS)-N,N-dimethyl-1,2,3,3a,4,5,6,6a-octahydrocyclopenta[c]pyrrol-4-amine

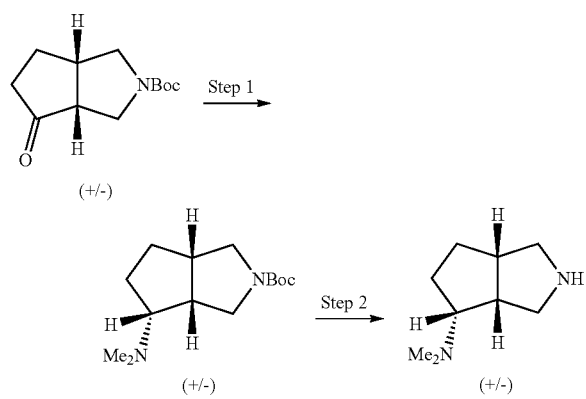

Step 1: Racemic tert-butyl 4-oxo-1,3,3a,5,6,6a-hexahydrocyclopenta[c]pyrrole-2-carboxylate (523.8 mg, 2.325 mmol), dichloromethane (5 mL), aqueous dimethylamine (2.0 mL, 40 wt. %, 6.8 equiv), and sodium triacetoxyborohydride (2.06 g, 9.72 mmol, 4.18 equiv) were combined and stirred at room temperature for 20 h. The reaction was partitioned between CH₂Cl₂ and aqueous sodium hydroxide (1.0 M) and the layers were separated. The aqueous layer was extracted twice with CH₂Cl₂/MeOH (9:1) and once with CHCl₃/iPrOH (7:3). The combined organic layers were dried over sodium sulfate, filtered and concentrated. The residue was purified by silica gel column chromatography eluting with a gradient of MeOH/CH₂Cl₂ (0-30% MeOH/NH₄OH, 2.5% NH₄OH v/v) to yield racemic tert-butyl (3aR,4R,6aS)-4-(dimethylamino)-3,3a,4,5,6,6a-hexahydro-1H-cyclopenta[c]pyrrole-2-carboxylate (452.4 mg, 76% yield).

MS m/z 255.3 [M+H]⁺; ¹H NMR (methanol-d₄) δ: 3.42-3.51 (m, 1H), 3.39 (dd, J=8.7, 4.1 Hz, 2H), 3.20 (br d, J=10.4 Hz, 1H), 2.80 (br s, 1H), 2.62-2.73 (m, 1H), 2.42-2.51 (m, 1H), 2.22 (s, 6H), 1.91-2.01 (m, 1H), 1.83-1.90 (m, 1H), 1.57 (quin, J=10.6 Hz, 1H), 1.45-1.50 (m, 1H), 1.43 (s, 9H).

Step 2: Racemic tert-butyl (3aR,4R,6aS)-4-(dimethylamino)-3,3a,4,5,6,6a-hexahydro-1H-cyclopenta[c]pyrrole-2-carboxylate (43.1 mg, 0.169 mmol) was dissolved in TFA (2 mL) and stirred at room temperature for 4 h. The reaction was concentrated and the residue used directly in subsequent reactions, assuming a quantitative yield of racemic (3aR, 4R,6aS)-N,N-dimethyl-1,2,3,3a,4,5,6,6a-octahydrocyclopenta[c]pyrrol-4-amine 2,2,2-trifluoroacetic acid. MS m/z 155.3 [M+H]⁺.

Preparation of Starting Material:
N-(tert-Butyl)pyrrolidin-3-amine

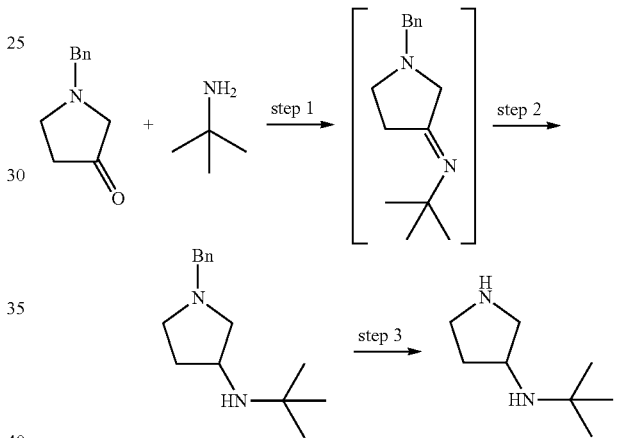

Step 1: A dry vial was charged with 1-benzylpyrrolidin-3-one (4.0 g, 22.8 mmol), 2-methylpropan-2-amine (3.8 g, 52.0 mmol) and Ti(OiPr)₄ (6.0 mL, 20.2 mmol). The mixture was purged with N₂ for 15 min and then allowed to stir at room temperature for 2 h. The resulting (E)-1-benzyl-N-(tert-butyl)pyrrolidin-3-imine was used without further purification.

Step 2: To the mixture from step 1 was added dry methanol (40 mL) and the reaction was cooled to 0° C. in an ice bath. NaBH₄ (1.6 g, 42.3 mmol) was added slowly in portions (caution: very exothermic reaction). Once evolution of the gas subsided, the mixture was warmed to room temperature and stirred for 2 h at room temperature. Upon completion, 0.1M NaOH solution (20 mL) was added to precipitate the titanium salts. The biphasic mixture was filtered through celite and washed with methanol. The solvent was removed under vacuum and the crude oil was purified by reverse phase chromatography using a acetonitrile/H₂O gradient (10%-100% acetonitrile) to afford 1-benzyl-N-(tert-butyl)pyrrolidine-3-amine (3.2 g, 60% yield) as a colorless oil.

Step 3: To an oven-dry round bottom flask containing palladium hydroxide on activated carbon (320 mg) was added 1-benzyl-N-(tert-butyl)pyrrolidine-3-amine (3.2 g, 13.8 mmol) dissolved in MeOH (20 mL). The mixture was sparged with H₂ for 5 minutes and a balloon of H₂ was placed on top of the flask and the reaction was stirred for 2 h at room temperature. The reaction mixture was filtered through celite, washed with MeOH and concentrated to afford N-(tert-butyl)pyrrolidin-3-amine (1.89 g, 96% yield) as a colorless oil which solidified upon standing.

$^1$H NMR (methanol-d$_4$) δ: 4.21 (dq, J=14.4, 7.0 Hz, 1H), 3.80 (dd, J=12.7, 8.0 Hz, 1H), 3.58-3.50 (m, 2H), 3.38-3.32 (m, 1H), 2.62-2.56 (m, 1H), 2.28-2.20 (m, 1H), 1.42 (s, 9H); 2NHs not observed.

Using the procedure described, additional compounds described herein may be prepared by substituting the appropriate starting material, suitable reagents and reaction conditions, obtaining compounds such as those selected from:

| Structure | Data |
|---|---|
| 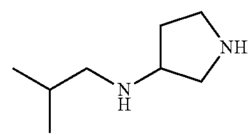 | $^1$H NMR (chloroform-d) δ: 0.93 (d, J = 6.71 Hz, 6H) 1.74 (dq, J = 13.28, 6.66 Hz, 2H) 1.98-2.15 (m, 1H) 2.42 (d, J = 6.71 Hz, 2H) 2.98 (dd, J = 11.60, 3.66 Hz, 1H) 3.06-3.21 (m, 2H) 3.29 (dt, J = 11.14, 7.40 Hz, 1H) 3.35-3.46 (m, 3H) |
| 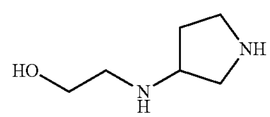 | $^1$H NMR (chloroform-d) δ: 1.57 (br d, J = 5.49 Hz, 1H) 2.02 (br dd, J = 13.12, 6.71 Hz, 1H) 2.38 (br s, 2H) 2.70-2.86 (m, 3H) 2.92 (br d, J = 8.09 Hz, 1H) 3.00 (br dd, J = 11.14, 5.80 Hz, 1H) 3.07-3.16 (m, 1H) 3.31 (br s, 1H) 3.49 (s, 1H) 3.67 (br t, J = 4.73 Hz, 2H) |
| 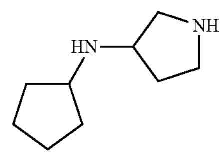 [SMILES: C1CCC(NC2CCNC2)C1] | MS m/z 155 [M + H]$^+$; $^1$H NMR (methanol-d$_4$) δ: 3.35-3.41 (m, 1H), 3.03-3.16 (m, 3H), 2.86-2.97 (m, 1H), 2.67-2.75 (m, 1H), 2.03-2.15 (m, 1H), 1.88-2.00 (m, 2H), 1.68-1.79 (m, 2H), 1.54-1.68 (m, 3H), 1.30-1.44 (m, 2H); 2NHs not observed |
| 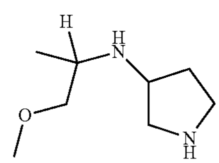 | MS m/z 159.2 [M + H]$^+$ |
| 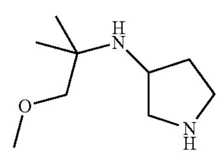 | MS m/z 173.3 [M + H]$^+$; $^1$H NMR (chloroform-d) δ: 3.46-3.39 (m, 1H), 3.36 (s, 3H), 3.27-3.17 (m, 3H), 3.09-3.01 (m, 2H), 2.75-2.65 (m, 1H), 2.18-2.07 (m, 1H), 1.65-1.53 (m, 1H), 1.65-1.53 (m, 1H), 1.08 (s, 3H), 1.07 (s, 3H); 1NH not observed |
| 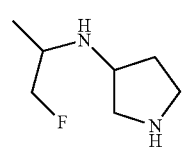 | $^1$H NMR (chloroform-d) δ: 4.45-4.20 (m, 2H), 3.81-3.68 (m, 1H), 3.31-3.15 (m, 2H), 3.12-2.88 (m, 3H), 2.40-2.23 (m, 1H), 1.95-1.80 (m, 1H), 1.12 (t, J = 7.9 Hz, 3H); 2NHs not observed |
| 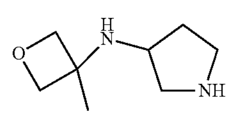 | $^1$H NMR (chloroform-d) δ: 4.57-4.44 (m, 2H), 4.43-4.28 (m, 2H), 3.54-3.41 (m, 1H), 2.81-2.64 (m, 2H), 2.62-2.50 (m, 1H), 2.34-2.13 (m, 2H), 1.60-1.41 (m, 4H); 2NHs not observed |
| 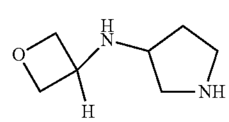 | MS m/z 143.3 [M + H]$^+$ |
| 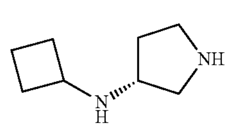 | $^1$H NMR (methanol-d$_4$) δ: 1.87-2.03 (m, 2H) 2.12-2.31 (m, 3H) 2.32-2.45 (m, 2H) 2.47-2.59 (m, 1H) 3.38-3.49 (m, 2H) 3.56 (br dd, J = 12.21, 6.41 Hz, 1H) 3.73 (br dd, J = 12.21, 8.24 Hz, 1H) 3.83-3.92 (m, 1H) 3.94-4.06 (m, 1H); 2NHs not observed |

| Structure | Data |
|---|---|
| (cyclobutyl-NH-pyrrolidin-3-yl, NH) | ¹H NMR (methanol-d₄) δ: 1.87-2.03 (m, 2H) 2.14-2.31 (m, 3H) 2.38 (br d, J = 3.66 Hz, 2H) 2.52 (br dd, J = 14.04, 7.02 Hz, 1H) 3.36-3.51 (m, 2H) 3.53-3.64 (m, 1H) 3.73 (br dd, J = 12.66, 8.09 Hz, 1H) 3.88 (br t, J = 8.09 Hz, 1H) 3.94-4.06 (m, 1H); 2NHs not observed |
| (1-methylcyclopropyl-NH-pyrrolidin-3-yl) | MS m/z 141.1 [M + H]⁺ |
| (4-methyltetrahydropyran-4-yl-NH-pyrrolidin-3-yl) | MS m/z 185.3 [M + H]⁺ |

Preparation of Starting Material:
N-(Pyrrolidin-3-ylmethyl)propan-2-amine hydrochloride

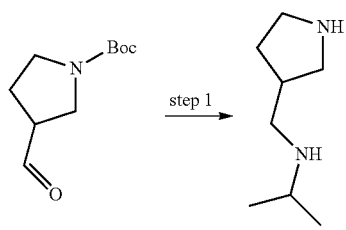

Step 1: To a round bottom flask were added 1-Boc-3-formylpyrrolidine (300 mg, 1.5 mmol), isopropyl amine (0.2 mL, 2.54 mmol) and methylene chloride (5 mL). The mixture was stirred for 30 min at room temperature followed by the portion-wise addition of sodium triacetoxyborohydride (636 mg, 3 mmol) and the mixture continued to stir for 16 h at room temperature. The reaction was quenched by the addition of 1.0 M NaOH and washed with water. The aqueous phase was extracted with $CH_2Cl_2$ (2 times) and the combined organic layers were dried over $Mg_2SO_4$. The solvent volume was reduced in vacuo and an HCl solution (2.0M in ether, 2 mL) was added. The mixture was stirred for 5 h at room temperature, and the solids were collected by filtration, and dried to provide N-(pyrrolidin-3-ylmethyl)propan-2-amine bishydrochloride salt (160 mg, 50% yield) as an off white solid.

¹H NMR (DMSO-d₆) δ: 9.70-9.45 (m, 2H), 9.19 (br s, 2H), 3.39-3.30 (m, 1H), 3.25 (dd, J=6.1, 11.9 Hz, 2H), 3.17-3.07 (m, 1H), 3.06-2.94 (m, 3H), 2.75-2.64 (m, 1H), 2.20-2.06 (m, 1H), 1.81-1.66 (m, 1H), 1.27 (d, J=6.3 Hz, 6H).

Using the procedure described, additional compounds described herein may be prepared by substituting the appropriate starting material, suitable reagents and reaction conditions, obtaining compounds such as those selected from:

| Structure | Data |
|---|---|
| (tert-butyl-NH-CH₂-pyrrolidin-3-yl) | ¹H NMR (methanol-d₄) δ: 3.66-3.55 (m, 1H), 3.53-3.43 (m, 1H), 3.38-3.29 (m, 2H), 3.25-3.13 (m, 2H), 3.13-3.02 (m, 1H), 2.77-2.63 (m, 1H), 2.42-2.30 (m, 1H), 1.92-1.77 (m, 1H), 1.41 (s, 9H); 1NH not observed. |
| (tetrahydropyran-4-yl-NH-CH₂-pyrrolidin-3-yl) | ¹H NMR (DMSO-d₆) δ: 9.25-8.98 (m, 2H), 8.96-8.74 (m, 2H), 4.00-3.87 (m, 2H), 3.45-3.36 (m, 1H), 3.35-3.23 (m, 4H), 3.23-3.12 (m, 1H), 3.12-3.02 (m, 2H), 2.93 (br s, 1H), 2.64-2.53 (m, 1H), 2.20-2.07 (m, 1H), 1.99-1.87 (m, 2H), 1.74-1.62 (m, 1H), 1.62-1.50 (m, 2H) |
| (cyclobutyl-NH-CH₂-pyrrolidin-3-yl) | ¹H NMR (methanol-d₄) δ: 1.76-1.87 (m, 1H) 1.95 (br d, J = 9.77 Hz, 2H) 2.17-2.29 (m, 2H) 2.29-2.44 (br s, 3H) 2.64-2.79 (m, 1H) 2.99-3.15 (m, 3H) 3.33 (br s, 1H) 3.46 (br d, J = 4.27 Hz, 1H) 3.53-3.65 (m, 1H) 3.80 (br t, J = 8.09 Hz, 1H); 2NHs not observed |

Preparation of Starting Material: N-(Pyrrolidin-3-ylmethyl)tetrahydrofuran-3-amine

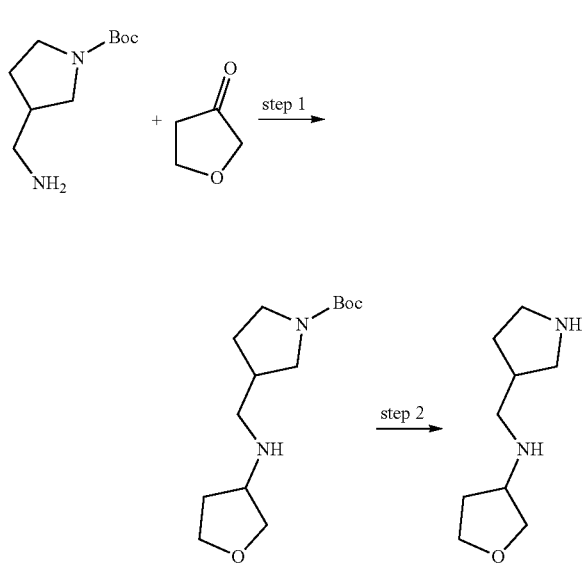

Step 1: To a solution of tert-butyl 3-(aminomethyl)pyrrolidine-1-carboxylate (50 mg, 0.25 mmol) and dihydrofuran-3(2H)-one (43 mg, 0.50 mmol) in CH$_2$Cl$_2$ (1.3 mL) was added sodium triacetoxyborohydride (110 mg, 0.050 mmol). The reaction was stirred at room temperature for 2 hours and then partitioned between EtOAc and aq. NaHCO$_3$. The organic phase was collected, and the aqueous layer was extracted once more with EtOAc. The organic phases were combined, washed with water, then brine, dried over Na$_2$SO$_4$ and then concentrated to afford tert-butyl 3-(((tetrahydrofuran-3-yl)amino)methyl)pyrrolidine-1-carboxylate which was used without further purification. MS m/z 271.4 [M+H]$^+$.

Step 2: 3-(((Tetrahydrofuran-3-yl)amino)methyl)pyrrolidine-1-carboxylate from step 1 was dissolved in CH$_2$Cl$_2$ (2 mL) and then trifluoroacetic acid (0.5 mL) was added. The reaction was stirred at room temperature for 1 hour and then concentrated under high vacuum to afford N-(pyrrolidin-3-ylmethyl)tetrahydrofuran-3-amine which was used without further purification. MS m/z 171.3 [M+H]$^+$.

Using the procedure described, additional compounds described herein may be prepared by substituting the appropriate starting material, suitable reagents and reaction conditions, obtaining compounds such as those selected from:

| Structure | Data |
|---|---|
| 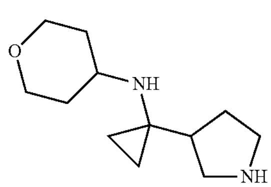 [SMILES: C1CC(C2(NC3CCOCC3)CC2)CN1] | MS m/z 211.2 [M + H]$^+$ |

Preparation of Starting Material (R)-N-(tert-Butyl)pyrrolidin-3-amine

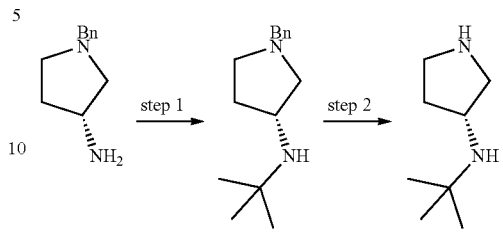

Step 1: (R)-1-Benzylpyrrolidin-3-amine (2.0 g, 11.3 mmol), molecular sieves (2.0 g), and acetone (4.2 mL, 57.0 mmol) were mixed in a microwave vial and the mixture was heated in a microwave at 60° C. for 4 h. The molecular sieves were filtered off and the red solution was concentrated. The crude red oil was diluted with THF (4.0 mL) and 1.6 M solution of methyl lithium (8.7 mL, 14.0 mmol) was added slowly at room temperature. The reaction was stirred at room temperature for 4 h. The reaction mixture was then quenched with water and extracted with EtOAc, and the organic layer was dried over Na$_2$SO$_4$ and concentrated. The residue was purified by silica gel chromatography using a MeOH/CH$_2$Cl$_2$ gradient (0-30%), followed by reverse phase purification using a gradient from 10% ACN/H$_2$O up to 100% ACN to afford (R)-1-benzyl-N-(tert-butyl)pyrrolidin-3-amine (0.2 g, 9% yield) as a colorless oil.

Step 2: To a round bottom flask containing Pd(OH)$_2$/C was added MeOH (10 mL) followed by (R)-1-benzyl-N-(tert-butyl)pyrrolidin-3-amine (0.2 g, 0.9 mmol) and the solvent was bubbled with H$_2$ for 5 min. A balloon containing H$_2$ was then placed on top of the flask and the reaction was allowed to stir for 2 h at room temperature. The solution was filtered over Celite and then concentrated to afford (R)-N-(tert-butyl)pyrrolidin-3-amine (0.12 g, 94% yield) as a colorless oil.

$^1$H NMR (methanol-d$_4$) δ: 4.23 (dq, J=14.0, 7.2 Hz, 1H), 3.83 (dd, J=12.5, 9.0 Hz, 1H), 3.62-3.50 (m, 2H), 3.40-3.33 (m, 1H), 2.66-2.58 (m, 1H), 2.30-2.23 (m, 1H), 1.46 (s, 9H).

Using the procedure described, additional compounds described herein may be prepared by substituting the appropriate starting material, suitable reagents and reaction conditions, obtaining compounds such as those selected from:

| Structure | Data |
|---|---|
| 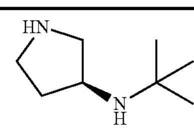 | $^1$H NMR (methanol-d$_4$) δ: 4.23 (dq, J = 15.0, 8.0 Hz, 1H), 3.83 (dd, J = 12.9, 8.3 Hz, 1H), 3.62-3.52 (m, 2H), 3.40-3.33 (m, 1H), 2.65-2.59 (m, 1H), 2.26 (dq, J = 16.3, 8.4 Hz, 1H), 1.46 (s, 9H) |

Example 1

Preparation of Compound 15

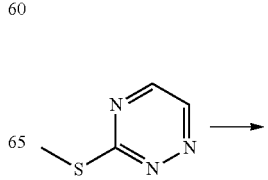

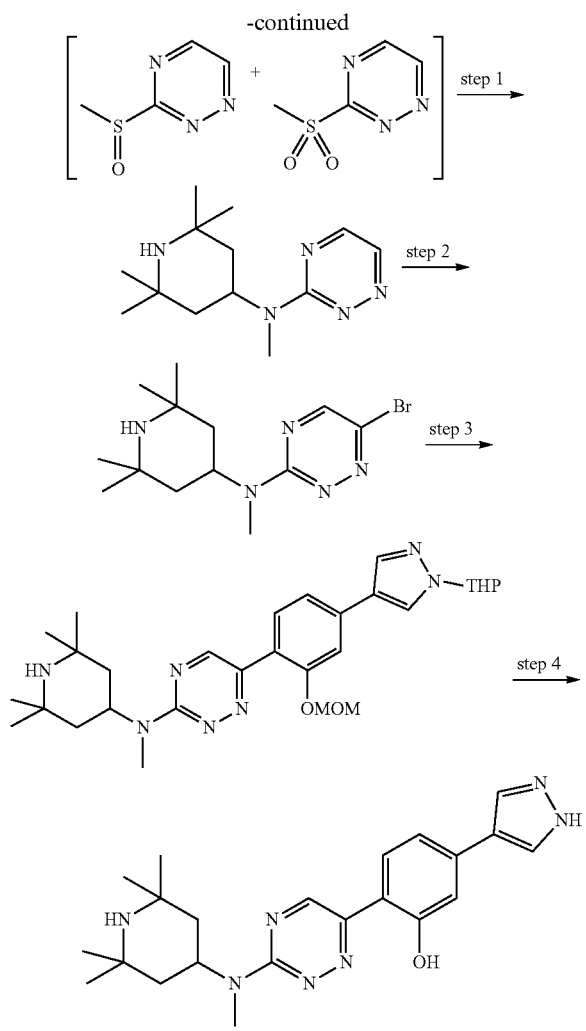

Step 1: A solution of 3-(methylthio)-1,2,4-triazine (500 mg, 3.9 mmol) in 10 mL of $CH_2Cl_2$ was cooled in an ice-water batch, and m-CPBA (958 mg, 3.9 mmol) was added. The reaction mixture was stirred at 0° C. for 1 h until UPLC showed complete consumption of the starting material. The solvent was removed under reduced pressure without heating. The residue was redissolved in 5 mL of n-BuOH, N,2,2,6,6-pentamethylpiperidin-4-amine (1.0 g, 5.9 mmol) was added, and the reaction mixture was heated to 100° C. for 16 h. The reaction mixture was cooled to room temperature, the solvent was removed under reduced pressure. The crude product, N-methyl-N-(2,2,6,6-tetramethylpiperidin-4-yl)-1,2,4-triazin-3-amine, was used as is in the next step.

Step 2: N-Methyl-N-(2,2,6,6-tetramethylpiperidin-4-yl)-1,2,4-triazin-3-amine prepared in step 1 was dissolved in 10 mL of MeOH and 5 mL of water. Bromine (200 μL, 3.9 mmol) was added, and the reaction mixture was stirred for 30 min at room temperature until UPLC showed full conversion. The solvents were removed under reduced pressure. The residue was dissolved in EtOAc (20 mL) and washed with water followed by brine. The organic layer was dried over $Na_2SO_4$, concentrated, and purified using silica gel chromatography eluting with a $MeOH/CH_2Cl_2$ gradient (0 to 30% MeOH) to yield 6-bromo-N-methyl-N-(2,2,6,6-tetramethylpiperidin-4-yl)-1,2,4-triazin-3-amine (367 mg, 29%) as brownish solid.

MS m/z 328.2, 330.3 [M+H]$^+$; $^1$H NMR (methanol-$d_4$) δ: 8.46 (s, 1H), 5.15-5.32 (m, 1H), 3.10 (s, 3H), 2.04-2.09 (m, 2H), 1.96-1.99 (m, 2H), 1.58 (s, 6H), 1.54 (s, 6H), NH not observed.

Step 3: An oven-dried flask was equipped with a magnetic stir bar and charged with 6-bromo-N-methyl-N-(2,2,6,6-tetramethylpiperidin-4-yl)-1,2,4-triazin-3-amine (40 mg, 0.12 mmol), 4-[3-(methoxymethoxy)-4-(4,4,5,5-tetramethyl-1,3,2-dioxaborolan-2-yl)phenyl]-1-tetrahydropyran-2-yl-pyrazole (61 mg, 0.15 mmol), [1,1'-bis(diphenylphosphino)ferrocene] dichloropalladium(II) (9 mg, 0.012 mmol), and $K_2CO_3$ (51 mg, 0.37 mmol). The flask was sealed with a rubber septum and then evacuated and backfilled with argon. Dioxane (2 mL) and water (0.5 mL) were added, and the reaction was heated to 90° C. for 16 h. The reaction was cooled to room temperature, diluted with water, and extracted with EtOAc. The combined organic layers were dried over $Na_2SO_4$, concentrated under reduced pressure, and purified by column chromatography eluting with a $MeOH/CH_2Cl_2$ gradient (0 to 30% MeOH) to provide 6-(2-(methoxymethoxy)-4-(1-(tetrahydro-2H-pyran-2-yl)-1H-pyrazol-4-yl)phenyl)-N-methyl-N-(2,2,6,6-tetramethylpiperidin-4-yl)-1,2,4-triazin-3-amine (41 mg, 63%) as a brownish solid. MS m/z 536.5 [M+H]$^+$.

Step 4: To a solution of 6-[2-(methoxymethoxy)-4-(1-tetrahydropyran-2-ylpyrazol-4-yl)phenyl]-N-methyl-N-(2,2,6,6-tetramethyl-4-piperidyl)-1,2,4-triazin-3-amine (41 mg, 0.077 mmol) in $CH_2Cl_2$ (1 mL) and 2 drops of MeOH was added HCl (4 mol/L) in 1,4-dioxane (38 μL, 0.15 mmol). The reaction was stirred for 5 h until UPLC showed complete consumption of the starting material. The solvents were removed under reduced pressure, and the product was purified by column chromatography eluting with a gradient $CH_2Cl_2$/MeOH (5 to 30% MeOH). Provided 2-[3-[methyl-(2,2,6,6-tetramethyl-4-piperidyl)amino]-1,2,4-triazin-6-yl]-5-(1H-pyrazol-4-yl)phenol;dihydrochloride (24 mg, 65%) as brownish solid.

MS m/z 408.5 [M+H]$^+$; $^1$H NMR (methanol-$d_4$) δ: 9.11 (s, 1H), 8.03 (br. s., 2), 7.84 (d, J=7.9 Hz, 1H), 7.25 (dd, J=8.2, 1.9 Hz, 1H), 7.21 (d, J=1.9 Hz, 1H), 5.32-5.46 (m, 1H), 3.23 (s, 3H), 1.93-2.10 (m, 3H), 1.65 (s, 6H), 1.54 (s, 6H); 3Hs not observed (2NHs and OH).

Using the procedure described for Example 1, additional compounds described herein may be prepared by substituting the appropriate starting material, suitable reagents and reaction conditions, obtaining compounds such as those selected from:

| Cpd | Data |
|---|---|
| 10 | MS m/z 422.5 [M + H]$^+$; $^1$H NMR (DMSO-$d_6$) δ: 11.78 (br s, 1H), 9.65 (s, 1H), 9.43 (s, br, 1H), 9.09 (s, 1H), 8.08 (d, J = 8.5 Hz, 1H), 8.03 (s, 1H), 7.38-7.35 (m, 2H), 5.21-5.29 (m, 1H), 3.13 (s, 3H), 2.38 (s, 3H), 2.09 (t, J = 12.0 Hz, 2H), 1.78 (d, J = 12.0 Hz, 2H), 1.52 (s, 6H), 1.51 (s, 6H) |

| Cpd | Data |
|---|---|
| 50 | MS m/z 426.6 [M + H]⁺; ¹H NMR (DMSO-d₆) δ: 11.64 (br s, 1H), 9.28 (br s, 1H), 9.10 (s, 1H), 8.22 (br s, 1H), 8.06 (s, 1H), 8.00 (d, J = 8.0 Hz, 1H), 7.56 (d, J = 8.0 Hz, 1H), 7.26 (d, J = 8.5 Hz, 1H), 7.24 (s, 1H), 5.22 (t, J = 13.0 Hz, 1H), 3.11 (s, 3H), 1.94-2.07 (m, 2H), 1.77 (d, J = 10.0 Hz, 2H), 1.49 (s, 6H), 1.46 (s, 6H); 1H is from HCl salt |
| 87 | MS m/z 406.5 [M + H]⁺. ¹H NMR (methanol-d₄) δ: 9.10 (s, 1H), 8.02 (s, 2H), 7.84, (d, J = 8.09 Hz, 1H), 7.24 (d, J = 8.00 Hz, 1H), 7.21 (s, 1H), 6.00-5.56 (m, 1H) 3.74 (s, 3H), 3.12 (s, 3H), 2.75-2.60 (m, 2H), 2.42-2.30 (m, 2H), 2.29-2.17 (m, 2H), 2.16-1.97 (m, 4H), 1.96-1.87 (m, 2H); 2NHs not observed (NH and OH) |
| 105 | MS m/z 393.5 [M + H]⁺; ¹H NMR (methanol-d₄) δ: 9.13 (s, 1H), 8.77 (dd, J = 4.6, 1.5 Hz, 1H), 8.41 (s, 1H), 8.37 (d, J = 7.3 Hz, 1H), 7.47 (s, 1H), 7.40 (dd, J = 8.2, 4.6 Hz, 1H), 5.36-5.48 (m, 1H), 3.26 (s, 3H), 1.95-2.09 (m, 4H), 1.65 (s, 6H), 1.55 (s, 6H); 2Hs not observed (NH and OH) |
| 125 | MS m/z 426.6 [M + H]⁺; ¹H NMR (methanol-d₄) δ: 9.11 (s, 1H), 7.66-7.83 (m, 2H), 7.50 (br s, 1H), 6.77 (t, J = 2.7 Hz, 1H), 5.32-5.45 (m, 1H), 3.23 (s, 3H), 1.92-2.01 (m, 4H), 1.62 (s, 6H), 1.51 (s, 6H); 3Hs not observed (2 NHs and OH) |

Example 2

Preparation of Compound 1

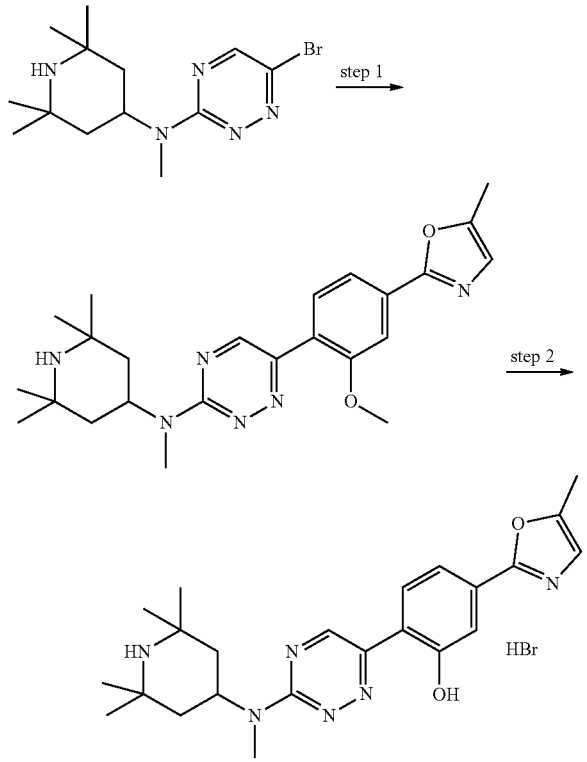

Step 1: An oven-dried flask was equipped with a magnetic stir bar and charged with 6-bromo-N-methyl-N-(2,2,6,6-tetramethyl-4-piperidyl)-1,2,4-triazin-3-amine (80 mg, 0.24 mmol), 2-[3-methoxy-4-(4,4,5,5-tetramethyl-1,3,2-dioxaborolan-2-yl)phenyl]-5-methyl-oxazole (92 mg, 0.29 mmol), tetrakis(triphenylphosphine)palladium(0) (28 mg, 0.024 mmol), and Na₂CO₃ (77.5 mg, 0.73 mmol). The flask was sealed with a rubber septum, and then evacuated and backfilled with argon. Dioxane (2 mL) and water (0.5 mL) were added, and the reaction was heated to 90° C. for 16 h. The reaction was cooled to room temperature, diluted with water, and extracted with EtOAc. The combined organic layers were dried over Na₂SO₄, concentrated under reduced pressure, and purified by column chromatography eluting with a MeOH/CH₂Cl₂ gradient (0 to 30% MeOH) to provide 6-(2-methoxy-4-(5-methyloxazol-2-yl)phenyl)-N-methyl-N-(2,2,6,6-tetramethylpiperidin-4-yl)-1,2,4-triazin-3-amine (38 mg, 36%) as a brownish solid. MS m/z 437.5 [M+H]⁺.

Step 2: 6-[2-Methoxy-4-(5-methyloxazol-2-yl)phenyl]-N-methyl-N-(2,2,6,6-tetramethyl-4-piperidyl)-1,2,4-triazin-3-amine (38 mg, 0.09 mmol) in CH₂Cl₂ (2 mL) was treated with BBr₃ in CH₂Cl₂ (1 mol/L, 0.87 mL). The reaction was stirred at room temperature for 4 h until UPLC showed complete consumption of the starting material. The precipitate was filtered and dried to give 2-(3-(methyl(2,2,6,6-tetramethylpiperidin-4-yl)amino)-1,2,4-triazin-6-yl)-5-(5-methyloxazol-2-yl)phenol hydrobromide (13 mg, 35%) as an orange solid.

MS m/z 423.5 [M+H]⁺; ¹H NMR (methanol-d₄) δ: 9.14 (s, 1H), 7.98 (d, J=8.2 Hz, 1H), 7.61 (dd, J=8.2, 1.6 Hz, 1H), 7.58 (d, J=1.6 Hz, 1H), 6.96 (d, J=1.3 Hz, 1H), 5.37-5.45 (m, 1H), 3.25 (s, 3H), 2.46 (s, 3H), 1.98-2.05 (m, 4H), 1.66 (s, 6H), 1.55 (s, 6H); 2Hs not observed (NH and OH).

Using the procedure described for Example 2, additional compounds described herein may be prepared by substituting the appropriate starting material, suitable reagents and reaction conditions, obtaining compounds such as those selected from:

| Cpd | Data |
|---|---|
| 17 | MS m/z 408.3 [M + H]⁺; ¹H NMR (methanol-d₄) δ: 8.33 (d, J = 2.1 Hz, 1H), 7.74-7.81 (m, 2H), 7.37-7.48 (m, 2H), 6.57 (s, 1H), 6.03 (s, 1H), 4.46-4.59 (m, 1H), 3.21 (s, 3H), 2.06-2.30 (m, 4H), 1.66 (s, 6H), 1.62 (s, 6H); 2Hs not observed (NH and OH). |
| 368 | MS m/z 438.5 [M + H]⁺. ¹H NMR (methanol-d₄): 9.11 (s, 1H), 7.71 (s, 1H), 7.40 (d, J = 8.00 Hz, 2H), 7.32 (d, J = 8.50 Hz, 2H), 7.31 (s, 1H), 6.80 (s, 1H), 5.51 (s, 3H), 5.36-5.39 (m, 1H), 4.01 (s, 3H), 1.96-2.05 (m, 4H), 1.66 (s, 6H), 1.54 (s, 6H) |
| 376 | MS m/z 410.5 [M + H]⁺. ¹H NMR (methanol-d₄): 8.89 (s, 1H), 8.06 (s, 2H), 6.85-6.91 (m, 2H), 4.31-4.26 (m, 1H), 4.25-4.17 (m, 1H), 4.02-3.96 (m, 1H), 3.93 (s, 3H), 3.81- |

| Cpd | Data |
|---|---|
| | 3.75 (m, 2H), 2.71-2.60 (m, 1H), 2.33-2.24 (m, 1H), 1.50 (s, 9H); 3Hs not observed (2NHs and OH) |

Example 3

Preparation of Compound 16

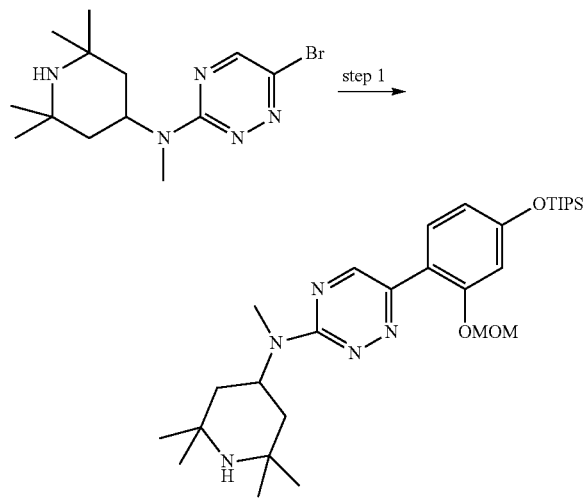

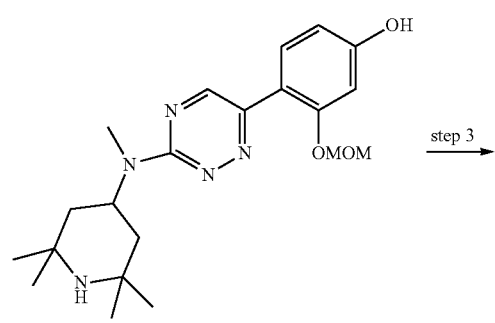

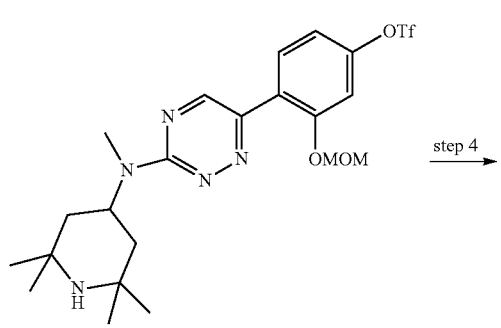

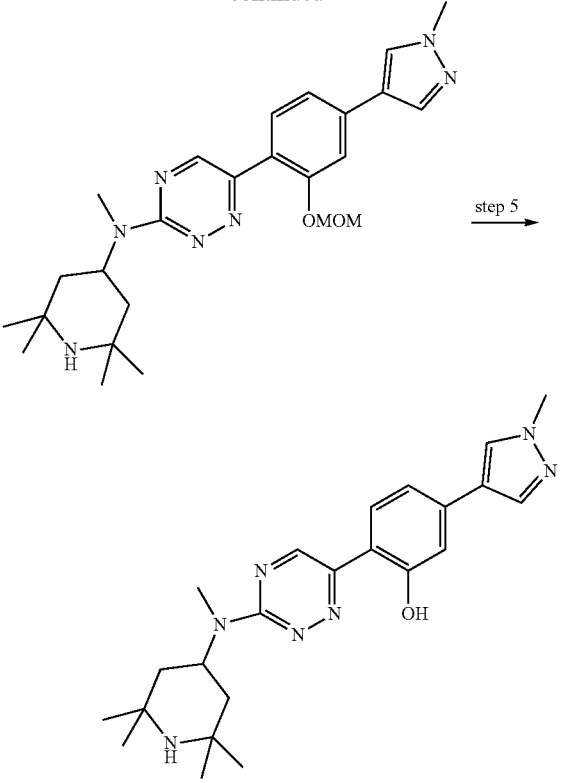

Step 1: An oven-dried flask was equipped with a magnetic stir bar and charged with 6-bromo-N-methyl-N-(2,2,6,6-tetramethyl-4-piperidyl)-1,2,4-triazin-3-amine (450 mg, 1.37 mmol), triisopropyl-[3-(methoxymethoxy)-4-(4,4,5,5-tetramethyl-1,3,2-dioxaborolan-2-yl)phenoxy]silane (658 mg, 1.51 mmol), [1,1'-bis(diphenylphosphino)ferrocene]dichloropalladium(II) (102 mg, 0.14 mmol) and $K_2CO_3$ (383 mg, 2.74 mmol). The flask was sealed with a rubber septum, and then evacuated and backfilled with argon. Dioxane (4 mL) and water (1 mL) were added and the reaction was heated to 90° C. for 16 h. The reaction was cooled to room temperature, diluted with water (5 mL), and extracted with EtOAc. The combined organic layers were dried over $Na_2SO_4$, concentrated under reduced pressure, and purified by column chromatography eluting with a $MeOH/CH_2Cl_2$ gradient (0 to 30% MeOH) to provide crude 6-(2-(methoxymethoxy)-4-((triisopropylsilyl)oxy)phenyl)-N-methyl-N-(2,2,6,6-tetramethylpiperidin-4-yl)-1,2,4-triazin-3-amine (316 mg, 41%) as a brownish solid. MS m/z 558.6 $[M+H]^+$.

Step 2: To a solution of 6-[2-(methoxymethoxy)-4-triisopropylsilyloxy-phenyl]-N-methyl-N-(2,2,6,6-tetramethyl-4-piperidyl)-1,2,4-triazin-3-amine (316 mg, 0.57 mmol) in dry THF (2 mL) was added a 1.0 M solution of TBAF in THF (1.1 mL, 1.1 mmol). The reaction mixture was stirred at room temperature for 10 min until TLC showed complete consumption of the starting material. The solvent was removed under reduced pressure, and the residue was purified by column chromatography eluting with a MeOH/CH$_2$Cl$_2$ gradient (0 to 30% MeOH) to yield 3-(methoxymethoxy)-4-(3-(methyl(2,2,6,6-tetramethylpiperidin-4-yl)amino)-1,2,4-triazin-6-yl)phenol (156 mg, 69%) as a tan oil.

Step 3: To a solution of 3-(methoxymethoxy)-4-(3-(methyl(2,2,6,6-tetramethylpiperidin-4-yl)amino)-1,2,4-triazin-6-yl)phenol in CH$_2$Cl$_2$ (3 mL) were added N,N-bis(trifluoromethylsulfonyl)aniline (280 mg, 0.78 mmol) and Et$_3$N (0.16 mL, 1.2 mmol). The reaction was stirred for 16 h until UPLC showed complete conversion. The solvent was removed under reduced pressure, the residue was purified by column chromatography on silica gel eluting with a EtOAc/hexanes gradient (30-100% EtOAc) to give 3-(methoxymethoxy)-4-(3-(methyl(2,2,6,6-tetramethylpiperidin-4-yl)amino)-1,2,4-triazin-6-yl)phenyl trifluoromethanesulfonate (154 mg, 74%). MS m/z 534.4 [M+H]$^+$.

Step 4: An oven-dried flask was equipped with a magnetic stir bar and charged with 3-(methoxymethoxy)-4-(3-(methyl(2,2,6,6-tetramethylpiperidin-4-yl)amino)-1,2,4-triazin-6-yl)phenyl trifluoromethanesulfonate (51 mg, 0.096 mmol), 1-methyl-4-(4,4,5,5-tetramethyl-1,3,2-dioxaborolan-2-yl)pyrazole (24 mg, 0.12 mmol), [1,1'-bis(diphenylphosphino)ferrocene]dichloropalladium(I) (7 mg, 0.01 mmol), and K$_2$CO$_3$ (40 mg, 029 mmol). The flask was sealed with a rubber septum and then evacuated and backfilled with argon. Dioxane (2 mL) and water (0.5 mL) were added and the reaction was heated to 90° C. for 16 h. The reaction was cooled to room temperature, diluted with water, and extracted with EtOAc. The combined organic layers were dried over Na$_2$SO$_4$, concentrated under reduced pressure, and purified by column chromatography eluting with a MeOH/CH$_2$Cl$_2$ gradient (0 to 30% MeOH) to provide 6-(2-(methoxymethoxy)-4-(1-methyl-1H-pyrazol-4-yl)phenyl)-N-methyl-N-(2,2,6,6-tetramethylpiperidin-4-yl)-1,2,4-triazin-3-amine (40 mg, 90%). MS m/z 466.6 [M+H]$^+$.

Step 5: To a solution of 6-(2-(methoxymethoxy)-4-(1-methyl-H-pyrazol-4-yl)phenyl)-N-methyl-N-(2,2,6,6-tetramethylpiperidin-4-yl)-1,2,4-triazin-3-amine (40 mg, 0.086 mmol) in CH$_2$Cl$_2$ (1 mL), were added 2 drops of MeOH and HCl (4 mol/L) in 1,4-dioxane (43 µL, 0.17 mmol). The reaction was stirred for 16 h at room temperature. The solvents were removed under reduced pressure, and the product was purified by column chromatography eluting with a MeOH/CH$_2$Cl$_2$ gradient (5 to 30% MeOH) to provide 2-(3-(methyl(2,2,6,6-tetramethylpiperidin-4-yl)amino)-1,2,4-triazin-6-yl)-5-(1-methyl-1H-pyrazol-4-yl)phenol.

MS m/z 422.5 [M+H]$^+$; $^1$H NMR (methanol-d$_4$) δ: 9.37-9.43 (m, 1H), 8.10 (s, 1H), 7.94 (s, 1H), 7.64 (d, J=8.2 Hz, 1H), 7.24 (dd, J=8.5, 1.8 Hz, 1H), 7.19 (d, J=1.8 Hz, 1H), 5.36-5.48 (m, 1H), 3.97 (s, 3H), 3.16 (s, 3H), 2.00-2.15 (m, 4H), 1.64 (s, 6H), 1.58 (s, 6H); 2Hs not observed (OH and NH).

Using the procedure described for Example 3, additional compounds described herein may be prepared by substituting the appropriate starting material, suitable reagents and reaction conditions, obtaining compounds such as those selected from:

| Cpd | Data |
|---|---|
| 8 | MS m/z 419.2 [M + H]$^+$; $^1$H NMR (DMSO-d$_6$) δ: 11.25 (br s, 1H), 9.09 (s, 1H), 8.58-8.71 (m, 2H), 8.00 (d, J = 8.3 Hz, 1H), 7.65-7.76 (m, 2H), 7.41-7.43 (m, 1H), 7.40 (s, 1H), 5.10-5.32 (m, 1H), 3.13 (s, 3H), 1.98 (t, J = 13.0 Hz, 2H), 1.82 (dd, J = 13.0, 3.7 Hz, 2H), 1.50 (s, 6H), 1.45 (s, 6H); 1H not observed (NH or OH). |
| 9 | MS m/z 433.3 [M + H]$^+$; $^1$H NMR (DMSO-d$_6$) δ: 9.08 (s, 1H), 8.51 (d, J = 5.1 Hz, 1H), 7.99 (d, J = 8.1 Hz, 1H), 7.54-7.63 (m, 1H), 7.49 (dd, J = 5.1, 1.5 Hz, 1H), 7.38 (dd, J = 8.1, 1.5 Hz, 1H), 7.35-7.36 (m, 1H), 5.11-5.32 (m, 1H), 3.08 (s, 3H), 2.54 (s, 3H), 1.54 (dd, J = 12.1, 3.4 Hz, 2H), 1.47 (t, J = 12.1 Hz, 2H), 1.24 (s, 6H), 1.10 (s, 6H); 2Hs not observed (NH and OH). |
| 60 | MS m/z 420.6 [M + H]$^+$; $^1$H NMR (methanol-d$_4$) δ: 9.61 (s, 1H), 9.28 (br d, J = 5.2 Hz, 1H), 9.16 (s, 1H), 8.10 (br d, J = 5.6, 2.5 Hz, 1H), 8.07 (d, J = 7.9 Hz, 1H), 7.52 (dd, J = 8.4, 1.7 Hz, 1H), 7.49 (d, J = 1.8 Hz, 1H), 5.35-5.48 (m, 1H), 3.25 (s, 3H), 1.95-2.09 (m, 4H), 1.66 (s, 6H), 1.56 (s, 6H); 2Hs not observed (NH and OH) |
| 61 | MS m/z 434.6 [M + H]$^+$; $^1$H NMR (methanol-d$_4$) δ: 9.39 (s, 1H), 9.13 (s, 1H), 8.04 (br d, J = 7.9 Hz, 1H), 7.95 (s, 1H), 7.37-7.53 (m, 2H), 5.29-5.46 (m, 1H), 3.21 (s, 3H), 2.78 (s, 3H), 1.67-1.85 (m, 4H), 1.47 (s, 6H), 1.35 (s, 6H); 2Hs not observed (NH and OH) |
| 70 | MS m/z 419.1 [M + H]$^+$; $^1$H NMR (DMSO-d$_6$) δ: 9.08 (s, 1H), 8.91 (s, 1H), 8.59 (d, J = 4.0 Hz, 1H), 8.09 (d, J = 8.0 Hz, 1H), 7.98 (d, J = 8.0 Hz, 1H), 7.48-7.52 (m, 1H), 7.30-7.33 (m, 2H), 5.19 (br s, 1H), 3.08 (s, 3H), 1.45-1.55 (m, 4H), 1.11 (s, 6H), 1.24 (s, 6H); 2Hs not observed (OH and NH) |
| 74 | MS m/z 423.5 [M + H]$^+$; $^1$H NMR (methanol-d$_4$) δ: 9.11 (s, 1H), 7.82 (d, J = 8.4 Hz, 1H), 7.69 (s, 1H), 7.54 (d, J = 1.1 Hz, 1H), 7.34-7.39 (m, 2H), 5.33-5.42 (m, 1H), 3.77-3.83 (m, 3H), 3.21 (s, 3H), 1.84-1.99 (m, 4H), 1.59 (br s, 6H), 1.47 (br s, 6H); 1H not observed |
| 77 | MS m/z 392.5 [M + H]$^+$. $^1$H NMR (methanol-d$_4$): 8.41 (s, 2H), 7.66 (dd, J = 8.32, 1.60 Hz, 1H), 7.31 (d, J = 8.33 Hz, 1H), 7.28 (s, 1H), 6.00 (s, 1H), 5.98 (s, 1H), 3.1 (s, 3H), 2.58-2.51 (m, 3H), 2.39-2.06 (m, 9H), 2.07-1.88 (m, 1H), 1.89-1.76 (m, 1H); 3Hs not observed (2NHs and OH) |
| 78 | MS m/z 364.4 [M + H]+. $^1$H NMR (methanol-d$_4$): 8.91 (s, 1H), 7.90 (s, 2H), 7.72, (d, J = 8.09 Hz, 1H), 7.12 (d, J = 8.00 Hz, 1H), 7.09, (s, 1H), 4.11-4.07 (m, 1H), 4.00-3.96 (m, 2H), 2.39-2.35 (m, 2H), 2.29-2.25 (m, 4H), 2.17-2.01 (m, 4H); 2Hs not observed (OH and NH) |
| 86 | MS m/z 420.2 [M + H]$^+$; $^1$H NMR (DMSO-d$_6$) δ: 9.21 (s, 1H), 9.15 (s, 2H), 9.10 (s, 1H), 8.36 (br s, 1H), 8.00 (d, J = 8.4 Hz, 1H), 7.38-7.42 (m, 2H), 5.23 (br s, 1H), 3.11 (s, 3H), 1.81-1.89 (m, 2H), 1.67-1.71 (m, 2H), 1.41 (s, 6H), 1.33 (s, 6H); 1H not observed (OH or NH) |
| 103 | MS m/z 434.3 [M + H]$^+$; $^1$H NMR (DMSO-d$_6$) δ: 9.07 (s, 1H), 8.35 (s, 1H), 7.87-7.90 (m, 1H), 7.50 (d, J = 8.8 Hz, 2H), 7.17-7.19 (m, 2H), 6.86 (d, J = 8.4 Hz, 2H), 5.21 (br s, 1H), 3.10 (s, 3H), 1.66-1.82 (m, 4H), 1.39 (s, 6H), 1.30 (s, 6H); 2Hs not observed (OH and NH) |

-continued

| Cpd | Data |
|---|---|
| 104 | MS m/z 435.1 [M + H]⁺; ¹H NMR (DMSO-d₆) δ: 9.07 (s, 1H), 7.89 (d, J = 8.4 Hz, 1H), 7.84 (dd, J = 9.6, 2.8 Hz, 1H), 7.75 (d, J = 2.8 Hz, 1H), 7.17 (dd, J = 8.0, 1.6 Hz, 2H), 7.13 (d, J = 1.6 Hz, 2H), 6.44 (d, J = 9.2 Hz, 1H), 5.19 (br s, 1H), 3.17 (s, 3H), 1.48-1.58 (m, 4H), 1.27 (s, 6H), 1.14 (s, 6H); 1H not observed (OH or NH) |
| 124 | MS m/z 422.4 [M + H]⁺; ¹H NMR (methanol-d₄) δ: 9.11 (br s, 1H), 7.88 (br d, J = 5.8 Hz, 1H), 7.52 (d, J = 1.5 Hz, 1H), 6.94-7.09 (m, 2H), 6.42 (d, J = 1.5 Hz, 1H), 5.24-5.42 (m, 1H), 3.94 (s, 3H), 3.16 (s, 3H), 1.70 (dd, J = 12.5, 3.4 Hz, 2H), 1.62 (t, J = 12.5 Hz, 2H), 1.38 (s, 6H), 1.26 (s, 6H); 2Hs not observed (NH and OH) |
| 131 | MS m/z 458.7 [M + H]⁺; ¹H NMR (DMSO- d₆) δ: 12.60 (br s, 1H), 11.30 (br s, 1H), 9.08 (s, 1H), 8.28 (s, 1H), 7.60-8.00 (m, 3H), 7.52 (br s, 1H), 7.28-7.31 (m, 2H), 5.21 (br s, 1H), 3.15 (s, 3H), 1.35-1.55 (m, 4H), 1.24 (s, 6H), 1.00 (s, 6H) |
| 176 | MS m/z 473.3 [M + H]⁺; ¹H NMR (DMSO-d₆) δ: 9.09 (s, 1H), 8.90 (d, J = 2.0 Hz, 1H), 8.51 (d, J = 2.0 Hz, 1H), 8.38 (br s, 2H), 8.23 (s, 1H), 7.98 (d, J = 6.0 Hz, 1H), 7.34-7.36 (m, 2H), 5.21 (m, 1H), 4.11 (s, 3H), 3.17 (s, 3H), 1.60-1.70 (m, 4H), 1.33 (s, 6H), 1.15 (s, 6H) |
| 177 | MS m/z 472.3 [M + H]⁺; ¹H NMR (DMSO-d₆) δ: 9.09 (s, 1H), 8.40 (s, 1H), 8.12 (s, 1H), 8.05 (s, 1H), 7.95 (d, J = 8.8 Hz, 1H), 7.74 (s, 2H), 7.30-7.32 (m, 2H), 5.21 (m, 1H), 4.08 (s, 3H), 3.10 (s, 3H), 1.63-1.78 (m, 4H), 1.37 (s, 6H), 1.27 (s, 6H); 1H not observed (OH or NH) |
| 188 | MS m/z 462.5 [M + H]⁺; ¹H NMR (methanol-d₄) δ: 9.09 (s, 1H), 7.82-7.87 (m, 1H), 7.18 (d, J = 7.9 Hz, 1H), 7.15 (d, J = 7.6 Hz, 3H), 6.90 (d, J = 7.9 Hz, 1H), 6.00 (s, 2H), 5.29-5.44 (m, 1H), 3.19 (s, 3H), 1.84-1.96 (m, 4H), 1.56 (s, 6H), 1.44 (s, 6H); 2Hs not observed (NH and OH) |
| 352 | MS m/z 395.2 [M + H]⁺; ¹H NMR (DMSO-d₆) δ: 8.98 (s, 1H), 8.41 (br s, 1H), 8.25 (s, 1H), 7.96 (d, J = 8.0 Hz, 1H), 7.62 (d, J = 1.6 Hz, 1H), 7.54 (dd, J = 8.0, 1.6 Hz, 1H), 7.41 (s, 1H), 4.38 (br s, 1H), 1.98 (d, J = 1.6 Hz, 2H), 1.39-1.54 (m, 2H), 1.27 (s, 6H), 1.02 (s, 6H); 2Hs not observed (OH and NH) |

Example 4

Preparation of Compound 23

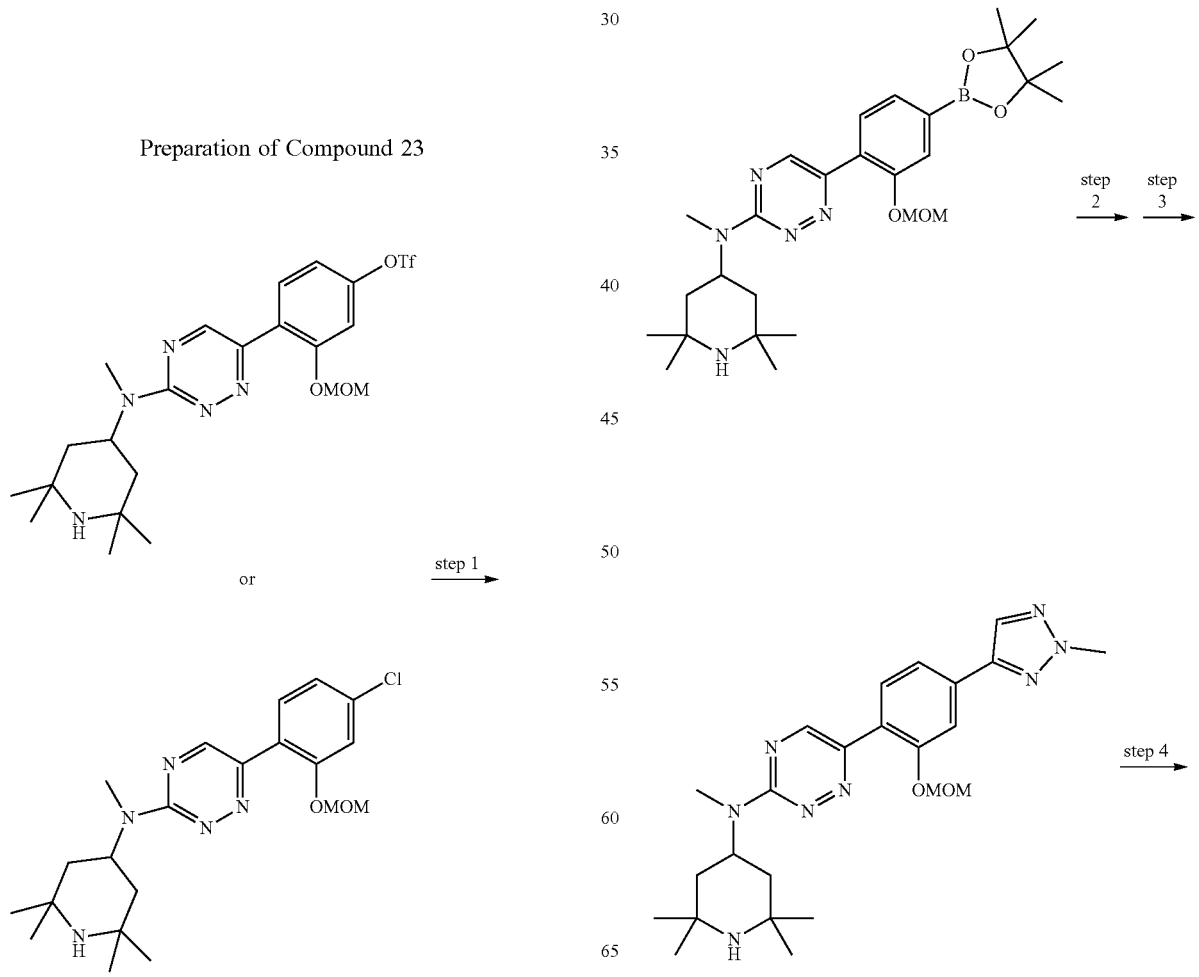

-continued

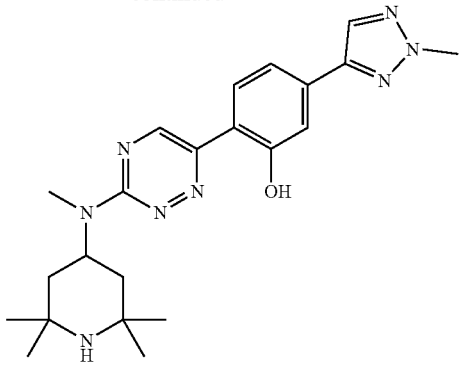

Step 1: A suspension of 3-(methoxymethoxy)-4-(3-(methyl(2,2,6,6-tetramethylpiperidin-4-yl)amino)-1,2,4-triazin-6-yl)phenyl trifluoromethanesulfonate (30 mg, 0.056 mmol, 1.0 equiv), $B_2Pin_2$ (20 mg, 0.078 mmol, 1.4 equiv), Pd(dppf)Cl$_2$ (4.6 mg, 0.0056 mmol, 0.1 equiv), and dry KOAc (16 mg, 0.168 mmol, 3.0 equiv) in dioxane (0.9 mL) was sparged with argon for 10 minutes, then heated to 90° C. under argon atmosphere for 2 h, after which complete conversion to 6-(2-(methoxymethoxy)-4-(4,4,5,5-tetramethyl-1,3,2-dioxaborolan-2-yl)phenyl)-N-methyl-N-(2,2,6,6-tetramethylpiperidin-4-yl)-1,2,4-triazin-3-amine was observed. The reaction mixture was then cooled to room temperature and used directly in the next step.

Alternatively, 6-(4-chloro-2-(methoxymethoxy)phenyl)-N-methyl-N-(2,2,6,6-tetramethylpiperidin-4-yl)-1,2,4-triazin-3-amine could be used as a starting material for step 1. XPhos Pd G3 (10 mol %) could be used as catalyst in this case, otherwise following the above procedure.

Step 2: To the mixture from Step 1 was added aq. K$_2$CO$_3$ (85 μL, 2M, 3.0 equiv), 4-bromo-2-methyl-2H-1,2,3-triazole (13.6 mg, 0.084 mmol, 1.5 equiv), and Pd(dppf)Cl$_2$ (4.6 mg, 0.0056 mmol, 0.1 equiv). The mixture was then heated to 95° C. under argon for 12 h. The reaction was cooled to room temperature, filtered over Celite (washed with 10% MeOH/CH$_2$Cl$_2$), concentrated, and purified by column chromatography eluting with MeOH/CH$_2$Cl$_2$ (5-15% MeOH) to afford 6-(2-(methoxymethoxy)-4-(2-methyl-2H-1,2,3-triazol-4-yl)phenyl)-N-methyl-N-(2,2,6,6-tetramethylpiperidin-4-yl)-1,2,4-triazin-3-amine which was used in the next step without further purification.

Step 3: 6-(2-(Methoxymethoxy)-4-(2-methyl-2H-1,2,3-triazol-4-yl)phenyl)-N-methyl-N-(2,2,6,6-tetramethylpiperidin-4-yl)-1,2,4-triazin-3-amine from Step 2 was dissolved in MeOH (0.5 mL), then HCl (0.5 mL, 4M in dioxane) was added. The solution was stirred at room temperature for 30 minutes. The reaction mixture was concentrated and purified by column chromatography eluting with MeOH/CH$_2$Cl$_2$ (10-30% MeOH) to afford 2-(3-(methyl(2,2,6,6-tetramethylpiperidin-4-yl)amino)-1,2,4-triazin-6-yl)-5-(2-methyl-2H-1,2,3-triazol-4-yl)phenol (11.5 mg, 50% over 3 steps).

MS m/z 423.3 [M+H]$^+$ $^1$H NMR (methanol-d) δ: 9.12 (s, 1H), 8.04 (s, 1H), 7.87-7.96 (m, 1H), 7.42-7.51 (m, 2H), 5.36-5.45 (m, 1H), 4.25 (s, 3H), 3.23 (s, 3H), 1.90-2.07 (m, 4H), 1.65 (s, 6H), 1.53 (s, 6H); 2Hs not observed (NH and OH).

Using the procedure described for Example 4, additional compounds described herein may be prepared by substituting the appropriate starting material, suitable reagents and reaction conditions, obtaining compounds such as those selected from:

| Cpd | Data |
|---|---|
| 2 | MS m/z 450.2 [M + H]$^+$; $^1$H NMR (DMSO-d$_6$) δ: 9.07 (s, 1H), 8.87 (d, J = 1.0 Hz, 1H), 8.35 (s, 1H), 7.99 (d, J = 8.3 Hz, 1H), 7.84 (d, J = 1.7 Hz, 1H), 7.75 (dd, J = 8.3, 1.7 Hz, 1H), 7.48 (d, J = 1.0 Hz, 1H), 5.13-5.30 (m, 1H), 3.99 (s, 3H), 3.09 (s, 3H), 1.59 (d, J = 7.8 Hz, 4H), 1.29 (s, 6H), 1.17 (s, 6H); 1H not observed (NH or OH). |
| 3 | MS m/z 449.2 [M + H]$^+$; $^1$H NMR (DMSO-d$_6$) δ: 9.07 (s, 1H), 8.33 (s, 1H), 8.25 (d, J = 5.4 Hz, 1H), 7.97 (d, J = 8.1 Hz, 1H), 7.33-7.40 (m, 2H), 7.30 (dd, J = 5.4, 1.5 Hz, 1H), 7.09 (d, J = 0.9 Hz, 1H), 5.11-5.32 (m, 1H), 3.90 (s, 4H), 3.10 (s, 3H), 1.60-1.79 (m, 3H), 1.35 (s, 6H), 1.25 (s, 6H); 1H not observed (NH or OH). |
| 4 | MS m/z 409.1 [M + H]$^+$; $^1$H NMR (DMSO-d$_6$) δ: 11.33 (br. s., 2H), 9.06 (s, 1H), 8.37 (s, 1H), 7.94 (d, J = 8.2 Hz, 1H), 7.50 (d, J = 1.6 Hz, 1H), 7.45 (dd, J = 8.2, 1.6 Hz, 1H), 5.05-5.34 (m, 1H), 3.08 (s, 3H), 1.54 (dd, J = 12.0, 3.7 Hz, 2H), 1.48 (t, J = 12.0 Hz, 2H), 1.24 (s, 6H), 1.11 (s, 6H); 1H not observed (NH or OH). |
| 5 | MS m/z 435.2 [M + H]$^+$; $^1$H NMR (DMSO-d$_6$) δ: 11.65 (br. s., 1H), 11.12 (br. s., 1H), 9.06 (s, 1H), 8.80 (br. s., 1H), 7.94 (d, J = 8.3 Hz, 1H), 7.47 (d, J = 6.8 Hz, 1H), 7.28 (dd, J = 8.3, 1.7 Hz, 1H), 7.25 (d, J = 1.6 Hz, 1H), 6.56 (d, J = 1.6 Hz, 1H), 6.48 (dd, J = 6.8, 1.6 Hz, 1H), 5.06-5.35 (m, 1H), 3.34 (s, 3H), 1.75-2.02 (m, 4H), 1.48 (s, 6H), 1.40 (s, 6H). |
| 6 | MS m/z 422.2 [M + H]$^+$; $^1$H NMR (DMSO-d$_6$) δ: 9.06 (s, 1H), 8.38 (br. s., 1H), 7.86 (d, J = 8.2 Hz, 1H), 7.82 (s, 1H), 7.10 (d, J = 1.6 Hz, 1H), 7.07 (dd, J = 8.2, 1.6 Hz, 1H), 5.07-5.28 (m, 1H), 3.10 (s, 3H), 2.41 (s, 3H), 1.85 (t, J = 12.5 Hz, 2H), 1.69 (dd, J = 12.5, 3.5 Hz, 2H), 1.41 (s, 6H), 1.33 (s, 6H); 2Hs not observed (NH and OH). |
| 7 | MS m/z 409.3 [M + H]$^+$; $^1$H NMR (DMSO-d$_6$) δ: 9.02 (s, 1H), 8.25 (s, 1H), 8.00 (d, J = 8.2 Hz, 1H), 7.60 (s, 1H), 7.56 (d, J = 8.2 Hz, 1H), 7.41 (s, 1H), 5.09-5.37 (m, 1H), 3.08 (s, 3H), 1.41-1.61 (m, 4H), 1.24 (s, 6H), 1.11 (s, 6H); 2Hs not observed (NH and OH). |
| 12 | MS m/z 426.4 [M + H]$^+$; $^1$H NMR (methanol-d$_4$) δ: 9.09 (s, 1H), 7.97 (d, J = 2.0 Hz, 1H), 7.84 (d, J = 8.5 Hz, 1H), 7.22-7.20 (m, 2H), 5.36 (dt, J = 17.0, 9.0 Hz, 1H), 3.20 (s, 3H), 1.96 (d, J = 8.0 Hz, 4H), 1.61 (s, 6H), 1.50 (s, 6H); 3Hs not observed (2NHs and OH). |
| 18 | MS m/z 440.3 [M + H]$^+$; $^1$H NMR (methanol-d$_4$) δ: 9.10 (s, 1H), 7.93 (d, J = 2.3 Hz, 1H), 7.85 (d, J = 8.9 Hz, 1H), 7.14-7.23 (m, 2H), 5.32-5.39 (m, 1H), 3.83 (s, 3H), 3.20 (s, 3H), 1.91-2.00 (m, 4H), 1.61 (s, 6H), 1.50 (s, 6H); 2H not observed (NH and OH). |
| 53 | MS m/z 424.5 [M + H]$^+$; $^1$H NMR (DMSO-d$_6$) δ: 8.97 (s, 1H), 7.82 (d, J = 8.09 Hz, 1H), 7.52 (dd, J = 5.04, 0.92 Hz, 1H), 7.47 (dd, J = 3.51, 0.91 Hz, 1H), 7.22-7.17 (m, 2H), 7.09-7.07 (m, 1H), 5.21-5.08 (m, 1H), 3.03 (s, 3H), 2.00-1.66 (m, 4H), 1.38, (s, 12H); 2Hs not observed (NH and OH) |
| 54 | MS m/z 438.5 [M + H]$^+$; $^1$H NMR (DMSO-d$_6$) δ: 9.05 (s, 1H), 7.89 (d, J = 8.09 Hz, 1H), 7.37 (s, 1H), 7.25 (dd, J = 8.24, 1.53 Hz, 1H), 7.22 (s, 1H), 7.17 (s, 1H), 5.28-5.17 (m, 1H), 3.12 (s, 3H), 2.27 (s, 3H), 2.04-1.74 (m, 4H), 1.38, (s, 12H); 2Hs not observed (NH and OH). |
| 56 | MS m/z 449.2 [M + H]$^+$; $^1$H NMR (DMSO-d$_6$) δ: 9.06 (s, 1H), 7.94 (d, J = 8.0 Hz, 1H), 7.82 (d, J = 6.8 Hz, 1H), 7.28-7.31 (m, 2H), 6.64 (d, J = 2.0 Hz, 1H), 6.55 (dd, J = 7.2, 2.0 Hz, 1H), 5.23 (br s, 1H), 3.92 (s, 3H), 3.11 (s, 3H), 1.83-1.91 (m, 2H), 1.68-1.73 (m, 2H), 1.43 (s, 6H), 1.37 (s, 6H); 2Hs not observed (OH and NH) |
| 57 | MS m/z 442.5 [M + H]+, 444.5 [M + 2 + H]$^+$; $^1$H NMR (methanol-d$_4$) δ: 9.09 (s, 1H), 8.29 (s, 1H), 7.92 (d, J = 11.0 Hz, 1H), 7.55-7.64 (m, 1H), 7.27-7.40 (m, 1H), 5.25-5.42 (m, 1H), 3.17 (s, 3H), 1.70 (ddd, J = 8.7, 5.3, 3.8 Hz, 2H), 1.60 (dd, J = 14.6, 12.5 Hz, 2H), 1.40 (s, 6H), 1.27 (s, 6H); 3Hs not observed (2 NHs and OH) |
| 58 | MS m/z 425.5 [M + H]$^+$; $^1$H NMR (methanol-d$_4$) δ: 9.14 (s, 1H), 7.98 (d, J = 8.9 Hz, 1H), 7.95-8.00 (m, 1H), 7.92 (d, J = 3.4 Hz, 1H), 7.67 (d, J = 3.2 Hz, 1H), 7.57-7.61 (m, 2H), 5.35-5.46 (m, 1H), 3.25 (s, 3H), 2.01 (s, 4H), 1.66 (s, 6H), 1.55 (s, 6H); 1H not observed (NH or OH) |
| 62 | MS m/z 423.6 [M + H]$^+$; $^1$H NMR (DMSO-d$_6$) δ: 9.04 (s, 1H), 8.55 (s, 1H), 7.92 (d, J = 8.2 Hz, 1H), 7.66 (d, J = 1.5 Hz, 1H), 7.59 (dd, J = 7.9, 1.5 Hz, 1H), 5.18-5.29 (m, 1H), 3.94 (s, 3H), 3.13 (s, 3H), 1.94-2.06 (m, 2H), 1.75-1.87 (m, 2H), 1.52 (s, 6H), 1.48 (s, 6H); 2Hs not observed (OH and NH) |

| Cpd | Data |
|---|---|
| 64 | MS m/z 439.5 [M + H]⁺; ¹H NMR (DMSO-d₆) δ: 8.78 (s, 1H), 8.20 (s, 1H), 7.82 (d, J = 7.93 Hz, 1H), 7.40 (s, 1H), 7.31 (d, J = 8.01, 1.60 Hz, 1H), 5.31-5.15 (m, 1H), 3.94 (s, 3H), 3.11 (s, 3H), 2.09-1.7 (m, 4H), 1.46 (s, 12H); 2Hs not observed (NH and OH) |
| 65 | MS m/z 426.5 [M + H]⁺; ¹H NMR (methanol-d₄) δ: 9.15 (s, 1H), 8.81 (s, 1H), 8.02 (d, J = 7.9 Hz, 1H), 7.65-7.70 (m, 2H), 5.34-5.47 (m, 1H), 3.25 (s, 3H), 1.96-2.03 (m, 4H), 1.64 (s, 6H), 1.53 (s, 6H); 2Hs not observed (NH and OH). |
| 66 | MS m/z 440.5 [M + H]⁺; ¹H NMR (chloroform-d) δ: 9.12 (s, 1H), 8.00 (d, J = 8.1 Hz, 1H), 7.96-8.04 (m, 1H), 7.57-7.62 (m, 2H), 5.29-5.46 (m, 1H), 3.22 (s, 3H), 2.69 (s, 3H), 1.93-2.01 (m, 4H), 1.61 (s, 6H), 1.50 (s, 6H); 1H not observed (NH or OH) |
| 71 | MS m/z 419.1 [M + H]⁺; ¹H NMR (DMSO-d₆) δ: 9.07 (s, 1H), 8.69 (d, J = 4.4 Hz, 1H), 8.38 (br s, 1H), 7.94-7.98 (m, 2H), 7.87-7.92 (m, 1H), 7.78 (d, J = 1.6 Hz, 1H), 7.66 (dd, J = 6.4, 1.6 Hz, 1H), 7.36-7.40 (m, 1H), 5.23 (br s, 1H), 3.10 (s, 3H), 1.75-1.82 (m, 2H), 1.64-1.68 (m, 2H), 1.38 (s, 6H), 1.29 (s, 6H); 1H not observed (OH or NH) |
| 75 | MS m/z 422.5 [M + H]⁺; ¹H NMR (methanol-d₄) δ: 9.10 (s, 1H), 7.84 (d, J = 8.9 Hz, 1H), 7.69 (s, 1H), 7.54 (d, J = 1.1 Hz, 1H), 7.34-7.38 (m, 2H), 5.32-5.46 (m, 1H), 3.80 (s, 3H), 3.21 (s, 3H), 1.87-1.98 (m, 4H), 1.59 (s, 6H), 1.47 (s, 6H); 2Hs not observed (NH and OH) |
| 76 | MS m/z 422.4 [M + H]⁺; ¹H NMR (methanol-d₄) δ: 9.00 (s, 1H), 7.75 (d, J = 7.78 Hz, 1H), 7.52 (d, J = 2.29 Hz, 1H), 7.31 (s, 1H), 7.29 (s, 1H), 6.55 (d, J = 2.29 Hz, 1H), 5.37-5.18 (m, 1H), 3.84 (s, 3H), 3.11 (s, 3H), 1.91-1.83 (m, 4H), 1.53 (s, 6H), 1.42 (s, 6H); 2Hs not observed (NH and OH) |
| 80 | MS m/z 459.4 [M + H]⁺; ¹H NMR (methanol-d₄) δ: 9.15-9.18 (m, 1H), 9.10 (br d, J = 13.3 Hz, 2H), 8.10-8.15 (m, 1H), 7.96 (d, J = 9.0 Hz, 1H), 7.86 (s, 1H), 7.69-7.72 (m, 1H), 7.63 (d, J = 7.0 Hz, 1H), 5.35-5.46 (m, 1H), 3.25 (s, 3H), 1.99-2.09 (m, 4H), 1.66 (s, 6H), 1.56 (s, 6H); 2Hs not observed (NH and OH) |
| 81 | MS m/z 424.6 [M + H]⁺; ¹H NMR (methanol-d₄) δ 9.13 (s, 1H), 7.98-8.12 (m, 1H), 7.55-7.72 (m, 2H), 5.34-5.47 (m, 1H), 3.24 (s, 3H), 2.66 (s, 3H), 1.86-2.01 (m, 4H), 1.62 (s, 6H), 1.51 (s, 6H); 2Hs not observed (OH and NH) |
| 83 | MS m/z 420.1 [M + H]⁺; ¹H NMR (DMSO-d₆) δ: 9.27 (d, J = 1.2 Hz, 1H), 9.07 (s, 1H), 8.74 (dd, J = 2.4, 1.6 Hz, 1H), 8.63 (d, J = 2.4 Hz, 1H), 8.01 (d, J = 8.0 Hz, 1H), 7.78 (d, J = 1.6 Hz, 1H), 7.74 (dd, J = 8.4, 1.6 Hz, 1H), 5.21 (br s, 1H), 3.09 (s, 3H), 1.45-1.58 (m, 4H), 1.25 (s, 6H), 1.06 (s, 6H); 2Hs not observed (OH and NH) |
| 84 | MS m/z 420.3 [M + H]⁺; ¹H NMR (DMSO-d₆) δ: 9.23 (dd, J = 4.8, 1.2 Hz, 1H), 9.09 (s, 1H), 8.36 (br s, 1H), 8.23 (d, J = 8.0 Hz, 1H), 8.03 (d, J = 8.0 Hz, 1H), 7.86 (d, J = 8.4 Hz, 1H), 7.70-7.82 (m, 1H), 7.72 (dd, J = 8.4, 1.6 Hz, 1H), 5.23 (br s, 1H), 3.07 (s, 3H), 1.78-1.85 (m, 2H), 1.67-1.71 (m, 2H), 1.40 (s, 6H), 1.24 (s, 6H); 1H not observed (OH or NH) |
| 85 | MS m/z 420.2 [M + H]⁺; ¹H NMR (DMSO-d₆) δ: 9.05 (s, 1H), 8.93 (d, J = 4.8 Hz, 2H), 8.06 (s, 1H), 7.99 (s, 2H), 7.47 (t, J = 4.8 Hz, 1H), 5.23 (br s, 1H), 3.08 (s, 3H), 1.44-1.56 (m, 4H), 1.25 (s, 6H), 1.11 (s, 6H); 2Hs not observed (OH and NH) |
| 88 | MS m/z 451.6 [M + H]⁺; ¹H NMR (methanol-d₄) δ: 9.08-9.24 (m, 1H), 8.95 (s, 1H), 8.00 (s, 1H), 7.78-7.92 (m, 2H), 5.27-5.42 (m, 1H), 3.37 (s, 3H), 3.16 (s, 3H), 1.53-1.76 (m, 4H), 1.36 (s, 6H), 1.24 (s, 6H); 2Hs not observed (NH and OH) |
| 91 | MS m/z 409.5 [M + H]⁺; ¹H NMR (methanol-d₄) δ: 9.09 (s, 1H), 8.29 (s, 1H), 7.90 (d, J = 7.2 Hz, 1H), 7.59 (s, 1H), 7.29-7.41 (m, 2H), 5.29-5.40 (m, 1H), 3.18 (s, 3H), 1.64-1.80 (m, 4H), 1.42 (s, 6H), 1.30 (s, 6H); 2Hs not observed (NH and OH) |
| 92 | MS m/z 459.6 [M + H]+; ¹H NMR (methanol-d₄) δ: 9.17 (s, 1H), 8.22 (s, 1H), 8.11 (d, J = 9.6 Hz, 1H), 8.03 (d, J = 7.9 Hz, 1H), 7.79-7.85 (m, 2H), 7.69-7.74 (m, 2H), 5.41 (br s, 1H), 3.25 (s, 3H), 1.96-2.03 (m, 4H), 1.65 (s, 6H), 1.53 (s, 6H); 2Hs not observed (NH and OH) |
| 97 | MS m/z 458.6 [M + H]⁺; ¹H NMR (DMSO-d₆) δ 9.37 (br d, J = 10.38 Hz, 1H), 9.09 (s, 1H), 8.29 (br d, J = 10.83 Hz, 1H), 8.15 (s, 1H), 8.05 (s, 1H), 7.94 (d, J = 7.93 Hz, 1H), 7.62-7.70 (m, 2H), 7.28-7.33 (m, 2H), 5.23 (br s, 1H), 3.12 (s, 3H), 2.06 (br t, J = 12.82 Hz, 2H), 1.74-1.82 (m, 2H), 1.52 (s, 6H), 1.50 (s, 6H); 1H not observed (NH or OH) |
| 98 | MS m/z 437.3 [M + H]⁺; ¹H NMR (DMSO-d₆) δ: 9.08 (s, 1H), 8.68-8.73 (m, 1H), 7.91-8.00 (m, 2H), 7.80 (s, 1H), 7.70 (d, J = 7.6 Hz, 1H), 7.32 (br s, 1H), 5.21 (br s, 1H), 3.08 (s, 3H), 1.44-1.55 (m, 4H), 1.24 (s, 6H), 1.03 (s, 6H); 2Hs not observed (OH and NH) |
| 101 | MS m/z 448.6 [M + H]⁺; ¹H NMR (methanol-d₄) δ: 9.09-9.11 (m, 1H), 8.09-8.13 (m, 1H), 7.86 (s, 1H), 7.82 (d, J = 8.2 Hz, 1H), 7.19 (dd, J = 6.6, 1.5 Hz, 1H), 7.17 (d, J = 1.7 Hz, 1H), 5.32-5.43 (m, 1H), 3.72 (tt, J = 7.3, 3.8 Hz, 1H), 3.22 (s, 3H), 1.97-2.00 (m, 4H), 1.63 (s, 6H), 1.52 (s, 6H), 1.14-1.18 (m, 2H), 1.07-1.13 (m, 2H); 2Hs not observed (NH and OH) |
| 102 | MS m/z 420.2 [M + H]⁺; ¹H NMR (DMSO-d₆) δ: 9.27 (s, 1H), 9.07 (s, 1H), 8.87 (d, J = 5.2 Hz, 1H), 8.36 (br s, 1H), 8.08 (d, J = 5.2 Hz, 1H), 8.02 (d, J = 8.4 Hz, 1H), 7.89 (s, 1H), 7.78 (d, J = 8.0 Hz, 1H), 5.23 (br s, 1H), 3.17 (s, 3H), 1.63-1.75 (m, 4H), 1.35 (s, 6H), 1.25 (s, 6H); 1H not observed (OH or NH) |
| 106 | MS m/z 410.3 [M + H]⁺; ¹H NMR (methanol-d₄) δ: 9.14 (s, 1H), 9.06 (s, 1H), 8.06 (d, J = 7.3 Hz, 1H), 7.63-7.75 (m, 2H), 5.31-5.48 (m, 1H), 3.22 (s, 3H), 1.74-1.96 (m, 4H), 1.54 (s, 6H), 1.42 (s, 6H); 2Hs not observed (OH and NH) |
| 107 | MS m/z 395.3 [M + H]⁺; ¹H NMR (methanol-d₄) δ: 9.27 (s, 1H), 8.82 (d, J = 12.0 Hz, 1H), 8.10 (d, J = 12.0 Hz, 1H), 7.91 (d, J = 8.0 Hz, 1H), 7.77 (s, 1H), 7.51 (s, 1H), 7.44 (dd, J = 8.0, 1.5 Hz, 1H), 6.72 (d, J = 2.0 Hz, 1H), 5.67-5.61 (m, 1H), 2.37 (dd, J = 13.5, 4.0 Hz, 2H), 1.82 (t, J = 12.0 Hz, 2H), 1.51 (s, 6H), 1.47 (s, 6H) |
| 108 | MS m/z 409.4 [M + H]⁺; ¹H NMR (DMSO-d₆) δ: 9.27 (s, 1H), 9.02 (d, J = 11.5 Hz, 1H), 8.25 (d, J = 11.5 Hz, 1H), 7.90 (d, J = 8.0 Hz, 1H), 7.77 (d, J = 2.0, 1H), 7.50 (d, J = 1.5 Hz, 1H), 7.41 (dd, J = 8.0, 1.5 Hz, 1H), 6.70 (d, J = 2.0 Hz, 1H), 5.65-5.60 (m, 1H), 3.90 (s, 3H), 2.35 (dd, J = 13.0, 3.5 Hz, 2H), 1.84 (t, J = 12.5 Hz, 2H), 1.52 (s, 6H), 1.49 (s, 6H) |
| 111 | MS m/z 408.5 [M + H]⁺; ¹H NMR (methanol-d₄) δ: 9.13 (s, 1H), 7.91 (d, J = 8.09 Hz, 1H), 7.71 (s, 1H), 7.43 (s, 2H), 6.73 (s, 1H), 5.42-5.35 (m, 1H), 3.23 (s, 3H), 2.04-1.97 (m, 4H), 1.66 (s, 6H), 1.54 (s, 6H); 3Hs not observed (2 NHs and OH) |
| 112 | MS m/z 438.3 [M + H]⁺; ¹H NMR (methanol-d₄) δ: 9.12-9.13 (m, 1H), 8.81 (s, 2H), 8.00-8.03 (m, 2H), 7.95 (d, J = 8.5 Hz, 1H), 5.32-5.43 (m, 1H), 3.21 (s, 3H), 1.77-1.88 (m, 4H), 1.50 (s, 6H), 1.38 (s, 6H); 2Hs not observed (NH and OH) |
| 123 | MS m/z 454.4 [M + H]⁺; ¹H NMR (methanol-d₄) δ: 9.15 (s, 1H), 8.22 (d, J = 8.9 Hz, 1H), 8.02 (d, J = 7.5 Hz, 1H), 7.84 (d, J = 9.0 Hz, 1H), 7.76 (s, 1H), 7.71 (br d, J = 8.2 Hz, 1H), 5.32-5.45 (m, 1H), 3.22 (s, 3H), 1.85-1.92 (m, 4H), 1.55 (s, 6H), 1.43 (s, 6H); 2Hs not observed (NH and OH) |
| 128 | MS m/z 434.4 [M + H]⁺; ¹H NMR (methanol-d₄) δ: 9.14 (s, 1H), 8.73 (s, 2H), 7.98-8.01 (m, 2H), 7.97 (s, 1H), 5.34-5.46 (m, 1H), 3.23 (s, 3H), 2.40 (s, 3H), 1.96-2.00 (m, 4H), 1.62 (s, 6H), 1.51 (s, 6H); 2Hs not observed (NH and OH) |
| 129 | MS m/z 434.3 [M + H]⁺; ¹H NMR (methanol-d₄) δ: 9.17 (s, 1H), 8.69 (d, J = 4.9 Hz, 1H), 8.01-8.07 (m, 2H), 7.98 (s, 1H), 7.28-7.31 (m, 1H), 5.36-5.45 (m, 1H), 3.24 (s, 3H), 2.62 (s, 3H), 1.99-2.05 (m, 4H), 1.66 (s, 6H), 1.55 (s, 6H); 2Hs not observed (NH and OH) |
| 130 | MS m/z 454.3 [M + H]⁺; ¹H NMR (methanol-d₄) δ: 9.15 (s, 1H), 8.70 (d, J = 5.0 Hz, 1H), 8.01 (d, J = 9.6 Hz, 1H), 7.97 (d, J = 5.2 Hz, 1H), 7.78-7.85 (m, 2H), 5.34-5.46 (m, 1H), 3.24 (s, 3H), 1.92-1.98 (m, 4H), 1.60 (s, 6H), 1.49 (s, 6H); 2Hs not observed (NH and OH) |
| 132 | MS m/z 459.3 [M + H]⁺; ¹H NMR (DMSO-d₆) δ: 9.10 (s, 1H), 8.85 (d, J = 2.0 Hz, 1H), 8.49 (d, J = 2.0 Hz, 1H), 8.39 (br s, 1H), 8.22 (s, 1H), 7.97 (d, J = 8.0 Hz, 1H), 7.33-7.36 (m, 2H), 5.23 (br s, 1H), 3.11 (s, 3H), 1.74-1.82 (m, 2H), 1.64-1.67 (m, 2H), 1.38 (s, 6H), 1.29 (s, 6H); 2Hs not observed (OH and NH) |
| 134 | MS m/z 436.3 [M + H]⁺; ¹H NMR (methanol-d₄) δ: 9.19-9.38 (m, 1H), 8.05 (d, J = 10.1 Hz, 1H), 7.82 (d, J = 7.9 Hz, 1H), 7.32 (s, 1H), 7.20 (dd, J = 7.9, 1.2 Hz, 1H), 7.07 (d, J = 10.1 Hz, 1H), 5.28-5.38 (m, 1H), 3.16 (s, 3H), 1.68 (br dd, J = 12.8, 2.2 Hz, 2H), 1.61 (t, J = 12.8 Hz, 2H), 1.37 (s, 6H), 1.25 (s, 6H); 3Hs not observed (NH and 2 OHs) |

| Cpd | Data |
|---|---|
| 136 | MS m/z 459.1 [M + H]⁺; ¹H NMR (DMSO-$d_6$) δ: 13.40 (br s, 1H), 11.30 (br s, 1H), 9.07 (s, 1H), 8.37 (s, 1H), 8.11 (d, J = 8.8 Hz, 1H), 7.97-8.00 (m, 2H), 7.82 (d, J = 1.2 Hz, 1H), 7.72 (d, J = 8.0 Hz, 1H), 5.19-5.22 (m, 1H), 3.08 (s, 3H), 1.44-1.55 (m, 4H), 1.25 (s, 6H), 1.11 (s, 6H); 1H not observed (OH or NH) |
| 141 | MS m/z 487.5 [M + H]⁺; ¹H NMR (methanol-$d_4$) δ: 9.14 (s, 1H), 7.97 (d, J = 8.4 Hz, 1H), 7.92 (s, 1H), 7.62-7.67 (m, 2H), 7.57 (s, 1H), 5.34-5.46 (m, 1H), 3.24 (s, 3H), 2.68 (s, 3H), 2.50 (s, 3H), 1.98-2.05 (m, 4H), 1.66 (s, 6H), 1.56 (s, 6H); 2Hs not observed (NH and OH) |
| 142 | MS m/z 473.5 [M + H]⁺; ¹H NMR (methanol-$d_4$) δ: 9.16 (s, 1H), 7.93-8.04 (m, 3H), 7.72 (d, J = 10.2 Hz, 1H), 7.65-7.70 (m, 2H), 5.34-5.47 (m, 1H), 3.25 (s, 3H), 2.51 (s, 3H), 2.01 (br d, J = 7.8 Hz, 4H), 1.65 (s, 6H), 1.55 (s, 6H); 2Hs not observed (NH and OH) |
| 143 | MS m/z 424.6 [M + H]⁺; ¹H NMR (DMSO-$d_6$) δ: 9.01-9.14 (m, 2H), 7.99-8.11 (m, 2H), 7.72 (d, J = 1.5 Hz, 1H), 7.65 (dd, J = 8.2, 1.5 Hz, 1H), 5.18-5.30 (m, 1H), 4.45 (s, 3H), 3.14 (s, 3H), 2.01 (t, J = 13.0 Hz, 2H), 1.78-1.87 (m, 2H), 1.52 (s, 6H), 1.48 (s, 6H) |
| 144 | MS m/z 451.4 [M + H]⁺; ¹H NMR (methanol-$d_4$) δ: 9.16 (s, 1H), 8.04 (d, J = 8.2 Hz, 2H), 7.74 (d, J = 1.5 Hz, 1H), 7.70 (dd, J = 8.2, 1.5 Hz, 1H), 5.36-5.46 (m, 1H), 4.23 (s, 3H), 3.25 (s, 3H), 1.94-2.08 (m, 4H), 1.65 (s, 6H), 1.54 (s, 6H); 2Hs not observed (NH and OH) |
| 145 | MS m/z 459.0 [M + H]⁺; ¹H NMR (DMSO-$d_6$) δ: 9.09 (s, 1H), 8.80 (s, 1H), 8.10 (d, J = 1.6 Hz, 1H), 7.97 (d, J = 8.0 Hz, 1H), 7.89 (d, J = 8.0 Hz, 1H), 7.73 (dd, J = 8.4, 1.6 Hz, 1H), 7.33-7.37 (m, 2H), 5.20 (br s, 1H), 3.09 (s, 3H), 1.44-1.56 (m, 4H), 1.24 (s, 6H), 1.09 (s, 6H); 2Hs not observed (OH and NH) |
| 146 | MS m/z 450.5 [M + H]⁺; ¹H NMR (DMSO-$d_6$) δ: 9.20-9.27 (m, 1H), 9.07 (s, 1H), 8.58 (s, 1H), 8.14-8.22 (m, 1H), 7.95 (d, J = 8.2 Hz, 1H), 7.73 (d, J = 1.8 Hz, 1H), 7.63 (dd, J = 8.2, 1.8 Hz, 1H), 6.93 (s, 1H), 5.18-5.30 (m, 1H), 3.45 (s, 3H), 3.13 (s, 3H), 2.04 (t, J = 12.8 Hz, 2H), 1.79-1.84 (m, 2H), 1.52 (s, 6H), 1.49 (s, 6H) |
| 147 | MS m/z 450.6 [M + H]⁺; ¹H NMR (DMSO-$d_6$) δ: 9.17-9.27 (m, 1H), 9.10 (s, 1H), 8.32 (d, J = 2.4 Hz, 1H), 8.12-8.21 (m, 1H), 8.00 (d, J = 8.2 Hz, 1H), 7.43 (dd, J = 8.1, 1.7 Hz, 1H), 7.39 (d, J = 1.5 Hz, 1H), 7.18 (d, J = 2.1 Hz, 1H), 5.18-5.30 (m, 1H), 3.70 (s, 3H), 3.13 (s, 3H), 2.04 (t, J = 12.8 Hz, 2H), 1.78-1.84 (m, 2H), 1.52 (s, 6H), 1.49 (s, 6H) |
| 152 | MS m/z 459.4 [M + H]⁺; ¹H NMR (DMSO-$d_6$) δ: 9.16 (d, J = 7.6 Hz, 1H), 9.12 (s, 1H), 8.90-8.98 (m, 1H), 8.28 (s, 1H), 8.27 (s, 1H), 8.02 (d, J = 8.2 Hz, 1H), 7.90-7.98 (m, 1H), 7.52 (d, J = 7.6 Hz, 1H), 7.46 (d, J = 8.2 Hz, 1H), 7.42 (s, 1H), 5.17-5.30 (m, 1H), 3.14 (s, 3H), 1.95-2.05 (m, 2H), 1.80-1.89 (m, 2H), 1.52 (s, 6H), 1.47 (s, 6H) |
| 155 | MS m/z 460.5 [M + H]⁺; ¹H NMR (DMSO-$d_6$) δ: 9.40 (d, J = 7.0 Hz, 1H), 9.09-9.15 (m, 2H), 8.53 (s, 1H), 8.03-8.12 (m, 2H), 7.80 (d, J = 7.3 Hz, 1H), 7.56 (d, J = 8.2 Hz, 1H), 7.52 (s, 1H), 5.19-5.30 (m, 1H), 3.14 (s, 3H), 2.03 (t, J = 13.0 Hz, 2H), 1.83 (d, J = 12.5 Hz, 2H), 1.53 (s, 6H), 1.49 (s, 6H) |
| 156 | MS m/z 426.3 [M + H]⁺; ¹H NMR (methanol-$d_4$) δ: 9.10 (s, 1H), 7.92 (d, J = 8.00 Hz, 1H), 7.68 (d, J = 4.00 Hz, 1H), 7.44 (s, 2H), 5.44-5.34, (m, 1H), 3.23 (s, 3H), 2.01 (d, J = 7.5 Hz, 4H), 1.65 (s, 6H), 1.54, (s, 6H); 3Hs not observed (2 NHs and OH) |
| 158 | MS m/z 459.5 [M + H]⁺; ¹H NMR (DMSO-$d_6$) δ: 12.16 (s, 1H), 9.07 (s, 1H), 8.86 (s, 1H), 8.38 (s, 1H), 7.97-7.99 (m, 1H), 7.92-7.93 (m, 1H), 7.80 (d, J = 1.2 Hz, 1H), 7.71-7.73 (m, 1H), 6.69 (d, J = 3.2 Hz, 1H), 5.21 (br s, 1H), 3.13 (s, 3H), 1.54-1.60 (m, 4H), 1.33 (s, 6H), 1.21 (s, 6H); 1H not observed (OH or NH) |
| 163 | MS m/z 473.5 [M + H]⁺; ¹H NMR (DMSO-$d_6$) δ: 9.65 (s, 1H), 9.11 (s, 1H), 8.41 (d, J = 8.54 Hz, 1H), 8.20 (d, J = 8.54 Hz, 1H), 8.03 (d, J = 8.09 Hz, 1H), 7.93 (s, 1H), 7.80 (d, J = 7.93 Hz, 1H), 5.26 (br s, 1H), 4.08 (s, 3H), 3.13 (s, 3H), 2.15 (t, J = 12.82 Hz, 2H), 1.75 (d, J = 12.36 Hz, 2H) 1.54 (s, 12H); 2Hs not observed (NH and OH) |
| 164 | MS m/z 473.3 [M + H]⁺; ¹H NMR (DMSO-$d_6$) δ: 9.09 (s, 1H), 8.48 (s, 1H), 8.14 (d, J = 8.09 Hz, 1H), 7.98 (d, J = 8.39 Hz, 1H), 7.92 (d, J = 8.39 Hz, 1H), 7.84-7.89 (m, 1H), 7.72 (d, J = 8.24 Hz, 1H), 5.26 (br s, 1H) 3.91 (s, 3 H), 3.13 (s, 3H), 2.11 (t, J = 12.82 Hz, 2H), 1.77 (d, J = 11.60 Hz, 2H), 1.54 (s, 6H), 1.53 (s, 6H); 2Hs not observed (NH and OH) |
| 168 | MS m/z 464.4 [M + H]⁺; ¹H NMR (methanol-$d_4$) δ: 9.10-9.13 (m, 1H), 7.87 (d, J = 7.9 Hz, 1H), 7.18-7.26 (m, 2H), 6.58 (s, 1H), 5.34-5.44 (m, 1H), 3.23 (s, 3H), 2.21 (s, 3H), 1.98-2.05 (m, 4H), 1.65 (s, 6H), 1.56 (s, 6H); 5Hs not observed (3 NHs and 2 OHs) |
| 169 | MS m/z 488.5 [M + H]⁺; ¹H NMR (methanol-$d_4$) δ: 9.13 (s, 1H), 7.95 (d, J = 7.8 Hz, 1H), 7.80 (s, 1H), 7.66-7.71 (m, 2H), 5.33-5.45 (m, 1H), 3.22 (s, 3H), 2.71 (s, 3H), 2.66-2.70 (m, 3H), 1.93 (t, J = 10.8 Hz, 4H), 1.59 (s, 6H), 1.47 (s, 6H); 2Hs not observed (NH and OH) |
| 173 | MS m/z 474.3 [M + H]⁺; ¹H NMR (DMSO-$d_6$) δ: 9.11 (s, 1H), 8.63 (d, J = 8.7 Hz, 1H), 8.09 (d, J = 8.7 Hz, 1H), 8.06-8.01 (m, 1H), 7.93 (s, 1H), 7.84 (d, J = 8.1 Hz, 1H), 5.33-5.17 (m, 1H), 4.37 (s, 3H), 3.14 (s, 3H), 2.14-2.01 (m, 2H), 1.84-1.72 (m, 2H), 1.53 (s, 6H), 1.51 (s, 6H); 2Hs not observed (NH and OH) |
| 178 | MS m/z 461.2 [M + H]⁺; ¹H NMR (DMSO-$d_6$) δ: 11.24 (br s, 1H), 9.11 (s, 1H), 8.97-9.07 (m, 1H), 8.90 (d, J = 9.5 Hz, 1H), 8.45 (d, J = 9.5 Hz, 1H), 8.10 (d, J = 7.9 Hz, 1H), 7.93-8.07 (m, 1H), 7.87 (s, 1H), 7.82 (d, J = 8.2 Hz, 1H), 5.15-5.35 (m, 1H), 3.15 (s, 3H), 1.97-2.06 (m, 2H), 1.80-1.88 (m, 2H), 1.53 (s, 6H), 1.48 (s, 6H); 1H from HCl salt |
| 179 | MS m/z 450.3 [M + H]⁺; ¹H NMR (DMSO-$d_6$) δ: 11.05 (br s, 1H), 9.15 (s, 1H), 9.07 (s, 1H), 8.00-8.08 (m, 2H), 7.87 (s, 1H), 7.78 (d, J = 8.2 Hz, 1H), 5.74 (t, J = 5.8 Hz, 1H), 5.14-5.32 (m, 1H), 4.64 (d, J = 5.8 Hz, 2H), 3.13 (s, 2H), 1.88-2.03 (m, 2H), 1.73-1.85 (m, 2H), 1.48 (s, 6H), 1.43 (s, 6H); 2Hs not observed (OH and NH) |
| 184 | MS m/z 459.5 [M + H]⁺; ¹H NMR (DMSO-$d_6$) δ: 13.75 (br s, 1H), 11.24 (br s, 1H), 9.15 (s, 1H), 9.08 (s, 1H), 8.33 (d, J = 0.8 Hz, 1H), 8.31 (m, 1H), 8.28 (s, 1H), 7.96 (d, J = 8.4 Hz, 1H), 7.80 (d, J = 1.6 Hz, 1H), 7.69-7.71 (m, 2H), 5.22 (br s, 1H), 3.42 (s, 3H), 1.63-1.64 (m, 4H), 1.33 (s, 6H), 1.21 (s, 6H) |
| 185 | MS m/z 469.5 [M + H]⁺; ¹H NMR (methanol-$d_4$) δ: 9.31 (d, J = 8.00 Hz, 1H), 9.27-9.23 (m, 2H), 8.69 (s, 1H), 8.61-8.55 (m, 1H), 8.37 (d, J = 9.00 Hz, 1H), 8.20-8.16 (m, 1H), 8.06 (d, J = 8.00 Hz, 1H), 7.54 (d, J = 10 Hz, 1H), 7.52 (s, 1H), 5.47-5.37 (m, 1H), 3.19, (s, 3H), 2.19-2.01 (m, 4H), 1.65, (s, 6H), 1.57 (s, 6H); 2Hs not observed (NH and OH) |
| 186 | MS m/z 474.3 [M + H]⁺; ¹H NMR (DMSO-$d_6$) δ: 9.02 (s, 1H), 8.41 (d, J = 8.70 Hz, 1H), 8.15 (d, J = 8.70 Hz, 1H), 7.94 (d, J = 8.09 Hz, 1H), 7.84 (s, 1H), 7.72 (d, J = 8.09 Hz, 1H), 5.17 (br s, 1H), 4.30 (s, 3H), 3.05 (s, 3H), 1.99 (t, J = 12.89 Hz, 2H) 1.71 (d, J = 12.51 Hz, 2H), 1.45 (s, 6H), 1.42 (m, 6H); 2Hs not observed (NH and OH) |
| 192 | MS m/z 459.5 [M + H]⁺; ¹H NMR (DMSO-$d_6$) δ: 9.57 (br s, 1H), 9.42 (s, 1H), 9.12 (s, 1H), 8.45 (br s, 1H), 8.25 (s, 1H), 8.08 (d, J = 10.1 Hz, 1H), 8.01 (d, J = 8.5 Hz, 1H), 7.76 (dd, J = 9.3, 1.4 Hz, 1H), 7.42-7.49 (m, 2H), 5.17-5.31 (m, 1H), 3.13 (s, 3H), 2.13 (t, J = 12.8 Hz, 2H), 1.73-1.80 (m, 2H), 1.54 (s, 6H), 1.53 (s, 6H) |
| 194 | MS m/z 460.3 [M + H]⁺; ¹H NMR (DMSO-$d_6$) δ: 9.22 (s, 1H), 9.08 (s, 1H), 8.52 (s, 1H), 8.34 (br s, 1H), 8.02 (d, J = 8.4 Hz, 1H), 7.84 (d, J = 2.0 Hz, 1H), 7.78 (dd, J = 8.0, 2.0 Hz, 1H), 5.22 (br s, 1H), 3.14 (s, 3H), 1.60-1.69 (m, 4H), 1.32 (s, 6H), 1.21 (s, 6H); 2Hs not observed (OH and NH) |
| 195 | MS m/z 460.3 [M + H]⁺; ¹H NMR (DMSO-$d_6$) δ: 9.46 (s, 1H), 9.07 (s, 1H), 8.50 (s, 1H), 8.42 (s, 1H), 8.14 (d, J = 1.6 Hz, 1H), 8.05 (dd, J = 8.0, 1.2 Hz, 1H), 8.00 (d, J = 8.4 Hz, 1H), 5.24 (s, 1H), 3.11 (s, 3H), 1.64-1.80 (m, 4H), 1.38 (s, 6H), 1.28 (s, 6H); 2Hs not observed (OH and NH) |
| 198 | MS m/z 473.3 [M + H]⁺; ¹H NMR (DMSO-$d_6$) δ: 9.07 (s, 1H), 8.37 (br s, 1H), 8.33 (s, 1H), 8.25 (d, J = 8.8 Hz, 1H), 8.04 (d, J = 8.8 Hz, 1H), 7.98 (d, J = 8.0 Hz, 1H), 7.83 (d, J = 1.6 Hz, 1H), 7.73 (dd, J = 8.4, 1.6 Hz, 1H), 5.22 (br, 1H), 4.11 (s, 3H), 3.10 (s, 3H), 1.64-1.74 (m, 4H), 1.35 (s, 6H), 1.25 (s, 6H); 1H not observed (OH or NH) |
| 200 | MS m/z 473.5 [M + H]⁺; ¹H NMR (DMSO-$d_6$) δ: 11.20 (br s, 1H), 9.11 (s, 1H), 8.30 (s, 1H), 7.93-8.03 (m, 2H), 7.87-7.93 (m, 1H), 7.40 (d, J = 8.2 Hz, 1H), 7.37 (s, 1H), 5.18-5.28 (m, 1H), 4.36 (s, 3H), 3.13 (s, 3H), 1.81-1.90 (m, 2H), |

| Cpd | Data |
|---|---|
| | 1.69-1.81 (m, 2H), 1.46 (s, 6H), 1.38 (s, 6H); 1H not observed (OH or NH) |
| 207 | MS m/z 431.5 [M + H]+; 1H NMR (DMSO-d6) δ: 9.24-9.38 (m, 2H), 9.11-9.18 (m, 2H), 8.27 (d, J = 7.3 Hz, 2H), 8.01 (d, J = 8.5 Hz, 1H), 7.52 (d, J = 7.3 Hz, 1H), 7.42-7.49 (m, 2H), 4.05-4.21 (m, 3H), 3.80-3.93 (m, 4H), 1.41 (s, 9H) |
| 208 | MS m/z 444.6 [M + H]+; 1H NMR (DMSO-d6) δ: 9.04-9.25 (m, 3H), 8.13 (s, 1H), 8.05 (s, 1H), 7.95 (d, J = 7.6 Hz, 1H), 7.74 (s, 2H), 7.29-7.38 (m, 2H), 4.13-4.25 (m, 3H), 4.09 (s, 3H), 3.76-3.97 (m, 4H), 1.40 (s, 9H) |
| 209 | MS m/z 392.5 [M + H]+; 1H NMR (DMSO-d6) δ: 9.29 (br s, 2H), 9.10 (s, 1H), 8.93 (dd, J = 4.7, 1.1 Hz, 2H), 8.09 (s, 1H), 7.96-8.03 (m, 2H), 7.44-7.51 (m, 1H), 4.05-4.22 (m, 3H), 3.77-3.98 (m, 4H), 1.41 (s, 9H) |
| 210 | MS m/z 395.5 [M + H]+; 1H NMR (DMSO-d6) δ: 9.17 (br s, 2H), 9.10 (s, 1H), 8.24 (s, 1H), 7.93 (d, J = 7.9 Hz, 1H), 7.48 (s, 1H), 7.44 (d, J = 8.2 Hz, 1H), 4.22 (s, 3H), 3.79-3.92 (m, 3H), 3.55-3.66 (m, 4H), 1.40 (s, 9H) |
| 211 | MS m/z 396.5 [M + H]+; 1H NMR (DMSO-d6) δ: 9.17 (br s, 2H), 9.10 (s, 1H), 8.24 (s, 1H), 7.93 (d, J = 7.9 Hz, 1H), 7.48 (s, 1H), 7.44 (d, J = 8.2 Hz, 1H), 4.22 (s, 3H), 3.79-3.92 (m, 3H), 3.55-3.66 (m, 4H), 1.40 (s, 9H); 1H from HCl salt |
| 214 | MS m/z 421.5 [M + H]+; 1H NMR (DMSO-d6) δ: 8.10 (d, J = 5.80 Hz, 1H), 7.79 (d, J = 7.78 Hz, 1H), 7.38 (d, J = 7.93 Hz, 1H), 7.35 (s, 1H), 7.23-7.21 (m, 1H), 7.16 (s, 1H), 4.36-4.34.32 (m, 2H), 4.12-4.17 (m, 1H), 3.99-3.88 (m, 2H), 3.84 (s, 3H), 3.79-3.71 (m, 1H), 2.66-2.69 (m, 1H), 2.41-2.48 (m, 1H), 1.51 (s, 9H); 2Hs not observed (NH and OH) |
| 215 | MS m/z 446.3 [M + H]+; 1H NMR (DMSO-d6) δ: 9.14 (s, 1H), 8.55-8.45 (m, 1H), 8.28-8.18 (m, 1H), 8.03-7.97 (m, 1H), 7.93 (br s, 1H), 7.85-7.77 (m, 1H), 4.38 (s, 3H), 3.93-3.81 (m, 4H), 3.72-3.55 (m, 1H), 1.41 (s, 9H); (4Hs overlapped with residual solvent peaks) |
| 216 | MS m/z 422.5 [M + H]+; 1H NMR (DMSO-d6) δ: 9.13 (s, 1H), 7.83 (d, J = 8.09 Hz, 1H), 7.5-7.50 (m, 2H), 7.02 (s, 1H), 6.03 (s, 1H), 4.42-4.32 (m, 1H), 4.22-4.18 (m, 1H), 4.03-3.91 (m, 2H), 3.82-3.74 (m, 1H), 3.63-3.69 (m, 3H), 2.73-2.65 (m, 1H), 2.54-2.42 (m, 1H), 1.53 (s, 9H); 2Hs not observed (NH and OH) |
| 217 | MS m/z 422.5 [M + H]+; 1H NMR (methanol-d4) δ: 9.16 (s, 1H), 8.81 (s, 1H), 7.99 (d, J = 8.5 Hz, 1H), 7.70 (s, 1H), 7.67 (d, J = 8.0 Hz, 1H), 7.33 (s, 1H), 4.31-4.21 (m, 2H), 4.06 (s, 3H), 4.01-3.97 (m,1H), 3.80-3.76 (m, 2H), 2.68-2.62 (m, 1H), 2.31-2.24 (m, 1H), 1.49 (s, 9H); 2Hs not observed (NH and OH) |
| 221 | MS m/z 445.3 [M + H]+; 1H NMR (methanol-d4) δ: 9.16 (s, 1H), 8.89 (s, 1H), 8.49 (s, 1H), 8.17 (s, 1H), 7.96 (d, J = 8.9 Hz, 1H), 7.29-7.38 (m, 2H), 4.18 (s, 4H), 3.99-4.07 (m, 1H), 3.92-3.99 (m, 1H), 3.67-3.77 (m, 1H), 3.54-3.63 (m, 1H), 2.47-2.60 (m, 1H), 2.08-2.19 (m, 1H), 1.36-1.40 (m, 9H); 2Hs not observed (NH and OH) |
| 222 | MS m/z 473.3 [M + H]+; 1H NMR (methanol-d4) δ: 9.19 (s, 1H), 9.13 (s, 1H), 8.41 (s, 1H), 8.15 (s, 1H), 7.94 (d, J = 7.9 Hz, 1H), 7.58-7.66 (m, 2H), 5.36 (br d, J = 1.7 Hz, 1H), 4.35 (s, 3H), 3.19 (s, 3H), 1.66-1.83 (m, 4H), 1.45 (s, 6H), 1.32 (s, 6H); 2Hs not observed (NH and OH) |
| 225 | MS m/z 381.3 [M + H]+; 1H NMR (methanol-d4) δ: 9.13 (s, 1H), 8.20 (s, 1H), 7.92 (d, J = 8.5 Hz, 1H), 7.47-7.46 (m, 2H), 4.26-4.18 (m, 2H), 3.99-3.95 (m, 1H), 3.75-3.72 (m, 2H), 2.65-2.59 (m, 1H), 2.30-2.23 (m, 1H), 1.47 (s, 9H); 1H not observed (NH or OH) |
| 227 | MS m/z 407.3 [M + H]+; 1H NMR (DMSO-d6) δ: 8.08 (d, J = 6.87 Hz, 1H), 7.80 (d, J = 8.24 Hz, 1H), 7.39 (d, J = 8.24 Hz, 1H), 7.36 (s, 1H), 7.18 (d, J = 6.71 Hz, 1H), 7.14 (s, 1H), 6.02 (d, J = 2.6 Hz, 1H), 4.38-4.24 (m, 1H), 4.19-4.09 (m, 1H), 4.06-3.88 (m, 2H), 3.83-3.79 (m, 4H), 3.64-3.53 (m, 1H), 2.73-2.59 (m, 1H), 2.55-2.38 (m, 1H), 1.41-1.53 (m, 6H); 2Hs not observed (NH and OH) |
| 234 | MS m/z 408.3 [M + H]+; 1H NMR (DMSO-d6) δ: 8.76 (s, 1H), 7.70 (d, J = 8.09 Hz, 1H), 7.54-7.50 (m, 2H), 6.92 (s, 1H), 5.94 (m, 1H), 4.29-4.20 (m, 2H), 4.17-4.08 (m, 1H), 4.06-3.90 (m, 1H), 3.82-3.72 (m, 1H), 3.68-3.59 (m, 3H), 3.59-3.45 (m, 1H), 2.69-2.39 (m, 2H), 1.47 (br s, 6H); 2Hs not observed (NH and OH) |
| 241 | MS m/z 419.4 [M + H]+; 1H NMR (DMSO-d6) δ: 10.18 (br s, 1H), 9.04 (s, 1H), 7.91 (d, J = 7.9 Hz, 1H), 7.79 (d, J = 7.2 Hz, 1H), 7.30 (d, J = 8.2 Hz, 1H), 7.28 (s, 1H), 6.64 (s, 1H), 6.54 (d, J = 7.0 Hz, 1H), 4.06 (br s, 2H), 3.98 (br s, 2H), 3.46 (s, 3H), 3.37 (m, 2H), 3.00 (dd, J = 22.1, 10.5 Hz, 2H), 2.74 (d, J = 4.43 Hz, 3H), 2.17 (d, 13.7 Hz, 2H), 2.00 (td, J = 13.7, 13.7, 3.5 Hz, 2H) |
| 242 | MS m/z 393.3 [M + H]+; 1H NMR (DMSO-d6) δ: 11.13 (br s, 1H), 9.29 (br s, 1H), 9.04 (s, 1H), 8.24 (s, 1H), 7.91 (d, J = 8.1 Hz, 1H), 7.46 (s, 1H), 7.44 (d, J = 8.1 Hz, 1H), 4.22 (s, 3H), 4.06 (br s, 2H), 3.97 (br s, 2H), 3.42 (d, J = 12.05 Hz, 2H), 3.03 (dd, J = 22.3, 11.4 Hz, 2H), 2.79 (d, J = 4.0 Hz, 3H), 2.20 (d, J = 13.7 Hz, 2H), 1.90 (ddd, J = 14.8, 8.9, 3.4 Hz, 2H); 1H from TFA salt |
| 243 | MS m/z 420.4 [M + H]+; 1H NMR (DMSO-d6) δ: 11.10 (br s, 1H), 9.26 (br dd, J = 3.5, 2.0 Hz, 1H), 9.06 (s, 1H), 8.88 (s, 1H), 7.96 (br d, J = 8.1 Hz, 1H), 7.84 (s, 1H), 7.76 (br d, J = 8.2 Hz, 1H), 7.47 (s, 1H), 4.07 (br s, 2H), 3.96-4.01 (m, 5H), 2.99-3.07 (m, 2H), 2.77-2.82 (m, 3H), 2.18-2.25 (m, 2H), 1.84-1.95 (m, 2H); 2Hs not observed (CH2 obscured by solvent peak); 1H from TFA salt |
| 244 | MS m/z 390.3 [M + H]+; 1H NMR (DMSO-d6) δ: 10.88 (br s, 1H), 9.25 (br s, 1H), 8.97 (s, 1H), 8.87 (d, J = 4.9 Hz, 2H), 8.00 (s, 1H), 7.93 (d, J = 8.4 Hz, 1H), 7.89 (d, J = 8.4 Hz, 1H), 7.40 (t, J = 4.7 Hz, 1H), 4.00 (br s, 2H), 3.91 (br s, 2H), 2.96 (dd, J = 22.1, 11.6 Hz, 2H), 2.73 (d, J = 4.1 Hz, 3H), 2.13 (d, J = 14.0 Hz, 2H) 1.83 (ddd, J = 14.2, 12.5, 3.4 Hz, 2H); 2Hs not observed (CH2 obscured by solvent peak); 1H from TFA salt |
| 245 | MS m/z 379.2 [M + H]+; 1H NMR (DMSO-d6) δ: 15.02 (br s, 1H), 11.12 (br s, 1H), 9.21 (br s, 1H), 9.05 (s, 1H), 8.27 (br s, 1H), 7.91 (d, J = 8.5 Hz, 1H), 7.51 (br s, 1H), 7.46 (d, J = 7.4 Hz, 1H), 4.06 (br s, 2H), 3.97 (br s, 2H), 3.03 (dd, J = 22.4, 11.6 Hz, 2H), 2.79 (d, J = 4.6 Hz, 3H), 2.20 (d, J = 13.6 Hz, 2H), 1.90 (ddd, J = 14.0, 12.8, 4.3 Hz, 2H); 2Hs not observed (CH2 obscured by solvent peak); 1H from TFA salt |
| 246 | MS m/z 454.5 [M + H]+; 1H NMR (methanol-d4) δ: 8.88 (s, 1H), 7.77 (d, J = 8.2 Hz, 1H), 7.63-7.46 (m, 2H), 6.97 (s, 1H), 6.04 (d, J = 8.9 Hz, 1H), 3.64 (s, 3H), 2.22-2.01 (m, 2H), 1.76-1.65 (m, 6H), 1.64-1.51 (m, 6H); 4Hs not observed (2 NHs, OH and 1 CH obscured by solvent peak) |
| 250 | MS m/z 381.3 [M + H]+; 1H NMR (methanol-d4) δ: 9.09 (s, 1H), 8.01 (s, 1H), 7.97 (d, J = 8.0 Hz, 1H), 7.63 (d, J = 9.0 Hz, 2H), 7.33 (s, 1H), 4.09-4.05 (m, 1H), 3.91-3.88 (m, 1H), 3.81-3.74 (m, 1H), 3.66-3.60 (m, 1H), 3.42-3.36 (m, 1H), 2.44-2.37 (m, 1H), 2.02-1.94 (m, 1H), 1.25 (s, 9H); 2Hs not observed (NH and OH) |
| 251 | MS m/z 394.3 [M + H]+; 1H NMR (DMSO-d6) δ: 11.06 (br s, 1H), 9.28 (br s, 1H), 9.01 (s, 1H), 7.98 (d, J = 8.1 Hz, 1H), 7.70 (s, 1H), 7.65 (d, J = 8.1 Hz, 1H), 4.45 (s, 3H), 4.07 (br s, 2H), 3.98 (br s, 2H), 3.03 (dd, J = 22.1, 11.0 Hz, 2H), 2.79 (d, J = 4.1 Hz, 3H), 2.20 (d, J = 14.0 Hz, 2H), 1.90 (ddd, J = 14.6, 12.4, 2.6 Hz, 2H); 2Hs not observed (CH2 obscured by solvent peak); 1H from TFA salt |
| 252 | MS m/z 379.3 [M + H]+; 1H NMR (DMSO-d6) δ: 11.08 (br s, 1H), 9.35 (br s, 1H), 9.00 (s, 1H), 8.24 (s, 1H), 7.95 (d, J = 8.1 Hz, 1H), 7.61 (s, 1H), 7.56 (d, J = 8.1 Hz, 1H), 7.41 (s, 1H), 4.06 (s, 2H), 3.96 (s, 2H), 3.02 (dd, J = 22.7, 10.8 Hz, 2H), 2.79 (d, J = 4.1 Hz, 3H), 2.20 (d, J = 14.0 Hz, 2H), 1.90 (ddd, J = 13.9, 13.0, 2.9 Hz, 2H); 2Hs not observed (CH2 obscured by solvent peak); 1H from TFA salt |
| 253 | MS m/z 408.5 [M + H]+; 1H NMR (DMSO-d6) δ: 9.01 (s, 1H), 8.22 (m, 1H), 7.86 (d, J = 8.4 Hz, 1H), 7.75 (d, J = 2.0 Hz, 1H), 7.42 (d, J = 2.0 Hz, 1H), 7.35-7.38 (m, 3H), 6.70 (d, J = 2.4 Hz, 1H), 4.40 (br s, 1H), 3.89 (m, 3H), 2.02-2.09 (m, 2H), 1.46-1.54 (m, 2H), 1.44 (s, 6H), 1.35 (s, 6H); 2Hs not observed (OH and NH) |
| 254 | MS m/z 436.5 [M + H]+; 1H NMR (DMSO-d6) δ: 9.02 (s, 1H), 8.87 (s, 1H), 8.38 (s, 1H), 7.97 (d, J = 8.4 Hz, 1H), 7.84 (d, J = 1.2 Hz ,1H), 7.73-7.76 (m, 1H), 7.48 (s, 1H), 4.35 (br s, 1H), 3.98 (s, 3H), 1.93-1.96 |

-continued

| Cpd | Data |
|---|---|
| | (m, 2H), 1.35-1.40 (m, 2H), 1.34 (s, 6H), 1.23 (s, 6H); 2Hs not observed (OH and NH) |
| 258 | MS m/z 367.4 [M + H]$^+$; $^1$H NMR (methanol-d$_4$) δ: 9.17 (s, 1H), 8.01 (d, J = 8.5 Hz, 1H), 7.84-7.77 (m, 1H), 7.74-7.72 (m, 2H), 4.25 (q, J = 6.3 Hz, 1H), 4.19 (dd, J = 12.1, 7.0 Hz, 1H), 4.03-3.99 (m, 1H), 3.86-3.78 (m, 2H), 3.63-3.57 (m, 1H), 2.63 (tt, J = 13.2, 6.3 Hz, 1H), 2.31 (dq, J = 14.2, 7.3 Hz, 1H), 1.45 (dd, J = 6.6, 4.0 Hz, 6H); 3Hs not observed (2NHs and OH) |
| 259 | MS m/z 382.2 [M + H]$^+$; $^1$H NMR (methanol-d$_4$) δ: 9.14 (s, 1H), 8.20 (s, 1H), 7.92 (d, J = 9.0 Hz, 1H), 7.48-7.46 (m, 2H), 4.23 (dt, J = 13.0, 7.0 Hz, 1H), 4.15 (dd, J = 12.5, 7.5 Hz, 1H), 3.98 (ddd, J = 11.5, 8.5, 5.5 Hz, 1H), 3.83-3.76 (m, 2H), 3.58 (quin, J = 6.5 Hz, 1H), 3.31 (s, 3H), 2.60 (td, J = 13.0, 7.5 Hz, 1H), 2.31-2.24 (m, 1H), 1.42 (dd, J = 6.5, 4.0 Hz, 6H); 1H not observed (NH or OH) |
| 265 | MS m/z 408.6 [M + H]$^+$; $^1$H NMR (methanol-d$_4$) δ: 9.02-9.22 (m, 1H), 8.70-8.83 (m, 1H), 7.84-7.97 (m, 1H), 7.50-7.67 (m, 2H), 7.22-7.38 (m, 1H), 4.05 (s, 3H), 3.93-4.01 (m, 1H), 3.82-3.91 (m, 1H), 3.61-3.70 (m, 2H), 3.36-3.46 (m, 1H), 2.94-3.03 (m, 1H), 2.30-2.39 (m, 1H), 1.85-1.99 (m, 1H), 1.14 (t, J = 6.7 Hz, 6H); 2Hs not observed (NH and OH) |
| 266 | MS m/z 409.6 [M + H]$^+$; $^1$H NMR (DMSO-d$_6$) δ: 9.06-9.13 (m, 1H), 9.04 (s, 1H), 8.25 (s, 1H), 8.12 (br s, 1H), 7.94-8.01 (m, 1H), 7.93 (d, J = 8.2 Hz, 1H), 7.47 (d, J = 1.2 Hz, 1H), 7.43 (dd, J = 8.2, 1.5 Hz, 1H), 4.36-4.46 (m, 1H), 4.22 (s, 3H), 2.05-2.12 (m, 2H), 1.62 (t, J = 12.7 Hz, 2H), 1.50 (s, 6H), 1.44 (s, 6H) |
| 267 | MS m/z 410.1 [M + H]$^+$; $^1$H NMR (DMSO-d$_6$) δ: 9.05-9.15 (m, 1H), 9.00 (s, 1H), 8.15 (br s, 1H), 7.92-8.03 (m, 2H), 7.72 (d, J = 1.5 Hz, 1H), 7.64 (dd, J = 8.2, 1.5 Hz, 1H), 4.33-4.50 (m, 4H), 2.02-2.16 (m, 2H), 1.62 (t, J = 12.8 Hz, 2H), 1.50 (s, 6H), 1.44 (s, 6H) |
| 268 | MS m/z 380.4 [M + H]$^+$; $^1$H NMR (methanol-d$_4$) δ: 9.10 (s, 1H), 8.80 (s, 1H), 7.97 (d, J = 8 Hz, 1H), 7.65-7.70 (m, 2H), 7.33 (s, 1H), 4.06 (s, 3H), 3.80-3.95 (m, 2H), 3.70-3.78 (m, 1H), 3.52-3.59 (m, 1H), 3.43-3.48 (m, 1H), 2.47 (s, 3H), 2.29-2.35 (m, 1H), 2.00-2.04 (m, 1H); 2Hs not observed (NH and OH) |
| 269 | MS m/z 356.3 [M + H]$^+$; $^1$H NMR (methanol-d$_4$) δ: 8.83 (s, 1H), 7.99 (d, J = 8 Hz, 1H), 7.61-7.72 (m, 2H), 6.04 (s, 1H), 4.03-4.15 (m, 2H), 3.78-3.95 (m, 2H), 3.50-3.54 (m, 1H), 2.65 (s, 3H), 2.58-2.66 (m, 1H), 2.42-2.53 (m, 1H); 2Hs not observed (NH and OH) |
| 270 | MS m/z 350.2 [M + H]$^+$; $^1$H NMR (methanol-d$_4$) δ: 8.93 (d, J = 5.0 Hz, 2H), 8.02-8.05 (m, 1H), 7.79 (d, J = 8.5 Hz, 2H), 7.48 (t, J = 5.0 Hz, 1H), 6.05 (s, 1H), 4.06-4.16 (m, 2H), 3.75-3.85 (m, 2H), 3.60-3.70 (m, 1H), 2.85 (s, 3H), 2.61-2.69 (m, 1H), 2.40-2.57 (m, 1H); 2Hs not observed (NH and OH) |
| 271 | MS m/z 403.3 [M + H]$^+$; $^1$H NMR (methanol-d$_4$) δ: 8.87 (d, J = 2 Hz, 1H), 8.53 (d, J = 2 Hz, 1H), 8.18 (d, J = 3.5 Hz, 1H), 7.76 (d, J = 8.5 Hz, 1H), 7.35 (dd, J = 8 Hz, 2 Hz, 1H), 7.32 (s, 1H), 6.01 (s, 1H), 4.16 (s, 3H), 4.00-4.15 (m, 2H), 3.88-3.95 (m, 2H), 3.80 (m, 1H), 2.84 (s, 3H), 2.60-2.70 (m, 1H), 2.35-2.50 (m, 1H); 2Hs not observed (NH and OH) |
| 277 | MS m/z 409.5 [M + H]$^+$; $^1$H NMR (methanol-d$_4$) δ: 7.76 (s, 1H), 7.72 (d, J = 8.2 Hz, 1H), 7.35 (d, J = 8.3 Hz, 1H), 7.31 (s, 1H), 5.98 (s, 1H), 4.42-4.32 (m, 1H), 2.67 (s, 3H), 2.30-2.17 (m, 2H), 1.86-1.73 (m, 2H), 1.63 (s, 3H), 1.62 (s, 3H), 1.55 (s, 3H), 1.53 (s, 3H); 2Hs not observed (NH and OH) |
| 279 | MS m/z 406.5 [M + H]$^+$; $^1$H NMR (DMSO-d$_6$) δ: 9.01 (s, 1H), 8.92 (d, J = 5.2 Hz, 2H), 8.06 (s, 1H), 7.98 (s, 2H), 7.47 (t, J = 5.0 Hz, 1H), 4.41 (br s, 1H), 2.02-2.12 (m, 2H), 1.48-1.56 (m, 2H), 1.44 (s, 6H), 1.35 (s, 6H); 3Hs not observed (OH and 2NHs) |
| 280 | MS m/z 475.8 [M + H]$^+$; $^1$H NMR (DMSO-d$_6$) δ: 9.08 (s, 1H), 8.33 (s, 1H), 7.95 (d, J = 8.0 Hz, 1H), 7.66 (br s, 1H), 7.29-7.37 (m, 3H), 6.56 (s, 1H), 6.32 (s, 1H), 5.20 (br s, 1H), 3.09 (s, 3H), 1.54-1.60 (m, 4H), 1.30 (s, 6H), 1.17 (s, 6H); 1H not observed (OH or NH) |
| 281 | MS m/z 474.2 [M + H]$^+$; $^1$H NMR (DMSO-d$_6$) δ: 9.58 (s, 1H), 9.05 (s, 1H), 8.45 (s, 1H), 8.12 (d, J = 1.6 Hz, 1H), 8.05 (dd, J = 8.0, 1.2 Hz, 1H), 8.00 (d, J = 8.0 Hz, 1H), 5.22 (br s, 1H), 4.23 (s, 3H), 3.05 (s, 3H), 1.47-1.58 (m, 4H), 1.26 (s, 6H), 1.06 (s, 6H); 2Hs not observed (OH and NH) |
| 283 | MS m/z 417.4 [M + H]$^+$; $^1$H NMR (DMSO-d$_6$) δ: 9.26 (s, 1H), 9.17 (s, 1H), 9.07 (s, 1H), 8.17 (s, 1H), 7.97 (d, J = 7.9 Hz, 1H), 7.86 (d, J = 0.9 Hz, 1H), 7.71 (s, 1H), 7.61 (dd, J = 8.5, 1.5 Hz, 1H), 3.67-3.86 (m, 2H), 3.47-3.54 (m, 1H), 3.18-3.38 (m, 2H), 2.84 (dt, J = 12.4, 6.3 Hz, 1H), 2.10-2.23 (m, 1H), 1.74-1.89 (m, 1H), 1.02 (t, J = 6.4 Hz, 6H); 2Hs not observed (NH and OH) |
| 284 | MS m/z 477.4 [M + H]$^+$; $^1$H NMR (DMSO-d$_6$) δ: 9.82-9.94 (m, 1H), 9.11 (s, 1H), 8.90 (d, J = 2.1 Hz, 1H), 8.52 (d, J = 2.1 Hz, 1H), 8.29 (br s, 1H), 8.23 (s, 1H), 8.08-8.17 (m, 1H), 7.99 (d, J = 8.9 Hz, 1H), 7.34-7.40 (m, 2H), 4.70-4.87 (m, 2H), 4.11 (s, 3H), 1.95-2.06 (m, 1H), 1.84-1.95 (m, 1H), 1.57 (d, J = 18.5 Hz, 6H), 1.48 (d, J = 6.4 Hz, 6H) |
| 285 | MS m/z 472.3 [M + H]$^+$; $^1$H NMR (DMSO-d$_6$) δ: 9.07 (s, 1H), 8.37 (br s, 2H), 8.25 (s, 1H), 7.93 (d, J = 7.2 Hz, 2H), 7.67 (d, J = 8.4 Hz, 1H), 7.61 (d, J = 8.40 Hz, 1H), 7.31 (d, J = 7.6 Hz, 2H), 5.22 (br s, 1H), 4.03 (s, 3H), 3.10 (s, 3H), 1.64-1.77 (m, 4H), 1.33 (s, 6H), 1.06 (s, 6H) |
| 287 | MS m/z 427.5 [M + H]$^+$; $^1$H NMR (DMSO-d$_6$) δ: 9.07 (s, 1H), 8.97 (d, J = 10.7 Hz, 1H), 8.25 (s, 1H), 8.20 (br d, J = 12.7 Hz, 1H), 7.94 (d, J = 8.1 Hz, 1H), 7.47 (d, J = 1.5 Hz, 1H), 7.44 (dd, J = 8.0, 1.6 Hz, 1H), 4.83 (d, J = 49.0 Hz, 1H), 4.22 (s, 3H), 2.00 (br d, J = 13.3 Hz, 1H), 1.90-1.96 (m, 1H), 1.53 (br d, J = 19.2 Hz, 6H), 1.45 (br d, J = 5.5 Hz, 6H); 2Hs not observed (1 NH and 1 CH obscured by solvent peak) |
| 288 | MS m/z 413.4 [M + H]$^+$; $^1$H NMR (DMSO-d$_6$) δ: 10.95-11.09 (m, 1H), 8.91-8.99 (m, 2H), 8.19 (d, J = 0.6 Hz, 1H), 8.12 (br dd, J = 11.7, 1.4 Hz, 1H), 7.92 (d, J = 8.2 Hz, 1H), 7.56 (d, J = 1.5 Hz, 1H), 7.51 (dd, J = 8.2, 1.7 Hz, 1H), 7.35 (d, J = 0.8 Hz, 1H), 4.71-4.86 (m, 1H), 1.90-1.98 (m, 1H), 1.83-1.90 (m, 1H), 1.46 (br d, J = 18.9 Hz, 6H), 1.38 (br d, J = 5.3 Hz, 6H); 1H not observed (1 CH obscured by solvent peak). |
| 290 | MS m/z 454.4 [M + H]$^+$; $^1$H NMR (DMSO-d$_6$) δ: 11.14 (bs, 1H), 9.08 (m, 2H), 8.88 (s, 1H), 8.20 (d, 12.5 Hz, 1H), 7.98 (d, J = 8.2 Hz, 1H), 7.84 (d, J = 1.7 Hz, 1H), 7.76 (dd, J = 8.2, 1.7 Hz, 1H), 7.47 (s, 1H), 4.85 (bd, J = 47.3 Hz, 1H), 3.99 (s, 3H), 2.01 (t, J = 13.4 Hz, 1H), 1.93 (dd, J = 13.7, 3.6 Hz, 1H), 1.55 (s, 3H), 1.51 (s, 3H), 1.46 (d, J = 1.4 Hz, 3H), 1.44 (s, 3H); 1H not observed (1 CH obscured by solvent peak) |
| 291 | MS m/z 428.5 [M + H]$^+$; $^1$H NMR (DMSO-d$_6$) δ: 9.03 (s, 2H), 8.98 (d, J = 10.8 Hz, 1H), 8.20 (br d, J = 11.3 Hz, 1H), 8.01 (d, J = 8.1 Hz, 1H), 7.72 (d, J = 1.4 Hz, 1H), 7.66 (dd, J = 8.1, 1.7 Hz, 1H), 4.86 (d, J = 47.9 Hz, 1H), 4.45 (s, 3H), 2.02 (d, J = 13.6 Hz, 1H), 1.91-1.98 (m, 1H), 1.55 (s, 3H), 1.51 (s, 3H), 1.46 (br d, J = 0.9 Hz, 3H), 1.45 (s, 3H); 1H not observed (1 CH obscured by solvent peak) |
| 292 | MS m/z 430.4 [M + H]$^+$; $^1$H NMR (DMSO-d$_6$) δ: 10.96-11.45 (m, 1H), 9.02-9.10 (m, 2H), 9.00 (s, 1H), 8.20 (br d, J = 13.1 Hz, 1H), 8.04 (d, J = 8.1 Hz, 1H), 7.69 (d, J = 1.7 Hz, 1H), 7.65 (dd, J = 8.1, 1.7 Hz, 1H), 4.86 (d, J = 47.5 Hz, 1H), 2.02 (br t, J = 13.4 Hz, 1H), 1.94 (br dd, J = 13.7, 4.0 Hz, 1H), 1.55 (s, 3H), 1.51 (s, 3H), 1.46 (br s, 3H), 1.45 (s, 3H); 1H not observed (1 CH obscured by solvent peak) |
| 294 | MS m/z 417.4 [M + H]$^+$; $^1$H NMR (DMSO-d$_6$) δ: 9.13 (br s, 1H), 8.32 (br s, 1H), 8.10-8.24 (m, 1H), 7.92-8.00 (m, 1H), 7.73-7.83 (m, 2H), 7.43-7.57 (m, 2H), 3.69-3.84 (m, 2H), 3.45-3.60 (m, 3H), 2.79-2.89 (m, 1H), 2.10-2.25 (m, 1H), 1.74-1.88 (m, 1H), 1.34 (t, J = 6.1 Hz, 6H); 2Hs not observed (NH and OH) |
| 295 | MS m/z 353.2 [M + H]$^+$; $^1$H NMR (DMSO-d$_6$) δ: 9.07 (s, 1H), 8.23 (s, 1H), 7.91 (d, J = 8 Hz, 1H), 7.42-7.48 (m, 2H), 4.20 (s, 3H), 3.75-4.00 (m, 4H), 3.65-3.75 (m, 1H), 2.66 (s, 3H), 2.40-2.50 (m, 1H), 2.29-2.35 (m, 1H); 2Hs not observed (NH and OH) |

| Cpd | Data |
|---|---|
| 300 | MS m/z 490.3 [M + H]⁺; ¹H NMR (DMSO-d₆) δ: 9.10 (s, 1H), 8.81 (d, J = 11.6 Hz, 1H), 8.41 (s, 1H), 7.89-7.96 (m, 2H), 7.80 (s, 1H), 7.47 (d, J = 12.8 Hz, 1H), 7.31-7.36 (m, 2H), 5.22 (br s, 1H), 4.03 (s, 3H), 3.13 (s, 3H), 1.93-2.00 (m, 2H), 1.83-1.87 (m, 2H), 1.51 (s, 6H), 1.44 (s, 6H |
| 301 | MS m/z 494.2 [M + H]⁺; ¹H NMR (DMSO-d₆) δ: 9.06 (s, 1H), 8.38 (s, 1H), 8.29 (s, 1H), 7.95 (d, J = 8.4 Hz, 1H), 7.49 (s, 1H), 7.16-7.20 (m, 2H), 5.22 (br s, 1H), 3.10 (s, 3H), 1.63-1.66 (m, 4H), 1.33 (s, 6H), 1.21 (s, 6H); 2Hs not observed (OH and NH) |
| 302 | MS m/z 508.3 [M + H]⁺; ¹H NMR (DMSO-d₆) δ: 9.06 (s, 1H), 8.35 (br s, 1H), 8.29 (s, 1H), 7.94 (d, J = 8.0 Hz, 1H), 7.59 (d, J = 5.2 Hz, 1H), 7.20 (s, 1H), 7.17 (d, J = 8.0 Hz, 1H), 5.20 (br s, 1H), 4.00 (s, 3H), 3.11 (s, 3H), 1.69-1.86 (m, 4H), 1.41 (s, 6H), 1.25 (s, 6H); 1H not observed (OH or NH) |
| 303 | MS m/z 473.3 [M + H]⁺; ¹H NMR (methanol-d₄) δ: 9.16 (s, 1H), 8.54 (br s, 2H), 8.18 (s, 1H), 8.01 (d, J = 8.8 Hz, 1H), 7.75 (d, J = 0.6 Hz, 1H), 7.66-7.70 (m, 3H), 5.38-5.42 (m, 1H), 3.24 (s, 3H), 2.72 (s, 3H), 1.92-1.99 (m, 4H), 1.63 (s, 6H), 1.51 (s, 6H) |
| 304 | MS m/z 489.2 [M + H]⁺; ¹H NMR (methanol-d₄) δ: 9.19 (s, 1H), 8.38 (d, J = 1.6 Hz, 1H), 8.06 (d, J = 8.8 Hz, 1H), 8.01 (s, 1H), 7.75-7.77 (m, 2H), 7.58 (s, 1H), 5.38-5.45 (m, 1H), 4.36 (s, 3H), 3.25 (s, 3H), 2.02 (d, J = 8.0 Hz, 4H), 1.66 (s, 6H), 1.54 (s, 6H); 2Hs not observed (OH and NH) |
| 305 | MS m/z 407.4 [M + H]⁺; ¹H NMR (DMSO-d₆) δ: 9.79 (s, 1H), 9.44 (s, 1H), 9.07 (s, 1H), 8.68 (br d, J = 12.8 Hz, 1H), 8.07 (d, J = 8.2 Hz, 1H), 7.89 (d, J = 1.7 Hz, 1H), 7.80-7.82 (m, 1H), 2.10-2.15 (m, 2H), 1.60 (br t, J = 12.7 Hz, 2H), 1.49 (s, 6H), 1.41 (s, 6H); 3Hs not observed (2 NHs, 1CH obscured by solvent peak) |
| 307 | MS m/z 431.4 [M + H]⁺; ¹H NMR (methanol-d₄) δ: 8.85 (d, J = 1.8 Hz, 1H), 8.80 (s, 1H), 8.47 (d, J = 1.8 Hz, 1H), 8.15 (s, 1H), 7.87 (d, J = 7.9 Hz, 1H), 7.56 (d, J = 0.9 Hz, 1H), 7.47 (d, J = 7.9 Hz, 1H), 4.15 (s, 3H), 3.80-4.03 (m, 2H), 3.55-3.72 (m, 2H), 3.36-3.43 (m, 1H), 2.94-3.03 (m, 1H), 2.28-2.43 (m, 1H), 1.86-1.99 (m, 1H), 1.14 (t, J = 5.8 Hz, 6H); 2Hs not observed (NH and OH) |
| 314 | MS m/z 406.4 [M + H]⁺; ¹H NMR (methanol-d₄) δ: 9.54 (s, 1H), 9.24 (d, J = 5.3 Hz, 1H), 9.06 (s, 1H), 8.52 (br s, 1H), 8.06 (dd, J = 5.3, 2.1 Hz, 1H), 7.99 (d, J = 8.2 Hz, 1H), 7.48 (br d, J = 8.1 Hz, 1H), 7.44 (s, 1H), 4.52 (br s, 1H), 2.19-2.29 (m, 2H), 1.67 (br t, J = 13.0 Hz, 2H), 1.61 (s, 6H), 1.50 (s, 6H); 2Hs not observed (NH and OH) |
| 320 | MS m/z 354.2 [M + H]⁺; ¹H NMR (DMSO-d₆) δ: 9.05 (s, 1H), 7.99 (d, J = 8 Hz, 1H), 7.73 (s, 1H), 7.66 (d, J = 8 Hz, 1H), 4.44 (s, 3H), 3.75-4.00 (m, 4H), 3.65-3.75 (m, 1H), 2.67 (s, 3H), 2.40-2.48 (m, 1H), 2.31 (m, 1H); 2Hs not observed (NH and OH) |
| 321 | MS m/z 459.4 [M + H]⁺; ¹H NMR (methanol-d₄) δ: 8.87 (s, 1H), 8.52 (s, 1H), 8.21 (s, 1H), 7.73 (d, J = 8 Hz, 1H), 7.35 (d, J = 8 Hz, 1H), 7.30 (s, 1H), 6.01 (s, 1H), 4.33 (m, 1H), 4.16 (s, 3H), 2.25 (t, J = 16 Hz, 2H), 1.7-1.82 (m, 2H), 1.62 (d, J = 8.5 Hz, 6H), 1.53 (d, J = 5.5 Hz, 6H); 2Hs not observed (NH and OH) |
| 344 | MS m/z 484.2 [M + H]⁺; ¹H NMR (methanol-d₄), δ: 9.15 (s, 1H), 8.39 (d, J = 1.2 Hz, 1H), 8.38 (s, 1H), 8.03 (d, J = 8.4 Hz, 1H), 7.94 (d, J = 1.2 Hz, 1H), 7.70-7.72 (m, 2H), 5.40-5.42 (m, 1H), 3.24 (s, 3H), 1.97-2.05 (m, 4H), 1.66 (s, 6H), 1.54 (s, 6H); 2Hs not observed (OH and NH) |
| 351 | MS m/z 488.3 [M + H]⁺; ¹H NMR (methanol-d₄), δ: 9.17 (s, 1H), 8.54 (br s, 2H), 8.25 (s, 1H), 8.03 (d, J = 8.0 Hz, 1H), 7.86 (s, 1H), 7.81 (s, 1H), 7.71-7.74 (m, 2H), 5.39-5.43 (m, 1H), 4.46 (s, 2H), 3.25 (s, 3H), 2.01 (d, J = 7.6 Hz, 4H), 1.65 (s, 6H), 1.54 (s, 6H); 2Hs not observed (OH and NH) |
| 359 | MS m/z 445.6 [M + H]⁺; ¹H NMR (methanol-d₄) δ: 9.48 (s, 1H), 8.87 (d, J = 4.0 Hz, 1H), 8.48 (s, 1H), 8.24-8.40 (m, 1H), 7.81 (d, J = 8.2 Hz, 1H), 7.27-7.39 (m, 2H), 5.96 (s, 1H), 4.29-4.49 (m, 1H), 2.15 (dd, J = 22.0, 13.7 Hz, 2H), 1.63-1.81 (m, 2H), 1.56 (d, J = 8.9 Hz, 6H), 1.46 (d, J = 5.2 Hz, 6H); 3Hs not observed (2NHs and OH) |
| 360 | MS m/z 444.7 [M + H]⁺; ¹H NMR (methanol-d₄) δ: 8.85 (d, J = 6.1 Hz, 1H), 8.71 (s, 1H), 8.02-8.11 (m, 1H), 7.95-8.00 (m, 1H), 7.83-7.92 (m, 1H), 7.52-7.61 (m, 3H), 5.80-6.24 (m, 1H), 4.24-4.57 (m, 1H), 2.28 (dd, J = 19.5, 15.0 Hz, 2H), 1.68-1.89 (m, 2H), 1.65 (d, J = 8.2 Hz, 6H), 1.56 (d, J = 5.2 Hz, 6H); 3Hs not observed (2NHs and OH) |
| 365 | MS m/z 414.4 [M + H]⁺; ¹H NMR (methanol-d₄) δ: 9.12 (s, 1H), 8.00 (s, 1H), 7.86 (d, J = 8.0 Hz, 1H), 7.30 (s, 1H), 7.26 (d, J = 7.5 Hz, 1H), 4.30-4.19 (m, 2H), 4.00-3.95 (m, 1H), 3.77-3.73 (m, 2H), 2.67-2.61 (m, 1H), 2.32-2.24 (m, 1H), 1.49 (s, 9H); 3Hs not observed (2NHs and OH) |
| 366 | MS m/z 405.3 [M + H]⁺; ¹H NMR (methanol-d₄) δ: 9.14 (s, 1H), 8.20 (s, 1H), 7.92 (d, J = 9.0 Hz, 1H), 7.34 (br s, 2H), 4.31-4.20 (m, 2H), 4.01-3.96 (m, 1H), 3.79-3.73 (m, 2H), 2.68-2.62 (m, 1H), 2.32-2.24 (m, 1H), 1.49 (s, 9H); 3Hs not observed (2NHs and OH) |
| 374 | MS m/z 398.4 [M + H]⁺; ¹H NMR (methanol-d₄) δ: 8.50 (s, 1H), 8.24 (d, J = 10.2 Hz, 1H), 7.99 (s, 1H), 7.21 (m, 2H), 3.96-4.04 (m, 1H), 3.77-3.88 (m, 2H), 3.62 (br d, J = 7.6 Hz, 1H), 3.44-3.50 (m, 1H), 2.39-2.52 (m, 1H), 1.93-2.10 (m, 1H), 1.27 (s, 9H); 3Hs not observed (2 NHs and OH) |
| 375 | MS m/z 394.3 [M + H]⁺; ¹H NMR (methanol-d₄) δ: 8.01 (br s, 1H), 7.67 (d, J = 8.0 Hz, 1H), 7.15 (d, J = 8.5 Hz, 1H), 7.12 (s, 1H), 5.99 (s, 1H), 4.41-4.33 (m, 1H), 4.22-4.18 (m, 1H), 4.02-3.91 (m, 2H), 3.80-3.76 (m, 1H), 2.73-2.66 (m, 1H), 2.53 (s, 3H), 2.50-2.46 (m, 1H), 1.54 (s, 9H); 3Hs not observed (2NHs and OH) |
| 383 | MS m/z 476.3 [M + H]⁺; ¹H NMR (DMSO-d₆) δ: 9.10 (s, 1H), 8.27 (d, J = 3.4 Hz, 1H), 7.84-8.02 (m, 2H), 7.55 (dd, J = 12.6, 0.9 Hz, 1H), 7.28-7.38 (m, 2H), 5.10-5.32 (m, 1H), 3.11 (s, 3H), 1.77-1.94 (m, 2H), 1.66-1.77 (m, 2H), 1.43 (s, 6H), 1.34 (s, 6H); 3Hs not observed (OH and 2 NHs) |

Example 5

Preparation of Compound 63

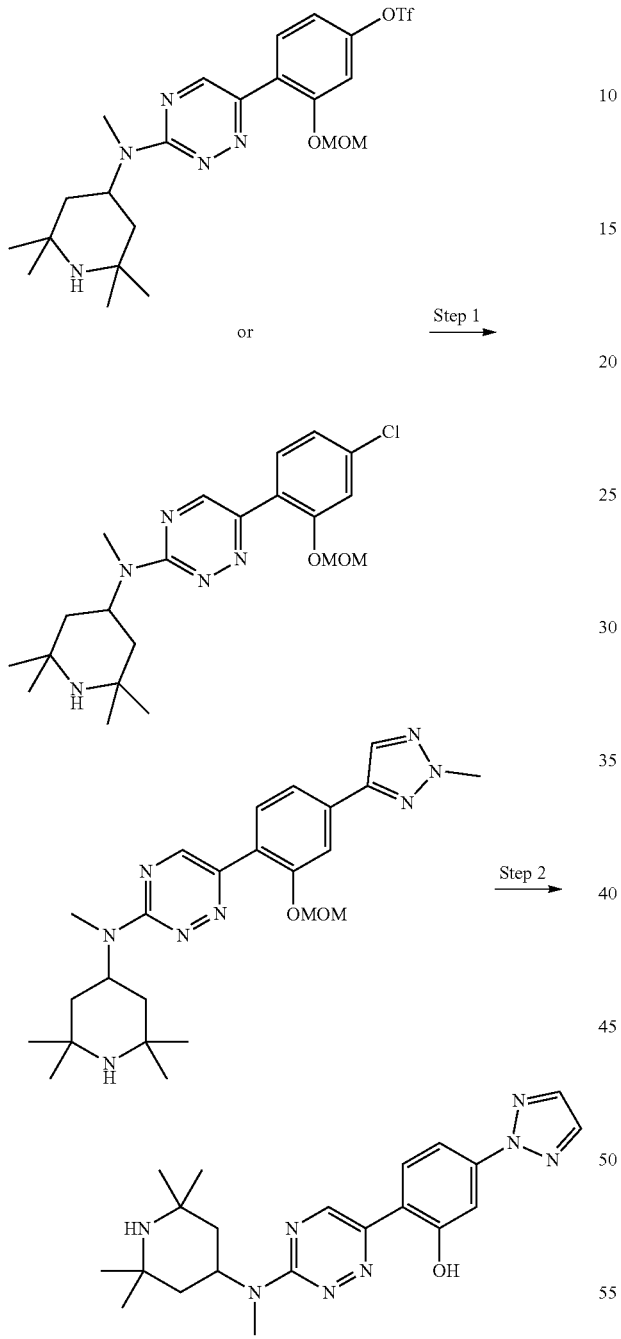

Step 1. Tris(dibenzylideneacetone)dipalladium(0) (4.5 mg, 0.005 mmol) and 2-di-tert-butylphosphino-3,4,5,6-tetramethyl-2',4',6'-triisopropyl-1,1'-biphenyl (6.0 mg, 0.0125 mmol) were suspended in 5:1 toluene/dioxane (1 mL). The purple solution was sparged with argon for 5 minutes, then heated to 120° C. for 5 minutes. The solution was cooled to room temperature and 3-(methoxymethoxy)-4-(3-(methyl(2,2,6,6-tetramethylpiperidin-4-yl)amino)-1,2,4-triazin-6-yl)phenyl trifluoromethanesulfonate (53 mg, 0.10 mmol), $K_3PO_4$ (64 mg, 0.30 mmol), and 1,2,3-triazole (9.0 mg, 0.013 mmol) were added. The suspension was sparged once more with argon, then heated to 120° C. for 1 h until complete consumption of aryl triflate or chloride occurred, as monitored by UPLC. The reaction was cooled to room temperature and the product was purified by chromatography on silica gel (ISCO), eluting with 5-30% MeOH in $CH_2Cl_2$ to afford 6-(2-(methoxymethoxy)-4-(2H-1,2,3-triazol-2-yl)phenyl)-N-methyl-N-(2,2,6,6-tetramethylpiperidin-4-yl)-1,2,4-triazin-3-amine (34 mg, 75% yield) as a dark solid. MS m/z 453.6 [M+H]$^+$.

Alternatively, 6-(4-chloro-2-(methoxymethoxy)phenyl)-N-methyl-N-(2,2,6,6-tetramethylpiperidin-4-yl)-1,2,4-triazin-3-amine could be used as a starting material for step 1.

Step 2. 6-(2-(methoxymethoxy)-4-(2H-1,2,3-triazol-2-yl)phenyl)-N-methyl-N-(2,2,6,6-tetramethylpiperidin-4-yl)-1,2,4-triazin-3-amine (34 mg, 0.075 mmol) was suspended in H (1 mL), then HCl (4 Min dioxane, 1 mL) was added. The solution was stirred at room temperature for 1 h. The reaction mixture was concentrated, and the product was purified by chromatography on silica gel (ISCO), eluting with 5-30% MeOH in $CH_2Cl_2$ to afford 2-(3-(methyl(2,2,6,6-tetramethylpiperidin-4-yl)amino)-1,2,4-triazin-6-yl)-5-(2H-1,2,3-triazol-2-yl)phenol (25 mg, 80% yield) as an orange solid.

MS m/z 409.5 [M+H]$^+$; $^1$H NMR (DMSO-$d_6$) δ: 9.03-9.15 (m, 2H), 8.16 (s, 2H), 7.99-8.13 (m, 2H), 7.72 (d, J=2.1 Hz, 1H), 7.64 (dd, J=8.5, 2.1 Hz, 1H), 5.14-5.32 (m, 1H), 3.13 (s, 3H), 1.98-2.04 (m, 2H), 1.80-1.85 (m, 2H), 1.52 (s, 6H), 1.48 (s, 6H).

Using the procedure described for Example 5, additional compounds described herein may be prepared by substituting the appropriate starting material, suitable reagents and reaction conditions, obtaining compounds such as those selected from:

| Cpd | Data |
|---|---|
| 51 | MS m/z 423.6 [M + H]$^+$; $^1$H NMR (methanol-$d_4$) δ: 9.12 (s, 1H), 9.02 (s, 1H), 8.01 (d, J = 8.5 Hz, 1H), 7.38-7.47 (m, 2H), 5.35-5.45 (m, 1H), 3.24 (s, 3H), 2.47 (s, 3H), 1.96-2.04 (m, 4H), 1.64 (s, 6H), 1.53 (s, 6H); 2Hs not observed (OH and NH) |
| 55 | MS m/z 438.6 [M + H]$^+$; $^1$H NMR (methanol-$d_4$) δ: 9.24 (s, 1H), 8.02 (s, 1H), 8.05 (s, 1H), 7.92 (d, J = 8.5 Hz, 1H), 7.71-7.78 (m, 1H), 7.49-7.57 (m, 2H), 7.32-7.42 (m, 4H), 5.99 (s, 1H), 5.36-5.46 (m, 1H), 4.41-4.52 (m, 1H), 3.85 (s, 6H), 3.25 (s, 3H), 3.16 (s, 3H), 1.98-2.19 (m, 8H); 1.56-1.70 (m, 24H); 2 rotamers (1:1), 2Hs not observed (NHs) |
| 59 | MS m/z 442.5 [M + H]$^+$; $^1$H NMR (DMSO-$d_6$) δ: 9.10 (s, 1H), 8.30 (s, 1H), 8.00 (d, J = 8.0 Hz, 1H), 7.94 (s, 1H), 7.27 (d, J = 8.5 Hz, 1H), 7.24 (s, 1H), 5.13-5.28 (m, 1H), 3.11 (s, 3H), 1.85-2.06 (m, 2H), 1.70-1.81 (m, 2H), 1.46 (s, 6H), 1.42 (s, 6H); 2Hs not observed (NH and OH) |
| 68 | MS m/z 450.5 [M + H]$^+$; $^1$H NMR (DMSO-$d_6$) δ: 11.42 (br s, 1H), 9.24 (s, 1H), 9.08-9.15 (m, 2H), 8.21 (s, 1H), 8.05-8.13 (m, 1H), 8.01 (d, J = 8.5 Hz, 1H), 7.59 (d, J = 2.1 Hz, 1H), 7.55 (dd, J = 8.5, 2.1 Hz, 1H), 5.16-5.29 (m, 1H), 3.90 (s, 3H), 3.13 (s, 3H), 2.01 (t, J = 13.0 Hz, 2H), 1.75-1.86 (m, 2H), 1.52 (s, 6H), 1.48 (s, 6H) |
| 69 | MS m/z 423.6 [M + H]$^+$; $^1$H NMR (DMSO-$d_6$) δ: 11.17 (br s, 1H), 9.04-9.13 (m, 1H), 9.02 (s, 1H), 8.01-8.09 (m, 1H), 7.99 (d, J = 8.5 Hz, 1H), 7.92 (s, 1H), 7.65 (d, J = 2.1 Hz, 1H), 7.57 (dd, J = 8.5, 2.1 Hz, 1H), 5.13-5.31 (m, 1H), 3.13 (s, 3H), 2.38 (s, 3H), 1.95-2.05 (m, 2H), 1.80-1.86 (m, 2H), 1.52 (s, 6H), 1.48 (s, 6H) |

-continued

| Cpd | Data |
|---|---|
| 79 | MS m/z 409.4 [M + H]$^+$; $^1$H NMR (DMSO-d$_6$) δ: 9.35 (s, 1H), 9.15-9.18 (m, 1H), 9.06 (s, 1H), 8.27 (s, 1H), 8.08-8.17 (m, 1H), 8.02 (d, J = 8.2 Hz, 1H), 7.47-7.55 (m, 2H), 5.16-5.30 (m, 1H), 3.13 (s, 3H), 2.03 (t, J = 13.0 Hz, 2H), 1.77-1.85 (m, 2H), 1.52 (s, 6H), 1.49 (s, 6H) |
| 89 | MS m/z 408.5 [M + H]$^+$; $^1$H NMR (methanol-d$_4$) δ: 9.12 (s, 1H), 8.23 (s, 1H), 8.01 (d, J = 8.0 Hz, 1H), 7.65 (s, 1H), 7.23 (d, J = 8.5 Hz, 1H), 7.21 (s, 2H), 5.39-5.43 (m, 1H), 3.24 (s, 3H), 2.00-2.01 (m, 4H), 1.65 (s, 6H), 1.54 (s, 6H); 2Hs not observed (NH and OH) |
| 90 | MS m/z 424.2 [M + H]$^+$; $^1$H NMR (DMSO-d$_6$) δ: 9.27-9.38 (m, 1H), 9.06 (s, 1H), 8.18-8.31 (m, 1H), 7.87-7.96 (m, 2H), 7.38-7.44 (m, 2H), 7.32 (d, J = 8.2 Hz, 1H), 3.12 (s, 3H), 2.05 (t, J = 13.0 Hz, 2H), 1.72-1.83 (m, 2H), 1.52 (s, 6H), 1.50 (s, 6H); 1H not observed |
| 93 | MS m/z 426.6 [M + H]$^+$; $^1$H NMR (DMSO-d$_6$) δ 9.13-9.27 (m, 1H), 9.06 (s, 1H), 8.73 (d, J = 4.3 Hz, 1H), 8.09-8.20 (m, 1H), 7.97 (d, J = 8.5 Hz, 1H), 7.88 (d, J = 4.0 Hz, 1H), 7.49 (s, 1H), 7.39 (d, J = 8.5 Hz, 1H), 5.18-5.26 (m, 1H), 3.12 (s, 3H), 2.03 (t, J = 13.0 Hz, 2H), 1.74-1.85 (m, 2H), 1.52 (s, 6H), 1.49 (s, 6H) |
| 94 | MS m/z 422.6 [M + H]$^+$; $^1$H NMR (DMSO-d$_6$) δ: 9.10-9.21 (m, 1H), 9.06 (s, 1H), 8.28 (s, 1H), 8.06-8.17 (m, 1H), 7.94 (d, J = 8.9 Hz, 1H), 7.59 (s, 1H), 7.46 (s, 1H), 7.38 (d, J = 8.2 Hz, 1H), 5.16-5.29 (m, 1H), 3.12 (s, 3H), 2.11 (s, 3H), 2.02 (t, J = 13.0 Hz, 2H), 1.77-1.84 (m, 2H), 1.52 (s, 6H), 1.48 (s, 6H) |
| 99 | MS m/z 454.5 [M + H]$^+$; $^1$H NMR (DMSO-d$_6$) δ: 9.15-9.26 (m, 1H), 9.05 (s, 1H), 9.03 (s, 1H), 8.12-8.21 (m, 1H), 8.09 (d, J = 8.5 Hz, 1H), 7.77 (d, J = 2.1 Hz, 1H), 7.69 (dd, J = 8.5, 2.1 Hz, 1H), 5.17-5.32 (m, 1H), 3.14 (s, 3H), 1.98-2.09 (m, 2H), 1.76-1.85 (m, 2H), 1.52 (s, 6H), 1.49 (s, 6H) |
| 119 | MS m/z 424.3 [M + H]$^+$; $^1$H NMR (DMSO-d$_6$) δ: 9.11-9.23 (m, 1H), 9.03 (s, 1H), 8.10-8.20 (m, 1H), 8.08 (d, J = 8.5 Hz, 1H), 7.73 (d, J = 1.8 Hz, 1H), 7.67 (dd, J = 8.5, 2.1 Hz, 1H), 5.16-5.33 (m, 1H), 3.14 (s, 3H), 2.61 (s, 3H), 2.03 (t, J = 12.8 Hz, 2H), 1.76-1.87 (m, 2H), 1.52 (s, 6H), 1.49 (s, 6H) |
| 121 | MS m/z 395.2 [M + H]$^+$; $^1$H NMR (DMSO-d$_6$) δ: 11.33 (br s, 1H), 9.35 (br s, 1H), 8.97 (s, 1H), 8.15 (s, 2H), 8.07 (br s, 1H), 8.00 (d, J = 8.5 Hz, 1H), 7.71 (d, J = 1.5 Hz, 1H), 7.62 (dd, J = 8.5, 2.0 Hz, 1H), 4.40 (br s, 1H), 2.06 (d, J = 12.5 Hz, 2H), 1.63 (t, J = 12.5 Hz, 2H), 1.50 (s, 6H), 1.45 (s, 6H) |
| 122 | MS m/z 396.3 [M + H]$^+$; $^1$H NMR (DMSO-d$_6$) δ: 11.18 (s, 1H), 9.24 (s, 1H), 9.18-9.13 (m, 1H), 8.37-8.30 (m, 1H), 8.17 (s, 2H), 8.03 (d, J = 8.5 Hz, 1H), 7.78 (d, J = 2.0 Hz, 1H), 7.68 (dd, J = 8.5, 2.0 Hz, 1H), 5.66-5.61 (m, 1H), 2.35 (dd, J = 13.0, 3.0 Hz, 2H), 1.86 (t, J = 12.5 Hz, 2H), 1.52 (s, 6H), 1.51 (s, 6H) |
| 133 | MS m/z 443.4 [M + H]$^+$; $^1$H NMR (DMSO-d$_6$) δ: 9.40 (s, 1H), 9.15-9.23 (m, 1H), 9.05 (s, 1H), 8.10-8.18 (m, 1H), 8.03 (d, J = 9.2 Hz, 1H), 7.43-7.49 (m, 2H), 5.18-5.29 (m, 1H), 3.13 (s, 3H), 2.03 (t, J = 12.8 Hz, 2H), 1.78-1.84 (m, 2H), 1.52 (s, 6H), 1.49 (s, 6H) |
| 135 | MS m/z 433.5 [M + H]$^+$; $^1$H NMR (DMSO-d$_6$) δ: 9.42 (s, 1H), 9.17 (s, 1H), 8.44 (s, 1H), 8.07 (d, J = 8.5 Hz, 1H), 7.56 (s, 1H), 7.40-7.47 (m, 1H), 5.20-5.36 (m, 1H), 3.16 (s, 3H), 1.64-1.72 (m, 2H), 1.51-1.58 (m, 2H), 1.32 (s, 6H), 1.18 (s, 6H); 2Hs not observed (OH and NH) |
| 139 | MS m/z 433.5 [M + H]$^+$; $^1$H NMR (DMSO-d$_6$) δ: 9.20 (s, 1H), 8.87 (s, 1H), 8.65 (s, 1H), 8.13 (d, J = 8.5 Hz, 1H), 7.32-7.42 (m, 2H), 5.22-5.40 (m, 1H), 3.18 (s, 3H), 1.52-1.69 (m, 4H), 1.34 (s, 6H), 1.20 (s, 6H); 2Hs not observed (OH and NH) |
| 140 | MS m/z 450.5 [M + H]$^+$; $^1$H NMR (DMSO-d$_6$) δ: 9.40 (s, 1H), 9.14-9.23 (m, 1H), 9.05 (s, 1H), 8.09-8.21 (m, 1H), 8.03 (d, J = 9.2 Hz, 1H), 7.41-7.51 (m, 2H), 5.17-5.31 (m, 1H), 3.17 (s, 3H), 3.13 (s, 3H), 2.03 (t, J = 12.8 Hz, 2H), 1.75-1.86 (m, 2H), 1.52 (s, 6H), 1.49 (s, 6H); 1H not observed (OH or NH) |
| 161 | MS m/z 438.6 [M + H]$^+$; $^1$H NMR (DMSO-d$_6$) δ: 9.31-9.44 (m, 1H), 9.06 (s, 1H), 8.38 (s, 1H), 8.24-8.34 (m, 1H), 7.95 (d, J = 8.5 Hz, 1H), 7.70 (s, 1H), 7.49 (s, 1H), 7.41 (d, J = 8.5 Hz, 1H), 5.16-5.30 (m, 1H), 4.45 (s, 2H), 3.12 (s, 3H), 2.07 (t, J = 12.8 Hz, 2H), 1.72-1.84 (m, 2H), 1.52 (s, 6H), 1.51 (s, 6H); 1H not observed (OH) |
| 172 | MS m/z 439.5 [M + H]$^+$; $^1$H NMR (DMSO-d$_6$) δ: 9.02 (s, 1H), 8.04 (s, 1H), 8.01 (d, J = 8.5 Hz, 1H), 7.65 (s, 1H), 7.59 (d, J = 8.9 Hz, 1H), 5.45 (t, J = 5.5 Hz, 1H), 5.15-5.29 (m, 1H), 4.66 (d, J = 5.8 Hz, 2H), 3.12 (s, 3H), 1.67-1.89 (m, 4H), 1.43 (s, 6H), 1.33 (s, 6H); 2Hs not observed (OH and NH) |
| 187 | MS m/z 380.3 [M + H]$^+$; $^1$H NMR (methanol-d$_4$) δ: 9.38 (br s, 1H), 9.16 (s, 1H), 8.11 (d, J = 9.0 Hz, 1H), 8.07 (s, 1H), 7.73 (s, 1H), 7.35-7.33 (m, 2H), 4.31-4.22 (m, 2H), 4.02-3.98 (m, 1H), 3.80-3.75 (m, 2H), 2.68-2.62 (m, 1H), 2.33-2.25 (m, 1H), 1.49 (s, 9H); 2Hs not observed (NH and OH) |
| 197 | MS m/z 394.3 [M + H]$^+$; $^1$H NMR (methanol-d$_4$) δ: 9.37 (s, 1H), 9.16 (s, 1H), 8.10 (d, J = 8.0 Hz, 1H), 7.83 (s, 1H), 7.32-7.30 (m, 2H), 4.31-4.22 (m, 2H), 4.02-3.98 (m,1H), 3.81-3.75 (m, 2H), 2.68-2.62 (m, 1H), 2.45 (s, 3H), 2.33-2.26 (m, 1H), 1.49 (s, 9H); 2Hs not observed (NH and OH) |
| 204 | MS m/z 381.5 [M + H]$^+$; $^1$H NMR (DMSO-d$_6$) δ: 11.37 (br s, 1H), 9.02 (s, 1H), 8.15 (s, 2H), 8.00 (d, J = 8.2 Hz, 1H), 7.72 (s, 1H), 7.63 (d, J = 8.2 Hz, 1H), 3.92-4.02 (m, 2H), 3.72-3.85 (m, 2H), 3.50-3.62 (m, 3H), 1.24 (s, 9H); 1 H not observed (OH or NH) |
| 218 | MS m/z 339.2 [M + H]$^+$; $^1$H NMR (DMSO-d$_6$) δ: 9.03 (s, 1H), 8.14 (s, 2H), 7.99 (d, J = 8.5 Hz, 1H), 7.71 (s, 1H), 7.64 (d, J = 8.5 Hz, 1H), 3.75-3.98 (m, 4H), 3.62-3.70 (br s, 1H), 2.66 (s, 3H), 2.40-2.48 (m, 1H), 2.25-2.35 (m, 1H); 2Hs not observed (NH and OH) |
| 219 | MS m/z 356.2 [M + H]$^+$; $^1$H NMR (DMSO-d$_6$) δ: 9.05 (s, 1H), 8.69 (d, J = 4 Hz, 1H), 7.94 (d, J = 8.5 Hz, 1H), 7.86 (d, J = 4 Hz, 1H), 7.47 (s, 1H), 7.39 (d, J = 8.5 Hz, 1H), 3.70-4.00 (m, 4H), 3.60-3.70 (m, 1H), 2.66 (s, 3H), 2.40-2.50 (m, 1H), 2.25-2.35 (m, 1H); 2Hs not observed (NH and OH) |
| 220 | MS m/z 338.2 [M + H]$^+$; $^1$H NMR (DMSO-d$_6$) δ: 9.76 (s, 1H), 9.10 (s, 1H), 8.31 (s, 1H), 8.08 (d, J = 5 Hz, 1H), 7.95 (s, 1H), 7.42 (m, 2H), 3.80-4.00 (m, 4H), 3.72 (m, 1H), 2.65 (s, 3H), 2.43 (m, 1H), 2.31 (m, 1H); 2Hs not observed (NH and OH) |
| 228 | MS m/z 392.5 [M + H]$^+$; $^1$H NMR (methanol-d$_4$) δ: 9.42 (s, 1H), 7.85 (s, 2H), 7.34-7.31 (m, 2H), 5.98 (s, 1H), 4.27 (s, 2H), 4.16 (s, 2H), 3.53 (d, J = 12.8 Hz, 3H), 3.20-3.12 (m, 2H), 2.91 (s, 3H), 2.45 (s, 3H), 2.37 (d, J = 14.5 Hz, 2H), 2.13 (t, J = 11.9 Hz, 2H); 1H not observed (OH) |
| 229 | MS m/z 396.5 [M + H]$^+$; $^1$H NMR (methanol-d$_4$) δ: 8.34 (d, J = 4.4 Hz, 1H), 7.73-7.64 (m, 2H), 7.41-7.33 (m, 2H), 5.94 (s, 1H), 4.26 (s, 2H), 4.14 (s, 2H), 3.53 (d, J = 12.7 Hz, 2H), 3.14 (t, J = 12.7 Hz, 2H), 2.90 (s, 3H), 2.37 (d, J = 14.6 Hz, 2H), 2.13 (t, J = 13.8 Hz, 2H); 1H not observed (OH) |
| 230 | MS m/z 396.4 [M + H]$^+$; $^1$H NMR (methanol-d$_4$) δ: 8.13 (s, 1H), 7.76 (d, J = 8.5 Hz, 1H), 7.41 (d, J = 7.5 Hz, 1H), 7.22 (d, J = 9.1 Hz, 1H), 7.20 (s, 1H), 5.95 (s, 1H), 4.26 (s, 2H), 4.15 (s, 2H), 3.53 (d, J = 12.4 Hz, 2H), 3.15 (t, J = 12.6 Hz, 2H), 2.90 (s, 3H), 2.37 (d, J = 14.4 Hz, 2H), 2.13 (t, J = 13.8 Hz, 2H); 1H not observed (OH) |
| 231 | MS m/z 378.4 [M + H]$^+$; $^1$H NMR (methanol-d$_4$) δ: 9.57 (s, 1H), 8.14 (s, 1H), 7.87 (d, J = 8.2 Hz, 1H), 7.80 (s, 1H), 7.37 (d, J = 8.9 Hz, 2H), 5.99 (s, 1H), 4.28 (s, 2H), 4.16 (s, 2H), 3.53 (d, J = 12.7 Hz, 2H), 3.15 (t, J = 12.6 Hz, 2H), 2.90 (s, 3H), 2.37 (d, J = 14.3 Hz, 2H), 2.14 (t, J = 13.6 Hz, 2H); 1H not observed (OH) |

| Cpd | Data |
|---|---|
| 232 | MS m/z 379.4 [M + H]+; 1H NMR (methanol-d4) δ: 9.06 (s, 1H), 8.00-7.90 (m, 3H), 7.73-7.65 (m, 2H), 4.09 (br d, J = 20.9 Hz, 4H), 3.51 (br s, 2H), 3.11 (br s, 2H), 2.90 (s, 3H), 2.30 (br s, 2H), 2.08 (br s, 2H); 1H not observed (OH) |
| 238 | MS m/z 381.5 [M + H]+; 1H NMR (DMSO-d6) δ: 11.37 (br s, 1H), 9.02 (s, 1H), 8.15 (s, 2H), 8.00 (d, J = 8.2 Hz, 1H), 7.72 (s, 1H), 7.63 (d, J = 8.2 Hz, 1H), 3.92-4.02 (m, 2H), 3.72-3.85 (m, 2H), 3.50-3.62 (m, 3H), 1.24 (s, 9H); 1H not observed (OH or NH) |
| 239 | MS m/z 426.5 [M + H]+; 1H NMR (DMSO-d6) δ: 10.06-10.18 (m, 1H), 9.66 (s, 1H), 9.08 (s, 1H), 8.36 (br s, 1H), 8.13 (d, J = 13.4 Hz, 1H), 8.07 (d, J = 8.2 Hz, 1H), 8.03 (s, 1H), 7.39 (s, 1H), 7.36 (d, J = 8.2 Hz, 1H), 4.74-4.84 (m, 2H), 2.38 (s, 3H), 1.96-2.07 (m, 1H), 1.84-1.93 (m, 1H), 1.57 (d, J = 18.5 Hz, 6H), 1.49 (d, J = 5.8 Hz, 6H) |
| 240 | MS m/z 430.5 [M + H]+; 1H NMR (DMSO-d6) δ: 9.94 (br s, 1H), 9.10 (s, 1H), 8.33 (br s, 1H), 8.13 (d, J = 13.1 Hz, 1H), 8.07 (s, 1H), 8.00 (d, J = 8.2 Hz, 1H), 7.57 (d, J = 8.2 Hz, 1H), 6.77-7.37 (m, 3H), 4.76-4.85 (m, 2H), 1.95-2.07 (m, 1H), 1.85-1.94 (m, 1H), 1.57 (d, J = 18.5 Hz, 6H), 1.48 (d, J = 6.1 Hz, 6H) |
| 264 | MS m/z 367.44 [M + H]+; 1H NMR (methanol-d4) δ: 9.06 (s, 1H), 7.87-7.98 (m, 3H), 7.59-7.68 (m, 2H), 3.96 (dd, J = 11.0, 7.0 Hz, 1H), 3.76-3.91 (m, 1H), 3.54-3.70 (m, 2H), 3.38 (br dd, J = 11.1, 6.6 Hz, 1H), 2.98 (dt, J = 12.5, 6.3 Hz, 1H), 2.29-2.39 (m, 1H), 1.86-1.97 (m, 1H), 1.14 (t, J = 6.1 Hz, 6H); 2Hs not observed (NH and OH) |
| 273 | MS m/z 394.4 [M + H]+; 1H NMR (methanol-d4) δ: 9.58 (s, 1H), 8.15 (s, 1H), 7.89 (d, J = 8.1 Hz, 1H), 7.81 (s, 1H), 7.41-7.36 (m, 2H), 6.01 (s, 1H), 4.49-4.40 (m, 1H), 2.31-2.18 (m, 2H), 1.87-1.74 (m, 2H), 1.65 (s, 3H), 1.63 (s, 3H), 1.55 (s, 3H), 1.54 (s, 3H); 3Hs not observed (2 NHs and OH) |
| 274 | MS m/z 408.4 [M + H]+; 1H NMR (methanol-d4) δ: 9.44 (s, 1H), 7.89-7.83 (m, 2H), 7.36-7.31 (m, 2H), 6.00 (s, 1H), 4.48-4.38 (m, 1H), 2.28-2.19 (m, 2H), 1.86-1.75 (m, 2H), 1.64 (s, 3H), 1.63 (s, 3H), 1.55 (s, 3H), 1.54 (s, 3H); 3Hs not observed (2NHs and OH) |
| 275 | MS m/z 412.5 [M + H]+; 1H NMR (methanol-d4) δ: 7.99 (s, 1H), 7.77 (d, J = 8.6 Hz, 1H), 7.35 (d, J = 9.5 Hz, 1H), 7.22 (d, J = 8.6 Hz, 1H), 7.19 (s, 1H), 5.98 (s, 1H), 4.37 (m, 1H), 2.29-2.18 (m, 2H), 1.78 (m, 2H), 1.63 (s, 3H), 1.61 (s, 3H), 1.55 (s, 3H), 1.53 (s, 3H); 2Hs not observed (NH and OH) |
| 276 | MS m/z 412.4 [M + H]+; 1H NMR (methanol-d4) δ: 8.35 (d, J = 4.5 Hz, 1H), 7.71 (d, J = 8.5 Hz, 1H), 7.69 (d, J = 4.0 Hz, 1H), 7.40-7.35 (m, 2H), 5.97 (s, 1H), 4.41-4.30 (m, 1H), 2.31-2.19 (m, 2H), 1.84-1.72 (m, 2H), 1.63 (s, 3H), 1.61 (s, 3H), 1.55 (s, 3H), 1.53 (s, 3H); 3Hs not observed (2NHs and OH |
| 315 | MS m/z 420.5 [M + H]+; 1H NMR (methanol-d4) δ: 9.00 (s, 1H), 8.47 (s, 2H), 8.37 (d, J = 2.6 Hz, 1H), 8.07 (d, J = 4.6 Hz, 1H), 7.73 (d, J = 8.5 Hz, 1H), 7.66 (d, J = 8.0 Hz, 1H), 7.34 (dd, J = 8.4, 4.9 Hz, 1H), 6.73 (dd, J = 8.5, 2.1 Hz, 1H), 6.70 (d, J = 2.1 Hz, 1H), 4.54 (br s, 1H), 2.29 (br dd, J = 13.9, 3.4 Hz, 2H), 1.62-1.66 (m, 2H), 1.61 (s, 6H), 1.49 (s, 6H) |
| 324 | MS m/z 413.4 [M + H]+; 1H NMR (methanol-d4) δ: 9.08 (s, 1H), 7.97 (d, J = 9.2 Hz, 1H), 7.93-7.97 (m, 2H), 7.69-7.75 (m, 2H), 4.71-4.83 (m, 1H), 4.42-4.65 (m, 1H), 1.74-1.86 (m, 2H), 1.41 (m, 6H), 1.28-1.31 (m, 6H); 3Hs not observed (2NHs and OH) |
| 326 | MS m/z 380.3 [M + H]+; 1H NMR (methanol-d4) δ: 9.08 (s, 1H), 8.07 (s, 1H), 7.95 (d, J = 8.5 Hz, 1H), 7.33 (s, 1H), 7.15 (d, J = 9.0 Hz, 1H), 7.13 (s, 1H), 4.06 (dd, J = 11.0, 6.5 Hz, 1H), 3.97-3.88 (m, 2H), 3.73-3.70 (m, 1H), 3.60 (dd, J = 11.5, 6.0 Hz, 1H), 3.29-3.25 (m, 1H), 2.51-2.42 (m, 1H), 2.26 (s, 3H), 2.15-2.06 (m, 1H), 1.28 (t, J = 5.0 Hz, 6H); 2Hs not observed (NH and OH) |
| 331 | MS m/z 366.4 [M + H]+; 1H NMR (methanol-d4) δ: 9.16 (s, 1H), 8.75 (br s, 1H), 8.07 (br d, J = 8.5 Hz, 1H), 7.85 (br s, 1H), 7.44 (m, 2H), 7.23-7.35 (m, 2H), 4.13-4.32 (m, 2H), 3.97-4.08 (m, 1H), 3.76-3.91 (m, 2H), 3.48-3.70 (m, 1H), 2.58-2.69 (m, 1H), 2.24-2.40 (m, 1H), 1.46 (t, J = 4.6 Hz, 6H); 2Hs not observed (NH and OH) |
| 338 | MS m/z 384.3 [M + H]+; 1H NMR (methanol-d4) δ: 9.13 (s, 1H), 8.33 (dd, J = 15.0, 4.0 Hz, 1H), 7.85 (dd, J = 111.5, 8.5 Hz, 1H), 7.68 (dd, J = 9.0, 3.5 Hz, 1H), 7.39-7.35 (m, 2H), 4.31-4.22 (m, 1H), 4.18-4.10 (m, 1H), 4.00-3.75 (m, 3H), 3.60-3.51 (m, 1H), 2.67-2.58 (m, 1H), 2.48-2.29 (m, 1H), 1.44 (t, J = 6.0 Hz, 6H); 2Hs not observed (NH and OH) |
| 381 | MS m/z 459.3 [M + H]+; 1H NMR (DMSO-d6) δ: 9.42 (s, 1H), 9.04 (s, 1H), 8.57 (s, 1H), 8.42 (d, J = 5.6 Hz, 1H), 8.30 (s, 1H), 8.06 (d, J = 9.0 Hz, 1H), 7.93 (dd, J = 5.5, 1.1 Hz, 1H), 7.47-7.55 (m, 2H), 5.20-5.27 (m, 1H), 3.11 (s, 3H), 1.57-1.71 (m, 4H), 1.33 (s, 6H), 1.21 (s, 6H); 1H not observed (OH or NH) |
| 417 | MS m/z 407.5 [M + H]+; 1H NMR (methanol-d4): 9.13 (s, 1H), 8.01 (d, J = 9.00 Hz, 1H), 7.96 (s, 2H), 7.73 (s, 2H), 5.41-5.30 (m, 1H), 3.22 (s, 3H), 2.37-2.31 (m, 2H), 2.15-2.01 (m, 6H), 1.57 (s, 6H); 2Hs not observed (NH and OH) |

Example 6

Preparation of Compound 13

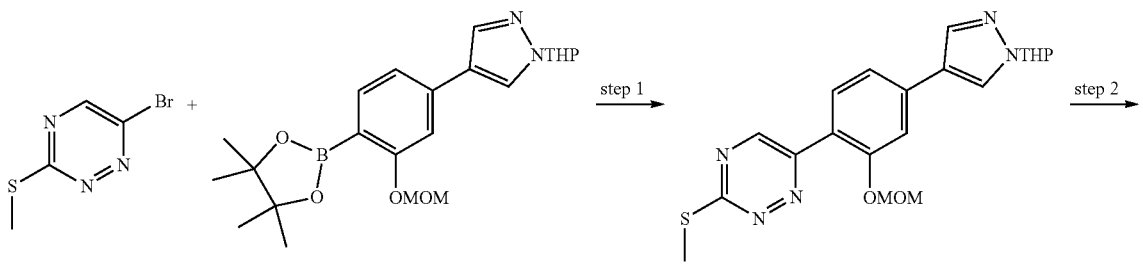

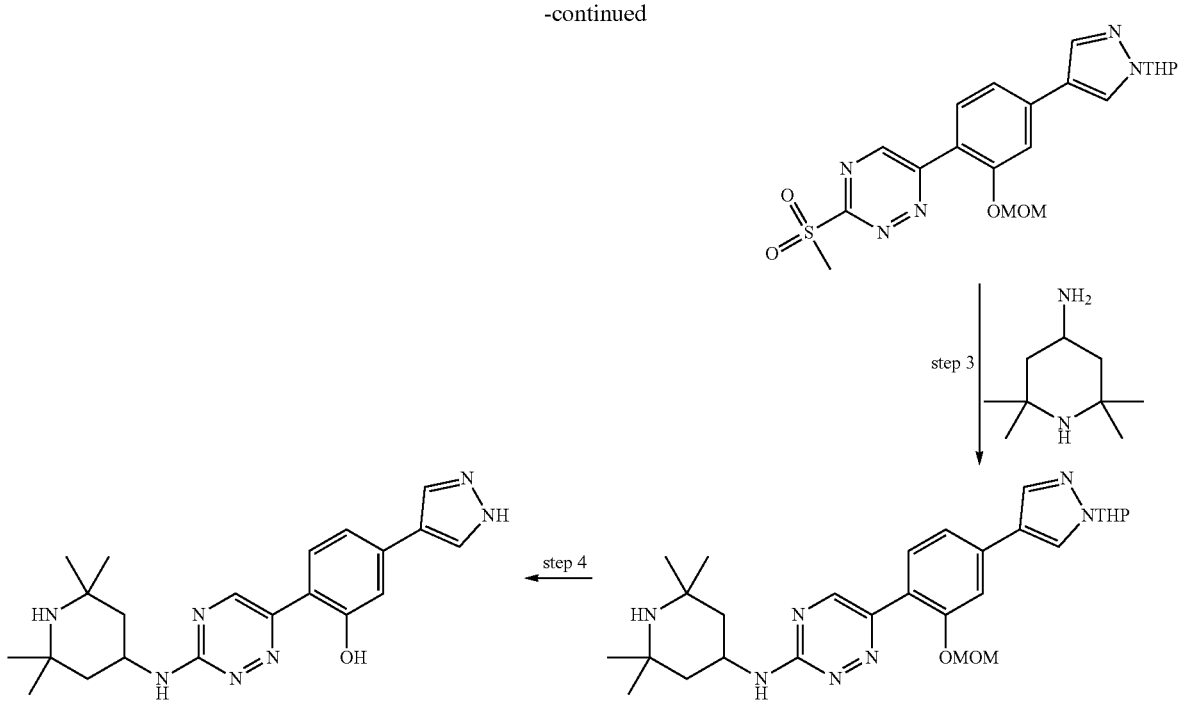

Step 1: A dry screw cap vial was equipped with a magnetic stir bar and charged with 6-bromo-3-(methylthio)-1,2,4-triazine (0.2 g, 0.9 mmol, 1.0 equiv), 4-(3-(methoxymethoxy)-4-(4,4,5,5-tetramethyl-1,3,2-dioxaborolan-2-yl)phenyl)-1-(tetrahydro-2H-pyran-2-yl)-1H-pyrazole (0.4 g, 1.0 mmol), [1,1'-bis(diphenylphosphino)ferrocene] dicholoropalladium(II) (0.08 g, 0.1 mmol), and $K_2CO_3$ (0.4 g, 2.6 mmol) and was purged with argon. Dioxane (4 mL) and water (1 mL) were added, and the reaction was stirred at 90° C. for 1 h. The crude mixture was partitioned between water and EtOAc, washed with water, and the organic layer was dried over $MgSO_4$, filtered, and concentrated. The crude oil was purified by silica gel chromatography eluting with a EtOAc/hexanes gradient (0-75% EtOAc) to afford 6-(2-(methoxymethoxy)-4-(1-(tetrahydro-2H-pyran-2-yl)-1H-pyrazol-4-yl)phenyl)-3-(methylthio)-1,2,4-triazine (0.2 g, 61% yield) as a yellow solid. MS m/z 414.2 $[M+H]^+$.

Step 2: To a solution of 6-(2-(methoxymethoxy)-4-(1-(tetrahydro-2H-pyran-2-yl)-1H-pyrazol-4-yl)phenyl)-3-(methylthio)-1,2,4-triazine (0.7 g, 1.7 mmol) in $CH_2Cl_2$ (15 mL) was added 3-chlorobenzoperoxoic acid (0.6 g, 3.4 mmol). The reaction mixture was stirred at 22° C. for 2 h. The crude mixture was purified by silica gel chromatography eluting with a EtOAc/hexanes gradient (0-100% EtOAc) to afford 6-(2-(methoxymethoxy)-4-(1-(tetrahydro-2H-pyran-2-yl)-1H-pyrazol-4-yl)phenyl)-3-(methylsulfonyl)-1,2,4-triazine (0.6 g, 1.3 mmol, 78%) as yellow solid. MS m/z 446.2 $[M+H]^+$.

Step 3: A vial was equipped with a magnetic stir bar and charged with 6-(2-(methoxymethoxy)-4-(1-(tetrahydro-2H-pyran-2-yl)-1H-pyrazol-4-yl)phenyl)-3-(methylsulfonyl)-1,2,4-triazine (0.06 g, 0.13 mmol), 2,2,6,6-tetramethylpiperidin-4-amine (0.03 g, 0.18 mmol), and dichloroethane (5 mL) and the reaction was stirred at room temperature for 48 h. The solvents were removed, and the crude solid was purified by silica gel chromatography, eluting with a MeOH/$CH_2Cl_2$ gradient (0-15% MeOH, containing 2.5% $NH_4OH$) to afford 6-(2-(methoxymethoxy)-4-(1-(tetrahydro-2H-pyran-2-yl)-1H-pyrazol-4-yl)phenyl)-N-(2,2,6,6-tetramethylpiperidin-4-yl)-1,2,4-triazin-3-amine (0.03 g, 36% yield) as yellow solid. MS m/z 522.3 $[M+H]^+$.

Step 4: To a solution of 6-(2-(methoxymethoxy)-4-(1-(tetrahydro-2H-pyran-2-yl)-1H-pyrazol-4-yl)phenyl)-N-(2,2,6,6-tetramethylpiperidin-4-yl)-1,2,4-triazin-3-amine (0.03 g, 0.05 mmol) in MeOH (1 mL) was added 4.0M HCl in dioxane (1 mL), and the mixture was stirred for 1 h at room temperature. The solvents were removed, and the crude residue was purified by silica gel chromatography eluting with a MeOH/$CH_2Cl_2$ gradient (0-15% MeOH, containing 2.5% $NH_4OH$) to afford 5-(1H-pyrazol-4-yl)-2-(3-((2,2,6,6-tetramethylpiperidin-4-yl)amino)-1,2,4-triazin-6-yl)phenol hydrochloride (0.02 g, 72% yield) as a yellow solid.

MS m/z 394.3 $[M+H]^+$; $^1H$ NMR (methanol-$d_4$) δ: 9.07 (s, 1H), 8.08 (br s, 1H), 7.96 (br s, 1H), 7.83 (d, J=8.5 Hz, 1H), 7.24, (dd, J=8.0, 1.5 Hz, 1H), 7.21 (d, J=2.0 Hz, 1H), 4.58 (t, J=12.5 Hz, 1H), 2.30 (dd, J=13.5, 2.5 Hz, 2H), 1.66-1.60 (m, 2H), 1.62 (s, 6H), 1.50 (s, 6H); 4 Hs not observed (3NHs and OH).

Using the procedure described for Example 6, additional compounds described herein may be prepared by substituting the appropriate starting material, suitable reagents and reaction conditions, obtaining compounds such as those selected from:

| Cpd | Data |
|---|---|
| 11 | MS m/z 395.5 $[M + H]^+$; $^1H$ NMR (DMSO-$d_6$) δ: 13.06 (br s, 1H), 10.96 (br s, 1H), 9.29 (s, 1H), 8.24 (br s, 1H), 7.94 (s, 1H), 7.90 (d, J = 8.0 Hz, 1H), 7.28 (dd, J = 8.0, 1.5 Hz, 1H), 7.25 (d, J = 1.5 Hz, 1H), 5.61 (t, J = 10.0 Hz, 1H), 2.27 (br s, 2H), 1.01-1.97 (m, 14H); 1H not observed (NH or OH) |
| 19 | MS m/z 352.4 $[M + H]^+$; $^1H$ NMR (methanol-$d_4$) δ: 9.10 (s, 1H), 8.02 (br. s, 2H), 7.85 (d, J = 8.5 Hz, 1H), 7.25 (dd, J = 8.0, 1.5 Hz, 1H), 7.21 (d, J = 1.5 Hz, 1H), 4.98 (dt, J = 12.0, 4.0 Hz, 1H), 3.59 (d, |

| Cpd | Data |
|---|---|
| | J = 13.0 Hz, 2H), 3.26 (d, J = 3.5 Hz, 1H), 3.24 (s, 3H), 3.21 (d, J = 2.5 Hz, 1H), 2.22 (dd, J = 13.0, 3.5 Hz, 2H), 2.07 (d, J = 3.0 Hz, 2H); 3Hs not observed (2NHs and OH). |
| 20 | MS m/z 352.2 [M + H]⁺; ¹H NMR (methanol-d₄) δ: 9.13 (s, 1H), 8.02 (br. s, 2H), 7.85 (d, J = 8.0 Hz, 1H), 7.25 (d, J = 8.5, 2.0 Hz, 1H), 7.21 (d, J = 1.5 Hz, 1H), 4.22 (dd, J = 15.5, 8.5 Hz, 1H), 4.01-3.95 (m, 1H), 3.92 (dd, J = 15.0, 3.5 Hz, 1H), 3.45 (dd, J = 18.5, 8.0 Hz, 1H), 3.39 (s, 3H), 2.34-2.28 (m, 1H), 2.22-2.01 (m, 3H), 1.87 (dd, J = 13.0, 9.5 Hz, 1H); 3Hs not observed (2NHs and OH). |
| 21 | MS m/z 378.3 [M + H]⁺; ¹H NMR (methanol-d₄): 9.09 (s, 1H), 8.01 (br. s, 2H), 7.83 (d, J = 8.5 Hz, 1H), 7.24 (dd, J = 8.0, 1.5 Hz, 1H), 7.20 (d, J = 1.5 Hz, 1H), 5.36-5.29 (m, 1H), 4.20 (br. s, 2H), 3.19 (s, 3H), 2.28 (dt, J = 3.5, 15 Hz, 4H), 2.23 (br. s, 4H), 2.0-1.94 (m, 2H); 1H not observed (NH or OH). |
| 22 | MS m/z 392.3 [M + H]⁺; ¹H NMR (methanol-d₄) δ: 9.10 (s, 1H), 8.02 (br. s, 2H), 7.84 (d, J = 10 Hz, 1H), 7.24 (dd, J = 8.0, 1.5 Hz, 1H), 7.21 (d, J = 1.5 Hz, 1H), 5.98-5.92 (m, 1H), 3.88 (br. s, 2H), 3.18 (s, 3H), 2.46 (dt, J = 3.6, 14 Hz, 2H), 2.31-2.16 (m, 4H), 2.13-2.06 (m, 4H), 1.92-1.89 (m, 2H); 1H not observed (NH or OH). |
| 52 | MS m/z 352.4 [M + H]⁺; ¹H NMR (methanol-d₄) δ: 9.07 (s, 1H), 8.01 (s, 2H), 7.83 (d, J = 8.5 Hz, 1H), 7.24 (dd, J = 8.5, 2.0 Hz, 1H), 7.21 (d, J = 2.0 Hz, 1H), 4.18-4.22 (m, 1H), 3.52-3.56 (m, 2H), 3.19-3.27 (m, 2H), 2.91 (s, 3H), 2.34-2.36 (m, 2H), 1.92-2.00 (m, 2H); 3Hs not observed (2NHs and OH) |
| 67 | MS m/z 426.6 [M + H]⁺; ¹H NMR (methanol-d₄) δ: 9.19 (s, 1H), 8.52-8.06 (m, 1H), 7.88 (d, J = 7.5 Hz, 1H), 7.28 (d, J = 8.3 Hz, 2H), 7.24 (s, 1H), 5.60 (dd, J = 33.5, 13.3 Hz, 1H), 3.34 (s, 3H), 2.52 (t, J = 13.5 Hz, 1H), 2.02 (d, J = 12.5 Hz, 1H), 1.72 (s, 3H), 1.68 (s, 3H), 1.62 (s, 3H), 1.58 (s, 3H), 0.94-0.86 (m, 1H); 3Hs not observed (2 NHs and OH) |
| 82 | MS m/z 367.4 [M + H]⁺; ¹H NMR (methanol-d₄) δ: 9.31 (s, 1H), 8.09 (br s, 1H), 7.94 (br s, 1H), 7.92 (d, J = 8.5 Hz, 1H), 7.27 (dd, J = 9.5 Hz, 1H), 7.22 (s, 1H), 5.40-5.46 (m, 1H), 3.44-3.49 (m, 2H), 2.58-2.61 (m, 2H), 1.68 (q, J = 12.5 Hz, 2H), 1.43 (s, 3H), 1.42 (s, 3H); 3Hs not observed (2 NHs and OH) |
| 95 | MS m/z 364.5 [M + H]⁺; ¹H NMR (methanol-d₄) δ: 9.06 (s, 1H), 7.81 (d, J = 8.0 Hz, 1H), 7.60 (d, J = 8.0 Hz, 1H), 7.25-7.19 (m, 3H), 4.00-3.93 (m, 6H), 3.70-3.65 (m, 2H), 2.15-2.09 (m, 2H), 2.00 (t, J = 5.7 Hz, 2H); 3Hs not observed (2NHs and OH) |
| 96 | MS m/z 364.5 [M + H]⁺; ¹H NMR (methanol-d₄) δ: 8.08 (s, 2H), 7.59 (d, J = 8.5 Hz, 1H), 7.25 (d, J = 8.5 Hz, 1H), 7.21 (s, 1H), 5.94 (s, 1H), 4.19 (s, 4H), 3.26 (t, J = 5.0 Hz, 4H), 2.19 (t, J = 5.0 Hz, 4H); 3Hs not observed (2NHs and OH) |
| 100 | MS m/z 336.4 [M + H]⁺; ¹H NMR (DMSO-d₆) δ: 9.07 (s, 1H), 8.27-8.19 (br s, 1H), 7.98-7.92 (br s, 1H), 7.83 (d, J = 8.0 Hz, 1H), 7.22 (dd, J = 8.0, 2.0 Hz, 1H), 7.19 (d, J = 1.5 Hz, 1H), 3.88-3.82 (m, 2H), 3.68-3.62 (m, 2H), 2.64 (t, J = 2.0 Hz, 1H), 1.93 (s, 2H); 3Hs not observed (2NHs and OH) |
| 109 | MS m/z 364.3 [M + H]⁺; ¹H NMR (DMSO-d₆) δ: 11.33 (br s, 1H), 9.07 (s, 1H), 8.20 (br s, 1H), 7.95 (s, 1H), 7.83 (d, J = 8.0 Hz, 1H), 7.23-7.20 (m, 2H), 3.98 (d, J = 9.0 Hz, 2H), 3.84 (d, J = 8.5, 2H), 3.01 (s, 2H), 2.75 (s, 2H), 1.81 (t, J = 5.0 Hz, 2H), 1.55 (t, J = 5.0 Hz, 2H); 2 H not observed (2 NHs) |
| 110 | MS m/z 350.2 [M + H]⁺; ¹H NMR (DMSO-d₆) δ: 9.14 (br s, 1H), 9.10 (s, 1H), 8.95 (br s, 1H), 8.08 (s, 2H), 7.84 (d, J = 8.0 Hz, 1H), 7.23-7.20 (m, 2H), 4.08-4.05 (m, 2H), 3.97-3.94 (m, 2H), 3.86 (br s, 2H), 3.64 (br s, 2H), 2.32 (t, J = 7.0 Hz, 2H); 1H not observed (NH or OH) |
| 120 | MS m/z 395.3 [M + H]⁺; ¹H NMR (methanol-d₄) δ: 9.22 (s, 1H), 7.93 (s, 2H), 7.82 (d, J = 8.5 Hz, 1H), 7.18 (dd, J = 8.00, 1.5 Hz, 1H), 7.12 (s, 1H), 5.37-5.30 (m, 1H), 2.64-2.61 (m, 2H), 1.83-1.75 (m, 2H), 1.63-1.49 (m, 4H), 0.98 (t, J = 10 Hz, 6H); 3Hs not |
| | observed (2NHs and OH); 2Hs (CH₂ signal) are obscured by the solvent peak at 3.33 ppm |
| 113 | MS m/z 378.3 [M + H]⁺; ¹H NMR (methanol-d₄) δ: 9.05 (s, 1H), 8.07 (br s, 1H), 7.92 (s, 1H), 7.82 (d, J = 8.0 Hz, 1H), 7.22 (dd, J = 8.0, 2.0 Hz, 1H), 7.19 (d, J = 2.0 Hz, 1H), 3.93-3.88 (m, 2H), 3.22-3.17 (m, 3H), 2.67 (s, 3H), 2.53 (t, J = 8.0 Hz, 2H), 2.24 (d, J = 11.0 Hz, 2H), 2.00 (td, J = 12.0, 4.0 Hz, 2H); 1H not observed (NH or OH) |
| 114 | MS m/z 338.3 [M + H]⁺; ¹H NMR (methanol-d₄) δ: 8.12 (s, 2H), 7.61 (d, J = 8.0 Hz, 1H), 7.22 (dd, J = 8.0, 2.0 Hz, 1H), 7.21 (s, 1H), 5.96 (s, 1H), 4.16-4.07 (m, 2H), 4.05-3.74 (m, 3H), 2.83 (s, 3H), 2.65-2.59 (m, 1H), 2.49-2.38 (m, 1H); 3Hs not observed (2NHs and OH) |
| 115 | MS m/z 350.2 [M + H]⁺; ¹H NMR (methanol-d₄) δ: 8.25 (br s, 2H), 7.64 (d, J = 8.0 Hz, 1H), 7.27 (d, J = 8.0 Hz, 1H), 7.24 (s, 1H), 5.97 (d, J = 12.5 Hz, 1H), 4.26-4.00 (m, 3H), 3.70 (dd, J = 20.0, 5.0 Hz, 1H), 3.45 (dd, J = 26.0, 10.5 Hz, 1H), 1.24 (dt, J = 10.0, 5.0 Hz, 1H), 1.09-1.04 (m, 2H), 1.00-0.95 (m, 1H); 4Hs not observed (3NHs and OH) |
| 116 | MS m/z 364.3 [M + H]⁺; ¹H NMR (methanol-d₄) δ: 9.13 (d, J = 5.0 Hz, 1H), 8.03 (br s, 2H), 7.84 (d, J = 8.0 Hz, 1H), 7.23 (dd, J = 8.0, 1.5 Hz, 1H), 7.20 (d, J = 1.5 Hz, 1H), 5.34-5.15 (m, 1H), 4.34 (d, J = 15.0, 4.0 Hz, 1H), 4.17-3.97 (m, 2H), 3.86-3.75 (m, 1H), 3.68-3.64 (m, 1H), 3.51-3.36 (m, 2H), 3.26-3.09 (m, 2H), 2.43-2.09 (m, 3H), 2.04-1.83 (m, 1H); 1H not observed (NH or OH) |
| 117 | MS m/z 364.3 [M + H]⁺; ¹H NMR (methanol-d₄) δ: 9.14 (s, 1H), 8.02 (br s, 2H), 7.84 (d, J = 8.0 Hz, 1H), 7.23 (d, J = 8.0, 1H), 7.20 (s, 1H), 4.39 (d, J = 13.5 Hz, 1H), 4.26 (t, J = 7.0 Hz, 1H), 4.03-3.75 (m, 5H), 3.49-3.45 (m, 1H), 3.07 (s, 3H), 2.67-2.59 (m, 1H), 2.02-1.95 (m, 1H); 2Hs not observed (NH and OH) |
| 118 | MS m/z 336.2 [M + H]⁺; ¹H NMR (methanol-d₄) δ: 9.08 (s, 1H), 8.06 (br s, 1H), 7.92 (br s, 1H), 7.82 (d, J = 8.0, 1H), 7.22 (dd, J = 8.0, 2.0 Hz, 1H), 7.18 (d, J = 1.5 Hz, 1H), 4.46 (s, 4H), 4.35 (s, 4H); 3Hs not observed (2NHs and OH) |
| 126 | MS m/z 412.5 [M + H]⁺; ¹H NMR (DMSO-d₆) δ: 13.00 (br s, 1H), 11.45 (br s, 1H), 9.08 (s, 1H), 8.24 (br s, 1H), 7.95 (br s, 1H), 7.86 (d, J = 7.9 Hz, 1H), 7.20-7.25 (m, 2H), 4.30-4.70 (m, 2H), 1.64 (t, J = 13.1 Hz, 1H), 1.56 (dd, J = 12.2, 3.1 Hz, 1H), 1.33-1.47 (m, 1H), 1.22 (br d, J = 14.0 Hz, 6H), 1.09 (br d, J = 14.0 Hz, 6H); 1H not observed (OH) |
| 127 | MS m/z 392.3 [M + H]⁺; ¹H NMR (methanol-d₄) δ: 9.04 (s, 1H), 8.10-7.89 (m, 2H), 7.80 (d, J = 8.5 Hz, 1H), 7.20 (dd, J = 8.0, 1.5 Hz, 1H), 7.17 (d, J = 1.5 Hz, 1H), 3.94 (d, J = 11.4 Hz, 2H), 3.69 (d, J = 11.4 Hz, 2H), 2.76 (q, J = 7.2 Hz, 4H), 1.93 (s, 2H), 1.64 (s, 1H), 1.14 (t, J = 7.2 Hz, 6H); 2Hs not observed (NH and OH) |
| 137 | MS m/z 364.3 [M + H]⁺; ¹H NMR (DMSO-d₆) δ: 13.00 (br s, 1H), 11.42 (s, 1H), 9.10 (s, 1H), 8.35-7.92 (m, 2H), 7.85 (d, J = 8.0 Hz, 1H), 7.23 (d, J = 8.5 Hz, 1H), 7.21 (s, 1H), 3.86 (br s, 2H), 3.76 (br s, 2H), 3.66 (s, 1H), 2.36-2.31 (m, 2H), 2.20-2.17 (m, 1H), 0.65 (br s, 4H); 1H not observed (NH or OH) |
| 138 | MS m/z 380.3 [M + H]⁺; ¹H NMR (methanol-d₄) δ: 8.44 (s, 2H), 7.67 (d, J = 8.0 Hz, 1H), 7.31 (d, J = 8.0 Hz, 1H), 7.29 (s, 1H), 5.98 (s, 1H), 4.29-4.40 (m, 1H), 4.14-4.19 (m, 1H), 3.87-3.98 (m, 2H), 3.71-3.80 (m, 1H), 2.64-2.74 (m, 1H), 2.39-2.51 (m, 1H), 1.52 (s, 9H); 3Hs not observed (2NHs or OH) |
| 148 | MS m/z 366.3 [M + H]⁺; ¹H NMR (methanol-d₄) δ: 9.06 (s, 1H), 7.99 (br s, 2H), 7.80 (d, J = 8.5 Hz, 1H), 7.20 (dd, J = 8.0, 1.5 Hz, 1H), 7.17 (d, J = 1.5 Hz, 1H), 4.03 (d, J = 11.5, 6.5 Hz, 1H), 3.92-3.86 (m, 2H), 3.68-3.65 (m, 1H), 3.55 (dd, J = 11.5, 6.5 Hz, 1H), 2.47-2.41 (m, 1H), 1.26 (t, J = 5.5 Hz, 6H), 1.20-1.16 (m, 1H); 3Hs not observed (2NHs and OH) |

| Cpd | Data |
|---|---|
| 154 | MS m/z 394.3 [M + H]⁺; ¹H NMR (methanol-d₄) δ: 9.08 (s, 1H), 8.00 (br s, 2H), 7.82 (d, J = 8.5 Hz, 1H), 7.22 (d, J = 8.0 Hz, 1H), 7.19 (s, 1H), 4.13-4.09 (m, 1H), 3.99-3.90 (m, 2H), 3.69-3.63 (m, 1H), 3.57-3.52 (m, 1H), 2.52-2.49 (m, 1H), 2.14-2.09 (m, 1H), 1.72-1.64 (m, 2H), 1.30 (s, 6H), 1.00 (t, J = 7.5 Hz, 3H); 3Hs not observed (2NHs and OH) |
| 157 | MS m/z 458.4 [M + H]⁺; ¹H NMR (DMSO-d₆) δ: 11.29 (s, br, 1H), 9.12 (s, 1H), 8.80-8.69 (m, 2H), 8.08 (s, br, 2H), 7.85 (d, J = 8.5 Hz, 1H), 7.23 (d, J = 8.0 Hz, 1H), 7.21 (s, 1H), 4.30-4.22 (m, 1H), 4.08-4.00 (m, 1H), 3.85-3.79 (m, 1H), 3.74-3.69 (m, 1H), 3.66-3.23 (m, 12H), 2.27-2.20 (m, 1H), 2.17 (s, 1H), 1.93 (q, J = 11.6 Hz, 2H), 1.67 (q, J = 12.3 Hz, 2H) |
| 159 | MS m/z 458.4 [M + H]⁺; ¹H NMR (DMSO-d₆) δ:9.13 (s, 1H), 8.62 (br s, 2H), 8.09 (s, 2H), 7.86 (d, J = 8.0 Hz, 1H), 7.24 (d, J = 8.0 Hz, 1H), 7.21 (s, 1H), 4.18-4.13 (m, 1H), 4.07-4.04 (m, 1H), 3.89-3.81 (m, 2H), 3.69-3.57 (m, 1H), 3.52 (s, 1H), 2.33-2.31 (m, 1H), 2.20 (br s, 2H), 2.04 (d, J = 14.0 Hz, 2H), 1.89-1.86 (m, 6H), 1.74 (br s, 2H), 1.64 (d, J = 12.5 Hz, 3H); 1H not observed (NH or OH) |
| 160 | MS m/z 486.3 [M + H]⁺; ¹H NMR (DMSO-d₆) δ: 11.28 (br s, 1H), 9.12 (s, 1H), 9.03-8.96 (m, 2H), 8.08 (s, 2H), 7.85 (d, J = 7.5 Hz, 1H), 7.23 (d, J = 8.0 Hz, 1H), 7.21 (s, 1H), 4.23 (br s, 1H), 4.04 (m, 1H), 3.82-3.78 (m, 2H), 3.76-3.73 (m, 3H), 2.32-2.28 (s, 1H), 1.84-1.77 (m, 2H), 1.65-1.56 (m, 4H), 1.38-1.29 (m, 4H), 1.21-1.15 (m, 2H), 0.90 (s, 6 |
| 162 | MS m/z 392.4 [M + H]⁺; ¹H NMR (methanol-d₄) δ: 8.58 (s, 2H), 7.68 (dd, J = 8.1, 4.7 Hz, 1H), 7.38-7.54 (m, 1H), 7.29-7.36 (m, 2H), 5.97 (d, J = 4.3 Hz, 1H), 3.83-4.09 (m, 4H), 3.59-3.73 (m, 1H), 3.38-3.42 (m, 1H), 3.08-3.20 (m, 1H), 3.03 (br d, J = 2.4 Hz, 3H), 2.99 (s, 3H), 2.30-2.40 (m, 1H), 2.12-2.28 (m, 1H), 1.74-1.86 (m, 1H); 2H not observed (NH and OH) |
| 166 | MS m/z 378.4 [M + H]⁺; ¹H NMR (methanol-d₄) δ: 9.09 (s, 1H), 7.94-8.11 (m, 2H), 7.84 (br d, J = 8.2 Hz, 1H), 7.61-7.77 (m, 1H), 7.18-7.28 (m, 1H), 3.77-3.88 (m, 2H), 3.71-3.76 (m, 1H), 3.67 (br dd, J = 10.8, 6.9 Hz, 1H), 2.96-3.07 (m, 1H), 2.74-2.94 (m, 4H), 2.72 (s, 3H), 2.61-2.66 (m, 1H), 2.02-2.14 (m, 1H), 1.81-1.91 (m, 1H); 2H not observed (NH and OH) |
| 167 | MS m/z 392.3 [M + H]⁺; ¹H NMR (methanol-d₄) δ: 8.32 (s, 2H), 7.63 (br d, J = 7.9 Hz, 1H), 7.29 (br d, J = 8.2 Hz, 1H), 7.26 (s, 1H), 5.94 (s, 1H), 4.07 (br s, 1H), 3.71-3.91 (m, 3H), 3.55-3.64 (m, 1H), 3.13-3.31 (m, 2H), 3.01 (br s, 3H), 2.89-2.97 (m, 3H), 2.38-2.50 (m, 1H), 2.18-2.29 (m, 1H), 1.98-2.12 (m, 1H), 1.64-1.79 (m, 1H); 2Hs not observed (NH and OH) |
| 170 | MS m/z 408.6 [M + H]⁺; ¹H NMR (methanol-d₄) δ: 9.11 (s, 1H), 8.08-7.99 (m, 2H), 7.82 (d, J = 8.0 Hz, 1H), 7.22 (d, J = 8.0 Hz, 1H), 7.19 (s, 1H), 4.29-4.21 (m, 2H), 4.01-3.96 (m, 1H), 3.77-3.69 (m, 2H), 2.67-2.61 (m, 1H), 2.34-2.27 (m, 1H), 1.94-1.75 (m, 4H), 1.41 (s, 3H), 1.03 (t, J = 7.5 Hz, 3H); 3Hs not observed (2 NHs and OH) |
| 171 | MS m/z 394.3 [M + H]⁺; ¹H NMR (methanol-d₄) δ: 9.15 (s, 1H), 8.24-7.98 (br s, 2H), 7.91 (d, J = 8.0 Hz, 1H), 7.30 (d, J = 8.2 Hz, 1H), 7.28 (s, 1H), 4.43-4.39 (m, 1H), 4.35-4.29 (m, 1H), 3.77-3.69 (m, 1H), 3.43 (t, J = 9.5 Hz, 1H), 2.76-2.71 (m, 1H), 1.83-1.77 (m, 1H), 1.51 (d, J = 6.0 Hz, 3H), 1.32 (s, 9H); 3Hs not observed (2NHs and OH) |
| 180 | MS m/z 392.4 [M + H]⁺; ¹H NMR (methanol-d₄) δ: 8.11 (br s, 2H), 7.58 (d, J = 8.2 Hz, 1H), 7.16-7.28 (m, 2H), 5.92 (s, 1H), 3.77-4.06 (m, 1H), 3.61-3.76 (m, 3H), 3.09-3.22 (m, 4H), 1.67-1.92 (m, 8H); 3Hs not observed (2 NHs and OH) |
| 181 | MS m/z 378.4 [M + H]⁺; ¹H NMR (methanol-d₄) δ: 8.08 (br s, 2H), 7.59 (d, J = 8.2 Hz, 1H), 7.14-7.28 (m, 2H), 5.92 (s, 1H), 3.81-4.06 (m, 1H), 3.64-3.80 (m, 3H), 3.43-3.50 (m, 2H), 3.20-3.27 (m, 2H), 2.06 (q, J = 7.3 Hz, 2H), 1.81-1.94 (m, 3H), 1.74-1.79 (m, 1H); 3Hs not observed (2 NHs and OH) |
| 182 | MS m/z 406.4 [M + H]⁺; ¹H NMR (methanol-d₄) δ: 8.65 (br s, 2H), 7.69 (d, J = 7.9 Hz, 1H), 7.31-7.38 (m, 2H), 5.96 (s, 1H), 3.80-3.88 (m, 1H), 3.66-3.78 (m, 3H), 3.61 (br d, J = 9.2 Hz, 1H), 3.53 (br d, J = 10.4 Hz, 1H), 3.16-3.22 (m, 1H), 2.89-3.01 (m, 4H), 1.95-2.18 (m, 4H), 1.84-1.95 (m, 2H), 1.73 (br s, 2H); 2Hs not observed (NH and OH) |
| 183 | MS m/z 392.5 [M + H]⁺; ¹H NMR (methanol-d₄) δ: 8.75 (br s, 2H), 7.72 (d, J = 8.2 Hz, 1H), 7.32-7.41 (m, 2H), 5.97 (s, 1H), 3.67-3.86 (m, 5H), 3.67-3.89 (m, 1H), 3.27-3.32 (m, 1H), 3.09 (br dd, J = 11.0, 8.9 Hz, 1H), 3.00 (s, 3H), 2.25 (br d, J = 8.2 Hz, 1H), 2.07-2.19 (m, 1H), 1.97 (br s, 3H), 1.84-2.04 (m, 1H); 2Hs not observed (NH and OH) |
| 193 | MS m/z 420.4 [M + H]⁺; ¹H NMR (methanol-d₄) δ: 9.08 (s, 1H), 8.18-7.88 (br s, 2H), 7.82 (d, J = 8.0 Hz, 1H), 7.22 (dd, J = 8.5, 2.0 Hz, 1H), 7.18 (d, J = 1.5 Hz, 1H), 3.92-3.86 (m, 2H), 3.79 (d, J = 4.0 Hz, 2H), 3.71 (dd, J = 12.0, 7.5 Hz, 1H), 3.22-3.16 (m, 1H), 3.01-2.95 (m, 1H), 2.25-2.11 (m, 2H), 1.98-1.89 (m, 1H), 1.69-1.64 (m, 1H), 1.44 (s, 9H); 3Hs not observed (2NHs and OH) |
| 199 | MS m/z 408.5 [M + H]⁺; ¹H NMR (methanol-d₄) δ: 9.03 (s, 1H), 8.02 (s, 1H), 7.86 (s, 1H), 7.78 (d, J = 7.9 Hz, 1H), 7.10-7.22 (m, 2H), 4.45 (br t, J = 11.6 Hz, 1H), 3.96 (s, 3H), 2.03 (br d, J = 11.0 Hz, 2H), 1.35 (s, 6H), 1.24-1.31 (m, 2H), 1.22 (s, 6H); 3Hs not observed (2 NHs and OH) |
| 201 | MS m/z 426.5 [M + H]⁺; ¹H NMR (methanol-d₄) δ: 9.05 (s, 1H), 7.99 (s, 1H), 7.85 (s, 1H), 7.78 (br d, J = 7.9 Hz, 1H), 7.05-7.26 (m, 2H), 4.65-4.75 (m, 1H), 3.93 (s, 3H), 1.70-1.80 (m, 2H), 1.35 (br d, J = 6.4 Hz, 6H), 1.16-1.27 (m, 7H); 3Hs not observed (2NHs and OH) |
| 202 | MS m/z 394.3 [M + H]⁺; ¹H NMR (methanol-d₄) δ: 9.07 (s, 1H), 8.02 (s, 1H), 7.86 (s, 1H), 7.79 (d, J = 7.9 Hz, 1H), 7.13-7.21 (m, 2H), 3.99-4.08 (m, 2H), 3.96 (s, 3H), 3.83-3.90 (m, 1H), 3.57-3.73 (m, 2H), 2.29-2.45 (m, 1H), 1.83-2.01 (m, 1H), 1.22 (s, 9H); 2Hs not observed (NH and OH) |
| 203 | MS m/z 380.3 [M + H]⁺; ¹H NMR (methanol-d₄) δ: 9.06 (s, 1H), 8.01 (s, 1H), 7.85 (s, 1H), 7.81 (d, J = 7.9 Hz, 1H), 7.18 (d, J = 7.6 Hz, 1H), 7.16 (s, 1H), 3.97-4.01 (m, 1H), 3.96 (s, 3H), 3.77-3.94 (m, 1H), 3.57-3.77 (m, 2H), 3.40 (dd, J = 10.8, 6.9 Hz, 1H), 2.95-3.05 (m, 1H), 2.28-2.42 (m, 1H), 1.86-2.00 (m, 1H), 1.16 (br t, J = 5.8 Hz, 6H); 2Hs not observed (NH and OH) |
| 205 | MS m/z 352.4 [M + H]⁺; ¹H NMR (methanol-d₄) δ: 9.07 (s, 1H), 8.02 (s, 1H), 7.86 (s, 1H), 7.80 (d, J = 7.9 Hz, 1H), 7.10-7.26 (m, 2H), 3.96 (s, 3H), 3.79-3.92 (m, 2H), 3.65-3.74 (m, 1H), 3.49-3.65 (m, 1H), 3.41-3.48 (m, 1H), 2.46 (s, 3H), 2.22-2.36 (m, 1H), 1.91-2.09 (m, 1H); 2Hs not observed (NH and OH) |
| 206 | MS m/z 394.3 [M + H]⁺; ¹H NMR (methanol-d₄) δ: 9.07 (s, 1H), 8.01, (s, 2H), 7.82 (d, J = 8.00 Hz, 1H), 7.23 (d, J = 8.00 Hz, 1H), 7.19 (s, 1H), 4.94 (d, J = 15 Hz, 2H), 3.79-3.71, (m, 1H), 3.20 (t, J = 14.50 Hz, 2H), 2.21 (d, J = 12.50 Hz, 2H), 1.78-1.67, (m, 2H), 1.46, (s, 9H); 3Hs not observed (2 NHs and OH) |
| 212 | MS m/z 394.4 [M + H]⁺; ¹H NMR (methanol-d₄) δ: 9.09 (s, 1H), 8.01 (s, 2H), 7.82 (d, J = 8.00 Hz, 1H), 7.23 (d, J = 8.50 Hz, 1H), 7.19 (s, 1H), 4.91 (d, J = 13.50 Hz, 1H), 4.58 (d, J = 13.50 Hz, 1H), 3.67-3.65, (m, 1H), 3.55-3.52, (m, 1H), 3.46-3.38 (m, 1H), 2.29-2.21, (m, 1H), 1.97-1.75, (m, 3H), 1.48 (s, 9H); 3Hs not observed (2 NHs and OH) |
| 226 | MS m/z 392.3 [M + H]⁺; ¹H NMR (DMSO-d₆) δ: 11.25 (s, 1H), 9.29 (br s, 1H), 9.07 (s, 1H), 8.17 (s, 1H), 7.87 (s, 1H), 7.83 (d, J = 8.1 Hz, 1H), 7.18 (d, J = 8.1 Hz, 1H), 7.15 (s, 1H), 4.04 (br s, 2H), 3.97 (br s, 2H), 3.88 (s, 3H), 3.40 (m, 2H), 3.02 (m, 2H), 2.78 (s, 3H), 2.18 (m, 2H), 1.91 (m, 2H) |
| 262 | MS m/z 352.2 [M + H]⁺; ¹H NMR (DMSO-d₆) δ: 9.13 (s, 1H), 8.17 (s, 2H), 7.87 (d, J = 8.5 Hz, 1H), 7.25 (dd, J = 2.6, 4.1 Hz, 2H), 4.81 (d, J = 13.3 Hz, 2H), 3.43-3.30 (m, 2H), 3.25-3.12 (m, 2H), 1.37 (d, J = 6.4 Hz, 6H); 3Hs not observed (2 NH and OH) |

| Cpd | Data |
|---|---|
| 278 | MS m/z 398.3 [M + H]$^+$; $^1$H NMR (DMSO-d$_6$) δ: 9.97 (br s, 1H), 9.69 (br s, 1H), 9.13(s, 1H), 8.08 (s, 2H), 7.85 (d, J = 8.0 Hz, 1H), 7.25-7.22 (m, 2H), 5.79 (d, J = 53.0 Hz, 2H), 4.39-4.26 (m, 2H), 4.13-3.99 (m, 1H), 3.94-3.80 (m, 2H), 1.44 (s, 9H) |
| 282 | MS m/z 380.4 [M + H]$^+$; $^1$H NMR (DMSO-d$_6$) δ: 9.11 (s, 1H), 8.21 (s, 2H), 7.88 (d, J = 8.5 Hz, 1H), 7.30-7.22 (m, 2H), 4.00 (s, 4H), 1.48 (s, 12H); 3Hs not observed (2 NHs and OH) |
| 297 | MS m/z 380.5 [M + H]$^+$; $^1$H NMR (methanol-d$_4$) δ: 8.30-8.62 (m, 2H), 7.68 (br d, J = 8.2 Hz, 1H), 7.32 (br d, J = 8.4 Hz, 1H), 7.29 (s, 1H), 5.98 (br s, 1H), 4.07-4.26 (m, 2H), 3.85-4.06 (m, 2H), 3.78 (br s, 1H), 3.37 (s, 2H), 2.93-3.12 (m, 1H), 2.59-2.76 (m, 1H), 2.39-2.58 (m, 2H), 2.15 (br dd, J = 13.0, 6.7 Hz, 1H), 1.12 (br d, J = 6.4 Hz, 6H); 1H not observed (NH or OH) |
| 298 | MS m/z 410.3 [M + H]$^+$; $^1$H NMR (methanol-d$_4$) δ: 8.93 (s, 1H), 7.89 (br s, 2H), 7.70 (d, J = 7.9 Hz, 1H), 7.11 (dd, J = 8.2, 1.8 Hz, 1H), 7.08 (d, J = 1.5 Hz, 1H), 4.64-4.73 (m, 1H), 3.39 (br d, J = 7.9 Hz, 1H), 2.15 (br dd, J = 13.3, 8.4 Hz, 1H), 1.78 (dd, J = 13.3, 6.3 Hz, 1H), 1.33 (s, 3H), 1.31 (s, 3H), 1.22 (s, 3H), 1.18 (s, 3H); 5Hs not observed (3 NHs and 2 OHs) |
| 306 | MS m/z 364.3 [M + H]$^+$; $^1$H NMR (DMSO-d$_6$) δ: 10.05 (br s, 1H), 9.13 (s, 1H), 8.91 (br s, 1H), 8.10 (s, 2H), 7.86 (d, J = 8.5 Hz, 1H), 7.42 (s, 1H), 7.32 (s, 1H), 7.17-7.26 (m, 3H), 3.76-4.01 (m, 4H), 3.51-3.69 (m, 1H), 2.85-2.97 (m, 1H), 2.73-2.85 (m, 1H), 1.64-1.88 (m, 5H) |
| 309 | MS m/z 339.3 [M + H]$^+$ |
| 310 | MS m/z 378.4 [M + H]$^+$; $^1$H NMR (DMSO-d$_6$) δ: 10.40 (br s, 1H), 9.10-9.19 (m, 1H), 8.12 (s, 2H), 7.86 (d, J = 7.9 Hz, 1H), 7.19-7.29 (m, 2H), 4.15-4.32 (m, 2H), 3.62-3.70 (m, 2H), 3.30-3.40 (m, 1H), 3.17 (s, 3H), 2.97-3.08 (m, 1H), 2.87-2.95 (m, 1H), 1.72-1.95 (m, 5H); 1H not observed (OH or NH) |
| 311 | MS m/z 380.3 [M + H]$^+$; $^1$H NMR (DMSO-d$_6$) δ: 12.38 (br s, 1H), 9.13 (s, 1H), 8.11 (s, 2H), 7.86 (d, J = 7.9 Hz, 1H), 7.18-7.30 (m, 2H), 5.76 (s, 1H), 4.50 (s, 3H), 4.14-4.22 (m, 2H), 3.99-4.03 (m, 2H), 3.86-3.95 (m, 2H), 3.80-3.84 (m, 2H), 3.36-3.49 (m, 1H), 3.26-3.29 (m, 1H) |
| 312 | MS m/z 380.4 [M + H]$^+$; $^1$H NMR (DMSO-d$_6$) δ: 9.08 (s, 1H), 8.27-7.95 (m, 2H), 7.84 (d, J = 7.9 Hz, 1H), 7.28-7.17 (m, 2H), 4.67 (q, J = 6.3 Hz, 2H), 4.52-4.31 (m, 2H), 4.07-3.86 (m, 2H), 3.76-3.53 (m, 4H), 2.14-2.02 (m, 1H), 1.82 (br s, 1H); 3Hs not observed (2NHs and OH) |
| 313 | MS m/z 394.4 [M + H]$^+$; $^1$H NMR (DMSO-d$_6$) δ: 9.10 (s, 1H), 8.16 (s, 1H), 7.90-7.82 (m, 2H), 7.20-7.14 (m, 2H), 4.80-4.871 (m, 2H), 4.58-4.55 (m, 2H), 4.45-4.34 (m, 1H), 3.88 (s, 3H), 3.85-3.72 (m, 3H), 3.70-3.59 (m, 2H), 2.35-2.22 (m, 1H), 2.15-2.03 (m, 1H); 2Hs not observed (NH and OH) |
| 316 | MS m/z 398.3 [M + H]$^+$; $^1$H NMR (methanol-d$_4$) δ: 9.10 (s, 1H), 8.00 (br s, 2H), 7.83 (d, J = 8.0 Hz, 1H), 7.22 (d, J = 8.5 Hz, 1H), 7.19 (s, 1H), 4.52 (d, J = 47.5 Hz, 2H), 4.18-4.13 (m, 2H), 3.96-3.93 (m, 1H), 3.72-3.64 (m, 2H), 2.58-2.55 (m, 1H), 2.24-2.16 (m, 1H), 1.41 (s, 6H); 3Hs not observed (2 NHs and OH) |
| 317 | MS m/z 352.4 [M + H]$^+$; $^1$H NMR (methanol-d$_4$) δ: 8.50 (s, 2H), 7.69 (br d, J = 7.9 Hz, 1H), 7.33 (br d, J = 8.5 Hz, 1H), 7.31 (s, 1H), 5.99 (s, 1H), 4.04-4.29 (m, 2H), 3.94 (br d, J = 12.2 Hz, 2H), 3.73-3.86 (m, 1H), 3.24 (dt, J = 12.6, 6.1 Hz, 2H), 2.57-2.75 (m, 1H), 2.33-2.56 (m, 1H), 1.43 (br t, J = 6.9 Hz, 3H) 3Hs not observed (2 NHs 1 OH) |
| 318 | MS m/z 352.4 [M + H]$^+$; $^1$H NMR (methanol-d$_4$) δ: 8.59 (br s, 2H), 7.70 (br d, J = 7.9 Hz, 1H), 7.34 (br d, J = 8.2 Hz, 1H), 7.32 (br s, 1H), 5.91-6.08 (m, 1H), 4.14-4.33 (m, 2H), 4.05-3.90 (m, 2H), 3.72-3.83 (m, 1H), 3.04 (s, 3H), 3.04 (s, 3H), 2.71 (br d, J = 6.1 Hz, 1H), 2.41-2.62 (m, 1H); 2Hs not observed (NH and OH) |
| 322 | MS m/z 412.4 [M + H]$^+$; $^1$H NMR (methanol-d$_4$) δ: 9.02 (s, 1H), 8.00 (br s, 2H), 7.78 (br d, J = 7.9 Hz, 1H), 7.20 (br d, J = 8.2 Hz, 1H), 7.18 (s, 1H), 4.65-4.80 (m, 1H), 4.45-4.60 (m, 1H), 1.78 (br d, J = 8.5 Hz, 2H), 1.38 (br d, J = 6.7 Hz, 6H), 1.27 (s, 6H); 4Hs not observed (3NHs and OH) |
| 323 | MS m/z 412.5 [M + H]$^+$; $^1$H NMR (methanol-d$_4$) δ: 9.05 (s, 1H), 8.01 (br s, 2H), 7.81 (br d, J = 7.9 Hz, 1H), 7.22 (br d, J = 8.2 Hz, 1H), 7.20 (s, 1H), 4.66-4.80 (m, 1H), 4.43-4.61 (m, 1H), 1.78 (br d, J = 8.5 Hz, 2H), 1.38 (br d, J = 7.0 Hz, 6H), 1.27 (s, 6H); 4Hs not observed (3NHs and OH) |
| 325 | MS m/z 394.4 [M + H]$^+$; $^1$H NMR (DMSO-d$_6$) δ: 9.13 (s, 1H), 8.08 (br s, 2H), 7.86 (d, J = 7.9 Hz, 1H), 7.31-7.16 (m, 2H), 4.84-4.70 (m, 2H), 4.48 (d, J = 6.9 Hz, 2H), 4.18-4.04 (m, 1H), 4.04-3.90 (m, 1H), 3.90-3.79 (m, 1H), 3.79-3.69 (m, 1H), 3.69-3.56 (m, 1H), 2.46-2.36 (m, 1H), 2.23-2.09 (m, 1H), 1.73 (s, 3H); 3Hs not observed (2 NH and OH) |
| 327 | MS m/z 364.2 [M + H]$^+$; $^1$H NMR (DMSO-d$_6$) δ: 9.08-9.24 (m, 2H), 8.94 (br s, 1H), 8.12 (s, 2H), 7.84 (d, J = 7.9 Hz, 1H), 7.19-7.28 (m, 2H), 3.56-3.80 (m, 4H), 3.20-3.29 (m, 1H), 3.00-3.13 (m, 3H), 2.67-2.78 (m, 1H), 2.57-2.67 (m, 1H), 1.91-2.04 (m, 1H), 1.68-1.81 (m, 1H); 1H not observed (OH or NH) |
| 328 | MS m/z 324.2 [M + H]$^+$; $^1$H NMR (DMSO-d$_6$) δ: 9.13 (s, 1H), 8.24 (s, 2H), 7.87 (br d, J = 7.8 Hz, 2H), 7.34-7.19 (m, 2H), 4.11 (br s, 4H), 3.22 (br s, 4H); 3Hs not observed (2 NHs and OH) |
| 329 | MS m/z 384.3 [M + H]$^+$; $^1$H NMR (methanol-d$_4$) δ: 9.17 (s, 1H), 8.20 (br s, 2H), 7.84 (d, J = 7.3 Hz, 1H), 7.26 (br s, 2H), 4.97-4.57 (m, 3H), 4.22-3.81 (m, 5H), 3.80-3.54 (m, 1H), 1.37 (br s, 3H); 3Hs was not observed (2 NHs and OH) |
| 332 | MS m/z 350.4 [M + H]$^+$; $^1$H NMR (methanol-d$_4$) δ: 8.48 (s, 2H), 7.70 (br d, J = 8.5 Hz, 1H), 7.33 (br d, J = 8.2 Hz, 1H), 7.30 (s, 1H), 6.00 (s, 1H), 3.93-4.05 (m, 2H), 3.82-3.92 (m, 1H), 3.48-3.62 (m, 2H), 3.39-3.48 (m, 1H), 2.46-2.68 (m, 3H), 2.27-2.45 (m, 2H); 3Hs not observed (2 NHs and OH) |
| 333 | MS m/z 368.5 [M + H]$^+$; $^1$H NMR (methanol-d$_4$) δ: 8.47 (s, 2H), 7.68 (br d, J = 8.7 Hz, 1H), 7.33 (br d, J = 8.4 Hz, 1H), 7.30 (s, 1H), 5.99 (s, 1H), 4.20-4.33 (m, 1H), 4.19-4.09 (m, 2H), 3.91 (br s, 5H), 3.75-3.85 (m, 1H), 3.37 (s, 3H), 2.60-2.76 (m, 1H), 2.38-2.57 (m, 1H); 3Hs not observed (2 NHs and OH) |
| 334 | MS m/z 366.3 [M + H]$^+$; $^1$H NMR (DMSO-d$_6$) δ: 13.00 (br s, 1H), 11.43 (br s, 1H), 9.09 (br s, 1H), 8.23 (br s, 1H), 7.95 (br s, 1H), 7.85 (d, J = 7.3 Hz, 1H), 7.20-7.24 (m, 2H), 4.80-4.88 (m, 1H), 4.40-4.52 (m, 3H), 3.82-4.01 (m, 2H), 3.49-3.73 (m, 3H); 2Hs not observed (OH and/or NH) |
| 335 | MS m/z 408.4 [M + H]$^+$ |
| 336 | MS m/z 396.4 [M + H]$^+$; $^1$H NMR (methanol-d$_4$) δ: 8.63 (br s, 2H), 7.70 (br s, 1H), 7.33 (br s, 2H), 5.99 (br s, 1H), 4.36 (br s, 1H), 4.15 (br s, 1H), 4.05-3.87 (m, 2H), 3.79 (m, 2H), 3.63-3.56 (m, 2H), 3.48 (br s, 3H), 2.78-2.33 (m, 2H), 1.47 (br s, 3H); 3Hs was observed (2NHs and OH) |
| 337 | MS m/z 350.3 [M + H]$^+$; $^1$H NMR (methanol-d$_4$) δ: 8.81 (s, 2H), 7.72 (d, J = 7.93 Hz, 1H), 7.40-7.35 (m, 2H), 5.98 (s, 1H), 3.98 (br s, 2H), 3.79-3.77 (m, 2H), 3.71-3.61 (m, 2H), 3.49-3.40 (m, 4H); 3Hs not observed (2 NHs and OH) |

| Cpd | Data |
|---|---|
| 339 | MS m/z 364.2 [M + H]⁺; ¹H NMR (DMSO-d₆) δ: 9.79 (br s, 1H), 9.68 (br s, 1H), 9.13 (s, 1H), 8.10 (s, 2H), 7.86 (d, J = 8.5 Hz, 1H), 7.19-7.27 (m, 2H), 4.11-4.24 (m, 1H), 3.78-3.85 (m, 1H), 3.66-3.69 (m, 1H), 3.28-3.33 (m, 2H), 2.55-2.61 (m, 1H), 2.25-2.39 (m, 2H), 1.96-2.17 (m, 4H); 1H not observed (OH or NH) |
| 340 | MS m/z 378.4 [M + H]⁺; ¹H NMR (methanol-d₄) δ: 8.65 (s, 2H), 7.68 (d, J = 8.1 Hz, 1H), 7.42-7.24 (m, 2H), 6.04-5.91 (m, 1H), 4.50-4.36 (m, 1H), 4.22-4.11 (m, 1H), 4.04-3.88 (m, 2H), 3.84-3.71 (m, 1H), 2.73-2.60 (m, 1H), 2.60-2.42 (m, 1H), 1.58 (d, J = 2.9 Hz, 3H), 1.31 (br s, 2H), 0.90 (br d, J = 4.0 Hz, 2H); 3Hs not observed (2 NHs and OH) |
| 341 | MS m/z 410.5 [M + H]⁺; ¹H NMR (methanol-d₄) δ: 8.69 (s, 2H), 7.71 (d, J = 8.1 Hz, 1H), 7.42-7.30 (m, 2H), 5.99 (s, 1H), 4.45-4.27 (m, 1H), 4.21-4.03 (m, 1H), 4.02-3.87 (m, 2H), 3.85-3.73 (m, 1H), 3.62-3.47 (m, 5H), 2.73-2.59 (m, 1H), 2.56-2.40 (m, 1H), 1.57-1.43 (m, 6H); 3Hs not observed (2 NHs and OH) |
| 345 | MS m/z 356.3 [M + H]⁺; ¹H NMR (methanol-d₄) δ: 8.60 (br s, 2H), 7.80-7.51 (m, 1H), 7.45-7.16 (m, 2H), 6.12-5.81 (m, 1H), 5.38-5.12 (m, 1H), 4.52-4.22 (m, 1H), 3.93-3.71 (m, 1H), 3.67-3.41 (m, 3H), 2.45-2.10 (m, 2H); 4Hs not observed (3 NHs and OH) |
| 346 | MS m/z 368.3 [M + H]⁺; ¹H NMR (methanol-d₄) δ: 8.55 (s, 2H), 7.63-7.55 (m, 1H), 7.30-7.15 (m, 2H), 5.89 (s, 1H), 4.38 (br s, 1H), 4.11-3.90 (m, 4H), 3.70-3.59 (m, 1H), 3.42 (d, J = 2.4 Hz, 3H), 2.78 (d, J = 3.8 Hz, 3H); 3Hs not observed (2 NHs and OH) |
| 347 | MS m/z 366.3 [M + H]⁺; ¹H NMR (methanol-d₄) δ: 9.05 (s, 1H), 7.99 (br s, 2H), 7.80 (d, J = 8.0 Hz, 1H), 7.20 (dd, J = 8.0, 2.0 Hz, 1H), 7.17 (d, J = 1.5 Hz, 1H), 3.99 (dd, J = 11.5, 6.5 Hz, 1H), 3.89-3.85 (m, 1H), 3.79-3.73 (m, 1H), 3.68-3.62 (m, 1H), 3.47 (dd, J = 11.5, 6.5 Hz, 1H), 3.10 (dt, J = 12.5, 6.0 Hz, 1H), 2.39 (dq, J = 12.0, 6.0 Hz, 1H), 2.03-1.97 (m, 1H), 1.20 (t, J = 5.5 Hz, 6H); 3Hs not observed (2 NHs and OH) |
| 348 | MS m/z 366.3 [M + H]⁺; ¹H NMR (methanol-d₄) δ: 9.05 (s, 1H), 7.99 (br s, 2H), 7.80 (d, J = 8.0 Hz, 1H), 7.20 (dd, J = 8.0, 2.0 Hz, 1H), 7.17 (d, J = 1.5 Hz, 1H), 3.99 (dd, J = 11.5, 6.5 Hz, 1H), 3.89-3.85 (m, 1H), 3.79-3.73 (m, 1H), 3.68-3.62 (m, 1H), 3.47 (dd, J = 11.5, 6.5 Hz, 1H), 3.10 (dt, J = 12.5, 6.0 Hz, 1H), 2.39 (dq, J = 12.0, 6.0 Hz, 1H), 2.03-1.97 (m, 1H), 1.20 (t, J = 5.5 Hz, 6H); 3Hs not observed (2 NHs and OH) |
| 349 | MS m/z 390.4 [M + H]⁺; ¹H NMR (DMSO-d₆) δ: 11.20-11.34 (m, 1H), 9.50-9.59 (m, 1H), 9.13 (s, 1H), 8.07-8.12 (m, 1H), 7.86 (d, J = 8.1 Hz, 1H), 7.24 (dd, J = 8.1, 1.7 Hz, 1H), 7.21 (d, J = 1.5 Hz, 1H), 4.03-4.08 (m, 1H), 3.95-4.00 (m, 1H), 3.78-3.84 (m, 2H), 3.66-3.75 (m, 3H), 2.74 (s, 1H), 2.11-2.15 (m, 6H); 2Hs not observed (2 NHs) |
| 353 | MS m/z 380.6 [M + H]⁺; ¹H NMR (methanol-d₄) δ: 8.64 (s, 2H), 7.70 (d, J = 8.1 Hz, 1H), 7.40-7.29 (m, 2H), 5.97 (d, J = 10.1 Hz, 1H), 4.12-4.04 (m, 2H), 4.02-3.95 (m, 1H), 3.94-3.70 (m, 3H), 3.59-3.44 (m, 2H), 2.68-2.53 (m, 1H), 2.37-2.20 (m, 1H); 2Hs not observed (overlapped with residual solvent peak); 3Hs not observed (2 NHs and OH) |
| 354 | MS m/z 364.5 [M + H]⁺; ¹H NMR (methanol-d₄) δ: 8.59 (br s, 2H), 7.68 (d, J = 8.2 Hz, 1H), 7.40-7.26 (m, 2H), 6.01-5.94 (m, 1H), 3.88-3.67 (m, 4H), 3.59-3.43 (m, 4H), 2.41-2.10 (m, 4H); 3Hs not observed (2 NHs and OH) |
| 355 | MS m/z 380.5 [M + H]⁺; ¹H NMR (methanol-d₄) δ: 8.25 (br s, 2H), 7.63 (d, J = 8.0 Hz, 1H), 7.28 (dd, J = 8.5, 1.5 Hz, 1H), 7.24 (d, J = 1.5 Hz, 1H), 5.96 (d, J = 3.0 Hz, 1H), 4.38-4.28 (m, 1H), 4.18-4.12 (m, 1H), 3.96-3.87 (m, 2H), 3.80-3.70 (m, 2H), 2.72-2.64 (m, 1H), 2.49-2.37 (m, 1H), 1.51 (s, 9H); 3Hs not observed (2NHs and OH) |
| 356 | MS m/z 380.5 [M + H]⁺; ¹H NMR (methanol-d₄) δ: 8.25-8.16 (m, 2H), 7.65 (d, J = 8.3 Hz, 1H), 7.29 (d, J = 8.5 Hz, 1H), 7.25 (s, 1H), 5.98 (d, J = 2.6 Hz, 1H), 4.40-4.29 (m, 1H), 4.20-4.13 (m, 1H), 3.96-3.87 (m, 2H), 3.80-3.71 (m, 1H), 2.76-2.64 (m, 1H), 2.49-2.37 (m, 1H), 1.53 (s, 9H); 3Hs not observed (2 NHs and OH) |
| 357 | MS m/z 392.5 [M + H]⁺; ¹H NMR (methanol-d₄) δ: 9.12 (s, 1H), 7.90-8.17 (m, 2H), 7.80 (d, J = 8.2 Hz, 1H), 7.21 (s, 2H), 4.09-4.16 (m, 1H), 4.02-4.09 (m, 1H), 3.89-4.00 (m, 1H), 3.74-3.83 (m, 2H), 3.59-3.70 (m, 1H), 2.46-2.65 (m, 1H), 2.13-2.32 (m, 3H), 1.80-1.92 (m, 2H), 1.58-1.78 (m, 4H); 3Hs not observed (2NHs and OH) |
| 361 | MS m/z 380.6 [M + H]⁺; ¹H NMR (methanol-d₄) δ: 8.62 (br s, 2H), 7.68 (d, J = 7.9 Hz, 1H), 7.42-7.28 (m, 2H), 5.95 (d, J = 7.2 Hz, 1H), 4.02-3.89 (m, 1H), 3.88-3.78 (m, 1H), 3.77-3.64 (m, 1H), 3.51-3.44 (m, 1H), 3.30-3.17 (m, 2H), 2.89 (br s, 1H), 2.44 (br s, 1H), 2.14-1.94 (m, 1H), 1.50-1.38 (m, 7H); 3Hs not observed (2NHs and OH) |
| 362 | MS m/z 422.4 [M + H]⁺; ¹H NMR (methanol-d₄) δ: 9.13 (s, 1H), 8.05 (d, J = 9.6 Hz, 2H), 7.30-7.16 (m, 2H), 5.96 (s, 1H), 4.47-4.29 (m, 1H), 4.27-4.09 (m, 1H), 4.04-3.98 (m, 2H), 3.83-3.69 (m, 2H), 3.65 (br t, J = 11.6 Hz, 3H), 2.75-2.58 (m, 1H), 2.51-2.25 (m, 1H), 2.07-1.95 (m, 2H), 1.94-1.82 (m, 2H), 1.64 (br s, 3H); 3Hs not observed (2 NHs and OH) |
| 367 | MS m/z 397.5 [M + H]⁺; ¹H NMR (methanol-d₄) δ: 8.11 (s, 1H), 7.95 (s, 1H), 7.62 (d, J = 8.2 Hz, 1H), 7.22 (d, J = 7.9 Hz, 1H), 7.19 (s, 1H), 5.97 (d, J = 2.1 Hz, 1H), 4.28-4.42 (m, 1H), 4.09-4.22 (m, 1H), 3.84-3.99 (m, 2H), 3.69-3.82 (m, 1H), 2.62-2.77 (m, 1H), 2.36-2.51 (m, 1H), 1.52 (s, 9H); 2Hs not observed (NH and OH) |
| 373 | MS m/z 411.5 [M + H]⁺; ¹H NMR (methanol-d₄) δ: 8.14 (s, 1H), 7.99 (s, 1H), 7.62 (d, J = 8.5 Hz, 1H), 7.23 (dd, J = 8.2, 1.5 Hz, 1H), 7.19 (d, J = 1.5 Hz, 1H), 5.92-6.03 (m, 1H), 4.23-4.43 (m, 1H), 2.20-2.33 (m, 2H), 1.68-1.87 (m, 2H), 1.63 (d, J = 8.9 Hz, 6H), 1.55 (d, J = 6.4 Hz, 6H); 3Hs not observed (2 NHs and OH) |
| 369 | MS m/z 378.4 [M + H]⁺; ¹H NMR (methanol-d₄) δ: 8.63 (s, 2H), 7.69 (d, J = 7.8 Hz, 1H), 7.41-7.27 (m, 2H), 5.96 (d, J = 6.4 Hz, 1H), 3.80 (br s, 3H), 3.32-3.19 (m, 4H), 2.36-2.08 (m, 2H), 2.02-1.76 (m, 5H); 3Hs not observed (2 NHs and OH) |
| 370 | MS m/z 350.3 [M + H]⁺; ¹H NMR (methanol-d₄) δ: 8.54 (s, 2H), 7.69 (d, J = 8.2 Hz, 1H), 7.37-7.26 (m, 2H), 5.99 (d, J = 9.0 Hz, 1H), 4.63-4.50 (m, 1H), 4.26-4.16 (m, 1H), 4.10 (dd, J = 6.3, 12.4 Hz, 1H), 4.06-.98 (m, 1H), 3.67-3.54 (m, 2H), 3.54-3.43 (m, 2H), 2.48-2.36 (m, 1H), 2.22-2.12 (m, 1H); 3Hs not observed (2 NHs and OH) |
| 371 | MS m/z 382.4 [M + H]⁺; ¹H NMR (methanol-d₄) δ: 9.15 (s, 1H), 8.15 (br s, 2H), 7.85 (d, J = 8.2 Hz, 1H), 7.29-7.20 (m, 2H), 3.98 (br s, 2H), 3.94-3.84 (m, 2H), 3.72-3.61 (m, 2H), 3.52 (br t, J = 5.7 Hz, 2H), 3.11-2.98 (m, 2H), 2.45-2.35 (m, 2H), 1.92-1.80 (m, 2H); 4Hs not observed (2 NHs and 2 OHs) |
| 372 | MS m/z 422.5 [M + H]⁺; ¹H NMR (methanol-d₄) δ: 8.95 (s, 1H), 7.99 (br s, 2H), 7.72 (d, J = 8.2 Hz, 1H), 7.18-7.08 (m, 2H), 4.09-4.02 (m, 2H), 3.94-3.86 (m, 1H), 3.82-3.74 (m, 1H), 3.58-3.44 (m, 3H), 3.30-3.23 (m, 1H), 3.21-3.14 (m, 1H), 2.75-2.64 (m, 1H), 2.37-2.25 (m, 1H), 2.11-2.01 (m, 1H), 1.91-1.79 (m, 1H), 1.76-1.64 (m, 2H); 1H not observed (overlapped with solvent peak); 3Hs not observed (2 NHs and OH) |
| 377 | MS m/z 429.5 [M + H]⁺; ¹H NMR (methanol-d₄) δ: 8.15 (s, 1H), 8.00 (s, 1H), 7.62 (d, J = 8.5 Hz, 1H), 7.23 (dd, J = 8.2, 1.2 Hz, 1H), 7.20 (s, 1H), 6.01 (d, J = 10.1 Hz, 1H), 4.62-4.82 (m, 1H), 1.97-2.27 (m, 3H), 1.65-1.72 (m, 6H), 1.55-1.63 (m, 6H); 3Hs not observed (2 NHs and OH) |
| 386 | MS m/z 406.5 [M + H]⁺; ¹H NMR (methanol-d₄) δ: 8.66 (s, 2H), 7.69 (d, J = 7.9 Hz, 1H), 7.42-7.29 (m, 2H), 6.02-5.89 (m, 1H), 4.04-3.88 (m, 1H), 3.87-3.76 (m, 1H), 3.74-3.59 (m, 2H), 3.51-3.42 (m, 1H), 3.31-3.20 (m, 2H), 3.00-2.81 (m, 1H), 2.53-2.37 (m, 1H), 2.25-2.14 (m, 2H), 2.12-1.97 (m, 1H), |

| Cpd | Data |
|---|---|
| | 1.89 (br s, 2H), 1.83-1.75 (m, 2H), 1.71 (br s, 2H); 3Hs not observed (2 NHs and OH) |
| 387 | MS m/z 378.5 [M + H]$^+$; $^1$H NMR (DMSO-d$_6$) δ: 9.17 (s, 1H), 8.19-8.09 (m, 2H), 7.80 (br d, J = 5.6 Hz, 1H), 7.25 (br s, 2H), 3.93-3.74 (m, 1H), 3.65-3.51 (m, 1H), 3.51-3.32 (m, 2H), 3.28-3.08 (m, 2H), 2.38-2.27 (m, 1H), 2.25-2.09 (m, 2H), 2.05-1.93 (m, 2H), 1.93-1.78 (m, 2H), 1.73-1.56 (m, 1H); 3Hs not observed (2 NHs and OH) |
| 388 | MS m/z 429.4 [M + H]$^+$; $^1$H NMR (DMSO-d$_6$) δ: 9.10 (s, 1H), 8.68 (s, 1H), 8.09 (s, 2H), 7.99-7.79 (m, 2H), 7.62-7.39 (m, 2H), 7.31-7.14 (m, 2H), 4.40 (br s, 2H), 3.98-3.87 (m, 1H), 3.80-3.75 (m, 1H), 3.66-3.52 (m, 1H), 3.51-3.38 (m, 1H), 3.19 (br s, 2H), 2.87-2.72 (m, 1H), 2.31-2.20 (m, 1H), 1.95-1.81 (m, 1H); 3Hs not observed (2 NHs and OH) |
| 389 | MS m/z 352.4 [M + H]$^+$; $^1$H NMR (methanol-d$_4$) δ: 9.08 (s, 1H), 8.02 (s, 1H), 7.86 (s, 1H), 7.82 (d, J = 8.00 Hz, 1H), 7.19 (d, J = 8.00 Hz, 1H), 7.16 (s, 1H), 3.96 (s, 3H), 3.92-3.81 (m, 2H), 3.75 (d, J = 11.00 Hz, 1H), 3.62 (d, J = 11.00 Hz, 1H), 2.16 (s, 2H), 1.49 (s, 3H); 3Hs not observed (2 NHs and OH) |
| 390 | MS m/z 394.5 [M + H]$^+$; $^1$H NMR (methanol-d$_4$) δ: 8.68 (s, 2H), 7.69 (d, J = 7.9 Hz, 1H), 7.40-7.29 (m, 2H), 5.96 (d, J = 7.8 Hz, 1H), 4.06-3.91 (m, 1H), 3.90-3.78 (m, 1H), 3.77-3.64 (m, 1H), 3.61-3.44 (m, 1H), 3.31-3.17 (m, 2H), 2.96-2.80 (m, 1H), 2.54-2.41 (m, 1H), 2.16-1.97 (m, 1H), 1.53-1.43 (s, 9H); 3Hs not observed (2 NHs and OH) |
| 391 | MS m/z 436.6 [M + H]$^+$; $^1$H NMR (DMSO-d$_6$) δ: 9.11 (s, 1H), 8.50-8.64 (m, 1H), 8.46 (br dd, J = 3.7, 1.8 Hz, 1H), 8.03-8.23 (m, 2H), 7.86 (br d, J = 8.4 Hz, 2H), 7.19-7.28 (m, 2H), 3.88-4.02 (m, 2H), 3.85 (br dd, J = 10.5, 2.0 Hz, 2H), 3.71-3.82 (m, 2H), 3.56-3.70 (m, 2H), 3.42-3.52 (m, 3H), 3.04-3.25 (m, 3H), 2.60-2.75 (m, 1H), 2.16-2.37 (m, 2H), 1.77-1.94 (m, 3H), 1.57-1.77 (m, 3H), 1.42 (s, 3H) |
| 392 | MS m/z 378.5 [M + H]$^+$; $^1$H NMR (DMSO-d$_6$) δ: 11.48 (br s, 1H), 9.09 (s, 1H), 8.15 (s, 1H), 7.99-8.12 (m, 1H), 7.85 (br d, J = 8.2 Hz, 1H), 7.17-7.26 (m, 2H), 3.77-3.91 (m, 1H), 3.66-3.77 (m, 1H), 3.50-3.62 (m, 1H), 2.77-2.93 (m, 2H), 2.26-2.35 (m, 1H), 2.08-2.25 (m, 1H), 1.80 (br d, J = 9.6 Hz, 1H), 0.51 (br d, J = 5.6 Hz, 2H), 0.44 (br s, 2H); 4H not observed (2NHs, 2 aliphatic CHs obscured by solvent peak) |
| 395 | MS m/z 408.5 [M + H]$^+$; $^1$H NMR (methanol-d$_4$) δ: 8.41 (s, 2H), 7.66 (d, J = 8.2 Hz, 1H), 7.24-7.36 (m, 2H), 5.95 (d, J = 6.7 Hz, 1H), 4.05-4.15 (m, 2H), 3.90-4.01 (m, 2H), 3.87-3.89 (m, 1H), 3.74-3.86 (m, 2H), 3.65-3.71 (m, 2H), 3.41-3.52 (m, 2H), 2.82-2.92 (m, 1H), 2.40-2.50 (m, 2H), 2.16 (br s, 1H), 2.00-2.17 (m, 2H); 3Hs not observed (OH and 2NHs) |
| 397 | MS m/z 422.4 [M + H]$^+$; $^1$H NMR (methanol-d$_4$) δ: 9.07 (s, 1H), 8.01 (br d, J = 0.9 Hz, 2H), 7.83 (br d, J = 7.3 Hz, 1H), 7.23 (br d, J = 8.2 Hz, 1H), 7.20 (s, 1H), 3.92-4.05 (m, 3H), 3.82-3.90 (m, 1H), 3.59-3.69 (m, 1H), 3.45 (br t, J = 11.7 Hz, 2H), 2.83 (br d, J = 7.0 Hz, 3H), 2.53-2.64 (m, 1H), 2.26-2.35 (m, 1H), 1.93 (br d, J = 12.8 Hz, 2H), 1.80-1.88 (m, 1H), 1.42-1.54 (m, 2H), 1.28-1.38 (m, 1H); 3Hs not observed (2NHs and OH) |
| 398 | MS m/z 422.4 [M + H]$^+$; $^1$H NMR (1:3 chloroform-d: methanol-d$_4$) δ: 9.04 (s, 1H), 7.94 (br s, 2H), 7.78 (br d, J = 7.9 Hz, 1H), 7.15-7.23 (m, 2H), 4.03 (br d, J = 11.0 Hz, 2H), 3.98 (br dd, J = 9.8, 8.9 Hz, 1H), 3.84-3.92 (m, 1H), 3.62-3.71 (m, 1H), 3.46 (br t, J = 11.6 Hz, 2H), 3.35-3.40 (m, 1H), 2.89-3.14 (m, 3H), 2.59-2.72 (m, 1H), 2.28-2.38 (m, 1H), 1.98 (br d, J = 11.9 Hz, 2H), 1.82-1.93 (m, 1H), 1.51-1.64 (m, 2H); 3Hs not observed (2 NHs and OH) |
| 399 | MS m/z 378.5 [M + H]$^+$; $^1$H NMR (methanol-d$_4$) δ: 1.94-2.09 (m, 2H) 2.28-2.52 (m, 4H) 2.54-2.69 (m, 1H) 3.37 (s, 1H), 3.71-4.02 (m, 4H) 4.03-4.18 (m, 2H) 5.98 (br s, 1H) 7.20-7.42 (m, 2H) 7.67 (br d, J = 8.24 Hz, 1H) 8.41 (br s, 2H); 3Hs not observed (2NHs and OH) |
| 400 | MS m/z 378.5 [M + H]$^+$; $^1$H NMR (methanol-d$_4$) δ: 1.91-2.09 (m, 2H) 2.28-2.50 (m, 5H) 2.52-2.71 (m, 1H) 3.37 (s, 2H) 3.68-4.01 (m, 4H) 4.03-4.19 (m, 2H) 5.93-6.03 (m, 1H) 7.31 (s, 1H) 7.32-7.37 (m, 1H) 7.69 (br d, J = 7.93 Hz, 1H) 8.55 (s, 2H); 1H not observed |
| 403 | MS m/z 440.7 [M + H]$^+$; $^1$H NMR (methanol-d$_4$) δ: 8.41 (s, 2H), 7.67 (d, J = 7.9 Hz, 1H), 7.25-7.34 (m, 2H), 5.95 (d, J = 7.3 Hz, 1H), 5.11-5.13 (m, 1H), 5.02-5.04 (m, 1H), 4.22 (t, J = 13.4 Hz, 1H), 4.09 (d, J = 10.4 Hz, 1H), 3.95-4.01 (m, 1H), 3.70-3.85 (m, 4H), 3.47-3.64 (m, 3H), 2.90-2.94 (m, 1H), 2.46-2.50 (m, 1H), 1.97-2.20 (m, 3H); 3Hs not observed (OH and 2NHs) |
| 404 | MS m/z 422.6 [M + H]$^+$; $^1$H NMR (methanol-d$_4$) δ: 8.40 (s, 2H), 7.66 (d, J = 7.9 Hz, 1H), 7.25-7.35 (m, 2H), 5.95 (d, J = 6.4 Hz, 1H), 3.90-4.05 (m, 2H), 3.74-3.87 (m, 3H), 3.68-3.72 (m, 3H), 3.47-3.52 (m, 2H), 3.35-3.37 (m, 2H), 2.88-2.94 (m, 1H), 2.44-2.48 (m, 1H), 2.19-2.22 (m, 1H), 1.92-2.10 (m, 3H), 1.68-1.72 (m, 1H); 3Hs not observed (OH and 2NHs) |
| 405 | MS m/z 448.7 [M + H]$^+$; $^1$H NMR (methanol-d$_4$) δ: 8.42 (br s, 2H), 7.67 (d, J = 8.5 Hz, 1H), 7.26-7.36 (m, 2H), 5.95 (d, J = 6.7 Hz, 1H), 4.50-4.52 (m, 2H), 3.92-3.96 (m, 1H), 3.79-3.83 (m, 1H), 3.66-3.72 (m, 1H), 3.47-3.52 (m, 1H), 3.15-3.28 (m, 2H), 2.85-2.89 (m, 1H), 2.65-2.72 (m, 1H), 2.40-2.46 (m, 1H), 2.00-2.10 (m, 2H), 1.82 (d, J = 7.3 Hz, 2H), 1.45-1.62 (m, 2H), 1.26-1.31 (m, 1H); 3Hs not observed (OH and 2NHs) |
| 406 | MS m/z 392.4 [M + H]$^+$; $^1$H NMR (methanol-d$_4$) δ: 1.97-2.07 (m, 2H) 2.29-2.52 (m, 5H) 2.53-2.69 (m, 1H) 3.71-4.02 (m, 4H) 4.08 (br s, 5H) 5.97 (br s, 1H) 7.24 (br s, 1H) 7.26 (br d, J = 8.24 Hz, 1H) 7.66 (br d, J = 8.24 Hz, 1H) 8.17-8.53 (m, 2H); 3Hs not observed (2NHs and OH) |
| 407 | MS m/z 392.4 [M + H]$^+$; $^1$H NMR (methanol-d$_4$) δ: 1.89-2.08 (m, 2H) 2.23-2.51 (m, 5H) 2.60 (br d, J = 5.80 Hz, 1H) 3.69-4.00 (m, 4H) 4.01-4.20 (m, 5H) 5.97 (br s, 1H) 7.22 (s, 1H) 7.25 (br d, J = 7.93 Hz, 1H) 7.65 (br d, J = 7.93 Hz, 1H) 8.17 (s, 1H) 8.29 (s, 1H); 3Hs not observed (2 NHs and OH) |
| 408 | MS m/z 420.6 [M + H]$^+$; $^1$H NMR (methanol-d$_4$) δ: 9.10 (s, 1H), 8.02 (s, 1H), 7.86 (s, 1H), 7.83 (d, J = 8.54 Hz, 1H), 7.21 (d, J = 8.09 Hz, 1H), 7.17 (s, 1H), 3.38-3.28 (m, 1H), 3.96 (s, 3H), 3.20 (s, 3H), 2.36-2.30 (m, 2H), 2.14-1.99 (m, 6H), 1.57 (s, 6H); 2Hs not observed (NH and OH) |
| 409 | MS m/z 428.4 [M + H]$^+$; $^1$H NMR (methanol-d$_4$) δ: 8.47 (br s, 2H), 7.69 (br d, J = 8.2 Hz, 1H), 7.33 (br d, J = 8.2 Hz, 1H), 7.30 (s, 1H), 5.99 (s, 1H), 4.20-4.30 (m, 1H), 4.07-4.19 (m, 2H), 3.86-4.07 (m, 3H), 3.75-3.86 (m, 1H), 2.75-2.88 (m, 1H), 2.60-2.74 (m, 1H), 2.32-2.56 (m, 4H), 2.15-2.30 (m, 1H), 2.02-2.12 (m, 1H); 3Hs not observed (2NHs and OH) |
| 410 | MS m/z 366.5 [M + H]$^+$; $^1$H NMR (methanol-d$_4$) δ: 8.42 (s, 2H), 7.66 (d, J = 7.8 Hz, 1H), 7.35-7.25 (m, 2H), 5.95 (d, J = 9.0 Hz, 1H), 4.07-3.92 (m, 1H), 3.89-3.76 (m, 1H), 3.74-3.61 (m, 1H), 3.56-3.46 (m, 1H), 3.45-3.38 (m, 2H), 3.00 (br s, 7H), 2.51-2.39 (m, 1H), 2.12-1.92 (m, 1H); 2Hs not observed (NH and OH) |
| 413 | MS m/z 352.4 [M + H]$^+$; $^1$H NMR (methanol-d$_4$) δ: 8.46 (s, 2H), 7.71-7.62 (m, 1H), 7.36-7.26 (m, 2H), 5.99-5.89 (m, 1H), 4.00-3.88 (m, 1H), 3.81 (br s, 1H), 3.74-3.63 (m, 1H), 3.56-3.47 (m, 1H), 3.28-3.25 (m, 2H), 2.95-2.84 (m, 1H), 2.84-2.77 (m, 3H), 2.43 (m, 1H), 2.13-1.93 (m, 1H); 3Hs not observed (2NHs and OH) |
| 414 | MS m/z 394.5 [M + H]$^+$; $^1$H NMR (methanol-d$_4$) δ: 8.51 (s, 2H), 7.67 (d, J = 7.8 Hz, 1H), 7.40-7.25 |

| Cpd | Data |
|---|---|
| | (m, 2H), 6.01-5.87 (m, 1H), 3.99-3.79 (m, 1H), 3.74-3.57 (m, 3H), 2.94-2.79 (m, 1H), 2.59-2.27 (m, 1H), 2.16-1.99 (m, 1H), 1.52-1.35 (m, 11H); 3Hs not observed (2NHs and OH) |
| 415 | MS m/z 392.4 [M + H]+; 1H NMR (methanol-d4) δ: 1.89-2.08 (m, 2H) 2.23-2.51 (m, 5H) 2.60 (br d, J = 5.80 Hz, 1H) 3.69-4.00 (m, 4H) 4.01-4.20 (m, 5H) 5.97 (br s, 1H) 7.22 (s, 1H) 7.25 (br d, J = 7.93 Hz, 1H) 7.65 (br d, J = 7.93 Hz, 1H) 8.17 (s, 1H) 8.29 (s, 1H); 3Hs not observed (2NHs and OH) |
| 416 | MS m/z 406.4 [M + H]+; 1H NMR (methanol-d4) δ: 1.20 (t, J = 6.87 Hz, 2H) 1.89-2.13 (m, 2H) 2.25-2.51 (m, 5H) 2.86 (br dd, J = 12.51, 6.10 Hz, 1H) 3.04-3.22 (m, 2H), 3.51 (q, J = 6.82 Hz, 2H) 3.69 (br d, J = 6.10 Hz, 1H) 3.75-3.98 (m, 3H) 4.00-4.08 (m, 3 H) 5.94 (br d, J = 7.32 Hz, 1H) 7.22 (s, 1H) 7.25 (br d, J = 8.24 Hz, 1H) 7.63 (br d, J = 8.54 Hz, 1H) 8.16 (s, 1H) 8.28 (s, 1H) |
| 418 | MS m/z 398.5 [M + H]+; 1H NMR (DMSO-d6) δ: 9.13 (s, 1H), 8.14 (s, 2H), 7.69 (d, J = 7 Hz, 1H), 7.33 (t, J = 7 Hz, 1H), 4.16 (m, 1H), 4.07 (m, 1H), 3.75-3.90 (m, 2H), 3.64 (m, 1H), 2.35 (m, 1H), 1.38 (s, 9H); 3Hs not observed (NH, OH, and one aliphatic multiplet peak obscured by solvent peak) |
| 420 | MS m/z 410.4 [M + H]+; 1H NMR (methanol-d4) δ: 8.81 (s, 2H), 7.69 (br d, J = 7.9 Hz, 1H), 7.30-7.42 (m, 2H), 5.98 (s, 1H), 5.27-5.35 (m, 1H), 4.28 (br s, 1H), 4.11-4.22 (m, 1H), 3.93-4.09 (m, 3H), 3.83 (br s, 1H), 2.69 (br d, J = 1.2 Hz, 1H), 2.48-2.64 (m, 2H), 2.43 (br s, 1H), 1.92-2.35 (m, 4H); 3Hs not observed (2 NHs and OH) |
| 421 | MS m/z 448.3 [M + H]+; 1H NMR (methanol-d4) δ: 8.72 (br s, 2H), 7.70 (br d, J = 7.9 Hz, 1H), 7.32-7.39 (m, 2H), 5.90-6.04 (m, 1H), 4.06 (br d, J = 7.6 Hz, 4H), 3.77-3.88 (m, 1H), 3.65-3.75 (m, 1H), 3.48-3.63 (m, 3H), 3.16-3.27 (m, 1H), 2.34 (br d, J = 4.6 Hz, 1H), 2.21 (br d, J = 6.1 Hz, 1H), 2.14 (br d, J = 11.9 Hz, 1H), 1.79 (br s, 3H), 1.14 (br d, J = 6.1 Hz, 4H); 3Hs not observed (2 NHs and OH) |
| 422 | MS m/z 394.5 [M + H]+; 1H NMR (methanol-d4) δ: 9.14 (s, 1H), 8.02 (s, 1H), 7.86 (s, 1H), 7.84 (d, J = 10.00 Hz, 1H), 7.21 (d, J = 10.00 Hz, 1H), 7.18 (s, 1H), 4.06-3.89 (m, 3H), 3.96 (s, 3H), 3.86-3.74 (m, 2H), 2.44-2.37 (m, 2H), 1.65 (s, 3H), 1.46 (t, J = 5.50 Hz, 6H); 2Hs not observed (NH and OH) |

Example 7

Preparation of Compound 14

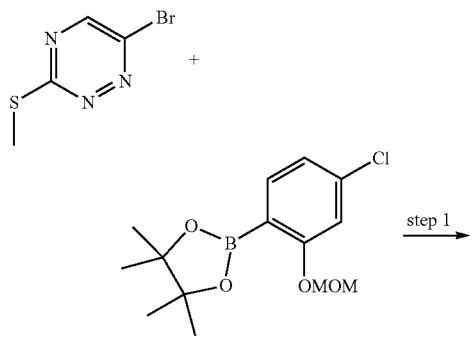

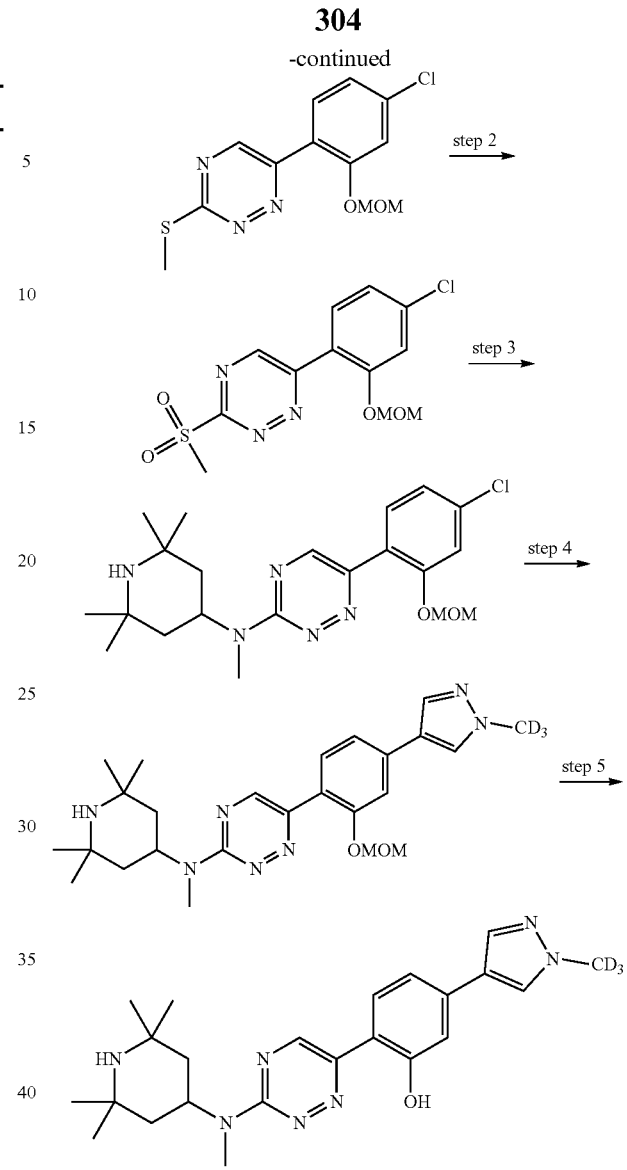

Step 1. To a dry round bottom flask were added: 6-bromo-3-methylsulfanyl-1,2,4-triazine (7.0 g, 34.0 mmol), 2-[4-chloro-2-(methoxymethoxy)phenyl]-4,4,5,5-tetramethyl-1,3,2-dioxaborolane (10 g, 33.5 mmol), $K_2CO_3$ (9.5 g, 68 mmol), and PddppfCl2 (3.8 g, 5.1 mmol). The mixture was degassed with argon for 10 min, then dioxane (100 mL) and water (20 mL) were added and the reaction was heated at 90° C. for 16 h (overnight). The reaction was cooled down to room temperature, partitioned between EtOAc and water, and then the organic phase was dried over $Na_2SO_4$, concentrated, and then purified by silica-gel column chromatography eluting with a gradient of 0-20% EtOAc in pentanes. This provided 6-[4-chloro-2-(methoxymethoxy)phenyl]-3-methylsulfanyl-1,2,4-triazine (4.5 g, 44% yield) as a yellow solid. MS m/z 298.1, 300.1 [M+H]+.

Step 2. 6-[4-Chloro-2-(methoxymethoxy)phenyl]-3-methylsulfanyl-1,2,4-triazine (1.84 g, 6.18 mmol) and mCPBA (2.67 g, 15.5 mmol) were dissolved in $CH_2Cl_2$ (26 mL). The reaction mixture was stirred at room temperature for 16 h. LCMS showed full conversion. The solvent was then removed in vacuo and the crude product was triturated in 20 mL $Et_2O$. Filtration provided 6-[4-chloro-2-

(methoxymethoxy)phenyl]-3-methylsulfonyl-1,2,4-triazine (1.69 g, 80.4% yield) as an off-white solid. MS m/z 330.1, 332.1 [M+H]⁺.

Step 3. 6-[4-Chloro-2-(methoxymethoxy)phenyl]-3-methylsulfonyl-1,2,4-triazine (1.0 g, 2.9 mmol) was dissolved in dry DMF (8 mL). Then N,2,2,6,6-pentamethylpiperidin-4-amine (790 mg, 4.41 mmol) and DIPEA (5.2 mL, 30 mmol) were added. The reaction mixture was stirred at 50° C. for 16 h (overnight). The reaction mixture was purified directly by silica-gel column chromatography using 20% MeOH/CH₂Cl₂ eluent to provide the desired product 6-[4-chloro-2-(methoxymethoxy)phenyl]-N-methyl-N-(2,2,6,6-tetramethyl-4-piperidyl)-1,2,4-triazin-3-amine (980 mg, 79% yield) as a yellow solid. MS m/z 420.5, 422.5 [M+H]⁺.

Step 4. To a dry screw-cap vial were added 6-[4-chloro-2-(methoxymethoxy)phenyl]-N-methyl-N-(2,2,6,6-tetramethyl-4-piperidyl)-1,2,4-triazin-3-amine (30 mg, 0.071 mmol), 4-(4,4,5,5-tetramethyl-1,3,2-dioxaborolan-2-yl)-1-(trideuteriomethyl)pyrazole (18.1 mg, 0.086 mmol), XPhos Pd G4 (6 mg, 0.007 mmol), and K₂CO₃ (30 mg, 0.2143 mmol). The mixture was degassed with argon for 10 min, then dioxane (2 mL) and water (0.5 mL) were added and the reaction was heated at 90° C. for 16 h (overnight). The reaction was cooled to room temperature, partitioned between EtOAc and water, and the organic phase was dried over Na₂SO₄, concentrated, and purified by silica-gel column chromatography eluting with a MeOH/CH₂Cl₂ gradient (0-20% MeOH) to provide 6-[2-(methoxymethoxy)-4-[1-(trideuteriomethyl)pyrazol-4-yl]phenyl]-N-methyl-N-(2,2,6,6-tetramethyl-4-piperidyl)-1,2,4-triazin-3-amine (24 mg, 72% yield) as a brownish solid. MS m/z 469.8 [M+H]⁺.

Step 5. To a solution 6-[2-(methoxymethoxy)-4-[1-(trideuteriomethyl)pyrazol-4-yl]phenyl]-N-methyl-N-(2,2,6,6-tetramethyl-4-piperidyl)-1,2,4-triazin-3-amine (24 mg, 0.051 mmol) in 1 mL of CH₂Cl₂ and a few drops of MeOH was added HCl (4 mol/L) in 1,4-dioxane (26 μL, 0.10 mmol) and the mixture was stirred 16 h at room temperature. UPLC showed complete consumption of the starting material. The solvents were evaporated and the residue was purified by silica-gel column chromatography eluting with a MeOH/CH₂Cl₂ gradient (0-30% MeOH/2.5% NH₄OH) to provided 2-[3-[methyl-(2,2,6,6-tetramethyl-4-piperidyl)amino]-1,2,4-triazin-6-yl]-5-[1-(trideuteriomethyl)pyrazol-4-yl]phenol; hydrochloride (7 mg, 30% yield) as a tan solid.

MS m/z 425.5 [M+H]⁺; ¹H NMR (methanol-d₄) δ: 9.58 (br s, 1H), 8.23 (s, 1H), 8.09 (s, 1H), 7.66 (d, J=8.2 Hz, 1H), 7.26 (dd, J=8.2, 1.8 Hz, 1H), 7.22 (d, J=1.8 Hz, 1H), 4.50-4.61 (m, 1H), 3.18 (s, 3H), 2.08-2.27 (m, 4H), 1.72 (s, 6H), 1.60 (s, 6H); 2Hs not observed (OH and NH).

Using the procedure described for Example 7, additional compounds described herein may be prepared by substituting the appropriate starting material, suitable reagents and reaction conditions, obtaining compounds such as those selected from:

| Cpd | Data |
|---|---|
| 72 | MS m/z 413.5 [M + H]⁺; ¹H NMR (methanol-d₄) δ: 9.34 (s, 1H), 8.00 (d, J = 2.0 Hz, 1H), 7.95 (d, J = 9.0 Hz, 1H), 7.27-7.28 (m, 2H), 5.72-5.76 (m, 1H), 2.43-2.45 (m, 2H), 1.76-1.88 (m, 2H), 1.57 (s, 6H), 1.51 (s, 6H); 3Hs not observed (2NHs and OH) |
| 213 | MS m/z 380.3 [M + H]⁺; ¹H MMR (methanol-d₄) δ: 9.14 (s, 1H), 7.88 (d, J = 8.2 Hz, 1H), 7.64 (s, 1H), 7.32-7.52 (m, 2H), 6.67 (s, 1H), 4.06-4.25 (m, 2H), 3.98-4.03 (m, 1H), 3.97 (s, 3H), 3.71-3.91 (m, 1H), 3.43-3.61 (m, 1H), 2.58 (s, 1H), 2.21-2.33 (m, 1H), 2.28 (td, J = 13.0, 6.3 Hz, 1H), 1.42 (br t, J = 5.2 Hz, 6H); 2Hs not observed (NH and OH) |
| 223 | MS m/z 442.4 [M + H]⁺; ¹H MMR (methanol-d₄) δ: 9.10 (s, 1H), 8.07 (s, 1H), 8.03 (s, 1H), 7.90 (d, J = 8.00 Hz, 1H). 7.7 (d, J = 8.50 Hz, 1H), 7.64 (d, J = 9.00 Hz, 1H), 7.31 (d, J = 8.5 Hz, 1H), 7.28 (s, 1H), 4.16 (s, 2H), 4.10 (s, 3H), 4.05 (s, 2H), 3.53 (d, J = 12.5 Hz, 2H), 3.11 (t, J = 12.5 Hz, 2H), 2.91 (s, 3H), 2.32 (d, J = 14.5 Hz, 2H), 2.05 (t, J = 12.50 Hz, 2H); 1H not observed (OH) |
| 233 | MS m/z 392.5 [M + H]⁺; ¹H MMR (methanol-d₄) δ: 7.82 (s, 1H), 7.66 (d, J = 8.3 Hz, 1H), 7.41 (d, J = 8.6 Hz, 1H), 7.39 (s, 1H), 6.81 (s, 1H), 5.95 (s, 1H), 4.25 (s, 2H), 4.14 (s, 2H), 4.02 (s, 3H), 3.53 (d, J = 12.6 Hz, 2H), 3.14 (t, J = 12.7 Hz, 2H), 2.90 (s, 3H), 2.36 (d, J = 14.4 Hz, 2H), 2.13 (t, J = 13.8 Hz, 2H); 1 OH not observed |
| 224 | MS m/z 443.5 [M + H]⁺; ¹H MMR (methanol-d₄) δ: 9.11 (s, 1H), 8.85 (s, 1H), 8.46 (s, 1H), 8.15 (s, 1H), 7.96 (d, J = 8.5 Hz, 1H), 7.32 (d, J = 8.00 Hz, 1H), 7.30 (s, 1H), 4.10-4.16 (m, 5H), 4.06 (s, 2H), 3.53 (d, J = 12.5 Hz, 2H), 3.12 (t, J = 10.00 Hz, 2H), 2.92 (s, 3H), 2.33 (d, J = 14.00 Hz, 2H), 2.05 (t, J = 14.50 Hz, 2H); 1H not observed (OH) |
| 235 | MS m/z 384.4 [M + H]⁺; ¹H MMR (methanol-d₄) δ: 9.04 (s, 1H), 7.95 (s, 1H), 7.81 (d, J = 6.7 Hz, 1H), 7.09-7.27 (m, 1H), 3.96 (br dd, J = 9.8, 6.7 Hz, 1H), 3.76-3.91 (m, 1H), 3.51-3.71 (m, 2H), 3.35-3.42 (m, 1H), 2.98 (dt, J = 12.5, 6.3 Hz, 1H), 2.20-2.40 (m, 1H), 1.84-1.98 (m, 1H), 1.14 (t, J = 5.8 Hz, 6H); 3Hs not observed (2NHs and OH) |
| 236 | MS m/z 381.5 [M + H]⁺; ¹H MMR (methanol-d₄) δ: 8.06 (s, 1H), 7.70 (d, J = 8.2 Hz, 1H), 7.38-7.55 (m, 2H), 6.00 (d, J = 3.1 Hz, 1H), 4.26-4.37 (m, 1H), 4.24 (s, 3H), 4.08-4.19 (m, 1H), 3.74-4.02 (m, 3H), 3.51-3.65 (m, 1H), 2.58-2.74 (m, 1H), 2.34-2.53 (m, 1H), 1.47 (d, J = 6.4 Hz, 6H); 2Hs not observed (NH and OH) |
| 237 | MS m/z 384.3 [M + H]⁺; ¹H MMR (methanol-d₄) δ: 8.82 (s, 1H), 7.82 (d, J = 7.9 Hz, 1H), 7.59-7.73 (m, 2H), 6.03 (d, J = 3.1 Hz, 1H), 4.25-4.37 (m, 1H), 4.09-4.19 (m, 1H), 3.85-4.03 (m, 2H), 3.75-3.84 (m, 1H), 3.51-3.65 (m, 1H), 2.58-2.74 (m, 1H), 2.36-2.56 (m, 1H), 1.47 (br d, J = 5.8 Hz, 6H); 2Hs not observed (NH and OH) |
| 260 | MS m/z 476.5 [M + H]⁺; ¹H MMR (DMSO-d₆) δ: 9.51 (br d, J = 11.3 Hz, 1H), 9.10 (s, 1H), 8.21-8.31 (m, 1H), 8.15 (br d, J = 13.4 Hz, 1H), 8.13 (s, 1H), 8.06 (s, 1H), 7.96 (d, J = 8.2 Hz, 1H), 7.75 (s, 1H), 7.31-7.36 (m, 2H), 4.71-4.92 (m, 2H), 4.09 (s, 3H), 1.97-2.06 (m, 1H), 1.92 (br dd, J = 13.3, 4.1 Hz, 1H), 1.58 (s, 3H), 1.54 (s, 3H), 1.48 (s, 3H); 1H not observed (OH) |
| 261 | MS m/z 426.5 [M + H]⁺; ¹H MMR (DMSO-d₆) δ: 9.75 (br d, J = 11.3 Hz, 1H), 9.06 (s, 1H), 8.22 (br s, 1H), 8.13 (br d, J = 11.6 Hz, 1H),7.87 (d, J = 7.9 Hz, 1H), 7.76 (d, J = 2.1 Hz, 1H), 7.45 (d, J = 1.5 Hz, 1H), 7.38 (dd, J = 8.2, 1.5 Hz, 1H), 6.70 (d, J = 2.1 Hz, 1H), 4.68-4.89 (m, 2H), 3.90 (s, 3H), 1.95-2.05 (m, 1H), 1.86-1.94 (m, 1H), 1.58 (s, 3H), 1.54 (s, 3H), 1.48 (br s, 3H), 1.47 (s, 3H) |
| 263 | MS m/z 366.4 [M + H]⁺; ¹H MMR (methanol-d₄) δ: 7.89 (d, J = 2.4 Hz, 1H), 7.75 (d, J = 8.2 Hz, 1H), 7.50-7.41 (m, 2H), 6.88 (d, J = 2.4 Hz, 1H), 6.05 (s, 1H), 4.36 (d, J = 14.5 Hz, 1H), 4.23 (s, 3H), 3.71-3.60 (m, 2H), 3.51-3.38 (m, 2H), 1.50 (d, J = 6.4 Hz, 3H), 1.48 (d, J = 6.4 Hz, 3H); 2Hs was not observed (NH and OH) |
| 289 | MS m/z 381.4 [M + H]⁺; ¹H MMR (methanol-d₄) δ: 7.95 (s, 1H), 7.76 (d, J = 8.2 Hz, 1H), 7.39 (br d, J = 8.2 Hz, 1H), 7.35-7.37 (m, 1H), 5.96-6.05 (m, 1H), 4.26-4.37 (m, 1H), 4.10-4.20 (m, 1H), 3.89-4.05 (m, 2H), 3.75-3.85 (m, 1H), 3.49-3.64 (m, 1H), 2.77 (s, 3H), 2.60-2.72 (m, 1H), 2.38-2.54 (m, 1H), 1.47 (dd, J = 6.4, 1.8 Hz, 6H); 2Hs not observed (NH and OH) |
| 296 | MS m/z 352.3 [M + H]⁺; ¹H MMR (methanol-d₄) δ: 7.72 (d, J = 2 Hz, 1H), 7.68 (d, J = 8 Hz, 1H), 7.43 (dd, J = 8.5 Hz, 1.5 Hz, 1H), 7.41 (s, 1H), 6.75 (d, J = 2 Hz, 1H), 5.99 (s, 1H), 4.03-4.18 (m, 2H), 4.00 (s, 3H), 3.87-3.95 (m, 2H), 3.81 (m, 1H), 2.85 (s, 3H), 2.59-2.74 (m, 1H), 2.37-2.53 (m, 1H); 2Hs not observed (NH and OH) |
| 299 | MS m/z 393.3 [M + H]⁺; ¹H MMR (methanol-d₄) δ: 9.06 (s, 1H), 7.87 (d, J = 8.2 Hz, 1H), 7.40 (s, 1H), 7.27 (d, J = 8.1 Hz, 1H), 7.24 (s, 1H), 4.10 (s, 4H), 3.51 (s, 2H), 3.11 (s, 2H), 2.90 (s, 3H), 2.54 (s, 3H), 2.29 (s, 2H), 2.09 (s, 2H); 1 OH not observed |

-continued

| Cpd | Data |
|---|---|
| 308 | MS m/z 367.3 [M + H]⁺; ¹H MMR (methanol-d₄) δ: 8.05 (s, 1H), 7.78 (d, J = 8.2 Hz, 1H), 7.64 (dd, J = 8.9, 1.5 Hz, 1H), 7.62 (d, J = 1.5 Hz, 1H), 7.37 (s, 1H), 6.01 (d, J = 3.1 Hz, 1H), 4.25-4.39 (m, 1H), 4.08-4.20 (m, 1H), 3.74-4.00 (m, 3H), 3.50-3.67 (m, 1H), 2.61-2.75 (m, 1H), 2.35-2.54 (m, 1H), 1.47 (dd, J = 6.1, 1.8 Hz, 6H); 2Hs not observed (NH and OH) |
| 319 | MS m/z 458.4 [M + H]⁺; ¹H MMR (methanol-d₄) δ: 8.07 (s, 1H), 7.83-7.88 (m, 2H), 7.74 (d, J = 8.5 Hz, 1H), 7.51 (d, J = 8.5 Hz, 1H), 7.41 (dd, J = 8.5 Hz, 1.5 Hz, 1H), 7.38 (s, 1H), 6.03 (s, 1H), 4.37 (m. 1H), 4.15 (s, 3H), 2.27 (m, 2H), 1.74-1.85 (m, 2H), 1.64 (d, J = 8.5 Hz, 6H), 1.56 (d, J = 6 Hz, 6H); 2Hs not observed (NH and OH) |
| 330 | MS m/z 430.5 [M + H]⁺; ¹H MMR (methanol-d₄) δ: 8.03 (s, 1H), 7.77-7.89 (m, 2H), 7.71 (d, J = 8.2 Hz, 1H), 7.47 (d, J = 8.2 Hz, 1H), 7.38 (d, J = 8.2 Hz, 1H), 7.34 (s, 1H), 5.97-6.05 (m, 1H), 4.22-4.38 (m, 1H), 4.12 (s, 3H), 3.71-4.03 (m, 4H), 3.50-3.64 (m, 1H), 2.58-2.71 (m, 1H), 2.35-2.54 (m, 1H), 1.46 (d, J = 5.8 Hz, 6H); 2Hs not observed (NH and OH) |
| 350 | MS m/z 353.5 [M + H]⁺; ¹H MMR (DMSO-d₆) δ: 9.05 (s, 1H), 7.91 (d, J = 8 Hz, 1H), 7.56 (s, 1H), 7.29 (dd, J = 8 Hz, 1.5 Hz, 1H), 7.27 (s, 1H), 3.93 (m, 2H), 3.75-3.90 (m, 2H), 3.71 (m, 1H), 2.67 (s, 3H), 2.40-2.48 (m, 1H), 2.27 (m, 1H); 2Hs not observed (NH and OH); and one methyl singlet obscured by the DMSO peak) |
| 358 | MS m/z 339.4 [M + H]⁺; ¹H MMR (methanol-d₄) δ: 8.05 (s, 1H), 7.77 (d, J = 8 Hz, 1H), 7.60-7.67 (m, 2H), 7.37 (s, 1H), 6.00 (s, 1H), 4.03-4.11 (m, 2H), 3.85-3.97 (m, 2H), 3.71-3.82 (m, 1H), 2.83 (s, 3H), 2.58-2.70 (m, 1H), 2.35-2.45 (m, 1H); 2Hs not observed (NH and OH) |

Example 8

Preparation of Compound 73

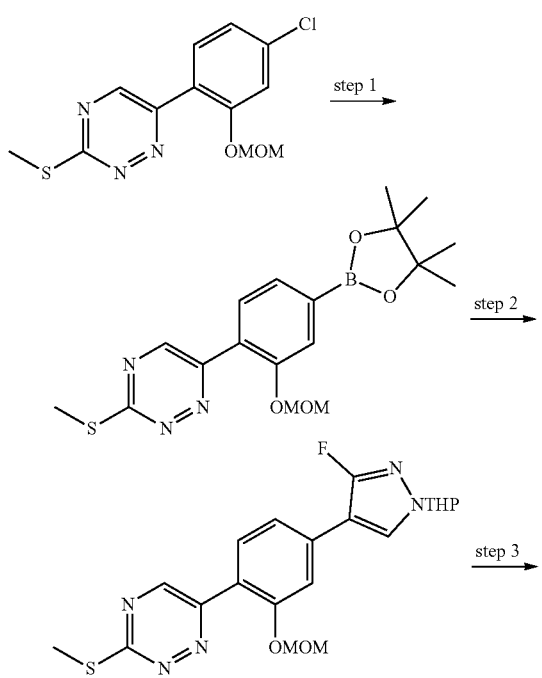

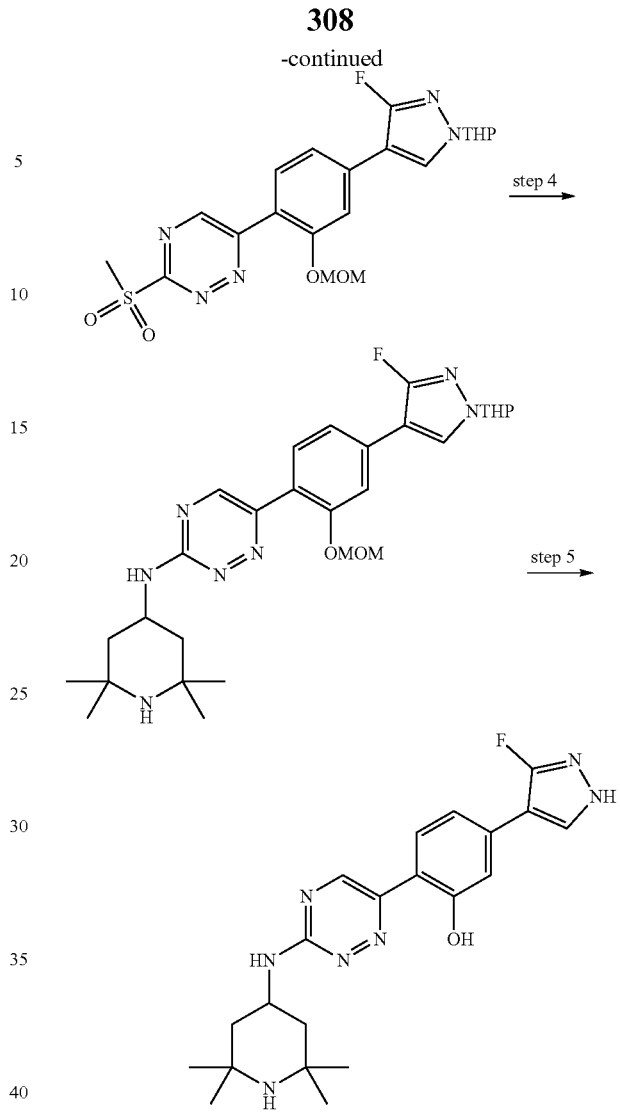

Step 1: To a suspension of 6-[4-chloro-2-(methoxymethoxy)phenyl]-3-methylsulfanyl-1,2,4-triazine (350 mg, 1.18 mmol) was added 4,4,5,5-tetramethyl-2-(4,4,5,5-tetramethyl-1,3,2-dioxaborolan-2-yl)-1,3,2-dioxaborolane (750 mg, 2.9 mmol), KOAc (575 mg, 5.86 mmol), X Phos Pd G4 (175 mg, 0.20 mmol) in dry dioxane (5 mL) which was sparged with argon for 10 minutes, then heated to 90° C. under an argon atmosphere for 2 h, after which complete conversion to 6-(2-(methoxymethoxy)-4-(4,4,5,5-tetramethyl-1,3,2-dioxaborolan-2-yl)phenyl)-3-(methylthio)-1,2,4-triazine was observed. The reaction mixture was then cooled to room temperature and used directly in the next step. MS m/z 390.4 [M+H]⁺.

Step 2: To the mixture from Step 1 was added aq. K₂CO₃ (350 mg, 2.5 mmol), 4-bromo-3-fluoro-1-tetrahydropyran-2-yl-pyrazole (200 mg, 0.80 mmol), X Phos Pd G4 (75 mg, 0.084 mmol) and water (1 mL). The reaction was degassed via bubbling with argon for 5 min and then heated to 90° C. for 12 h. The reaction was cooled to room temperature, diluted with water and extracted with EtOAc. The combined organic layers were dried over MgSO₄ and then filtered and concentrated under reduced pressure. The residue was purified by column chromatography eluting with EtOAc/hexanes (0-50%) to afford 6-[4-(3-fluoro-1-tetrahydropyran-2-yl-pyrazol-4-yl)-2-(methoxymethoxy)phenyl]-3- methylsulfanyl-1,2,4-triazine (140 mg, 40% yield) as a yellow oil. MS m/z 432.4 [M+H]+.

Step 3: To a stirred solution of 6-[4-(3-fluoro-1-tetrahydropyran-2-yl-pyrazol-4-yl)-2-(methoxymethoxy)phenyl]-3-methylsulfanyl-1,2,4-triazine (140 mg, 0.32 mmol) in $CH_2Cl_2$ (5 mL) was added mCPBA (120 mg, 0.70 mmol) and the reaction was allowed to stir at room temperature for 1 h. It was then quenched with saturated aqueous $NaHCO_3$. The organic layer was dried over $MgSO_4$ and concentrated. The residue was purified by silica gel column chromatography eluting with EtOAc/hexanes (0-100% EtOAc) to afford 6-[4-(3-fluoro-1-tetrahydropyran-2-yl-pyrazol-4-yl)-2-(methoxymethoxy)phenyl]-3-methylsulfonyl-1,2,4-triazine (95 mg, 63% yield) as a yellow solid. MS m/z 464.5 [M+H]+.

Step 4: A mixture of 6-[4-(3-fluoro-1-tetrahydropyran-2-yl-pyrazol-4-yl)-2-(methoxymethoxy)phenyl]-3-methylsulfonyl-1,2,4-triazine (25 mg, 0.054 mmol), 2,2,6,6-tetramethylpiperidin-4-amine (17 mg, 0.11 mmol) and DIPEA (30 μL, 0.168 mmol) in dry DMF was heated to 50° C. for 1 h. UPLC showed full conversion. The solvent was removed by blowing a stream of air and the residue was purified by silica gel column chromatography eluting with $MeOH/CH_2Cl_2$ (0-30% MeOH) to afford 6-[4-(3-fluoro-1-tetrahydropyran-2-yl-pyrazol-4-yl)-2-(methoxymethoxy)phenyl]-N-(2,2,6,6-tetramethyl-4-piperidyl)-1,2,4-triazin-3-amine (20 mg, 69% yield). MS m/z 540.7 [M+H]+.

Step 5: 6-[4-(3-Fluoro-1-tetrahydropyran-2-yl-pyrazol-4-yl)-2-(methoxymethoxy)phenyl]-N-(2,2,6,6-tetramethyl-4-piperidyl)-1,2,4-triazin-3-amine (20 mg, 0.037 mmol) was dissolved in MeOH (1 mL) and HCl (4 mol/L) in 1,4-dioxane (1.0 mL, 4 mmol) was then added. The reaction mixture was heated to 50° C. for 2 h. The solvents were removed and the residue was purified by silica gel column chromatography eluting with $MeOH/CH_2Cl_2$ (0-30% MeOH) to afford 5-(3-fluoro-1H-pyrazol-4-yl)-2-[3-[(2,2,6,6-tetramethyl-4-piperidyl)amino]-1,2,4-triazin-6-yl]phenol (12 mg, 77% yield) as a yellow solid.

MS m/z 412.5 [M+H]+; 1H NMR (methanol-d4) δ: 9.05 (s, 1H), 7.97 (d, J=2.0 Hz, 1H), 7.83 (d, J=9.0 Hz, 1H), 7.20-7.22 (m, 2H), 4.54-4.58 (m, 1H), 2.30 (dd, J=13.5, 3.5 Hz, 2H), 1.62-1.64 (m, 2H), 1.61 (s, 6H), 1.49 (s, 6H); 4Hs not observed (3NHs and OH).

Using the procedure described for Example 8, additional compounds described herein may be prepared by substituting the appropriate starting material, suitable reagents and reaction conditions, obtaining compounds such as those selected from:

| Cpd | Data |
|---|---|
| 149 | MS m/z 396.4 [M + H]+; 1H NMR (DMSO-d6) δ: 9.00 (s, 1H), 7.81 (d, J = 1.8 Hz, 1H), 7.76 (d, J = 8.2 Hz, 1H), 7.15-7.23 (m, 2H), 4.06 (s, 4H), 2.84-3.25 (m, 4H), 2.74 (br s, 3H), 2.15 (br s, 4H); 2Hs not observed (NH and OH) |
| 150 | MS m/z 382.4 [M + H]+; 1H NMR (1:1 chloroform-d: methanol-d4) δ: 8.90 (s, 1H), 7.74 (d, J = 1.8 Hz, 1H), 7.68 (d, J = 7.9 Hz, 1H), 7.08-7.13 (m, 2H), 4.31 (dt, J = 14.0, 4.9 Hz, 1H), 4.12 (dd, J = 14.3, 6.1 Hz, 1H), 3.84-3.93 (m, 2H), 3.52 (ddd, J = 13.7, 9.8, 3.7 Hz, 1H), 3.39 (dq, J = 11.9, 4.7 Hz, 1H), 3.26-3.33 (m, 1H), 2.57-2.68 (m, 1H), 2.06-2.19 (m, 2H), 1.78-1.92 (m, 2H); 3Hs not observed (2NHs and OH) |
| 151 | MS m/z 382.4 [M + H]+; 1H NMR (1:1 chloroform-d: methanol-d4) δ: 7.85 (d, J = 1.8 Hz, 1H), 7.50 (d, J = 8.9 Hz, 1H), 7.16-7.21 (m, 2H), 5.84 (s, 1H), 4.10-4.27 (m, 4H), 3.20-3.29 (m, 4H), 2.20 (br s, 4H); 3Hs not observed (2NHs and OH) |
| 153 | MS m/z 396.3 [M + H]+; 1H NMR (DMSO-d6) δ: 12.63-12.73 (m, 2H), 11.04-11.30 (m, 4H), 9.03-9.08 (m, 1H), 8.22 (br s, 1H), 7.88 (br d, J = 7.9 Hz, 1H), 7.21 (br s, 2H), 4.62-4.71 (m, 1H), 4.48-4.56 (m, 1H), 4.19-4.30 (m, 1H), 3.35-3.43 (m, 1H), 3.18 (s, 3H), 3.07-3.13 (m, 1H), 2.89 (br d, J = 4.6 Hz, 2H), 2.74-2.81 (m, 1H), 2.18-2.28 (m, 1H), 2.08-2.16 (m, 1H), 1.98-2.07 (m, 1H), 1.63-1.72 (m, 1H); 2H not observed (1 NH 1 OH). |
| 174 | MS m/z 398.3 [M + H]+; 1H MMR (DMSO-d6) δ: 12.66 (br s, 1H), 11.31 (br s, 1H), 9.04 (s, 1H), 8.21 (s, 1H), 7.86 (d, J = 8.5 Hz, 1H), 7.19-7.16 (m, 2H), 3.96-3.82 (m, 1H), 3.79-3.68 (m, 1H), 3.66-3.58 (m, 1H), 3.56-3.46 (m, 1H), 3.23-3.20 (m, 1H), 2.25-2.18 (m, 1H), 1.87-1.79 (m, 1H), 1.12 (s, 9H);); 1H not observed (NH or OH) |
| 175 | MS m/z 394.3 [M + H]+; 1H MMR (DMSO-d6) δ: 11.19 (br s, 1H), 9.03 (s, 1H), 7.86 (d, J = 8.0 Hz, 1H), 7.74 (s, 1H), 7.41 (s, 1H), 7.36 (d, J = 8.0 Hz, 1H), 6.69 (s, 1H), 3.90 (s, 3H), 3.79-3.65 (m, 2H), 3.59-3.45 (m, 2H), 3.23-3.08 (m, 1H), 2.23-2.13 (m, 1H), 1.83-1.70 (m, 1H), 1.09 (s, 9H); 1H not observed (NH or OH) |
| 189 | MS m/z 430.5 [M + H]+; 1H MMR (methanol-d4) δ: 9.10 (s, 1H), 7.98 (s, 1H), 7.86 (d, J = 8.5 Hz, 1H), 7.20-7.27 (m, 2H), 4.53-4.67 (m, 1H), 2.01-2.26 (m, 3H), 1.68 (s, 3H), 1.65 (s, 3H), 1.59 (s, 3H), 1.56 (s, 3H); 4H not observed (3NHs and OH) |
| 247 | MS m/z 413.5 [M + H]+; 1H MMR (DMSO-d6) δ: 9.75 (br d, J = 12.2 Hz, 1H), 9.07 (s, 1H), 8.38 (br s, 1H), 8.27 (br s, 1H), 8.14 (br d, J = 12.2 Hz, 1H), 7.94 (d, J = 8.2 Hz, 1H), 7.53 (s, 1H), 7.46 (br d, J = 7.9 Hz, 1H), 4.77 (br s, 2H), 1.96-2.05 (m, 1H), 1.87-1.95 (m, 1H), 1.58 (s, 3H), 1.54 (s, 3H), 1.48 (br d, J = 6.4 Hz, 6H); 1H not observed (NH or OH) |
| 248 | MS m/z 463.5 [M + H]+; 1H MMR (DMSO-d6) δ: 11.24 (br s, 1H), 9.28 (s, 1H), 9.19 (s, 1H), 9.07 (s, 1H), 8.16 (s, 1H), 8.00 (d, J = 8.5 Hz, 1H), 7.87 (s, 1H), 7.74 (s, 1H), 7.62 (br d, J = 8.2 Hz, 1H), 4.41-4.73 (m, 2H), 1.57-1.79 (m, 2H), 1.06-1.37 (m, 12H); 2Hs not observed (NH and OH) |
| 249 | MS m/z 463.5 [M + H]+; 1H MMR (DMSO-d6) δ: 11.28 (br s, 1H), 9.91-10.07 (m, 1H), 9.09 (s, 1H), 8.69 (s, 1H), 8.52 (br d, J = 9.5 Hz, 1H), 8.28 (br s, 1H), 8.25 (br d, J = 9.8 Hz, 1H), 8.13 (br d, J = 13.1 Hz, 1H), 8.08 (d, J = 8.2 Hz, 1H), 7.80 (s, 1H), 7.74 (br d, J = 8.2 Hz, 1H), 4.75-4.89 (m, 2H), 1.98-2.06 (m, 1H), 1.87-1.94 (m, 1H), 1.59 (s, 3H), 1.56 (s, 3H), 1.49 (br s, 3H), 1.48 (br s, 3H) |
| 256 | MS m/z 429.4 [M + H]+; 1H MMR (methanol-d4) δ: 9.14 (s, 1H), 8.40 (s, 1H), 8,29 (d, J = 8.50 Hz, 1H), 8.11 (d, J = 10.00 Hz, 1H), 8.05 (s, 1H), 8.03 (s, 1H), 7.73 (d, J = 8.50 Hz, 1H), 7.73 (d, J = 12.50 Hz, 1H), 4.17 (s, 2H), 4.07 (s, 2H), 3.54 (d, J = 14.50 Hz, 2H), 3.12 (t, J = 10.0 Hz, 2H), 2.91 (s, 3H), 2.32 (d, J = 14.50 Hz, 2H), 2.06 (t, J = 15.00 Hz, 2H); 1H not observed (OH) |
| 257 | MS m/z 429.4 [M + H]+; 1H MMR (methanol-d4) δ: 9.42 (s, 1H), 9.38 (s, 1H), 8.37 (s, 1H), 8.23 (s, 1H), 7.80-7.75 (m, 2H), 7.74-7.70 (m, 1H), 6.00 (s, 1H), 4.26 (s, 2H), 4.15 (s, 2H), 3.48 (d, J = 7.00 Hz, 2H), 3.12 (t, J = 13.00 Hz, 2H), 2.91 (s, 3H), 2.38 (d, J = 16.00 Hz, 2H), 2.11 (t, J = 14.00 Hz, 2H); 1H not observed (OH) |
| 272 | MS m/z 396.4 [M + H]+; 1H MMR (methanol-d4) δ: 9.10 (s, 1H), 8.78 (s, 1H), 8.01 (d, J = 8.09 Hz, 1H), 7.76-7.61 (m, 2H), 4.17 (s, 2H), 4.07 (s, 2H), 3.51 (d, J = 12.13 Hz, 2H), 3.11 (t, J = 12.50 Hz, 2H), 2.91 (s, 3H), 2.32 (d, J = 14.50 Hz, 2H), 2.06 (t, J = 15.00 Hz, 2H); 1H not observed (NH or OH) |
| 378 | MS m/z 398.5 [M + H]+; 1H MMR (methanol-d4) δ: 9.07 (s, 1H), 7.96 (s, 1H), 7.82 (d, J = 8.5 Hz, 1H), 7.19 (d, J = 8.5 Hz, 1H), 7.18 (s, 1H), 4.08 (dd, J = 11.5, 7.5 Hz, 1H), 3.91-3.37 (m, 2H), 3.66-3.61 (m, 1H), 3.51-3.47 (m, 1H), 2.49-2.44 (m, 1H), 2.10-2.03 (m, 1H), 1.32 (s, 9H); 3Hs not observed (2NHs and OH) |
| 379 | MS m/z 398.5 [M + H]+; 1H MMR (methanol-d4) δ: 9.07 (s, 1H), 7.96 (s, 1H), 7.82 (d, J = 8.5 Hz, 1H), 7.19 (d, J = 8.5 Hz, 1H), 7.18 (s, 1H), 4.08 (dd, J = 11.5, 7.5 Hz, 1H), 3.91-3.37 (m, 2H), 3.66-3.61 (m, 1H), 3.51-3.47 (m, 1H), 2.49-2.44 (m, 1H), 2.10-2.03 (m, 1H), 1.32 (s, 9H); 3Hs not observed (2NHs and OH) |
| 385 | MS m/z 403.6 [M + H]+; 1H MMR (methanol-d4) δ: 9.21 (s, 1H), 8.57 (s, 1H), 8.50 (d, J = 9.8 Hz, 1H), 8.44-8.38 (m, 1H), 8.25 (s, 1H), 8.14-8.07 (m, 1H), 7.83-7.73 (m, 2H), 5.18-5.04 (m, 2H), 3.59-3.44 (m, 2H), 3.18-3.02 (m, 2H), 1.47 (d, J = 6.4 Hz, 6H); 2Hs not observed (NH and OH) |

Example 9

Preparation of Compound 380

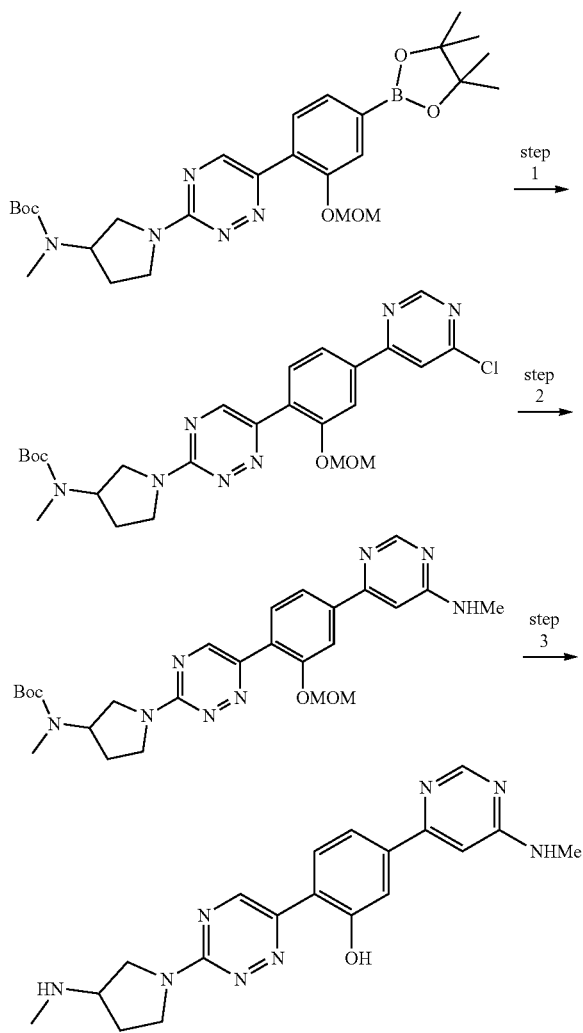

Step 1: A mixture of tert-butyl N-[1-[6-[2-(methoxymethoxy)-4-(4,4,5,5-tetramethyl-1,3,2-dioxaborolan-2-yl)phenyl]-1,2,4-triazin-3-yl]pyrrolidin-3-yl]-N-methyl-carbamate (425 mg, 0.63 mmol), 4,6-dichloropyrimidine (450 mg, 3.02 mmol), Pd(dppf)Cl$_2$—CH$_2$Cl$_2$ (50 mg, 0.06 mmol), 1,4-dioxane (3 mL), and aqueous K$_2$CO$_3$ (2 M, 1.5 mL, 3.0 mmol) was purged with argon for 10 min. The reaction was then heated at 90° C. for 16 h. The reaction mixture was partitioned between water and CH$_2$Cl$_2$. The organic layer was dried over MgSO$_4$, filtered, and concentrated under vacuum. Purification by silica gel chromatography with MeOH/CH$_2$Cl$_2$ (0 to 5% MeOH) yielded tert-butyl N-[1-[6-[4-(6-chloropyrimidin-4-yl)-2-(methoxymethoxy)phenyl]-1,2,4-triazin-3-yl]pyrrolidin-3-yl]-N-methyl-carbamate (318 mg, 86% yield) as an orange oil.

$^1$H NMR (acetone-d$_6$) δ: 9.08 (s, 1H), 8.84 (s, 1H), 8.23 (s, 2H), 8.04-8.11 (m, 2H), 5.49 (s, 2H), 4.94 (m, 1H), 3.80-4.10 (m, 2H), 3.55-3.75 (m, 2H), 3.51 (s, 3H), 2.91 (s, 3H), 2.27 (m, 2H), 1.50 (s, 9H).

Step 2: tert-Butyl N-[1-[6-[4-(6-chloropyrimidin-4-yl)-2-(methoxymethoxy)phenyl]-1,2,4-triazin-3-yl]pyrrolidin-3-yl]-N-methyl-carbamate (40 mg, 0.068 mmol) and methylamine (33% in EtOH) (0.5 mL, 6 mmol) were stirred at room temperature for 1 h. The volatiles were removed by a nitrogen stream. The residue was purified by silica gel chromatography eluting with MeOH/CH$_2$Cl$_2$ (0 to 5% MeOH) to afford tert-butyl N-[1-[6-[2-(methoxymethoxy)-4-[6-(methylamino)pyrimidin-4-yl]phenyl]-1,2,4-triazin-3-yl]pyrrolidin-3-yl]-N-methyl-carbamate (32 mg, 90% yield) as an off-white solid.

$^1$H NMR (methanol-d$_4$) δ: 8.86 (s, 1H), 8.51 (s, 1H), 7.90 (m, 2H), 7.71 (d, J=7.5 Hz, 1H), 6.94 (s, 1H), 5.39 (s, 2H), 4.87 (s, 1H), 3.90-4.00 (m, 2H), 3.55-3.70 (m, 2H), 3.48 (s, 3H), 3.00 (s, 3H), 2.90 (s, 3H), 2.29 (m, 2H), 1.52 (s, 9H).

Step 3: To a solution of tert-butyl N-[1-[6-[2-(methoxymethoxy)-4-[6-(methylamino)pyrimidin-4-yl]phenyl]-1,2,4-triazin-3-yl]pyrrolidin-3-yl]-N-methyl-carbamate (30 mg, 0.057 mmol) in MeOH (0.4 mL) was added 4N HCl in dioxane (0.4 mL, 1.6 mmol). The reaction mixture was stirred at room temperature for 1 h. The solvents were then removed by a nitrogen stream. The product was dissolved in sat. aq. NaHCO$_3$, and the free base was extracted with CH$_2$Cl$_2$. The organic layer was dried over MgSO$_4$, filtered, and concentrated under vacuum. The title product, 5-[6-(methylamino)pyrimidin-4-yl]-2-[3-[3-(methylamino)pyrrolidin-1-yl]-1,2,4-triazin-6-yl]phenol (15 mg, 69% yield), was obtained as a yellow solid.

MS m/z 379.3 [M+H]$^+$; H NMR (DMSO-d$_6$) δ: 9.03 (s, 1H), 8.51 (s, 1H), 7.94 (d, J=8 Hz, 1H), 7.50-7.80 (m, 2H), 7.40 (br s, 1H), 6.92 (s, 1H), 3.55-3.80 (m, 3H), 3.44 (m, 1H), 3.30 (m, 1H), 2.87 (s, 3H), 2.31 (s, 3H), 2.11 (m, 1H), 1.89 (m, 1H); 2Hs not observed (NH and OH).

Using the procedure described for Example 9, additional compounds described herein may be prepared by substituting the appropriate starting material, suitable reagents and reaction conditions, obtaining compounds such as those selected from:

| Cpd | Data |
| --- | --- |
| 33 | MS m/z 437.6 [M + H]$^+$; $^1$H MMR (methanol-d$_4$) δ: 9.13-9.28 (m, 2H), 8.10-8.23 (m, 1H), 7.38-7.61 (m, 2H), 5.33-5.52 (m, 1H), 3.26 (s, 3H), 2.04-2.14 (m, 2H), 2.00 (dd, J = 13.1, 2.4 Hz, 2H), 1.66 (s, 6H), 1.58 (s, 6H); 3Hs not observed (NH and 2 OHs) |
| 364 | MS m/z 396.3 [M + H]$^+$; $^1$H MMR (DMSO-d$_6$) δ: 9.10 (s, 1H), 9.01 (s, 1H), 7.95-8.03 (m, 2H), 7.88 (s, 1H), 7.80 (d, J = 8 Hz, 1H), 3.80-4.00 (m, 4H), 3.63-3.76 (m, 1H), 2.66 (s, 3H), 2.62 (s, 3H), 2.40-2.48 (m, 1H), 2.30 (m, 1H); 2Hs not observed (NH and OH) |

Example 10

Preparation of Compound 396

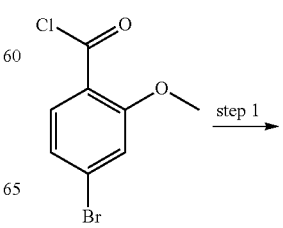

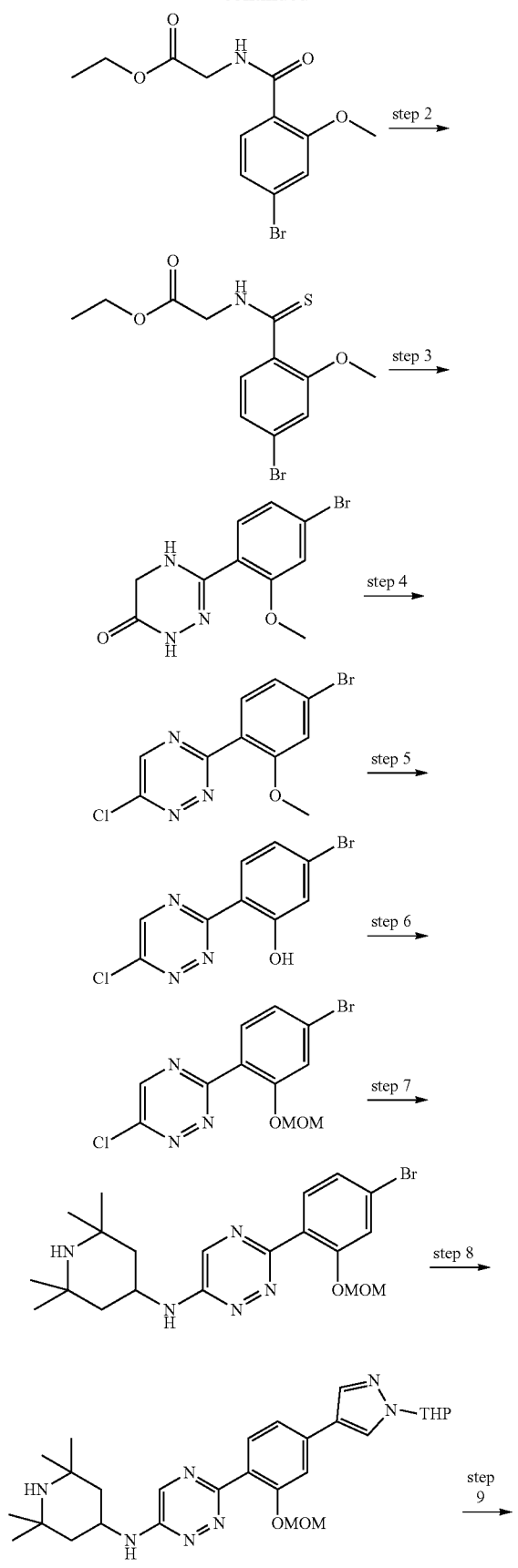

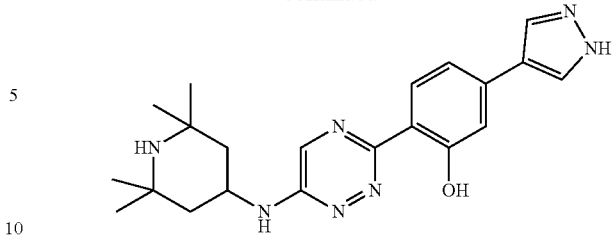

Step 1: To a stirred solution of 4-bromo-2-methoxybenzoyl chloride (2.53 g, 10.1 mmol) in dry dichloromethane (80 mL) were added ethyl 2-aminoacetate hydrochloride (2.12 g, 15.2 mmol) and Et$_3$N (4.28 mL, 30.4 mmol). After stirring for 1 h, the mixture was diluted with saturated NaHCO$_3$ and the aqueous layer extracted twice with dichloromethane. The combined organic layers were dried over Na$_2$SO$_4$ and evaporated to dryness in vacuo to give ethyl (4-bromo-2-methoxybenzoyl)glycinate (3.2 g, 99% yield) which was taken on without further purification. MS m/z 316.0, 318.0 [M+H]$^+$.

Step 2: To a stirred solution of ethyl (4-bromo-2-methoxybenzoyl)glycinate (3.2 g, 10.0 mmol) in dry toluene (150 mL) was added phosphorous pentasulfide (2.5 g, 11.0 mmol) and the mixture was heated to 120° C. for 1 h. The mixture was filtered, evaporated to dryness and purified by silica gel chromatography eluting with a gradient EtOAc/hexanes (0-100% EtOAc) to yield ethyl 2-[(4-bromo-2-methoxybenzenecarbothioyl)amino]acetate (1.38 g, 41% yield). MS m/z 331.3, 333.3 [M+H]$^+$.

Step 3: To a solution of ethyl 2-[(4-bromo-2-methoxybenzenecarbothioyl)amino]acetate (1.38 g, 4.2 mmol) in ethanol (10 mL) was added hydrazine (1.02 g, 31.4 mmol). The mixture was heated to 90° C. for 5 h until UPLC showed complete consumption of the starting material and allowed to cool to room temperature. Concentration in vacuo gave a yellow solid that was purified by silica gel chromatography eluting with a MeOH/CH$_2$Cl$_2$ gradient (0-10% MeOH) to give 3-(4-bromo-2-methoxy-phenyl)-4,5-dihydro-1H-1,2,4-triazin-6-one (560 mg, 47%) as an off-white solid. MS m/z 284.0, 286.0 [M+H]$^+$.

Step 4: 3-(4-bromo-2-methoxy-phenyl)-4,5-dihydro-1H-1,2,4-triazin-6-one (1.0 g, 3.5 mmol) was dissolved in POCl$_3$ (10 mL, 108 mmol) and heated to 85° C. for 16 h. The mixture was allowed to cool to room temperature and evaporated to dryness in vacuo. The residue was dissolved in dioxane (20 mL) and manganese dioxide (3.5 g, 40 mmol) was added. The mixture was stirred at 90° C. for 36 h. After filtering through celite and rinsing with hot dioxane, the combined organic phases were evaporated to dryness in vacuo. The crude residue was purified by silica gel chromatography eluting with a MeOH/CH$_2$Cl$_2$ gradient (0-10% MeOH) to give 3-(4-bromo-2-methoxy-phenyl)-6-chloro-1,2,4-triazine (420 mg, 40% yield) as a tan solid. MS m/z 299.9, 301.9 [M+H]$^+$.

Step 5: 3-(4-Bromo-2-methoxy-phenyl)-6-chloro-1,2,4-triazine (1.0 g, 3.3 mmol) was dissolved in CH$_2$Cl$_2$ (10 mL) and cooled to −50° C. Boron tribromide (5.0 mL, 5.0 mmol) was added slowly and the reaction mixture was stirred for 5 h at −50° C. Upon completion (as shown by LCMS), the reaction was quenched with water and saturated sodium bicarbonate solution (final pH=7-8) and extracted with CH$_2$Cl$_2$ three times. The combined organic layers were dried over Na$_2$SO$_4$, concentrated in vacuo and purified by silica gel column chromatography eluting with a EtOAc/hexanes gradient (10-80% EtOAc) to give 5-bromo-2-(6-chloro-1,2,4-triazin-3-yl)phenol (650 mg, 68% yield) as a brownish solid. MS m/z 285.8, 287.9 [M+H]⁺.

Step 6: A solution of 5-bromo-2-(6-chloro-1,2,4-triazin-3-yl)phenol (0.65 g, 2.3 mmol) in dry THF (5 mL) was cooled to 0° C. Sodium hydride (0.12 g, 3.0 mmol, 60 mass % in mineral oil) was added and the mixture was stirred for 1.5 h at 0° C. Bromo(methoxy)methane (0.37 g, 3.0 mmol) was added and the reaction mixture was stirred for an additional 3 h at 0° C. The reaction was quenched with water (10 mL) and extracted with EtOAc three times. The combined organic layers were dried over $Na_2SO_4$, concentrated in vacuo and purified by silica-gel column chromatography eluting with a EtOAc/hexanes gradient (10-80% EtOAc) to give 3-[4-bromo-2-(methoxymethoxy)phenyl]-6-chloro-1,2,4-triazine (430 mg, 57% yield). MS m/z 329.9, 331.9 [M+H]⁺; ¹H NMR (methanol-d₄) δ: 8.95 (s, 1H), 7.70 (d, J=8.2 Hz, 1H), 7.55 (s, 1H), 7.37 (d, J=7.9 Hz, 1H), 4.87 (s, 2H), 3.33 (s, 3H).

Step 7: To a solution of 3-[4-bromo-2-(methoxymethoxy)phenyl]-6-chloro-1,2,4-triazine (500 mg, 1.51 mmol) and 2,2,6,6-tetramethylpiperidin-4-amine (285 mg, 1.82 mmol) in dry DMSO (5 mL) was added DIPEA (0.67 mL, 3.8 mmol). The mixture was heated at 100° C. for 16 hours. LCMS showed complete conversion. The reaction was quenched with water (100 mL) and extracted with EtOAc five times. The combined organic layers were dried over $Na_2SO_4$, concentrated in vacuo and purified by silica gel column chromatography eluting with a MeOH/$CH_2Cl_2$ gradient (0-20% MeOH) to give 3-(4-bromo-2-(methoxymethoxy)phenyl)-N-(2,2,6,6-tetramethylpiperidin-4-yl)-1,2,4-triazin-6-amine (340 mg, 50% yield) as a greyish solid. MS m/z 449.9, 451.9 [M+H]⁺; ¹H NMR (methanol-d₄) δ: 8.19 (s, 1H), 7.52 (br d, J=7.9 Hz, 1H), 7.48 (s, 1H), 7.30 (d, J=8.2 Hz, 1H), 5.21 (s, 2H), 4.41-4.60 (m, 1H), 3.45 (s, 3H), 2.10 (br d, J=11.9 Hz, 2H), 1.37 (s, 6H), 1.24 (s, 6H), 1.18-1.23 (m, 2H), 2 Hs is not observed (NHs).

Step 8: To a dry screw-cap vial were added 3-[4-bromo-2-(methoxymethoxy)phenyl]-N-(2,2,6,6-tetramethyl-4-piperidyl)-1,2,4-triazin-6-amine (67 mg, 0.15 mmol), (1-tetrahydropyran-2-yl-4-(4,4,5,5-tetramethyl-1,3,2-dioxaborolan-2-yl)pyrazole (50 mg, 0.18 mmol), $K_2CO_3$ (62 mg, 0.45 mmol), and $PddppfCl_2$ (11 mg, 0.015 mmol). The mixture was degassed with argon for 10 min, and then dioxane (2 mL) and water (0.5 mL) were added and the reaction was heated at 90° C. for 16 h (overnight). The reaction was cooled to room temperature, partitioned between EtOAc and water, and the organic phase was dried over $Na_2SO_4$ and concentrated. The crude product was purified by silica gel column chromatography, eluting with a MeOH/$CH_2Cl_2$ gradient (0-20% MeOH) to provide 3-[2-(methoxymethoxy)-4-(1-tetrahydropyran-2-ylpyrazol-4-yl)phenyl]-N-(2,2,6,6-tetramethyl-4-piperidyl)-1,2,4-triazin-6-amine (59 mg, 76% yield) as a brownish solid. MS m/z 522.7 [M+H]⁺.

Step 9: To a solution of 3-[2-(methoxymethoxy)-4-(1-tetrahydropyran-2-ylpyrazol-4-yl)phenyl]-N-(2,2,6,6-tetramethyl-4-piperidyl)-1,2,4-triazin-6-amine (59 mg, 0.11 mmol) in 1 mL of $CH_2Cl_2$ and MeOH (0.5 mL) was added HCl (4 mol/L) in 1,4-dioxane (56 μL, 0.23 mmol) and the mixture was stirred for 16 h at room temperature. UPLC showed complete consumption of the starting material. The solvents were evaporated, and the residue was purified by silica gel column chromatography eluting with a MeOH/$CH_2Cl_2$/2.5% $NH_4OH$ gradient (0-30% MeOH/$NH_4OH$) to provide 5-(1H-pyrazol-4-yl)-2-[6-[(2,2,6,6-tetramethyl-4-piperidyl)amino]-1,2,4-triazin-3-yl]phenol (30 mg, 62% yield) as a tan solid MS m/z 394.5 [M+H]⁺; ¹H NMR (methanol-d₄) δ: 8.32 (s, 1H), 8.18 (d, J=7.0 Hz, 1H), 8.02 (s, 2H), 7.13-7.25 (m, 2H), 4.43 (br t, J=11.3 Hz, 1H), 2.08 (br d, J=12.8 Hz, 2H), 1.39 (s, 6H), 1.20-1.32 (m, 8H); 4Hs not observed (3NHs and OH).

Using the procedure described for Example 11, additional compounds described herein may be prepared by substituting the appropriate starting material, suitable reagents and reaction conditions, obtaining compounds such as those selected from:

| Cpd | Data |
|---|---|
| 24 | MS m/z 408.3 [M + H]⁺; ¹H MMR (methanol-d₄) δ: 8.64 (s, 1H), 8.25 (d, J = 7.6 Hz, 1H), 7.92-8.13 (m, 2H), 7.19-7.24 (m, 2H), 5.22-5.31 (m, 1H), 3.13 (s, 3H), 1.82-2.01 (m, 4H), 1.53-1.64 (m, 6H), 1.38-1.52 (m, 6H); 3Hs not observed (2NHs and OH) |
| 190 | MS m/z 426.4 [M + H]⁺; ¹H MMR (methanol-d₄) δ: 8.08 (s, 1H), 7.60 (d, J = 7.9 Hz, 1H), 7.27-7.37 (m, 2H), 5.75 (br s, 1H), 4.47-4.80 (m, 1H), 3.04 (s, 3H), 1.88-2.12 (m, 4H), 1.58-1.66 (m, 6H), 1.57 (s, 6H); 3Hs not observed (2 NHs and OH) |
| 191 | MS m/z 425.5 [M + H]⁺; ¹H MMR (methanol-d₄) δ: 8.63 (s, 1H), 8.23 (d, J = 8.2 Hz, 1H), 8.01 (s, 1H), 7.86 (br s, 1H), 7.09-7.21 (m, 2H), 5.16-5.57 (m, 1H), 3.14 (s, 3H), 1.92-2.09 (m, 4H), 1.66 (s, 6H), 1.56 (s, 6H); 2Hs not observed (NH and OH) |
| 196 | MS m/z 422.5 [M + H]⁺; ¹H MMR (methanol-d₄) δ: 9.96 (s, 1H), 9.46 (d, J = 7.9 Hz, 1H), 9.34 (s, 1H), 9.14 (s, 1H), 8.39-8.53 (m, 2H), 6.52-6.64 (m, 1H), 5.20 (s, 3H), 4.44 (s, 3H), 3.46 (br t, J = 12.2 Hz, 2H), 3.28 (br d, J = 12.8 Hz, 2H), 2.95 (s, 6H), 2.86 (s, 6H); 2Hs not observed (NH and OH) |
| 342 | MS m/z 472.4 [M + H]⁺; ¹H MMR (methanol-d₄) δ: 8.67 (s, 1H), 8.37 (d, J = 8.5 Hz, 1H), 8.04 (s, 1H), 7.78-7.89 (m, 2H), 7.52 (d, J = 9.5 Hz, 1H), 7.32-7.43 (m, 2H), 5.23-5.41 (m, 1H), 4.15 (s, 3H), 3.15 (s, 3H), 1.88-2.15 (m, 4H), 1.65 (s, 6H), 1.52 (s, 6H); 2Hs not observed (NH and OH) |
| 343 | MS m/z 422.4 [M + H]⁺; ¹H MMR (methanol-d₄) δ: 8.57 (s, 1H), 8.23 (d, J = 8.9 Hz, 1H), 7.64 (d, J = 2.1 Hz, 1H), 7.33-7.43 (m, 2H), 6.69 (d, J = 2.4 Hz, 1H), 5.12-5.36 (m, 1H), 3.97 (s, 3H), 3.10 (s, 3H), 1.83-2.04 (m, 4H), 1.61 (s, 6H), 1.50 (s, 6H); 2Hs not observed (NH and OH) |
| 363 | MS m/z 380.4 [M + H]⁺; ¹H MMR (methanol-d₄) δ: 8.57 (s, 1H), 8.27 (d, J = 8.7 Hz, 1H), 8.05-8.15 (m, 1H), 7.90-8.02 (m, 1H), 7.21-7.25 (m, 2H), 4.21-4.31 (m, 1H), 4.17 (br dd, J = 11.3, 7.5 Hz, 1H), 3.93 (s, 1H), 3.68-3.77 (m, 2H), 2.60-2.72 (m, 1H), 2.24-2.36 (m, 1H), 1.49 (s, 9H); 3Hs not observed (2NHs and OH) |
| 382 | MS m/z 419.3 [M + H]⁺; ¹H MMR (DMSO-d₆) δ: 12.74 (br s, 1H), 8.78 (s, 1H), 8.65 (d, J = 4.6 Hz, 2H), 8.29 (d, J = 8.8 Hz, 1H), 7.78 (d, J = 4.9 Hz, 2H), 7.45 (br s, 2H), 4.84-5.08 (m, 1H), 3.04 (s, 3H), 1.53-1.64 (m, 2H), 1.39-1.53 (m, 2H), 1.26 (s, 6H), 1.10 (s, 6H); 1H not observed (OH or NH) |
| 384 | MS m/z 419.3 [M + H]⁺; ¹H MMR (DMSO-d₆) δ:12.72 (br s, 1H), 8.97 (br s, 1H), 8.78 (s, 1H), 8.60 (br s, 1H), 8.20-8.33 (m, 1H), 8.16 (dt, J = 8.2, 1.9 Hz, 1H), 7.51 (dd, J = 7.8, 4.6 Hz, 1H), 7.32-7.41 (m, 2H), 4.85-5.05 (m, 1H), 3.04 (s, 3H), 1.55-1.59 (m, 2H), 1.44-1.48 (m, 2H), 1.26 (s, 6H), 1.10 (s, 6H); 1H not observed (OH or NH) |
| 393 | MS m/z 419.3 [M + H]⁺; ¹H MMR (DMSO-d₆) δ: 12.64 (s, 1H), 8.77 (s, 1H), 8.69 (d, J = 4.0 Hz, 1H), 8.27 (d, J = 8.3 Hz, 1H), 8.04 (d, J = 8.0 Hz, 1H), 7.83-7.95 (m, 1H), 7.66-7.79 (m, 2H), 7.39 (dd, J = 7.0, 5.0 Hz, 1H), 4.86-5.03 (m, 1H), 3.04 (s, 3H), 1.57 (d, J = 11.8 Hz, 2H), 1.46 (t, J = 12.0 Hz, 2H), 1.26 (s, 6H), 1.10 (s, 6H); 1H not observed (OH or NH) |
| 394 | MS m/z 473.3 [M + H]⁺; ¹H MMR (DMSO-d₆) δ: 12.64 (s, 1H), 8.77 (s, 1H), 8.31-8.37 (m, 1H), 8.27 (t, J = 8.5 Hz, 2H), 8.11 (d, J = 9.0 Hz, 1H), 7.81 (dd, J = 8.3, 1.8 Hz, 1H), 7.77 (d, J = 1.8 Hz, 1H), 4.87-5.05 (m, 1H), 4.12 (s, 3H), 3.05 (s, 3H), 1.52-1.63 (m, 2H), 1.39-1.52 (m, 2H), 1.26 (s, 6H), 1.10 (s, 6H); 1H not observed (OH or NH) |
| 402 | MS m/z 420.3 [M + H]⁺; ¹H MMR (DMSO-d₆) δ: 12.61 (s, 1H), 9.10-9.14 (br s, 1H), 8.95 (d, J = 5.0 Hz, 2H), 8.89 (s, 1H), 8.32 (d, J = 8.5 Hz, 1H), 8.03 (d, J = 8.3 Hz, 1H), 7.98 (d, J = 1.8 Hz, 1H), 7.49 (t, J = 4.9 Hz, 1H), 4.92-5.10 (m, |

| Cpd | Data |
|---|---|
|  | 1H), 3.09 (s, 3H), 1.97-2.01 (m, 2H), 1.81-1.85 (m, 2H), 1.52 (s, 6H), 1.46 (s, 6H) |
| 411 | MS m/z 420.3 [M + H]$^+$; $^1$H MMR (DMSO-d$_6$) δ: 12.57 (br s, 1H), 9.27 (d, J = 1.0 Hz, 1H), 8.89 (d, J = 5.5 Hz, 1H), 8.78 (s, 1H), 8.32 (d, J = 8.3 Hz, 1H), 8.17 (dd, J = 5.3, 1.3 Hz, 1H), 7.80-7.90 (m, 2H), 4.94-4.99 (m, 1H), 3.05 (s, 3H), 1.57 (dd, J = 12.0, 3.3 Hz, 2H), 1.46 (t, J = 12.2 Hz, 2H), 1.25 (s, 6H), 1.09 (s, 6H); 1H not observed (OH or NH) |
| 412 | MS m/z 420.3 [M + H]$^+$; $^1$H MMR (DMSO-d$_6$) δ: 12.72 (br s, 1H), 9.33 (d, J = 1.3 Hz, 1H), 8.75 (s, 1H), 8.77 (s, 1H), 8.65 (d, J = 2.5 Hz, 1H), 8.30 (d, J = 8.3 Hz, 1H), 7.70-7.86 (m, 2H), 4.83-5.08 (m, 1H), 3.05 (s, 3H), 1.57 (dd, J = 11.9, 3.4 Hz, 2H), 1.46 (t, J = 12.2 Hz, 2H), 1.26 (s, 6H), 1.10 (s, 6H); 1H not observed (OH and NH) |
| 419 | MS m/z 395.5 [M + H]$^+$; $^1$H MMR (methanol-d$_4$) δ: 8.61 (s, 1H), 8.32 (d, J = 8.2 Hz, 1H), 8.14 (br s, 1H), 7.99 (br s, 1H), 7.25 (br s, 2H), 5.79 (br t, J = 10.4 Hz, 1H), 2.51 (br dd, J = 13.4, 2.5 Hz, 2H), 1.93 (br t, J = 12.1 Hz, 2H), 1.65 (s, 6H), 1.56-1.62 (m, 6H); 3Hs not observed (2NHs and OH) |
| 423 | MS m/z 412.4 [M + H]$^+$; $^1$H MMR (methanol-d$_4$) δ: 8.40 (s, 1H), 8.22 (br d, J = 7.9 Hz, 1H), 7.90-8.11 (m, 2H), 7.11-7.27 (m, 2H), 4.63-4.83 (m, 1H), 1.73-2.00 (m, 2H), 1.48 (br d, J = 6.4 Hz, 6H), 1.19-1.41 (m, 7H); 4Hs not observed (3NHs and OH) |
| 424 | MS m/z 411.6 [M + H]$^+$; $^1$H MMR (methanol-d$_4$) δ: 8.21 (s, 1H), 8.03 (s, 1H), 7.57 (br d, J = 7.9 Hz, 1H), 7.31 (br d, J = 7.9 Hz, 1H), 7.24 (s, 1H), 5.38 (s, 1H), 4.23-4.43 (m, 1H), 2.16-2.43 (m, 2H), 1.61-1.69 (m, 2H), 1.59 (br d, J = 4.9 Hz, 6H), 1.54 (s, 6H); 3Hs not observed (2NHs and OH) |

Example 11

Preparation of Compound 401

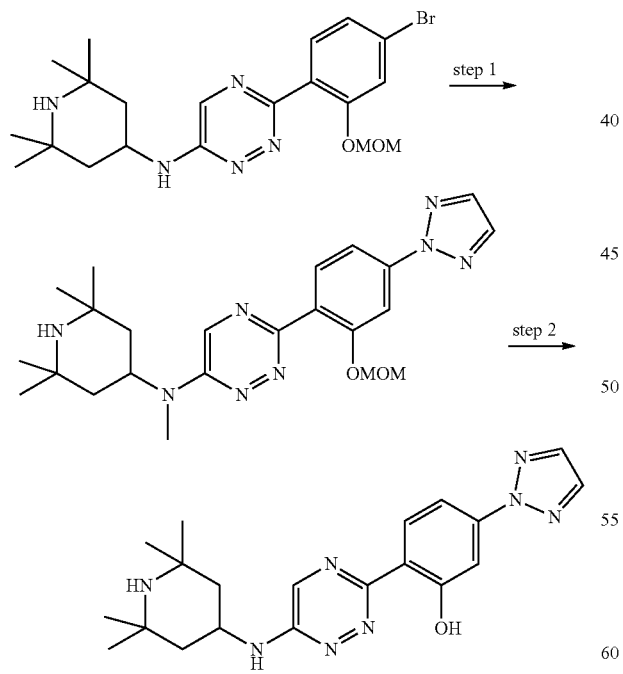

Step 1: A mixture of tris(dibenzylideneacetone)dipalladium(0) (15 mg, 0.016 mmol) and 2-di-tert-butylphosphino-3,4,5,6-tetramethyl-2',4',6'-triisopropyl-1,1'-biphenyl (21 mg, 0.042 mmol) in dioxane (0.2 mL) and toluene (0.8 mL) was purged with argon, then heated to 120° C. for 5 min. The solution was cooled to room temperature and 3-[4-bromo-2-(methoxymethoxy)phenyl]-N-(2,2,6,6-tetramethyl-4-piperidyl)-1,2,4-triazin-6-amine (150 mg, 0.33 mmol), K$_3$PO$_4$ (145 mg, 0.67 mmol), and 1H-triazole (11 μL, 0.19 mmol) were added. Argon was bubbled thorough the reaction mixture for 5 min, and then the mixture was heated to 120° C. for 30 min. The reaction mixture was cooled to room temperature and purified by silica gel column chromatography eluting with a MeOH/CH$_2$Cl$_2$ gradient (0-25% MeOH) to afford 3-[2-(methoxymethoxy)-4-(triazol-2-yl)phenyl]-N-(2,2,6,6-tetramethyl-4-piperidyl)-1,2,4-triazin-6-amine (43 mg, 29% yield) as a clear foam. MS m/z 439.6 [M+H]$^+$.

Step 2: To a solution of 3-[2-(methoxymethoxy)-4-(triazol-2-yl)phenyl]-N-(2,2,6,6-tetramethyl-4-piperidyl)-1,2,4-triazin-6-amine (43 mg, 0.098 mmol) in 1 mL of CH$_2$Cl$_2$ and MeOH (0.5 mL) was added HCl (4 mol/L) in 1,4-dioxane (50 μL, 0.2 mmol) and the mixture was stirred 5 h at room temperature until UPLC showed complete consumption of the starting material. After concentration, the residue was purified by silica gel chromatography eluting with a MeOH/CH$_2$Cl$_2$/2.5% NH$_4$OH gradient (0-30% MeOH/NH$_4$OH) to provide 2-[6-[(2,2,6,6-tetramethyl-4-piperidyl)amino]-1,2,4-triazin-3-yl]-5-(triazol-2-yl)phenol hydrochloride (35 mg, 82% yield) as a yellow solid.

MS m/z 395.5 [M+H]$^+$; $^1$H NMR (methanol-d$_4$) δ: 8.02 (s, 2H), 7.86 (s, 1H), 7.82 (br d, J=8.5 Hz, 1H), 7.70 (d, J=8.5 Hz, 1H), 5.41 (s, 1H), 4.34 (br t, J=11.9 Hz, 1H), 2.37 (br d, J=12.5 Hz, 1H), 2.26 (d, J=12.5 Hz, 1H), 1.62-1.84 (m, 2H), 1.59 (br d, J=4.6 Hz, 6H), 1.53 (s, 6H); 3Hs not observed (2NHs and OH).

Using the procedure described for Example 12, additional compounds described herein may be prepared by substituting the appropriate starting material, suitable reagents and reaction conditions, obtaining compounds such as those selected from:

| Cpd | Data |
|---|---|
| 255 | MS m/z 409.4 [M + H]$^+$; $^1$H MMR (methanol-d$_4$) δ: 8.68 (s, 1H), 8.39 (d, J = 8.5 Hz, 1H), 7.94 (s, 2H), 7.64-7.74 (m, 2H), 5.23-5.39 (m, 1H), 3.14 (s, 3H), 1.94-2.08 (m, 4H), 1.64 (s, 6H), 1.51 (s, 6H); 2Hs not observed (NH and OH) |

Example 12

Preparation of Compound 286

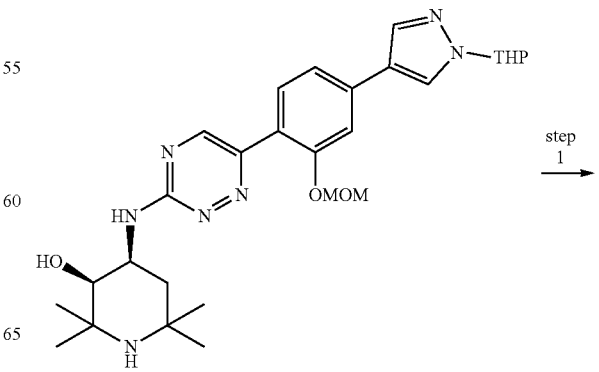

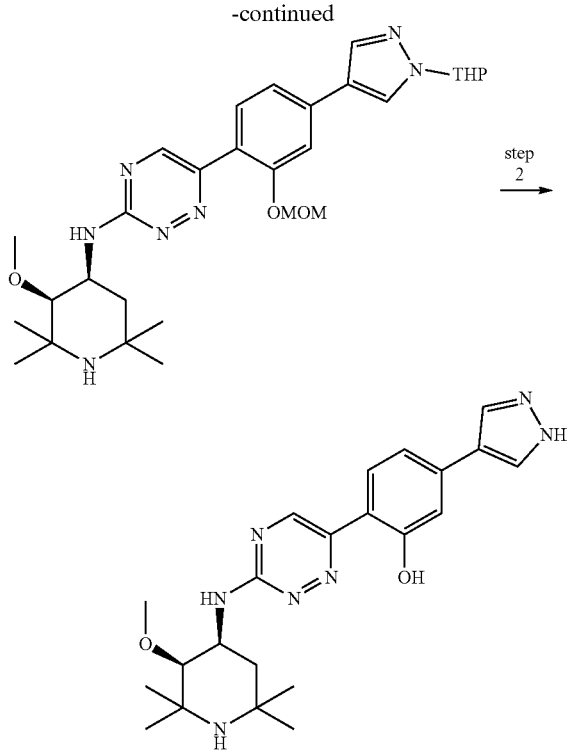

Step 1: A solution of racemic (3S,4S)-4-[[6-[2-(methoxymethoxy)-4-(1-tetrahydropyran-2-ylpyrazol-4-yl)phenyl]-1,2,4-triazin-3-yl]amino]-2,2,6,6-tetramethyl-piperidin-3-ol (20 mg, 0.038 mmol) in DMF (0.3 mL) was cooled to 0° C. Sodium hydride (60 mass % in mineral oil) (4.2 mg, 0.11 mmol) was added and stirring at 0° C. was continued for 15 minutes. A stock solution of iodomethane (0.027 mL) in DMF (2.0 mL) was prepared. A portion of this stock solution (0.20 mL) containing iodomethane (0.0027 mL, 0.043 mmol, 1.15 equiv) was added to the reaction and stirring was continued for 10 minutes at 0° C. H$_2$O was added to quench the sodium hydride and the reaction was partitioned between brine and EtOAc. The layers were separated, and the aqueous layer was extracted twice with EtOAc. The combined organic layers were washed twice with brine, dried over sodium sulfate, filtered and concentrated. The residue was purified by silica-gel column chromatography eluting with 0-30% MeOH/CH$_2$Cl$_2$ to yield 6-[2-(methoxymethoxy)-4-(1-tetrahydropyran-2-ylpyrazol-4-yl)phenyl]-N-[(3S,4S)-3-methoxy-2,2,6,6-tetramethyl-4-piperidyl]-1,2,4-triazin-3-amine (16.7 mg, 81% yield). MS m/z 552.7 [M+H]$^+$.

Step 2: 6-[2-(Methoxymethoxy)-4-(1-tetrahydropyran-2-ylpyrazol-4-yl)phenyl]-N-[(3S,4S)-3-methoxy-2,2,6,6-tetramethyl-4-piperidyl]-1,2,4-triazin-3-amine (16.7 mg, 0.030 mmol) was dissolved in methanol (0.5 mL) and a hydrogen chloride solution (2 mL, 4.0 M in dioxane) was added. The reaction mixture was stirred at room temperature for 16 h. The reaction was concentrated and the residue was purified by silica-gel column chromatography eluting with 0-100% MeOH (2.5% v/v NH$_4$OH) in CH$_2$Cl$_2$ to yield 2-[3-[[(3S,4S)-3-methoxy-2,2,6,6-tetramethyl-4-piperidyl]amino]-1,2,4-triazin-6-yl]-5-(1H-pyrazol-4-yl)phenol (2.5 mg, 20%).

MS m/z 424.5 [M+H]$^+$; $^1$H NMR (methanol-d$_4$) δ: 9.07 (s, 1H), 7.99 (br s, 2H), 7.81 (d, J=8.2 Hz, 1H), 7.21 (dd, J=8.1, 1.7 Hz, 1H), 7.18 (d, J=1.5 Hz, 1H), 5.52-5.63 (m, 1H), 3.48-3.61 (m, 1H), 3.20 (s, 3H), 1.94-2.08 (m, 2H), 1.40 (s, 3H), 1.36 (s, 3H), 1.24 (s, 3H), 1.14 (s, 3H); 4Hs not observed (3 NHs and OH).

Using the procedure described for Example 13, additional compounds described herein may be prepared by substituting the appropriate starting material, suitable reagents and reaction conditions, obtaining compounds such as those selected from:

| Cpd | Data |
|---|---|
| 293 | MS m/z 438.5 [M + H]$^+$; $^1$H NMR (methanol-d$_4$) δ: 9.06 (s, 1H), 7.99 (br s, 2H), 7.81 (d, J = 8.2 Hz, 1H), 7.21 (dd, J = 8.2, 1.5 Hz, 1H), 7.18 (d, J = 1.5 Hz, 1H), 5.35 (br s, 1H), 3.23 (s, 3H), 3.05-3.18 (m, 1H), 2.44-2.69 (m, 3H), 2.05 (br dd, J = 13.1, 9.5 Hz, 1H), 1.79-1.97 (m, 1H), 1.27 (br d, J = 9.2 Hz, 6H), 1.23 (s, 3H), 1.14 (br s, 3H); 3Hs not observed (2NHs and OH) |

Example 13

Preparation of Compound 165

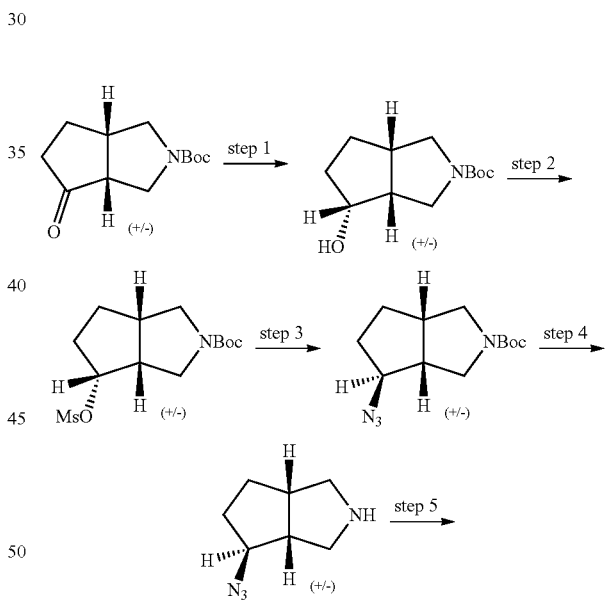

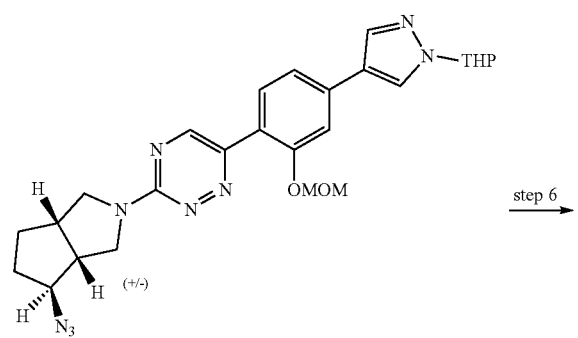

-continued

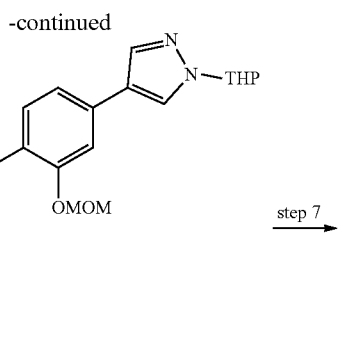

step 7

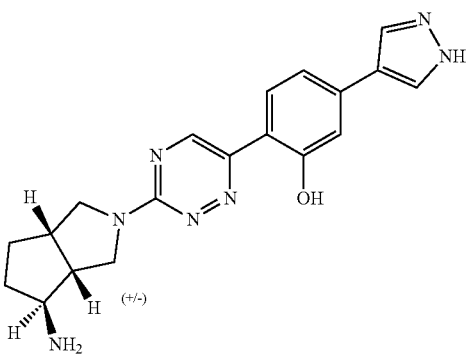

Step 1: A solution of racemic tert-butyl 4-oxo-1,3,3a,5,6,6a-hexahydrocyclopenta[c]pyrrole-2-carboxylate (606 mg, 2.69 mmol) in THF (4 mL) was cooled to −78° C. A THF solution of lithium tri-sec-butylborohydride (3.2 mL, 1.0 M) was added dropwise over 20 minutes. Stirring was continued following complete addition at −78° C. and the reaction was slowly warmed to room temperature over 16 h. Upon completion, the reaction was quenched with methanol, and then concentrated in vacuo. The residue was partitioned between EtOAc and saturated aqueous sodium bicarbonate and the layers were separated. The aqueous layer was extracted once with EtOAc and the combined organic layers were dried over sodium sulfate, filtered and concentrated.

The residue was purified by silica-gel column chromatography eluting with 0-100% EtOAc/hexanes to yield racemic tert-butyl (3aR,4R,6aS)-4-hydroxy-3,3a,4,5,6,6a-hexahydro-1H-cyclopenta[c]pyrrole-2-carboxylate (583 mg, 95% yield).

MS m/z 250.2 [M+Na]$^+$; $^1$H NMR (chloroform-d) δ: 4.28 (q, J=5.5 Hz, 1H), 3.64 (dd, J=11.9, 3.1 Hz, 1H), 3.57 (br dd, J=10.8, 7.8 Hz, 1H), 3.37 (br dd, J=11.7, 8.1 Hz, 1H), 3.18 (dd, J=11.0, 3.4 Hz, 1H), 2.63-2.74 (m, 2H), 1.83-1.93 (m, 2H), 1.75-1.82 (m, 1H), 1.55-1.64 (m, 1H), 1.48 (s, 9H); 1H not observed (OH).

Step 2: Racemic tert-butyl (3aR,4R,6aS)-4-hydroxy-3,3a,4,5,6,6a-hexahydro-1H-cyclopenta[c]pyrrole-2-carboxylate (583 mg, 2.56 mmol) was cycled under N$_2$, followed by the addition of CH$_2$Cl$_2$ (5 mL). The reaction was cooled to −78° C. with stirring. Methanesulfonyl chloride (0.34 mL, 4.39 mmol) was added followed by trimethylamine (0.69 mL, 4.95 mmol) and the reaction was stirred at −78° C. for 30 minutes, and then allowed to warm to room temperature over 3 h. The reaction was partitioned between saturated aqueous sodium bicarbonate and CH$_2$Cl$_2$ and the layers were separated. The organic layer was washed once with saturated aqueous sodium bicarbonate, dilute aqueous acetic acid, and saturated aqueous sodium bicarbonate, and then dried over sodium sulfate, filtered and concentrated to yield tert-butyl (3aR,4R,6aS)-4-methylsulfonyloxy-3,3a,4,5,6,6a-hexahydro-1H-cyclopenta[c]pyrrole-2-carboxylate (566 mg, 72% yield).

MS m/z 328.3 [M+Na]$^+$; $^1$H NMR (chloroform-d) δ: 5.03 (q, J=6.1 Hz, 1H), 3.45-3.58 (m, 2H), 3.30-3.39 (m, 1H), 3.15 (br dd, J=11.0, 4.0 Hz, 1H), 2.96 (s, 3H), 2.77-2.86 (m, 1H), 2.60-2.71 (m, 1H), 1.99-2.09 (m, 1H), 1.92-1.97 (m, 1H), 1.82-1.91 (m, 1H), 1.50-1.63 (m, 1H), 1.34-1.44 (m, 9H).

Step 3: To a vial containing racemic tert-butyl (3aR,4R,6aS)-4-methylsulfonyloxy-3,3a,4,5,6,6a-hexahydro-1H-cyclopenta[c]pyrrole-2-carboxylate (566 mg, 1.85 mmol) was added DMAc (3 mL) and sodium azide (155 mg, 2.38 mmol), which was sealed and warmed to 90° C. with stirring for 20 h. After cooling to room temperature, the reaction was partitioned between EtOAc and saturated aqueous sodium carbonate. The layers were separated, and the organic layer was washed twice with brine, dried over sodium sulfate, filtered and then concentrated to yield racemic tert-butyl (3aR,4S,6aS)-4-azido-3,3a,4,5,6,6a-hexahydro-1H-cyclopenta[c]pyrrole-2-carboxylate (288 mg, 62% yield).

MS m/z 197.1 [M+H-tBu]$^+$; $^1$H NMR (chloroform-d) δ: 3.65 (br s, 1H), 3.39-3.51 (m, 2H), 3.17 (br d, J=8.9 Hz, 1H), 3.11 (br d, J=8.5 Hz, 1H), 2.67-2.76 (m, 1H), 2.52 (tt, J=8.5, 4.2 Hz, 1H), 1.92-2.00 (m, 2H), 1.64-1.74 (m, 1H), 1.42-1.47 (m, 1H), 1.38 (s, 9H).

Step 4: Racemic tert-butyl (3aR,4S,6aS)-4-azido-3,3a,4,5,6,6a-hexahydro-1H-cyclopenta[c]pyrrole-2-carboxylate (70 mg, 0.28 mmol) was dissolved in TFA (2.0 mL) and stirred at room temperature for 10 minutes. The reaction was concentrated, azeotroped with CH$_2$Cl$_2$, and then carried forward without purification. MS m/z 153.3 [M+H]$^+$.

Step 5: The residue from step 4 containing racemic (3aR,4S,6aS)-4-azido-1,2,3,3a,4,5,6,6a-octahydrocyclopenta[c]pyrrole;2,2,2-trifluoroacetic acid (106 mg, 0.28 mmol) was dissolved in DMF (2 mL), followed by the addition of N,N-diisopropylethylamine (0.4 mL, 2.29 mmol) and 6-[2-(methoxymethoxy)-4-(1-tetrahydropyran-2-ylpyrazol-4-yl)phenyl]-3-methylsulfonyl-1,2,4-triazine (86.0 mg, 0.19 mmol). The reaction was warmed to 80° C. with stirring for 3 h, and then cooled to room temperature and concentrated. The residue was purified by column chromatography eluting with 0-100% EtOAc in hexanes to yield racemic (3aR,4S,6aS)-4-azido-2-[6-[2-(methoxymethoxy)-4-(1-tetrahydropyran-2-ylpyrazol-4-yl)phenyl]-1,2,4-triazin-3-yl]-3,3a,4,5,6,6a-hexahydro-1H-cyclopenta[c]pyrrole (64 mg, 64% yield). MS m/z 518.4 [M+H]$^+$.

Step 6: Racemic (3aR,4S,6aS)-4-azido-2-[6-[2-(methoxymethoxy)-4-(1-tetrahydropyran-2-ylpyrazol-4-yl)phenyl]-1,2,4-triazin-3-yl]-3,3a,4,5,6,6a-hexahydro-1H-cyclopenta[c]pyrrole (64 mg, 0.12 mmol), triphenylphosphine (48 mg, 0.18 mmol), THF (2 mL), and H$_2$O (1 mL) were combined and warmed to 80° C. with stirring for 3 h. The reaction was cooled to room temperature and concentrated. The residue was purified by column chromatography eluting with 0-100% EtOAc/hexanes to yield racemic (3aR,4S,6aS)-2-[6-[2-(methoxymethoxy)-4-(1-tetrahydropyran-2-ylpyrazol-4-yl)phenyl]-1,2,4-triazin-3-yl]-3,3a,4,5,6,6a-hexahydro-1H-cyclopenta[c]pyrrol-4-amine (45 mg, 75% yield).

MS m/z 492.4 [M+H]$^+$; $^1$H NMR (methanol-d$_4$) δ: 8.74 (s, 1H), 8.23 (s, 1H), 7.93 (s, 1H), 7.72 (d, J=7.9 Hz, 1H), 7.42 (s, 1H), 7.34 (br d, J=7.9 Hz, 1H), 5.42 (br d, J=10.1 Hz, 1H), 5.32 (s, 2H), 4.06 (br d, J=11.6 Hz, 1H), 3.69-3.88 (m, 4H), 3.55 (br dd, J=11.6, 4.0 Hz, 1H), 3.45 (s, 3H), 3.39-3.44 (m, 1H), 3.00-3.10 (m, 1H), 2.70-2.79 (m, 1H), 2.12-2.29

(m, 3H), 2.04 (br d, J=8.9 Hz, 2H), 1.67-1.82 (m, 3H), 1.57-1.66 (m, 2H); 2Hs not observed (2 NHs).

Step 7: Racemic (3aR,4S,6aS)-2-[6-[2-(methoxymethoxy)-4-(1-tetrahydropyran-2-ylpyrazol-4-yl)phenyl]-1,2,4-triazin-3-yl]-3,3a,4,5,6,6a-hexahydro-1H-cyclopenta[c]pyrrol-4-amine (3 mg, 0.0053 mmol) was dissolved in methanol (0.5 mL) and a hydrogen chloride solution in dioxane (2.0 mL, 4.0 M) and stirred at room temperature for 1 h. The reaction was concentrated, and the residue was dissolved in MeOH, followed by $Et_2O$ addition to precipitate solid. The solid was filtered, then rinsed through the filter with MeOH and the methanolic filtrate was concentrated to yield racemic 2-[3-[(3aR,4S,6aS)-4-amino-3,3a,4,5,6,6a-hexahydro-1H-cyclopenta[c]pyrrol-2-yl]-1,2,4-triazin-6-yl]-5-(1H-pyrazol-4-yl)phenol;dihydrochloride (2.1 mg, 91% yield).

MS m/z 364.3 $[M+H]^+$; $^1H$ NMR (methanol-$d_4$) δ: 8.18 (br s, 2H), 7.53 (d, J=8.2 Hz, 1H), 7.18 (br d, J=8.5 Hz, 1H), 7.15 (s, 1H), 5.83 (br s, 1H), 3.88 (br t, J=9.2 Hz, 1H), 3.72-3.81 (m, 1H), 3.52-3.71 (m, 2H), 3.40 (br t, J=11.0 Hz, 1H), 3.02-3.15 (m, 1H), 2.83-2.95 (m, 1H), 2.24-2.37 (m, 1H), 2.13 (br dd, J=12.8, 5.2 Hz, 1H), 1.69-1.81 (m, 1H), 1.54-1.69 (m, 1H); 4Hs not observed (3NHs and OH).

BIOLOGICAL EXAMPLES

The following in vitro biological examples demonstrate the usefulness of the compounds of the present description for treating Huntington's disease.

To describe in more detail and assist in understanding the present description, the following non-limiting biological examples are offered to more fully illustrate the scope of the description and are not to be construed as specifically limiting the scope thereof. Such variations of the present description that may be now known or later developed, which would be within the purview of one skilled in the art to ascertain, are considered to fall within the scope of the present description and as hereinafter claimed.

Compounds of Formula (I) or Formula (II) were tested using the Meso Scale Discovery (MSD) Assay provided in International Application No. PCT/US2016/066042, filed on Dec. 11, 2016 and claiming priority to U.S. Provisional Application 62/265,652 filed on Dec. 10, 2015, the entire contents of which are incorporated herein by reference.

The Endogenous Huntingtin Protein assay used in Example 1 was developed using the ELISA-based MSD electrochemiluminescence assay platform.

Example 1

Endogenous Huntingtin Protein Assay

Meso Scale Discovery (MSD) 96-well or 384-well plates were coated overnight at 4° C. with MW1 (expanded polyglutamine) or MAB2166 monoclonal antibody (for capture) at a concentration of 1 μg/mL in PBS (30 μL per well). Plates were then washed three times with 300 μL wash buffer (0.05% Tween-20 in PBS) and blocked (100 μL blocking buffer; 5% BSA in PBS) for 4-5 hours at room temperature with rotational shaking and then washed three times with wash buffer.

Samples (25 μL) were transferred to the antibody-coated MSD plate and incubated overnight at 4° C. After removal of the lysates, the plate was washed three times with wash buffer, and 25 μL of #5656S (Cell signaling; rabbit monoclonal) secondary antibody (diluted to 0.25 μg/mL in 0.05% Tween-20 in blocking buffer) was added to each well and incubated with shaking for 1 Hour at room temperature.

Following incubation with the secondary antibody, the wells were rinsed with wash buffer after which 25 μL of goat anti-rabbit SULFO TAG secondary detection antibody (required aspect of the MSD system) (diluted to 0.25 μg/mL in 0.05% Tween-20 in blocking buffer) was added to each well and incubated with shaking for 1 hour at room temperature. After rinsing three times with wash buffer, 150 μL of read buffer T with surfactant (MSD) were added to each empty well, and the plate was imaged on a SI 6000 imager (MSD) according to manufacturers' instructions provided for 96- or 384-well plates. The resulting $IC_{50}$ values (μM) for compounds tested are shown in Table 1.

As shown in Table 1, test compounds described herein had the following $IC_{50}$ values, an $IC_{50}$ value between >3 μM and ≤9 μM is indicated by a single star (*), an $IC_{50}$ value between >1 μM and ≤3 μM is indicated by two stars (), an $IC_{50}$ value between >0.5 μM and ≤1 μM is indicated by three stars (*), an $IC_{50}$ value between >0.1 μM and ≤0.5 μM is indicated by four stars (**) and an $IC_{50}$ value of ≤0.1 μM is indicated by five stars (***).

TABLE 1

| Cpd | $IC_{50}$ |
|---|---|
| 1 | *** |
| 2 | ***** |
| 3 | ***** |
| 4 | ***** |
| 5 | ***** |
| 6 | ***** |
| 7 | ***** |
| 8 | ***** |
| 9 | ***** |
| 10 | ***** |
| 11 | ***** |
| 12 | ***** |
| 13 | ***** |
| 14 | ***** |
| 15 | ***** |
| 16 | ***** |
| 17 | **** |
| 18 | ***** |
| 19 | ***** |
| 20 | *** |
| 21 | ***** |
| 22 | ***** |
| 23 | ***** |
| 24 | **** |
| 33 | ** |
| 50 | ***** |
| 51 | *** |
| 52 | **** |
| 53 | **** |
| 54 | *** |
| 55 | ***** |
| 56 | ***** |
| 57 | ***** |
| 58 | ***** |
| 59 | ***** |
| 60 | ***** |
| 61 | ***** |
| 62 | **** |
| 63 | ***** |
| 64 | ***** |
| 65 | ***** |
| 66 | ***** |
| 67 | **** |
| 68 | ***** |
| 69 | ***** |
| 70 | **** |
| 71 | ***** |
| 72 | ***** |
| 73 | ***** |
| 74 | ***** |
| 75 | *** |
| 76 | ***** |

TABLE 1-continued

| Cpd | IC$_{50}$ |
|---|---|
| 77 | ***** |
| 78 | ***** |
| 79 | ***** |
| 80 | ***** |
| 81 | ***** |
| 82 | **** |
| 83 | ***** |
| 84 | ***** |
| 85 | ***** |
| 86 | **** |
| 87 | ***** |
| 88 | ***** |
| 89 | ***** |
| 90 | ***** |
| 91 | ***** |
| 92 | ***** |
| 93 | ***** |
| 94 | **** |
| 95 | **** |
| 96 | ***** |
| 97 | ***** |
| 98 | **** |
| 99 | ***** |
| 100 | ***** |
| 101 | **** |
| 102 | ***** |
| 103 | ***** |
| 104 | ***** |
| 105 | **** |
| 106 | ***** |
| 107 | ** |
| 108 | *** |
| 109 | **** |
| 110 | **** |
| 111 | ***** |
| 112 | **** |
| 113 | **** |
| 114 | ***** |
| 115 | **** |
| 116 | **** |
| 117 | **** |
| 118 | **** |
| 119 | ***** |
| 120 | **** |
| 121 | ***** |
| 122 | **** |
| 123 | ***** |
| 124 | **** |
| 125 | ***** |
| 126 | ***** |
| 127 | **** |
| 128 | **** |
| 129 | **** |
| 130 | **** |
| 131 | ***** |
| 132 | **** |
| 133 | ***** |
| 134 | ***** |
| 135 | **** |
| 136 | ***** |
| 137 | ***** |
| 138 | ***** |
| 139 | **** |
| 140 | ***** |
| 141 | ***** |
| 142 | ***** |
| 143 | ***** |
| 144 | ***** |
| 145 | ***** |
| 146 | ***** |
| 147 | ***** |
| 148 | ***** |
| 149 | ***** |
| 150 | ***** |
| 151 | ***** |
| 152 | ***** |
| 153 | **** |
| 154 | ***** |

TABLE 1-continued

| Cpd | IC$_{50}$ |
|---|---|
| 155 | ***** |
| 156 | ***** |
| 157 | **** |
| 158 | ** |
| 159 | ** |
| 160 | ** |
| 161 | ***** |
| 162 | **** |
| 163 | ** |
| 164 | **** |
| 165 | ***** |
| 166 | ***** |
| 167 | ***** |
| 168 | **** |
| 169 | ***** |
| 170 | ***** |
| 171 | ***** |
| 172 | ***** |
| 173 | ***** |
| 174 | ***** |
| 175 | ** |
| 176 | ***** |
| 177 | ***** |
| 178 | ***** |
| 179 | ***** |
| 180 | ** |
| 181 | *** |
| 182 | *** |
| 183 | **** |
| 184 | ***** |
| 185 | ***** |
| 186 | ***** |
| 187 | **** |
| 188 | ***** |
| 189 | ***** |
| 190 | ***** |
| 191 | ***** |
| 192 | **** |
| 193 | ** |
| 194 | ***** |
| 195 | ***** |
| 196 | ***** |
| 197 | **** |
| 198 | ***** |
| 199 | ***** |
| 200 | ***** |
| 201 | ***** |
| 202 | ***** |
| 203 | ***** |
| 204 | ***** |
| 205 | ***** |
| 206 | ** |
| 207 | ** |
| 208 | **** |
| 209 | ** |
| 210 | ***** |
| 211 | ***** |
| 212 | **** |
| 213 | ** |
| 214 | ***** |
| 215 | **** |
| 216 | **** |
| 217 | ***** |
| 218 | **** |
| 219 | **** |
| 220 | *** |
| 221 | *** |
| 222 | ***** |
| 223 | **** |
| 224 | ** |
| 225 | ***** |
| 226 | ***** |
| 227 | ***** |
| 228 | ***** |
| 229 | *** |
| 230 | *** |
| 231 | **** |
| 232 | ***** |

TABLE 1-continued

| Cpd | IC$_{50}$ |
|---|---|
| 233 | ** |
| 234 | **** |
| 235 | ***** |
| 236 | ***** |
| 237 | **** |
| 238 | **** |
| 239 | ***** |
| 240 | ***** |
| 241 | ***** |
| 242 | ***** |
| 243 | ***** |
| 244 | * |
| 245 | ***** |
| 246 | ***** |
| 247 | ***** |
| 248 | ***** |
| 249 | ***** |
| 250 | **** |
| 251 | **** |
| 252 | *** |
| 253 | ***** |
| 254 | ***** |
| 255 | ***** |
| 256 | **** |
| 257 | ** |
| 258 | **** |
| 259 | **** |
| 260 | ***** |
| 261 | ***** |
| 262 | ***** |
| 263 | **** |
| 264 | **** |
| 265 | ***** |
| 266 | ***** |
| 267 | ***** |
| 268 | ***** |
| 269 | **** |
| 270 | ** |
| 271 | **** |
| 272 | **** |
| 273 | ***** |
| 274 | ***** |
| 275 | ***** |
| 276 | ***** |
| 277 | ***** |
| 278 | ***** |
| 279 | ***** |
| 280 | ***** |
| 281 | ***** |
| 282 | *** |
| 283 | ** |
| 284 | ***** |
| 285 | ***** |
| 286 | **** |
| 287 | ***** |
| 288 | ***** |
| 289 | ***** |
| 290 | ***** |
| 291 | ***** |
| 292 | ***** |
| 293 | **** |
| 294 | ***** |
| 295 | ***** |
| 296 | ** |
| 297 | ***** |
| 298 | ** |
| 299 | ***** |
| 300 | ** |
| 301 | ***** |
| 302 | *** |
| 303 | ***** |
| 304 | ***** |
| 305 | ***** |
| 306 | **** |
| 307 | *** |
| 308 | **** |
| 309 | *** |
| 310 | **** |

TABLE 1-continued

| Cpd | IC$_{50}$ |
|---|---|
| 311 | ** |
| 312 | ** |
| 313 | ** |
| 314 | ***** |
| 315 | ***** |
| 316 | ***** |
| 317 | ***** |
| 318 | **** |
| 319 | ***** |
| 320 | **** |
| 321 | ***** |
| 322 | ***** |
| 323 | ***** |
| 324 | ***** |
| 325 | **** |
| 326 | ***** |
| 327 | ***** |
| 328 | **** |
| 329 | **** |
| 330 | ** |
| 331 | **** |
| 332 | ***** |
| 333 | ***** |
| 334 | ** |
| 335 | ***** |
| 336 | ***** |
| 337 | ***** |
| 338 | **** |
| 339 | ***** |
| 340 | ***** |
| 341 | ***** |
| 342 | **** |
| 343 | ***** |
| 344 | ***** |
| 345 | **** |
| 346 | *** |
| 347 | ***** |
| 348 | ***** |
| 349 | **** |
| 350 | ***** |
| 351 | ***** |
| 352 | ***** |
| 353 | ** |
| 354 | ***** |
| 355 | ***** |
| 356 | ***** |
| 357 | ***** |
| 358 | **** |
| 359 | ***** |
| 360 | **** |
| 361 | ***** |
| 362 | ***** |
| 363 | ***** |
| 364 | **** |
| 365 | ***** |
| 366 | ***** |
| 367 | ***** |
| 368 | **** |
| 369 | ***** |
| 370 | ***** |
| 371 | ***** |
| 372 | ***** |
| 373 | ***** |
| 374 | ***** |
| 375 | ***** |
| 376 | ***** |
| 377 | ***** |
| 378 | ***** |
| 379 | ***** |
| 380 | ***** |
| 381 | ***** |
| 382 | ***** |
| 383 | ***** |
| 384 | ***** |
| 385 | ***** |
| 386 | **** |
| 387 | ***** |
| 388 | ***** |

TABLE 1-continued

| Cpd | IC$_{50}$ |
|---|---|
| 389 | ***** |
| 390 | ***** |
| 391 | ***** |
| 392 | ***** |
| 393 | ***** |
| 394 | ***** |
| 395 | ***** |
| 396 | ***** |
| 397 | ***** |
| 398 | ***** |
| 399 | ***** |
| 400 | ***** |
| 401 | ***** |
| 402 | ***** |
| 403 | ***** |
| 404 | ***** |
| 405 | ***** |
| 406 | ***** |
| 407 | ***** |
| 408 | ***** |
| 409 | ***** |
| 410 | ***** |
| 411 | ***** |
| 412 | ***** |
| 413 | ***** |
| 414 | ***** |
| 415 | ***** |
| 416 | ***** |
| 417 | ***** |
| 418 | ***** |
| 419 | ***** |
| 420 | ***** |
| 421 | ***** |
| 422 | ***** |
| 423 | ***** |
| 424 | ***** |

Without regard to whether a document cited herein was specifically and individually indicated as being incorporated by reference, all documents referred to herein are incorporated by reference into the present application for any and all purposes to the same extent as if each individual reference was fully set forth herein.

Having now fully described the subject matter of the claims, it will be understood by those having ordinary skill in the art that the same can be performed within a wide range of equivalents without affecting the scope of the subject matter or particular aspects described herein. It is intended that the appended claims be interpreted to include all such equivalents.

What is claimed is:

1. A compound selected from the group consisting of:
   5-(5-methyl-1,3-oxazol-2-yl)-2-{3-[methyl(2,2,6,6-tetramethylpiperidin-4-yl)amino]-1,2,4-triazin-6-yl}phenol;
   5-(2-methoxypyridin-4-yl)-2-{3-[methyl(2,2,6,6-tetramethylpiperidin-4-yl)amino]-1,2,4-triazin-6-yl}phenol;
   2-{3-[methyl(2,2,6,6-tetramethylpiperidin-4-yl)amino]-1,2,4-triazin-6-yl}-5-(1H-1,2,3-triazol-4-yl)phenol;
   4-(3-hydroxy-4-{3-[methyl(2,2,6,6-tetramethylpiperidin-4-yl)amino]-1,2,4-triazin-6-yl}phenyl)pyridin-2-ol;
   5-(3-methyl-1H-pyrazol-4-yl)-2-{3-[methyl(2,2,6,6-tetramethylpiperidin-4-yl)amino]-1,2,4-triazin-6-yl}phenol;
   2-{3-[methyl(2,2,6,6-tetramethylpiperidin-4-yl)amino]-1,2,4-triazin-6-yl}-5-(1,3-oxazol-2-yl)phenol;
   2-{3-[methyl(2,2,6,6-tetramethylpiperidin-4-yl)amino]-1,2,4-triazin-6-yl}-5-(pyridin-4-yl)phenol;
   5-(2-methylpyridin-4-yl)-2-{3-[methyl(2,2,6,6-tetramethylpiperidin-4-yl)amino]-1,2,4-triazin-6-yl}phenol;
   5-(4-methyl-1H-imidazol-1-yl)-2-{3-[methyl(2,2,6,6-tetramethylpiperidin-4-yl)amino]-1,2,4-triazin-6-yl}phenol;
   5-(1H-pyrazol-4-yl)-2-{3-[(2,2,6,6-tetramethylpiperidin-4-yl)oxy]-1,2,4-triazin-6-yl}phenol;
   5-(3-fluoro-1H-pyrazol-4-yl)-2-{3-[methyl(2,2,6,6-tetramethylpiperidin-4-yl)amino]-1,2,4-triazin-6-yl}phenol;
   5-(1H-pyrazol-4-yl)-2-{3-[(2,2,6,6-tetramethylpiperidin-4-yl)amino]-1,2,4-triazin-6-yl}phenol;
   5-[1-($^{2}$H$_{3}$)methyl-1H-pyrazol-4-yl]-2-{3-[methyl(2,2,6,6-tetramethylpiperidin-4-yl)amino]-1,2,4-triazin-6-yl}phenol;
   2-{3-[methyl(2,2,6,6-tetramethylpiperidin-4-yl)amino]-1,2,4-triazin-6-yl}-5-(1H-pyrazol-4-yl)phenol;
   5-(1-methyl-1H-pyrazol-4-yl)-2-{3-[methyl(2,2,6,6-tetramethylpiperidin-4-yl)amino]-1,2,4-triazin-6-yl}phenol;
   2-{3-[methyl(2,2,6,6-tetramethylpiperidin-4-yl)amino]-1,2,4-triazin-6-yl}-5-(1H-pyrazol-1-yl)phenol;
   5-(3-fluoro-1-methyl-1H-pyrazol-4-yl)-2-{3-[methyl(2,2,6,6-tetramethylpiperidin-4-yl)amino]-1,2,4-triazin-6-yl}phenol;
   2-{3-[methyl(piperidin-4-yl)amino]-1,2,4-triazin-6-yl}-5-(1H-pyrazol-4-yl)phenol;
   2-{3-[methyl(piperidin-3-yl)amino]-1,2,4-triazin-6-yl}-5-(1H-pyrazol-4-yl)phenol;
   2-(3-{[(1R,3S,5S)-8-azabicyclo[3.2.1]octan-3-yl](methyl)amino}-1,2,4-triazin-6-yl)-5-(1H-pyrazol-4-yl)phenol;
   2-(3-{[(1R,3S,5S)-9-azabicyclo[3.3.1]nonan-3-yl](methyl)amino}-1,2,4-triazin-6-yl)-5-(1H-pyrazol-4-yl)phenol;
   2-{3-[methyl(2,2,6,6-tetramethylpiperidin-4-yl)amino]-1,2,4-triazin-6-yl}-5-(2-methyl-2H-1,2,3-triazol-4-yl)phenol;
   2-{6-[methyl(2,2,6,6-tetramethylpiperidin-4-yl)amino]-1,2,4-triazin-3-yl}-5-(1H-pyrazol-4-yl)phenol;
   (6-(2-hydroxy-4-(1H-pyrazol-4-yl)phenyl)-1,2,4-triazin-3-yl)(2,2,6,6-tetramethylpiperidin-4-yl)methanone;
   (3-(2-hydroxy-4-(1H-pyrazol-4-yl)phenyl)-1,2,4-triazin-6-yl)(2,2,6,6-tetramethylpiperidin-4-yl)methanone;
   2-(6-(2-hydroxy-4-(1H-pyrazol-4-yl)phenyl)-1,2,4-triazin-3-yl)-2-(2,2,6,6-tetramethylpiperidin-4-yl)acetonitrile;
   2-(3-(2-hydroxy-4-(1H-pyrazol-4-yl)phenyl)-1,2,4-triazin-6-yl)-2-(2,2,6,6-tetramethylpiperidin-4-yl)acetonitrile;
   2-(3-(amino(2,2,6,6-tetramethylpiperidin-4-yl)methyl)-1,2,4-triazin-6-yl)-5-(1H-pyrazol-4-yl)phenol;
   2-(6-(amino(2,2,6,6-tetramethylpiperidin-4-yl)methyl)-1,2,4-triazin-3-yl)-5-(1H-pyrazol-4-yl)phenol;
   2-(3-(methyl(2,2,6,6-tetramethylpiperidin-4-yl)amino)-1,2,4-triazin-6-yl)-5-(1,3,5-triazin-2-yl)phenol;
   2-(6-(methyl(2,2,6,6-tetramethylpiperidin-4-yl)amino)-1,2,4-triazin-3-yl)-5-(1,3,5-triazin-2-yl)phenol;
   4-(3-hydroxy-4-{3-[methyl(2,2,6,6-tetramethylpiperidin-4-yl)amino]-1,2,4-triazin-6-yl}phenyl)-1,3,5-triazin-2-ol;
   4-(3-hydroxy-4-(6-(methyl(2,2,6,6-tetramethylpiperidin-4-yl)amino)-1,2,4-triazin-3-yl)phenyl)-1,3,5-triazin-2-ol;
   5-(4-amino-1,3,5-triazin-2-yl)-2-(3-(methyl(2,2,6,6-tetramethylpiperidin-4-yl)amino)-1,2,4-triazin-6-yl)phenol;

5-(4-amino-1,3,5-triazin-2-yl)-2-(6-(methyl(2,2,6,6-tetramethylpiperidin-4-yl)amino)-1,2,4-triazin-3-yl)phenol;
5-(4-chloro-1,3,5-triazin-2-yl)-2-(3-(methyl(2,2,6,6-tetramethylpiperidin-4-yl)amino)-1,2,4-triazin-6-yl)phenol
5-(4-chloro-1,3,5-triazin-2-yl)-2-(6-(methyl(2,2,6,6-tetramethylpiperidin-4-yl)amino)-1,2,4-triazin-3-yl)phenol;
2-(3-(methyl(2,2,6,6-tetramethylpiperidin-4-yl)amino)-1,2,4-triazin-6-yl)-5-(5-methyl-1H-pyrazol-4-yl)phenol;
2-(6-(methyl(2,2,6,6-tetramethylpiperidin-4-yl)amino)-1,2,4-triazin-3-yl)-5-(5-methyl-1H-pyrazol-4-yl)phenol;
5-(5-chloro-1H-pyrazol-4-yl)-2-(3-(methyl(2,2,6,6-tetramethylpiperidin-4-yl)amino)-1,2,4-triazin-6-yl)phenol;
5-(5-chloro-1H-pyrazol-4-yl)-2-(6-(methyl(2,2,6,6-tetramethylpiperidin-4-yl)amino)-1,2,4-triazin-3-yl)phenol;
4-(3-hydroxy-4-(3-(methyl(2,2,6,6-tetramethylpiperidin-4-yl)amino)-1,2,4-triazin-6-yl)phenyl)-1H-pyrazole-5-carbonitrile;
4-(3-hydroxy-4-(6-(methyl(2,2,6,6-tetramethylpiperidin-4-yl)amino)-1,2,4-triazin-3-yl)phenyl)-1H-pyrazole-5-carbonitrile;
5-(1,5-dimethyl-1H-pyrazol-4-yl)-2-(3-(methyl(2,2,6,6-tetramethylpiperidin-4-yl)amino)-1,2,4-triazin-6-yl)phenol;
5-(1,5-dimethyl-1H-pyrazol-4-yl)-2-(6-(methyl(2,2,6,6-tetramethylpiperidin-4-yl)amino)-1,2,4-triazin-3-yl)phenol;
5-(5-chloro-1-methyl-1H-pyrazol-4-yl)-2-(3-(methyl(2,2,6,6-tetramethylpiperidin-4-yl)amino)-1,2,4-triazin-6-yl)phenol;
5-(5-chloro-1-methyl-1H-pyrazol-4-yl)-2-(6-(methyl(2,2,6,6-tetramethylpiperidin-4-yl)amino)-1,2,4-triazin-3-yl)phenol;
4-(3-hydroxy-4-(3-(methyl(2,2,6,6-tetramethylpiperidin-4-yl)amino)-1,2,4-triazin-6-yl)phenyl)-1-methyl-1H-pyrazole-5-carbonitrile;
4-(3-hydroxy-4-(6-(methyl(2,2,6,6-tetramethylpiperidin-4-yl)amino)-1,2,4-triazin-3-yl)phenyl)-1-methyl-1H-pyrazole-5-carbonitrile;
5-(4-fluoro-1H-imidazol-1-yl)-2-{3-[methyl(2,2,6,6-tetramethylpiperidin-4-yl)amino]-1,2,4-triazin-6-yl}phenol;
2-{3-[methyl(2,2,6,6-tetramethylpiperidin-4-yl)amino]-1,2,4-triazin-6-yl}-5-(3-methyl-1H-1,2,4-triazol-1-yl)phenol;
2-{3-[(1-methylpiperidin-4-yl)amino]-1,2,4-triazin-6-yl}-5-(1H-pyrazol-4-yl)phenol;
2-{3-[methyl(2,2,6,6-tetramethylpiperidin-4-yl)amino]-1,2,4-triazin-6-yl}-5-(thiophen-2-yl)phenol;
2-{3-[methyl(2,2,6,6-tetramethylpiperidin-4-yl)amino]-1,2,4-triazin-6-yl}-5-(4-methylthiophen-2-yl)phenol;
5-(4-methoxy-1H-pyrazol-1-yl)-2-{3-[methyl(2,2,6,6-tetramethylpiperidin-4-yl)amino]-1,2,4-triazin-6-yl}phenol;
4-(3-hydroxy-4-{3-[methyl(2,2,6,6-tetramethylpiperidin-4-yl)amino]-1,2,4-triazin-6-yl}phenyl)-1-methylpyridin-2(1H)-one;
5-(3-chloro-1H-pyrazol-4-yl)-2-{3-[methyl(2,2,6,6-tetramethylpiperidin-4-yl)amino]-1,2,4-triazin-6-yl}phenol;
2-{3-[methyl(2,2,6,6-tetramethylpiperidin-4-yl)amino]-1,2,4-triazin-6-yl}-5-(1,3-thiazol-2-yl)phenol;
5-(4-chloro-1H-imidazol-1-yl)-2-{3-[methyl(2,2,6,6-tetramethylpiperidin-4-yl)amino]-1,2,4-triazin-6-yl}phenol;
2-{3-[methyl(2,2,6,6-tetramethylpiperidin-4-yl)amino]-1,2,4-triazin-6-yl}-5-(pyridazin-4-yl)phenol;
5-(6-methylpyridazin-4-yl)-2-{3-[methyl(2,2,6,6-tetramethylpiperidin-4-yl)amino]-1,2,4-triazin-6-yl}phenol;
2-{3-[methyl(2,2,6,6-tetramethylpiperidin-4-yl)amino]-1,2,4-triazin-6-yl}-5-(1-methyl-1H-1,2,4-triazol-3-yl)phenol;
2-{3-[methyl(2,2,6,6-tetramethylpiperidin-4-yl)amino]-1,2,4-triazin-6-yl}-5-(2H-1,2,3-triazol-2-yl)phenol;
2-{3-[methyl(2,2,6,6-tetramethylpiperidin-4-yl)amino]-1,2,4-triazin-6-yl}-5-(2-methyl-1,3-thiazol-5-yl)phenol;
2-{3-[methyl(2,2,6,6-tetramethylpiperidin-4-yl)amino]-1,2,4-triazin-6-yl}-5-(1,2,4-thiadiazol-5-yl)phenol;
2-{3-[methyl(2,2,6,6-tetramethylpiperidin-4-yl)amino]-1,2,4-triazin-6-yl}-5-(3-methyl-1,2,4-thiadiazol-5-yl)phenol;
2-{3-[(3-fluoro-2,2,6,6-tetramethylpiperidin-4-yl)(methyl)amino]-1,2,4-triazin-6-yl}-5-(1H-pyrazol-4-yl)phenol;
1-[1-(3-hydroxy-4-{3-[methyl(2,2,6,6-tetramethylpiperidin-4-yl)amino]-1,2,4-triazin-6-yl}phenyl)-1H-pyrazol-4-yl]ethan-1-one;
2-{3-[methyl(2,2,6,6-tetramethylpiperidin-4-yl)amino]-1,2,4-triazin-6-yl}-5-(4-methyl-2H-1,2,3-triazol-2-yl)phenol;
2-{3-[methyl(2,2,6,6-tetramethylpiperidin-4-yl)amino]-1,2,4-triazin-6-yl}-5-(pyridin-3-yl)phenol;
2-{3-[methyl(2,2,6,6-tetramethylpiperidin-4-yl)amino]-1,2,4-triazin-6-yl}-5-(pyridin-2-yl)phenol;
5-(3-fluoro-1H-pyrazol-4-yl)-2-{3-[(2,2,6,6-tetramethylpiperidin-4-yl)oxy]-1,2,4-triazin-6-yl}phenol;
5-(3-fluoro-1H-pyrazol-4-yl)-2-{3-[(2,2,6,6-tetramethylpiperidin-4-yl)amino]-1,2,4-triazin-6-yl}phenol;
5-(2-methyl-1,3-oxazol-5-yl)-2-{3-[methyl(2,2,6,6-tetramethylpiperidin-4-yl)amino]-1,2,4-triazin-6-yl}phenol;
5-(1-methyl-1H-imidazol-4-yl)-2-{3-[methyl(2,2,6,6-tetramethylpiperidin-4-yl)amino]-1,2,4-triazin-6-yl}phenol;
5-(1-methyl-1H-pyrazol-3-yl)-2-{3-[methyl(2,2,6,6-tetramethylpiperidin-4-yl)amino]-1,2,4-triazin-6-yl}phenol;
2-(3-{[(1R,3s,5S)-9-methyl-9-azabicyclo[3.3.1]nonan-3-yl]amino}-1,2,4-triazin-6-yl)-5-(1H-pyrazol-4-yl)phenol;
2-(3-{[(1R,3r,5S)-8-azabicyclo[3.2.1]octan-3-yl]amino}-1,2,4-triazin-6-yl)-5-(1H-pyrazol-4-yl)phenol;
2-{3-[methyl(2,2,6,6-tetramethylpiperidin-4-yl)amino]-1,2,4-triazin-6-yl}-5-(1H-1,2,4-triazol-1-yl)phenol;
5-(imidazo[1,2-a]pyrazin-6-yl)-2-{3-[methyl(2,2,6,6-tetramethylpiperidin-4-yl)amino]-1,2,4-triazin-6-yl}phenol;
5-(5-methyl-1,3,4-oxadiazol-2-yl)-2-{3-[methyl(2,2,6,6-tetramethylpiperidin-4-yl)amino]-1,2,4-triazin-6-yl}phenol;
2-{3-[(2,6-dimethylpiperidin-4-yl)oxy]-1,2,4-triazin-6-yl}-5-(1H-pyrazol-4-yl)phenol;
2-{3-[methyl(2,2,6,6-tetramethylpiperidin-4-yl)amino]-1,2,4-triazin-6-yl}-5-(pyrazin-2-yl)phenol;
2-{3-[methyl(2,2,6,6-tetramethylpiperidin-4-yl)amino]-1,2,4-triazin-6-yl}-5-(pyridazin-3-yl)phenol;

2-{3-[methyl(2,2,6,6-tetramethylpiperidin-4-yl)amino]-1,2,4-triazin-6-yl}-5-2-{3-[methyl(2,2,6,6-tetramethylpiperidin-4-yl)amino]-1,2,4-triazin-6-yl}-5-(pyrimidin-2-yl)phenol;

2-{3-[methyl(2,2,6,6-tetramethylpiperidin-4-yl)amino]-1,2,4-triazin-6-yl}-5-(pyrimidin-5-yl)phenol;

2-(3-{methyl[(1R,3s,5S)-9-methyl-9-azabicyclo[3.3.1]nonan-3-yl]amino}-1,2,4-triazin-6-yl)-5-(1H-pyrazol-4-yl)phenol;

5-(4-methoxy-1,3,5-triazin-2-yl)-2-{3-[methyl(2,2,6,6-tetramethylpiperidin-4-yl)amino]-1,2,4-triazin-6-yl}phenol;

5-(1H-imidazol-1-yl)-2-{3-[methyl(2,2,6,6-tetramethylpiperidin-4-yl)amino]-1,2,4-triazin-6-yl}phenol;

1-(3-hydroxy-4-{3-[methyl(2,2,6,6-tetramethylpiperidin-4-yl)amino]-1,2,4-triazin-6-yl}phenyl)-1H-pyrazol-4-ol;

2-{3-[methyl(2,2,6,6-tetramethylpiperidin-4-yl)amino]-1,2,4-triazin-6-yl}-5-(1,3-oxazol-5-yl)phenol;

5-(imidazo[1,2-b]pyridazin-6-yl)-2-{3-[methyl(2,2,6,6-tetramethylpiperidin-4-yl)amino]-1,2,4-triazin-6-yl}phenol;

5-(4-fluoro-1H-pyrazol-1-yl)-2-{3-[methyl(2,2,6,6-tetramethylpiperidin-4-yl)amino]-1,2,4-triazin-6-yl}phenol;

5-(4-methyl-1H-pyrazol-1-yl)-2-{3-[methyl(2,2,6,6-tetramethylpiperidin-4-yl)amino]-1,2,4-triazin-6-yl}phenol;

2-[3-(2,7-diazaspiro[3.5]nonan-7-yl)-1,2,4-triazin-6-yl]-5-(1H-pyrazol-4-yl)phenol;

2-[3-(2,7-diazaspiro[3.5]nonan-2-yl)-1,2,4-triazin-6-yl]-5-(1H-pyrazol-4-yl)phenol;

5-(1H-indazol-5-yl)-2-{3-[methyl(2,2,6,6-tetramethylpiperidin-4-yl)amino]-1,2,4-triazin-6-yl}phenol;

5-(4-fluoropyridin-2-yl)-2-{3-[methyl(2,2,6,6-tetramethylpiperidin-4-yl)amino]-1,2,4-triazin-6-yl}phenol;

2-{3-[methyl(2,2,6,6-tetramethylpiperidin-4-yl)amino]-1,2,4-triazin-6-yl}-5-(4-nitro-2H-1,2,3-triazol-2-yl)phenol;

2-[3-(6-amino-3-azabicyclo[3.1.0]hexan-3-yl)-1,2,4-triazin-6-yl]-5-(1H-pyrazol-4-yl)phenol;

5-(1-cyclopropyl-1H-pyrazol-4-yl)-2-{3-[methyl(2,2,6,6-tetramethylpiperidin-4-yl)amino]-1,2,4-triazin-6-yl}phenol;

2-{3-[methyl(2,2,6,6-tetramethylpiperidin-4-yl)amino]-1,2,4-triazin-6-yl}-5-(pyrimidin-4-yl)phenol;

4-{3-[methyl(2,2,6,6-tetramethylpiperidin-4-yl)amino]-1,2,4-triazin-6-yl}[1,1'-biphenyl]-3,4'-diol;

5-(3-hydroxy-4-{3-[methyl(2,2,6,6-tetramethylpiperidin-4-yl)amino]-1,2,4-triazin-6-yl}phenyl)pyridin-2(1H)-one;

6-{3-[methyl(2,2,6,6-tetramethylpiperidin-4-yl)amino]-1,2,4-triazin-6-yl}quinolin-7-ol;

2-{3-[methyl(2,2,6,6-tetramethylpiperidin-4-yl)amino]-1,2,4-triazin-6-yl}-5-(1,3,4-oxadiazol-2-yl)phenol;

5-(1H-pyrazol-3-yl)-2-{3-[(2,2,6,6-tetramethylpiperidin-4-yl)oxy]-1,2,4-triazin-6-yl}phenol;

5-(1-methyl-1H-pyrazol-3-yl)-2-{3-[(2,2,6,6-tetramethylpiperidin-4-yl)oxy]-1,2,4-triazin-6-yl}phenol;

2-[3-(2,6-diazaspiro[3.5]nonan-2-yl)-1,2,4-triazin-6-yl]-5-(1H-pyrazol-4-yl)phenol;

2-[3-(2,6-diazaspiro[3.4]octan-6-yl)-1,2,4-triazin-6-yl]-5-(1H-pyrazol-4-yl)phenol;

2-{3-[methyl(2,2,6,6-tetramethylpiperidin-4-yl)amino]-1,2,4-triazin-6-yl}-5-(1H-pyrazol-3-yl)phenol;

5-(5-fluoropyrimidin-2-yl)-2-{3-[methyl(2,2,6,6-tetramethylpiperidin-4-yl)amino]-1,2,4-triazin-6-yl}phenol;

2-[3-(1-methyl-1,7-diazaspiro[3.5]nonan-7-yl)-1,2,4-triazin-6-yl]-5-(1H-pyrazol-4-yl)phenol;

2-{3-[(3S)-3-(methylamino)pyrrolidin-1-yl]-1,2,4-triazin-6-yl}-5-(1H-pyrazol-4-yl)phenol;

2-{3-[(7S)-7-amino-5-azaspiro[2.4]heptan-5-yl]-1,2,4-triazin-6-yl}-5-(1H-pyrazol-4-yl)phenol;

2-{3-[(8aS)-hexahydropyrrolo[1,2-a]pyrazin-2(1H)-yl]-1,2,4-triazin-6-yl}-5-(1H-pyrazol-4-yl)phenol;

2-{3-[(3aR,6aR)-1-methylhexahydropyrrolo[3,4-b]pyrrol-5(1H)-yl]-1,2,4-triazin-6-yl}-5-(1H-pyrazol-4-yl)phenol;

2-[3-(2,6-diazaspiro[3.3]heptan-2-yl)-1,2,4-triazin-6-yl]-5-(1H-pyrazol-4-yl)phenol;

2-{3-[methyl(2,2,6,6-tetramethylpiperidin-4-yl)amino]-1,2,4-triazin-6-yl}-5-(5-methyl-2H-tetrazol-2-yl)phenol;

2-(3-{[(2R,4s,6S)-2,6-diethylpiperidin-4-yl]oxy}-1,2,4-triazin-6-yl)-5-(1H-pyrazol-4-yl)phenol;

2-{3-[(2,2,6,6-tetramethylpiperidin-4-yl)amino]-1,2,4-triazin-6-yl}-5-(2H-1,2,3-triazol-2-yl)phenol;

2-{3-[(2,2,6,6-tetramethylpiperidin-4-yl)oxy]-1,2,4-triazin-6-yl}-5-(2H-1,2,3-triazol-2-yl)phenol;

5-(6-chloropyridazin-3-yl)-2-{3-[methyl(2,2,6,6-tetramethylpiperidin-4-yl)amino]-1,2,4-triazin-6-yl}phenol;

5-(1-methyl-1H-pyrazol-5-yl)-2-{3-[methyl(2,2,6,6-tetramethylpiperidin-4-yl)amino]-1,2,4-triazin-6-yl}phenol;

4-fluoro-2-{3-[methyl(2,2,6,6-tetramethylpiperidin-4-yl)amino]-1,2,4-triazin-6-yl}-5-(1H-pyrazol-5-yl)phenol;

2-{3-[(3-fluoro-2,2,6,6-tetramethylpiperidin-4-yl)amino]-1,2,4-triazin-6-yl}-5-(1H-pyrazol-4-yl)phenol;

2-{3-[6-(diethylamino)-3-azabicyclo[3.1.0]hexan-3-yl]-1,2,4-triazin-6-yl}-5-(1H-pyrazol-4-yl)phenol;

5-(5-methylpyrimidin-2-yl)-2-{3-[methyl(2,2,6,6-tetramethylpiperidin-4-yl)amino]-1,2,4-triazin-6-yl}phenol;

5-(4-methylpyrimidin-2-yl)-2-{3-[methyl(2,2,6,6-tetramethylpiperidin-4-yl)amino]-1,2,4-triazin-6-yl}phenol;

5-(2-chloropyrimidin-4-yl)-2-{3-[methyl(2,2,6,6-tetramethylpiperidin-4-yl)amino]-1,2,4-triazin-6-yl}phenol;

5-(1H-benzimidazol-5-yl)-2-{3-[methyl(2,2,6,6-tetramethylpiperidin-4-yl)amino]-1,2,4-triazin-6-yl}phenol;

2-{3-[methyl(2,2,6,6-tetramethylpiperidin-4-yl)amino]-1,2,4-triazin-6-yl}-5-(1H-pyrazolo[3,4-b]pyridin-5-yl)phenol;

5-(3-chloro-1H-1,2,4-triazol-1-yl)-2-{3-[methyl(2,2,6,6-tetramethylpiperidin-4-yl)amino]-1,2,4-triazin-6-yl}phenol;

6-(3-hydroxy-4-{3-[methyl(2,2,6,6-tetramethylpiperidin-4-yl)amino]-1,2,4-triazin-6-yl}phenyl)pyridazin-3-ol;

1-(3-hydroxy-4-{3-[methyl(2,2,6,6-tetramethylpiperidin-4-yl)amino]-1,2,4-triazin-6-yl}phenyl)-1H-pyrazole-4-carbonitrile;

2-{3-[methyl(2,2,6,6-tetramethylpiperidin-4-yl)amino]-1,2,4-triazin-6-yl}-5-(1H-pyrazolo[4,3-b]pyridin-5-yl)phenol;

2-{3-[3-(cyclopropylamino)pyrrolidin-1-yl]-1,2,4-triazin-6-yl}-5-(1H-pyrazol-4-yl)phenol;

2-{3-[3-(tert-butylamino)pyrrolidin-1-yl]-1,2,4-triazin-6-yl}-5-(1H-pyrazol-4-yl)phenol;

1-(3-hydroxy-4-{3-[methyl(2,2,6,6-tetramethylpiperidin-4-yl)amino]-1,2,4-triazin-6-yl}phenyl)-1H-imidazole-4-carbonitrile;

1-[1-(3-hydroxy-4-{3-[methyl(2,2,6,6-tetramethylpiperidin-4-yl)amino]-1,2,4-triazin-6-yl}phenyl)-1H-imidazol-4-yl]ethan-1-one;

5-(2,8-dimethylimidazo[1,2-b]pyridazin-6-yl)-2-{3-[methyl(2,2,6,6-tetramethylpiperidin-4-yl)amino]-1,2,4-triazin-6-yl}phenol;

5-(2-methylimidazo[1,2-b]pyridazin-6-yl)-2-{3-[methyl(2,2,6,6-tetramethylpiperidin-4-yl)amino]-1,2,4-triazin-6-yl}phenol;

2-{3-[methyl(2,2,6,6-tetramethylpiperidin-4-yl)amino]-1,2,4-triazin-6-yl}-5-(2-methyl-2H-tetrazol-5-yl)phenol;

5-(6-methoxy-1,2,4-triazin-3-yl)-2-{3-[methyl(2,2,6,6-tetramethylpiperidin-4-yl)amino]-1,2,4-triazin-6-yl}phenol;

5-(1,3-benzoxazol-6-yl)-2-{3-[methyl(2,2,6,6-tetramethylpiperidin-4-yl)amino]-1,2,4-triazin-6-yl}phenol;

6-(3-hydroxy-4-{3-[methyl(2,2,6,6-tetramethylpiperidin-4-yl)amino]-1,2,4-triazin-6-yl}phenyl)-3-methylpyrimidin-4(3H)-one;

5-(3-hydroxy-4-{3-[methyl(2,2,6,6-tetramethylpiperidin-4-yl)amino]-1,2,4-triazin-6-yl}phenyl)-2-methylpyridazin-3(2H)-one;

2-(3-{3-[(propan-2-yl)amino]pyrrolidin-1-yl}-1,2,4-triazin-6-yl)-5-(1H-pyrazol-4-yl)phenol;

5-(3-fluoro-1H-pyrazol-4-yl)-2-[3-(7-methyl-2,7-diazaspiro[3.5]nonan-2-yl)-1,2,4-triazin-6-yl]phenol;

5-(3-fluoro-1H-pyrazol-4-yl)-2-{3-[(3aS,7aR)-octahydro-5H-pyrrolo[3,2-c]pyridin-5-yl]-1,2,4-triazin-6-yl}phenol;

2-[3-(2,7-diazaspiro[3.5]nonan-2-yl)-1,2,4-triazin-6-yl]-5-(3-fluoro-1H-pyrazol-4-yl)phenol;

2-{3-[methyl(2,2,6,6-tetramethylpiperidin-4-yl)amino]-1,2,4-triazin-6-yl}-5-([1,2,3]triazolo[1,5-a]pyridin-5-yl)phenol;

5-(3-fluoro-1H-pyrazol-4-yl)-2-{3-[(3aS,7aR)-1-methyloctahydro-5H-pyrrolo[3,2-c]pyridin-5-yl]-1,2,4-triazin-6-yl}phenol;

2-(3-{3-[(2-methylbutan-2-yl)amino]pyrrolidin-1-yl}-1,2,4-triazin-6-yl)-5-(1H-pyrazol-4-yl)phenol;

2-{3-[methyl(2,2,6,6-tetramethylpiperidin-4-yl)amino]-1,2,4-triazin-6-yl}-5-(tetrazolo[1,5-a]pyridin-7-yl)phenol;

5-(4-fluoro-1H-pyrazol-3-yl)-2-{3-[methyl(2,2,6,6-tetramethylpiperidin-4-yl)amino]-1,2,4-triazin-6-yl}phenol;

2-(3-{3-[(adamantan-1-yl)amino]pyrrolidin-1-yl}-1,2,4-triazin-6-yl)-5-(1H-pyrazol-4-yl)phenol;

2-{3-[methyl(2,2,6,6-tetramethylpiperidin-4-yl)amino]-1,2,4-triazin-6-yl}-5-(5H-pyrrolo[2,3-b]pyrazin-2-yl)phenol;

2-(3-{3-[(adamantan-2-yl)amino]pyrrolidin-1-yl}-1,2,4-triazin-6-yl)-5-(1H-pyrazol-4-yl)phenol;

2-(3-{3-[(3,5-dimethyladamantan-1-yl)amino]pyrrolidin-1-yl}-1,2,4-triazin-6-yl)-5-(1H-pyrazol-4-yl)phenol;

5-[4-(hydroxymethyl)-1H-pyrazol-1-yl]-2-{3-[methyl(2,2,6,6-tetramethylpiperidin-4-yl)amino]-1,2,4-triazin-6-yl}phenol;

2-{3-[(3aR,4R,6aS)-4-(dimethylamino)hexahydrocyclopenta[c]pyrrol-2(1H)-yl]-1,2,4-triazin-6-yl}-5-(1H-pyrazol-4-yl)phenol;

5-(3-methyl-3H-imidazo[4,5-b]pyridin-5-yl)-2-{3-[methyl(2,2,6,6-tetramethylpiperidin-4-yl)amino]-1,2,4-triazin-6-yl}phenol;

5-(1-methyl-1H-imidazo[4,5-b]pyridin-5-yl)-2-{3-[methyl(2,2,6,6-tetramethylpiperidin-4-yl)amino]-1,2,4-triazin-6-yl}phenol;

2-{3-[(3aR,4S,6aS)-4-aminohexahydrocyclopenta[c]pyrrol-2(1H)-yl]-1,2,4-triazin-6-yl}-5-(1H-pyrazol-4-yl)phenol;

2-[3-(5-methyloctahydro-2H-pyrrolo[3,4-c]pyridin-2-yl)-1,2,4-triazin-6-yl]-5-(1H-pyrazol-4-yl)phenol;

2-{3-[(3aR,4S,6aS)-4-(dimethylamino)hexahydrocyclopenta[c]pyrrol-2(1H)-yl]-1,2,4-triazin-6-yl}-5-(1H-pyrazol-4-yl)phenol;

3-amino-6-(3-hydroxy-4-{3-[methyl(2,2,6,6-tetramethylpiperidin-4-yl)amino]-1,2,4-triazin-6-yl}phenyl)-4-methylpyridin-2-ol;

5-(2,7-dimethyl[1,3]oxazolo[5,4-b]pyridin-5-yl)-2-{3-[methyl(2,2,6,6-tetramethylpiperidin-4-yl)amino]-1,2,4-triazin-6-yl}phenol;

2-(3-{3-[(3-methylpentan-3-yl)amino]pyrrolidin-1-yl}-1,2,4-triazin-6-yl)-5-(1H-pyrazol-4-yl)phenol;

2-{3-[4-(tert-butylamino)-2-methylpyrrolidin-1-yl]-1,2,4-triazin-6-yl}-5-(1H-pyrazol-4-yl)phenol;

5-[4-(hydroxymethyl)-2H-1,2,3-triazol-2-yl]-2-{3-[methyl(2,2,6,6-tetramethylpiperidin-4-yl)amino]-1,2,4-triazin-6-yl}phenol;

2-{3-[methyl(2,2,6,6-tetramethylpiperidin-4-yl)amino]-1,2,4-triazin-6-yl}-5-(3-methyl-3H-[1,2,3]triazolo[4,5-b]pyridin-5-yl)phenol;

2-{3-[3-(tert-butylamino)pyrrolidin-1-yl]-1,2,4-triazin-6-yl}-5-(3-fluoro-1H-pyrazol-4-yl)phenol;

2-{3-[3-(tert-butylamino)pyrrolidin-1-yl]-1,2,4-triazin-6-yl}-5-(1-methyl-1H-pyrazol-3-yl)phenol;

5-(1-methyl-1H-pyrazolo[3,4-b]pyridin-5-yl)-2-{3-[methyl(2,2,6,6-tetramethylpiperidin-4-yl)amino]-1,2,4-triazin-6-yl}phenol;

5-(1-methyl-1H-indazol-5-yl)-2-{3-[methyl(2,2,6,6-tetramethylpiperidin-4-yl)amino]-1,2,4-triazin-6-yl}phenol;

2-{3-[methyl(2,2,6,6-tetramethylpiperidin-4-yl)amino]-1,2,4-triazin-6-yl}-5-(tetrazolo[1,5-b]pyridazin-6-yl)phenol;

5-[6-(hydroxymethyl)pyrimidin-4-yl]-2-{3-[methyl(2,2,6,6-tetramethylpiperidin-4-yl)amino]-1,2,4-triazin-6-yl}phenol;

2-[3-(2,9-diazaspiro[5.5]undecan-9-yl)-1,2,4-triazin-6-yl]-5-(1H-pyrazol-4-yl)phenol;

2-[3-(2,8-diazaspiro[4.5]decan-8-yl)-1,2,4-triazin-6-yl]-5-(1H-pyrazol-4-yl)phenol;

2-[3-(2-methyl-2,9-diazaspiro[5.5]undecan-9-yl)-1,2,4-triazin-6-yl]-5-(1H-pyrazol-4-yl)phenol;

2-[3-(2-methyl-2,8-diazaspiro[4.5]decan-8-yl)-1,2,4-triazin-6-yl]-5-(1H-pyrazol-4-yl)phenol;

2-{3-[methyl(2,2,6,6-tetramethylpiperidin-4-yl)amino]-1,2,4-triazin-6-yl}-5-(1H-pyrazolo[3,4-c]pyridin-5-yl)phenol;

2-{3-[methyl(2,2,6,6-tetramethylpiperidin-4-yl)amino]-1,2,4-triazin-6-yl}-5-(quinolin-6-yl)phenol;

2-{3-[methyl(2,2,6,6-tetramethylpiperidin-4-yl)amino]-1,2,4-triazin-6-yl}-5-(1-methyl-1H-[1,2,3]triazolo[4,5-b]pyridin-5-yl)phenol;

2-{3-[3-(tert-butylamino)pyrrolidin-1-yl]-1,2,4-triazin-6-yl}-5-(1H-imidazol-1-yl)phenol;

5-(2H-1,3-benzodioxol-5-yl)-2-{3-[methyl(2,2,6,6-tetramethylpiperidin-4-yl)amino]-1,2,4-triazin-6-yl}phenol;

5-(3-fluoro-1H-pyrazol-4-yl)-2-(3-{[(3R,4R)-3-fluoro-2,2,6,6-tetramethylpiperidin-4-yl]amino}-1,2,4-triazin-6-yl)phenol;

2-(3-{[(2S)-2-aminopropyl](methyl)amino}-1,2,4-triazin-6-yl)-5-(1H-pyrazol-4-yl)phenol;

5-(5-fluoro-1H-pyrazol-4-yl)-2-{6-[methyl(2,2,6,6-tetramethylpiperidin-4-yl)amino]-1,2,4-triazin-3-yl}phenol;

5-[1-(²H₃)methyl-1H-pyrazol-4-yl]-2-{6-[methyl(2,2,6,6-tetramethylpiperidin-4-yl)amino]-1,2,4-triazin-3-yl}phenol;

2-{3-[(3aR,4R,6aS)-4-(tert-butylamino)hexahydrocyclopenta[c]pyrrol-2(1H)-yl]-1,2,4-triazin-6-yl}-5-(1H-pyrazol-4-yl)phenol;

2-{3-[methyl(2,2,6,6-tetramethylpiperidin-4-yl)amino]-1,2,4-triazin-6-yl}-5-(1H-pyrazolo[3,4-b]pyrazin-5-yl)phenol;

2-{3-[methyl(2,2,6,6-tetramethylpiperidin-4-yl)amino]-1,2,4-triazin-6-yl}-5-(1H-pyrazolo[4,3-d]pyrimidin-5-yl)phenol;

5-(1-methyl-1H-pyrazol-4-yl)-2-{6-[methyl(2,2,6,6-tetramethylpiperidin-4-yl)amino]-1,2,4-triazin-3-yl}phenol;

2-{3-[3-(tert-butylamino)pyrrolidin-1-yl]-1,2,4-triazin-6-yl}-5-(4-methyl-1H-imidazol-1-yl)phenol;

5-(1-methyl-1H-pyrazolo[4,3-b]pyridin-5-yl)-2-{3-[methyl(2,2,6,6-tetramethylpiperidin-4-yl)amino]-1,2,4-triazin-6-yl}phenol;

5-(1-methyl-1H-pyrazol-4-yl)-2-{3-[(2,2,6,6-tetramethylpiperidin-4-yl)amino]-1,2,4-triazin-6-yl}phenol;

5-(1-methyl-1H-benzotriazol-5-yl)-2-{3-[methyl(2,2,6,6-tetramethylpiperidin-4-yl)amino]-1,2,4-triazin-6-yl}phenol;

2-(3-{[(3S,4S)-3-fluoro-2,2,6,6-tetramethylpiperidin-4-yl]amino}-1,2,4-triazin-6-yl)-5-(1-methyl-1H-pyrazol-4-yl)phenol;

2-{3-[3-(tert-butylamino)pyrrolidin-1-yl]-1,2,4-triazin-6-yl}-5-(1-methyl-1H-pyrazol-4-yl)phenol;

5-(1-methyl-1H-pyrazol-4-yl)-2-(3-{3-[(propan-2-yl)amino]pyrrolidin-1-yl}-1,2,4-triazin-6-yl)phenol;

2-{3-[3-(tert-butylamino)pyrrolidin-1-yl]-1,2,4-triazin-6-yl}-5-(2H-1,2,3-triazol-2-yl)phenol;

2-{3-[3-(methylamino)pyrrolidin-1-yl]-1,2,4-triazin-6-yl}-5-(1-methyl-1H-pyrazol-4-yl)phenol;

2-{3-[4-(tert-butylamino)piperidin-1-yl]-1,2,4-triazin-6-yl}-5-(1H-pyrazol-4-yl)phenol;

2-{3-[3-(tert-butylamino)pyrrolidin-1-yl]-1,2,4-triazin-6-yl}-5-([1,2,3]triazolo[1,5-a]pyridin-5-yl)phenol;

2-{3-[3-(tert-butylamino)pyrrolidin-1-yl]-1,2,4-triazin-6-yl}-5-(1-methyl-1H-indazol-5-yl)phenol;

2-{3-[3-(tert-butylamino)pyrrolidin-1-yl]-1,2,4-triazin-6-yl}-5-(pyrimidin-2-yl)phenol;

2-{3-[3-(tert-butylamino)pyrrolidin-1-yl]-1,2,4-triazin-6-yl}-5-(2-methyl-2H-1,2,3-triazol-4-yl)phenol;

2-{3-[3-(tert-butylamino)pyrrolidin-1-yl]-1,2,4-triazin-6-yl}-5-(2-methyl-2H-tetrazol-5-yl)phenol;

2-{3-[3-(tert-butylamino)piperidin-1-yl]-1,2,4-triazin-6-yl}-5-(1H-pyrazol-4-yl)phenol;

5-(1-methyl-1H-pyrazol-3-yl)-2-(3-{3-[(propan-2-yl)amino]pyrrolidin-1-yl}-1,2,4-triazin-6-yl)phenol;

4-(4-{3-[3-(tert-butylamino)pyrrolidin-1-yl]-1,2,4-triazin-6-yl}-3-hydroxyphenyl)-1-methylpyridin-2(1H)-one;

2-{3-[3-(tert-butylamino)pyrrolidin-1-yl]-1,2,4-triazin-6-yl}-5-(1-methyl-1H-[1,2,3]triazolo[4,5-b]pyridin-5-yl)phenol;

6-(4-{3-[3-(tert-butylamino)pyrrolidin-1-yl]-1,2,4-triazin-6-yl}-3-hydroxyphenyl)-3-methylpyrimidin-4(3H)-one;

2-{3-[3-(tert-butylamino)pyrrolidin-1-yl]-1,2,4-triazin-6-yl}-5-(6-methoxypyrimidin-4-yl)phenol;

2-{3-[3-(methylamino)pyrrolidin-1-yl]-1,2,4-triazin-6-yl}-5-(2H-1,2,3-triazol-2-yl)phenol;

5-(4-fluoro-1H-pyrazol-1-yl)-2-{3-[3-(methylamino)pyrrolidin-1-yl]-1,2,4-triazin-6-yl}phenol;

5-(1H-imidazol-1-yl)-2-{3-[3-(methylamino)pyrrolidin-1-yl]-1,2,4-triazin-6-yl}phenol;

2-{3-[3-(tert-butylamino)pyrrolidin-1-yl]-1,2,4-triazin-6-yl}-5-(1-methyl-1H-pyrazolo[3,4-b]pyridin-5-yl)phenol;

5-(1-methyl-1H-pyrazolo[3,4-c]pyridin-5-yl)-2-{3-[methyl(2,2,6,6-tetramethylpiperidin-4-yl)amino]-1,2,4-triazin-6-yl}phenol;

2-[3-(7-methyl-2,7-diazaspiro[3.5]nonan-2-yl)-1,2,4-triazin-6-yl]-5-(1-methyl-1H-indazol-5-yl)phenol;

2-[3-(7-methyl-2,7-diazaspiro[3.5]nonan-2-yl)-1,2,4-triazin-6-yl]-5-(1-methyl-1H-2-[3-(7-methyl-2,7-diazaspiro[3.5]nonan-2-yl)-1,2,4-triazin-6-yl]-5-(1-methyl-1H-pyrazolo[3,4-b]pyridin-5-yl)phenol;

2-{3-[3-(tert-butylamino)pyrrolidin-1-yl]-1,2,4-triazin-6-yl}-5-(1H-1,2,3-triazol-4-yl)phenol;

2-[3-(7-methyl-2,7-diazaspiro[3.5]nonan-2-yl)-1,2,4-triazin-6-yl]-5-(1-methyl-1H-pyrazol-4-yl)phenol;

4-[3-hydroxy-4-(3-{3-[(propan-2-yl)amino]pyrrolidin-1-yl}-1,2,4-triazin-6-yl)phenyl]-1-methylpyridin-2(1H)-one;

2-[3-(7-methyl-2,7-diazaspiro[3.5]nonan-2-yl)-1,2,4-triazin-6-yl]-5-(4-methyl-1H-imidazol-1-yl)phenol 5-(4-fluoro-1H-pyrazol-1-yl)-2-[3-(7-methyl-2,7-diazaspiro[3.5]nonan-2-yl)-1,2,4-triazin-6-yl]phenol;

5-(4-fluoro-1H-imidazol-1-yl)-2-[3-(7-methyl-2,7-diazaspiro[3.5]nonan-2-yl)-1,2,4-triazin-6-yl]phenol;

5-(1H-imidazol-1-yl)-2-[3-(7-methyl-2,7-diazaspiro[3.5]nonan-2-yl)-1,2,4-triazin-6-yl]phenol;

2-[3-(7-methyl-2,7-diazaspiro[3.5]nonan-2-yl)-1,2,4-triazin-6-yl]-5-(2H-1,2,3-triazol-2-yl)phenol;

2-[3-(7-methyl-2,7-diazaspiro[3.5]nonan-2-yl)-1,2,4-triazin-6-yl]-5-(1-methyl-1H-pyrazol-3-yl)phenol;

6-[3-hydroxy-4-(3-{3-[(propan-2-yl)amino]pyrrolidin-1-yl}-1,2,4-triazin-6-yl)phenyl]-3-methylpyrimidin-4(3H)-one;

5-(5-fluoro-1H-pyrazol-4-yl)-2-(3-{3-[(propan-2-yl)amino]pyrrolidin-1-yl}-1,2,4-triazin-6-yl)phenol;

5-(2-methyl-2H-1,2,3-triazol-4-yl)-2-(3-{3-[(propan-2-yl)amino]pyrrolidin-1-yl}-1,2,4-triazin-6-yl)phenol;

2-(3-{3-[(propan-2-yl)amino]pyrrolidin-1-yl}-1,2,4-triazin-6-yl)-5-(1,2,4-thiadiazol-5-yl)phenol;

2-(3-{[(3S,4S)-3-fluoro-2,2,6,6-tetramethylpiperidin-4-yl]amino}-1,2,4-triazin-6-yl)-5-(1H-imidazol-1-yl)phenol;

2-(3-{[(3S,4S)-3-fluoro-2,2,6,6-tetramethylpiperidin-4-yl]amino}-1,2,4-triazin-6-yl)-5-2-(3-{[(3S,4S)-3-fluoro-2,2,6,6-tetramethylpiperidin-4-yl]amino}-1,2,4-triazin-6-yl)-5-(4-methyl-1H-imidazol-1-yl)phenol;

5-(4-fluoro-1H-imidazol-1-yl)-2-(3-{[(3S,4S)-3-fluoro-2,2,6,6-tetramethylpiperidin-4-yl]amino}-1,2,4-triazin-6-yl)phenol;

4-{3-hydroxy-4-[3-(7-methyl-2,7-diazaspiro[3.5]nonan-2-yl)-1,2,4-triazin-6-yl]phenyl}-1-methylpyridin-2(1H)-one;

2-[3-(7-methyl-2,7-diazaspiro[3.5]nonan-2-yl)-1,2,4-triazin-6-yl]-5-(2-methyl-2H-1,2,3-triazol-4-yl)phenol;

5-(6-methoxypyrimidin-4-yl)-2-[3-(7-methyl-2,7-diazaspiro[3.5]nonan-2-yl)-1,2,4-triazin-6-yl]phenol;

2-[3-(7-methyl-2,7-diazaspiro[3.5]nonan-2-yl)-1,2,4-triazin-6-yl]-5-(pyrimidin-2-yl)phenol;

2-[3-(7-methyl-2,7-diazaspiro[3.5]nonan-2-yl)-1,2,4-triazin-6-yl]-5-(1H-1,2,3-triazol-4-yl)phenol;

6-[4-(3-{[(3S,4S)-3-fluoro-2,2,6,6-tetramethylpiperidin-4-yl]amino}-1,2,4-triazin-6-yl)-3-hydroxyphenyl]-3-methylpyrimidin-4(3H)-one;

2-(3-{[(3S,4S)-3-fluoro-2,2,6,6-tetramethylpiperidin-4-yl]amino}-1,2,4-triazin-6-yl)-5-(1H-1,2,3-triazol-4-yl)phenol;
2-(3-{[(3S,4S)-3-fluoro-2,2,6,6-tetramethylpiperidin-4-yl]amino}-1,2,4-triazin-6-yl)-5-2-(3-{[(3S,4S)-3-fluoro-2,2,6,6-tetramethylpiperidin-4-yl]amino}-1,2,4-triazin-6-yl)-5-(imidazo[1,2-a]pyrazin-6-yl)phenol;
2-(3-{[(3S,4S)-3-fluoro-2,2,6,6-tetramethylpiperidin-4-yl]amino}-1,2,4-triazin-6-yl)-5-2-(3-{[(3S,4S)-3-fluoro-2,2,6,6-tetramethylpiperidin-4-yl]amino}-1,2,4-triazin-6-yl)-5-(imidazo[1,2-b]pyridazin-6-yl)phenol;
2-{3-[3-(tert-butylamino)pyrrolidin-1-yl]-1,2,4-triazin-6-yl}-5-(1,3-oxazol-2-yl)phenol;
2-[3-(7-methyl-2,7-diazaspiro[3.5]nonan-2-yl)-1,2,4-triazin-6-yl]-5-(2-methyl-2H-tetrazol-5-yl)phenol;
2-[3-(7-methyl-2,7-diazaspiro[3.5]nonan-2-yl)-1,2,4-triazin-6-yl]-5-(1,3-oxazol-2-yl)phenol;
5-(1-methyl-1H-pyrazol-3-yl)-2-{3-[(2,2,6,6-tetramethylpiperidin-4-yl)amino]-1,2,4-triazin-6-yl}phenol;
5-(6-methoxypyrimidin-4-yl)-2-{3-[(2,2,6,6-tetramethylpiperidin-4-yl)amino]-1,2,4-triazin-6-yl}phenol;
2-{6-[methyl(2,2,6,6-tetramethylpiperidin-4-yl)amino]-1,2,4-triazin-3-yl}-5-(2H-1,2,3-triazol-2-yl)phenol;
5-(imidazo[1,2-b]pyridazin-6-yl)-2-[3-(7-methyl-2,7-diazaspiro[3.5]nonan-2-yl)-1,2,4-triazin-6-yl]phenol;
5-(imidazo[1,2-a]pyrazin-6-yl)-2-[3-(7-methyl-2,7-diazaspiro[3.5]nonan-2-yl)-1,2,4-triazin-6-yl]phenol;
2-(3-{3-[(propan-2-yl)amino]pyrrolidin-1-yl}-1,2,4-triazin-6-yl)-5-(1H-1,2,3-triazol-4-yl)phenol;
5-(2-methyl-2H-tetrazol-5-yl)-2-(3-{3-[(propan-2-yl)amino]pyrrolidin-1-yl}-1,2,4-triazin-6-yl)phenol;
2-(3-{[(3S,4S)-3-fluoro-2,2,6,6-tetramethylpiperidin-4-yl]amino}-1,2,4-triazin-6-yl)-5-(1-methyl-1H-indazol-5-yl)phenol;
2-(3-{[(3S,4S)-3-fluoro-2,2,6,6-tetramethylpiperidin-4-yl]amino}-1,2,4-triazin-6-yl)-5-2-(3-{[(3S,4S)-3-fluoro-2,2,6,6-tetramethylpiperidin-4-yl]amino}-1,2,4-triazin-6-yl)-5-(1-methyl-1H-pyrazol-3-yl)phenol;
2-[3-(3,5-dimethylpiperazin-1-yl)-1,2,4-triazin-6-yl]-5-(1H-pyrazol-4-yl)phenol;
2-[3-(3,5-dimethylpiperazin-1-yl)-1,2,4-triazin-6-yl]-5-(1-methyl-1H-pyrazol-3-yl)phenol;
2-(3-{3-[(propan-2-yl)amino]pyrrolidin-1-yl}-1,2,4-triazin-6-yl)-5-(2H-1,2,3-triazol-2-yl)phenol;
5-(6-methoxypyrimidin-4-yl)-2-(3-{3-[(propan-2-yl)amino]pyrrolidin-1-yl}-1,2,4-triazin-6-yl)phenol;
5-(2-methyl-2H-1,2,3-triazol-4-yl)-2-{3-[(2,2,6,6-tetramethylpiperidin-4-yl)amino]-1,2,4-triazin-6-yl}phenol;
5-(2-methyl-2H-tetrazol-5-yl)-2-{3-[(2,2,6,6-tetramethylpiperidin-4-yl)amino]-1,2,4-triazin-6-yl}phenol;
5-(6-methoxypyrimidin-4-yl)-2-{3-[3-(methylamino)pyrrolidin-1-yl]-1,2,4-triazin-6-yl}phenol;
2-{3-[3-(methylamino)pyrrolidin-1-yl]-1,2,4-triazin-6-yl}-5-(1,2,4-thiadiazol-5-yl)phenol;
2-{3-[3-(methylamino)pyrrolidin-1-yl]-1,2,4-triazin-6-yl}-5-(pyrimidin-2-yl)phenol;
2-{3-[3-(methylamino)pyrrolidin-1-yl]-1,2,4-triazin-6-yl}-5-(1-methyl-1H-pyrazolo[3,4-b]pyridin-5-yl)phenol;
2-[3-(7-methyl-2,7-diazaspiro[3.5]nonan-2-yl)-1,2,4-triazin-6-yl]-5-(1,2,4-thiadiazol-5-yl)phenol;
5-(1H-imidazol-1-yl)-2-{3-[(2,2,6,6-tetramethylpiperidin-4-yl)amino]-1,2,4-triazin-6-yl}phenol;
5-(4-methyl-1H-imidazol-1-yl)-2-{3-[(2,2,6,6-tetramethylpiperidin-4-yl)amino]-1,2,4-triazin-6-yl}phenol;
5-(4-fluoro-1H-imidazol-1-yl)-2-{3-[(2,2,6,6-tetramethylpiperidin-4-yl)amino]-1,2,4-triazin-6-yl}phenol;
5-(4-fluoro-1H-pyrazol-1-yl)-2-{3-[(2,2,6,6-tetramethylpiperidin-4-yl)amino]-1,2,4-triazin-6-yl}phenol;
5-(2-methyl-1,3-oxazol-5-yl)-2-{3-[(2,2,6,6-tetramethylpiperidin-4-yl)amino]-1,2,4-triazin-6-yl}phenol;
2-{3-[3-(tert-butylamino)-4-fluoropyrrolidin-1-yl]-1,2,4-triazin-6-yl}-5-(1H-pyrazol-4-yl)phenol;
5-(pyrimidin-2-yl)-2-{3-[(2,2,6,6-tetramethylpiperidin-4-yl)amino]-1,2,4-triazin-6-yl}phenol;
5-(7-fluoro-1H-benzimidazol-5-yl)-2-{3-[methyl(2,2,6,6-tetramethylpiperidin-4-yl)amino]-1,2,4-triazin-6-yl}phenol;
5-(1-methyl-1H-pyrazolo[4,3-d]pyrimidin-5-yl)-2-{3-[methyl(2,2,6,6-tetramethylpiperidin-4-yl)amino]-1,2,4-triazin-6-yl}phenol;
5-(1H-pyrazol-4-yl)-2-[3-(3,3,5,5-tetramethylpiperazin-1-yl)-1,2,4-triazin-6-yl]phenol;
5-(imidazo[1,2-a]pyrazin-6-yl)-2-(3-{3-[(propan-2-yl)amino]pyrrolidin-1-yl}-1,2,4-triazin-6-yl)phenol;
2-(3-{[(3S,4S)-3-fluoro-2,2,6,6-tetramethylpiperidin-4-yl]amino}-1,2,4-triazin-6-yl)-5-(1-methyl-1H-pyrazolo[3,4-b]pyridin-5-yl)phenol;
5-(1-methyl-1H-benzimidazol-5-yl)-2-{3-[methyl(2,2,6,6-tetramethylpiperidin-4-yl)amino]-1,2,4-triazin-6-yl}phenol;
2-(3-{[(3S,4S)-3-methoxy-2,2,6,6-tetramethylpiperidin-4-yl]amino}-1,2,4-triazin-6-yl)-5-(1H-pyrazol-4-yl)phenol;
2-(3-{[(3S,4S)-3-fluoro-2,2,6,6-tetramethylpiperidin-4-yl]amino}-1,2,4-triazin-6-yl)-5-(2-methyl-2H-1,2,3-triazol-4-yl)phenol;
2-(3-{[(3S,4S)-3-fluoro-2,2,6,6-tetramethylpiperidin-4-yl]amino}-1,2,4-triazin-6-yl)-5-(1,3-oxazol-2-yl)phenol;
5-(2-methyl-1,3-oxazol-5-yl)-2-(3-{3-[(propan-2-yl)amino]pyrrolidin-1-yl}-1,2,4-triazin-6-yl)phenol;
2-(3-{[(3S,4S)-3-fluoro-2,2,6,6-tetramethylpiperidin-4-yl]amino}-1,2,4-triazin-6-yl)-5-(6-methoxypyrimidin-4-yl)phenol;
2-(3-{[(3S,4S)-3-fluoro-2,2,6,6-tetramethylpiperidin-4-yl]amino}-1,2,4-triazin-6-yl)-5-2-(3-{[(3S,4S)-3-fluoro-2,2,6,6-tetramethylpiperidin-4-yl]amino}-1,2,4-triazin-6-yl)-5-(2-methyl-2H-tetrazol-5-yl)phenol;
2-(3-{[(3S,4S)-3-fluoro-2,2,6,6-tetramethylpiperidin-4-yl]amino}-1,2,4-triazin-6-yl)-5-(1,2,4-thiadiazol-5-yl)phenol;
2-(3-{[(3S,4S)-3-methoxy-2,2,6,6-tetramethylpiperidin-4-yl](methyl)amino}-1,2,4-triazin-6-yl)-5-(1H-pyrazol-4-yl)phenol;
5-(imidazo[1,2-b]pyridazin-6-yl)-2-(3-{3-[(propan-2-yl)amino]pyrrolidin-1-yl}-1,2,4-triazin-6-yl)phenol;
2-{3-[3-(methylamino)pyrrolidin-1-yl]-1,2,4-triazin-6-yl}-5-(2-methyl-2H-1,2,3-triazol-4-yl)phenol;
2-{3-[3-(methylamino)pyrrolidin-1-yl]-1,2,4-triazin-6-yl}-5-(1-methyl-1H-pyrazol-3-yl)phenol;
2-(3-{3-[(2-methylpropyl)amino]pyrrolidin-1-yl}-1,2,4-triazin-6-yl)-5-(1H-pyrazol-4-yl)phenol;
(3S,4S)-4-({6-[2-hydroxy-4-(1H-pyrazol-4-yl)phenyl]-1,2,4-triazin-3-yl}amino)-2,2,6,6-tetramethylpiperidin-3-ol;
2-[3-(7-methyl-2,7-diazaspiro[3.5]nonan-2-yl)-1,2,4-triazin-6-yl]-5-(2-methyl-1,3-oxazol-5-yl)phenol;
5-(7-fluoro-1-methyl-1H-benzimidazol-5-yl)-2-{3-[methyl(2,2,6,6-tetramethylpiperidin-4-yl)amino]-1,2,4-triazin-6-yl}phenol;
5-(6,7-difluoro-1H-benzimidazol-5-yl)-2-{3-[methyl(2,2,6,6-tetramethylpiperidin-4-yl)amino]-1,2,4-triazin-6-yl}phenol;

5-(6,7-difluoro-1-methyl-1H-benzimidazol-5-yl)-2-{3-[methyl(2,2,6,6-tetramethylpiperidin-4-yl)amino]-1,2,4-triazin-6-yl}phenol;

5-(8-methylimidazo[1,2-b]pyridazin-6-yl)-2-{3-[methyl(2,2,6,6-tetramethylpiperidin-4-yl)amino]-1,2,4-triazin-6-yl}phenol;

5-(8-methoxyimidazo[1,2-b]pyridazin-6-yl)-2-{3-[methyl(2,2,6,6-tetramethylpiperidin-4-yl)amino]-1,2,4-triazin-6-yl}phenol;

2-{3-[(2,2,6,6-tetramethylpiperidin-4-yl)amino]-1,2,4-triazin-6-yl}-5-(1,2,4-triazin-6-yl)phenol;

2-{3-[(4aS,7aS)-octahydro-6H-pyrrolo[3,4-b]pyridin-6-yl]-1,2,4-triazin-6-yl}-5-(1H-pyrazol-4-yl)phenol;

5-(1-methyl-1H-pyrazolo[3,4-b]pyridin-5-yl)-2-(3-{3-[(propan-2-yl)amino]pyrrolidin-1-yl}-1,2,4-triazin-6-yl)phenol;

5-(1,3-oxazol-2-yl)-2-(3-{3-[(propan-2-yl)amino]pyrrolidin-1-yl}-1,2,4-triazin-6-yl)phenol;

2-(3-{[(3S)-1-methylpyrrolidin-3-yl]oxy}-1,2,4-triazin-6-yl)-5-(1H-pyrazol-4-yl)phenol;

2-{3-[(4aS,7aS)-1-methyloctahydro-6H-pyrrolo[3,4-b]pyridin-6-yl]-1,2,4-triazin-6-yl}-5-(1H-pyrazol-4-yl)phenol;

2-{3-[(4aS,7aR)-4-methylhexahydropyrrolo[3,4-b][1,4]oxazin-6(2H)-yl]-1,2,4-triazin-6-yl}-5-(1H-pyrazol-4-yl)phenol;

2-(3-{3-[(oxetan-3-yl)amino]pyrrolidin-1-yl}-1,2,4-triazin-6-yl)-5-(1H-pyrazol-4-yl)phenol;

5-(1-methyl-1H-pyrazol-4-yl)-2-(3-{3-[(oxetan-3-yl)amino]pyrrolidin-1-yl}-1,2,4-triazin-6-yl)phenol;

5-(pyridazin-4-yl)-2-{3-[(2,2,6,6-tetramethylpiperidin-4-yl)amino]-1,2,4-triazin-6-yl}phenol;

5-[(pyridin-3-yl)amino]-2-{3-[(2,2,6,6-tetramethylpiperidin-4-yl)amino]-1,2,4-triazin-6-yl}phenol;

2-(3-{3-[(1-fluoro-2-methylpropan-2-yl)amino]pyrrolidin-1-yl}-1,2,4-triazin-6-yl)-5-(1H-pyrazol-4-yl)phenol;

2-{3-[3-(ethylamino)pyrrolidin-1-yl]-1,2,4-triazin-6-yl}-5-(1H-pyrazol-4-yl)phenol;

2-{3-[3-(dimethylamino)pyrrolidin-1-yl]-1,2,4-triazin-6-yl}-5-(1H-pyrazol-4-yl)phenol;

5-(1-methyl-1H-indazol-5-yl)-2-{3-[(2,2,6,6-tetramethylpiperidin-4-yl)amino]-1,2,4-triazin-6-yl}phenol;

2-{3-[3-(methylamino)pyrrolidin-1-yl]-1,2,4-triazin-6-yl}-5-(2-methyl-2H-tetrazol-5-yl)phenol;

5-(1-methyl-1H-pyrazolo[3,4-b]pyridin-5-yl)-2-{3-[(2,2,6,6-tetramethylpiperidin-4-yl)amino]-1,2,4-triazin-6-yl}phenol;

2-(3-{[(3S,4S)-3-fluoro-2,2,6,6-tetramethylpiperidin-4-yl]amino}-1,2,4-triazin-6-yl)-5-(1H-pyrazol-4-yl)phenol;

2-(3-{[(3R,4R)-3-fluoro-2,2,6,6-tetramethylpiperidin-4-yl]amino}-1,2,4-triazin-6-yl)-5-(1H-pyrazol-4-yl)phenol;

2-{3-[(3-fluoro-2,2,6,6-tetramethylpiperidin-4-yl)amino]-1,2,4-triazin-6-yl}-5-(2H-1,2,3-triazol-2-yl)phenol;

2-(3-{3-[(3-methyloxetan-3-yl)amino]pyrrolidin-1-yl}-1,2,4-triazin-6-yl)-5-(1H-pyrazol-4-yl)phenol;

5-(4-methyl-1H-imidazol-1-yl)-2-(3-{3-[(propan-2-yl)amino]pyrrolidin-1-yl}-1,2,4-triazin-6-yl)phenol;

2-{3-[(3aR,7aR)-octahydro-2H-pyrrolo[3,4-c]pyridin-2-yl]-1,2,4-triazin-6-yl}-5-(1H-pyrazol-4-yl)phenol;

2-[3-(piperazin-1-yl)-1,2,4-triazin-6-yl]-5-(1H-pyrazol-4-yl)phenol;

2-{3-[(3S)-3-{[(2R)-1-fluoropropan-2-yl]amino}pyrrolidin-1-yl]-1,2,4-triazin-6-yl}-5-(1H-pyrazol-4-yl)phenol;

5-(1-methyl-1H-indazol-5-yl)-2-(3-{3-[(propan-2-yl)amino]pyrrolidin-1-yl}-1,2,4-triazin-6-yl)phenol;

5-(1H-imidazol-1-yl)-2-(3-{3-[(propan-2-yl)amino]pyrrolidin-1-yl}-1,2,4-triazin-6-yl)phenol;

2-{3-[(3aR,6aS)-hexahydropyrrolo[3,2-b]pyrrol-1(2H)-yl]-1,2,4-triazin-6-yl}-5-(1H-pyrazol-4-yl)phenol;

2-(3-{3-[(2-hydroxyethyl)amino]pyrrolidin-1-yl}-1,2,4-triazin-6-yl)-5-(1H-pyrazol-4-yl)phenol;

2-[3-(8-amino-2-oxa-6-azaspiro[3.4]octan-6-yl)-1,2,4-triazin-6-yl]-5-(1H-pyrazol-4-yl)phenol;

2-(3-{3-[(oxan-4-yl)amino]pyrrolidin-1-yl}-1,2,4-triazin-6-yl)-5-(1H-pyrazol-4-yl)phenol;

2-(3-{3-[(1-methoxypropan-2-yl)amino]pyrrolidin-1-yl}-1,2,4-triazin-6-yl)-5-(1H-pyrazol-4-yl)phenol;

2-[3-(hexahydropyrrolo[3,4-c]pyrrol-2(1H)-yl)-1,2,4-triazin-6-yl]-5-(1H-pyrazol-4-yl)phenol;

5-(4-fluoro-1H-pyrazol-1-yl)-2-(3-{3-[(propan-2-yl)amino]pyrrolidin-1-yl}-1,2,4-triazin-6-yl)phenol;

2-[3-(1,7-diazaspiro[4.4]nonan-7-yl)-1,2,4-triazin-6-yl]-5-(1H-pyrazol-4-yl)phenol;

2-(3-{3-[(1-methylcyclopropyl)amino]pyrrolidin-1-yl}-1,2,4-triazin-6-yl)-5-(1H-pyrazol-4-yl)phenol;

2-(3-{3-[(1-methoxy-2-methylpropan-2-yl)amino]pyrrolidin-1-yl}-1,2,4-triazin-6-yl)-5-(1H-pyrazol-4-yl)phenol;

5-(1-methyl-1H-indazol-5-yl)-2-{6-[methyl(2,2,6,6-tetramethylpiperidin-4-yl)amino]-1,2,4-triazin-3-yl}phenol;

5-(1-methyl-1H-pyrazol-3-yl)-2-{6-[methyl(2,2,6,6-tetramethylpiperidin-4-yl)amino]-1,2,4-triazin-3-yl}phenol;

6-(3-hydroxy-4-{3-[methyl(2,2,6,6-tetramethylpiperidin-4-yl)amino]-1,2,4-triazin-6-yl}phenyl)imidazo[1,2-b]pyridazine-8-carbonitrile;

2-(3-{[(3R,4S)-3-fluoropiperidin-4-yl]amino}-1,2,4-triazin-6-yl)-5-(1H-pyrazol-4-yl)phenol;

2-{3-[(3R,4R)-3-methoxy-4-(methylamino)pyrrolidin-1-yl]-1,2,4-triazin-6-yl}-5-(1H-pyrazol-4-yl)phenol;

2-(3-{(3S)-3-[(propan-2-yl)amino]pyrrolidin-1-yl}-1,2,4-triazin-6-yl)-5-(1H-pyrazol-4-yl)phenol;

2-(3-{(3R)-3-[(propan-2-yl)amino]pyrrolidin-1-yl}-1,2,4-triazin-6-yl)-5-(1H-pyrazol-4-yl)phenol;

2-{3-[3-(bicyclo[1.1.1]pentan-1-yl)amino]pyrrolidin-1-yl]-1,2,4-triazin-6-yl}-5-(1H-pyrazol-4-yl)phenol;

2-{3-[3-(methylamino)pyrrolidin-1-yl]-1,2,4-triazin-6-yl}-5-(2-methyl-1,3-oxazol-5-yl)phenol;

5-[8-(aminomethyl)imidazo[1,2-b]pyridazin-6-yl]-2-{3-[methyl(2,2,6,6-tetramethylpiperidin-4-yl)amino]-1,2,4-triazin-6-yl}phenol;

5-(1,3-oxazol-2-yl)-2-{3-[(2,2,6,6-tetramethylpiperidin-4-yl)amino]-1,2,4-triazin-6-yl}phenol;

2-[3-(6-oxa-2,9-diazaspiro[4.5]decan-2-yl)-1,2,4-triazin-6-yl]-5-(1H-pyrazol-4-yl)phenol;

2-[3-(2,7-diazaspiro[4.4]nonan-2-yl)-1,2,4-triazin-6-yl]-5-(1H-pyrazol-4-yl)phenol;

2-{3-[(3S)-3-(tert-butylamino)pyrrolidin-1-yl]-1,2,4-triazin-6-yl}-5-(1H-pyrazol-4-yl)phenol 2-{3-[(3R)-3-(tert-butylamino)pyrrolidin-1-yl]-1,2,4-triazin-6-yl}-5-(1H-pyrazol-4-yl)phenol;

2-{3-[3-(cyclopentylamino)pyrrolidin-1-yl]-1,2,4-triazin-6-yl}-5-(1H-pyrazol-4-yl)phenol;

2-{3-[3-(methylamino)pyrrolidin-1-yl]-1,2,4-triazin-6-yl}-5-(1,3-oxazol-2-yl)phenol;

5-(imidazo[1,2-a]pyrazin-2-yl)-2-{3-[(2,2,6,6-tetramethylpiperidin-4-yl)amino]-1,2,4-triazin-6-yl}phenol;
5-(imidazo[1,2-a]pyridin-2-yl)-2-{3-[(2,2,6,6-tetramethylpiperidin-4-yl)amino]-1,2,4-triazin-6-yl}phenol;
2-[3-(3-{[(propan-2-yl)amino]methyl}pyrrolidin-1-yl)-1,2,4-triazin-6-yl]-5-(1H-pyrazol-4-yl)phenol;
2-(3-{3-[(4-methyloxan-4-yl)amino]pyrrolidin-1-yl}-1,2,4-triazin-6-yl)-5-(1H-pyrazol-4-yl)phenol;
2-{6-[3-(tert-butylamino)pyrrolidin-1-yl]-1,2,4-triazin-3-yl}-5-(1H-pyrazol-4-yl)phenol;
2-{3-[3-(methylamino)pyrrolidin-1-yl]-1,2,4-triazin-6-yl}-5-[6-(methylsulfanyl)pyrimidin-4-yl]phenol;
2-{3-[3-(tert-butylamino)pyrrolidin-1-yl]-1,2,4-triazin-6-yl}-5-(3-chloro-1H-pyrazol-4-yl)phenol;
4-(4-{3-[3-(tert-butylamino)pyrrolidin-1-yl]-1,2,4-triazin-6-yl}-3-hydroxyphenyl)-1H-pyrazole-3-carbonitrile;
2-{3-[3-(tert-butylamino)pyrrolidin-1-yl]-1,2,4-triazin-6-yl}-5-[1-($^{2}H_{3}$)methyl-1H-pyrazol-4-yl]phenol;
3-(1-methyl-1H-pyrazol-3-yl)-6-{3-[methyl(2,2,6,6-tetramethylpiperidin-4-yl)amino]-1,2,4-triazin-6-yl}benzene-1,2-diol;
2-[3-(2,7-diazaspiro[4.5]decan-2-yl)-1,2,4-triazin-6-yl]-5-(1H-pyrazol-4-yl)phenol;
2-[3-(hexahydropyrrolo[3,4-b]pyrrol-5(1H)-yl)-1,2,4-triazin-6-yl]-5-(1H-pyrazol-4-yl)phenol;
2-(3-{3-[(3-hydroxypropyl)amino]pyrrolidin-1-yl}-1,2,4-triazin-6-yl)-5-(1H-pyrazol-4-yl)phenol;
2-[3-(3-{[(oxan-4-yl)amino]methyl}pyrrolidin-1-yl)-1,2,4-triazin-6-yl]-5-(1H-pyrazol-4-yl)phenol;
5-[1-($^{2}H_{3}$)methyl-1H-pyrazol-4-yl]-2-{3-[(2,2,6,6-tetramethylpiperidin-4-yl)amino]-1,2,4-triazin-6-yl}phenol;
2-{6-[3-(tert-butylamino)pyrrolidin-1-yl]-1,2,4-triazin-3-yl}-5-(3-fluoro-1H-pyrazol-4-yl)phenol;
2-{3-[3-(tert-butylamino)pyrrolidin-1-yl]-1,2,4-triazin-6-yl}-5-(3-methyl-1H-pyrazol-4-yl)phenol;
2-{3-[3-(tert-butylamino)pyrrolidin-1-yl]-1,2,4-triazin-6-yl}-3-methoxy-5-(1H-pyrazol-4-yl)phenol;
2-(3-{[(3S,4S)-3-fluoro-2,2,6,6-tetramethylpiperidin-4-yl]amino}-1,2,4-triazin-6-yl)-5-[1-($^{2}H_{3}$)methyl-1H-pyrazol-4-yl]phenol;
2-{3-[(3S)-3-(tert-butylamino)pyrrolidin-1-yl]-1,2,4-triazin-6-yl}-5-(3-fluoro-1H-pyrazol-4-yl)phenol;
2-{3-[(3R)-3-(tert-butylamino)pyrrolidin-1-yl]-1,2,4-triazin-6-yl}-5-(3-fluoro-1H-pyrazol-4-yl)phenol;
5-[6-(methylamino)pyrimidin-4-yl]-2-{3-[3-(methylamino)pyrrolidin-1-yl]-1,2,4-triazin-6-yl}phenol;
2-{3-[methyl(2,2,6,6-tetramethylpiperidin-4-yl)amino]-1,2,4-triazin-6-yl}-5-(1H-pyrazolo[3,4-c]pyridin-1-yl)phenol;
2-{6-[methyl(2,2,6,6-tetramethylpiperidin-4-yl)amino]-1,2,4-triazin-3-yl}-5-(pyridin-4-yl)phenol;
5-(7-fluoro-1H-indazol-5-yl)-2-{3-[methyl(2,2,6,6-tetramethylpiperidin-4-yl)amino]-1,2,4-triazin-6-yl}phenol;
2-{6-[methyl(2,2,6,6-tetramethylpiperidin-4-yl)amino]-1,2,4-triazin-3-yl}-5-(pyridin-3-yl)phenol;
2-{3-[(3R,5S)-3,5-dimethylpiperazin-1-yl]-1,2,4-triazin-6-yl}-5-(imidazo[1,2-b]pyridazin-6-yl)phenol;
2-(3-{3-[(cyclopentylamino)methyl]pyrrolidin-1-yl}-1,2,4-triazin-6-yl)-5-(1H-pyrazol-4-yl)phenol;
2-[3-([2,3'-bipyrrolidin]-1'-yl)-1,2,4-triazin-6-yl]-5-(1H-pyrazol-4-yl)phenol;
5-(1H-pyrazol-4-yl)-2-{3-[3-({[(pyridin-2-yl)methyl]amino}methyl)pyrrolidin-1-yl]-1,2,4-triazin-6-yl}phenol;
2-[3-(3-amino-3-methylpyrrolidin-1-yl)-1,2,4-triazin-6-yl]-5-(1-methyl-1H-pyrazol-4-yl)phenol;
2-(3-{3-[(tert-butylamino)methyl]pyrrolidin-1-yl}-1,2,4-triazin-6-yl)-5-(1H-pyrazol-4-yl)phenol;
2-(3-{3-{[(4-methyloxan-4-yl)amino]methyl}pyrrolidin-1-yl)-1,2,4-triazin-6-yl)-5-(1H-pyrazol-4-yl)phenol;
2-(3-{3-[(cyclopropylamino)methyl]pyrrolidin-1-yl}-1,2,4-triazin-6-yl)-5-(1H-pyrazol-4-yl)phenol
2-{6-[methyl(2,2,6,6-tetramethylpiperidin-4-yl)amino]-1,2,4-triazin-3-yl}-5-(pyridin-2-yl)phenol;
5-(1-methyl-1H-pyrazolo[4,3-b]pyridin-5-yl)-2-{6-[methyl(2,2,6,6-tetramethylpiperidin-4-yl)amino]-1,2,4-triazin-3-yl}phenol;
2-[3-(3-{[(oxolan-3-yl)amino]methyl}pyrrolidin-1-yl)-1,2,4-triazin-6-yl]-5-(1H-pyrazol-4-yl)phenol;
5-(1H-pyrazol-4-yl)-2-{6-[(2,2,6,6-tetramethylpiperidin-4-yl)amino]-1,2,4-triazin-3-yl}phenol;
2-{3-[(3S)-3-{[(oxan-4-yl)amino]methyl}pyrrolidin-1-yl]-1,2,4-triazin-6-yl}-5-(1H-pyrazol-4-yl)phenol;
2-{3-[(3R)-3-{[(oxan-4-yl)amino]methyl}pyrrolidin-1-yl]-1,2,4-triazin-6-yl}-5-(1H-pyrazol-4-yl)phenol;
2-{3-[(3R)-3-(cyclobutylamino)pyrrolidin-1-yl]-1,2,4-triazin-6-yl}-5-(1H-pyrazol-4-yl)phenol;
2-{3-[(3S)-3-(cyclobutylamino)pyrrolidin-1-yl]-1,2,4-triazin-6-yl}-5-(1H-pyrazol-4-yl)phenol;
2-{6-[(2,2,6,6-tetramethylpiperidin-4-yl)amino]-1,2,4-triazin-3-yl}-5-(2H-1,2,3-triazol-2-yl)phenol;
2-{6-[methyl(2,2,6,6-tetramethylpiperidin-4-yl)amino]-1,2,4-triazin-3-yl}-5-(pyrimidin-2-yl)phenol;
2-(3-{3-{[(3-fluorooxan-4-yl)amino]methyl}pyrrolidin-1-yl)-1,2,4-triazin-6-yl)-5-(1H-pyrazol-4-yl)phenol;
2-[3-(3-{[(oxan-3-yl)amino]methyl}pyrrolidin-1-yl)-1,2,4-triazin-6-yl]-5-(1H-pyrazol-4-yl)phenol;
2-[3-(3-{[(8-oxabicyclo[3.2.1]octan-3-yl)amino]methyl}pyrrolidin-1-yl)-1,2,4-triazin-6-yl]-5-(1H-pyrazol-4-yl)phenol;
2-{3-[(3R)-3-(cyclobutylamino)pyrrolidin-1-yl]-1,2,4-triazin-6-yl}-5-(1-methyl-1H-pyrazol-4-yl)phenol;
2-{3-[(3S)-3-(cyclobutylamino)pyrrolidin-1-yl]-1,2,4-triazin-6-yl}-5-(1-methyl-1H-pyrazol-4-yl)phenol;
2-(3-{[(1R,3s,5S)-1,5-dimethyl-8-azabicyclo[3.2.1]octan-3-yl](methyl)amino}-1,2,4-triazin-6-yl)-5-(1-methyl-1H-pyrazol-4-yl)phenol;
2-(3-{3-[(3,3-difluorocyclopentyl)amino]pyrrolidin-1-yl}-1,2,4-triazin-6-yl)-5-(1H-pyrazol-4-yl)phenol;
2-(3-{3-[(dimethylamino)methyl]pyrrolidin-1-yl}-1,2,4-triazin-6-yl)-5-(1H-pyrazol-4-yl)phenol;
2-{6-[methyl(2,2,6,6-tetramethylpiperidin-4-yl)amino]-1,2,4-triazin-3-yl}-5-(pyrimidin-4-yl)phenol;
2-{6-[methyl(2,2,6,6-tetramethylpiperidin-4-yl)amino]-1,2,4-triazin-3-yl}-5-(pyrazin-2-yl)phenol;
2-(3-{3-[(methylamino)methyl]pyrrolidin-1-yl}-1,2,4-triazin-6-yl)-5-(1H-pyrazol-4-yl)phenol;
2-[3-(3-{1-[(propan-2-yl)amino]ethyl}pyrrolidin-1-yl)-1,2,4-triazin-6-yl]-5-(1H-pyrazol-4-yl)phenol;
2-(3-{3-[(cyclobutylamino)methyl]pyrrolidin-1-yl}-1,2,4-triazin-6-yl)-5-(1H-pyrazol-4-yl)phenol;
2-(3-{3-[(cyclobutylamino)methyl]pyrrolidin-1-yl}-1,2,4-triazin-6-yl)-5-(1-methyl-1H-pyrazol-4-yl)phenol;
2-(3-{[(1R,3s,5S)-1,5-dimethyl-8-azabicyclo[3.2.1]octan-3-yl](methyl)amino}-1,2,4-triazin-6-yl)-5-(2H-1,2,3-triazol-2-yl)phenol;
6-{3-[3-(tert-butylamino)pyrrolidin-1-yl]-1,2,4-triazin-6-yl}-2-fluoro-3-(1H-pyrazol-4-yl)phenol;
5-(1H-pyrazol-4-yl)-2-{6-[(2,2,6,6-tetramethylpiperidin-4-yl)oxy]-1,2,4-triazin-3-yl}phenol;

2-(3-{3-[(3-fluorocyclopentyl)amino]pyrrolidin-1-yl}-1,2,4-triazin-6-yl)-5-(1H-pyrazol-4-yl)phenol;

2-[3-(3-{1-[(oxan-4-yl)amino]cyclopropyl}pyrrolidin-1-yl)-1,2,4-triazin-6-yl]-5-(1H-pyrazol-4-yl)phenol;

2-(3-{3-methyl-3-[(propan-2-yl)amino]pyrrolidin-1-yl}-1,2,4-triazin-6-yl)-5-(1-methyl-1H-pyrazol-4-yl)phenol;

2-{6-[(3-fluoro-2,2,6,6-tetramethylpiperidin-4-yl)amino]-1,2,4-triazin-3-yl}-5-(1H-pyrazol-4-yl)phenol; and 5-[1-($^2$H$_3$)methyl-1H-pyrazol-4-yl]-2-{6-[(2,2,6,6-tetramethylpiperidin-4-yl)amino]-1,2,4-triazin-3-yl}phenol, wherein a form of the compound is selected from the group consisting of a salt, hydrate, solvate, racemate, enantiomer, diastereomer, stereoisomer, and tautomer form thereof.

2. The compound of claim 1 wherein the form of the compound is a compound salt selected from hydrochloride, hydrobromide, trifluoroacetate, formate, dihydrochloride, dihydroiodide, trihydrochloride, tetrahydrochloride, dihydrobromide and ditrifluoroacetate.

3. A compound, wherein the compound is a compound salt or a form thereof selected from the group consisting of:

5-(5-methyl-1,3-oxazol-2-yl)-2-{3-[methyl(2,2,6,6-tetramethylpiperidin-4-yl)amino]-1,2,4-triazin-6-yl}phenol hydrobromide;

5-(6-methoxypyrimidin-4-yl)-2-{3-[methyl(2,2,6,6-tetramethylpiperidin-4-yl)amino]-1,2,4-triazin-6-yl}phenol formate;

5-(2-methoxypyridin-4-yl)-2-{3-[methyl(2,2,6,6-tetramethylpiperidin-4-yl)amino]-1,2,4-triazin-6-yl}phenol formate;

5-(3-methyl-1H-pyrazol-4-yl)-2-{3-[methyl(2,2,6,6-tetramethylpiperidin-4-yl)amino]-1,2,4-triazin-6-yl}phenol formate;

5-(4-methyl-1H-imidazol-1-yl)-2-{3-[methyl(2,2,6,6-tetramethylpiperidin-4-yl)amino]-1,2,4-triazin-6-yl}phenol hydrochloride;

5-(1H-pyrazol-4-yl)-2-{3-[(2,2,6,6-tetramethylpiperidin-4-yl)oxy]-1,2,4-triazin-6-yl}phenol dihydrochloride;

5-(3-fluoro-1H-pyrazol-4-yl)-2-{3-[methyl(2,2,6,6-tetramethylpiperidin-4-yl)amino]-1,2,4-triazin-6-yl}phenol ditrifluoroacetate;

5-(1H-pyrazol-4-yl)-2-{3-[(2,2,6,6-tetramethylpiperidin-4-yl)amino]-1,2,4-triazin-6-yl}phenol dihydrochloride;

5-[1-($^2$H$_3$)methyl-1H-pyrazol-4-yl]-2-{3-[methyl(2,2,6,6-tetramethylpiperidin-4-yl)amino]-1,2,4-triazin-6-yl}phenol dihydrochloride;

2-{3-[methyl(2,2,6,6-tetramethylpiperidin-4-yl)amino]-1,2,4-triazin-6-yl}-5-(1H-pyrazol-4-yl)phenol hydrochloride;

5-(1-methyl-1H-pyrazol-4-yl)-2-{3-[methyl(2,2,6,6-tetramethylpiperidin-4-yl)amino]-1,2,4-triazin-6-yl}phenol dihydrochloride;

5-(3-fluoro-1-methyl-1H-pyrazol-4-yl)-2-{3-[methyl(2,2,6,6-tetramethylpiperidin-4-yl)amino]-1,2,4-triazin-6-yl}phenol hydrochloride;

2-{3-[methyl(piperidin-4-yl)amino]-1,2,4-triazin-6-yl}-5-(1H-pyrazol-4-yl)phenol dihydrochloride;

2-{3-[methyl(piperidin-3-yl)amino]-1,2,4-triazin-6-yl}-5-(1H-pyrazol-4-yl)phenol dihydrochloride;

2-{3-[methyl(2,2,6,6-tetramethylpiperidin-4-yl)amino]-1,2,4-triazin-6-yl}-5-(2-methyl-2H-1,2,3-triazol-4-yl)phenol hydrochloride;

2-{6-[methyl(2,2,6,6-tetramethylpiperidin-4-yl)amino]-1,2,4-triazin-3-yl}-5-(1H-pyrazol-4-yl)phenol hydrobromide;

5-(4-fluoro-1H-imidazol-1-yl)-2-{3-[methyl(2,2,6,6-tetramethylpiperidin-4-yl)amino]-1,2,4-triazin-6-yl}phenol dihydrochloride;

2-{3-[methyl(2,2,6,6-tetramethylpiperidin-4-yl)amino]-1,2,4-triazin-6-yl}-5-(3-methyl-1H-1,2,4-triazol-1-yl)phenol hydrochloride;

2-{3-[(1-methylpiperidin-4-yl)amino]-1,2,4-triazin-6-yl}-5-(1H-pyrazol-4-yl)phenol trihydrochloride;

5-(4-methoxy-1H-pyrazol-1-yl)-2-{3-[methyl(2,2,6,6-tetramethylpiperidin-4-yl)amino]-1,2,4-triazin-6-yl}phenol dihydrochloride;

5-(3-chloro-1H-pyrazol-4-yl)-2-{3-[methyl(2,2,6,6-tetramethylpiperidin-4-yl)amino]-1,2,4-triazin-6-yl}phenol hydrochloride;

2-{3-[methyl(2,2,6,6-tetramethylpiperidin-4-yl)amino]-1,2,4-triazin-6-yl}-5-(1,3-thiazol-2-yl)phenol hydrochloride;

5-(4-chloro-1H-imidazol-1-yl)-2-{3-[methyl(2,2,6,6-tetramethylpiperidin-4-yl)amino]-1,2,4-triazin-6-yl}phenol dihydrochloride;

2-{3-[methyl(2,2,6,6-tetramethylpiperidin-4-yl)amino]-1,2,4-triazin-6-yl}-5-(pyridazin-4-yl)phenol dihydrochloride;

5-(6-methylpyridazin-4-yl)-2-{3-[methyl(2,2,6,6-tetramethylpiperidin-4-yl)amino]-1,2,4-triazin-6-yl}phenol dihydrochloride;

2-{3-[methyl(2,2,6,6-tetramethylpiperidin-4-yl)amino]-1,2,4-triazin-6-yl}-5-(1-methyl-1H-1,2,4-triazol-3-yl)phenol dihydrochloride;

2-{3-[methyl(2,2,6,6-tetramethylpiperidin-4-yl)amino]-1,2,4-triazin-6-yl}-5-(2H-1,2,3-triazol-2-yl)phenol dihydrochloride;

2-{3-[methyl(2,2,6,6-tetramethylpiperidin-4-yl)amino]-1,2,4-triazin-6-yl}-5-(1,2,4-thiadiazol-5-yl)phenol hydrochloride;

2-{3-[methyl(2,2,6,6-tetramethylpiperidin-4-yl)amino]-1,2,4-triazin-6-yl}-5-(3-methyl-1,2,4-thiadiazol-5-yl)phenol hydrochloride;

2-{3-[(3-fluoro-2,2,6,6-tetramethylpiperidin-4-yl)(methyl)amino]-1,2,4-triazin-6-yl}-5-(1H-pyrazol-4-yl)phenol dihydrochloride;

1-[1-(3-hydroxy-4-{3-[methyl(2,2,6,6-tetramethylpiperidin-4-yl)amino]-1,2,4-triazin-6-yl}phenyl)-1H-pyrazol-4-yl]ethan-1-one dihydrochloride;

2-{3-[methyl(2,2,6,6-tetramethylpiperidin-4-yl)amino]-1,2,4-triazin-6-yl}-5-(4-methyl-2H-1,2,3-triazol-2-yl)phenol dihydrochloride;

2-{3-[methyl(2,2,6,6-tetramethylpiperidin-4-yl)amino]-1,2,4-triazin-6-yl}-5-(pyridin-2-yl)phenol formate;

5-(3-fluoro-1H-pyrazol-4-yl)-2-{3-[(2,2,6,6-tetramethylpiperidin-4-yl)oxy]-1,2,4-triazin-6-yl}phenol dihydrochloride;

5-(3-fluoro-1H-pyrazol-4-yl)-2-{3-[(2,2,6,6-tetramethylpiperidin-4-yl)amino]-1,2,4-triazin-6-yl}phenol trihydrochloride;

5-(2-methyl-1,3-oxazol-5-yl)-2-{3-[methyl(2,2,6,6-tetramethylpiperidin-4-yl)amino]-1,2,4-triazin-6-yl}phenol hydrochloride;

5-(1-methyl-1H-imidazol-4-yl)-2-{3-[methyl(2,2,6,6-tetramethylpiperidin-4-yl)amino]-1,2,4-triazin-6-yl}phenol hydrochloride;

5-(1-methyl-1H-pyrazol-3-yl)-2-{3-[methyl(2,2,6,6-tetramethylpiperidin-4-yl)amino]-1,2,4-triazin-6-yl}phenol hydrochloride;

2-(3-{[(1R,3s,5S)-9-methyl-9-azabicyclo[3.3.1]nonan-3-yl]amino}-1,2,4-triazin-6-yl)-5-(1H-pyrazol-4-yl)phenol dihydrochloride;

2-{3-[methyl(2,2,6,6-tetramethylpiperidin-4-yl)amino]-1,2,4-triazin-6-yl}-5-(1H-1,2,4-triazol-1-yl)phenol dihydrochloride;

5-(imidazo[1,2-a]pyrazin-6-yl)-2-{3-[methyl(2,2,6,6-tetramethylpiperidin-4-yl)amino]-1,2,4-triazin-6-yl}phenol hydrochloride;

5-(5-methyl-1,3,4-oxadiazol-2-yl)-2-{3-[methyl(2,2,6,6-tetramethylpiperidin-4-yl)amino]-1,2,4-triazin-6-yl}phenol hydrochloride;

2-{3-[(2,6-dimethylpiperidin-4-yl)oxy]-1,2,4-triazin-6-yl}-5-(1H-pyrazol-4-yl)phenol dihydrochloride;

2-{3-[methyl(2,2,6,6-tetramethylpiperidin-4-yl)amino]-1,2,4-triazin-6-yl}-5-(pyridazin-3-yl)phenol formate;

2-{3-[methyl(2,2,6,6-tetramethylpiperidin-4-yl)amino]-1,2,4-triazin-6-yl}-5-2-{3-[methyl(2,2,6,6-tetramethylpiperidin-4-yl)amino]-1,2,4-triazin-6-yl}-5-(pyrimidin-5-yl)phenol formate;

5-(4-methoxy-1,3,5-triazin-2-yl)-2-{3-[methyl(2,2,6,6-tetramethylpiperidin-4-yl)amino]-1,2,4-triazin-6-yl}phenol dihydrochloride;

5-(1H-imidazol-1-yl)-2-{3-[methyl(2,2,6,6-tetramethylpiperidin-4-yl)amino]-1,2,4-triazin-6-yl}phenol dihydrochloride;

1-(3-hydroxy-4-{3-[methyl(2,2,6,6-tetramethylpiperidin-4-yl)amino]-1,2,4-triazin-6-yl}phenyl)-1H-pyrazol-4-ol dihydrochloride;

2-{3-[methyl(2,2,6,6-tetramethylpiperidin-4-yl)amino]-1,2,4-triazin-6-yl}-5-(1,3-oxazol-5-yl)phenol hydrochloride;

5-(imidazo[1,2-b]pyridazin-6-yl)-2-{3-[methyl(2,2,6,6-tetramethylpiperidin-4-yl)amino]-1,2,4-triazin-6-yl}phenol hydrochloride;

5-(4-fluoro-1H-pyrazol-1-yl)-2-{3-[methyl(2,2,6,6-tetramethylpiperidin-4-yl)amino]-1,2,4-triazin-6-yl}phenol dihydrochloride;

5-(4-methyl-1H-pyrazol-1-yl)-2-{3-[methyl(2,2,6,6-tetramethylpiperidin-4-yl)amino]-1,2,4-triazin-6-yl}phenol dihydrochloride;

2-[3-(2,7-diazaspiro[3.5]nonan-7-yl)-1,2,4-triazin-6-yl]-5-(1H-pyrazol-4-yl)phenol dihydrochloride;

2-[3-(2,7-diazaspiro[3.5]nonan-2-yl)-1,2,4-triazin-6-yl]-5-(1H-pyrazol-4-yl)phenol dihydrochloride;

5-(1H-indazol-5-yl)-2-{3-[methyl(2,2,6,6-tetramethylpiperidin-4-yl)amino]-1,2,4-triazin-6-yl}phenol dihydrochloride;

2-{3-[methyl(2,2,6,6-tetramethylpiperidin-4-yl)amino]-1,2,4-triazin-6-yl}-5-(4-nitro-2H-1,2,3-triazol-2-yl)phenol dihydrochloride;

5-(1-cyclopropyl-1H-pyrazol-4-yl)-2-{3-[methyl(2,2,6,6-tetramethylpiperidin-4-yl)amino]-1,2,4-triazin-6-yl}phenol hydrochloride;

2-{3-[methyl(2,2,6,6-tetramethylpiperidin-4-yl)amino]-1,2,4-triazin-6-yl}-5-(pyrimidin-4-yl)phenol formate;

4-{3-[methyl(2,2,6,6-tetramethylpiperidin-4-yl)amino]-1,2,4-triazin-6-yl}[1,1'-biphenyl]-3,4'-diol formate;

6-{3-[methyl(2,2,6,6-tetramethylpiperidin-4-yl)amino]-1,2,4-triazin-6-yl}quinolin-7-ol hydrobromide;

5-(1H-pyrazol-3-yl)-2-{3-[(2,2,6,6-tetramethylpiperidin-4-yl)oxy]-1,2,4-triazin-6-yl}phenol ditrifluoroacetate;

5-(1-methyl-1H-pyrazol-3-yl)-2-{3-[(2,2,6,6-tetramethylpiperidin-4-yl)oxy]-1,2,4-triazin-6-yl}phenol trifluoroacetate;

2-[3-(2,6-diazaspiro[3.5]nonan-2-yl)-1,2,4-triazin-6-yl]-5-(1H-pyrazol-4-yl)phenol dihydrochloride;

2-[3-(2,6-diazaspiro[3.4]octan-6-yl)-1,2,4-triazin-6-yl]-5-(1H-pyrazol-4-yl)phenol dihydrochloride;

2-{3-[methyl(2,2,6,6-tetramethylpiperidin-4-yl)amino]-1,2,4-triazin-6-yl}-5-(1H-pyrazol-3-yl)phenol trifluoroacetate;

5-(5-fluoropyrimidin-2-yl)-2-{3-[methyl(2,2,6,6-tetramethylpiperidin-4-yl)amino]-1,2,4-triazin-6-yl}phenol hydrochloride;

2-[3-(1-methyl-1,7-diazaspiro[3.5]nonan-7-yl)-1,2,4-triazin-6-yl]-5-(1H-pyrazol-4-yl)phenol dihydrochloride;

2-{3-[(3S)-3-(methylamino)pyrrolidin-1-yl]-1,2,4-triazin-6-yl}-5-(1H-pyrazol-4-yl)phenol dihydrochloride;

2-{3-[(7S)-7-amino-5-azaspiro[2.4]heptan-5-yl]-1,2,4-triazin-6-yl}-5-(1H-pyrazol-4-yl)phenol dihydrochloride;

2-{3-[(8aS)-hexahydropyrrolo[1,2-a]pyrazin-2(1H)-yl]-1,2,4-triazin-6-yl}-5-(1H-pyrazol-4-yl)phenol dihydrochloride;

2-{3-[(3aR,6aR)-1-methylhexahydropyrrolo[3,4-b]pyrrol-5(1H)-yl]-1,2,4-triazin-6-yl}-5-(1H-pyrazol-4-yl)phenol dihydrochloride;

2-[3-(2,6-diazaspiro[3.3]heptan-2-yl)-1,2,4-triazin-6-yl]-5-(1H-pyrazol-4-yl)phenol dihydrochloride;

2-{3-[methyl(2,2,6,6-tetramethylpiperidin-4-yl)amino]-1,2,4-triazin-6-yl}-5-(5-methyl-2H-tetrazol-2-yl)phenol dihydrochloride;

2-(3-{[(2R,4s,6S)-2,6-diethylpiperidin-4-yl]oxy}-1,2,4-triazin-6-yl)-5-(1H-pyrazol-4-yl)phenol trifluoroacetate;

2-{3-[(2,2,6,6-tetramethylpiperidin-4-yl)amino]-1,2,4-triazin-6-yl}-5-(2H-1,2,3-triazol-2-yl)phenol dihydrochloride;

2-{3-[(2,2,6,6-tetramethylpiperidin-4-yl)oxy]-1,2,4-triazin-6-yl}-5-(2H-1,2,3-triazol-2-yl)phenol hydrochloride;

5-(6-chloropyridazin-3-yl)-2-{3-[methyl(2,2,6,6-tetramethylpiperidin-4-yl)amino]-1,2,4-triazin-6-yl}phenol hydrochloride;

5-(1-methyl-1H-pyrazol-5-yl)-2-{3-[methyl(2,2,6,6-tetramethylpiperidin-4-yl)amino]-1,2,4-triazin-6-yl}phenol dihydrochloride;

2-{3-[(3-fluoro-2,2,6,6-tetramethylpiperidin-4-yl)amino]-1,2,4-triazin-6-yl}-5-(1H-pyrazol-4-yl)phenol dihydrochloride;

2-{3-[6-(diethylamino)-3-azabicyclo[3.1.0]hexan-3-yl]-1,2,4-triazin-6-yl}-5-(1H-pyrazol-4-yl)phenol hydrochloride;

5-(5-methylpyrimidin-2-yl)-2-{3-[methyl(2,2,6,6-tetramethylpiperidin-4-yl)amino]-1,2,4-triazin-6-yl}phenol hydrochloride;

5-(4-methylpyrimidin-2-yl)-2-{3-[methyl(2,2,6,6-tetramethylpiperidin-4-yl)amino]-1,2,4-triazin-6-yl}phenol hydrochloride;

5-(2-chloropyrimidin-4-yl)-2-{3-[methyl(2,2,6,6-tetramethylpiperidin-4-yl)amino]-1,2,4-triazin-6-yl}phenol hydrochloride;

2-{3-[methyl(2,2,6,6-tetramethylpiperidin-4-yl)amino]-1,2,4-triazin-6-yl}-5-(1H-pyrazolo[3,4-b]pyridin-5-yl)phenol formate;

5-(3-chloro-1H-1,2,4-triazol-1-yl)-2-{3-[methyl(2,2,6,6-tetramethylpiperidin-4-yl)amino]-1,2,4-triazin-6-yl}phenol dihydrochloride;

6-(3-hydroxy-4-{3-[methyl(2,2,6,6-tetramethylpiperidin-4-yl)amino]-1,2,4-triazin-6-yl}phenyl)pyridazin-3-ol hydrochloride;

1-[1-(3-hydroxy-4-{3-[methyl(2,2,6,6-tetramethylpiperidin-4-yl)amino]-1,2,4-triazin-6-yl}phenyl)-1H-imidazol-4-yl]ethan-1-one dihydrochloride;
5-(2,8-dimethylimidazo[1,2-b]pyridazin-6-yl)-2-{3-[methyl(2,2,6,6-tetramethylpiperidin-4-yl)amino]-1,2,4-triazin-6-yl}phenol dihydrochloride;
5-(2-methylimidazo[1,2-b]pyridazin-6-yl)-2-{3-[methyl(2,2,6,6-tetramethylpiperidin-4-yl)amino]-1,2,4-triazin-6-yl}phenol dihydrochloride;
2-{3-[methyl(2,2,6,6-tetramethylpiperidin-4-yl)amino]-1,2,4-triazin-6-yl}-5-(2-methyl-2H-tetrazol-5-yl)phenol dihydrochloride;
6-(3-hydroxy-4-{3-[methyl(2,2,6,6-tetramethylpiperidin-4-yl)amino]-1,2,4-triazin-6-yl}phenyl)-3-methylpyrimidin-4(3H)-one dihydrochloride;
5-(3-hydroxy-4-{3-[methyl(2,2,6,6-tetramethylpiperidin-4-yl)amino]-1,2,4-triazin-6-yl}phenyl)-2-methylpyridazin-3(2H)-one dihydrochloride;
2-(3-{3-[(propan-2-yl)amino]pyrrolidin-1-yl}-1,2,4-triazin-6-yl)-5-(1H-pyrazol-4-yl)phenol hydrochloride;
2-[3-(2,7-diazaspiro[3.5]nonan-2-yl)-1,2,4-triazin-6-yl]-5-(3-fluoro-1H-pyrazol-4-yl)phenol dihydrochloride;
2-{3-[methyl(2,2,6,6-tetramethylpiperidin-4-yl)amino]-1,2,4-triazin-6-yl}-5-([1,2,3]triazolo[1,5-a]pyridin-5-yl)phenol dihydrochloride;
5-(3-fluoro-1H-pyrazol-4-yl)-2-{3-[(3aS,7aR)-1-methyloctahydro-5H-pyrrolo[3,2-c]pyridin-5-yl]-1,2,4-triazin-6-yl}phenol dihydrochloride;
2-{3-[methyl(2,2,6,6-tetramethylpiperidin-4-yl)amino]-1,2,4-triazin-6-yl}-5-(tetrazolo[1,5-a]pyridin-7-yl)phenol dihydrochloride;
5-(4-fluoro-1H-pyrazol-3-yl)-2-{3-[methyl(2,2,6,6-tetramethylpiperidin-4-yl)amino]-1,2,4-triazin-6-yl}phenol trifluoroacetate;
2-(3-{3-[(adamantan-1-yl)amino]pyrrolidin-1-yl}-1,2,4-triazin-6-yl)-5-(1H-pyrazol-4-yl)phenol ditrifluoroacetate;
2-{3-[methyl(2,2,6,6-tetramethylpiperidin-4-yl)amino]-1,2,4-triazin-6-yl}-5-(5H-pyrrolo[2,3-b]pyrazin-2-yl)phenol formate;
2-(3-{3-[(adamantan-2-yl)amino]pyrrolidin-1-yl}-1,2,4-triazin-6-yl)-5-(1H-pyrazol-4-yl)phenol ditrifluoroacetate;
2-(3-{3-[(3,5-dimethyladamantan-1-yl)amino]pyrrolidin-1-yl}-1,2,4-triazin-6-yl)-5-(1H-pyrazol-4-yl)phenol ditrifluoroacetate;
5-[4-(hydroxymethyl)-1H-pyrazol-1-yl]-2-{3-[methyl(2,2,6,6-tetramethylpiperidin-4-yl)amino]-1,2,4-triazin-6-yl}phenol hydrochloride;
2-{3-[(3aR,4R,6aS)-4-(dimethylamino)hexahydrocyclopenta[c]pyrrol-2(1H)-yl]-1,2,4-triazin-6-yl}-5-(1H-pyrazol-4-yl)phenol dihydrochloride;
5-(1-methyl-1H-imidazo[4,5-b]pyridin-5-yl)-2-{3-[methyl(2,2,6,6-tetramethylpiperidin-4-yl)amino]-1,2,4-triazin-6-yl}phenol hydrochloride;
2-{3-[(3aR,4S,6aS)-4-aminohexahydrocyclopenta[c]pyrrol-2(1H)-yl]-1,2,4-triazin-6-yl}-5-(1H-pyrazol-4-yl)phenol dihydrochloride;
2-[3-(5-methyloctahydro-2H-pyrrolo[3,4-c]pyridin-2-yl)-1,2,4-triazin-6-yl]-5-(1H-pyrazol-4-yl)phenol dihydrochloride;
2-{3-[(3aR,4S,6aS)-4-(dimethylamino)hexahydrocyclopenta[c]pyrrol-2(1H)-yl]-1,2,4-triazin-6-yl}-5-(1H-pyrazol-4-yl)phenol dihydrochloride;
3-amino-6-(3-hydroxy-4-{3-[methyl(2,2,6,6-tetramethylpiperidin-4-yl)amino]-1,2,4-triazin-6-yl}phenyl)-4-methylpyridin-2-ol dihydrochloride;
5-(2,7-dimethyl[1,3]oxazolo[5,4-b]pyridin-5-yl)-2-{3-[methyl(2,2,6,6-tetramethylpiperidin-4-yl)amino]-1,2,4-triazin-6-yl}phenol diformate;
5-[4-(hydroxymethyl)-2H-1,2,3-triazol-2-yl]-2-{3-[methyl(2,2,6,6-tetramethylpiperidin-4-yl)amino]-1,2,4-triazin-6-yl}phenol hydrochloride;
2-{3-[methyl(2,2,6,6-tetramethylpiperidin-4-yl)amino]-1,2,4-triazin-6-yl}-5-(3-methyl-3H-[1,2,3]triazolo[4,5-b]pyridin-5-yl)phenol hydrochloride;
2-{3-[3-(tert-butylamino)pyrrolidin-1-yl]-1,2,4-triazin-6-yl}-5-(3-fluoro-1H-pyrazol-4-yl)phenol hydrochloride;
2-{3-[3-(tert-butylamino)pyrrolidin-1-yl]-1,2,4-triazin-6-yl}-5-(1-methyl-1H-pyrazol-3-yl)phenol trifluoroacetate;
5-(1-methyl-1H-pyrazolo[3,4-b]pyridin-5-yl)-2-{3-[methyl(2,2,6,6-tetramethylpiperidin-4-yl)amino]-1,2,4-triazin-6-yl}phenol formate;
5-(1-methyl-1H-indazol-5-yl)-2-{3-[methyl(2,2,6,6-tetramethylpiperidin-4-yl)amino]-1,2,4-triazin-6-yl}phenol formate;
2-{3-[methyl(2,2,6,6-tetramethylpiperidin-4-yl)amino]-1,2,4-triazin-6-yl}-5-(tetrazolo[1,5-b]pyridazin-6-yl)phenol dihydrochloride;
5-[6-(hydroxymethyl)pyrimidin-4-yl]-2-{3-[methyl(2,2,6,6-tetramethylpiperidin-4-yl)amino]-1,2,4-triazin-6-yl}phenol hydrochloride;
2-[3-(2,9-diazaspiro[5.5]undecan-9-yl)-1,2,4-triazin-6-yl]-5-(1H-pyrazol-4-yl)phenol dihydrochloride;
2-[3-(2,8-diazaspiro[4.5]decan-8-yl)-1,2,4-triazin-6-yl]-5-(1H-pyrazol-4-yl)phenol dihydrochloride;
2-[3-(2-methyl-2,9-diazaspiro[5.5]undecan-9-yl)-1,2,4-triazin-6-yl]-5-(1H-pyrazol-4-yl)phenol dihydrochloride;
2-[3-(2-methyl-2,8-diazaspiro[4.5]decan-8-yl)-1,2,4-triazin-6-yl]-5-(1H-pyrazol-4-yl)phenol dihydrochloride;
2-{3-[methyl(2,2,6,6-tetramethylpiperidin-4-yl)amino]-1,2,4-triazin-6-yl}-5-(1H-pyrazolo[3,4-c]pyridin-5-yl)phenol formate;
2-{3-[methyl(2,2,6,6-tetramethylpiperidin-4-yl)amino]-1,2,4-triazin-6-yl}-5-(quinolin-6-yl)phenol trifluoroacetate;
2-{3-[methyl(2,2,6,6-tetramethylpiperidin-4-yl)amino]-1,2,4-triazin-6-yl}-5-(1-methyl-1H-[1,2,3]triazolo[4,5-b]pyridin-5-yl)phenol hydrochloride;
2-{3-[3-(tert-butylamino)pyrrolidin-1-yl]-1,2,4-triazin-6-yl}-5-(1H-imidazol-1-yl)phenol ditrifluoroacetate;
5-(2H-1,3-benzodioxol-5-yl)-2-{3-[methyl(2,2,6,6-tetramethylpiperidin-4-yl)amino]-1,2,4-triazin-6-yl}phenol dihydrochloride;
5-(3-fluoro-1H-pyrazol-4-yl)-2-(3-{[(3R,4R)-3-fluoro-2,2,6,6-tetramethylpiperidin-4-yl]amino}-1,2,4-triazin-6-yl)phenol dihydrochloride;
2-(3-{[(2S)-2-aminopropyl](methyl)amino}-1,2,4-triazin-6-yl)-5-(1H-pyrazol-4-yl)phenol dihydrochloride;
5-(5-fluoro-1H-pyrazol-4-yl)-2-{6-[methyl(2,2,6,6-tetramethylpiperidin-4-yl)amino]-1,2,4-triazin-3-yl}phenol hydrochloride;
2-{3-[(3aR,4R,6aS)-4-(tert-butylamino)hexahydrocyclopenta[c]pyrrol-2(1H)-yl]-1,2,4-triazin-6-yl}-5-(1H-pyrazol-4-yl)phenol dihydrochloride;
2-{3-[methyl(2,2,6,6-tetramethylpiperidin-4-yl)amino]-1,2,4-triazin-6-yl}-5-(1H-pyrazolo[3,4-b]pyrazin-5-yl)phenol formate;
2-{3-[methyl(2,2,6,6-tetramethylpiperidin-4-yl)amino]-1,2,4-triazin-6-yl}-5-(1H-pyrazolo[4,3-d]pyrimidin-5-yl)phenol formate;

5-(1-methyl-1H-pyrazol-4-yl)-2-{6-[methyl(2,2,6,6-tetramethylpiperidin-4-yl)amino]-1,2,4-triazin-3-yl}phenol hydrochloride;

2-{3-[3-(tert-butylamino)pyrrolidin-1-yl]-1,2,4-triazin-6-yl}-5-(4-methyl-1H-imidazol-1-yl)phenol ditrifluoroacetate;

5-(1-methyl-1H-pyrazolo[4,3-b]pyridin-5-yl)-2-{3-[methyl(2,2,6,6-tetramethylpiperidin-4-yl)amino]-1,2,4-triazin-6-yl}phenol formate;

5-(1-methyl-1H-pyrazol-4-yl)-2-{3-[(2,2,6,6-tetramethylpiperidin-4-yl)amino]-1,2,4-triazin-6-yl}phenol hydrochloride;

5-(1-methyl-1H-benzotriazol-5-yl)-2-{3-[methyl(2,2,6,6-tetramethylpiperidin-4-yl)amino]-1,2,4-triazin-6-yl}phenol hydrochloride;

2-{3-[3-(tert-butylamino)pyrrolidin-1-yl]-1,2,4-triazin-6-yl}-5-(1-methyl-1H-pyrazol-4-yl)phenol hydrochloride;

5-(1-methyl-1H-pyrazol-4-yl)-2-(3-{3-[(propan-2-yl)amino]pyrrolidin-1-yl}-1,2,4-triazin-6-yl)phenol hydrochloride;

2-{3-[3-(tert-butylamino)pyrrolidin-1-yl]-1,2,4-triazin-6-yl}-5-(2H-1,2,3-triazol-2-yl)phenol hydrochloride;

2-{3-[3-(methylamino)pyrrolidin-1-yl]-1,2,4-triazin-6-yl}-5-(1-methyl-1H-pyrazol-4-yl)phenol hydrochloride;

2-{3-[4-(tert-butylamino)piperidin-1-yl]-1,2,4-triazin-6-yl}-5-(1H-pyrazol-4-yl)phenol trifluoroacetate;

2-{3-[3-(tert-butylamino)pyrrolidin-1-yl]-1,2,4-triazin-6-yl}-5-([1,2,3]triazolo[1,5-a]pyridin-5-yl)phenol dihydrochloride;

2-{3-[3-(tert-butylamino)pyrrolidin-1-yl]-1,2,4-triazin-6-yl}-5-(1-methyl-1H-indazol-5-yl)phenol dihydrochloride;

2-{3-[3-(tert-butylamino)pyrrolidin-1-yl]-1,2,4-triazin-6-yl}-5-(pyrimidin-2-yl)phenol dihydrochloride;

2-{3-[3-(tert-butylamino)pyrrolidin-1-yl]-1,2,4-triazin-6-yl}-5-(2-methyl-2H-1,2,3-triazol-4-yl)phenol dihydrochloride;

2-{3-[3-(tert-butylamino)pyrrolidin-1-yl]-1,2,4-triazin-6-yl}-5-(2-methyl-2H-tetrazol-5-yl)phenol dihydrochloride;

2-{3-[3-(tert-butylamino)piperidin-1-yl]-1,2,4-triazin-6-yl}-5-(1H-pyrazol-4-yl)phenol trifluoroacetate;

5-(1-methyl-1H-pyrazol-3-yl)-2-(3-{3-[(propan-2-yl)amino]pyrrolidin-1-yl}-1,2,4-triazin-6-yl)phenol hydrochloride;

4-(4-{3-[3-(tert-butylamino)pyrrolidin-1-yl]-1,2,4-triazin-6-yl}-3-hydroxyphenyl)-1-methylpyridin-2(1H)-one hydrochloride;

2-{3-[3-(tert-butylamino)pyrrolidin-1-yl]-1,2,4-triazin-6-yl}-5-(1-methyl-1H-[1,2,3]triazolo[4,5-b]pyridin-5-yl)phenol hydrochloride;

6-(4-{3-[3-(tert-butylamino)pyrrolidin-1-yl]-1,2,4-triazin-6-yl}-3-hydroxyphenyl)-3-methylpyrimidin-4(3H)-one hydrochloride;

2-{3-[3-(tert-butylamino)pyrrolidin-1-yl]-1,2,4-triazin-6-yl}-5-(6-methoxypyrimidin-4-yl)phenol ditrifluoroacetate;

2-{3-[3-(methylamino)pyrrolidin-1-yl]-1,2,4-triazin-6-yl}-5-(2H-1,2,3-triazol-2-yl)phenol trihydrochloride;

5-(4-fluoro-1H-pyrazol-1-yl)-2-{3-[3-(methylamino)pyrrolidin-1-yl]-1,2,4-triazin-6-yl}phenol trihydrochloride;

5-(1H-imidazol-1-yl)-2-{3-[3-(methylamino)pyrrolidin-1-yl]-1,2,4-triazin-6-yl}phenol trihydrochloride;

2-{3-[3-(tert-butylamino)pyrrolidin-1-yl]-1,2,4-triazin-6-yl}-5-(1-methyl-1H-pyrazolo[3,4-b]pyridin-5-yl)phenol dihydrochloride;

5-(1-methyl-1H-pyrazolo[3,4-c]pyridin-5-yl)-2-{3-[methyl(2,2,6,6-tetramethylpiperidin-4-yl)amino]-1,2,4-triazin-6-yl}phenol dihydrochloride;

2-[3-(7-methyl-2,7-diazaspiro[3.5]nonan-2-yl)-1,2,4-triazin-6-yl]-5-(1-methyl-1H-indazol-5-yl)phenol trifluoroacetate;

2-[3-(7-methyl-2,7-diazaspiro[3.5]nonan-2-yl)-1,2,4-triazin-6-yl]-5-(1-methyl-1H-pyrazolo[3,4-b]pyridin-5-yl)phenol trifluoroacetate;

2-[3-(7-methyl-2,7-diazaspiro[3.5]nonan-2-yl)-1,2,4-triazin-6-yl]-5-(1-methyl-1H-pyrazol-4-yl)phenol trifluoroacetate;

4-[3-hydroxy-4-(3-{3-[(propan-2-yl)amino]pyrrolidin-1-yl}-1,2,4-triazin-6-yl)phenyl]-1-methylpyridin-2(1H)-one hydrochloride;

2-[3-(7-methyl-2,7-diazaspiro[3.5]nonan-2-yl)-1,2,4-triazin-6-yl]-5-(4-methyl-1H-imidazol-1-yl)phenol hydrochloride;

5-(4-fluoro-1H-pyrazol-1-yl)-2-[3-(7-methyl-2,7-diazaspiro[3.5]nonan-2-yl)-1,2,4-triazin-6-yl]phenol hydrochloride;

5-(4-fluoro-1H-imidazol-1-yl)-2-[3-(7-methyl-2,7-diazaspiro[3.5]nonan-2-yl)-1,2,4-triazin-6-yl]phenol hydrochloride;

5-(1H-imidazol-1-yl)-2-[3-(7-methyl-2,7-diazaspiro[3.5]nonan-2-yl)-1,2,4-triazin-6-yl]phenol hydrochloride;

2-[3-(7-methyl-2,7-diazaspiro[3.5]nonan-2-yl)-1,2,4-triazin-6-yl]-5-(2H-1,2,3-triazol-2-yl)phenol hydrochloride;

2-[3-(7-methyl-2,7-diazaspiro[3.5]nonan-2-yl)-1,2,4-triazin-6-yl]-5-(1-methyl-1H-pyrazol-3-yl)phenol hydrochloride;

6-[3-hydroxy-4-(3-{3-[(propan-2-yl)amino]pyrrolidin-1-yl}-1,2,4-triazin-6-yl)phenyl]-3-methylpyrimidin-4(3H)-one hydrochloride;

5-(5-fluoro-1H-pyrazol-4-yl)-2-(3-{3-[(propan-2-yl)amino]pyrrolidin-1-yl}-1,2,4-triazin-6-yl)phenol hydrochloride;

5-(2-methyl-2H-1,2,3-triazol-4-yl)-2-(3-{3-[(propan-2-yl)amino]pyrrolidin-1-yl}-1,2,4-triazin-6-yl)phenol hydrochloride;

2-(3-{3-[(propan-2-yl)amino]pyrrolidin-1-yl}-1,2,4-triazin-6-yl)-5-(1,2,4-thiadiazol-5-yl)phenol hydrochloride;

2-(3-{[(3S,4S)-3-fluoro-2,2,6,6-tetramethylpiperidin-4-yl]amino}-1,2,4-triazin-6-yl)-5-(1H-imidazol-1-yl)phenol dihydrochloride;

2-(3-{[(3S,4S)-3-fluoro-2,2,6,6-tetramethylpiperidin-4-yl]amino}-1,2,4-triazin-6-yl)-5-(4-methyl-1H-imidazol-1-yl)phenol dihydrochloride;

5-(4-fluoro-1H-imidazol-1-yl)-2-(3-{[(3S,4S)-3-fluoro-2,2,6,6-tetramethylpiperidin-4-yl]amino}-1,2,4-triazin-6-yl)phenol dihydrochloride;

4-{3-hydroxy-4-[3-(7-methyl-2,7-diazaspiro[3.5]nonan-2-yl)-1,2,4-triazin-6-yl]phenyl}-1-methylpyridin-2(1H)-one hydrochloride;

2-[3-(7-methyl-2,7-diazaspiro[3.5]nonan-2-yl)-1,2,4-triazin-6-yl]-5-(2-methyl-2H-1,2,3-triazol-4-yl)phenol trifluoroacetate;

5-(6-methoxypyrimidin-4-yl)-2-[3-(7-methyl-2,7-diazaspiro[3.5]nonan-2-yl)-1,2,4-triazin-6-yl]phenol ditrifluoroacetate;

2-[3-(7-methyl-2,7-diazaspiro[3.5]nonan-2-yl)-1,2,4-triazin-6-yl]-5-(pyrimidin-2-yl)phenol trifluoroacetate;

2-[3-(7-methyl-2,7-diazaspiro[3.5]nonan-2-yl)-1,2,4-triazin-6-yl]-5-(1H-1,2,3-triazol-4-yl)phenol trifluoroacetate;

6-[4-(3-{[(3S,4S)-3-fluoro-2,2,6,6-tetramethylpiperidin-4-yl]amino}-1,2,4-triazin-6-yl)-3-hydroxyphenyl]-3-methylpyrimidin-4(3H)-one dihydrochloride;

2-(3-{[(3S,4S)-3-fluoro-2,2,6,6-tetramethylpiperidin-4-yl]amino}-1,2,4-triazin-6-yl)-5-(1H-1,2,3-triazol-4-yl)phenol dihydrochloride;

2-(3-{[(3S,4S)-3-fluoro-2,2,6,6-tetramethylpiperidin-4-yl]amino}-1,2,4-triazin-6-yl)-5-(imidazo[1,2-b]pyridazin-6-yl)phenol dihydrochloride;

2-{3-[3-(tert-butylamino)pyrrolidin-1-yl]-1,2,4-triazin-6-yl}-5-(1,3-oxazol-2-yl)phenol hydrochloride;

2-[3-(7-methyl-2,7-diazaspiro[3.5]nonan-2-yl)-1,2,4-triazin-6-yl]-5-(2-methyl-2H-tetrazol-5-yl)phenol trifluoroacetate;

2-[3-(7-methyl-2,7-diazaspiro[3.5]nonan-2-yl)-1,2,4-triazin-6-yl]-5-(1,3-oxazol-2-yl)phenol trifluoroacetate;

5-(1-methyl-1H-pyrazol-3-yl)-2-{3-[(2,2,6,6-tetramethylpiperidin-4-yl)amino]-1,2,4-triazin-6-yl}phenol formate;

5-(6-methoxypyrimidin-4-yl)-2-{3-[(2,2,6,6-tetramethylpiperidin-4-yl)amino]-1,2,4-triazin-6-yl}phenol formate;

5-(imidazo[1,2-b]pyridazin-6-yl)-2-[3-(7-methyl-2,7-diazaspiro[3.5]nonan-2-yl)-1,2,4-triazin-6-yl]phenol trifluoroacetate;

5-(imidazo[1,2-a]pyrazin-6-yl)-2-[3-(7-methyl-2,7-diazaspiro[3.5]nonan-2-yl)-1,2,4-triazin-6-yl]phenol hydrochloride;

2-(3-{3-[(propan-2-yl)amino]pyrrolidin-1-yl}-1,2,4-triazin-6-yl)-5-(1H-1,2,3-triazol-4-yl)phenol diftrifluoroacetate;

5-(2-methyl-2H-tetrazol-5-yl)-2-(3-{3-[(propan-2-yl)amino]pyrrolidin-1-yl}-1,2,4-triazin-6-yl)phenol ftrifluoroacetate;

2-(3-{[(3S,4S)-3-fluoro-2,2,6,6-tetramethylpiperidin-4-yl]amino}-1,2,4-triazin-6-yl)-5-(1-methyl-1H-indazol-5-yl)phenol dihydrochloride 2-(3-{[(3S,4S)-3-fluoro-2,2,6,6-tetramethylpiperidin-4-yl]amino}-1,2,4-triazin-6-yl)-5-2-(3-{[(3S,4S)-3-fluoro-2,2,6,6-tetramethylpiperidin-4-yl]amino}-1,2,4-triazin-6-yl)-5-(1-methyl-1H-pyrazol-3-yl)phenol dihydrochloride;

2-[3-(3,5-dimethylpiperazin-1-yl)-1,2,4-triazin-6-yl]-5-(1H-pyrazol-4-yl)phenol dihydrochloride;

2-[3-(3,5-dimethylpiperazin-1-yl)-1,2,4-triazin-6-yl]-5-(1-methyl-1H-pyrazol-3-yl)phenol hydrochloride;

2-(3-{3-[(propan-2-yl)amino]pyrrolidin-1-yl}-1,2,4-triazin-6-yl)-5-(2H-1,2,3-triazol-2-yl)phenol hydrochloride;

5-(6-methoxypyrimidin-4-yl)-2-(3-{3-[(propan-2-yl)amino]pyrrolidin-1-yl}-1,2,4-triazin-6-yl)phenol hydrochloride;

5-(2-methyl-2H-1,2,3-triazol-4-yl)-2-{3-[(2,2,6,6-tetramethylpiperidin-4-yl)amino]-1,2,4-triazin-6-yl}phenol dihydrochloride;

5-(2-methyl-2H-tetrazol-5-yl)-2-{3-[(2,2,6,6-tetramethylpiperidin-4-yl)amino]-1,2,4-triazin-6-yl}phenol dihydrochloride;

5-(6-methoxypyrimidin-4-yl)-2-{3-[3-(methylamino)pyrrolidin-1-yl]-1,2,4-triazin-6-yl}phenol diftrifluoroacetate;

2-{3-[3-(methylamino)pyrrolidin-1-yl]-1,2,4-triazin-6-yl}-5-(1,2,4-thiadiazol-5-yl)phenol dihydrochloride;

2-{3-[3-(methylamino)pyrrolidin-1-yl]-1,2,4-triazin-6-yl}-5-(pyrimidin-2-yl)phenol dihydrochloride;

2-{3-[3-(methylamino)pyrrolidin-1-yl]-1,2,4-triazin-6-yl}-5-(1-methyl-1H-pyrazolo[3,4-b]pyridin-5-yl)phenol dihydrochloride;

2-[3-(7-methyl-2,7-diazaspiro[3.5]nonan-2-yl)-1,2,4-triazin-6-yl]-5-(1,2,4-thiadiazol-5-yl)phenol ftrifluoroacetate;

5-(1H-imidazol-1-yl)-2-{3-[(2,2,6,6-tetramethylpiperidin-4-yl)amino]-1,2,4-triazin-6-yl}phenol hydrochloride;

5-(4-methyl-1H-imidazol-1-yl)-2-{3-[(2,2,6,6-tetramethylpiperidin-4-yl)amino]-1,2,4-triazin-6-yl}phenol hydrochloride;

5-(4-fluoro-1H-imidazol-1-yl)-2-{3-[(2,2,6,6-tetramethylpiperidin-4-yl)amino]-1,2,4-triazin-6-yl}phenol hydrochloride;

5-(4-fluoro-1H-pyrazol-1-yl)-2-{3-[(2,2,6,6-tetramethylpiperidin-4-yl)amino]-1,2,4-triazin-6-yl}phenol hydrochloride;

5-(2-methyl-1,3-oxazol-5-yl)-2-{3-[(2,2,6,6-tetramethylpiperidin-4-yl)amino]-1,2,4-triazin-6-yl}phenol hydrochloride;

2-{3-[3-(tert-butylamino)-4-fluoropyrrolidin-1-yl]-1,2,4-triazin-6-yl}-5-(1H-pyrazol-4-yl)phenol hydrochloride;

5-(pyrimidin-2-yl)-2-{3-[(2,2,6,6-tetramethylpiperidin-4-yl)amino]-1,2,4-triazin-6-yl}phenol formate;

5-(1H-pyrazol-4-yl)-2-[3-(3,3,5,5-tetramethylpiperazin-1-yl)-1,2,4-triazin-6-yl]phenol dihydrochloride;

5-(imidazo[1,2-a]pyrazin-6-yl)-2-(3-{3-[(propan-2-yl)amino]pyrrolidin-1-yl}-1,2,4-triazin-6-yl)phenol hydrochloride;

2-(3-{[(3S,4S)-3-fluoro-2,2,6,6-tetramethylpiperidin-4-yl]amino}-1,2,4-triazin-6-yl)-5-(1-methyl-1H-pyrazolo[3,4-b]pyridin-5-yl)phenol dihydrochloride;

5-(1-methyl-1H-benzimidazol-5-yl)-2-{3-[methyl(2,2,6,6-tetramethylpiperidin-4-yl)amino]-1,2,4-triazin-6-yl}phenol formate;

2-(3-{[(3S,4S)-3-fluoro-2,2,6,6-tetramethylpiperidin-4-yl]amino}-1,2,4-triazin-6-yl)-5-(2-methyl-2H-1,2,3-triazol-4-yl)phenol ftrifluoroacetate;

2-(3-{[(3S,4S)-3-fluoro-2,2,6,6-tetramethylpiperidin-4-yl]amino}-1,2,4-triazin-6-yl)-5-(1,3-oxazol-2-yl)phenol ftrifluoroacetate;

5-(2-methyl-1,3-oxazol-5-yl)-2-(3-{3-[(propan-2-yl)amino]pyrrolidin-1-yl}-1,2,4-triazin-6-yl)phenol hydrochloride;

2-(3-{[(3S,4S)-3-fluoro-2,2,6,6-tetramethylpiperidin-4-yl]amino}-1,2,4-triazin-6-yl)-5-(6-methoxypyrimidin-4-yl)phenol ftrifluoroacetate;

2-(3-{[(3S,4S)-3-fluoro-2,2,6,6-tetramethylpiperidin-4-yl]amino}-1,2,4-triazin-6-yl)-5-2-(3-{[(3S,4S)-3-fluoro-2,2,6,6-tetramethylpiperidin-4-yl]amino}-1,2,4-triazin-6-yl)-5-(2-methyl-2H-tetrazol-5-yl)phenol ftrifluoroacetate;

2-(3-{[(3S,4S)-3-fluoro-2,2,6,6-tetramethylpiperidin-4-yl]amino}-1,2,4-triazin-6-yl)-5-2-(3-{[(3S,4S)-3-fluoro-2,2,6,6-tetramethylpiperidin-4-yl]amino}-1,2,4-triazin-6-yl)-5-(1,2,4-thiadiazol-5-yl)phenol ftrifluoroacetate;

2-(3-{[(3S,4S)-3-methoxy-2,2,6,6-tetramethylpiperidin-4-yl](methyl)amino}-1,2,4-triazin-6-yl)-5-(1H-pyrazol-4-yl)phenol dihydrochloride;

5-(imidazo[1,2-b]pyridazin-6-yl)-2-(3-{3-[(propan-2-yl)amino]pyrrolidin-1-yl}-1,2,4-triazin-6-yl)phenol hydrochloride;

2-{3-[3-(methylamino)pyrrolidin-1-yl]-1,2,4-triazin-6-yl}-5-(2-methyl-2H-1,2,3-triazol-4-yl)phenol dihydrochloride;
2-{3-[3-(methylamino)pyrrolidin-1-yl]-1,2,4-triazin-6-yl}-5-(1-methyl-1H-pyrazol-3-yl)phenol dihydrochloride;
2-(3-{3-[(2-methylpropyl)amino]pyrrolidin-1-yl}-1,2,4-triazin-6-yl)-5-(1H-pyrazol-4-yl)phenol dihydrochloride;
(3S,4S)-4-({6-[2-hydroxy-4-(1H-pyrazol-4-yl)phenyl]-1,2,4-triazin-3-yl}amino)-2,2,6,6-tetramethylpiperidin-3-ol dihydrochloride;
2-[3-(7-methyl-2,7-diazaspiro[3.5]nonan-2-yl)-1,2,4-triazin-6-yl]-5-(2-methyl-1,3-oxazol-5-yl)phenol ftrifluoroacetate;
5-(7-fluoro-1-methyl-1H-benzimidazol-5-yl)-2-{3-[methyl(2,2,6,6-tetramethylpiperidin-4-yl)amino]-1,2,4-triazin-6-yl}phenol formate;
5-(6,7-difluoro-1H-benzimidazol-5-yl)-2-{3-[methyl(2,2,6,6-tetramethylpiperidin-4-yl)amino]-1,2,4-triazin-6-yl}phenol formate;
5-(6,7-difluoro-1-methyl-1H-benzimidazol-5-yl)-2-{3-[methyl(2,2,6,6-tetramethylpiperidin-4-yl)amino]-1,2,4-triazin-6-yl}phenol formate;
5-(8-methylimidazo[1,2-b]pyridazin-6-yl)-2-{3-[methyl(2,2,6,6-tetramethylpiperidin-4-yl)amino]-1,2,4-triazin-6-yl}phenol formate;
5-(8-methoxyimidazo[1,2-b]pyridazin-6-yl)-2-{3-[methyl(2,2,6,6-tetramethylpiperidin-4-yl)amino]-1,2,4-triazin-6-yl}phenol formate;
2-{3-[(2,2,6,6-tetramethylpiperidin-4-yl)amino]-1,2,4-triazin-6-yl}-5-(1,2,4-triazin-6-yl)phenol ftrifluoroacetate;
2-{3-[(4aS,7aS)-octahydro-6H-pyrrolo[3,4-b]pyridin-6-yl]-1,2,4-triazin-6-yl}-5-(1H-pyrazol-4-yl)phenol dihydrochloride;
5-(1-methyl-1H-pyrazolo[3,4-b]pyridin-5-yl)-2-(3-{3-[(propan-2-yl)amino]pyrrolidin-1-yl}-1,2,4-triazin-6-yl)phenol hydrochloride;
5-(1,3-oxazol-2-yl)-2-(3-{3-[(propan-2-yl)amino]pyrrolidin-1-yl}-1,2,4-triazin-6-yl)phenol hydrochloride;
2-(3-{[(3S)-1-methylpyrrolidin-3-yl]oxy}-1,2,4-triazin-6-yl)-5-(1H-pyrazol-4-yl)phenol hydrochloride;
2-{3-[(4aS,7aS)-1-methyloctahydro-6H-pyrrolo[3,4-b]pyridin-6-yl]-1,2,4-triazin-6-yl}-5-(1H-pyrazol-4-yl)phenol trihydrochloride;
2-{3-[(4aS,7aR)-4-methylhexahydropyrrolo[3,4-b][1,4]oxazin-6(2H)-yl]-1,2,4-triazin-6-yl}-5-(1H-pyrazol-4-yl)phenol trihydrochloride;
5-(pyridazin-4-yl)-2-{3-[(2,2,6,6-tetramethylpiperidin-4-yl)amino]-1,2,4-triazin-6-yl}phenol formate;
5-[(pyridin-3-yl)amino]-2-{3-[(2,2,6,6-tetramethylpiperidin-4-yl)amino]-1,2,4-triazin-6-yl}phenol formate;
2-(3-{3-[(1-fluoro-2-methylpropan-2-yl)amino]pyrrolidin-1-yl}-1,2,4-triazin-6-yl)-5-(1H-pyrazol-4-yl)phenol hydrochloride;
2-{3-[3-(ethylamino)pyrrolidin-1-yl]-1,2,4-triazin-6-yl}-5-(1H-pyrazol-4-yl)phenol dihydrochloride;
2-{3-[3-(dimethylamino)pyrrolidin-1-yl]-1,2,4-triazin-6-yl}-5-(1H-pyrazol-4-yl)phenol dihydroiodide;
5-(1-methyl-1H-indazol-5-yl)-2-{3-[(2,2,6,6-tetramethylpiperidin-4-yl)amino]-1,2,4-triazin-6-yl}phenol trihydrochloride;
2-{3-[(methylamino)pyrrolidin-1-yl]-1,2,4-triazin-6-yl}-5-(2-methyl-2H-tetrazol-5-yl)phenol trihydrochloride;
5-(1-methyl-1H-pyrazolo[3,4-b]pyridin-5-yl)-2-{3-[(2,2,6,6-tetramethylpiperidin-4-yl)amino]-1,2,4-triazin-6-yl}phenol trihydrochloride;
2-(3-{[(3S,4S)-3-fluoro-2,2,6,6-tetramethylpiperidin-4-yl]amino}-1,2,4-triazin-6-yl)-5-(1H-pyrazol-4-yl)phenol dihydrochloride;
2-(3-{[(3R,4R)-3-fluoro-2,2,6,6-tetramethylpiperidin-4-yl]amino}-1,2,4-triazin-6-yl)-5-(1H-pyrazol-4-yl)phenol dihydrochloride;
2-{3-[(3-fluoro-2,2,6,6-tetramethylpiperidin-4-yl)amino]-1,2,4-triazin-6-yl}-5-(2H-1,2,3-triazol-2-yl)phenol dihydrochloride;
5-(4-methyl-1H-imidazol-1-yl)-2-(3-{3-[(propan-2-yl)amino]pyrrolidin-1-yl}-1,2,4-triazin-6-yl)phenol hydrochloride;
2-{3-[(3aR,7aR)-octahydro-2H-pyrrolo[3,4-c]pyridin-2-yl]-1,2,4-triazin-6-yl}-5-(1H-pyrazol-4-yl)phenol trihydrochloride;
2-[3-(piperazin-1-yl)-1,2,4-triazin-6-yl]-5-(1H-pyrazol-4-yl)phenol dihydrochloride;
2-{3-[(3S)-3-{[(2R)-1-fluoropropan-2-yl]amino}pyrrolidin-1-yl]-1,2,4-triazin-6-yl}-5-(1H-pyrazol-4-yl)phenol dihydrochloride;
5-(1-methyl-1H-indazol-5-yl)-2-(3-{3-[(propan-2-yl)amino]pyrrolidin-1-yl}-1,2,4-triazin-6-yl)phenol hydrochloride;
5-(1H-imidazol-1-yl)-2-(3-{3-[(propan-2-yl)amino]pyrrolidin-1-yl}-1,2,4-triazin-6-yl)phenol hydrochloride;
2-{3-[(3aR,6aS)-hexahydropyrrolo[3,2-b]pyrrol-1(2H)-yl]-1,2,4-triazin-6-yl}-5-(1H-pyrazol-4-yl)phenol dihydrochloride;
2-(3-{3-[(2-hydroxyethyl)amino]pyrrolidin-1-yl}-1,2,4-triazin-6-yl)-5-(1H-pyrazol-4-yl)phenol dihydrochloride;
2-(3-{3-[(oxan-4-yl)amino]pyrrolidin-1-yl}-1,2,4-triazin-6-yl)-5-(1H-pyrazol-4-yl)phenol dihydrochloride;
2-(3-{3-[(1-methoxypropan-2-yl)amino]pyrrolidin-1-yl}-1,2,4-triazin-6-yl)-5-(1H-pyrazol-4-yl)phenol dihydrochloride;
2-[3-(hexahydropyrrolo[3,4-c]pyrrol-2(1H)-yl)-1,2,4-triazin-6-yl]-5-(1H-pyrazol-4-yl)phenol dihydrochloride;
5-(4-fluoro-1H-pyrazol-1-yl)-2-(3-{3-[(propan-2-yl)amino]pyrrolidin-1-yl}-1,2,4-triazin-6-yl)phenol hydrochloride;
2-[3-(1,7-diazaspiro[4.4]nonan-7-yl)-1,2,4-triazin-6-yl]-5-(1H-pyrazol-4-yl)phenol dihydrochloride;
2-(3-{3-[(1-methylcyclopropyl)amino]pyrrolidin-1-yl}-1,2,4-triazin-6-yl)-5-(1H-pyrazol-4-yl)phenol dihydrochloride;
2-(3-{3-[(1-methoxy-2-methylpropan-2-yl)amino]pyrrolidin-1-yl}-1,2,4-triazin-6-yl)-5-(1H-pyrazol-4-yl)phenol dihydrochloride;
6-(3-hydroxy-4-{3-[methyl(2,2,6,6-tetramethylpiperidin-4-yl)amino]-1,2,4-triazin-6-yl}phenyl)imidazo[1,2-b]pyridazine-8-carbonitrile formate;
2-(3-{[(3R,4S)-3-fluoropiperidin-4-yl]amino}-1,2,4-triazin-6-yl)-5-(1H-pyrazol-4-yl)phenol dihydrochloride;
2-{3-[(3R,4R)-3-methoxy-4-(methylamino)pyrrolidin-1-yl]-1,2,4-triazin-6-yl}-5-(1H-pyrazol-4-yl)phenol dihydrochloride;
2-(3-{(3S)-3-[(propan-2-yl)amino]pyrrolidin-1-yl}-1,2,4-triazin-6-yl)-5-(1H-pyrazol-4-yl)phenol ftrifluoroacetate;
2-(3-{(3R)-3-[(propan-2-yl)amino]pyrrolidin-1-yl}-1,2,4-triazin-6-yl)-5-(1H-pyrazol-4-yl)phenol ftrifluoroacetate;

2-(3-{3-[(bicyclo[1.1.1]pentan-1-yl)amino]pyrrolidin-1-yl}-1,2,4-triazin-6-yl)-5-(1H-pyrazol-4-yl)phenol ftrifluoroacetate;

2-{3-[3-(methylamino)pyrrolidin-1-yl]-1,2,4-triazin-6-yl}-5-(2-methyl-1,3-oxazol-5-yl)phenol dihydrochloride;

5-[8-(aminomethyl)imidazo[1,2-b]pyridazin-6-yl]-2-{3-[methyl(2,2,6,6-tetramethylpiperidin-4-yl)amino]-1,2,4-triazin-6-yl}phenol formate;

5-(1,3-oxazol-2-yl)-2-{3-[(2,2,6,6-tetramethylpiperidin-4-yl)amino]-1,2,4-triazin-6-yl}phenol formate;

2-[3-(6-oxa-2,9-diazaspiro[4.5]decan-2-yl)-1,2,4-triazin-6-yl]-5-(1H-pyrazol-4-yl)phenol dihydrochloride;

2-[3-(2,7-diazaspiro[4.4]nonan-2-yl)-1,2,4-triazin-6-yl]-5-(1H-pyrazol-4-yl)phenol dihydrochloride;

2-{3-[(3S)-3-(tert-butylamino)pyrrolidin-1-yl]-1,2,4-triazin-6-yl}-5-(1H-pyrazol-4-yl)phenol dihydrochloride;

2-{3-[(3R)-3-(tert-butylamino)pyrrolidin-1-yl]-1,2,4-triazin-6-yl}-5-(1H-pyrazol-4-yl)phenol dihydrochloride;

2-{3-[3-(cyclopentylamino)pyrrolidin-1-yl]-1,2,4-triazin-6-yl}-5-(1H-pyrazol-4-yl)phenol dihydrochloride;

2-{3-[3-(methylamino)pyrrolidin-1-yl]-1,2,4-triazin-6-yl}-5-(1,3-oxazol-2-yl)phenol dihydrochloride;

5-(imidazo[1,2-a]pyrazin-2-yl)-2-{3-[(2,2,6,6-tetramethylpiperidin-4-yl)amino]-1,2,4-triazin-6-yl}phenol hydrochloride;

5-(imidazo[1,2-a]pyridin-2-yl)-2-{3-[(2,2,6,6-tetramethylpiperidin-4-yl)amino]-1,2,4-triazin-6-yl}phenol hydrochloride;

2-[3-(3-{[(propan-2-yl)amino]methyl}pyrrolidin-1-yl)-1,2,4-triazin-6-yl]-5-(1H-pyrazol-4-yl)phenol dihydrochloride;

2-(3-{3-[(4-methyloxan-4-yl)amino]pyrrolidin-1-yl}-1,2,4-triazin-6-yl)-5-(1H-pyrazol-4-yl)phenol diftrifluoroacetate;

2-{6-[3-(tert-butylamino)pyrrolidin-1-yl]-1,2,4-triazin-3-yl}-5-(1H-pyrazol-4-yl)phenol dihydrochloride;

2-{3-[3-(methylamino)pyrrolidin-1-yl]-1,2,4-triazin-6-yl}-5-[6-(methylsulfanyl)pyrimidin-4-yl]phenol trihydrochloride;

2-{3-[3-(tert-butylamino)pyrrolidin-1-yl]-1,2,4-triazin-6-yl}-5-(3-chloro-1H-pyrazol-4-yl)phenol dihydrochloride;

4-(4-{3-[3-(tert-butylamino)pyrrolidin-1-yl]-1,2,4-triazin-6-yl}-3-hydroxyphenyl)-1H-pyrazole-3-carbonitrile dihydrochloride;

2-{3-[3-(tert-butylamino)pyrrolidin-1-yl]-1,2,4-triazin-6-yl}-5-[1-($^2$H$_3$)methyl-1H-pyrazol-4-yl]phenol hydrochloride;

3-(1-methyl-1H-pyrazol-3-yl)-6-{3-[methyl(2,2,6,6-tetramethylpiperidin-4-yl)amino]-1,2,4-triazin-6-yl}benzene-1,2-diol ftrifluoroacetate;

2-[3-(2,7-diazaspiro[4.5]decan-2-yl)-1,2,4-triazin-6-yl]-5-(1H-pyrazol-4-yl)phenol dihydrochloride;

2-[3-(hexahydropyrrolo[3,4-b]pyrrol-5(1H)-yl)-1,2,4-triazin-6-yl]-5-(1H-pyrazol-4-yl)phenol dihydrochloride;

2-(3-{3-[(3-hydroxypropyl)amino]pyrrolidin-1-yl}-1,2,4-triazin-6-yl)-5-(1H-pyrazol-4-yl)phenol dihydrochloride;

2-[3-(3-{[(oxan-4-yl)amino]methyl}pyrrolidin-1-yl)-1,2,4-triazin-6-yl]-5-(1H-pyrazol-4-yl)phenol diftrifluoroacetate;

5-[1-($^2$H$_3$)methyl-1H-pyrazol-4-yl]-2-{3-[(2,2,6,6-tetramethylpiperidin-4-yl)amino]-1,2,4-triazin-6-yl}phenol hydrochloride;

2-{6-[3-(tert-butylamino)pyrrolidin-1-yl]-1,2,4-triazin-3-yl}-5-(3-fluoro-1H-pyrazol-4-yl)phenol dihydrochloride;

2-{3-[3-(tert-butylamino)pyrrolidin-1-yl]-1,2,4-triazin-6-yl}-5-(3-methyl-1H-pyrazol-4-yl)phenol dihydrochloride;

2-{3-[3-(tert-butylamino)pyrrolidin-1-yl]-1,2,4-triazin-6-yl}-3-methoxy-5-(1H-pyrazol-4-yl)phenol ftrifluoroacetate;

2-(3-{[(3S,4S)-3-fluoro-2,2,6,6-tetramethylpiperidin-4-yl]amino}-1,2,4-triazin-6-yl)-5-[1-($^2$H$_3$)methyl-1H-pyrazol-4-yl]phenol hydrochloride;

2-{3-[(3S)-3-(tert-butylamino)pyrrolidin-1-yl]-1,2,4-triazin-6-yl}-5-(3-fluoro-1H-pyrazol-4-yl)phenol dihydrochloride;

2-{3-[(3R)-3-(tert-butylamino)pyrrolidin-1-yl]-1,2,4-triazin-6-yl}-5-(3-fluoro-1H-pyrazol-4-yl)phenol dihydrochloride;

2-{3-[methyl(2,2,6,6-tetramethylpiperidin-4-yl)amino]-1,2,4-triazin-6-yl}-5-(1H-pyrazolo[3,4-c]pyridin-1-yl)phenol formate;

2-{3-[(3R,5S)-3,5-dimethylpiperazin-1-yl]-1,2,4-triazin-6-yl}-5-(imidazo[1,2-b]pyridazin-6-yl)phenol ftrifluoroacetate;

2-(3-{3-[(cyclopentylamino)methyl]pyrrolidin-1-yl}-1,2,4-triazin-6-yl)-5-(1H-pyrazol-4-yl)phenol dihydrochloride;

2-[3-([2,3'-bipyrrolidin]-1'-yl)-1,2,4-triazin-6-yl]-5-(1H-pyrazol-4-yl)phenol dihydrochloride;

5-(1H-pyrazol-4-yl)-2-{3-[3-({[(pyridin-2-yl)methyl]amino}methyl)pyrrolidin-1-yl]-1,2,4-triazin-6-yl}phenol diftrifluoroacetate;

2-(3-{3-[(tert-butylamino)methyl]pyrrolidin-1-yl}-1,2,4-triazin-6-yl)-5-(1H-pyrazol-4-yl)phenol dihydrochloride;

2-(3-(3-{[(4-methyloxan-4-yl)amino]methyl}pyrrolidin-1-yl)-1,2,4-triazin-6-yl)-5-(1H-pyrazol-4-yl)phenol ftrifluoroacetate;

2-(3-{3-[(cyclopropylamino)methyl]pyrrolidin-1-yl}-1,2,4-triazin-6-yl)-5-(1H-pyrazol-4-yl)phenol formate;

2-[3-(3-{[(oxolan-3-yl)amino]methyl}pyrrolidin-1-yl)-1,2,4-triazin-6-yl]-5-(1H-pyrazol-4-yl)phenol hydrochloride;

5-(1H-pyrazol-4-yl)-2-{6-[(2,2,6,6-tetramethylpiperidin-4-yl)amino]-1,2,4-triazin-3-yl}phenol hydrochloride;

2-{3-[(3R)-3-(cyclobutylamino)pyrrolidin-1-yl]-1,2,4-triazin-6-yl}-5-(1H-pyrazol-4-yl)phenol dihydrochloride;

2-{3-[(3S)-3-(cyclobutylamino)pyrrolidin-1-yl]-1,2,4-triazin-6-yl}-5-(1H-pyrazol-4-yl)phenol dihydrochloride;

2-{6-[(2,2,6,6-tetramethylpiperidin-4-yl)amino]-1,2,4-triazin-3-yl}-5-(2H-1,2,3-triazol-2-yl)phenol hydrochloride;

2-[3-(3-{[(3-fluorooxan-4-yl)amino]methyl}pyrrolidin-1-yl)-1,2,4-triazin-6-yl]-5-(1H-pyrazol-4-yl)phenol hydrochloride;

2-[3-(3-{[(oxan-3-yl)amino]methyl}pyrrolidin-1-yl)-1,2,4-triazin-6-yl]-5-(1H-pyrazol-4-yl)phenol hydrochloride;

2-[3-(3-{[(8-oxabicyclo[3.2.1]octan-3-yl)amino]methyl}pyrrolidin-1-yl)-1,2,4-triazin-6-yl]-5-(1H-pyrazol-4-yl)phenol hydrochloride;

2-{3-[(3R)-3-(cyclobutylamino)pyrrolidin-1-yl]-1,2,4-triazin-6-yl}-5-(1-methyl-1H-pyrazol-4-yl)phenol hydrochloride;

2-{3-[(3S)-3-(cyclobutylamino)pyrrolidin-1-yl]-1,2,4-triazin-6-yl}-5-(1-methyl-1H-pyrazol-4-yl)phenol hydrochloride;

2-(3-{[(1R,3s,5S)-1,5-dimethyl-8-azabicyclo[3.2.1]octan-3-yl](methyl)amino}-1,2,4-triazin-6-yl)-5-(1-methyl-1H-pyrazol-4-yl)phenol ftrifluoroacetate;

2-(3-{3-[(3,3-difluorocyclopentyl)amino]pyrrolidin-1-yl}-1,2,4-triazin-6-yl)-5-(1H-pyrazol-4-yl)phenol dihydrochloride;

2-(3-{3-[(dimethylamino)methyl]pyrrolidin-1-yl}-1,2,4-triazin-6-yl)-5-(1H-pyrazol-4-yl)phenol dihydrochloride;

2-(3-{3-[(methylamino)methyl]pyrrolidin-1-yl}-1,2,4-triazin-6-yl)-5-(1H-pyrazol-4-yl)phenol dihydrochloride;

2-[3-(3-{1-[(propan-2-yl)amino]ethyl}pyrrolidin-1-yl)-1,2,4-triazin-6-yl]-5-(1H-pyrazol-4-yl)phenol dihydrochloride;

2-(3-{3-[(cyclobutylamino)methyl]pyrrolidin-1-yl}-1,2,4-triazin-6-yl)-5-(1H-pyrazol-4-yl)phenol dihydrochloride;

2-(3-{3-[(cyclobutylamino)methyl]pyrrolidin-1-yl}-1,2,4-triazin-6-yl)-5-(1-methyl-1H-pyrazol-4-yl)phenol hydrochloride;

2-(3-{[(1R,3s,5S)-1,5-dimethyl-8-azabicyclo[3.2.1]octan-3-yl](methyl)amino}-1,2,4-triazin-6-yl)-5-(2H-1,2,3-triazol-2-yl)phenol ftrifluoroacetate;

6-{3-[3-(tert-butylamino)pyrrolidin-1-yl]-1,2,4-triazin-6-yl}-2-fluoro-3-(1H-pyrazol-4-yl)phenol dihydrochloride;

5-(1H-pyrazol-4-yl)-2-{6-[(2,2,6,6-tetramethylpiperidin-4-yl)oxy]-1,2,4-triazin-3-yl}phenol hydrochloride;

2-(3-{3-[(3-fluorocyclopentyl)amino]pyrrolidin-1-yl}-1,2,4-triazin-6-yl)-5-(1H-pyrazol-4-yl)phenol dihydrochloride;

2-[3-(3-{1-[(oxan-4-yl)amino]cyclopropyl}pyrrolidin-1-yl)-1,2,4-triazin-6-yl]-5-(1H-pyrazol-4-yl)phenol dihydrochloride;

2-(3-{3-methyl-3-[(propan-2-yl)amino]pyrrolidin-1-yl}-1,2,4-triazin-6-yl)-5-(1-methyl-1H-pyrazol-4-yl)phenol trifluoroacetate;

2-{6-[(3-fluoro-2,2,6,6-tetramethylpiperidin-4-yl)amino]-1,2,4-triazin-3-yl}-5-(1H-pyrazol-4-yl)phenol hydrochloride; and 5-[1-($^2$H$_3$)methyl-1H-pyrazol-4-yl]-2-{6-[(2,2,6,6-tetramethylpiperidin-4-yl)amino]-1,2,4-triazin-3-yl}phenol hydrochloride, wherein a form of the compound is selected from the group consisting of a salt, hydrate, solvate, racemate, enantiomer, diastereomer, stereoisomer, and tautomer form thereof.

4. A pharmaceutical composition comprising the compound, or form thereof, of claim 1 in admixture with one or more pharmaceutically acceptable excipients.

5. A pharmaceutical composition comprising the compound salt of claim 2 in admixture with one or more pharmaceutically acceptable excipients.

6. A pharmaceutical composition comprising the compound, or form thereof, of claim 3 in admixture with one or more pharmaceutically acceptable excipients.

7. A method for treating or ameliorating Huntington's Disease (HD) in a subject in need thereof comprising, administering to the subject an effective amount of the compound, or form thereof, of claim 1.

8. The method of claim 7, wherein the effective amount of the compound, or form thereof, is in a range of from about 0.001 mg/kg/day to about 500 mg/kg/day.

9. A method for treating or ameliorating Huntington's Disease (HD) in a subject in need thereof comprising, administering to the subject an effective amount of the compound salt of claim 2.

10. The method of claim 9, wherein the effective amount of the compound salt is in a range of from about 0.001 mg/kg/day to about 500 mg/kg/day.

11. A method for treating or ameliorating Huntington's Disease (HD) in a subject in need thereof comprising, administering to the subject an effective amount of the compound, or form thereof, of claim 3.

12. The method of claim 11, wherein the effective amount of the compound or form thereof is in a range of from about 0.001 mg/kg/day to about 500 mg/kg/day.

\* \* \* \* \*